(12) United States Patent
Chen et al.

(10) Patent No.: US 11,820,800 B2
(45) Date of Patent: Nov. 21, 2023

(54) ORTHOGONAL PROTEIN HETERODIMERS

(71) Applicant: UNIVERSITY OF WASHINGTON, Seattle, WA (US)

(72) Inventors: Zibo Chen, Seattle, WA (US); Scott Boyken, Seattle, WA (US); Sherry Bermeo, Seattle, WA (US); Robert A. Langan, Seattle, WA (US); David Baker, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 75 days.

(21) Appl. No.: 17/285,033

(22) PCT Filed: Nov. 4, 2019

(86) PCT No.: PCT/US2019/059654
§ 371 (c)(1),
(2) Date: Apr. 13, 2021

(87) PCT Pub. No.: WO2020/093043
PCT Pub. Date: May 7, 2020

(65) Prior Publication Data
US 2021/0355175 A1 Nov. 18, 2021

Related U.S. Application Data

(60) Provisional application No. 62/904,800, filed on Sep. 24, 2019, provisional application No. 62/755,264, filed on Nov. 2, 2018.

(51) Int. Cl.
| | |
|---|---|
| *C07K 14/00* | (2006.01) |
| *C07K 14/435* | (2006.01) |
| *G01N 33/53* | (2006.01) |
| *G16B 15/00* | (2019.01) |
| *G16B 5/00* | (2019.01) |
| *B82Y 10/00* | (2011.01) |
| *G06N 3/00* | (2023.01) |
| *H03K 19/00* | (2006.01) |
| *B82Y 5/00* | (2011.01) |
| *C07K 19/00* | (2006.01) |
| *G16B 5/10* | (2019.01) |
| *G16B 5/30* | (2019.01) |
| *G01N 33/542* | (2006.01) |

(52) U.S. Cl.
CPC .............. *C07K 14/435* (2013.01); *B82Y 5/00* (2013.01); *B82Y 10/00* (2013.01); *C07K 14/00* (2013.01); *C07K 19/00* (2013.01); *G01N 33/53* (2013.01); *G06N 3/002* (2013.01); *G16B 5/00* (2019.02); *G16B 15/00* (2019.02); *H03K 19/00* (2013.01); *C07K 2319/00* (2013.01); *G01N 33/542* (2013.01); *G16B 5/10* (2019.02); *G16B 5/30* (2019.02); *Y10S 977/914* (2013.01)

(58) Field of Classification Search
None
See application file for complete search history.

(56) References Cited

U.S. PATENT DOCUMENTS

| | | | |
|---|---|---|---|
| 10,851,135 B2 * | 12/2020 | Langan | ................ C07K 14/001 |
| 2007/0287170 A1 | 12/2007 | Davis et al. | |
| 2011/0224404 A1 | 9/2011 | Blaber et al. | |
| 2022/0025003 A1 * | 1/2022 | Baker | ................... C12N 9/506 |
| 2022/0073565 A1 * | 3/2022 | Langan | .................. C07K 14/00 |
| 2022/0119467 A1 * | 4/2022 | Baker | ................... C12N 15/86 |
| 2023/0065495 A1 * | 3/2023 | Klima | ................... C12N 15/64 |

FOREIGN PATENT DOCUMENTS

| | | |
|---|---|---|
| WO | 1997/012988 | 4/1997 |
| WO | 1997/12988 A1 | 4/1997 |
| WO | 2009/030780 | 3/2009 |
| WO | 2009/030780 A2 | 3/2009 |

OTHER PUBLICATIONS

Litowski, Jennifer R. and Hodges, Robert S.; "Designing heterodimeric two stranded alpha helical coiled coils." J. Biol. Chem. (2002) 277(40) p. 37272-37279.*
Rocklin, Gabriel J.et al; "Global analysis of protein folding using massively parallel design, synthesis, and testing." Science (2017) 357 p. 168-175.*
Howes, Laura; "Deepmind ai predicts protein structures." (C&EN (2020).*
Lowe, Derek, "Not alphafold's fault." blog "in the Pipeline" entry of Sep. 7, 2022.*
Rinaudo et al., Nat. Biotechnol. 25, 795-801 (2007).
Rocklin, et al., (2017) Science 357: 168-175.
Roquet, et al., Science. 353, aad8559 (2016).
Rothemund, et al., (2006) Nature 440: 297-302.
Roybal et al., Cell. 164, 770-779 (2016).
Ruotolo, et al., (2006) Curr. Opin. Chem. Biol. 19: 402-408.
Sahasrabuddhe, et al. (2018) Proc. Natl. Acad. Sci. 115: 1268-1273.
Sandrock, et al., J. Biol. Chem. 276, 35328-35333 (2001).
Schiestl, et al. (1989) Curr. Genet. 16: 339-346.
Schneidman-Duhovny, et al. (2010) Nucleic Acids Res. 38: W540-4.
Schneidman-Duhovny, et al. (2013) Biophys J. 105: 962-974.
Schrodinger, LLC The PyMOL Molecular Graphics System Version 1.8 (2015).
Seelig, et al., (2006) Science 314: 1585-1588.
Silverman, et al., (2019) ACS Synth. Biol. 8: 403-414.
Siuti, et al., Nat. Biotechnol. 31, 448-452 (2013).

(Continued)

*Primary Examiner* — Fred H Reynolds
(74) *Attorney, Agent, or Firm* — MCDONNELL BOEHNEN HULBERT & BERGHOFF LLP

(57) ABSTRACT

Disclosed herein are designed heterodimer proteins, monomeric polypeptides capable of forming heterodimer proteins, protein scaffolds including such polypeptides, and methods for using the heterodimer proteins and subunit polypeptides for designing logic gates.

10 Claims, 19 Drawing Sheets
Specification includes a Sequence Listing.

(56) References Cited

OTHER PUBLICATIONS

Skerker, et al., (2008) Cell 133: 1043-1054.
Studier, et al., (2005) Protein Expr. Purif. 41: 207-234.
Swartz, et al., in Recombinant Gene Expression Reviews and Protocols (Humana Press, Totowa, NJ, 2004) pp. 169-182.
Tamsir, et al., Nature. 469, 212-215 (2011).
Tatko, et al. (2006) J. Am. Chem. Soc. 128: 4170-4171.
Terwilliger, et al., (2008) Acta Crystallogr. D. Biol. Crystallogr. 64: 61-69.
Testa, et al., (2009) Nucleic acids, 37: D315-22.
Thomas, et al. (2013) J. Am. Chem. Soc. 135: 5161-5166.
Thompson,et al. (2012) ACS Synth Biol. 1:118-129.
VanAernum, et al., (2019) Anal. Chem. 91: 3611-3618.
Waitt, et al., (2008) J. Am. Soc. Mass Spectrom. 19: 239-245.
Weinberg et al., Nat. Biotechnol. 35, 453-462 (2017).
Wherry et al., Immunity. 27 (2007), doi:10.1016/j.immuni.2007.11.006.
Wherry, et al., Nat. Rev. Immunol. 15, 486 499 (2015).
Wood, et al., (2018) Protein Science, 27: 103-111.
Wroblewska et al., Nat. Biotechnol. 33, 839-841 (2015).
Yeh, et al., Nature. 447, 596-600 (2007).
Yu et al., Cell. 140, 246-256 (2010).
Zarrinpar, et al., (2003) Nature 426: 676-680.
Zhang, et al., (2005) Nucleic Acids Res. 33: 2302-2309.
Zhou, et al. (2012) Anal Chem. 84:6016-6023.
Zhou, et al. (2014) Acc. Chem. Res. 47: 1010-1018.
Grigoryan, et al., (2006) J. Mol. Bio. 355: 1125-1142.
Grigoryan, et al., (2009) Nature 458: 859-864.
Guzman, et al., (2014) PLoS One 9: e92444.
Harbury, et al. (1993) Science, 262: 1401-1407.
Harbury, et al., (1994) Nature, 371: 80-83.
Harris, et al., (2001) J. Cell. Sci. 114: 3219-3231.
Havranek, et al., (2003) Nat Struct, Biol. 10: 45-52.
Howard, et al., Proc. Natl. Acad. Sci. 100, 11267-11272 (2003).
Huang, et al., (2014) Science 346: 481-485.
Jewett, et al., (2004) Biotechnol. Bioeng. 86: 19-26.
Joachimiak, et al. (2006) J. Mol. Biol. 361: 195-208.
Jones, et al., (1996) Proc. Natl Acad. Sci. 93: 13-20.
Jones, et al., (1999) J. Mol. Biol. 292: 195-202.
June, et al., Science. 359, 1361-1365 (2018).
Kabsch (2010) Acta Crystallogr. D. Biol. Crystallogr. 66: 125-132.
Keating, et al., (2001) Proc. Natl. Acad. Sci., 98: 14825-14830.
Khalil et al., Cell. 150, 647-658 (2012).
Khalil, et al., Nat Rev Genet. 2010, 11(5): 367.
Kwon, et al., (2015) Sci. Rep. 5: 8663.
Leaver-Fay, et al. (2011) Methods Enzymol. 487: 545-574.
Lee, et al., (2015) ACS Synth. Biol 4: 975-986.
Lohmueller, et al., Nucleic Acids Res. 40, 5180-5187 (2012).
Long et al., Nat. Med. 21, 581-590 (2015).
Marketsmarkets, protein engineering Market Worth $1,463.0 Million by 2020, 2015.
Marty, et al., (2015) Anal Chem. 87: 4370-4376.
Maude et al., N. Engl. J. Med. 378, 439-448 (2018).
McCoy, et al., (2007) J. Appl. Crystallogr. 40: 658-674.
McNew, et al., (2000) Nature, 407: 153-159.
Morsut et al., Cell. 164, 780-791 (2016).
Moutevelis, et al., (2009) J. Mol. Biol. 385: 726-732.
Myers, et al., (1995) Protein Sci 4: 2138-2148.
Nautiyal, et al., (1999) Protein Sci, 8: 84-90.
Neelapu et al., N. Engl. J. Med. 377, 2531-2544 (2017).
Nussinov, Mol. Biosyst. 8, 22-26 (2012).
O'Shea, et al. (1993) Current Biology, Current Science 3(10): 658-667.
Otwinowski, et al., (1997) Methods Enzymol 276: 307-326.
Park, et al., Science. 299, 1061-1064 (2003).
Pauken et al., Science. 354, 1160-1165 (2016).
Pause, et al., Proc. Natl. Acad. Sci. 96, 9533-9538 (1999).
Perisic, et al., (2018) Pharmaceuticals, 11(29): 1-26.
Porter, et al., J. Am. Chem. Soc. 130, 6488-6497 (2008).

Potapov, et al., (2015) PLoS Comput Biol 11:e1004046.
Prehoda, et al., Science. 290, 801-806 (2000).
Qian, et al., (2011) Science 332: 1196-1201.
Rambo, et al. (2011) Biopolymers, 95: 559-571.
Reinke, et al., (2013), Science 340: 730-734.
The International Search Report (ISR) with Written Opinion for PCT/US2019/059654 dated Dec. 18, 2019, pp. 1-22.
O'Shea, Erin K. et al. "Peptide 'Velcro' Design of a heterodimeric coiled coil" Current Biology (1993) vol. 3(10), pp. 658-667.
Gradisar, Helena et al. "De novo design of orthogonal peptide pairs forming parallel coiled-coil heterodimers" Journal of Peptide Science 2010) vol. 17(2), pp. 100-106.
Crooks, Richard O. et al. "Deriving Heterospecific Self-Assembling Protein-Protein Interactions Using a Computational Interactome Screen" Journal of Molecular Biology (2015) vol. 428(2), pp. 385-398.
Reinke, Aaron W. et al. "A Synthetic Coiled-Coil Interactome Provides Heterospecific Modules for Molecular Engineering" Journal of the American Chemical Society (2010) vol. 132(17), pp. 6025-6031.
Edwards, Amanda L. et al. "Challenges in Targeting a Basic Helix-Loop-Helix Transcription Factor with Hydrocarbon-Stapled Peptides" ACS Chemical Biology (2016), vol. 11, pp. 3146-3153.
Gradisar, Helena et al. "Design of a single-chain polypeptide tetrahedron assembled from coiled-coil segments" Nature Chemical Biology (2013) vol. 9(6), pp. 362-366.
Chen, Zibo et al. "Programmable design of orthogonal protein heterodimers" Nature (2018) vol. 565(7737), pp. 106-111.
Aakre, et al., (2015). Cell, 163: 594-606.
Acharya, et al., (2006) Biochemistry 45: 11324-11332.
Adams, et al., (2010) Acta Crystallogr. D. Biol. Crystallogr. 66: 213-221.
Afonine, et al., (2010) Acta Crystallogr. D. Biol. Crystallogr. 66: 1153-1163.
Anderson, et al., (2018) ACS Omega 3:4810-4815.
Andrews, et al., Science. 361, eaap8987 (2018).
Angelici, et al., Cell Rep. 16, 2525-2537 (2016).
Antebi, et al., (2017) Cell 170: 1184-1196.
Apostolovic, et al., Chem Soc Rev, 2010, 39(9): 3541.
Aranda-Diaz, et al. (2017) ACS Synth. Biol. 6: 545-554.
Auslander, et al., Nature. 487, 123-127 (2012).
12. Bartel, et al., (1996) Nat Genet. 12: 72-77.
Bern, et al., (2018) J. Proteome Res 17: 1216-1226.
Bernado, et al., (2006) Biophys J. 91: 4536-4543.
Bolon, et al., (2005) Proc. Natl. Acad. Sci., 102: 12724-12729.
Bonnet, et al., Science. 340, 599-603 (2013).
Boyken, et al., (2016) Science 352: 680-687.
Bromley, et al., (2009) J. Am. Chem. Soc. 131: 928-930.
Burkhard, et al. (2001) Trend Cell Biol, 11: 82-88.
Chen, et al., (2018) Nature 565: 106-111.
Chien, et al., (1991) Proc. Natl. Acad. Sci. 88: 9578-9582.
23. Crick (1953) Acta Crystallogr. 6: 685-689.
Crooks, et al., (2017) Biochemistry, 56 (11): 1573-1584.
Davis, et al., (2007) Nucleic Acids Res. 35: W375-83.
De Ronde, et al., Biophys J., 2012, 103(5): 1097.
Diss, et al., (2008) J. Am. Chem. Soc. 103: 1321-1327.
Dixon et al., ACS Chem. Biol. 11, 400-408 (2016).
Dueber, et al., Nat. Biotechnol. 25, 660-662 (2007).
Dueber, et al., Science. 301, 1904-1908 (2003).
Dyachenko, et al., (2015) Anal. Chem. 87: 6095-6102.
Dyer, et al., (2014) Methods Mol. Biol. 1091: 245-258.
Edwards, et al., (2016) ACS Chem. Biol. 11(11): 3146-3153.
Elowitz, et al., Nature. 403, 335-338 (2000).
Ernsley, et al., (2004) Acta Crystallogr. D. Biol. Crystallogr. 60: 2126-2132.
Estrada, et al., (2009) BMC Bioinformatics 10: 104.
Fink et al., Nat. Chem. Biol. 15, 115-122 (2019).
Fletcher, et al., (2012) ACS Synth. Biol. 1: 240-250.
Fraietta et al., Nat. Med. 24, 563-571 (2018).
Gao, et al., Science. 361, 1252-1258 (2018).
Gardner, et al., Nature. 403, 339-342 (2000).
Gillingham, et al., (2003) Biochim. Biophys. Acta 1641: 71-85.
Gonzalez, et al., (1996) Nat. Struct. Biol. 3: 1011-1018.

(56) References Cited

OTHER PUBLICATIONS

Gordley et al., Proc. Natl. Acad. Sci. 13, 13528-13533 (2016).
Gradisar, et al., (2011) J. Pept. Sci. 17: 100-106.
Gradisar, et al., (2013) Nature Chem. Biol. 9(6): 362-366.
Green et al., Nature. 548, 117-121 (2017).
Green, et al., Cell. 159, 925-939 (2014).
Grigoryan, et al. (2011) J. Mol. Biol. 405: 1079-1100.
Taylor et al. "Selbstorganisation von funktionellen diskreten dreidimensionalen Architekturen in Wasser". Angewandte Chemie 131(5): 1292-1320, (Dec. 2018).
Grigoryan, et al., "Structure-based predication of bZIP partnering specificity" (2006) Mol. Biol. 355: 1125-1142.
Grigoryan & Keating, et al., "Structural specificity in coiled-coil interactions," Curr Opin Struct Biol, 2008, 18(4): 477-483.
Lumb, et al., "A buried polar interaction imparts structural uniqueness in a designed heterodimeric coiled coil" (1995) Biochemistry 34: 8642-8648.
Munoz, et al., "Elucidating the Folding Problem of Helical Peptides using Empirical Parameters. III. Temperature and pH Dependence," (1995) J. Mol. Biol. 245: 297-308.
Munoz, et al., "Elucidating the folding problem of helical peptides using empirical parameters," (1994) Nature Structura Biology 1(6):399-409.

\* cited by examiner

A

B

| Monomer A SEQ ID No. | Monomer B SEQ ID NO: |
|---|---|
| 1 | 2 |
| 331 | 2 |
| 3 | 4 |
| 5 | 6 |
| 5 | 332 |
| 7 | 8 |
| 7 | 334 |
| 9 | 10 |
| 11 | 12 |
| 13 | 14 |
| 13 | 336 |
| 15 | 16 |
| 15 | 338 |
| 17 | 18 |
| 19 | 20 |
| 21 | 22 |
| 23 | 24 |
| 25 | 26 |
| 25 | 340 |
| 27 | 28 |
| 29 | 30 |
| 29 | 342 |
| 31 | 32 |
| 31 | 344 |
| 33 | 34 |
| 33 | 346 |
| 35 | 36 |
| 35 | 348 |
| 37 | 38 |
| 37 | 418 |
| 39 | 40 |
| 39 | 350 |
| 41 | 42 |
| 41 | 352 |
| 43 | 44 |
| 45 | 46 |
| 45 | 354 |
| 47 | 48 |
| 47 | 356 |
| 49 | 50 |
| 51 | 52 |
| 53 | 54 |
| 53 | 358 |

| Monomer A SEQ ID No. | Monomer B SEQ ID NO: |
|---|---|
| 55 | 56 |
| 55 | 360 |
| 57 | 58 |
| 57 | 362 |
| 59 | 60 |
| 59 | 364 |
| 61 | 62 |
| 61 | 366 |
| 63 | 64 |
| 65 | 66 |
| 65 | 368 |
| 67 | 68 |
| 67 | 370 |
| 69 | 70 |
| 69 | 372 |
| 71 | 72 |
| 71 | 374 |
| 73 | 74 |
| 73 | 376 |
| 75 | 76 |
| 75 | 378 |
| 77 | 78 |
| 77 | 380 |
| 79 | 80 |
| 79 | 382 |
| 81 | 82 |
| 337 | 384 |
| 83 | 84 |
| 339 | 386 |
| 85 | 86 |
| 85 | 388 |
| 87 | 88 |
| 87 | 390 |
| 89 | 90 |
| 89 | 392 |
| 91 | 92 |
| 91 | 394 |
| 93 | 94 |
| 93 | 396 |
| 95 | 96 |
| 95 | 398 |
| 97 | 98 |
| 97 | 400 |

| Monomer A SEQ ID No. | Monomer B SEQ ID NO: |
|---|---|
| 99 | 100 |
| 99 | 402 |
| 101 | 102 |
| 341 | 404 |
| 103 | 104 |
| 103 | 406 |
| 105 | 106 |
| 343 | 408 |
| 107 | 108 |
| 107 | 410 |
| 109 | 110 |
| 109 | 412 |
| 111 | 112 |
| 111 | 424 |
| 113 | 114 |
| 113 | 416 |
| 115 | 116 |
| 459 | 420 |
| 117 | 118 |
| 345 | 422 |
| 119 | 120 |
| 347 | 424 |
| 121 | 122 |
| 349 | 426 |
| 123 | 124 |
| 351 | 428 |
| 125 | 126 |
| 353 | 126 |
| 127 | 128 |
| 355 | 430 |
| 129 | 130 |
| 357 | 432 |
| 131 | 132 |
| 359 | 434 |
| 133 | 134 |
| 361 | 436 |
| 135 | 136 |
| 363 | 438 |
| 137 | 138 |
| 365 | 440 |
| 139 | 140 |
| 367 | 442 |
| 141 | 142 |

FIGURE 16

| Monomer A SEQ ID No. | Monomer B SEQ ID NO: | Monomer A SEQ ID No. | Monomer B SEQ ID NO: | Monomer A SEQ ID No. | Monomer B SEQ ID NO: |
|---|---|---|---|---|---|
| 369 | 444 | 411 | 484 | 259 | 260 |
| 143 | 144 | 185 | 186 | 261 | 262 |
|  |  | 413 | 486 | 263 | 264 |
| 371 | 446 | 187 | 188 | 265 | 266 |
| 145 | 146 | 415 | 488 | 267 | 268 |
| 373 | 448 | 189 | 190 | 269 | 270 |
| 147 | 148 | 417 | 490 | 271 | 272 |
| 375 | 450 | 191 | 192 | 273 | 274 |
| 149 | 150 | 419 | 492 | 275 | 276 |
| 377 | 452 | 193 | 194 | 277 | 278 |
| 151 | 152 | 421 | 494 | 279 | 280 |
| 379 | 454 | 195 | 196 | 281 | 282 |
| 153 | 154 | 197 | 198 | 283 | 284 |
| 381 | 456 | 199 | 200 | 285 | 286 |
| 155 | 156 | 201 | 202 | 287 | 288 |
| 383 | 458 | 203 | 204 | 289 | 290 |
| 157 | 158 | 205 | 206 |  |  |
| 385 | 460 | 207 | 208 |  |  |
| 159 | 160 | 209 | 210 |  |  |
| 387 | 462 | 211 | 212 |  |  |
| 161 | 162 | 213 | 214 |  |  |
| 389 | 464 | 215 | 216 |  |  |
| 163 | 164 | 217 | 218 |  |  |
| 391 | 466 | 219 | 220 |  |  |
| 165 | 166 | 221 | 222 |  |  |
| 393 | 468 | 223 | 224 |  |  |
| 167 | 168 | 225 | 226 |  |  |
| 395 | 470 | 227 | 228 |  |  |
| 169 | 170 | 229 | 230 |  |  |
| 397 | 472 | 231 | 232 |  |  |
| 171 | 172 | 233 | 234 |  |  |
| 399 | 474 | 235 | 236 |  |  |
| 173 | 174 | 237 | 238 |  |  |
| 401 | 174 | 239 | 240 |  |  |
| 175 | 176 | 241 | 242 |  |  |
| 403 | 476 | 243 | 244 |  |  |
| 177 | 178 | 245 | 246 |  |  |
| 405 | 478 | 247 | 248 |  |  |
| 179 | 180 | 249 | 250 |  |  |
| 407 | 480 | 251 | 252 |  |  |
| 181 | 182 | 253 | 254 |  |  |
| 409 | 482 | 255 | 256 |  |  |
| 183 | 184 | 257 | 258 |  |  |

FIGURE 16 (cont.)

ORTHOGONAL PROTEIN HETERODIMERS

CROSS REFERENCE

This application is a U.S. national phase of International Application No. PCT/US2019/059654, filed on Nov. 4, 2019, which claims priority to U.S. Provisional Application No. 62/904,800, filed on Sep. 24, 2019 and U.S. Provisional Application No. 62/755,264, filed on Nov. 2, 2018, all of which are incorporated by reference herein in their entirety.

FEDERAL FUNDING STATEMENT

This invention was made with government support under Grant No. GM103533 awarded by the National Institutes of Health. The government has certain rights in the invention

BACKGROUND

Heterodimeric interaction specificity between two DNA strands, and between protein and DNA, is often achieved by varying side chains or bases coming off the protein or DNA backbone—for example, the bases participating in Watson-Crick base pairing in the double helix, or the side chains of protein contacting DNA in TALEN-DNA complexes. This modularity enables the generation of an essentially unlimited number of orthogonal DNA-DNA and protein-DNA heterodimers. In contrast, protein-protein interaction specificity is often achieved through backbone shape complementarity, which is less modular and hence harder to generalize.

SUMMARY

In one aspect, the disclosure provides designed heterodimer proteins, comprising:
 (a) a monomer A polypeptide, wherein the monomer A polypeptide is a non-naturally occurring polypeptide comprising 1-5 alpha helices connected by amino acid linkers; and
 (b) a monomer B polypeptide, wherein the monomer B polypeptide is a non-naturally occurring polypeptide comprising 1-5 alpha helices connected by amino acid linkers, wherein monomer A and monomer B non-covalently interact to form the designed heterodimer protein. In one embodiment,
  (i) monomer A comprises a polypeptide having at least 70%, 75%, 80%, 85%, 90%, 91%, 92%, 93%, 94%, 95%, 96%, 97%, 98%, 99%, or 100% sequence identity along the length of the amino acid sequence of an odd-numbered SEQ ID NO selected from the group consisting of selected from the group SEQ ID NOS: 1-290; and
  (ii) monomer B comprises a polypeptide having at least 70%, 75%, 80%, 85%, 90%, 91%, 92%, 93%, 94%, 95%, 96%, 97%, 98%, 99%, or 100% sequence identity along the length of the amino acid sequence of an even-numbered SEQ ID NO selected from the group consisting of selected from the group SEQ ID NOS: 1-290, wherein the even-numbered SEQ ID NO is the binding partner of the odd-numbered SEQ ID NO. in step (i).

In another aspect, the disclosure provides non-naturally occurring polypeptide comprising a polypeptide having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 1-290.

In another aspect, the disclosure provides non-naturally occurring polypeptide comprising a polypeptide having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494.

In another aspect, the disclosure provides proteins comprising 2, 3, 4, or more non-naturally occurring polypeptides having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 1-290, wherein the 2, 3, 4, or more naturally occurring polypeptides are covalently linked. In one embodiment, each of the 2, 3, 4, or more non-naturally occurring polypeptides are different. In another embodiment, each of the 2, 3, 4, or more non-naturally occurring polypeptides are present in a fusion protein.

In another aspect, the disclosure provides proteins comprising 2, 3, 4, or more non-naturally occurring polypeptides having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 1-290, 1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 wherein the 2, 3, 4, or more naturally occurring polypeptides are covalently linked. In one embodiment, each of the 2, 3, 4, or more non-naturally occurring polypeptides are different. In another embodiment, each of the 2, 3, 4, or more non-naturally occurring polypeptides are present in a fusion protein. In each of these aspects, amino acid changes from the reference amino acid sequence may be conservative amino acid substitutions. In another embodiment, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of amino acid residues at defined interface positions are invariant compared to the reference amino acid sequence.

In another aspect, the disclosure provides protein scaffolds, comprising
 a) a first designed component comprised of any number of monomer A polypeptides and/or monomer B polypeptides, each from different heterodimers, connected into a single component by amino acid linkers.
 b) a second designed component, comprising corresponding monomers for each monomer A and/or monomer B in the first designed component one;
 wherein the first and second designed components interact to form the protein scaffold, and wherein each monomer A only interacts in the scaffold with its monomer B mate.

In another aspect, the disclosure provides methods of forming the designed heterodimer protein of any embodiment of the disclosure, comprising:
 a) providing two of the monomers as unlinked monomers;
 b) providing the other two monomers as linked monomers;

whereby the unlinked monomers associate with their respective monomer of the same heterodimer, and not with any of the other monomers.

In another aspect, the disclosure provides designed heterodimer proteins, comprising:
a) asymmetric buried hydrogen bond networks incorporated into regularly repeating backbone structures; and
b) helix hairpin helix monomers wherein the supercoil phases of the helices are fixed at 0, 90, 180, or 270 degrees and the supercoil twist ($\omega 0$) and helical twist ($\omega 1$) are held constant for either a two layer left handed super coil ($\omega 0=-2.85$ and $\omega 1=102.85$), or a 5 layer untwisted bundle ($\omega 0=0$ and $\omega 1=100$)

In another aspect, the disclosure provides fusion proteins comprising a polypeptide of the formula X-B-Z, wherein:
(a) the X domain is a non-naturally occurring polypeptide comprising 1, 2, or 3 alpha helices, wherein the X domain is capable of non-covalently binding to a first target;
(b) the Z domain is a non-naturally occurring polypeptide comprising 1, 2, or 3 alpha helices, wherein the Z domain is capable of non-covalently binding to either (i) a second target that differs from the first target, or (ii) a different non-naturally occurring polypeptide comprising 1, 2, or 3 alpha helices; and
(c) the B domain is an amino acid linker;
wherein a combined number of alpha helices from the X domain and the Z domain is 4, 5, or 6; and
wherein the X domain and the Z domain interact at a binding interface, wherein the binding interface comprises a hydrogen bond network in which at least one side chain in each alpha helix hydrogen of the X domain bonds with a side chain in an alpha helix in the Z domain, and wherein the binding interface comprises a plurality of hydrophobic residues.

In another aspect, the disclosure provides kits or compositions, comprising at least two fusion proteins comprising the formula X-B-Z, wherein
the B domain in each fusion protein is independently a polypeptide linker;
the X domain in each fusion protein comprises a first non-naturally occurring polypeptide comprising 1, 2, or 3 alpha helices;
the Z domain in each fusion protein comprises a second non-naturally occurring polypeptide comprising 1, 2, or 3 alpha helices, wherein a combined number of alpha helices from the X domain and the Z domain in each individual fusion protein is 4, 5, or 6; wherein the X domain and the Z domain interact at a binding interface, wherein the binding interface comprises a hydrogen bond network in which at least one side chain in each X domain alpha helix bonds with a side chain in an alpha helix in the Z domain; wherein
the X domain in a first fusion protein is capable of non-covalently binding to a first target;
the Z domain in a second fusion protein is capable of non-covalently binding to a second target; and
the X domains and Z domains in each individual fusion protein that are not capable of non-covalently binding to the first target or the second target are capable of non-covalently binding to an X or a Z domain of a different fusion protein in the plurality of fusion proteins.

In one embodiment of the fusion proteins, kits, or compositions, each X domain and each Z domain comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide comprising the amino acid sequence selected from SEQ ID NO:1-290, with the proviso that the X domain and the Z domain do not do not form a heterodimer (a-b) pair. In another embodiment at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of amino acid residues at defined interface positions of each X domain and each Z domain are invariant compared to the reference amino acid sequence.

In one aspect, the disclosure provides methods, comprising:
(i) contacting a fusion protein according to any embodiment of the disclosure with a biological sample under conditions to promote non-covalent binding of the fusion protein with first target and second target present in the sample, and
(ii) detecting non-covalent binding of the one or more fusion proteins to the first target and/or the second target in the biological sample.

In one embodiment, the method comprises detecting cooperative non-covalently binding of the one or more fusion proteins to the first target and the second target in the biological sample. In another embodiment, the method comprises detecting non-covalent binding of the one or more fusion proteins to the first target or the second target in the biological sample.

In another aspect, the disclosure provides methods for target detection, comprising
(a) contacting a biological sample with at least two fusion proteins, wherein each of the at least two fusion proteins comprises the formula X-B-Z, wherein
each B is independently a polypeptide linker;
each X domain comprises a first non-naturally occurring polypeptide comprising 1, 2, or 3 alpha helices;
each Z domain comprises a second non-naturally occurring polypeptide comprising 1, 2, or 3 alpha helices, wherein a combined number of alpha helices from the X domain and the Z domain in each individual fusion protein is 4, 5, or 6; wherein the X domain and the Z domain interact at a binding interface, wherein the binding interface comprises a hydrogen bond network in which at least one side chain in each X domain alpha helix bonds with a side chain in an alpha helix in the Z domain; wherein
the X domain in a first fusion protein is capable of non-covalently binding to a first target;
the Z domain in a second fusion protein is capable of non-covalently binding to a second target; and
the X domains and Z domains in each individual fusion protein that are not capable of non-covalently binding to the first target or the second target are capable of non-covalently binding to an X or a Z domain of a different fusion protein in the plurality of fusion proteins;
(b) detecting non-covalent binding of the two or more fusion proteins to the first target and/or the second target in the biological sample.

In one aspect, the disclosure provides compositions comprising
(a) a first polypeptide comprising 2 alpha helices, wherein the first polypeptide is capable of non-covalently binding a first target; and
(b) a second polypeptide comprising 2 alpha helices, wherein the first polypeptide is capable of non-covalently binding to the second polypeptide, and wherein the second polypeptide is capable of non-covalently binding a second target that differs from the first target; wherein:
  (i) a binding affinity of the first polypeptide for the first target is approximately equal to a binding affinity of the second polypeptide for the second target; and
  (ii) the binding affinity of the first polypeptide for the first target and the binding affinity of the second polypeptide for the second target are greater than the binding affinity of the first target and the second target for each other.

In one aspect, the disclosure provides compositions comprising
  (a) a first polypeptide comprising 2 alpha helices, wherein the first polypeptide is capable of non-covalently binding a first target; and
  (b) a second polypeptide comprising 2 alpha helices, wherein the first polypeptide is capable of non-covalently binding to the second polypeptide, and wherein the second polypeptide is capable of non-covalently binding a second target that differs from the first target; wherein:
  (i) a binding affinity of the first polypeptide for the second polypeptide is greater than a binding affinity of the second polypeptide for the second target;
  (ii) a binding affinity of the first polypeptide for the first target is approximately equal to a binding affinity of the second polypeptide for the second target; and
  (iii) the binding affinity of the first polypeptide for the first target and the binding affinity of the second polypeptide for the second target are greater than the binding affinity of the first target and the second target for each other.

In another aspect, the disclosure provides compositions comprising
  (a) a first polypeptide comprising 4 alpha helices, wherein the first polypeptide is capable of non-covalently binding a first target; and
  (b) a second polypeptide comprising 4 alpha helices, wherein the second polypeptide is capable of non-covalently binding a second target that differs from the first target; wherein:
  (i) a binding affinity of the first target for the second target is greater than a binding affinity of the first polypeptide for the first target;
  (ii) a binding affinity of the first polypeptide for the first target is approximately equal to a binding affinity of the second polypeptide for the second target; and
  (iii) the sum of the binding affinity of (A) the first polypeptide for the first target and (B) the binding affinity of the second polypeptide for the second target, is greater than the binding affinity of the first target and the second target.

In various embodiments for each composition of the disclosure, the composition may further comprise the first target and the second target, and the first target and/or the second target further may comprise one or more effector polypeptide domains. In one embodiment, the first polypeptide and/or the second polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide comprising the amino acid sequence selected from the group consisting of SEQ ID NO:1-290, or the group consisting of SEQ ID NOS:1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494. In another embodiment, the first target and/or the second target each comprise a polypeptide that is 50%, 55%, 60% 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide comprising the amino acid sequence selected from the group consisting of SEQ ID NO:1-290, or the group consisting of SEQ ID NOS:1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, with the proviso that the first target forms a heterodimer (a-b) pair with the first polypeptide, and the second target forms a heterodimer (a-b) pair with the second polypeptide. In another embodiment, the compositions are contacted with a biological sample and binding is detected, such as detecting an output signal caused by actions of effector polypeptides upon binding.

The disclosure also provides nucleic acids encoding the polypeptides, proteins, and fusion proteins of the disclosure; expression vectors comprising the nucleic acids operatively linked to a promoter; and host cells comprising the nucleic acids, expression vectors, and/or polypeptides, proteins, fusion proteins, scaffolds, and designed heterodimer pairs of the disclosure.

DESCRIPTION OF THE FIGURES

FIG. 1A shows individual helix generation: the helical phase (AO, supercoil radius (R) and offset along the Z-axis (Z offset) were exhaustively sampled; a total of 11 free parameters since there is no z offset for the first helix. FIG. 1B shows top-down view of the parallel twisted backbone. FIG. 1C shows representative hydrogen bond networks identified using HBNET™. FIG. 1D shows matches of multiple HBNET™ containing heptads to a single full length backbone. FIG. 1E shows addition of loops to connect the 4 helices into two helix hairpins. FIGS. 1F, 1G, and 1H show SEC trace, CD spectra and (inset) temperature melt, and SAXS (black, experimental SAXS data; red, spectra computed from the designed backbones) profile of the design DHD37_ABXB. Experiments were performed once.

FIGS. 2A-2D show crystal structures superimposed on design models with monomers; cross-sections on backbones (left) indicate locations of designed hydrogen-bond networks (middle panels). Solid and dashed boxes compare networks in design model and crystal structure. Black boxes compare overall hydrophobic packing. FIG. 2A shows DHD_131, 2.4 Å resolution with 1.0 Å Cα RMSD. FIG. 2B shows DHD37_1:234, 3.3 Å resolution with 1.4 Å RMSD. FIG. 2C shows DHD_127, 1.8 Å resolution with 1.7 Å RMSD. FIG. 2D shows DHD_15, 3.4 Å resolution with 0.9 Å RMSD; hydrogen bond networks were not well resolved. FIGS. 2E-2F show DHD_39 and DHD_120 backbones and designed hydrogen bond networks. Experimental SAXS data (black) are similar to spectra computed from the designed backbones.

FIG. 3A shows induced dimerizer formed from "b" component of DHD13_XAAA fused to "b" component of DHD37_ABXB with an intervening flexible linker. The "a" components of the two heterodimers are brought into close proximity by the heterodimerizer. FIG.

3B shows Y2H data on 4 induced dimerization systems. For each pair of bars: left, without heterodimerizer fusion; right, with heterodimerizer fusion. Dashed line indicates background growth with unfused AD and DBD. Data are mean±s.d. from 3 biological repeats. FIG. 3C shows 9_a, 13_XAAA_a and 37_ABXB_a were covalently linked to form a scaffold, recruiting 9_b (hexahistidine tagged), 13_XAAA_b and 37_ABXB_b.

FIG. 4A shows Y2H for 21 heterodimers show heterodimer formation with little homodimer formation. First letter at bottom indicates monomer fused to AD, second letter, to DBD. FIG. 4B shows Y2H all by all testing of 9 pairs of heterodimers, colors indicate growth. Boxes indicate designed cognate heterodimer pairs, dashed black box indicates a set of 6 orthogonal heterodimers. FIG. 4C shows Off-target binding of DHD15_a and DHD13_XAAA_b, in the absence (left) or presence (right) of DHD15_b and DHD13_XAAA_a. Data are mean±s.d. Red dashed line indicates background growth with unfused AD and DBD.

FIG. 5A shows overlay of 50 backbones with different Crick parameters for each helix. FIG. 5B shows example hydrogen bond networks from the systematic search, each involving at least 4 residues and contacting all 4 helices.

FIGS. 6A and 6B show CD spectra for thermal denaturation of DHD_15 and DHD_20, respectively. Top, wavelength scan at 25° C., 75° C., 95° C., and final 25° C. Designs were alpha helical and stable up to 95° C. Bottom, CD temperature melts, monitoring absorption at 222 nm as temperature was increased from 25° C. to 95° C. FIG. 6C shows GdnHCl denaturation of DHD_127 by CD monitoring absorption at 222 nm. All CD experiments were performed once.

FIG. 7A shows on a 2+2 backbone (left), two loops were designed to connect the 4 helices into a single monomer in 2 different ways (middle), after which 4 different cut points were introduced to generate 4 possible backbone permuted heterodimers of a single helix and a three helix bundle (3+1 heterodimers, right). For example, 2:134 refers to a heterodimer where the original helix 2 is a single helix, and helices 1, 3, and 4 were connected into a 3 helix bundle. FIG. 7B shows hydrogen bond network permutation. Each unique network was assigned a letter (Networks "A" and "B" in this case), and with the hydrophobic packing assigned X. The backbone on the left reads "ABXB", with its first heptad accommodates network "A", its second and fourth heptad accommodate network "B", and its third heptad accommodates hydrophobic packing only.

FIG. 8A shows crystal structure of DHD_15 at pH 6.5, with 2.25 Å resolution. FIG. 8B shows superposition of design models in color onto both halves of the crystal structure in white, with backbone RMSD of 1.83 Å. FIGS. 8C to 8F show SEC traces of the induced dimerization DHD_9-13 fusion, DHD_15-37 fusion, DHD_13-37 fusion, and the scaffolding complex in FIG. 3C (the peak at around 15 mL corresponds to the fully assembled complex, followed by a peak representing excess of individual components). FIG. 8G shows CD thermal melt curves for the scaffolding complex in FIG. 3C. Wavelength scan was performed at 25° C., 75° C., 95° C., and final 25° C. Design was alpha helical and stable up to 95° C. FIG. 8H, CD chemical denaturation profile of the scaffolding complex in FIG. 3C. 2 (FIG. 8C to 8F) or 1 (FIG. 8G to 8H) biologically independent repeats were performed.

FIG. 9A shows Y2H assay with cell growth on agar plates containing 100 mM 3-AT, lacking tryptophan, leucine and histidine. Plates were imaged at Day 5. White, no growth on agar plates; grey, weak growth forming non-circular colonies; black, strong growth. FIG. 9B shows Y2H result by growing yeast culture in liquid media containing 100 mM 3-AT, lacking tryptophan, leucine and histidine. OD 600 values were measured at Day 2 to evaluate cell growth. FIG. 9C shows an additional set of DHDs tested by Y2H showing improved orthogonality. FIG. 9D shows distribution of OD 600 values for non-cognate interactions in FIG. 9B, the majority of cells grew to OD 600 values less than 0.4, indicating weak interactions for non-cognate binding. FIG. 9E shows more buried bulky polar residues strongly correlates with design success. f, Successful designs tend to have bigger polar interface surface area. FIG. 9G shows designs with better hydrophobic packing (as reported by the ROSETTA™ filter value Average Degree on Ile, Leu and Val residues) tend to have a higher chance of being constitutive heterodimers. Two (FIGS. 9A to 9C) independent experiments were performed.

FIG. 11A shows backbone structure of A:A' heterodimer building block, with hydrogen bond network detail in inset. Bottom right, condensed representation used throughout figures. FIG. 11B shows thermodynamic cycle describing the induced dimerization system. FIG. 11C shows simulation of the induced dimerization system under thermodynamic equilibrium. A and B' monomers were held constant while titrating in various initial amounts of the A'-B dimerizer proteins. If binding is not cooperative (small c), the final amount of trimeric complexes decreases when the dimerizer protein is in excess. FIG. 11D shows equilibrium denaturation experiments monitored by CD for designs with 6- and 12-amino acid (AA) linkers. Circles represent experimental data, and lines are fits to the 3-state unimolecular unfolding model. Design models are shown on the side. FIG. 11E shows experimental SAXS profile of 1'-2' with a 6-residue linker (in black), fitted to the calculated profile of 1:1' heterodimer. FIG. 11F shows an induced dimerization system using a 6-residue linker. FIG. 11G shows a two-input AND gate schematic. FIG. 11H shows a three-input AND gate.

FIG. 12A shows CIPHR gates are built from DHDs (top) with monomers or covalently connected monomers as inputs (left); some gates utilize only the designed cognate interactions (left side of middle panel), while others take advantage of observed inter and intramolecular binding affinity hierarchies (right side of middle panel). FIGS. 12B and 12C show two-input AND (12B) and OR (12C) CIPHR logic gates based on orthogonal DHD interactions. FIGS. 12D to 12G show NOT (12D), NOR (12E), XNOR (12F), and NAND (12G) CIPHR logic gates made from multispecific and competitive protein binding. For each gate, black dots represent individual Y2H growth measurement corrected over background growth, with their average values shown in bars. * indicates no yeast growth over background. 0s and 1s in the middle and right blocks represent different input states and expected outputs, respectively. \

FIG. 13A shows schematic of a three-input AND gate. FIG. 13B shows schematic of a three-input OR gate. FIG. 13C shows Y2H results confirmed activation of the 3-input OR gate with either of the inputs. FIG. 13D shows schematic of a DNF gate. FIG. 13 E shows Y2H results confirmed proper activation of the gate. For each gate, black dots represent individual measurements corrected over background growth, with their average values shown in bars.

FIG. 15A shows the 8:8' heterodimer binds more tightly than the homodimers of its monomers. FIG. 15B shows binding affinity gradient among the monomers of 1:1', 9:9', and 10:10' pairs.

FIG. 16 shows exemplary heterodimer proteins comprising combinations of monomer A and monomer B.

DETAILED DESCRIPTION

Figures 1A, 1B, 1C, 1D, 1E, 1F, 1G, 1H:
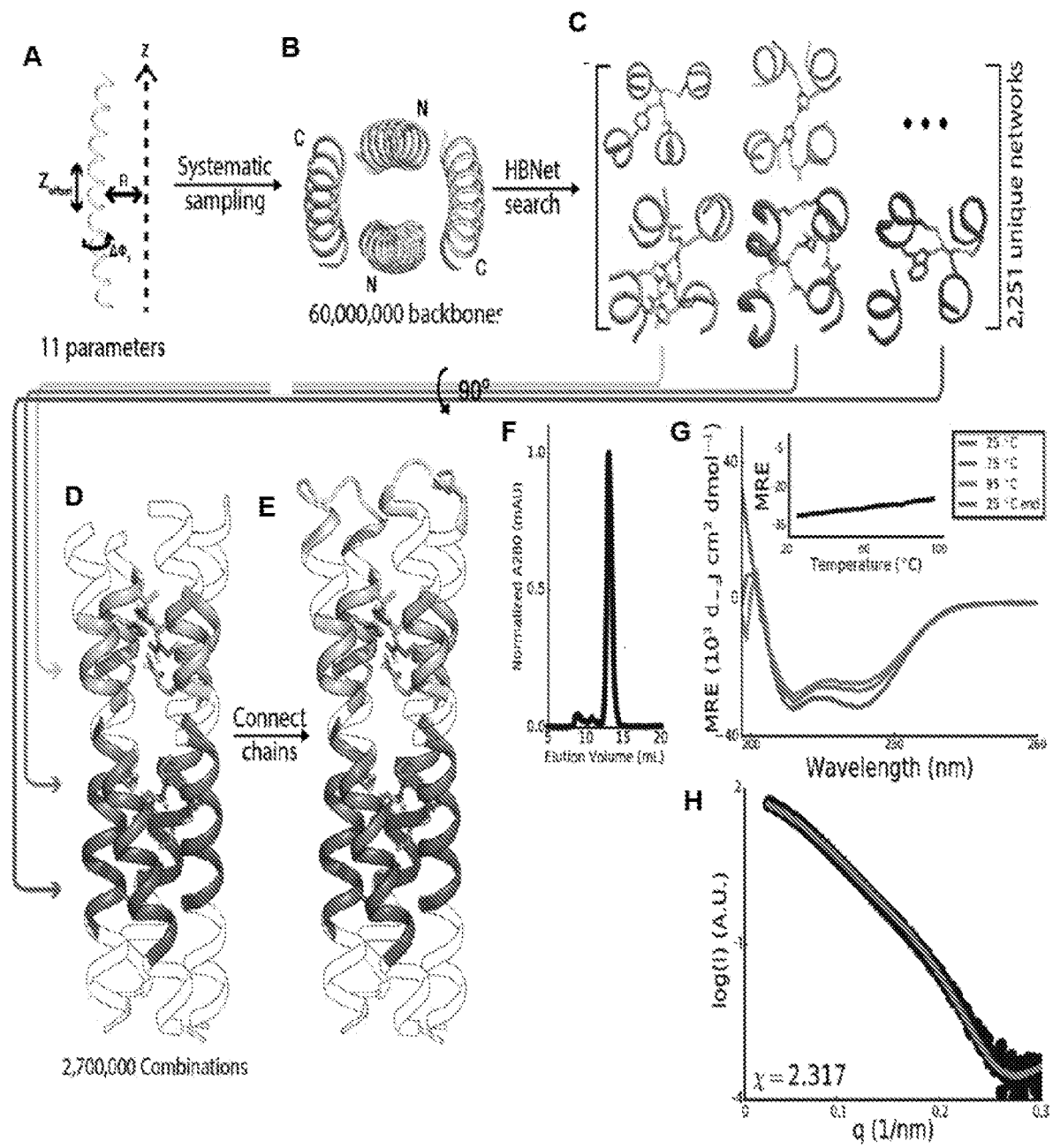
FIGS. 1A to 1H shows modular heterodimer design.
Figures 2A, 2B, 2C, 2D, 2E, 2F:
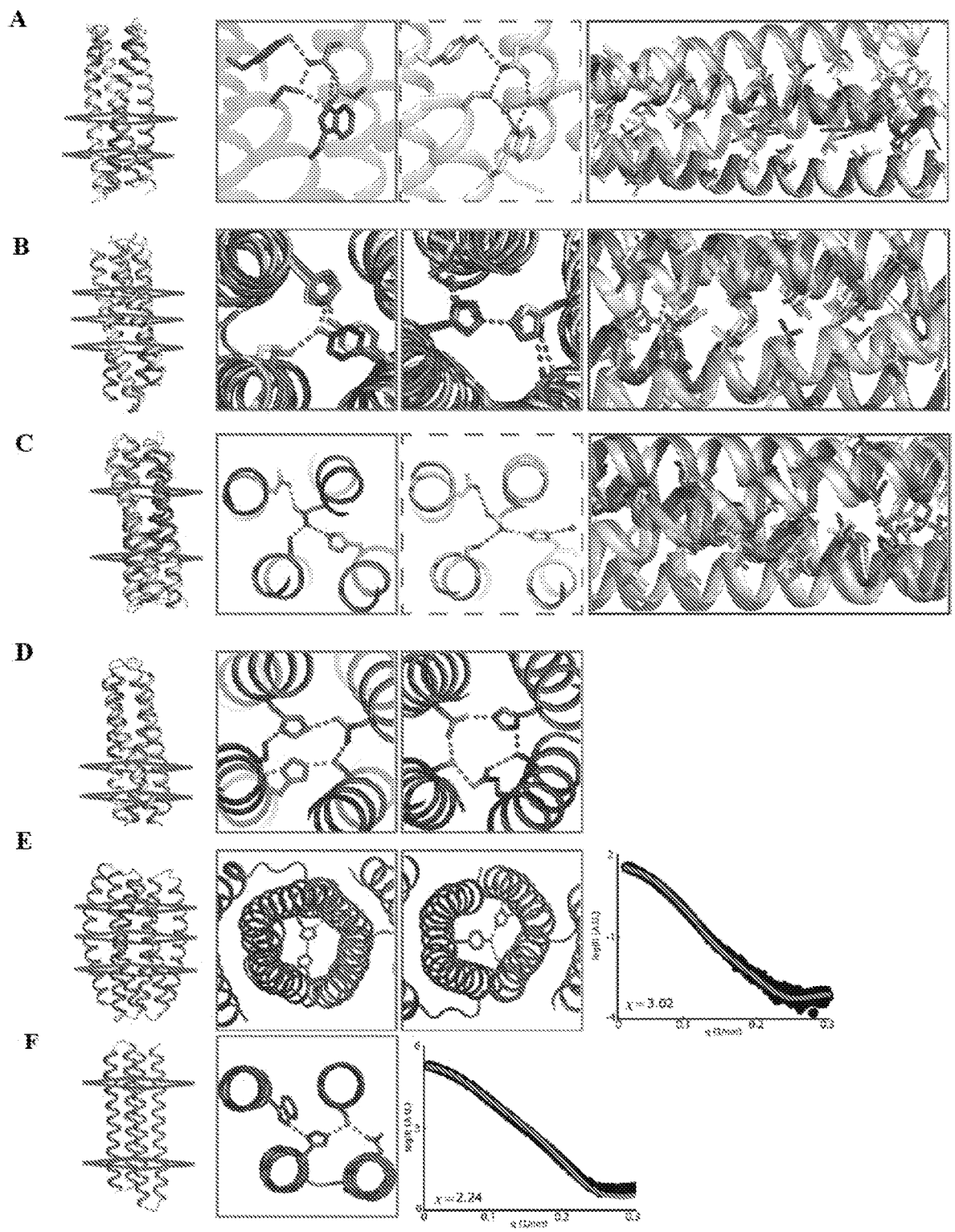
FIGS. 2A to 2F show structural characterization of designed heterodimers.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique*, 2$^{nd}$ Ed. (R.I. Freshney. 1987. Liss, Inc. New York, NY), *Gene Transfer and Expression Protocols*, pp. 109-128, ed. E. J. Murray, The Humana Press Inc., Clifton, N.J.), and the Ambion 1998 Catalog (Ambion, Austin, TX).

As used herein, the singular forms "a", "an" and "the" include plural referents unless the context clearly dictates otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (He; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

It is understood that wherever aspects are described herein with the language "comprising," otherwise analogous aspects described in terms of "consisting of" and/or "consisting essentially of" are also provided.

The term "interface residue" or "interface position", as used herein, means amino acid residues or positions that are interacting between at least two monomers in heterodimer, heterotrimer, heterotetramer, etc. The interaction comprises a hydrogen bond network in which at least a hydrogen from an alpha helix in the first monomer binds to a side chain in an alpha helix in the second monomer. In some aspects, the interaction comprises at least one hydrogen bond, at least two hydrogen bonds, at least three hydrogen bonds, at least four hydrogen bonds, at least five hydrogen bonds, at least six hydrogen bonds, at least seven hydrogen bonds, at least eight hydrogen bonds, at least nine hydrogen bonds, and at least ten hydrogen bonds. In some aspects, the interface residue comprises hydrophobic residues.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect the disclosure provide designed heterodimer proteins, comprising:
(a) a monomer A polypeptide, wherein the monomer A polypeptide is a non-naturally occurring polypeptide comprising 1-5 alpha helices connected by amino acid linkers; and
(b) a monomer B polypeptide, wherein the monomer B polypeptide is a non-naturally occurring polypeptide comprising 1-5 alpha helices connected by amino acid linkers,
wherein monomer A and monomer B non-covalently interact to form the designed heterodimer protein.

The disclosure provides designed heterodimer proteins according to this aspect formed by the non-covalent interaction of two different alpha-helix-containing polypeptides (monomer A and monomer B).

By doubling the interaction surface area of protein coiled coils with an additional helix, and incorporating modular hydrogen bond networks, a wide range of heterodimeric interaction specificities can be achieved, as described herein. Millions of helical backbones with varying degrees of supercoiling around a central axis were generated and searched for those accommodating extensive hydrogen bond networks, followed by connecting the helices with short loops and designing the remainder of the sequence. As disclosed in the examples that follow, designs expressed in

*E coli* exclusively formed heterodimers, and crystal structures of exemplary designs fit the computational models and confirmed the designed hydrogen bond networks. Following mixing of independently expressed and purified heterodimer designs, the vast majority of the interactions observed by native mass spectrometry were between the designed cognate pairs. The large sets of orthogonal polypeptide heterodimers disclosed herein can be used, for example, to generate synthetic protein logic gates, transcriptional networks and other synthetic biology applications.

Heterodimers are generally more useful than homodimers in bioengineering because of their ability to bring together two different entities (often fusion proteins). A long standing challenge in the field has been to come up with a set of orthogonally interacting protein heterodimers—monomers that selectively form cognate pairs and in the meantime avoid binding to other non-cognate monomers. Disclosed herein include such sets of orthogonal heterodimers, which can be programmably expanded into an even bigger set. The ability to bring together two different fusion proteins via genetically fused heterodimers allowed the design of protein-based logic gates, as also disclosed herein.

In one embodiment, monomer A and monomer B have their interaction specificity determined by at least one designed hydrogen bond network at the interface between monomer A and monomer B. In some aspects, (i) monomer A comprises 1 helix, and monomer B comprises 1 helix; (ii) monomer A comprises 1 helix and monomer B comprises 2 helices; (iii) monomer A comprises 1 helix and monomer B comprises 3 helices, (iv) monomer A comprises 1 helix and monomer B comprises 4 helices; or (v) monomer A comprises 1 helix and monomer B comprises 5 helices. In some aspects, (i) monomer A comprises 2 helices, and monomer B comprises 1 helix; (ii) monomer A comprises 2 helices and monomer B comprises 2 helices; (iii) monomer A comprises 2 helices and monomer B comprises 3 helices, (iv) monomer A comprises 2 helices and monomer B comprises 4 helices; or (v) monomer A comprises 2 helices and monomer B comprises 5 helices. In some aspects, (i) monomer A comprises 3 helices, and monomer B comprises 1 helix; (ii) monomer A comprises 3 helices and monomer B comprises 2 helices; (iii) monomer A comprises 3 helices and monomer B comprises 3 helices, (iv) monomer A comprises 3 helices and monomer B comprises 4 helices; or (v) monomer A comprises 3 helices and monomer B comprises 5 helices. In some aspects, (i) monomer A comprises 4 helices, and monomer B comprises 1 helix; (ii) monomer A comprises 4 helices and monomer B comprises 2 helices; (iii) monomer A comprises 4 helices and monomer B comprises 3 helices, (iv) monomer A comprises 4 helices and monomer B comprises 4 helices; or (v) monomer A comprises 4 helices and monomer B comprises 5 helices. In some aspects, (i) monomer A comprises 5 helices, and monomer B comprises 1 helix; (ii) monomer A comprises 5 helices and monomer B comprises 2 helices; (iii) monomer A comprises 5 helices and monomer B comprises 3 helices, (iv) monomer A comprises 5 helices and monomer B comprises 4 helices; or (v) monomer A comprises 5 helices and monomer B comprises 5 helices.

Any suitable amino acid linkers can be used to separate the alpha helices in each monomer. The length and amino acid content may vary based on an intended use, and can be determined by one of skill in the art based on the teachings herein. The polypeptide monomers may include any other useful sequences, including detectable tags and purification tags. In one non-limiting embodiment, at least one of monomer A and monomer B comprises a hexahistidine tag.

In another embodiment, the disclosure provides heterodimers, comprising:
(a) a monomer A polypeptide, wherein the monomer A polypeptide is a non-naturally occurring polypeptide comprising 1-5 alpha helices, wherein adjacent alpha helices may optionally be connected by an amino acid linker; and
(b) a monomer B polypeptide, wherein the monomer B polypeptide is a non-naturally occurring polypeptide comprising 1-5 alpha helices, wherein adjacent alpha helices may optionally be connected by an amino acid linker;
wherein the monomer A polypeptide and the monomer B polypeptide non-covalently interact to form the designed heterodimer protein.

In one embodiment, the monomer A polypeptide and the monomer B polypeptide have their interaction specificity determined by at least one hydrogen bond network at the interface between the monomer A polypeptide and the monomer B polypeptide. In another embodiment,
(i) the monomer A polypeptide comprises 2 alpha helices, and the monomer B polypeptide comprises 3 alpha helices;
(ii) the monomer A polypeptide comprises 3 alpha helices and the monomer B polypeptide comprises 3 alpha helices;
(iii) the monomer A polypeptide comprises 3 alpha helices and the monomer B polypeptide comprises 4 alpha helices,
(iv) the monomer A polypeptide comprises 4 alpha helices and the monomer B polypeptide 3 alpha helices;
(v) the monomer A polypeptide comprises 4 alpha helices and the monomer B polypeptide comprises 4 alpha helices;
(vi) the monomer A polypeptide comprises 5 alpha helices and the monomer B polypeptide comprises 4 alpha helices;
(vii) the monomer A polypeptide comprises 4 alpha helices and the monomer B polypeptide comprises 5 alpha helices;
(viii) the monomer A polypeptide comprises 5 alpha helices and the monomer B polypeptide comprises 5 alpha helices;
(ix) the monomer A polypeptide comprises 2 alpha helices and the monomer B polypeptide comprises 2 alpha helices; or
(x) the monomer A polypeptide comprises 3 alpha helices and the monomer B polypeptide comprises 2 alpha helices.

In one embodiment of any of the above embodiments,
(i) monomer A comprises a polypeptide having at least 70%, 75%, 80%, 85%, 90%, 91%, 92%, 93%, 94%, 95%, 96%, 97%, 98%, 99%, or 100% sequence identity along the length of the amino acid sequence of an odd-numbered SEQ ID NO selected from the group consisting of selected from the group SEQ ID NOS: 1-290; and
(ii) monomer B comprises a polypeptide having at least 70%, 75%, 80%, 85%, 90%, 91%, 92%, 93%, 94%, 95%, 96%, 97%, 98%, 99%, or 100% sequence identity along the length of the amino acid sequence of an even-numbered SEQ ID NO selected from the group consisting of selected from the group SEQ ID NOS: 1-290, wherein the even-numbered SEQ ID NO is the binding partner of the odd-numbered SEQ ID NO. in step (i).

The amino acid sequences of SEQ ID NOS:1-290 are provided in Table 1A. The "binding partners" are sequentially numbered (and similarly named) as shown in the Table. For example, SEQ ID NO:1 (DHD9 A) and SEQ ID NO:2 (DHD9 B) are binding partners, so that if monomer A comprises the polypeptide having at least 70%, 75%, 80%, 85%, 90%, 91%, 92%, 93%, 94%, 95%, 96%, 97%, 98%, 99%, or 100% sequence identity along the length of the amino acid sequence of SEQ ID NO:1, then monomer B comprises the polypeptide having at least 70%, 75%, 80%, 85%, 90%, 91%, 92%, 93%, 94%, 95%, 96%, 97%, 98%, 99%, or 100% sequence identity along the length of the amino acid sequence of SEQ ID NO:2. Similarly, SEQ ID NOS:3-4 are binding partners, SEQ ID NO:5-6 are binding partners . . . . SEQ ID NOS:289-290 are binding partners. Those of skill in the art will clearly understand what is meant by binding partner based on the teachings herein.

| Design name | Oligomerization State | Chain | Design sequene |
|---|---|---|---|
| DHD9 | Heterodimer | a | GSPKEEARELIRKQKELIKEQKKLIKEAKQKSDSRDAERIWKRSREINRES KKINKRIKELIKS SEQ ID NO: 1 |
| DHD9 | Heterodimer | b | PKKEAEELAEESEELHDRSEKLKERAEQSSNSEEARKILEDIERISERIEE ISDRIERLLRS SEQ ID NO: 2 |
| DHD13_XAAA | Keterodimer | a | GTKEDILERQRKIIERAQEIKRRQQEILEELERIIRKPGSSEEAMKRMLKL LEESLRLLKELLELSEESAQLLYEQR SEQ ID NO: 3 |
| DHD13_XAAA | Heterodimer | b | GTEKRLLEEAERAKREQKEIIKKAQELHRRLEEIVRQSGSSEEAKKEAKKI LEEIRELSKRSLELLREILYLSQEQKGSLVPP SEQ ID NO: 4 |
| DHD13_XAXA | Keterodimer | a | TKEDILERQRKIIERAQEIIRRQQEILEELERIIRKPGSSEEAMKRMLKLL EESLRLLKELLELLEESAQLLYEQP SEQ ID NO: 5 |
| DHD13_XAXA | Heterodimer | b | GSTEKRLLEEAERAKREAKEIIKKAQELKRRLEEIVRQSGSSEEAKKEAKK ILEEIRELSKRLLELLREILYLSQEQK SEQ ID NO: 6 |
| DHD13_XAAX | Keterodimer | a | TKEDILERARKIIERAQEIHRRQQEILEELERIIRKPGSSEEAMKRMLKLL EESLRLLKELLELSEELAQLLYEQP SEQ ID NO: 7 |
| DHD13_XAAX | Keterodimer | b | GSTEKRLLEEAERAIREQKEIIKKAQELKRRLEEIVRQSGSSEEAKKEAKK ILEEIRELSKRSLELLREILYLLQEQK SEQ ID NO: 8 |
| DHD13_2:341 | Keterodimer | a | TKEDILERQRKIIERAQEIHRRQQEILEELEYIIR SEQ ID NO: 9 |
| DHD13_2:341 | Keterodimer | b | MSEEAMKRMLKLLEESLRLLKELLELSEESAQLLYEQRKANNGSETEKRLL EEAERAHREQKEIIKKAQELKRRLEEIVRQSGSSEEAKKEAKKILEEIREL SKRSLELLREILYLSQEQK SEQ ID NO: 10 |
| DHD13_AAAA | Keterodimer | a | MTKEDILERQRKIIEPAQEIKRRQQEILKEQEKIIRKPGSSEEAMKRSLKL IEESLRLLKELLELSEESAQLLYEQR SEQ ID NO: 11 |
| DHD13_AAAA | Keterodimer | b | GTEKRLLEEAERAKREQKEIIKKAQELhKELTKIHQQSGSSEEAKKRALKI SQEIRELSKRSLELLREILYLSQEQK SEQ ID NO: 12 |
| DHD13_BAAA | Keterodimer | a | TKEDILERQRKIIERAQEIKRRQQEILKRSEEIIRKPGSSEEALETLRELQ EESLRLLKELLELSEESAQLLYEQR SEQ ID NO: 13 |
| DHD13_BAAA | Keterodimer | b | GSTEKRLLEEAEPAKREQKEIIKKAQELKRRTEEIIRQSGSSEEAKDELRR IQEEIRELSKRSLELLREILYLSQEQK SEQ ID NO: 14 |
| DHD13_4:123 | Keterodimer | a | TTKRYLEEAERAKREQKEIIKKAQELKRRLEEIVRQ SEQ ID NO: 15 |
| DHD13_4:123 | Keterodimer | b | GSSEEAKKEAKKILEEIRELSKRSLELLREILYLSQQVKDVDEKALERQRK IIERAQEIHRRQQEILEELERIIRKPGSSEEAMKRMLKLLEESLRLLKELL ELSEESAQLLYEAR SEQ ID NO: 16 |
| DHD13_1:234 | Keterodimer | a | EAMKRMLKLLEESLRLLKELLELSEESAQLLYEAR SEQ ID NO: 17 |
| DHD13_1:234 | Keterodimer | b | TTKRYLEEAERAKREQKEIIKKAQELKRRLEEIVRQSGSSEEAKKEAKKIL EEIRELSKRSLELLREILYLSQQVNDVDEKALERQRKIIERAQEIHRRQQE ILEELERIIRKPGS SEQ ID NO: 18 |
| DHD15 | Keterodimer | a | TREELLRENIELAKEHIEIMREILELLQKMEELLEKARGADEDVAKTIKEL LRRLKEIIERNQRIAKEHEYIARERS SEQ ID NO: 19 |
| DHD15 | Keterodimer | b | GTERKLLERSRRLQEESKRLLDEMAEIMRRIKKLLKKARGADEKVLDELRK IIERIRELLDRSRKIHERSEEIAYKEE SEQ ID NO: 20 |
| DHD20 | Keterodimer | a | GDRQELIRRNIELLKEHIKILEEISQLIEELSELLDKSSSEEVVKRYKKIL ERYKQLLRKSQEIHKESSEIAKKES SEQ ID NO: 21 |

-continued

| Design name | Oligomerization State | Chain | Design sequene |
|---|---|---|---|
| DHD20 | Heterodimer | b | GDEQKLIERSQRMQKESLELLKEIIKILDTIEKLLDKPDSEELLDTIKKLH DTLKKIHDRNKKLLKEHEEILRQRSGSLVPR SEQ ID NO: 22 |
| DHD21 | Heterodimer | a | DKEEEYKRLLDEIKEILKESKEVLKDSKRVLEDIKRKVPDDDLVKLLEKHV RLLEEHVKLLEQLIREAEKSSK SEQ ID NO: 23 |
| DHD21 | Heterodimer | b | QGSSAEELLKKIKESEKKIRDSLRKIKEIIKKSRKEGVDDKQLDLIRKVVE SHRDLLRLHRDLLRLLREETS SEQ ID NO: 24 |
| DHD25 | Heterodimer | a | DIDESIKEVEKLLEEVEQSLQKLDDSLKKLLEKVNQDPDVDDSVRKIVKRH VEILKRHEEVLKRLIEVVKEHTKTVK SEQ ID NO: 25 |
| DHD25 | Heterodimer | b | GSDREEVHKEIVKLIREIIKIHKKILKIHEKIKNGEIDPSEILKLSEEIKK LTDTIIKIIEDLEQLTRDLRR SEQ ID NO: 26 |
| DHD27 | Heterodimer | a | DRKEIVKRHQKVVELLKESSKLLRESSKLLQRLLDKTGDENLQKAVDDQDK AIKRQETAIRKSQEASKKLD SEQ ID NO: 27 |
| DHD27 | Heterodimer | b | DNSEEIKKVAKTSREVAEYSERVAKENDKVVKTLEEGKIDESELLRLLEES IKIFDTALKLHEEAYKLHQDLVRKVS SEQ ID NO: 28 |
| DHD30 | Heterodimer | a | DESEAASVAIESVQILVESVKLLEESVRILLDAVKKNGVEDLLRVAQRWEK LVDEWLKVVKRWLDNVRDIQR SEQ ID NO: 29 |
| DHD30 | Heterodimer | b | GSDKAEEVEKSVRKIEESIKKIRKSIKKAEDAVQLLKEGKIDAKDFLRIVR EDLEVVKEDVEIVKEDVENVREFSS SEQ ID NO: 30 |
| DHD33 | Heterodimer | a | SDKEVSDKLLKASKKLLKVSEELLEVVRRLLKALKDDELIKKIADLLRKII DKDKKFIRTSEEIVKESR SEQ ID NO: 31 |
| DHD33 | Heterodimer | b | GSDLKEVLKTVEEAVKEIIKSSEELLQISRKILEISRVGVDEHEYISAIRE YLKALEKHIQILKKFIEILKELIRAVS SEQ ID NO: 32 |
| DHD34_XAAXA | Heterodimer | a | SKEEIDKIVKKHKKKIEEHKKKVDELKKLVEEKDKRVSQDKDDKVKKLSEE VKKIIKRLEEVSKRLEEVSKKLLKVISDKR SEQ ID NO: 33 |
| DHD34_XAAXA | Heterodimer | b | GSNDEELKKILETLDRILKKLDKILTRLIEVLKKSEDPNLDDKDYTELVKQ FIELIKKYEEVVKEYEEVVRQLIRLFS SEQ ID NO: 34 |
| DHD34_XAXXA | Heterodimer | a | SKEEIDKIVKKHKKKIEELKKLVDELKKLVEEHDKRVSQDKDDKVKKLSEE VKKIIKRVEEVAKRLEEVSKKLLKVISDKR SEQ ID NO: 35 |
| DHD34_XAXXA | Heterodimer | b | GSNDEELKKILETLDRILKKLEKILTRLIEVLKKSEDPNLDDKDYTELVKQ FIELIKKFEEVIKEYEEVVRQLIRLFS SEQ ID NO: 36 |
| DHD34_XAAAA | Heterodimer | a | SKEEIDKIVKKHKKKIEEHKKKVDEHKKLVEEHDKRVSQDKDDKVKKLSEE LKKISKRLEEVSKRLEEVSKKLLKVISDKR SEQ ID NO: 37 |
| DHD34_XAAAA | Heterodimer | b | GSNDEELKKILETLDRILKKLDKILTRLDEVLKKSEDPNLDDKDYTELVKQ YIELVKKYEEVVKEYEEVVRQLIRLFS SEQ ID NO: 38 |
| DHD36 | Heterodimer | a | DHSRKLKEILDRLRKHVKRLKEHDELRDLVRQVPEDKLLEHVVKLSDKIL QISERAVREFTKSVDKDS SEQ ID NO: 39 |
| DHD36 | Heterodimer | b | GSDKKDELERILDEIRRLIERLDEILSRLNKLLELLKHGVPNAKEVVKDYI RLLKEYLELVKEFLKLVKRHADLVS SEQ ID NO: 40 |
| DHD37_ABXB | Heterodimer | a | DSDEHLKKLKTFLENLRRHLDRLDKHIKQLRDILSENPEDERVKDVIDLSE RSVRIVKTVIKIFEDSVRKKE SEQ ID NO: 41 |
| DHD37_ABXB | Heterodimer | b | GSDDKELDKLLDTLEKILQTATKIIDDANKLLEKLRRSERKDPKVVETYVE LLKRHEKAVKELLEIAKTHAKKVE SEQ ID NO: 42 |
| DHD37_BBBB | Heterodimer | a | MDEEDHLKKLKTHLEKLERHLKLLEDHAKKLEDILKERPEDSAVKESIDEL RRSIELVRESIEIFRQSVEEEE SEQ ID NO: 43 |
| DHD37_BBBB | Heterodimer | b | GDVKELTKILDTLTKILETATKVIKDATKLLEEHRKSDKPDPRLIETHKKL VEEHETLVRQHKELAEEHLKRTR SEQ ID NO: 44 |
| DHD37_XBXB | Heterodimer | a | DSDEHLKKLKTFLENLRRHLDRLDKLLKELRDILSENPEDERVKDVIDELE RVIRIVKTVIKIFEDSVRKKE SEQ ID NO: 45 |
| DHD37_XBXB | Heterodimer | b | GSDDKELDKLLDTLEKILQTATKIIDDLNKVLEKLRRSERKDPKVIETVVE LLKRHEKAVKELLEIAKTHAKKVE SEQ ID NO: 46 |

| Design name | Oligomerization State | Chain | Design sequene |
|---|---|---|---|
| DHD37_AXXB | Heterodimer | a | DSDEHLKKLKTFLENLRRLEDLLDKHIKQLRDILSENPEDERVKDVIDLSE RVVRTVKTVIKIFEDSVRKKE SEQ ID NO: 47 |
| DHD37_AXXB | Heterodimer | b | GSDDKELDKLLDTLEKILQTATKVVDDANKLLEKLRRSERKDPKVVETYVE LLKRLEKLIKELLEIAKTHAKKVE SEQ ID NO: 48 |
| DHD37_3:124 | Heterodimer | a | DSDEHLKKLKTFLENLRRHLDRLDKHIKQLRDILSEN SEQ ID NO: 49 |
| DHD37_3:124 | Heterodimer | b | EDERVKDVIDLSERSVRIVKTVIKIFEDSVRKLEKTKPDSKTAKELDKLLD TLEKILQTATKIIDDANKLLEKLRRSERKDPKVVETYVELLKRHEKAVKEL LEIAKTHAKKVE SEQ ID NO: 50 |
| DHD37_1:234 | Heterodimer | a | DSDEHLYKLKTFLENLRRHLDRLDKHIKQLRDILSENPEDERVKDAIDLSE RSVRIVKTVIKIFEDSVRKKEKRPIDKRDDKELDKLLDTLEKILQTATKII DDANKLLEYLRR SEQ ID NO: 51 |
| DHD37_1:234 | Heterodimer | b | GDPKVVETYVELLKRHEKAVKELLEIAKTHAKKVE SEQ ID NO: 52 |
| DHD37_AXBB | Heterodimer | a | DSDEHLDRLDKHLKKLKTFLENLRRHIKQLRDILSENPEDERVKDVIDLSK TVIKIFEDSVRKKERSVRIVE SEQ ID NO: 53 |
| DHD37_AXBB | Heterodimer | b | GSDDKEATKIIDDLDKLLDTLEKILQTANKLLEKLRRSERKDPKVVETYVK AVKELLEIAKTHAELLKRHEKKVE SEQ ID NO: 54 |
| DHD37_XBBA | Heterodimer | a | DSDEHIKQLRDHLDRLDKHLKKLKTFLENLRRILSENPEDERVKTVIKIFE DSVRKKERSVRIVKDVIDLSE SEQ ID NO: 55 |
| DHD37_XBBA | Heterodimer | b | GSDDKEANKLLEKATKIIDDLDKLLDTLEKILQTLRRSERKDPKAVKELLE IAKTHAELLKRHEKVVETYVKKVE SEQ ID NO: 56 |
| DHD39 | Heterodimer | a | DHSRKLEEILDRLRKHVKRLLEHLRELLSLVKENPEDKDLVEVLELSLAIL RRSLEAVEAFLKSVTKKDPDDEDLRRKADEIRKEVEEIKKSLAEVEKEIYK LK SEQ ID NO: 57 |
| DHD39 | Heterodimer | b | GSSADDVLEDILKIIRELIEILDQILSLLNQLLKLLRHGVPNAKKVVEKYK EILELYLQLVSLFLKIVKTHADAVSGKIDKKAEEEIKKEEEKIKEKLRQAK DILKKLQEEIDKTR SEQ ID NO: 58 |
| DHD40 | Heterodimer | a | DRDAHLYKLLTFLEQLVRHLDRLVKHITQLRDIVKKDPEDERAVDVIRQSV RSLEIVITVLKIFVDSVSDAARSKEAEKIVRKIRKEIDEIRQKLREIDKEV KKTTS SEQ ID NO: 59 |
| DHD40 | Heterodimer | b | GSNDKVLDKILDILDRILRLATRVIDLANKLLQVKKKSTHKDPRIVETYKE LLKIHETAVRLLLELADLHRRLKSKDEEANKRVETELDRIRKKVKDIEDKV RKLEDKVRKTAS SEQ ID NO: 60 |
| DHD43 | Heterodimer | a | NDLSKEVLKKLEKSVEELLRRVQKSVKEAQKRGLLSDELVDRHLKILNQLV KRHLELLQEVIKRSDKK SEQ ID NO: 61 |
| DHD43 | Heterodimer | b | GSDEAVKRVVEKSLKILDEVIKKSLDILRELIELQIRHAKDDESVIRASKS ALKDAIEALKKSLDEIKKALKRSADEG SEQ ID NO: 62 |
| DHD65 | Heterodimer | a | SSEEVVKVHEKVVKLHKEILELLKKIIKIHETAARDPDDKDSIKKLSDEIK KIVKRIEDISDQAKRESSDAQRKQS SEQ ID NO: 63 |
| DHD65 | Heterodimer | b | DKEEESKELLKKLKEILKRSEELLEESKELLKLAKNGEIDESELADADRKL NKKHEKLVQDIQDLLREHERQDR SEQ ID NO: 64 |
| DHD70 | Heterodimer | a | DEKKKIDKIVKETEDLLQKSEKLLQQSKEAVKRIRSQVKENEIVDRLLRIS EELLKISRRLVEISRRIASTLS SEQ ID NO: 65 |
| DHD70 | Heterodimer | b | GSSKEEVIRLLKENVRLIKENLELLTRNLKLITDLVRGSNGSEEKIKTLKE LLKEYRELLKRYRKLVEDYKRLVDKHD SEQ ID NO: 66 |
| DHD88 | Heterodimer | a | EIQELIKSSRRIIEESKELIKESEEVLRRIKEILDRIRNGVDNQEDLLREI LKLLTKNLKIIQRNLKLLQDNAEILKRLVS SEQ ID NO: 67 |
| DHD88 | Heterodimer | b | GSYIEDVIKKILDVSRELIKLSRTIIKISEEINKQLQQGRDTKDLVKKYDE IIKKYTRIVQHYTELIKELQKLLS SEQ ID NO: 68 |
| DHD89 | Heterodimer | a | SPTEEAIQLSQRVIELSKRVIELSKEILKLLKRVLDLLPDLDKNEEKRLDD YDKELKEYDKELKKYEKRLKDLAS SEQ ID NO: 69 |

-continued

| Design name | Oligomerization State | Chain | Design sequene |
|---|---|---|---|
| DHD89 | Heterodimer | b | GSEEEEILKIQKELLRIQSEILDKQKKILDTLRSNGAVTEEVRSILEKVER LSEEAKELSKEAKELTKEVSKLIS SEQ ID NO: 70 |
| DHD90 | Heterodimer | a | SPLKELNNQLLRLLRELVKVSKKIVDLSKTIIEVLKHTDLDPRLLDSLEKS QQELDKSQKELDKVVKELTKVNKKLQ SEQ ID NO: 71 |
| DHD90 | Heterodimer | b | GSPLEDLVRKYDELVKTYEKLVEEFKKAVDKYDKAVKKAPVSKEATDSLDL IRKVLELLDRNLKLIKENAKLIKELLK SEQ ID NO: 72 |
| DHD91 | Heterodimer | a | SPTREKEKVIKENEKVISDNERVLEEVVKVVETATDRKEIQDAVDEVRKSV DKLRDSVRKLEESVRTLD SEQ ID NO: 73 |
| DHD91 | Heterodimer | b | GSPIKDISKRLLEISKRLVEISDRIVELLQRIADSKDPNKDLQKEVKDVLE EYKRLVREYREVVKEYEKVVS SEQ ID NO: 74 |
| DHD92 | Heterodimer | a | DEDEHVKQLIKNADLLRKHAELLKELVKLFQEIASQIPDDRVAKKVTDVVD RIDKILKQTEKLVRRTKQILDYSR SEQ ID NO: 75 |
| DHD92 | Heterodimer | b | GSNLEELVKLLKEVLEMHERLLRIHEDLVEAKKSNASDKESERKLKKSDKD IKESLKKIKSIIDQVRYIQS SEQ ID NO: 76 |
| DHD93 | Heterodimer | a | PVEDIIEESLRLLEESLKLLNRILKLLEDSLRKLPRSEEWRQRLDEFRKKL EDWKEELERWIEDVRYKKT SEQ ID NO: 77 |
| DHD93 | Heterodimer | b | GSDEDYESREIIDEIRKLLDRSKKIVHRSQRLVERVKSTPLSEDQEDLIRR HEETINRHRELVKELEKVLEDHERHIR SEQ ID NO: 78 |
| DHD94 | Heterodimer | a | PEEDSRRVLERFVRVSREVLKVLEEFLRVSEELLREADRDRDRRLEEYERQ VDELREEIRRYKEEVDKFDKEVKYYKK SEQ ID NO: 79 |
| DHD94 | Heterodimer | b | GSPEKDENRKLLDKVRKLVEKSRRLVEELRKLVDQSTKNGLIDEKALRKQQ EVLRKVEEVLEKQERVLRELEEISYRVI SEQ ID NO: 80 |
| DHD94_3:214 | Heterodimer | a | GSPERDENRKLLDKVRKLVEKSRRLVEELRKLVDQSTKN SEQ ID NO: 81 |
| DHD94_3:214 | Heterodimer | b | GSDEKALRKQQEVLRKVEEVLEKQERVLRELEEISYRVITRGEDHKAEEDS RRVLERFVRVSREVLKVLEEFLRVSEELLREADRDRDRRLEEYERQVDELR EEIRRYKEEVDKFDKEVKYYKK SEQ ID NO: 82 |
| DHD94_2:143 | Heterodimer | a | GSDRRLEEYERQVDELREEIRRYKEEVDKFDKEVKYYKK SEQ ID NO: 83 |
| DHD94_2:143 | Heterodimer | b | GSPERDENRKLLDKVRKLVEKSRRLVEELRKLVDQSTKNGLIDEKALRKQQ EVLRKVEEVLEKQERVLRELEEISYRVITRGEDHKAEEDSRRVLERFVRVS REVLKVLEEFLRVSEELLREADR SEQ ID NO: 84 |
| DHD95 | Heterodimer | a | DLSEESKKFVEKVKKLEKESRELEKQVKKIEEDSRSVENDVQKEFLELLKR LLDIQKKVVEVLREVVKVQQYVDS SEQ ID NO: 85 |
| DHD95 | Heterodimer | b | GSDSEYESRQVLRELDTVLKDSHTVLEALRQVIRDSQDVVSKSDEESRRVI DDLEKVIQDSKKVLDDIKRLIDKSKSIKS SEQ ID NO: 86 |
| DHD96 | Heterodimer | a | NEDELLKLLTENLKLLDENLKLLRENLSLLRQANNITDKNRIREIVKQSKE IVKQSREILKQSKEIVERIKYIVS SEQ ID NO: 87 |
| DHD96 | Heterodimer | b | GSSLYELTQRYEKLVQQYEELVKDYRRLVKKLEKLKRDNKPDKRLLKEIVD VIKKSVEIIDRSLKLLEESIKILEETD SEQ ID NO: 88 |
| DHD97 | Heterodimer | a | SQERSLEILKRILDVLKESLEILKESLSILRQLASRIKNPNRKIEEILKES DKIIKESDKVLKEIEEVIRYSS SEQ ID NO: 89 |
| DHD97 | Heterodimer | b | GSDIEYESKEILELIKELLKLSRELLKESRRALELVRKSRDDSIVEEVIQV HKKVLDIHKEVLKIVRKVVEVHRRVKS SEQ ID NO: 90 |
| DHD98 | Heterodimer | a | SKKDESTKLERLAEKIDEITKRIEELVKDVKRKSSEGVDKDQQQKIDEVFQ KLLDLQREILEILDRILKVQQYILD SEQ ID NO: 91 |
| DHD98 | Heterodimer | b | GSDLEYLNRRLLQLIKTLIDLNRHLLKLIDKLKKLNSREGDEEKIKEESKQ IQEQFKEIVERSKEIIKQIKEIIKRSQ SEQ ID NO: 92 |
| DHD99 | Heterodimer | a | DFERSSRRLEKVVEDLRRSSDRLREVIDELRKSADEKDEDEDLRRARKEHR DLIEELKRALEKQEEIIKHLQELVYRQL SEQ ID NO: 93 |
| DHD99 | Heterodimer | b | GSEESEEVRKVVERIKKISRELEEVVKELDRVSKEFDRHGETDEIVREHER IVEKLEEIVKKHTKIVEELAEIVYKQQ SEQ ID NO: 94 |

-continued

| Design name | Oligomerization State | Chain | Design sequene |
|---|---|---|---|
| DHD100 | Heterodimer | a | SDDDSVRVLDEIVKILDESVKLLKESLKLLDDFLRTKPDDHLKEVVKESKK VVEQSKKVLDRIKKIIYESK SEQ ID NO: 95 |
| DHD100 | Heterodimer | b | GSDLLYLSKELLKLVRELLKLSRELVELSRRLVNSTHKSPELVKKYDKLVK KYQDLLKKLADVADEYLRQRS SEQ ID NO: 96 |
| DHD101 | Heterodimer | a | DEKDYHRRLIEHLEDLVRRHEELIKRQKKVVEELERRGLDERLRRVVDRFR RSSERWEEVIERFRQVVDKLRKSVE SEQ ID NO: 97 |
| DHD101 | Heterodimer | b | GSDAYDLDRIVKEHRRLVEEQRELVEELEKLVRRQEDHRVDKKESHEILER LERIIRRSTRILTELEKLTDEFERRTR SEQ ID NO: 98 |
| DHD102 | Heterodimer | a | DERYRAREHIRRVEEHTKRLRHILKRLREHEEKLRRELKPGDEITESVDRF KKIVDQFEESIKKFETVSEELRKSDS SEQ ID NO: 99 |
| DHD102 | Heterodimer | b | GSDRQRILDRLDKILEKLDDILKKLKDILETLSKDDVSDRRHKDLVEKFRE LVDTHHKLVERYRELVYQNR SEQ ID NO: 100 |
| DHD102_1:243 | Heterodimer | a | GSDEITESVDRFKKIVDQFEESIKKFETVSEELRKSIS SEQ ID NO: 101 |
| DHD102_1:243 | Heterodimer | b | GSDPQRAADRLDKILEKLDDILKKLKDILETLSKDDVKDRRAKDLVEKFRE LVDTHKKLVERYRELVYTATAGSDLARELIRRVEEHTKRLRHILKRLREHE EKLRR SEQ ID NO: 102 |
| DHD103 | Heterodimer | a | NADDQLATSIKKLEDSIDQLIKIVRKFEESVKKLQKHGVDQHHVEILRKIV EIFRQHIEKLKKHLEKLRYTSS SEQ ID NO: 103 |
| DHD103 | Heterodimer | b | GSDKEYLVTEHEKLVREHEKIVSEIEKLVKKHEAGVDESELEEILKKVEKL LRKLDEILEQLTQLLRKTE SEQ ID NO: 104 |
| DHD103_1:423 | Heterodimer | a | GSDQHWEILRKIVEIFRQHIEKLKKHLEKLRYTSS SEQ ID NO: 105 |
| DHD103_1:423 | Heterodimer | b | GSDAEYLVTEHEKLVREHEKIVSEIEKLVKKKEKGVDESELEEILKKVEKL LRKLDEILEQLTQLLRKAEKHIDKHSKAADQLATSIKKLEDSIDQLIKIVR KFEESVKKLQKH SEQ ID NO: 106 |
| DHD104 | Heterodimer | a | DEDDDIRRVLDESRRVLEHSRRVLKRSEEVLEKASRKKEKDTEEIEKHLKR LREHAKKLEKHRRELDDFLYKEI SEQ ID NO: 107 |
| DHD104 | Heterodimer | b | GSRDKYLLERLNDILKKLDEIVDKLSDILKRLKDVRHDDRLQELVERYKEI VKEYKRIVEEYEKLVREFEEQQR SEQ ID NO: 108 |
| DHD105 | Heterodimer | a | DRDYEDKEFKKIIKELEDVQEELKKLQEKIKRFSSELEEPNELLKEQLKVV EEQLEVNKKILKILRDQLKQNE SEQ ID NO: 109 |
| DHD105 | Heterodimer | b | GSDAEYKVRESVKRSKESVKHSEDVVDKLNKSVKLSESGHSDAEKASRELV KLVREVVELSREVIKLSEKVLRVIS SEQ ID NO: 110 |
| DHD106 | Heterodimer | a | DLQYKQEKLIRHFDRVVREWDKLVRKFSKVLEKQKHESKDKELEEASRRVD ELIKRLREQLKRSKEILRRLKELSRKSS SEQ ID NO: 111 |
| DHD106 | Heterodimer | b | GSDWEELLRRLEKVLQEYEEIVKELIDLIERLIKVSEDKSKDASEYKKLVT ELEKLISKLEEISKKLEELVKEYEYKTE SEQ ID NO: 112 |
| DHD107 | Heterodimer | a | DAKDELEKSLQEIEESLKELKKLLEELDKSLRELTSQGRNKKLEEHIKKVQ KFIELVKKYIKAVQDYLKEVRYDNS SEQ ID NO: 113 |
| DHD107 | Heterodimer | b | GSDKERAARATEEMVKLTKKLLKAVEDLVRDVRRLLKEGLISEKHARIAET ILEVFKKHAKIIKKHVDIVKYDES SEQ ID NO: 114 |
| DHD108 | Heterodimer | a | GSPLKERLLEIQRDLDRVLEEVVERLLRIQERLDSVVERKPPDVHEEYKYI VDEIREIVERVVREYEEIVKRIDEEVR SEQ ID NO: 115 |
| DHD108 | Heterodimer | b | GSEEDERIRYDLDRIRKDVRRKLEEIRQRVRELEKKLRDAGHRRDEKELLR ELIETSKDILRLVEELLKKIIDKSEDLLRKTE SEQ ID NO: 116 |
| DHD109 | Heterodimer | a | GSDEEDYINENVEKDVRDIEDDVRRINERIRELLEKIRTEEVLQRVLEEHH ELVERVLRKLVEILRKHEEENR SEQ ID NO: 117 |
| DHD109 | Heterodimer | b | GSDEEEYYKEKLHKLLREIEEELLKKYRELVRRLEELVKRGELDKDTAAHIL ERLSELLERIIRRVAHTLRRLSEERR SEQ ID NO: 118 |

-continued

| Design name | Oligomerization State | Chain | Design sequene |
|---|---|---|---|
| DHD110 | Heterodimer | a | GSDEDEISYDSKRRVEEIVRQAREKSEKSRKDIEDVAEVLRKGDVSEKEVV DELVKVLEEQVKVLREAVERLREVLKKQVDDVR SEQ ID NO: 119 |
| DHD110 | Heterodimer | b | GSDIVELVDHLLKRSLKLLEELAELVRRLLEKSTELLKRRTEEHKEEVVEE SEYMVRELEERLRRVVDESEKLVRDADKHIR SEQ ID NO: 120 |
| DHD111 | Heterodimer | a | GSKEKDIVKTLVDLLRENLETLERLIEEVVRLLKENVDVRDEGRDDKDSER ILRDIKRRIDEAAKESREIIERIEKEVEYRSR SEQ ID NO: 121 |
| DHD111 | Heterodimer | b | GSPEVDVLRRIVREILKASEELLRLLRKLIDEALKLSERKRDSQEYREVVD RVKKELERLLDEYRKLVEELKEKLRYDTR SEQ ID NO: 122 |
| DHD112 | Heterodimer | a | GSDKRYESEKLKRRLDEAVEKVREVVERVERESDRVLEEVRRRRESKEVVD KVIEDNDKALEDVLRVVDEVAKVVRDVVRENTR SEQ ID NO: 123 |
| DHD112 | Heterodimer | b | GSPREYKSKDILRKVDEILERIRRHADRVKKKSERLKRENVDVNEHSKDVK RVIRELLELVKELLRLAKKHSDDQQE SEQ ID NO: 124 |
| DHD113 | Heterodimer | a | GSDEDEILYHSERLLQKLKKELDDLKEKSRELLEELKKEDPDDRLIERIIR LHDEVLKDLDEVLKNILEVHREVLERLR SEQ ID NO: 125 |
| DHD113 | Heterodimer | b | DKLDRLLKIHEEALRRAEELIKRLLDIHRRALDLARRGELDDYLLKESERE LREIIRRAREELKESRDRLEEISR SEQ ID NO: 126 |
| DHD114 | Heterodimer | a | GSPKEELIRRVLEEVKRLNEKLLEIIRRAAELVKRANDELPETEKLREIDR ELEKKLKEIEDELRRIDKELDDALYEIED SEQ ID NO: 127 |
| DHD114 | Heterodimer | b | GSPKLDKLRELLERKLEKLREILEEVLKILRTNLERVREDIRDEDVLQEYE RLIRKAEEDLRRVLKEYDDLLKKLVYELR SEQ ID NO: 128 |
| DHD115 | Heterodimer | a | GSKEDESVKRAEEIVRTLLKLLEDSLREAERSLRDIKNGEDEHNLRRISEK LEELSKRITETIERLLRELQYTSR SEQ ID NO: 129 |
| DHD115 | Heterodimer | b | GSPNQELLDRVRKILEDLLRLNEELVRLNKELLKRALEMRRKNRDSEEVLE RLAEEYRKRLEEYRRELEKLLEELEETIYRYKR SEQ ID NO: 130 |
| DHD116 | Heterodimer | a | GSDESEEAQHEVEKVLDDIRRLSEKLQKRLEEVLEEVYELRREGSDRTEVV ELLKEVIREIVRVNREALERLLRVVEEAVKRNE SEQ ID NO: 131 |
| DHD116 | Heterodimer | b | GSDEEELVETVKRIQKEILDRLTELAKLLVEIQREIKKLKDEGEDDKELKR LSDELEEKVRQVVEEIKRLSDELEETVEYVSR SEQ ID NO: 132 |
| DHD117 | Heterodimer | a | GSDEEEEVVRRAEELVKEHEELIERVIRTHEELVYKLEDQGADKKLVDVLK RVVEESERVAREIVKVSRELIRLLEEASR SEQ ID NO: 133 |
| DHD117 | Heterodimer | b | GSSKEEILKELEDLQRRLIEEELKKLQERVVELLEELIKRLRDRGRDDKHLK RLVKEVRRLSEEVLRSIKEVSDRVRYQLR SEQ ID NO: 134 |
| DHD118 | Heterodimer | a | GSDKEEESEYLLRDLVRLLEKVKEKIEEVNREVEKLLKKVKDGRLDRREVL REILRLNRELAEIIKEVVDRIRHVVERSER SEQ ID NO: 135 |
| DHD118 | Heterodimer | b | GSDLHEVVYETKELLKRIEEVVEELRKKSEDIIRKAERGEISEDELKRLQE EIAREAKKLLLDEIKRVLERHLEQTL SEQ ID NO: 136 |
| DHD119 | Heterodimer | a | GSPVEEIIKEVVKRVIEVQEKVLRIISHAVKRVVEVQKKYDPGSEESNRVV EEVKKTIEDAIRESDEVVDEVVKRIQYTVR SEQ ID NO: 137 |
| DHD119 | Heterodimer | b | GSPEQEIADRILTEIRESQKELERLARKILKLLDESQEKAKRGRLSEEESD ELLERIKKELDELLERSKELLKKIEYELR SEQ ID NO: 138 |
| DHD120 | Heterodimer | a | GSDEDKEANRVLDEVLKTVRDLLETANEVLKEVLYRLKRTDDQEKVVRTLT EVLKEKLKLVEEIVRILDKVLKEHLETEK SEQ ID NO: 139 |
| DHD120 | Heterodimer | b | GSPEDDVLRRLEEVSEKILRVAEDVARQLREVSEKITQGKVDRKEWEEDIK RLKRELEELLREVVKEEIERLTYELR SEQ ID NO: 140 |
| DHD121 | Heterodimer | a | GSRREEVVKRIRELLKRNKELIDRIRELLEENEYLDKDARDKDVLRRSVEL LEELVRILEESVELAKEIIKLLREVVE SEQ ID NO: 141 |
| DHD121 | Heterodimer | b | GSDEKEDNRRLQHKIERILEKNEDLQRKLEEILELLERGEADEEKIDRLRK AVEDYRRVVEEIKEDVKRHKYTVR SEQ ID NO: 142 |
| DHD122 | Heterodimer | a | GSDEKEEAKKASEESVRTVERILEELLKASEESVELLRRGEDAKDVVERSK EALKRVKELLDEVVKRSDEILKYIHN SEQ ID NO: 143 |

| Design name | Oligomerization State | Chain | Design sequence |
|---|---|---|---|
| DHD122 | Heterodimer | b | GSDEKKLINEVVETQKRLIKEAAKRLSEVVRHQTELIRELREKNVDDKDVE KLLKESLDLAEEIVRRIKELLDESKKLVEYVSN SEQ ID NO: 144 |
| DHD123 | Heterodimer | a | GSPDMDEVKRVLDELIEIQEEILREIKRVLEKLIKIQEDNGSEYESREVVR EIVEIARKLVERSRRVVKKITETLQ SEQ ID NO: 145 |
| DHD123 | Heterodimer | b | GSDERYATREIVERIERIAREILKRTEEIVREVREVLSRDVDQEEVVRRLA DLLRESVELVQHLVRRVEELLQESVERKK SEQ ID NO: 146 |
| DHD124 | Heterodimer | a | GSPEREALREVLEDLKRVTDRLRELVERVLEELKKVTDHVDSERILRESRR VLKELKDIIEEILRESEKVLEKLKYTED SEQ ID NO: 147 |
| DHD124 | Heterodimer | b | GSPAREILEEVVKKHLEVVEDAARILEEIIREKEKAVREDRDKKELEEISR DLLRKAREALKKVKDISDDLSREIEYVAS SEQ ID NO: 148 |
| DHD125 | Heterodimer | a | GSPVEEAIKKVIDDLRDVQRKIRELVEELIRLLEEVQRDNDKRESEYVVER VEEILRRITETSREVVRKAVEDLS SEQ ID NO: 149 |
| DHD125 | Heterodimer | b | GSDSDEKAEYLLKEMERVVRESDEVVKKILRDLEEVLRERLRRGEISEDDVT EILKELAERHIRAIEELVRRLRELLERHKR SEQ ID NO: 150 |
| DHD126 | Heterodimer | a | GSPVEEVLKELSEVNERVRDIAREIIERLSEVNEEVKETDDEDELKKISKK VVDEVEDLLRKILEVSEEVVRRVEYHDR SEQ ID NO: 151 |
| DHD126 | Heterodimer | b | GSPKEDILREVLRRHKEIVREIVRLVREAVETKLELVKRNSDDRDAQDVIR KLEEDLERLVRHAQEVIEEIFYRLH SEQ ID NO: 152 |
| DHD127 | Heterodimer | a | GSPRSYLLKELADLSQHLVRLLERLVRESERVVEVLERGEVDEEELKRLED LHRELEKAVREVRETHREIRERSR SEQ ID NO: 153 |
| DHD127 | Heterodimer | b | GSDREYIIKDILDSQEHLLRLIEELLETQKELLEILKRRPDSVERVRELVR RSKEIADEIRRQSDRNVRLLEEVSK SEQ ID NO: 154 |
| DHD128 | Heterodimer | a | GSDEKDEIRHVIESVERLIEDIKRLLKTLRELAHDDSDKKTVKEVLDRVKE MIERHRRELEEHRKELERAEYEVR SEQ ID NO: 155 |
| DHD128 | Heterodimer | b | GSESEDRIKELLKRHIELVERHEELLHEIKKLIDLEEKDDKDREEAVKRID DAIKESEEMLEESKEILEEIEYLNR SEQ ID NO: 156 |
| DHD129 | Heterodimer | a | GSSLEDSVRLNDEVVKVVERVVRLNQEVVRLIKHATDVEDEETVKYVLERV REVLDESREVLKRVHELLEESERRLE SEQ ID NO: 157 |
| DHD129 | Heterodimer | b | GSHEKDIVYKVEDLVRKSDRIAERAREIVKRSRDIMREIRKDKDNKKLSDD LLKVTRDLQRVVDELEELSRELLRVAEESRK SEQ ID NO: 158 |
| DHD130 | Heterodimer | a | GSPELDEVKKLIDELKKSVERLEESIREVKESIKKLRKGDIDAEENIKLLK ENIKIVRENIKIIKEIIDVVQYVLR SEQ ID NO: 159 |
| DHD130 | Heterodimer | b | GSDEEEIEELLRELEKLLKKSEEALEESKKLIDESEELLRRDRLDKEKHVR ASEEHVKLSEEHLRISREIVKILEKAVYSTR SEQ ID NO: 160 |
| DHD131 | Heterodimer | a | GSDESDRIRKIVEESDEIVKESRKLAERARELIKESEDKRVSEERNERLLE ELLRILDENAELLKRNLELLKEVLYRTR SEQ ID NO: 161 |
| DHD131 | Heterodimer | b | GSDEDDELERLLREYHRVLREYEKLLEELRRLYEEYKRGEVSEEEESDRILR EIKEILDKSERLWDLSEEVWRTLLYQAE SEQ ID NO: 162 |
| DHD132 | Heterodimer | a | GSDKKDASRRAIRVLKEFVRVSEEVLEVLRKSVESLKRLDVDEKIKRTHDR IEEELRRWKRELEELIERLREWEYHQD SEQ ID NO: 163 |
| DHD132 | Heterodimer | b | GSDDEEEDKRLLEEVKRSLDTDERILEKLRHSLERQLEDVDKDEDSRRVLR ELDEITKRSREVVKRLRKLAYESK SEQ ID NO: 164 |
| DHD133 | Heterodimer | a | GSDKEYKLDRILRRLDELIKQLSRILEEIERLVDELEREPLDDKEVQDVIE RIVELIDEHLELLKEYIKLLEEYIKTTK SEQ ID NO: 165 |
| DHD133 | Heterodimer | b | GSPSKEYQEKSAERQKELLHEYEKLVRHLRELVEKLQRRELDKEEVLRRLV EILERLKDLHKKIEDAHRKNEEAHKENK SEQ ID NO: 166 |
| DHD134 | Heterodimer | a | GSRDRKISEELIKALEDHIRMLEELIRAIEEHIKLAERGVDEKELRESLEE LKKIVDELEKSLEELRKLAERYKYETR SEQ ID NO: 167 |
| DHD134 | Heterodimer | b | GSPKEESVEELKRVIDKHEEILRELKRVLEEHERVSHDEDENELRRSLERL KHILDRLHESLKELKELLKKNEYTER SEQ ID NO: 168 |

-continued

| Design name | Oligomerization State | Chain | Design sequene |
|---|---|---|---|
| DHD135 | Heterodimer | a | GSDHEYWVKIVERILRVMEKHAEIVKKHLEIVERVVREGPSEDLRRKLKES LREIEESLRELKELLDELDELSEKTR SEQ ID NO: 169 |
| DHD135 | Heterodimer | b | GSDEEYVTRSQRRLKRLLEEYIKVVEEHARLVERNERDDKELKRSIDELDK LTKELLELVKRYKELVDKTET SEQ ID NO: 170 |
| DHD136 | Heterodimer | a | GSDKEEIVKLQDEVIKTLERHLDILRKHIDLLEKLKDHLSEELKERVDRSI KKLEESIKRLERIIEELQELAEYSL SEQ ID NO: 171 |
| DHD136 | Heterodimer | b | GSREEELKESAEELERSVRELKKEADKYKEEVDRLHYRGKVDKDWRVVEK LIKLVEEHLELIREHLELLKEERR SEQ ID NO: 172 |
| DHD137 | Heterodimer | a | GSDMEYELKKSAEELRKSLEELKRILDELHKSLRELRRHGDDEEYVQTVEE LRKELEEHAKKLEEHLKELERVAT SEQ ID NO: 173 |
| DHD137 | Heterodimer | b | PEYELKKSVDDLKRDVDRLVEEVEEVFELSKERLREDRKHLELVEEMVRLI EKHLELIKEHLKLADDHVR SEQ ID NO: 174 |
| DHD138 | Heterodimer | a | GSREKDESKELNDEYKKLLEEYERLLRRSEELVKRAKGPRDEKELKRILEE NEDILRRTKEILERTKEISEEQKYRRR SEQ ID NO: 175 |
| DHD138 | Heterodimer | b | GSDKDERQERLNEESDKSNEESERSNRESEELNRRARGPNDEKELQEILDR HLELLERNQRLLDENKEILRESQYLND SEQ ID NO: 176 |
| DHD139 | Heterodimer | a | GSENKYILKEILKLLRENLKLLHDILRLLDENLEELEKHGAKDLDDYRRKI EEIRKKVEDYREKIEEIEKKVERDR SEQ ID NO: 177 |
| DHD139 | Heterodimer | b | GSESEYTQEEILELLKESIKLLREILRLLEESEELWRRENTKSERSEEIKE RAKEAIKRSEEILERVKRLSDHSR SEQ ID NO: 178 |
| DHD140 | Heterodimer | a | GSDEEEANYVSDKAVKIAEDVQELLKELLELSEVVRRGEVDEDEYDRVLRK LQEVMKEYEEVLKEYEEVSRKHE SEQ ID NO: 179 |
| DHD140 | Heterodimer | b | GSPEKYLIKTQEELLRRHAEILEDLIRKVERQVDLRRKVDERDEDLKRELE RSLRELERLVRESSRLVEEIRELSKEIKR SEQ ID NO: 180 |
| DHD141 | Heterodimer | a | GSDEEYELERISRESKELLERYKRLLREYQELLKELRHVKDLDRAVKIIHE LMRVSKELVEISHRLLELHERLVRRRK SEQ ID NO: 181 |
| DHD141 | Heterodimer | b | GSEKEYIEKLSRKIEEDIRRSEERAKDSERLVRRLEELAKRKRLDLDDVLR VAEENLEILEDNLRILEEILKEQDKSNR SEQ ID NO: 182 |
| DHD142 | Heterodimer | a | GSPHEEVVELHERVMEISERAVELIQRIIDIIRRIREDDKDIEKLVKTIRD LVREYEELHRELEEIDEEIYKKSE SEQ ID NO: 183 |
| DHD142 | Heterodimer | b | GSDHEDVVRLHEDLVRKQEDARRVLEEIVRLAEEIVEVIKKDEKDKDRVTR LVEEIEKLVEEYKKKVDEMRKISDEIKYRSR SEQ ID NO: 184 |
| DHD143 | Heterodimer | a | GSRAREVVKRAKRIIEEWQKILEEWRRILEEWRRLLEDERVDDRDNERIIR ENERVIRENEKIIRDVIRLLEELLYERR SEQ ID NO: 185 |
| DHD143 | Heterodimer | b | GSREDEELEEEIDRIRQMVEEYEELVKEYEELTEKYKQGKVDKEESKKIIE KSERLLDLSQDAVRKVKEIIRRILYTNR SEQ ID NO: 186 |
| DHD144 | Heterodimer | a | GSPKEEIVKLHDESAELHRRSVEVADEILKMKERSKDVDDERESRELSKEI ERLIREVEEVSKRIKRLSEEVEYLVR SEQ ID NO: 187 |
| DHD144 | Heterodimer | b | GSPLEEILKIQRRINKIQDDINKILHEILRMQEKLNRSSDKDEVEESLRRI RELIKRIKDLSKEIEDLSREVKYRTT SEQ ID NO: 188 |
| DHD145 | Heterodimer | a | GSPEDEHVYVVREIYEVLREHAEVLEENREVIERLLEAKKRGDKSEELVKE LKKSIDKLKEISRKLEEIVKELEKVSEKLK SEQ ID NO: 189 |
| DHD145 | Heterodimer | b | GSDEDETSYRILELLREIVRASRELIRLSEELLEVARRDDKDETVLETLIR EYKELLDRYRRLIEELTRLVEEYEERSR SEQ ID NO: 190 |
| DHD146 | Heterodimer | a | GSTQEEINRIQHEVLRIQEEIDEILRDIVEKLKAISRGELDHEVVKDVEDK VREALEKSEELLDKSRKVEYKSE SEQ ID NO: 191 |
| DHD146 | Heterodimer | b | GSDEEELNRELLEKSKRLVDINRDIIRTAQELIEMLKDSKDGRVDEDTKRE LRDKLRKLEEKLERVREELRKYEELLRYVQR SEQ ID NO: 192 |
| DHD147 | Heterodimer | a | GSDEKDRVYEILKEVQRLVKEYRDISKEIEDLVKHYEHITDDEAQEVSKEL IDKSLRASEIVRELIRLIKELLDELE SEQ ID NO: 193 |

-continued

| Design name | Oligomerization State | Chain | Design sequene |
|---|---|---|---|
| DHD147 | Heterodimer | b | GSDEEDVLYHLRELLEELKRVSDDYERLVREIKETSERKDRDTKENKDMLD ELVKAHREQEKLLERLVRLLEELFERKR SEQ ID NO: 194 |
| DHD1 | Heterodimer | a | PREQAIRISEEIIRISKKIIEILERTRSSTAREAMKWAKDSIRLAEESKYL LDK SEQ ID NO: 195 |
| DHD1 | Heterodimer | b | IEDDVKKIQDSTKKAQKETIEALERSTSSTARKQMEEQKEQIRLQKEAMYL LKK SEQ ID NO: 196 |
| DHD2 | Heterodimer | a | SREEIAKLQEEVIKLQRRVIELQKEVIELQRRAKELTSSYTKEILEIQRRI EEIQREIEEIQKRIEEIQEEIQRRT SEQ ID NO: 197 |
| DHD2 | Heterodimer | b | SDEEIKRLSEEVIQLSRRVIKMSREAIKLSREVQKLTPSYQKRIKEIADRS IELARESIEIAKRSEKIAEESQRRT SEQ ID NO: 198 |
| DHD3 | Heterodimer | a | PAKDEALKMANESLELAKKSARLIQESSSKEILERIEKIQRRIAELQDRIA YLIKK SEQ ID NO: 199 |
| DHD3 | Heterodimer | b | PAKDEALRMIDESRE1IKKSNELIQRSSSKEILERILEIQRKIAELQKRIQ YLLKS SEQ ID NO: 200 |
| DHD4 | Heterodimer | a | TDEARYRSERIVKEAKRLLDEARRRSEKIVREAKQRSNSEDAKRIMEENLR ESEEAARRLREIIRRNLEESRETG SEQ ID NO: 201 |
| DHD4 | Heterodimer | b | TREALEYQRKMAEEIEDLLREALRRQEEMVREAKQRSLSEEFKRIMERILE EQERVMRLAKEALERILEEQKRTG SEQ ID NO: 202 |
| DHD5 | Heterodimer | a | SERTKREAKRSQEEILREAKEAMRRAKESQDHRQNRDGSNSEDLERLSQEQ KRELEEVERRLKELAREQKYKLEDS SEQ ID NO: 203 |
| DHD5 | Heterodimer | b | SEDLKRILKEITERELKLMQDLMEILKKITEDENNLDSNNSEDLKRSIEKA RRILDEALRKLEESARRAKYIQEDN SEQ ID NO: 204 |
| DHD6 | Heterodimer | a | TEDEIRESLKWLDEVLQELREIARESNEVLERNRQKSRSDKLREDIERYKK RMEEARKKLDDQLNKYKKRMDENRS SEQ ID NO: 205 |
| DHD6 | Heterodimer | b | TEEELKESKKFAEDLARSARRALKESKRVLEEISQASRSKKLEEIVRRYKE QVKRWQDEWDERAREYRKRMKENRS SEQ ID NO: 206 |
| DHD7 | Heterodimer | a | TKTEEIERLAREIKKLSEKVERLAQEIEELSRRVKEENSTDRELKEANREI ERAIREIEKANKRMEEALRRMKYNG SEQ ID NO: 207 |
| DHD7 | Heterodimer | b | TKTEEHERLAREISKLADEHRKLAKIIEELARRIKEENLTDDELREAIRKI EDALRKNKEALKIMKEAAERNRYNT SEQ ID NO: 208 |
| DHD8 | Heterodimer | a | TKKEESRELARESEELARESEKLARKSLELARRAESSGSEEEKRRIIDENR KIIERNREIIERNKEIIEYNKELIS SEQ ID NO: 209 |
| DHD8 | Heterodimer | b | TKDEESLELNRESEELNRKSEELKRKSKELNDRAESSNSEEEEKEILREKK EILREHLEILRRHKEILRRHKYLTS SEQ ID NO: 210 |
| DHD16 | Heterodimer | a | TREELLRENIELAKEHIELMRELLELLQKMEELLERQSSEDILEELRKIIE RIRELLDRSRKIHERSEEIAYKEE SEQ ID NO: 211 |
| DHD16 | Heterodimer | b | SEDIAREIKELLRRLKEIIERNQRIAKEHEYIARERKKLDPSNEKERKLLE RSRRLQEESKRLLDEMAEIMRRIKKLLD SEQ ID NO: 212 |
| DHD18 | Heterodimer | a | DRQKLIEENIKLLDKHIKILEEILRLLKKDIDLLKKSSSEEVLEELKKIHR RIDKLLDESKKIHKRSSEIVKKRS SEQ ID NO: 213 |
| DHD18 | Heterodimer | b | DEQKLIETSQRLQEKSERLLEKFEQILREASDLYRKPDSEELLRRVEKLLR ELEKLIRENQDLARKHEKILRDQS SEQ ID NO: 214 |
| DHD19 | Heterodimer | a | DRQELIRENIELLKKHIKIVKEIQKLIETFIELLKKSSSEEILRRLKKILK RIEKLYRESQEIHKRSEEIAKKRQ SEQ ID NO: 215 |
| DHD19 | Heterodimer | b | DEERLIDKSRELQKESEELLKELLKIFKRIEELLEKPDSEELIREIKKLLE TLSEIHKRNEKLARTHEEILRQQS SEQ ID NO: 216 |
| DHD22 | Heterodimer | a | STRDVQREIAKAFKKMADVQKKLAEEIKRHVKKVEKKNKDNDEYRKIATEL LKKATESQKKLKELLDRIRKSDS SEQ ID NO: 217 |
| DHD22 | Heterodimer | b | DKDDRSTSLLKRVEKLIDESDRIIDKFTTLIELSRNGKIDDDQYKKELKEI LELLKKYDKHVKEVEELLKRLNS SEQ ID NO: 218 |

| Design name | Oligomerization State | Chain | Design sequene |
|---|---|---|---|
| DHD23 | Heterodimer | a | SKRKALEVSERVVRISEKVVRVLDESSDLLKKSYDDSDKFAELIDRHEEKI KKWKKLIKEWLEIIQRHKS SEQ ID NO: 219 |
| DHD23 | Heterodimer | b | SAEEFVKLSEEAVKRSKEILDIVRKQVKLVKAGVDKHEITDSLRKSEKLIE EHKELIKTHRDLLRREN SEQ ID NO: 220 |
| DHD24 | Heterodimer | a | SSTEILKRFKRALRESEKIVKHSRRVLKIIREVLKQKPTQAVHDLVRIIET QVKALEEQLKVLKRIVEALERQS SEQ ID NO: 221 |
| DHD24 | Heterodimer | b | DKQKEIKDILEKTRRIAEESRKIAEKFDEIIKRSTEGKIDESLTKELEELV KEVIKLSEDDARTSDDLVRKES SEQ ID NO: 222 |
| DHD26 | Heterodimer | a | DEDESIKLTRKSIEETRKSLKIIKEVVELIREVLKHIKDLDKEIFERIDKI LDKYKKQVDTYDEILKEYEKKQR SEQ ID NO: 223 |
| DHD26 | Heterodimer | b | SELDEQKELIKKQEKLIEEQQRLLSKIRRMFKERVKDQELLREIQKVLKRS QEIVETSKKILDRSDKTTE SEQ ID NO: 224 |
| DHD28 | Heterodimer | a | DQKEINTRIVEKLERIFKKSKEIVRQSERVISTIEKKTEDERELDLLRRHV KIVREHLKLLEELLKIIKEVQKESE SEQ ID NO: 225 |
| DHD28 | Heterodimer | b | DTEELVKRLNELLKELSKLVKEFIKILETYRKDQTKDTSKISERVDRILKT YEDLLQKYKEILEKIEKQLS SEQ ID NO: 226 |
| DHD29 | Heterodimer | a | DYARLIDQAVEVTRKVVEVNVTVARVNDKFAKHLGDEELRRVSEKLKEVSK DLQEVAKKSKDAARQVK SEQ ID NO: 227 |
| DHD29 | Heterodimer | b | DVSKVAEEYLQISKTLVDISRTLLEISERLVRLVRTVADDRSEVKKAIEDS IEVLKTSEEVVRQIKRASDKLVKAIS SEQ ID NO: 228 |
| DHD31 | Heterodimer | a | DAKEIQRRVVEIQTEVVKLQKKAVDIIRKIIEAFNNSNIDQSLLEAAKEIV KEIDKLEKLTESLLEESKKLLKRSS SEQ ID NO: 229 |
| DHD31 | Heterodimer | b | SAEEVVKLAKIFLELLRESIKLLKRSVDLLRKSSDPSLDKSEAEKVSREIE KVSDTSLKLSKKALDVVKRALKVAS SEQ ID NO: 230 |
| DHD32 | Heterodimer | a | DEKDAARKARKVSEEAKEASKKIEKALEESKRILNTLKQKKDEQEVKVIKE HEDVLRQIEKIQKQVLEIQKEVAKLLESLD SEQ ID NO: 231 |
| DHD32 | Heterodimer | b | SADDVARASEKVLRVARESAKAADKSLEVFKEVVKRGDKEAFLQVVKINEE VVKINITVIRILIEVSKTAT SEQ ID NO: 232 |
| DHD38 | Heterodimer | a | DEYVKETLKQLREALASLREADKRITELVKEARKKPLSEAARKFAEAIVTH VKVVVEHVEVVLRHVEVLVEAKKNGVIDKSILDNALRIIENVIRLLSNVIR VVDEVLQDLD SEQ ID NO: 233 |
| DHD38 | Heterodimer | b | DASDVIRRIHELFEEVHRLIEAVHRAIEDVAKAAQKKGLDESAVEILAELS KELAKLSRRLAEISREIQKVVTDPDDKEAVERLKEIIKEIKKQLDELRDRL RKLQDLLYKLK SEQ ID NO: 234 |
| DHD60 | Heterodimer | a | SEDKAHHDIVRVLEELIKIHDELMKISEEILKATSDSTATDETKEELKRRS KEAQKKSDTLVKIVKELEKESRKAQS SEQ ID NO: 235 |
| DHD60 | Heterodimer | b | DDEEKYRQIIREAQEISKTAKRILRDAQEISKRIRHQGVDRSEHQRLVDLL RELIKEHHKLLRRQQEADTRND SEQ ID NO: 236 |
| DHD63 | Heterodimer | a | DRKDKARKASEKLEEVIQRWKTVADKWKKMVDLVSNGKLSQEEVARVTEEL LKIQTELAKLLEEHAKVLQESAS SEQ ID NO: 237 |
| DHD63 | Heterodimer | b | SDEESIKTQSELIKTSEELLKDVKRIDEELQKLRDDPTLDESELKKRVKEW SDRVRKAKEISRKIQEIVKESKKRSS SEQ ID NO: 238 |
| DHD66 | Heterodimer | a | DKDEELRKVIEKYREMVKEYRKVIREYEEVIKSSKTIDKSSLISLSRKMVE LSQRVIDVSDEVAKVLSRKQS SEQ ID NO: 239 |
| DHD66 | Heterodimer | b | TDEERLKKQTKELKEQTKQLEKQKDLLEKISKGEISKDEIQEIIKESKKIA KESQKALDSSRKALEEVS SEQ ID NO: 240 |
| DHD67 | Heterodimer | a | DEKEVSKEIIKVLKDIAKVQQKVIEVSQRLASVLRADDDNVVKRALEEYEK ILEELRELNKEIEKLTDKYRKVTS SEQ ID NO: 241 |
| DHD67 | Heterodimer | b | DSDEQTKELEKLTELHKRHVEKLKKQTKESREVDSNKLWKSKDVKDKLSES EKELQKLSDQDKKAKDALESSRRKND SEQ ID NO: 242 |
| DHD69 | Heterodimer | a | DAEEQLKLLTKLLRHQQRLLQLIKESLKLIEKIDQSSQENQDEIRKWREVT KKLRELIKTSEKLVRELEKSYKKSS SEQ ID NO: 243 |

-continued

| Design name | Oligomerization State | Chain | Design sequene |
|---|---|---|---|
| DHD69 | Heterodimer | b | SLRDVVRRYQELVRRYDELIKTLTEILKKYQKKGAEDKDASTELVKAVRTS LKLSKELLKLNSELLKEDS SEQ ID NO: 244 |
| DHD71 | Heterodimer | a | SKEELKRKLDELKKRSDTLKELSKKLKEISERNPDDKSVHRTIIRIHREFV KNHKEIVRVIEEIVSDKS SEQ ID NO: 245 |
| DHD71 | Heterodimer | b | SKQDEHDRLLKIHDKLVKQHDELLKLLTKLSRAGDSVTKKKLEEILRKLQE VSKQLEESLKDADKVSKDIN SEQ ID NO: 246 |
| DHD72 | Heterodimer | a | TVQSLLEQHVKIVKRSIEILERHTQILQDIARSQGVSKELEDVERQVKEYR KEVKKLEEDLRQLSRNSK SEQ ID NO: 247 |
| DHD72 | Heterodimer | b | SDSDRIEKLIRESTELLKEQQKLAKRSRELAETVESLPLTEEYLKQQREKQ KKIEKLLKDSEKHLEELKRLVKSEK SEQ ID NO: 248 |
| DHD73 | Heterodimer | a | DSEKRIEDILRTDLELAKRDAELVKEHIKLVKRIDLSEELKKQVEDVEKES KKLEDSSEKLVQKVRKRSS SEQ ID NO: 249 |
| DHD73 | Heterodimer | b | DEEERAKDLRKYLEEQTQYYRTVTEHLRNLEKVVEEELERRGKPSSELQQIL ERSQRIYKETTEIYDTSKKLIEELDKHHR SEQ ID NO: 250 |
| DHD148 | Heterodimer | a | PLEDILKRHLDKVRELVRLSEEVNKLAKEVLDILKDKRVDEKELDKVLKEL EKVVEEYERAVKESRDLLRELRETTR SEQ ID NO: 251 |
| DHD148 | Heterodimer | b | DKERLLEIHERIQKLLDRNLEIIERLLRLLREARDIKDDDKLDKVIKRLKE LSEESKDILDKIKELLKESEKELT SEQ ID NO: 252 |
| DHD149 | Heterodimer | a | PEDEVIRVIEELLRIAAEVDEVHRRNVEVQEEASRVTDRERLERLNRESEE LIKRSRELIEEQRKLIERLERLAT SEQ ID NO: 253 |
| DHD149 | Heterodimer | b | DLEELIKEYAEVVRRHHKAVRDLERLVRELANAKHASEEELKRIATEILRI VKELIRVQERLIKLSEDSNEESR SEQ ID NO: 254 |
| DHD150 | Heterodimer | a | PTDEVIEVLKELLRIHRENLRVNEEIVEVNERASRVTDREELERLLRRSNE LIKRSRELNEESKKLIEKLERLAT SEQ ID NO: 255 |
| DHD150 | Heterodimer | b | DNEEIIKEARRVVEEYKKAVDRLEELVRRAENAKHASEKELKDIVREILRI SKELNKVSERLIELWERSQERAR SEQ ID NO: 256 |
| DHD151 | Heterodimer | a | PKEDIDRVSRELVRVHKELLEVLRKSTEIVEAVARNEKDERTIEEVLEEQE RAVRKLEEVSKKHKEAVKRLK SEQ ID NO: 257 |
| DHD151 | Heterodimer | b | ELERLSEEIQKLSDRLIELIRRHSKVLEEIVRLLKHKDNDEREVRRLLKLL RDLTRRYEEVLRKVEEIVKRQEDESR SEQ ID NO: 258 |
| DHD152 | Heterodimer | a | PEEDILRLLRKLVEVDKELLEVVRESTEVVRLVARNEKDVETVERVLRKQE EVVRKYERVSRELEEAVRRLK SEQ ID NO: 259 |
| DHD152 | Heterodimer | b | ELKDLVEEIVKLSKENLKLWEDHSRVLEEIVRLLKHKDNDEREVRRLLKLL EDLTRRAEETSRRIEEIVKEAEDRAR SEQ ID NO: 260 |
| DHD153 | Heterodimer | a | DEERELREVLRKHHRWREVVTKVVEEELKRVVELLKRGETSEEDLLRVLKKL LEMDKRILEVNREVLRVLEKRLT SEQ ID NO: 261 |
| DHD153 | Heterodimer | b | SLEEIIEELVELVRRSVEIAKESDEVARRIVESEDKKKELIDTLRDLHREW QEVTKRAEELVREAEKEVR SEQ ID NO: 262 |
| DHD154 | Heterodimer | a | TAEELLEVHKKSDRVTKEHLRVSEEILKVVEVLTRGEVSSEVLKRVLRKLE ELTDKLRRVTEEQRRVVEKLN SEQ ID NO: 263 |
| DHD154 | Heterodimer | b | DLEDLLRRLRRLVDEQRRLVEELERVSRRLEKAVRDNEDERELARLSREHS DIQDKKDKLAREILEVLKRLLERTE SEQ ID NO: 264 |
| DHD155 | Heterodimer | a | PEDDVVRIIKEDLESNREVLREQKEIHRILELVTRGEVSEEAIDRVLKRQE DLLKKQKESTDKARKVVEERR SEQ ID NO: 265 |
| DHD155 | Heterodimer | b | DEVRLITEWLKLSEESTRLLKELVELTRLLRNNVPNVEEILREHERISREL ERLSRRLKDLADKLERTRR SEQ ID NO: 266 |
| DHD156 | Heterodimer | a | DEDEVVKVHEEHVKSHEEIHRSHEEVVRAAEEDKRDSRELRTLMEEHRKLL EENEKSIEEVKKIHERVKR SEQ ID NO: 267 |
| DHD156 | Heterodimer | b | KKEELIDISKEVLDLDDEINKISKEILELIKKLLRLKEEGREDKDKAREVK RRIRELHRRIQELNKRLRELHKRVQETKR SEQ ID NO: 268 |

| Design name | Oligomerization State | Chain | Design sequence |
|---|---|---|---|
| DHD157 | Heterodimer | a | PEEDIARRVEDLLRKSEELIKESEKILKESKRLLDRNDSDKRVLETNLRLI DKHTKLLERNLELLEELLKLAEDVAK SEQ ID NO: 269 |
| DHD157 | Heterodimer | b | RFKDLSREYIEVVKRLLELSREALEVLREIKDTDKTDKKRIKELIDRLRKL IEEYKRIIDRLRKLSKDLEEEIIR SEQ ID NO: 270 |
| DHD158 | Heterodimer | a | DEEELVKILKELQRLSEESLEINKRLVEILRLLRRGEVPKEEVEKKLREIK KEQEKLDREHEKIKKRIEEITK SEQ ID NO: 271 |
| DHD158 | Heterodimer | b | SLKEKILEIIERNMKLVELSNRSVEIVARILKGEKDDEETLERLLREWDKI TRDYEEIIKESRKLVKELEEEAK SEQ ID NO: 272 |
| DHD159 | Heterodimer | a | SKTEILRKALEIHKEQIDIVRKLIELSEEVLKLVEESKEKNLEKLKRIDEE TDRLLERLDELHKRLTELAERLK SEQ ID NO: 273 |
| DHD159 | Heterodimer | b | SDDEARKQLEEMKRRLREVEKKSKRVEERVRELERLVRENREDEDRVLKTL EDLLRENEKLVRTIERHVREQRELSKEVK SEQ ID NO: 274 |
| DHD160 | Heterodimer | a | SEEELEKKADELRKLSEEWRKLQEEDKRLSEMVEKGELDLQEVDEHSLRVL ERATEVHRTVDKVIEEILRTTN SEQ ID NO: 275 |
| DHD160 | Heterodimer | b | SEKERHRESQETQEEIRRTHEEIIRKLEEILRRAKAGELPEETLDRLRRIM ERLKELSERLDDLVRKLRDDHRREQK SEQ ID NO: 276 |
| DHD161 | Heterodimer | a | SEKEILEELKRILKRVKDISDRLEELDKRTEEIARREPTKELVDELVKIHR DWLRLHEEILKLVDDALKKVEDATK SEQ ID NO: 277 |
| DHD161 | Heterodimer | b | DLRELLELQREASRLHRELVKLLTELVKKLELIAKGEDIREEDLKRIKERL EEIKKRSKRIKEESDEIDKKTK SEQ ID NO: 278 |
| DHD162 | Heterodimer | a | SERELQRELNKIVRRILEIHREVSELHQRAVKLIRENDNSEELEEISRRIE ELSKELEKLVREHDEIVKTIE SEQ ID NO: 279 |
| DHD162 | Heterodimer | b | SEREKLDRNDEELKEINKRVEEIKERSDRITEAIEKNERSEEEIRRLSREQ NEALQRLLELHKKLVKLHRELLEDTR SEQ ID NO: 280 |
| DHD163 | Heterodimer | a | DKEDVIRVHDEQHKLIEEQLELTRRIAELVREIAKNTASEEEIKEMLKEIK RLDDRSREIQDRLQKLLEEIRRKTK SEQ ID NO: 281 |
| DHD163 | Heterodimer | b | TEEEIVELNKDIQRKSKEHIDLQKELVKKIERAIRENNITEELLEELERLL RESEKIVEEIRRITDKIRKDAK SEQ ID NO: 282 |
| DHD164 | Heterodimer | a | SEKEILERLLRLSKEQNEISEEIHRLTERLVELKRRKDDDERLKRILDRQK RLVERAREISKEYEDLLRKLE SEQ ID NO: 283 |
| DHD164 | Heterodimer | b | SMEELLRKNARLSRKQLKIIDEHLELSTKLTRGEAGDETLEEIERRSREML EEQRRVDEESKRIREKLK SEQ ID NO: 284 |
| DHD165 | Heterodimer | a | SEEEIRDIVEKLLRTHEEVLKEIKKLLDDSERVRRELDKKDLDRIQKEQR DIQEENKEKAKRFDELVKELKKAAK SEQ ID NO: 285 |
| DHD165 | Heterodimer | b | SEEEHRRTMEKVEKEVRDIKRRSEEVKKKVKANTLSEEDLVRLLERLVEDH KRLQDLSQEIIERDEKATK SEQ ID NO: 286 |
| DHD166 | Heterodimer | a | DEDELAKEIEDVQRRKKESQEEHDKSVKKLEAAERGEIDEDSLLRVLEEDI KVLEKDIEVLERSIEVIEKAE SEQ ID NO: 287 |
| DHD166 | Heterodimer | b | SEKELIRRLLEQQRQKLRLSERLIELSRRLVEBBRKGKDNRDLLRELKKLS EEHKKHSKDDHEKVREIREREK SEQ ID NO: 288 |
| DHS 17 | Heterodimer | a | DRKDLLKRNIKLLDRHLKILDTILKLLEKLSELLKKSSSEEVVKEYKKILD EIRKLLEESKEIHKESKEILERES SEQ ID NO: 289 |
| DHD17 | Heterodimer | b | DEEKLIERSKRLQEESEQLLEKFEQILRELTELLEKPDSEELARKIKKLHD ELRKIIKRNQELIREIIEEILRKRD SEQ ID NO: 290 |

In one aspect, the monomer A polypeptide comprises a polypeptide having at least 70%, 75%, 80%, 85%, 90%, 91%, 92%, 93%, 94%, 95%, 96%, 97%, 98%, 99%, or 100% sequence identity along the length of the amino acid sequence of an odd-numbered SEQ ID NO selected from the group consisting of selected from the group SEQ ID NOS: 1-290; wherein GlySer at amino acids 1 and 2 of SEQ ID NO: 1, 55, 81, 83, 101, 105, 115, 117, 119, 121, 123, 125, 127, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, or 193 are optional, e.g., GlySer at amino acids 1 and 2 of SEQ ID NO: 1, 55, 81, 83, 101, 105, 115, 117, 119, 121, 123, 125, 127, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, or 193 are not present, and wherein the odd-numbered SEQ ID NO ("chain a") is the binding partner of the SEQ ID NO. ("chain b") in Tables 1A.

In another aspect, the monomer B polypeptide comprises a polypeptide having at least 70%, 75%, 80%, 85%, 90%, 91%, 92%, 93%, 94%, 95%, 96%, 97%, 98%, 99%, or 100% sequence identity along the length of the amino acid sequence of an even-numbered SEQ ID NO selected from the group consisting of selected from the group SEQ ID NOS: 1-290, wherein GlySer at amino acids 1 and 2 of SEQ ID NO: 6, 8, 14, 16, 26, 30, 32, 34, 36, 38, 40, 42, 46, 48, 54, 56, 58, 60, 62, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 128, 130, 132, 134, 136, 138, 140, 142, 144, 146, 148, 150, 152, 154, 156, 158, 160, 162, 164, 166, 168, 170, 172, 176, 178, 180, 182, 184, 186, 188, 190, 192, or 194 are optional, e.g., GlySer at amino acids 1 and 2 of SEQ ID NO: 6, 8, 14, 16, 26, 30, 32, 34, 36, 38, 40, 42, 46, 48, 54, 56, 58, 60, 62, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 128, 130, 132, 134, 136, 138, 140, 142, 144, 146, 148, 150, 152, 154, 156, 158, 160, 162, 164, 166, 168, 170, 172, 176, 178, 180, 182, 184, 186, 188, 190, 192, or 194 are not present, wherein the even-numbered SEQ ID NO ("chain b") is the binding partner of the SEQ ID NO. ("chain a") in Table 1A.

In another embodiment of any of the above embodiments,
(i) monomer A comprises a polypeptide having at least 70%, 75%, 80%, 85%, 90%, 91%, 92%, 93%, 94%, 95%, 96%, 97%, 98%, 99%, or 100% sequence identity along the length of the amino acid sequence of an odd-numbered SEQ ID NO selected from the group consisting of selected from the group SEQ ID NOS: 1-290, 331, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494; and
(ii) monomer B comprises a polypeptide having at least 70%, 75%, 80%, 85%, 90%, 91%, 92%, 93%, 94%, 95%, 96%, 97%, 98%, 99%, or 100% sequence identity along the length of the amino acid sequence of an even-numbered SEQ ID NO selected from the group consisting of selected from the group SEQ ID NOS: 1-290, 331, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, wherein the even-numbered SEQ ID NO is the binding partner of the odd-numbered SEQ ID NO. in step (i).

The amino acid sequences of SEQ ID NOS:1-290, 331, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 are provided in Table 1B. The "binding partners" have similar design names as shown in Table 1B. For example, SEQ ID NO:1 (DHD9 A) and SEQ ID NO:2 (DHD9 B) are binding partners, and For example, SEQ ID NO:331 (DHD9 A) and SEQ ID NO:2 (DHD9 B) are binding partners, so that if monomer A comprises the polypeptide having at least 70%, 75%, 80%, 85%, 90%, 91%, 92%, 93%, 94%, 95%, 96%, 97%, 98%, 99%, or 100% sequence identity along the length of the amino acid sequence of SEQ ID NO:1 or SEQ ID NO:331, then monomer B comprises the polypeptide having at least 70%, 75%, 80%, 85%, 90%, 91%, 92%, 93%, 94%, 95%, 96%, 97%, 98%, 99%, or 100% sequence identity along the length of the amino acid sequence of SEQ ID NO:2. Similarly, SEQ ID NOS:3-4 are binding partners, SEQ ID NO:5-6 and 5-332 are binding partners, etc. Those of skill in the art will clearly understand what is meant by binding partner based on the teachings herein.

TABLE 1B

| Design name | Oligomer- ization State | Chain | Design sequence |
|---|---|---|---|
| DHD9 | Heterodimer | a | GSPKEEARELIRKQKELIKEQKKLIKEAKQKSDSRDAERIWKRSREINRES KKINKRIKELIKS SEQ ID NO: 1<br>PKEEARELIRKQKELIKEQKKLIKEAKQKSDSRDAERIWKRSREINRESKK INKRIKELIKS SEQ ID NO: 331 |
| DHD9 | Heterodimer | b | PKKEAEELAEESEELHDRSEKLHERAEQSSNSEEARKILEDIERISERIEE ISDRIERLLRS SEQ ID NO: 2 |
| DHD13_X AAA | Heterodimer | a | GTKEDILERQRKIIERAQEIHRRQQEILEELERIIRKPGSSEEAMKRMLKL LEESLRLLKELLELSEESAQLLYEQR SEQ ID NO: 3 |
| DHD13_X AAA | Heterodimer | b | GTEKRLLEEAERAKREQKEIIKKAQELHRRLEEIVRQSGSSEEAKKEAKKI LEEIRELSKRSLELLREILYLSQEQKGSLVPR SEQ ID NO: 4 |
| DHD13_X AXA | Heterodimer | a | TKEDILERQRKIIERAQEIIRRQQEILEELERIIRKPGSSEEAMKRMLKLL EESLRLLKELLELLEESAQLLYEQR SEQ ID NO: 5 |
| DHD13_X AXA | Heterodimer | b | GSTEKRLLEEAERAHREAKEIIKKAQELHRRLEEIVRQSGSSEEAKKEAKK ILEEIRELSKRLLELLREILYLSQEQK SEQ ID NO: 6<br>TEKRLLEEAERAHREAKEIIKKAQELHRRLEEIVRQSGSSEEAKKEAKKIL EEIRELSKRLLELLREILYLSQEQK SEQ ID NO: 332 |
| DHD13_X AAX | Heterodimer | a | TKEDILERARKIIERAQEIHRRQQEILEELERIIRKPGSSEEAMKRMLKLL EESLRLLKELLELSEELAQLLYEQR SEQ ID NO: 7 |
| DHD13_X AAX | Heterodimer | b | GSTEKRLLEEAERAIREQKEIIKKAQELHRRLEEIVRQSGSSEEAKKEAKK ILEEIRELSKRSLELLREILYLLQEQK SEQ ID NO: 8<br>TEKRLLEEAERAIREQKEIIKKAQELHRRLEEIVRQSGSSEEAKKEAKKIL EEIRELSKRSLELLREILYLLQEQK SEQ ID NO: 334 |

TABLE 1B-continued

| Design name | Oligomer- ization State | Chain | Design sequence |
|---|---|---|---|
| DHD13_2: 341 | Heterodimer | a | TKEDILERQRKIIERAQEIHRRQQEILEELEYIIR SEQ ID NO: 9 |
| DHD13_2: 341 | Heterodimer | b | MSEEAMKRMLKLLEESLRLLKELLELSEESAQLLYEQRKANNGSETEKRLL EEAERAHREQKEIIKKAQELHRRLEEIVRQSGSSEEAKKEAKKILEEIREL SKRSLELLREILYLSQEQK SEQ ID NO: 10 |
| DHD13_A AAA | Heterodimer | a | MTKEDILERQRKIIERAQEIHRRQQEILKEQEKIIRKPGSSEEAMKRSLKL IEESLRLLKELLELSEESAQLLYEQR SEQ ID NO: 11 |
| DHD13_A AAA | Heterodimer | b | GTEKRLLEEAERAKREQKEIIKKAQELHKELTKIHQQSGSSEEAKKRALKI SQEIRELSKRSLELLREILYLSQEQK SEQ ID NO: 12 |
| DHD13_B AAA | Heterodimer | a | TKEDILERQRKIIERAQEIHRRQQEILKRSEEIIRKPGSSEEALETLRELQ EESLRLLKELLELSEESAQLLYEQR SEQ ID NO: 13 |
| DHD13_B AAA | Heterodimer | b | GSTEKRLLEEAERAHREQKEIIKKAQELHRRTEEIIRQSGSSEEAKDELRR IQEEIRELSKRSLELLREILYLSQEQK SEQ ID NO: 14 TEKRLLEEAERAHREQKEIIKKAQELHRRTEEIIRQSGSSEEAKDELRRIQ EEIRELSKRSLELLREILYLSQEQK SEQ ID NO: 336 |
| DHD13_4: 123 | Heterodimer | a | TTKRYLEEAERAHREQKEIIKKAQELHRRLEEIVRQ SEQ ID NO: 15 |
| DHD13_4: 123 | Heterodimer | b | GSSEEAKKEAKKILEEIRELSKRSLELLREILYLSQQVNDVDEKALERQRK IIERAQEIHRRQQEILEELERIIRKPGSSEEAMKRMLKLLEESLRLLKELL ELSEESAQLLYEAR SEQ ID NO: 16 SEEAKKEAKKILEEIRELSKRSLELLREILYLSQQVNDVDEKALERQRKII ERAQEIHRRQQEILEELERIIRKPGSSEEAMKRMLKLLEESLRLLKELLEL SEESAQLLYEAR SEQ ID NO: 338 |
| DHD13_1: 234 | Heterodimer | a | EAMKRMLKLLEESLRLLKELLELSEESAQLLYEAR SEQ ID NO: 17 |
| DHD13_1: 234 | Heterodimer | b | TTKRYLEEAERAHREQKEIIKKAQELHRRLEEIVRQSGSSEEAKKEAKKIL EEIRELSKRSLELLREILYLSQQVNDVDEKALERQRKIIERAQEIHRRQQE ILEELERIIRKPGS SEQ ID NO: 18 |
| DHD15 | Heterodimer | a | TREELLRENIELAKEHIEIMREILELLQKMEELLEKARGADEDVAKTIKEL LRRLKEIIERNQRIAKEHEYIARERS SEQ ID NO: 19 |
| DHD15 | Heterodimer | b | GTERKLLERSRRLQEESKRLLDEMAEIMRRIKKLLKKARGADEKVLDELRK IIERIRELLDRSRKIHERSEEIAYKEE SEQ ID NO: 20 |
| DHD20 | Heterodimer | a | GDRQELIRRNIELLKEIIIKILEEISQLIEELSELLDKSSSEEWKRYKKIL ERYKQLLRKSQEIHKESSEIAKKES SEQ ID NO: 21 |
| DHD20 | Heterodimer | b | GDEQKLIERSQRMQKESLELLKEIIKILDTIEKLLDKPDSEELLDTIKKLH DTLKKIHDRNKKLLKEHEEILRQRSGSLVPR SEQ ID NO: 22 |
| DHD21 | Heterodimer | a | DKEEEYKRLLDEIKEILKESKEVLKDSKRVLEDIKRKVPDDDLVKLLEKHV RLLEEHVKLLEQLIREAEKSSK SEQ ID NO: 23 |
| DHD21 | Heterodimer | b | QGSSAEELLKKIKESEKKIRDSLRKIKEIIKKSRKEGVDDKQLDLIRKVVE SHRDLLRLHRDLLRLLREETS SEQ ID NO: 24 |
| DHD25 | Heterodimer | a | DIDESIKEVEKLLEEVEQSLQKLDDSLKKLLEKVNQDPDVDDSVRKIVKRH VEILKRHEEVLKRLIEWKEHTKTVK SEQ ID NO: 25 |
| DHD25 | Heterodimer | b | GSDREEVHKEIVKLIREIIKIHKKILKIHEKIKNGEIDPSE1LKLSEEIKK LTDTIIKIIEDLEQLTRDLRR SEQ ID NO: 26 DREEVHKEIVKLIREIIKIHKKILKIHEKIKNGEIDPSE1LKLSEEIKKLT DTIIKIIEDLEQLTRDLRR SEQ ID NO: 340 |
| DHD27 | Heterodimer | a | DRKEIVKRHQKVVELLKESSKLLRESSKLLQRLLDKTGDENLQKAVDDQDK AIKRQETAIRKSQEASKKLD SEQ ID NO: 27 |
| DHD27 | Heterodimer | b | DNSEEIKKVAKTSREVAEYSERVAKENDKVVKTLEEGKIDESELLRLLEES IKIFDTALKLHEEAYKLIIQDLVRKVS SEQ ID NO: 28 |
| DHD30 | Heterodimer | a | DESEAASVAIESVQILVESVKLLEESVRILLDAVKKNGVEDLLRVAQRWEK LVDEWLKWKRWLDNVRDIQR SEQ ID NO: 29 |

TABLE 1B-continued

| Design name | Oligomer- ization State | Chain | Design sequence |
|---|---|---|---|
| DHD30 | Heterodimer | b | GSDKAEEVEKSVRKIEESIKKIRKSIKKAEDAVQLLKEGKIDAKDFLRIVR EDLEWKEDVEIVKEDVENVREFSS SEQ ID NO: 30 DKAEEVEKSVRKIEESIKKIRKSIKKAEDAVQLLKEGKIDAKDFLRIVRED LEWKEDVEIVKEDVENVREFSS SEQ ID NO: 342 |
| DHD33 | Heterodimer | a | SDKEVSDKLLKASKKLLKVSEELLEVVRRLLKALKDDELIKKIADLLRKII DKDKKFIRTSEEIVKESR SEQ ID NO: 31 |
| DHD33 | Heterodimer | b | GSDLKEVLKTVEEAVKEIIKSSEELLQISRKILEISRVGVDEHEYISAIRE YLKALEKHIQILKKFIEILKELIRAVSSEQIDNO:32 DLKEVLKTVEEAVKEIIKSSEELLQISRKILEISRVGVDEHEYISAIREYL KALEKHIQILKKFIEILKELIRAVS SEQ ID NO: 344 |
| DHD34_X AAXA | Heterodimer | a | SKEEIDKIVKKHKKKIEEHKKKVDELKKLVEEHDKRVSQDKDDVKKLSEE VKKIIKRLEEVSKRLEEVSKKLLKVISDKR SEQ ID NO: 33 |
| DHD34_X AAXA | Heterodimer | b | GSNDEELKKILETLDRILKKLDKILTRLIEVLKKSEDPNLDDKDYTELVKQ FIELIKKYEEWKEYEEWRQLIRLFS SEQ ID NO: 34 NDEELKKILETLDRILKKLDKILTRLIEVLKKSEDPNLDDKDYTELVKQFI ELIKKYEEWKEYEEWRQLIRLFS SEQ ID NO: 346 |
| DHD34_X AXXA | Heterodimer | a | SKEEIDKIVKKHKKKIEELKKLVDELKKLVEEHDKRVSQDKDDVKKLSEE VKKIIKRVEEVAKRLEEVSKKLLKVISDKR SEQ ID NO: 35 |
| DHD34_X AXXA | Heterodimer | b | GSNDEELKKILETLDRILKKLEKILTRLIEVLKKSEDPNLDDKDYTELVKQ FIELIKKFEEVIKEYEEWRQLIRLFS SEQ ID NO: 36 NDEELKKILETLDRILKKLEKILTRLIEVLKKSEDPNLDDKDYTELVKQFI ELIKKFEEVIKEYEEWRQLIRLFS SEQ ID NO: 348 |
| DHD34_X AAAA | Heterodimer | a | SKEEIDKIVKKHKKKIEEHKKKVDEHKKLVEEHDKRVSQDKDDVKKLSEE LKKISKRLEEVSKRLEEVSKKLLKVISDKR SEQ ID NO: 37 |
| DHD34_X AAAA | Heterodimer | b | GSNDEELKKILETLDRILKKLDKILTRLDEVLKKSEDPNLDDKDYTELVKQ YIELVKKYEEWKEYEEWRQLIRLFS SEQ ID NO: 38 NDEELKKILETLDRILKKLDKILTRLDEVLKKSEDPNLDDKDYTELVKQYI ELVKKYEEWKEYEEWRQLIRLFS SEQ ID NO: 418 |
| DHD36 | Heterodimer | a | DHSRKLKEILDRLRKHVKRLKEHDELRDLVRQVPEDKLLEHVVKLSDKIL QISERAVREFTKSVDKDS SEQ ID NO: 39 |
| DHD36 | Heterodimer | b | GSDKKDELERILDEIRRLIERLDEILSRLNKLLELLKHGVPNAKEVVKDYI RLLKEYLELVKEFLKLVKRHADLVS SEQ ID NO: 40 DKKDELERILDEIRRLIERLDEILSRLNKLLELLKHGVPNAKEVVKDYIRL LKEYLELVKEFLKLVKRHADLVS SEQ ID NO: 350 |
| DHD37_A BXB | Heterodimer | a | DSDEHLKKLKTFLENLRRHLDRLDKHIKQLRDILSENPEDERVKDVIDLSE RSVRIVKTVIKIFEDSVRKKE SEQ ID NO: 41 |
| DHD37_A BXB | Heterodimer | b | GSDDKELDKLLDTLEKILQTATKIIDDANKLLEKLRRSERKDPKVVETYVE LLKRHEKAVKELLEIAKTHAKKVE SEQ ID NO: 42 DDKELDKLLDTLEKILQTATKIIDDANKLLEKLRRSERKDPKVVETYVELL KRHEKAVKELLEIAKTHAKKVE SEQ ID NO: 352 |
| DHD37_B BBB | Heterodimer | a | MDEEDHLKKLKTHLEKLERHLKLLEDHAKKLEDILKERPEDSAVKESIDEL RRSIELVRESIElFRQSVEEEE SEQ ID NO: 43 |
| DHD37_B BBB | Heterodimer | b | GDVKELTKILDTLTKILETATKVIKDATKLLEEHRKSDKPDPRLIETHKKL VEEHETLVRQHKELAEEHLKRTR SEQ ID NO: 44 |
| DHD37_X BXB | Heterodimer | a | DSDEHLKKLKTFLENLRRHLDRLDKLLKELRDILSENPEDERVKDVIDELE RVIRIVKTVIKIFEDSVRKKE SEQ ID NO: 45 |
| DHD37_X BXB | Heterodimer | b | GSDDKELDKLLDTLEKILQTATKIIDDLNKVLEKLRRSERKDPKVIETVVE LLKRHEKAVKELLEIAKTHAKKVE SEQ ID NO: 46 DDKELDKLLDTLEKILQTATKIIDDLNKVLEKLRRSERKDPKVIETVVELL KRHEKAVKELLEIAKTHAKKVE SEQ ID NO: 354 |
| DHD37_A XXB | Heterodimer | a | DSDEHLKKLKTFLENLRRLEDLLDKHIKQLRDILSENPEDERVKDVIDLSE RWRTVKTVIKIFEDSVRKKE SEQ ID NO: 47 |
| DHD37_A XXB | Heterodimer | b | GSDDKELDKLLDTLEKILQTATKVVDDANKLLEKLRRSERKDPKVVETYVE LLKRLEKLIKELLEIAKTHAKKVE SEQ ID NO: 48 DDKELDKLLDTLEKILQTATKVVDDANKLLEKLRRSERKDPKVVETYVELL KRLEKLIKELLEIAKTHAKKVE SEQ ID NO: 356 |

TABLE 1B-continued

| Design name | Oligomerization State | Chain | Design sequence |
|---|---|---|---|
| DHD37_3: 124 | Heterodimer | a | DSDEHLKKLKTFLENLRRHLDRLDKHIKQLRDILSEN SEQ ID NO: 49 |
| DHD37_3: 124 | Heterodimer | b | EDERVKDVIDLSERSVRIVKTVIKIFEDSVRKLEKTKPDSKTAKELDKLLD TLEKILQTATKIIDDANKLLEKLRRSERKDPKVVETYVELLKRHEKAVKEL LEIAKTHAKKVE SEQ ID NO: 50 |
| DHD37_1: 234 | Heterodimer | a | DSDEHLYKLKTFLENLRRHLDRLDKHIKQLRDILSENPEDERVKDAIDLSE RSVRIVKTVIKIFEDSVRKKEKRPIDKRDDKELDKLLDTLEKILQTATKII DDANKLLEYLRR SEQ ID NO: 51 |
| DHD37_1: 234 | Heterodimer | b | GDPKVVETYVELLKRHEKAVKELLEIAKTHAKKVE SEQ ID NO: 52 |
| DHD37_A XBB | Heterodimer | a | DSDEHLDRLDKHLKKLKTFLENLRRHIKQLRDILSENPEDERVKDVIDLSK TVIKIFEDSVRKKERSVRIVE SEQ ID NO: 53 |
| DHD37_A XBB | Heterodimer | b | GSDDKEATKIIDDLDKLLDTLEKILQTANKLLEKLRRSERKDPKVVETYVK AVKELLEIAKTHAELLKRHEKKVE SEQ ID NO: 54 DDKEATKIIDDLDKLLDTLEKILQTANKLLEKLRRSERKDPKVVETYVKAV KELLEIAKTHAELLKRHEKKVE SEQ ID NO: 358 |
| DHD37_X BBA | Heterodimer | a | DSDEHIKQLRDHLDRLDKHLKKLKTFLENLRRILSENPEDERVKTVIKIFE DSVRKKERSVRIVKDVIDLSE SEQ ID NO: 55 |
| DHD37_X BBA | Heterodimer | b | GSDDKEANKLLEKATKIIDDLDKLLDTLEKILQTLRRSERKDPKAVKELLE IAKTHAELLKRHEKVVETYVKKVE SEQ ID NO: 56 DDKEANKLLEKATKIIDDLDKLLDTLEKILQTLRRSERKDPKAVKELLEIA KTHAELLKRHEKVVETYVKKVE SEQ ID NO: 360 |
| DHD39 | Heterodimer | a | DHSRKLEEILDRLRKHVKRLLEHLRELLSLVKENPEDKDLVEVLELSLAIL RRSLEAVEAFLKSVTKKDPDDEDLRRKADEIRKEVEEIKKSLAEVEKEIYK LK SEQ ID NO: 57 |
| DHD39 | Heterodimer | b | GSSADDVLEDILKIIRELIE1LDQILSLLNQLLKLLRHGVPNAKKVVEKYK EILELYLQLVSLFLKIVKTHADAVSGKIDKKAEEEIKKEEEKIKEKLRQAK DILKKLQEEIDKTR SEQ ID NO: 58 SADDVLEDILKIIRELIE1LDQILSLLNQLLKLLRHGVPNAKKVVEKYKEI LELYLQLVSLFLKIVKTHADAVSGKIDKKAEEEIKKEEEKIKEKLRQAKDI LKKLQEEIDKTR SEQ ID NO: 362 |
| DHD40 | Heterodimer | a | DRDAHLYKLLTFLEQLVRHLDRLVKHITQLRDIVKKDPEDERAVDVIRQSV RSLEIVITVLKIFVDSVSDAARSKEAEKIVRKIRKEIDEIRQKLREIDKEV KKTTS SEQ ID NO: 59 |
| DHD40 | Heterodimer | b | GSNDKVLDKILDILDRILRLATRVIDLANKLLQVKKKSTHKDPRIVETYKE LLKIHETAVRLLLELADLHRRLKSKDEEANKRVETELDRIRKKVKDIEDKV RKLEDKVRKTAS SEQ ID NO: 60 NDKVLDKILDILDRILRLATRVIDLANKLLQVKKKSTHKDPRIVETYKELL KIHETAVRLLLELADLHRRLKSKDEEANKRVETELDRIRKKVKDIEDKVRK LEDKVRKTAS SEQ ID NO: 364 |
| DHD43 | Heterodimer | a | NDLSKEVLKKLEKSVEELLRRVQKSVKEAQKRGLLSDELVDRHLKILNQLV KRHLELLQEVIKRSDKK SEQ ID NO: 61 |
| DHD43 | Heterodimer | b | GSDEAVKRVVEKSLKILDEVIKKSLDILRELIELQIRHAKDDESVIRASKS ALKDAIEALKKSLDEIKKALKRSADEG SEQ ID NO: 62 DEAVKRVVEKSLKILDEVIKKSLDILRELIELQIRHAKDDESVIRASKSAL KDAIEALKKSLDEIKKALKRSADEG SEQ ID NO: 366 |
| DHD65 | Heterodimer | a | SSEEVVKVHEKVVKLHKEILELLKKIIKIHETAARDPDDKDSIKKLSDEIK KIVKRIEDISDQAKRESSDAQRKQS SEQ ID NO: 63 |
| DHD65 | Heterodimer | b | DKEEESKELLKKLKEILKRSEELLEESKELLKLAKNGEIDESELADADRKL NKKHEKLVQDIQDLLREHERQDR SEQ ID NO: 64 |
| DHD70 | Heterodimer | a | DEKKKIDKIVKETEDLLQKSEKLLQQSKEAVKRIRSQVKENEIVDRLLRIS EELLKISRRLVEISRRIASTLS SEQ ID NO: 65 |
| DHD70 | Heterodimer | b | GSSKEEVIRLLKENVRLIKENLELLTRNLKLITDLVRGSNGSEEKIKTLKE LLKEYRELLKRYRKLVEDYKRLVDKHD SEQ ID NO: 66 SKEEVIRLLKENVRLIKENLELLTRNLKLITDLVRGSNGSEEKIKTLKELL KEYRELLKRYRKLVEDYKRLVDKHD SEQ ID NO: 368 |

TABLE 1B-continued

| Design name | Oligomerization State | Chain | Design sequence |
|---|---|---|---|
| DHD88 | Heterodimer | a | EIQELIKSSRRIIEESKELIKESEEVLRRIKEILDRIRNGVDNQEDLLREI LKLLTKNLKIIQRNLKLLQDNAEILKRLVS SEQ ID NO: 67 |
| DHD88 | Heterodimer | b | GSYIEDVIKKILDVSRELIKLSRTIIKISEEINKQLQQGRDTKDLVKKYDE IIKKYTRIVQHYTELIKELQKLLS SEQ ID NO: 68 YIEDVIKKILDVSRELIKLSRTIIKISEEINKQLQQGRDTKDLVKKYDEII KKYTRIVQHYTELIKELQKLLS SEQ ID NO: 370 |
| DHD89 | Heterodimer | a | SPTEEAIQLSQRVIELSKRVIELSKEILKLLKRVLDLLPDLDKNEEKRLDD YDKELKEYDKELKKYEKRLKDLAS SEQ ID NO: 69 |
| DHD89 | Heterodimer | b | GSEEEEILKIQKELLRIQSEILDKQKKILDTLRSNGAVTEEVRSILEKVER LSEEAKELSKEAKELTKEVSKLIS SEQ ID NO: 70 EEEEILKIQKELLRIQSEILDKQKKILDTLRSNGAVTEEVRSILEKVERLS EEAKELSKEAKELTKEVSKLIS SEQ ID NO: 372 |
| DHD90 | Heterodimer | a | SPLKELNNQLLRLLRELVKVSKKIVDLSKTIIEVLKHTDLDPRLLDSLEKS QQELDKSQKELDKWKELTKVNKKLQ SEQ ID NO: 71 |
| DHD90 | Heterodimer | b | GSPLEDLVRKYDELVKTYEKLVEEFKKAVDKYDKAVKKAPVSKEATDSLDL IRKVLELLDRNLKLIKENAKLIKELLK SEQ ID NO: 72 PLEDLVRKYDELVKTYEKLVEEFKKAVDKYDKAVKKAPVSKEATDSLDLIR KVLELLDRNLKLIKENAKLIKELLK SEQ ID NO: 374 |
| DHD91 | Heterodimer | a | SPTRENEKVIKENEKVISDNERVLEEVVKVVETATDRKEIQDAVDEVRKSV DKLRDSVRKLEESVRTLD SEQ ID NO: 73 |
| DHD91 | Heterodimer | b | GSPIKDISKRLLEISKRLVEISDRIVELLQRIADSKDPNKDLQKEVKDVLE EYKRLVREYREVVKEYEKVVS SEQ ID NO: 74 PIKDISKRLLEISKRLVEISDRIVELLQRIADSKDPNKDLQKEVKDVLEEY KRLVREYREVVKEYEKVVS SEQ ID NO: 376 |
| DHD92 | Heterodimer | a | DEDEHVKQLIKNADLLRKIIAELLKELVKLFQEIASQIPDDRVAKKVTDWD RIDKILKQTEKLVRRTKQILDYSR SEQ ID NO: 75 |
| DHD92 | Heterodimer | b | GSNLEELVKLLKEVLEMHERLLRIHEDLVEAKKSNASDKESERKLKKSDKD IKESLKKIKSIIDQVRYIQS SEQ ID NO: 76 NLEELVKLLKEVLEMHERLLRIHEDLVEAHKSNASDKESERKLKKSDKDIK ESLKKIKSIIDQVRYIQS SEQ ID NO: 378 |
| DHD93 | Heterodimer | a | PVEDIIEESLRLLEESLKLLNRILKLLEDSLRKLPRSEEWRQRLDEFRKKL EDWKEELERWIEDVRYKKT SEQ ID NO: 77 |
| DHD93 | Heterodimer | b | GSDEDYESREIIDEIRKLLDRSKKIVHRSQRLVERVKSTPLSEDQEDLIRR HEETINRHRELVKELEKVLEDHERHIR SEQ ID NO: 78 DEDYESREIIDEIRKLLDRSKKIVHRSQRLVERVKSTPLSEDQEDLIRRHE ETINRHRELVKELEKVLEDHERHIR SEQ ID NO: 380 |
| DHD94 | Heterodimer | a | PEEDSRRVLERFVRVSREVLKVLEEFLRVSEELLREADRDRDRRLEEYERQ VDELREEIRRYKEEVDKFDKEVKYYKK SEQ ID NO: 79 |
| DHD94 | Heterodimer | b | GSPEKDENRKLLDKVRKLVEKSRRLVEELRKLVDQSTKNGLIDEKALRKQQ EVLRKVEEVLEKQERVLRELEEISYRVI SEQ ID NO: 80 PEKDENRKLLDKVRKLVEKSRRLVEELRKLVDQSTKNGLIDEKALRKQQEV LRKVEEVLEKQERVLRELEEISYRVT SEQ ID NO: 382 |
| DHD94_3: 214 | Heterodimer | a | GSPERDENRKLLDKVRKLVEKSRRLVEELRKLVDQSTKN SEQ ID NO: 81 PERDENRKLLDKVRKLVEKSRRLVEELRKLVDQSTKN SEQ ID NO: 337 |
| DHD94_3: 214 | Heterodimer | b | GSDEKALRKQQEVLRKVEEVLEKQERVLRELEEISYRVITRGEDHKAEEDS RRVLERFVRVSREVLKVLEEFLRVSEELLREADRDRDRRLEEYERQVDELR EEIRRYKEEVDKFDKEVKYYKK SEQ ID NO: 82 DEKALRKQQEVLRKVEEVLEKQERVLRELEEISYRVITRGEDHKAEEDSRR VLERFVRVSREVLKVLEEFLRVSEELLREADRDRDRRLEEYERQVDELREE IRRYKEEVDKFDKEVKYYKK SEQ ID NO: 384 |
| DHD94_2: 143 | Heterodimer | a | GSDRRLEEYERQVDELREEIRRYKEEVDKFDKEVKYYKK SEQ ID NO: 83 DRRLEEYERQVDELREEIRRYKEEVDKFDKEVKYYKK SEQ ID NO: 339 |
| DHD94_2: 143 | Heterodimer | b | GSPERDENRKLLDKVRKLVEKSRRLVEELRKLVDQSTKNGLIDEKALRKQQ EVLRKVEEVLEKQERVLRELEEISYRVITRGEDHKAEEDSRRVLERFVRVS REVLKVLEEFLRVSEELLREADR SEQ ID NO: 84 |

TABLE 1B-continued

| Design name | Oligomerization State | Chain | Design sequence |
|---|---|---|---|
| | | | PERDENRKLLDKVRKLVEKSRRLVEELRKLVDQSTKNGLIDEKALRKQQEV LRKVEEVLEKQERVLRELEEISYRVITRGEDHKAEEDSRRVLERFVRVSRE VLKVLEEFLRVSEELLREADR SEQ ID NO: 386 |
| DHD95 | Heterodimer | a | DLSEESKKFVEKVKKLEKESRELEKQVKKIEEDSRSVENDVQKEFLELLKR LLDIQKKWEVLREWKVQQYVDS SEQ ID NO: 85 |
| DHD95 | Heterodimer | b | GSDSEYESRQVLRELDTVLKDSHTVLEALRQVIRDSQDVVSKSDEESRRVI DDLEKVIQDSKKVLDDIKRLIDKSKSIKS SEQ ID NO: 86 DSEYESRQVLRELDTVLKDSHTVLEALRQVIRDSQDVVSKSDEESRRVIDD LEKVIQDSKKVLDDIKRLIDKSKSIKS SEQ ID NO: 388 |
| DHD96 | Heterodimer | a | NEDELLKLLTENLKLLDENLKLLRENLSLLRQANNITDKNRIREIVKQSKE IVKQSREILKQSKEIVERIKYIVS SEQ ID NO: 87 |
| DHD96 | Heterodimer | b | GSSLYELTQRYEKLVQQYEELVKDYRRLVKKLEKLKRDNKPDKRLLKEIVD VIKKSVEIIDRSLKLLEESIKILEETD SEQ ID NO: 88 SLYELTQRYEKLVQQYEELVKDYRRLVKKLEKLKRDNKPDKRLLKEIVDVI KKSVEIIDRSLKLLEESIKILEETD SEQ ID NO: 390 |
| DHD97 | Heterodimer | a | SQERSLEILKRILDVLKESLEILKESLSILRQLASRIKNPNRKIEEILKES DKIIKESDKVLKEIEEVIRYSS SEQ ID NO: 89 |
| DHD97 | Heterodimer | b | GSDIEYESKEILELIKELLKLSRELLKESRRALELVRKSRDDSIVEEVIQV HKKVLDIHKEVLKIVRKVVEVHRRVKS SEQ ID NO: 90 DIEYESKEILELIKELLKLSRELLKESRRALELVRKSRDDSIVEEVIQVHK KVLDIHKEVLKIVRKVVEVHRRVKS SEQ ID NO: 392 |
| DHD98 | Heterodimer | a | SKKDESTKLERLAEKIDEITKRIEELVKDVKRKSSEGVDKDQQQKIDEVFQ KLLDLQREILEILDRILKVQQYILD SEQ ID NO: 91 |
| DHD98 | Heterodimer | b | GSDLEYLNRRLLQLIKTLIDLNRHLLKLIDKLKKLNSREGDEEKIKEESKQ IQEQFKEIVERSKEIIKQIKEIIKRSQ SEQ ID NO: 92 DLEYLNRRLLQLIKTLIDLNRHLLKLIDKLKKLNSREGDEEKIKEESKQIQ EQFKEIVERSKEIIKQIKEIIKRSQ SEQ ID NO: 394 |
| DHD99 | Heterodimer | a | DFERSSRRLEKVVEDLRRSSDRLREVIDELRKSADEKDEDEDLRRARKEHR DLIEELKRALEKQEEIIKHLQELVYRQL SEQ ID NO: 93 |
| DHD99 | Heterodimer | b | GSEESEEVRKVVERIKKISRELEEVVKELDRVSKEFDRHGETDEIVREHER IVEKLEEIVKKHTKIVEELAEIVYKQQ SEQ ID NO: 94 EESEEVRKVVERIKKISRELEEVVKELDRVSKEFDRHGETDEIVREHERIV EKLEEIVKKHTKIVEELAEIVYKQQ SEQ ID NO: 396 |
| DHD100 | Heterodimer | a | SDDDSVRVLDEIVKILDESVKLLKESLKLLDDFLRTKPDDHLKEVVKESKK WEQSKKVLDRIKKIIYESK SEQ ID NO: 95 |
| DHDIOO | Heterodimer | b | GSDLLYLSKELLKLVRELLKLSRELVELSRRLVNSTHKSPELVKKYDKLVK KYQDLLKKLADVADEYLRQRS SEQ ID NO: 96 DLLYLSKELLKLVRELLKLSRELVELSRRLVNSTHKSPELVKKYDKLVKKY QDLLKKLADVADEYLRQRS SEQ ID NO: 398 |
| DHD101 | Heterodimer | a | DEKDYHRRLIEHLEDLVRRHEELIKRQKKVVEELERRGLDERLRRVVDRFR RSSERWEEVIERFRQVVDKLRKSVE SEQ ID NO: 97 |
| DHD101 | Heterodimer | b | GSDAYDLDRIVKEHRRLVEEQRELVEELEKLVRRQEDHRVDKKESHEILER LERIIRRSTRILTELEKLTDEFERRTR SEQ ID NO: 98 DAYDLDRIVKEHRRLVEEQRELVEELEKLVRRQEDHRVDKKESHEILERLE RIIRRSTRILTELEKLTDEFERRTR SEQ ID NO: 400 |
| DHD102 | Heterodimer | a | DERYRAREHIRRVEEHTKRLRHILKRLREHEEKLRRELKPGDEITESVDRF KKIVDQFEESIKKFETVSEELRKSDS SEQ ID NO: 99 |
| DHD102 | Heterodimer | b | GSDRQRILDRLDKILEKLDDILKKLKDILETLSKDDVSDRRHKDLVEKFRE LVDTHHKLVERYRELVYQNR SEQ ID NO: 100 DRQRILDRLDKILEKLDDILKKLKDILETLSKDDVSDRRHKDLVEKFRELV DTHHKLVERYRELVYQNR SEQ ID NO: 402 |
| DHD102_1: 243 | Heterodimer | a | GSDEITESVDRFKKIVDQFEESIKKFETVSEELRKSIS SEQ ID NO: 101 DEITESVDRFKKIVDQFEESIKKFETVSEELRKSIS SEQ ID NO: 341 |
| DHD102_1: 243 | Heterodimer | b | GSDPQRAADRLDKILEKLDDILKKLKDILETLSKDDVKDRRAKDLVEKFRE LVDTHHKLVERYRELVYTATAGSDLARELIRRVEEHTKRLRHILKRLREHE EKLRR SEQ ID NO: 102 |

TABLE 1B-continued

| Design name | Oligomer- ization State | Chain | Design sequence |
|---|---|---|---|
| | | | DPQRAADRLDKILEKLDDILKKLKDILETLSKDDVKDRRAKDLVEKFRELV DTHHKLVERYRELVYTATAGSDLARELIRRVEEHTKRLRHILKRLREHEEK LRR SEQ ID NO: 404 |
| DHD103 | Heterodimer | a | NADDQLATSIKKLEDSIDQLIKIVRKFEESVKKLQKHGVDQHHVEILRKIV EIFRQHIEKLKKHLEKLRYTSS SEQ ID NO: 103 |
| DHD103 | Heterodimer | b | GSDKEYLVTEHEKLVREHEKIVSEIEKLVKKHEAGVDESELEEILKKVEKL LRKLDEILEQLTQLLRKTE SEQ ID NO: 104 DKEYLVTEHEKLVREHEKIVSEIEKLVKKHEAGVDESELEEILKKVEKLLR KLDEILEQLTQLLRKTE SEQ ID NO: 406 |
| DHD103_1: 423 | Heterodimer | a | GSDQHVVEILRKIVEIFRQHIEKLKKHLEKLRYTSS SEQ ID NO: 105 DQHVVEILRKIVEIFRQHIEKLKKHLEKLRYTSS SEQ ID NO: 343 |
| DHD103_2: 423 | Heterodimer | b | GSDAEYLVTEHEKLVREHEKIVSEIEKLVKKHEKGVDESELEEILKKVEKL LRKLDEILEQLTQLLRKAEKHIDKHSKAADQLATSIKKLEDSIDQLIKIVR KFEESVKKLQKH SEQ ID NO: 106 DAEYLVTEHEKLVREHEKIVSEIEKLVKKHEKGVDESELEEILKKVEKLLR KLDEILEQLTQLLRKAEKHIDKHSKAADQLATSIKKLEDSIDQLIKIVRKF EESVKKLQKH SEQ ID NO: 408 |
| DHD104 | Heterodimer | a | DEDDDIRRVLDESRRVLEHSRRVLKRSEEVLEKASRKKEKDTEEIEKHLKR LREHAKKLEKHRRELDDFLYKEI SEQ ID NO: 107 |
| DHD104 | Heterodimer | b | GSRDKYLLERLNDILKKLDEIVDKLSDILKRLKDVRHDDRLQELVERYKEI VKEYKRIVEEYEKLVREFEEQQR SEQ ID NO: 108 RDKYLLERLNDILKKLDEIVDKLSDILKRLKDVRHDDRLQELVERYKEIVK EYKRIVEEYEKLVREFEEQQR SEQ ID NO: 410 |
| DHD105 | Heterodimer | a | DRDYEDKEFKKIIKELEDVQEELKKLQEKIKRFSSELEEPNELLKEQLKVN EEQLEVNKKILKILRDQLKQNE SEQ ID NO: 109 |
| DHD105 | Heterodimer | b | GSDAEYKVRESVKRSKESVKHSEDVVDKLNKSVKLSESGHSDAEKASRELV KLVREWELSREVIKLSEKVLRVTS SEQ ID NO: 110 DAEYKVRESVKRSKESVKIISEDWDKLNKSVKLSESGHSDAEKASRELVKL VREWELSREVIKLSEKVLRVIS SEQ ID NO: 412 |
| DHD106 | Heterodimer | a | DLQYKQEKLIRHFDRVVREWDKLVRKFSKVLEKQKHESKDKELEEASRRVD ELIKRLREQLKRSKEILRRLKELSRKSS SEQ ID NO: 111 |
| DHD106 | Heterodimer | b | GSDWEELLRRLEKVLQEYEEIVKELIDLIERLIKVSEDKSKDASEYKKLVT ELEKLISKLEEISKKLEELVKEYEYKTE SEQ ID NO: 112 DWEELLRRLEKVLQEYEEIVKELIDLIERLIKVSEDKSKDASEYKKLVTEL EKLISKLEEISKKLEELVKEYEYKTE SEQ ID NO: 414 |
| DHD107 | Heterodimer | a | DAKDELEKSLQEIEESLKELKKLLEELDKSLRELTSQGRNKKLEEHIKKVQ KFIELVKKYIKAVQDYLKEVRYDNS SEQ ID NO: 113 |
| DHD107 | Heterodimer | b | GSDKERAARATEEMVKLTKKLLKAVEDLVRDVRRLLKEGLISEKHARIAET ILEVFKKHAKIIKKHVDIVKYDES SEQ ID NO: 114 DKERAARATEEMVKLTKKLLKAVEDLVRDVRRLLKEGLISEKHARIAETIL EVFKKHAKIIKKHVDIVKYDES SEQ ID NO: 416 |
| DHD108 | Heterodimer | a | GSPLKERLLEIQRDLDRVLEEVVERLLRIQERLDSVVERKPPDVHEEYKYI VDEIREIVERWREYEEIVKRIDEEVR SEQ ID NO: 115 PLKERLLEIQRDLDRVLEEVVERLLRIQERLDSVVERKPPDVHEEYKYIVD EIREIVERWREYEEIVKRIDEEVR SEQ ID NO: 459 |
| DHD108 | Heterodimer | b | GSEEDERIRYDLDRIRKDVRRKLEEIRQRVRELEKKLRDAGHRRDEKELLR ELIETSKDILRLVEELLKKIIDKSEDLLRKTE SEQ ID NO: 116 EEDERIRYDLDRIRKDVRRKLEEIRQRVRELEKKLRDAGHRRDEKELLREL IETSKDILRLVEELLKKIIDKSEDLLRKTE SEQ ID NO: 420 |
| DHD109 | Heterodimer | a | GSDEEDYINENVEKDVRDIEDDVRRINERIRELLEKIRTEEVLQRVLEEHH ELVERVLRKLVEILRKIIEEENR SEQ ID NO: 117 DEEDYINENVEKDVRDIEDDVRRINERIRELLEKIRTEEVLQRVLEEHHEL VERVLRKLVEILRKHEEENR SEQ ID NO: 345 |
| DHD109 | Heterodimer | b | GSDEEEYYKEKLHKLLREIEELLKHYRELVRRLEELVKRGELDKDTAAHIL ERLSELLERIIRRVAHTLRRLSEERR SEQ ID NO: 118 DEEEYYKEKLKKLLREIEELLKHYRELVRRLEELVKRGELDKDTAAHILER LSELLERIIRRVAHTLRRLSEERR SEQ ID NO: 422 |
| DHD110 | Heterodimer | a | GSDEDEISYDSKRRVEEIVRQAREKSEKSRKDIEDVAEVLRKGDVSEKEVV DELVKVLEEQVKVLREAVERLREVLKKQVDDVR SEQ ID NO: 119 |

TABLE 1B-continued

| Design name | Oligomerization State | Chain | Design sequence |
|---|---|---|---|
| | | | DEDEISYDSKRRVEEIVRQAREKSEKSRKDIEDVAEVLRKGDVSEKEVVDE LVKVLEEQVKVLREAVERLREVLKKQVDDVR SEQ ID NO: 347 |
| DHD110 | Heterodimer | b | GSDIVELVDHLLKRSLKLLEELAELVRRLLEKSTELLKRRTEEHKEEVVEE SEYMVRELEERLRRWDESEKLVRDADKHIR SEQ ID NO: 120 DIVELVDHLLKRSLKLLEELAELVRRLLEKSTELLKRRTEEHKEEVVEESE YMVRELEERLRRWDESEKLVRDADKHIR SEQ ID NO: 424 |
| DHD111 | Heterodimer | a | GSKEKDIVKTLVDLLRENLETLERLIEEVVRLLKENVDVRDEGRDDKDSER ILRDIKRRIDEAAKESREIIERIEKEVEYRSR SEQ ID NO: 121 KEKDIVKTLVDLLRENLETLERLIEEVVRLLKENVDVRDEGRDDKDSERIL RDIKRRIDEAAKESREIIERIEKEVEYRSR SEQ ID NO: 349 |
| DHD111 | Heterodimer | b | GSPEVDVLRRIVREILKASEELLRLLRKLIDEALKLSERKRDSQEYREWD RVKKELERLLDEYRKLVEELKEKLRYDTR SEQ ID NO: 122 PEVDVLRRIVREILKASEELLRLLRKLIDEALKLSERKRDSQEYREWDRV KKELERLLDEYRKLVEELKEKLRYDTR SEQ ID NO: 426 |
| DHD112 | Heterodimer | a | GSDKRYESEKLKRRLDEAVEKVREWERVERESDRVLEEVRRRESKEVVD KVIEDNDKALEDVLRVVDEVAKWRDVVRENTR SEQ ID NO: 123 DKRYESEKLKRRLDEAVEKVREWERVERESDRVLEEVRRRESKEVVDKV IEDNDKALEDVLRVVDEVAKWRDVVRENTR SEQ ID NO: 351 |
| DHD112 | Heterodimer | b | GSPREYHSKDILRKVDEILERIRRHADRVKKKSERLKRENVDVNEHSKDVK RVIRELLELVKELLRLAKKHSDDQQE SEQ ID NO: 124 PREYHSKDILRKVDEILERIRRHADRVKKKSERLKRENVDVNEHSKDVKRV IRELLELVKELLRLAKKHSDDQQE SEQ ID NO: 428 |
| DHD113 | Heterodimer | a | GSDEDEILYHSERLLQKLKKELDDLKEKSRELLEELKKEDPDDRLIERIIR LHDEVLKDLDEVLKNILEVHREVLERLR SEQ ID NO: 125 DEDEILYHSERLLQKLKKELDDLKEKSRELLEELKKEDPDDRLIERIIRLH DEVLKDLDEVLKNILEVHREVLERLR SEQ ID NO: 353 |
| DHD113 | Heterodimer | b | DKLDRLLKIHEEALRRAEELIKRLLDIHRRALDLARRGELDDYLLKESERE LREIIRRAREELKESRDRLEEISR SEQ ID NO: 126 |
| DHD114 | Heterodimer | a | GSPKEELIRRVLEEVKRLNEKLLEIIRRAAELVKRANDELPETEKLREIDR ELEKKLKEIEDELRRRIDKELDDALYEIED SEQ ID NO: 127 PKEELIRRVLEEVKRLNEKLLEIIRRAAELVKRANDELPETEKLREIDREL EKKLKEIEDELRRRIDKELDDALYEIED SEQ ID NO: 355 |
| DHD114 | Heterodimer | b | GSPKLDKLRELLERNLEKLREILEEVLKILRTNLERVREDIRDEDVLQEYE RLIRKAEEDLRRVLKEYDDLLKKLVYELR SEQ ID NO: 128 PKLDKLRELLERNLEKLREILEEVLKILRTNLERVREDIRDEDVLQEYERL IRKAEEDLRRVLKEYDDLLKKLVYELR SEQ ID NO: 430 |
| DHD115 | Heterodimer | a | GSKEDESVKRAEEIVRTLLKLLEDSLREAERSLRDIKNGEDEHNLRRISEK LEELSKRITETIERLLRELQYTSR SEQ ID NO: 129 KEDESVKRAEEIVRTLLKLLEDSLREAERSLRDIKNGEDEHNLRRISEKLE ELSKRITETIERLLRELQYTSR SEQ ID NO: 357 |
| DHD115 | Heterodimer | b | GSPNQELLDRVRKILEDLLRLNEELVRLNKELLKRALEMRRKNRDSEEVLE RLAEEYRKRLEEYRRELEKLLEELEETIYRYKR SEQ ID NO: 130 PNQELLDRVRKILEDLLRLNEELVRLNKELLKRALEMRRKNRDSEEVLERL AEEYRKRLEEYRRELEKLLEELEETIYRYKR SEQ ID NO: 432 |
| DHD116 | Heterodimer | a | GSDESEEAQHEVEKVLDDIRRLSEHLQKRLEEVLEEVYELRREGSDRTEVV ELLKEVIREIVRVNREALERLLRWEEAVKRNE SEQ ID NO: 131 DESEEAQHEVEKVLDDIRRLSEHLQKRLEEVLEEVYELRREGSDRTEVVEL LKEVIREIVRVNREALERLLRWEEAVKRNE SEQ ID NO: 359 |
| DHD116 | Heterodimer | b | GSDEEELVETVKRIQKEILDRLTELAKLLVEIQREIKKLKDEGEDDKELKR LSDELEEKVRQWEEIKRLSDELEETVEYVSR SEQ ID NO: 132 DEEELVETVKRIQKEILDRLTELAKLLVEIQREIKKLKDEGEDDKELKRLS DELEEKVRQWEEIKRLSDELEETVEYVSR SEQ ID NO: 434 |
| DHD117 | Heterodimer | a | GSDEEEVVRRAEELVKEHEELIERVIRTHEELVYKLEDQGADKKLVDVLK RVVEESERVAREIVKVSRELIRLLEEASR SEQ ID NO: 133 DEEEEVVRRAEELVKEHEELIERVIRTHEELVYKLEDQGADKKLVDVLKRV VEESERVAREIVKVSRELIRLLEEASR SEQ ID NO: 361 |
| DHD117 | Heterodimer | b | GSSKEEILKELEDLQRRLIEELKKLQERVVELLEELIKRLRDRGRDDKHLK RLVKEVRRLSEEVLRSIKEVSDRVRYQLR SEQ ID NO: 134 SKEEILKELEDLQRRLIEELKKLQERVVELLEELIKRLRDRGRDDKHLKRL VKEVRRLSEEVLRSIKEVSDRVRYQLR SEQ ID NO: 436 |

TABLE 1B-continued

| Design name | Oligomerization State | Chain | Design sequence |
|---|---|---|---|
| DHD118 | Heterodimer | a | GSDKEEESEYLLRDLVRLLEKVKEKIEEVNREVEKLLKKVKDGRLDRREVL REILRLNRELAEIIKEWDRIRHWERSER SEQ ID NO: 135 DKEEESEYLLRDLVRLLEKVKEKIEEVNREVEKLLKKVKDGRLDRREVLRE ILRLNRELAEIIKEWDRIRHWERSER SEQ ID NO: 363 |
| DHD118 | Heterodimer | b | GSDLHEVVYETKELLKRIEEVVEELRKKSEDIIRKAERGEISEDELKRLQE EIAREAKKLLLDEIKRVLERHLEQTL SEQ ID NO: 136 DLHEVVYETKELLKRIEEVVEELRKKSEDIIRKAERGEISEDELKRLQEEI AREAKKLLLDEIKRVLERHLEQTL SEQ ID NO: 438 |
| DHD119 | Heterodimer | a | GSPVEEIIKEVVKRVIEVQEKVLRIISHAVKRVVEVQKKYDPGSEESNRVV EEVKKTIEDAIRESDEVVDEVVKRIQYTVR SEQ ID NO: 137 PVEEIIKEVVKRVIEVQEKVLRIISHAVKRVVEVQKKYDPGSEESNRVVEE VKKTIEDAIRESDEVVDEVVKRIQYTVR SEQ ID NO: 365 |
| DHD119 | Heterodimer | b | GSPEQEIADRILTEIRESQKELERLARKILKLLDESQEKAKRGRLSEEESD ELLERIKKELDELLERSKELLKKIEYELR SEQ ID NO: 138 PEQEIADRILTEIRESQKELERLARKILKLLDESQEKAKRGRLSEEESDEL LERIKKELDELLERSKELLKKIEYELR SEQ ID NO: 440 |
| DHD120 | Heterodimer | a | GSDEDKEANRVLDEVLKTVRDLLETANEVLKEVLYRLKRTDDQEKVVRTLT EVLKEHLKLVEEIVRILDKVLKEHLETEK SEQ ID NO: 139 DEDKEANRVLDEVLKTVRDLLETANEVLKEVLYRLKRTDDQEKVVRTLTEV LKEHLKLVEEIVRILDKVLKEHLETEK SEQ ID NO: 367 |
| DHD120 | Heterodimer | b | GSPEDDVLRRLEEVSEKILRVAEDVARQLREVSEKITQGKVDRKEWEEDIK RLKRELEELLREV7KEEIERLTYELR SEQ ID NO: 140 PEDDVLRRLEEVSEKILRVAEDVARQLREVSEKITQGKVDRKEWEEDIKRL KRELEELLREWKEEIERLTYELR SEQ ID NO: 442 |
| DHD121 | Heterodimer | a | GSRREEVVKRIRELLKRNKELIDRIRELLEENEYLDKDARDKDVLRRSVEL LEELVRILEESVELAKEIIKLLREWE SEQ ID NO: 141 RREEVVKRIRELLKRNKELIDRIRELLEENEYLDKDARDKDVLRRSVELLE ELVRILEESVELAKEIIKLLREWE SEQ ID NO: 369 |
| DHD121 | Heterodimer | b | GSDEKEDNRRLQHKIERILEKNEDLQRKLEEILELLERGEADEEKIDRLRK AVEDYRRVVEEIKEDVKRHKYTVR SEQ ID NO: 142 DEKEDNRRLQKKIERILEKNEDLQRKLEEILELLERGEADEEKIDRLRKAV EDYRRVVEEIKEDVKRHKYTVR SEQ ID NO: 444 |
| DHD122 | Heterodimer | a | GSDEKEEAKKASEESVRTVERILEELLKASEESVELLRRGEDAKDVVERSK EALKRVKELLDEVVKRSDEILKYIHN SEQ ID NO: 143 DEKEEAKKASEESVRTVERILEELLKASEESVELLRRGEDAKDVVERSKEA LKRVKELLDEVVKRSDEILKYIHN SEQ ID NO: 371 |
| DHD122 | Heterodimer | b | GSDEKKLINEVVETQKRLIKEAAKRLSEVVRHQTELIRELREKNVDDKDVE KLLKESLDLAEEIVRRIKELLDESKKLVEYVSN SEQ ID NO: 144 DEKKLINEVVETQKRLIKEAAKRLSEVVRHQTELIRELREKNVDDKDVEKL LKESLDLAEEIVRRIKELLDESKKLVEYVSN SEQ ID NO: 446 |
| DHD123 | Heterodimer | a | GSPDMDEVKRVLDELIEIQEEILREIKRVLEKLIKIQEDNGSEYESREVVR EIVEIARKLVERSRRVVKKITETLQ SEQ ID NO: 145 PDMDEVKRVLDELIEIQEEILREIKRVLEKLIKIQEDNGSEYESREVVREI VEIARKLVERSRRVVKKITETLQ SEQ ID NO: 373 |
| DHD123 | Heterodimer | b | GSDERYATREIVERIERIAREILKRTEEIVREVREVLSRDVDQEEVVRRLA DLLRESVELVQHLVRRVEELLQESVERKK SEQ ID NO: 146 DERYATREIVERIERIAREILKRTEEIVREVREVLSRDVDQEEVVRRLADL LRESVELVQHLVRRVEELLQESVERKK SEQ ID NO: 448 |
| DHD124 | Heterodimer | a | GSPEREALREVLEDLKRVTDRLRELVERVLEELKKVTDHVDSERILRESRR VLKELKDIIEEILRESEKVLEKLKYTED SEQ ID NO: 147 PEREALREVLEDLKRVTDRLRELVERVLEELKKVTDHVDSERILRESRRVL KELKDIIEEILRESEKVLEKLKYTED SEQ ID NO: 375 |
| DHD124 | Heterodimer | b | GSPAREILEEVVKKHLEVVEDAARILEEIIREHEKAVREDRDKKELEEISR DLLRKAREALKKVKDISDDLSREIEYVAS SEQ ID NO: 148 PAREILEEVVKKHLEVVEDAARILEEIIREHEKAVREDRDKKELEEISRDL LRKAREALKKVKDISDDLSREIEYVAS SEQ ID NO: 450 |
| DHD125 | Heterodimer | a | GSPVEEAIKKVIDDLRDVQRKIRELVEELIRLLEEVQRDNDKRESEYVVER VEEILRRITETSREVVRKAVEDLS SEQ ID NO: 149 PVEEAIKKVIDDLRDVQRKIRELVEELIRLLEEVQRDNDKRESEYVVERVE EILRRITETSREVVRKAVEDLS SEQ ID NO: 377 |

TABLE 1B-continued

| Design name | Oligomerization State | Chain | Design sequence |
|---|---|---|---|
| DHD125 | Heterodimer | b | GSDSDEKAEYLLKEMERVVRESDEVVKKILRDLEEVLERLRRGEISEDDVT E1LKELAERHIRAIEELVRRLRELLERHKR SEQ ID NO: 150 DSDEKAEYLLKEMERVVRESDEVVKKILRDLEEVLERLRRGEISEDDVTEI LKELAERHIRAIEELVRRLRELLERHKR SEQ ID NO: 452 |
| DHD126 | Heterodimer | a | GSPVEEVLKELSEVNERVRDIAREIIERLSEVNEEVKETDDEDELKKISKK VVDEVEDLLRKILEVSEEVVRRVEYHDR SEQ ID NO: 151 PVEEVLKELSEVNERVRDIAREIIERLSEVNEEVKETDDEDELKKISKKVV DEVEDLLRKILEVSEEVVRRVEYHDR SEQ ID NO: 379 |
| DHD126 | Heterodimer | b | GSPKEDILREVLRRHKEIVREIVRLVREAVETHLELVKRNSDDRDAQDVTR KLEEDLERLVRHAQEVIEEIFYRLH SEQ ID NO: 152 PKEDILREVLRRHKEIVREIVRLVREAVETHLELVKRNSDDRDAQDVIRKL EEDLERLVRHAQEVIEEIFYRLH SEQ ID NO: 454 |
| DHD127 | Heterodimer | a | GSPRSYLLKELADLSQHLVRLLERLVRESERVVEVLERGEVDEEELKRLED LHRELEKAVREVRETHREIRERSR SEQ ID NO: 153 PRSYLLKELADLSQHLVRLLERLVRESERVVEVLERGEVDEEELKRLEDLH RELEKAVREVRETHREIRERSR SEQ ID NO: 381 |
| DHD127 | Heterodimer | b | GSDREYIIKDILDSQEHLLRLIEELLETQKELLEILKRRPDSVERVRELVR RSKEIADEIRRQSDRNVRLLEEVSK SEQ ID NO: 154 DREYIIKDILDSQEHLLRLIEELLETQKELLEILKRRPDSVERVRELVRRS KEIADEIRRQSDRNVRLLEEVSK SEQ ID NO: 456 |
| DHD128 | Heterodimer | a | GSDEKDEIRHVIESVERLIEDIKRLLKTLRELAHDDSDKKTVKEVLDRVKE MIERHRRELEEHRKELERAEYEVR SEQ ID NO: 155 DEKDEIRHVIESVERLIEDIKRLLKTLRELAHDDSDKKTVKEVLDRVKEMI ERHRRELEEHRKELERAEYEVR SEQ ID NO: 383 |
| DHD128 | Heterodimer | b | GSESEDRIKELLKRHIELVERHEELLHEIKKLIDLEEKDDKDREEAVKRID DAIKESEEMLEESKEILEEIEYLNR SEQ ID NO: 156 ESEDRIKELLKRHIELVERHEELLHEIKKLIDLEEKDDKDREEAVKRIDDA IKESEEMLEESKEILEEIEYLNR SEQ ID NO: 458 |
| DHD129 | Heterodimer | a | GSSLEDSVRLNDEVVKVVERVVRLNQEVVRLIKHATDVEDEETVKYVLERV REVLDESREVLKRVHELLEESERRLE SEQ ID NO: 157 SLEDSVRLNDEVVKVVERVVRLNQEVVRLIKHATDVEDEETVKYVLERVRE VLDESREVLKRVHELLEESERRLE SEQ ID NO: 385 |
| DHD129 | Heterodimer | b | GSHEKDIVYKVEDLVRKSDRIAERAREIVKRSRDIMREIRKDKDNKKLSDD LLKVTRDLQRVVDELEELSRELLRVAEESRK SEQ ID NO: 158 KEKDIVYKVEDLVRKSDRIAERAREIVKRSRDIMREIRKDKDNKKLSDDLL KVTRDLQRVVDELEELSRELLRVAEESRK SEQ ID NO: 460 |
| DHD130 | Heterodimer | a | GSPELDEVKKLIDELKKSVERLEESIREVKESIKKLRKGDIDAEENIKLLK ENIKIVRENIKIIKEIIDVVQYVLR SEQ ID NO: 159 PELDEVKKLIDELKKSVERLEESIREVKESIKKLRKGDIDAEENIKLLKEN IKIVRENIKIIKEIIDVVQYVLR SEQ ID NO: 387 |
| DHD130 | Heterodimer | b | GSDEEEIEELLRELEKLLKKSEEALEESKKLIDESEELLRRDRLDKEKHVR ASEEHVKLSEEHLRISREIVKILEKAVYSTR SEQ ID NO: 160 DEEEIEELLRELEKLLKKSEEALEESKKLIDESEELLRRDRLDKEKHVRAS EEHVKLSEEHLRISREIVKILEKAVYSTR SEQ ID NO: 462 |
| DHD131 | Heterodimer | a | GSDESDRIRKIVEESDEIVKESRKLAERARELIKESEDKRVSEERNERLLE ELLRILDENAELLKRNLELLKEVLYRTR SEQ ID NO: 161 DESDRIRKIVEESDEIVKESRKLAERARELIKESEDKRVSEERNERLLEEL LRILDENAELLKRNLELLKEVLYRTR SEQ ID NO: 389 |
| DHD131 | Heterodimer | b | GSDEDDELERLLREYKRVLREYEKLLEELRRLYEEYKRGEVSEEESDRILR EIKEILDKSERLWDLSEEVWRTLLYQAE SEQ ID NO: 162 DEDDELERLLREYHRVLREYEKLLEELRRLYEEYKRGEVSEEESDRILREI KEILDKSERLWDLSEEVWRTLLYQAE SEQ ID NO: 464 |
| DHD132 | Heterodimer | a | GSDKKDASRRAIRVLEEFVRVSEEVLEVLRKSVESLKRLDVDEKIKRTHDR IEEELRRWKRELEELIERLREWEYHQD SEQ ID NO: 163 DKKDASRRAIRVLHEFVRVSEEVLEVLRKSVESLKRLDVDEKIKRTHDRIE EELRRWKRELEELIERLREWEYHQD SEQ ID NO: 391 |
| DHD132 | Heterodimer | b | GSDDEEEDKRLLEEVKRSLDTDERILEKLRHSLERQLEDVDKDEDSRRVLR ELDEITKRSREVVKRLRKLAYESK SEQ ID NO: 164 DDEEEDKRLLEEVKRSLDTDERILEKLRHSLERQLEDVDKDEDSRRVLREL DEITKRSREVVKRLRKLAYESK SEQ ID NO: 466 |

TABLE 1B-continued

| Design name | Oligomer- ization State | Chain | Design sequence |
|---|---|---|---|
| DHD133 | Heterodimer | a | GSDKEYKLDRILRRLDELIKQLSRILEEIERLVDELEREPLDDKEVQDVIE RIVELIDEHLELLKEYIKLLEEYIKTTK SEQ ID NO: 165 DKEYKLDRILRRLDELIKQLSRILEEIERLVDELEREPLDDKEVQDVIERI VELIDEHLELLKEYIKLLEEYIKTTK SEQ ID NO: 393 |
| DHD133 | Heterodimer | b | GSPSKEYQEKSAERQKELLHEYEKLVRHLRELVEKLQRRELDKEEVLRRLV ElLERLKDLHKKIEDAHRKNEEAHKENK SEQ ID NO: 166 PSKEYQEKSAERQKELLHEYEKLVRHLRELVEKLQRRELDKEEVLRRLVEI LERLKDLHKKIEDAHRKNEEAHKENK SEQ ID NO: 468 |
| DHD134 | Heterodimer | a | GSRDRKISEELIKALEDHIRMLEELIRAIEEHIKLAERGVDEKELRESLEE LKKIVDELEKSLEELRKLAERYKYETR SEQ ID NO: 167 RDRKISEELIKALEDHIRMLEELIRAIEEHIKLAERGVDEKELRESLEELK KIVDELEKSLEELRKLAERYKYETR SEQ ID NO: 395 |
| DHD134 | Heterodimer | b | GSPKEESVEELKRVIDKHEEILRELKRVLEEHERVSHDEDENELRRSLERL KHILDRLHESLKELHELLKKNEYTER SEQ ID NO: 168 PKEESVEELKRVIDKHEEILRELKRVLEEHERVSHDEDENELRRSLERLKH ILDRLHESLKELHELLKKNEYTER SEQ ID NO: 470 |
| DHD135 | Heterodimer | a | GSDHEYWVKIVERILRVMEKHAEIVKKHLEIVERVVREGPSEDLRRKLKES LREIEESLRELKELLDELDELSEKTR SEQ ID NO: 169 DHEYWVKIVERILRVMEKHAEIVKKHLEIVERVVREGPSEDLRRKLKESLR EIEESLRELKELLDELDELSEKTR SEQ ID NO: 397 |
| DHD135 | Heterodimer | b | GSDEEYVTRSQRRLKRLLEEYIKVVEEHARLVERNERDDKELKRSIDELDK LTKELLELVKRYKELVDKTET SEQ ID NO: 170 DEEYVTRSQRRLKRLLEEYIKVVEEHARLVERNERDDKELKRSIDELDKLT KELLELVKRYKELVDKTET SEQ ID NO: 472 |
| DHD136 | Heterodimer | a | GSDKEEIVKLQDEVIKTLERHLDILRKHIDLLEKLKDHLSEELKERVDRSI KKLEESIKRLERIIEELQELAEYSL SEQ ID NO: 171 DKEEIVKLQDEVIKTLERHLDILRKHIDLLEKLKDHLSEELKERVDRSIKK LEESIKRLERIIEELQELAEYSL SEQ ID NO: 399 |
| DHD136 | Heterodimer | b | GSREEELKESAEELERSVRELKKEADKYKEEVDRLHYRGKVDKDWVRVVEK LIKLVEEHLELIREHLELLKEERR SEQ ID NO: 172 REEELKESAEELERSVRELKKEADKYKEEVDRLHYRGKVDKDWVRVVEKLI KLVEEHLELIREHLELLKEERR SEQ ID NO: 474 |
| DHD137 | Heterodimer | a | GSDMEYELKKSAEELRKSLEELKRILDELHKSLRELRRHGDDEEYVQTVEE LRKELEEHAKKLEEHLKELERVAT SEQ ID NO: 173 DMEYELKKSAEELRKSLEELKRILDELHKSLRELRRHGDDEEYVQTVEELR KELEEHAKKLEEHLKELERVAT SEQ ID NO: 401 |
| DHD137 | Heterodimer | b | PEYELKKSVDDLKRDVDRLVEEVEEVFELSKERLREDRKHLELVEEMVRLI EKHLELIKEHLKLADDHVR SEQ ID NO: 174 |
| DHD138 | Heterodimer | a | GSREKDESKELNDEYKKLLEEYERLLRRSEELVKRAKGPRDEKELKRILEE NEDILRRTKEILERTKEISEEQKYRRR SEQ ID NO: 175 REKDESKELNDEYKKLLEEYERLLRRSEELVKRAKGPRDEKELKRILEENE DILRRTKEILERTKEISEEQKYRRR SEQ ID NO: 403 |
| DHD138 | Heterodimer | b | GSDKDERQERLNEESDKSNEESERSNRESEELNRRARGPNDEKELQEILDR HLELLERNQRLLDENKEILRESQYLND SEQ ID NO: 176 DKDERQERLNEESDKSNEESERSNRESEELNRRARGPNDEKELQEILDRHL ELLERNQRLLDENKEILRESQYLND SEQ ID NO: 476 |
| DHD139 | Heterodimer | a | GSENKYILKEILKLLRENLKLLHDILRLLDENLEELEKHGAKDLDDYRRKI EEIRKKVEDYREKIEEIEKKVERDR SEQ ID NO: 177 ENKYILKEILKLLRENLKLLHDILRLLDENLEELEKHGAKDLDDYRRKIEE IRKKVEDYREKIEEIEKKVERDR SEQ ID NO: 405 |
| DHD139 | Heterodimer | b | GSESEYTQEEILELLKESIKLLREILRLLEESEELWRRENTKSERSEEIKE RAKEAIKRSEEILERVKRLSDHSR SEQ ID NO: 178 ESEYTQEEILELLKESIKLLREILRLLEESEELWRRENTKSERSEEIKERA KEAIKRSEEILERVKRLSDHSR SEQ ID NO: 478 |
| DHD140 | Heterodimer | a | GSDEEEANYVSDKAVKIAEDVQELLKELLELSEVVRRGEVDEDEYDRVLRK LQEVMKEYEEVLKEYEEVSRKHE SEQ ID NO: 179 DEEEANYVSDKAVKIAEDVQELLKELLELSEVVRRGEVDEDEYDRVLRKLQ EVMKEYEEVLKEYEEVSRKHE SEQ ID NO: 407 |

TABLE 1B-continued

| Design name | Oligomerization State | Chain | Design sequence |
|---|---|---|---|
| DHD140 | Heterodimer | b | GSPEKYLIKTQEELLRRHAEILEDLIRKVERQVDLRRKVDERDEDLKRELE RSLRELERLVRESSRLVEEIRELSKEIKR SEQ ID NO: 180 PEKYLIKTQEELLRRHAEILEDLIRKVERQVDLRRKVDERDEDLKRELERS LRELERLVRESSRLVEEIRELSKEIKR SEQ ID NO: 480 |
| DHD141 | Heterodimer | a | GSDEEYELERISRESKELLERYKRLLREYQELLKELRHVKDLDRAVKIIHE LMRVSKELVEISHRLLELHERLVRRRK SEQ ID NO: 181 DEEYELERISRESKELLERYKRLLREYQELLKELRHVKDLDRAVKIIHELM RVSKELVEISHRLLELHERLVRRRK SEQ ID NO: 409 |
| DHD141 | Heterodimer | b | GSEKEYIEKLSRKIEEDIRRSEERAKDSERLVRRLEELAKRKRLDLDDVLR VAEENLEILEDNLRILEEILKEQDKSNR SEQ ID NO: 182 EKEYIEKLSRKIEEDIRRSEERAKDSERLVRRLEELAKRKRLDLDDVLRVA EENLEILEDNLRILEEILKEQDKSNR SEQ ID NO: 482 |
| DHD142 | Heterodimer | a | GSPHEEVVELHERVMEISERAVELIQRIIDIIRRIREDDKDIEKLVKTIRD LVREYEELHRELEEIDEEIYKKSE SEQ ID NO: 183 PHEEVVELHERVMEISERAVELIQRIIDIIRRIREDDKDIEKLVKTIRDLV REYEELHRELEEIDEEIYKKSE SEQ ID NO: 411 |
| DHD142 | Heterodimer | b | GSDHEDVVRLHEDLVRKQEDARRVLEEIVRLAEEIVEVIKKDEKDKDRVTR LVEEIEKLVEEYKKKVDEMRKISDEIKYRSR SEQ ID NO: 184 DHEDVVRLHEDLVRKQEDARRVLEEIVRLAEEIVEVIKKDEKDKDRVTRLV EEIEKLVEEYKKKVDEMRKISDEIKYRSR SEQ ID NO: 484 |
| DHD143 | Heterodimer | a | GSRAREVVKRAKRIIEEWQKILEEWRRILEEWRRLLEDERVDDRDNERIIR ENERVIRENEKIIRDVIRLLEELLYERR SEQ ID NO: 185 RAREVVKRAKRIIEEWQKILEEWRRILEEWRRLLEDERVDDRDNERIIREN ERVIRENEKIIRDVIRLLEELLYERR SEQ ID NO: 413 |
| DHD143 | Heterodimer | b | GSREDEELEEEIDRIRQMVEEYEELVKEYEELTEKYKQGKVDKEESKKIIE KSERLLDLSQDAVRKVKEIIRRILYTNR SEQ ID NO: 186 REDEELEEEIDRIRQMVEEYEELVKEYEELTEKYKQGKVDKEESKKIIEKS ERLLDLSQDAVRKVKEIIRRILYTNR SEQ ID NO: 486 |
| DHD144 | Heterodimer | a | GSPKEEIVKLHDESAELHRRSVEVADEILKMHERSKDVDDERESRELSKEI ERLIREVEEVSKRIKRLSEEVEYLVR SEQ ID NO: 187 PKEEIVKLHDESAELHRRSVEVADEILKMHERSKDVDDERESRELSKEIER LIREVEEVSKRIKRLSEEVEYLVR SEQ ID NO: 415 |
| DHD144 | Heterodimer | b | GSPLEEILKIQRRINKIQDDINKILHEILRMQEKLNRSSDKDEVEESLRRI RELIKRIKDLSKEIEDLSREVKYRTT SEQ ID NO: 188 PLEEILKIQRRINKIQDDINKILKEILRMQEKLNRSSDKDEVEESLRRIRE LIKRIKDLSKEIEDLSREVKYRTT SEQ ID NO: 488 |
| DHD145 | Heterodimer | a | GSPEDEHVYVVREIYEVLREHAEVLEENREVIERLLEAKKRGDKSEELVKE LKKSIDKLKEISRKLEEIVKELEKVSEKLK SEQ ID NO: 189 PEDEHVYVVREIYEVLREHAEVLEENREVIERLLEAKKRGDKSEELVKELK KSIDKLKEISRKLEEIVKELEKVSEKLK SEQ ID NO: 417 |
| DHD145 | Heterodimer | b | GSDEDETSYRILELLREIVRASRELIRLSEELLEVARRDDKDETVLETLIR EYKELLDRYRRLIEELTRLVEEYEERSR SEQ ID NO: 190 DEDETSYRILELLREIVRASRELIRLSEELLEVARRDDKDETVLETLIREY KELLDRYRRLIEELTRLVEEYEERSR SEQ ID NO: 490 |
| DHD146 | Heterodimer | a | GSTQEEINRIQHEVLRIQEEIDEILRDIVEKLKAISRGELDHEVVKDVEDK VREALEKSEELLDKSRKVEYKSE SEQ ID NO: 191 TQEEINRIQHEVLRIQEEIDEILRDIVEKLKAISRGELDHEVVKDVEDKVR EALEKSEELLDKSRKVEYKSE SEQ ID NO: 419 |
| DHD146 | Heterodimer | b | GSDEEELNRELLEKSKRLVDINRDIIRTAQELIEMLKDSKDGRVDEDTKRE LRDKLRKLEEKLERVREELRKYEELLRYVQR SEQ ID NO: 192 DEEELNRELLEKSKRLVDINRDIIRTAQELIEMLKDSKDGRVDEDTKRELR DKLRKLEEKLERVREELRKYEELLRYVQR SEQ ID NO: 492 |
| DHD147 | Heterodimer | a | GSDEKDRVYEILKEVQRLVKEYRDISKEIEDLVKHYEHITDDEAQEVSKEL IDKSLRASEIVRELIRLIKELLDELE SEQ ID NO: 193 DEKDRVYEILKEVQRLVKEYRDISKEIEDLVKHYEHITDDEAQEVSKELID KSLRASElVRELIRLIKELLDELE SEQ ID NO: 421 |
| DHD147 | Heterodimer | b | GSDEEDVLYHLRELLEELKRVSDDYERLVREIKETSERKDRDTKENKDMLD ELVKAHREQEKLLERLVRLLEELFERKR SEQ ID NO: 194 DEEDVLYHLRELLEELKRVSDDYERLVREIKETSERKDRDTKENKDMLDEL VKAHREQEKLLERLVRLLEELFERKR SEQ ID NO: 494 |

TABLE 1B-continued

| Design name | Oligomerization State | Chain | Design sequence |
|---|---|---|---|
| DHD1 | Heterodimer | a | PREQAIRISEEIIRISKKIIEILERTRSSTAREAMKWAKDSIRLAEESKYL LDK SEQ ID NO: 195 |
| DHD1 | Heterodimer | b | IEDDVKKIQDSTKKAQKETIEALERSTSSTARKQMEEQKEQIRLQKEAMYL LKK SEQ ID NO: 196 |
| DHD2 | Heterodimer | a | SREEIAKLQEEVIKLQRRVIE1QKEVIELQRRAKELTSSYTKEILEIQRRI EEIQREIEEIQKRIEEIQEEIQRRT SEQ ID NO: 197 |
| DHD2 | Heterodimer | b | SDEEIKRLSEEVIQLSRRVIKMSREAIKLSREVQKLTPSYQKRIKEIADRS IELARESIEIAKRSEKIAEESQRRT SEQ ID NO: 198 |
| DHD3 | Heterodimer | a | PAKDEALKMANESLELAKKSARLIQESSSKEILERIEKIQRRIAELQDRIA YLIKK SEQ ID NO: 199 |
| DHD3 | Heterodimer | b | PAKDEALRMIDESRELIKKSNELIQRSSSKEILERILEIQRKIAELQKRIQ YLLKS SEQ ID NO: 200 |
| DHD4 | Heterodimer | a | TDEARYRSERIVKEAKRLLDEARRRSEKIVREAKQRSNSEDAKRIMEENLR ESEEAARRLREIIRRNLEESRETG SEQ ID NO: 201 |
| DHD4 | Heterodimer | b | TREALEYQRKMAEEIEDLLREALRRQEEMVREAKQRSLSEEFKRIMERILE EQERVMRLAKEALERILEEQKRTG SEQ ID NO: 202 |
| DHD5 | Heterodimer | a | SERTKREAKRSQEEILREAKEAMRRAKESQDHRQNRDGSNSEDLERLSQEQ KRELEEVERRLKELAREQKYKLEDS SEQ ID NO: 203 |
| DHD5 | Heterodimer | b | SEDLKRILKEITERELKLMQDLMEILKKITEDENNLDSNNSEDLKRSIEKA RRILDEALRKLEESARRAKYIQEDN SEQ ID NO: 204 |
| DHD6 | Heterodimer | a | TEDEIRESLKV7LDEVLQELREIARESNEVLERNRQKSRSDKLREDIERYKK RMEEARKKLDDQLNKYKKRMDENRS SEQ ID NO: 205 |
| DHD6 | Heterodimer | b | TEEELKESKKFAEDLARSARRALKESKRVLEEISQASRSKKLEEIVRRYKE QVKRWQDEWDERAREYRKRMKENRS SEQ ID NO: 206 |
| DHD7 | Heterodimer | a | TKTEEIERLAREIKKLSEKVERLAQEIEELSRRVKEENSTDRELKEANREI ERAIREIEKANKRMEEALRRMKYNG SEQ ID NO: 207 |
| DHD7 | Heterodimer | b | TKTEEHERLAREISKLADEHRKLAKIIEELARRIKEENLTDDELREAIRKI EDALRKNKEALKIMKEAAERNRYNT SEQ ID NO: 208 |
| DHD8 | Heterodimer | a | TKKEESRELARESEELARESEKLARKSLELARRAESSGSEEEKRRIIDENR KIIERNREIIERNKEIIEYNKELIS SEQ ID NO: 209 |
| DHD8 | Heterodimer | b | TKDEESLELNRESEELNRKSEELKRKSKELNDRAESSNSEEEEKEILREHK EILREHLEILRRHKEILRRHKYLTS SEQ ID NO: 210 |
| DHD16 | Heterodimer | a | TREELLREKIELAKEHIEIMREILELLQKMEELLERQSSEDILEELRKIIE RIRELLDRSRKIHERSEEIAYKEE SEQ ID NO: 211 |
| DHD16 | Heterodimer | b | SEDIAREIKELLRRLKEIIERNQRIAKEHEYIARERKKLDPSNEKERKLLE RSRRLQEESKRLLDEMAEIMRRIKKLLD SEQ ID NO: 212 |
| DHD18 | Heterodimer | a | DRQKLIEENIKLLDKHIKILEEILRLLKKDIDLLKKSSSEEVLEELKKIHR RIDKLLDESKKIHKRSSEIVKKRS SEQ ID NO: 213 |
| DHD18 | Heterodimer | b | DEQKLIETSQRLQEKSERLLEKFEQILREASDLYRKPDSEELLRRVEKLLR ELEKLIRENQDLARKHEKILRDQS SEQ ID NO: 214 |
| DHD19 | Heterodimer | a | DRQELIRENIELLKKHIKIVKEIQKLIETFIELLKKSSSEEILRRLKKILK RIEKLYRESQEIHKRSEEIAKKRQ SEQ ID NO: 215 |
| DHD19 | Heterodimer | b | DEERLIDKSRELQKESEELLKELLKIFKRIEELLEKPDSEELIREIKKLLE TLSEIHKRNEKLARTHEEILRQQS SEQ ID NO: 216 |
| DHD22 | Heterodimer | a | STRDVQREIAKAFKKMADVQKKLAEEIKRHVKNVEKKNKDNDEYRKIATEL LKKATESQKKLKELLDRIRKSDS SEQ ID NO: 217 |
| DHD22 | Heterodimer | b | DKDDRSTSLLKRVEKLIDESDRIIDKFTTLIELSRNGKIDDDQYKKELKEI LELLKKYDKHVKEVEELLKRLNS SEQ ID NO: 218 |
| DHD23 | Heterodimer | a | SKRKALEVSERVVRISEKVVRVLDESSDLLKKSYDDSDKFAELIDRHEEKI KKV7KKLIKEWLEIIQRHKS SEQ ID NO: 219 |

TABLE 1B-continued

| Design name | Oligomerization State | Chain | Design sequence |
|---|---|---|---|
| DHD23 | Heterodimer | b | SAEEFVKLSEEAVKRSKEILDIVRKQVKLVKAGVDKHEITDSLRKSEKLIE EHKELIKTHRDLLRREN SEQ ID NO: 220 |
| DHD24 | Heterodimer | a | SSTEILKRFKRALRESEKIVKHSRRVLKIIREVLKQKPTQAVHDLVRIIET QVKALEEQLKVLKRIVEALERQS SEQ ID NO: 221 |
| DHD24 | Heterodimer | b | DKQKEIKDILEKTRRIAEESRKIAEKFDEIIKRSTEGKIDESLTKELEELV KEVIKLSEDDARTSDDLVRKES SEQ ID NO: 222 |
| DHD26 | Heterodimer | a | DEDESIKLTRKSIEETRKSLKIIKEVVELIREVLKHIKDLDKEIFERIDKI LDKYKKQVDTYDEILKEYEKKQR SEQ ID NO: 223 |
| DHD26 | Heterodimer | b | SELDEQKELIKKQEKLIEEQQRLLSKIRRMFKERVKDQELLREIQKVLKRS QEIVETSKKILDRSDKTTE SEQ ID NO: 224 |
| DHD28 | Heterodimer | a | DQKEINTRIVEKLERIFKKSKEIVRQSERVISTIEKKTEDERELDLLRRHV KIVREHLKLLEELLKIIKEVQKESE SEQ ID NO: 225 |
| DHD28 | Heterodimer | b | DTEELVKRLNELLKELSKLVKEFIKILETYRKDQTKDTSKISERVDRILKT YEDLLQKYKEILEKIEKQLS SEQ ID NO: 226 |
| DHD29 | Heterodimer | a | DYARLIDQAVEVTRKVVEVNVTVARVNDKFAKHLGDEELRRVSEHLKEVSK DLQEVAKKSKDAARQVK SEQ ID NO: 227 |
| DHD29 | Heterodimer | b | DVSKVAEEYLQISKTLVDISRTLLEISERLVRLVRTVADDRSEVKKAIEDS IEVLKTSEEVVRQIKRASDKLVKAIS SEQ ID NO: 228 |
| DHD31 | Heterodimer | a | DAKEIQRRVVEIQTEVVKLQKKAVDIIRKIIEAFNNSNIDQSLLEAAKEIV KEIDKLEKLTESLLEESKKLLKRSS SEQ ID NO: 229 |
| DHD31 | Heterodimer | b | SAEEVVKLAKIFLELLRESIKLLKRSVDLLRKSSDPSLDKSEAAKVSREIE KVSDTSLKLSKKALDVVKRALKVAS SEQ ID NO: 230 |
| DHD32 | Heterodimer | a | DEKDAARKARKVSEEAKEASKKIEKALEESKRILNTLQKKDEQEVKVIKE HEDVLRQIEKIQKQVLEIQKEVAKLLESLD SEQ ID NO: 231 |
| DHD32 | Heterodimer | b | SADDVARASEKVLRVARESAKAADKSLEVFKEVVKRGDKEAFLQVVKINEE VVKINITVIRILIEVSKTAT SEQ ID NO: 232 |
| DHD38 | Heterodimer | a | DEYVKETLKQLREALASLREADKRITELVKEARKKPLSEAARKFAEAIVTH VKVVVEHVEVVLRHVEVLVEAKKNGVIDKSILDNALRIIENVIRLLSNVIR VVDEVLQDLD SEQ ID NO: 233 |
| DHD38 | Heterodimer | b | DASDVIRRIHELFEEVHRLIEAVHRAIEDVAKAAQKKGLDESAVEILAELS KELAKLSRRLAEISREIQKVVTDPDDKEAVERLKEIIKEIKKQLDELRDRL RKLQDLLYKLK SEQ ID NO: 234 |
| DHD60 | Heterodimer | a | SEDKAHHDIVRVLEELIKIHDELMKISEEILKATSDSTATDETKEELKRRS KEAQKKSDTLVKIVKELEKESRKAQS SEQ ID NO: 235 |
| DHD60 | Heterodimer | b | DDEEKYRQIIREAQEISKTAKRILRDAQEISKRIRHQGVDRSEHQRLVDLL RELIKEHHKLLRRQQEADTRND SEQ ID NO: 236 |
| DHD63 | Heterodimer | a | DRKDKARKASEKLEEVIQRWKTVADKWKKMVDLVSNGKLSQEEVARVTEEL LKIQTELAKLLEEHAKVLQESAS SEQ ID NO: 237 |
| DHD63 | Heterodimer | b | SDEESIKTQSELIKTSEELLKDVKRIDEELQKLRDDPTLDESELKKRVKEW SDRVRKAKEISRKIQEIVKESKKRSS SEQ ID NO: 238 |
| DHD66 | Heterodimer | a | DKDEELRKVIEKYREMVKEYRKVIREYEEVIKSSKTIDKSSLISLSRKMVE LSQRVIDVSDEVAKVLSRKQS SEQ ID NO: 239 |
| DHD66 | Heterodimer | b | TDEERLKKQTKELKEQTKQLEKQKDLLEKISNGEISKDEIQEIIKESKKIA KESQKALDSSRKALEEVS SEQ ID NO: 240 |
| DHD67 | Heterodimer | a | DEKEVSKEIIKVLKDIAKVQQKVIEVSQRLASVLRADDDNVVKRALEEYEK ILEELRELNKEIEKLTDKYRKVTS SEQ ID NO: 241 |
| DHD67 | Heterodimer | b | DSDEQTKELEKLTELHKRHVEKLKKQTKESREVDSNKLWKSKDVKDKLSES EKELQKLSDQDKKAKDALESSRRKND SEQ ID NO: 242 |
| DHD69 | Heterodimer | a | DAEEQLKLLTKLLRHQQRLLQLIKESLKLIEKIDQSSQENQDEIRKWREVT KKLRELIKTSEKLVRELEKSYKKSS SEQ ID NO: 243 |

TABLE 1B-continued

| Design name | Oligomerization State | Chain | Design sequence |
|---|---|---|---|
| DHD69 | Heterodimer | b | SLRDVVRRYQELVRRYDELIKTLTEILKKYQKKGAEDKDASTELVKAVRTS LKLSKELLKLNSELLKEDS SEQ ID NO: 244 |
| DHD71 | Heterodimer | a | SKEELKRKLDELKKRSDTLKELSKKLKEISERNPDDKSVHRT11RIHREFV KNIIKEIVRVIEEIVSDKS SEQ ID NO: 245 |
| DHD71 | Heterodimer | b | SKQDEHDRLLKIHDKLVKQHDELLKLLTKLSRAGDSVTKKKLEEILRKLQE VSKQLEESLKDADKVSKDIN SEQ ID NO: 246 |
| DHD72 | Heterodimer | a | TVQSLLEQHVKIVKRSIEILERHTQILQDIARSQGVSKELEDVERQVKEYR KEVKKLEEDLRQLSRNSK SEQ ID NO: 247 |
| DHD72 | Heterodimer | b | SDSDRIEKLIRESTELLKEQQKLAKRSRELAETVESLPLTEEYLKQQREHQ KKIEKLLKDSEKHLEELKRLVKSEK SEQ ID NO: 248 |
| DHD73 | Heterodimer | a | DSEKRIEDILRTDLELAKRDAELVKEHIKLVKRIDLSEELKKQVEDVEKES KKLEDSSEKLVQKVRKRSS SEQ ID NO: 249 |
| DHD73 | Heterodimer | b | DEEERAKDLRKYLEEQTQYYRTVTEHLRNLEKVVEELERRGKPSSELQQIL ERSQRIYKETTEIYDTSKKLIEELDKHHR SEQ ID NO: 250 |
| DHD148 | Heterodimer | a | PLEDILKRHLDKVRELVRLSEEVNKLAKEVLDILKDKRVDEKELDKVLKEL EKVVEEYERAVKESRDLLRELRETTR SEQ ID NO: 251 |
| DHD148 | Heterodimer | b | DKERLLEIHERIQKLLDRNLEIIERLLRLLREARDIKDDDKLDKVIKRLKE LSEESKDILDKIKELLKESEKELT SEQ ID NO: 252 |
| DHD149 | Heterodimer | a | PEDEVIRVIEELLRIAAEVDEVHRRNVEVQEEASRVTDRERLERLNRESEE LIKRSRELIEEQRKLIERLERLAT SEQ ID NO: 253 |
| DHD149 | Heterodimer | b | DLEELIKEYAEVVRRKHKAVRDLERLVRELANAKHASEEELKRIATEILRI VKELIRVQERLIKLSEDSNEESR SEQ ID NO: 254 |
| DHD150 | Heterodimer | a | PTDEVIEVLKELLRIHRENLRVNEEIVEVNERASRVTDREELERLLRRSNE LIKRSRELKEESKKLIEKLERLAT SEQ ID NO: 255 |
| DHD150 | Heterodimer | b | DNEEIIKEARRVVEEYKKAVDRLEELVRRAEKAKHASEKELKDIVREILRI SKELNKVSERLIELV7ERSQERAR SEQ ID NO: 256 |
| DHD151 | Heterodimer | a | PKEDIDRVSRELVRVHKELLEVLRKSTEIVEAVARNEKDERTIEEVLEEQE RAVRKLEEVSKKHKEAVKRLK SEQ ID NO: 257 |
| DHD151 | Heterodimer | b | ELERLSEEIQKLSDRLIELIRRHSKVLEEIVRLLKHKDNDEREVRRLLKLL RDLTRRYEEVLRKVEEIVKRQEDESR SEQ ID NO: 258 |
| DHD152 | Heterodimer | a | PEEDILRLLRKLVEVDKELLEVVRESTEVVRLVARNEKDVETVERVLRKQE EVVRKYERVSRELEEAVRRLK SEQ ID NO: 259 |
| DHD152 | Heterodimer | b | ELKDLVEEIVKLSKENLKLWEDHSRVLEEIVRLLKHKDNDEREVRRLLKLL EDLTRRAEETSRRIEEIVKEAEDRAR SEQ ID NO: 260 |
| DHD153 | Heterodimer | a | DEERELREVLRKHHRVVREWTKVVEELKRVVELLKRGETSEEDLLRVLKKL LEMDKRILEVNREVLRVLEKRLT SEQ ID NO: 261 |
| DHD153 | Heterodimer | b | SLEEIIEELVELVRRSVEIAKESDEVARRIVESEDKKKELIDTLRDLHREW QEVTKRAEELVREAEKEVR SEQ ID NO: 262 |
| DHD154 | Heterodimer | a | TAEELLEVHKKSDRVTKEHLRVSEEILKVVEVLTRGEVSSEVLKRVLRKLE ELTDKLRRVTEEQRRWEKLN SEQ ID NO: 263 |
| DHD154 | Heterodimer | b | DLEDLLRRLRRLVDEQRRLVEELERVSRRLEKAVRDNEDERELARLSREHS DIQDKHDKLAREILEVLKRLLERTE SEQ ID NO: 264 |
| DHD155 | Heterodimer | a | PEDDVVRIIKEDLESNREVLREQKEIHRILELVTRGEVSEEAIDRVLKRQE DLLKKQKESTDKARKWEERR SEQ ID NO: 265 |
| DHD155 | Heterodimer | b | DEVRLITEWLKLSEESTRLLKELVELTRLLRNNVPNVEEILREHERISREL ERLSRRLKDLADKLERTRR SEQ ID NO: 266 |
| DHD156 | Heterodimer | a | DEDEVVKVHEEHVKSHEEIHRSHEEVVRAAEEDKRDSRELRTLMEEHRKLL EENEKSIEEVKKIHERVKR SEQ ID NO: 267 |
| DHD156 | Heterodimer | b | KKEELIDISKEVLDLDDEINKISKEILELIKKLLRLKEEGREDKDKAREVK RRIRELHRRIQELNKRLRELKKRVQETKR SEQ ID NO: 268 |

TABLE 1B-continued

| Design name | Oligomerization State | Chain | Design sequence |
|---|---|---|---|
| DHD157 | Heterodimer | a | PEEDIARRVEDLLRKSEELIKESEKILKESKRLLDRNDSDKRVLETNLRLI DKHTKLLERNLELLEELLKLAEDVAK SEQ ID NO: 269 |
| DHD157 | Heterodimer | b | RFKDLSREYIEVVKRLLELSREALEVLREIKDTDKTDKKRIKELIDRLRKL IEEYKRIIDRLRKLSKDLEEEHR SEQ ID NO: 270 |
| DHD158 | Heterodimer | a | DEEELVKILKELQRLSEESLEINKRLVEILRLLRRGEVPKEEVEKKLREIK KEQEKLDREHEKIKKRIEEITK SEQ ID NO: 271 |
| DHD158 | Heterodimer | b | SLKEKILEIIERNMKLVELSNRSVEIVARILKGEKDDEETLERLLREWDKI TRDYEEIIKESRKLVKELEEEAK SEQ ID NO: 272 |
| DHD159 | Heterodimer | a | SKTEILRKALEIHKEQIDIVRKLIELSEEVLKLVEESKEKNLEKLKRIDEE TDRLLERLDELHKRLTELAERLK SEQ ID NO: 273 |
| DHD159 | Heterodimer | b | SDDEARKQLEEMKRRLREVEKKSKRVEERVRELERLVRENREDEDRVLKTL EDLLRENEKLVRTIERIIVREQRELSKEVK SEQ ID NO: 274 |
| DHD160 | Heterodimer | a | SEEELEKKADELRKLSEEWRKLQEEDKRLSEMVEKGELDLQEVDEHSLRVL ERATEVHRTVDKVIEEILRTTN SEQ ID NO: 275 |
| DHD160 | Heterodimer | b | SEKERIIRESQETQEEIRRTHEEHRKLEEILRRAKAGELPEETLDRLRRIM ERLKELSERLDDLVRKLRDDHRREQK SEQ ID NO: 276 |
| DHD161 | Heterodimer | a | SEKEILEELKRILKRVKDISDRLEELDKRTEEIARREPTKELVDELVKIHR DV7LRLHEEILKLVDDALKKVEDATK SEQ ID NO: 277 |
| DHD161 | Heterodimer | b | DLRELLELQREASRLHRELVKLLTELVKKLELIAKGEDIREEDLKRIKERL EEIKKRSKRIKEESDEIDKKTK SEQ ID NO: 278 |
| DHD162 | Heterodimer | a | SERELQRELNKIVRRILEIHREVSELHQRAVKLIRENDNSEELEEISRRIE ELSKELEKLVREHDEIVKTIE SEQ ID NO: 279 |
| DHD162 | Heterodimer | b | SEREKLDRKDEELKEINKRVEEIKERSDRITEAIEKNERSEEEIRRLSREQ NEALQRLLELHKKLVKLHRELLEDTR SEQ ID NO: 280 |
| DHD163 | Heterodimer | a | DKEDVIRVHDEQHKLIEEQLELTRRIAELVREIAKNTASEEEIKEMLKEIK RLDDRSREIQDRLQKLLEEIRRKTK SEQ ID NO: 281 |
| DHD163 | Heterodimer | b | TEEEIVELNKDIQRKSKEHIDLQNELVKKIERAIRENNITEELLEELERLL RESEKIVEEIRRITDKIRKDAK SEQ ID NO: 282 |
| DHD164 | Heterodimer | a | SEKEILERLLRLSKEQNEISEEIHRLTERLVELKRRKDDDERLKRILDRQK RLVERAREISKEYEDLLRKLE SEQ ID NO: 283 |
| DHD164 | Heterodimer | b | SMEELLRKNARLSRKQLKIIDEHLELSTKLTRGEAGDETLEEIERRSREML EEQRRVDEESKRIREKLK SEQ ID NO: 284 |
| DHD165 | Heterodimer | a | SEEEIRDIVEKLLRTHEEVLKEIKKLLDDSERVRRRELDKKDLDRIQKEQR DIQEENKEKAKRFDELVKELKKAAK SEQ ID NO: 285 |
| DHD165 | Heterodimer | b | SEEEHRRTMEKVEKEVRDIKRRSEEVKKKVKANTLSEEDLVRLLERLVEDH KRLQDLSQEIIERDEKATK SEQ ID NO: 286 |
| DHD166 | Heterodimer | a | DEDELAKEIEDVQRRNKESQEEHDKSVKKLEAAERGEIDEDSLLRVLEEDI KVLEKDIEVLERSIEVIEKAE SEQ ID NO: 287 |
| DHD166 | Heterodimer | b | SEKELIRRLLEQQRQHLRLSERLIELSRRLVEVVRKGKDNRDLLRELKKLS EEHKKHSKDDHEKVREIREREK SEQ ID NO: 288 |
| DHS 17 | Heterodimer | a | DRKDLLKRNIKLLDRHLKILDTILKLLEKLSELLKKSSSEEVVKEYKKILD EIRKLLEESKEIHKESKEILERES SEQ ID NO: 289 |
| DHD17 | Heterodimer | b | DEEKLIERSKRLQEESEQLLEKFEQILRELTELLEKPDSEELARKIKKLHD ELRKIIKRKQELIREHEEILRKRD SEQ ID NO: 290 |

In some aspects, non-limiting examples of the monomer A polypeptide and monomer B polypeptide pairs are shown in FIG. 16.

In some aspects, the amino acid sequence of SEQ ID NOs: 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 useful for the monomer A polypeptide or the monomer B polypeptide is not linked to GlySer at the N terminus of the sequence or does not comprise GlySer at the N terminus. In some aspects, the monomer A polypeptide and/or the monomer B polypeptide comprises at least one amino acid, at least two amino acids, at least three amino acids, at least four amino acids, at least five amino acids, at least six amino acids, at least seven amino acids, at least eight amino acids, at least nine amino acids, or at least ten amino acids at the N terminus or the C terminus of the amino acid sequence. In some aspects, the additional amino acids are not GlySer at the N terminus.

In some aspects, the protein of the present disclosure comprises a heterodimer comprising a monomer A polypeptide and a monomer B polypeptide, wherein the monomer A polypeptide comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence as set forth in SEQ ID NO: 331, 5, 7, 13, 15, 25, 29, 31, 33, 35, 37, 39, 41, 45, 47, 53, 55, 57, 59, 61, 65, 67, 69, 71, 73, 75, 77, 79, 337, 339, 85, 87, 89, 91, 93, 95, 97, 99, 341, 103, 343, 107, 109, 111, 113, 459, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, or 421 and the monomer B polypeptide comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence as set forth in SEQ ID NO: 2, 332, 334, 336, 338, 340, 342, 344, 346, 348, 418, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 420, 422, 424, 426, 428, 126, 430, 432, 434, 436, 438, 440, 442, 444, 446, 448, 450, 452, 454, 456, 458, 460, 462, 464, 466, 468, 470, 472, 474, 174, 476, 478, 480, 482, 484, 486, 488, 490, 492, or 494, respectively.

In some aspects, the protein of the present disclosure comprises a heterodimer comprising a monomer A polypeptide and a monomer B polypeptide, wherein the monomer A polypeptide comprises an amino acid sequence at least 70%, 75%, 80%, 85%, 90%, 91%, 92%, 93%, 94%, 95%, 96%, 97%, 98%, 99%, or 100% sequence identity along the length of SEQ ID NO: 331, 5, 7, 13, 15, 25, 29, 31, 33, 35, 37, 39, 41, 45, 47, 53, 55, 57, 59, 61, 65, 67, 69, 71, 73, 75, 77, 79, 337, 339, 85, 87, 89, 91, 93, 95, 97, 99, 341, 103, 343, 107, 109, 111, 113, 459, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, or 421, wherein the amino acid sequence of the monomer A polypeptide does not comprise GlySer at the N terminus, and the monomer B polypeptide comprises an amino acid sequence at least 70%, 75%, 80%, 85%, 90%, 91%, 92%, 93%, 94%, 95%, 96%, 97%, 98%, 99%, or 100% sequence identity along the length of SEQ ID NO: 2, 332, 334, 336, 338, 340, 342, 344, 346, 348, 418, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 420, 422, 424, 426, 428, 126, 430, 432, 434, 436, 438, 440, 442, 444, 446, 448, 450, 452, 454, 456, 458, 460, 462, 464, 466, 468, 470, 472, 474, 174, 476, 478, 480, 482, 484, 486, 488, 490, 492, or 494, respectively, wherein the amino acid sequence of the monomer B polypeptide does not comprise GlySer at the N terminus.

In some aspects, the protein of the present disclosure comprises a heterodimer comprising a monomer A polypeptide and a monomer B polypeptide, wherein the monomer A polypeptide consists of an amino acid sequence at least 70%, 75%, 80%, 85%, 90%, 91%, 92%, 93%, 94%, 95%, 96%, 97%, 98%, 99%, or 100% sequence identity along the length of the amino acid sequence as set forth in SEQ ID NO: 331, 5, 7, 13, 15, 25, 29, 31, 33, 35, 37, 39, 41, 45, 47, 53, 55, 57, 59, 61, 65, 67, 69, 71, 73, 75, 77, 79, 337, 339, 85, 87, 89, 91, 93, 95, 97, 99, 341, 103, 343, 107, 109, 111, 113, 459, 345, 347, 349, 351, 353, 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, or 421 and the monomer B polypeptide consists of an amino acid sequence at least 70%, 75%, 80%, 85%, 90%, 91%, 92%, 93%, 94%, 95%, 96%, 97%, 98%, 99%, or 100% sequence identity along the length of the amino acid sequence as set forth in SEQ ID NO: 2, 332, 334, 336, 338, 340, 342, 344, 346, 348, 418, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 420, 422, 424, 426, 428, 126, 430, 432, 434, 436, 438, 440, 442, 444, 446, 448, 450, 452, 454, 456, 458, 460, 462, 464, 466, 468, 470, 472, 474, 174, 476, 478, 480, 482, 484, 486, 488, 490, 492, or 494, respectively.

In one embodiment of any of the above embodiments, amino acid changes from the reference amino acid sequence are conservative amino acid substitutions. As used herein, "conservative amino acid substitution" means an amino acid substitution that does not alter or substantially alter polypeptide function or other characteristics. A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In another embodiment of any of the above embodiments, amino acid residues at 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of defined interface positions are invariant compared to the reference amino acid sequence. Table 2 below provides the residue numbers within each A and B monomer that are present at the interface in the heterodimer. The position of interface residues are the same for A-B binding partners. Table 2 is organized by heterodimer design name (see the left-hand column in Tables 1A and 1B). Note that for purpose of defining the position of interface residues for each polypeptide in Table 1A and 1B, the "GS" residues at the amino terminus, if present, are not included.

TABLE 2

Interface residues by position number across both chains 'a' and 'b'

DHD_1
[5, 6, 8, 9, 12, 13, 16, 19, 20, 22, 23, 31, 34, 35, 38, 41, 42, 45, 48, 52, 55, 59, 63, 66, 70, 73, 74, 77, 80, 81, 85, 88, 89, 92, 95, 96, 99, 102, 103, 106]

DHD_2
[5, 6, 9, 12, 13, 16, 19, 20, 23, 26, 27, 30, 33, 36, 37, 38, 41, 44, 45, 48, 51, 55, 58, 62, 65, 69, 72, 73, 76, 81, 85, 88, 89, 92, 95, 96, 99, 102, 103, 106, 109, 110, 112, 114, 117, 120, 123, 124, 127, 128, 131, 134, 135, 137, 138, 141, 144, 145, 148, 149, 152]

DHD_3
[6, 7, 10, 11, 13, 14, 17, 20, 21, 24, 25, 28, 33, 36, 40, 43, 44, 47, 50, 51, 54, 62, 63, 66, 69, 73, 76, 77, 80, 81, 84, 89, 92, 93, 96, 99, 100, 103, 106, 107, 110, 112]

DHD_4
[1, 8, 11, 12, 15, 19, 22, 26, 29, 30, 33, 38, 39, 42, 45, 46, 49, 50, 53, 56, 57, 60, 63, 64, 67, 68, 71, 75, 76, 80, 83, 87, 90, 94, 98, 101, 105, 108, 113, 114, 117, 121, 124, 125, 128, 132, 135, 139, 142, 143, 146, 150]

DHD_5
[4, 8, 12, 15, 16, 19, 22, 23, 26, 30, 34, 38, 39, 44, 48, 51, 55, 58, 62, 66, 69, 73, 76, 80, 84, 87, 88, 92, 95, 96, 98, 99, 102, 105, 106, 110, 114, 115, 117, 120, 124, 127, 131, 135, 138, 142, 145, 149, 152]

DHD_6
[1, 5, 8, 9, 11, 12, 15, 16, 19, 22, 23, 26, 27, 30, 33, 35, 37, 42, 46, 49, 53, 56, 60, 64, 67, 71, 74, 77, 81, 84, 87, 88, 91, 92, 95, 99, 102, 105, 106, 109, 110, 111, 112, 113, 118, 122, 125, 129, 132, 133, 136, 140, 143, 147, 150]

DHD_7
[3, 6, 10, 13, 17, 20, 24, 27, 31, 34, 44, 47, 48, 51, 55, 58, 61, 62, 65, 69, 72, 75, 76, 79, 82, 86, 89, 90, 93, 96, 100, 103, 107, 110, 115, 120, 124, 127, 130, 131, 134, 138, 141, 145, 148, 151, 152]

DHD_8
[6, 10, 13, 17, 20, 24, 27, 28, 31, 34, 47, 50, 54, 57, 61, 64, 68, 71, 75, 76, 82, 83, 86, 89, 93, 96, 100, 103, 107, 110, 123, 126, 130, 133, 134, 137, 140, 144, 147, 150, 151, 152]

DHD_9
[12, 16, 19, 23, 26, 30, 33, 38, 39, 42, 46, 49, 52, 53, 56, 59, 60, 63, 67, 69, 88, 92, 95, 99, 102, 106, 109, 115, 122, 125, 129, 132, 136, 139, 143, 145]

DHD_16
[6, 9, 10, 13, 16, 17, 20, 23, 24, 27, 28, 30, 34, 43, 46, 50, 53, 57, 60, 64, 67, 71, 72, 5, 8, 12, 15, 19, 22, 23, 26, 29, 33, 41, 50, 57, 60, 64, 67, 68, 71, 74, 78]

DHD_18
[3, 6, 9, 10, 13, 16, 17, 20, 23, 24, 27, 31, 34, 38, 43, 46, 50, 53, 57, 60, 64, 67, 68, 71, 75, 78, 81, 85, 88, 91, 95, 98, 102, 105, 106, 109, 118, 121, 125, 128, 132, 135, 136, 139, 142, 146, 149, 150]

DHD_19
[3, 6, 9, 10, 13, 16, 17, 20, 23, 24, 27, 30, 31, 34, 38, 43, 46, 50, 53, 57, 60, 61, 64, 67, 71, 75, 81, 88, 91, 95, 98, 99, 102, 105, 109, 118, 121, 125, 128, 129, 132, 135, 139, 142, 146, 149, 150]

DHD_22
[1, 2, 5, 6, 9, 10, 12, 13, 16, 19, 20, 23, 27, 30, 31, 33, 34, 38, 41, 44, 47, 48, 51, 55, 58, 62, 65, 69, 72, 80, 81, 84, 87, 91, 94, 97, 98, 101, 102, 105, 108, 118, 122, 125, 126, 129, 132, 136, 139, 143, 146, 147, 148]

DHD_23
[1, 5, 6, 8, 9, 12, 15, 16, 19, 22, 23, 26, 29, 30, 33, 34, 40, 43, 47, 51, 54, 57, 58, 61, 64, 65, 68, 72, 75, 76, 79, 82, 83, 86, 89, 90, 93, 96, 97, 100, 104, 109, 110, 113, 116, 120, 123, 126, 127, 130, 134, 138]

DHD_24
[1, 5, 9, 12, 16, 19, 22, 26, 29, 30, 33, 40, 41, 42, 45, 48, 49, 51, 52, 55, 56, 59, 62, 63, 66, 69, 70, 73, 77, 80, 83, 84, 87, 91, 94, 98, 101, 105, 108, 109, 113, 118, 121, 125, 128, 129, 132, 136, 139, 142, 143, 147]

DHD_26
[5, 8, 9, 12, 16, 19, 22, 23, 26, 29, 30, 33, 37, 40, 44, 45, 48, 51, 52, 55, 58, 59, 62, 65, 66, 69, 73, 77, 80, 84, 87, 91, 94, 95, 98, 101, 105, 109, 112, 114, 115, 118, 119, 122, 125, 126, 129, 132, 136, 139, 143]

DHD_28
[2, 5, 6, 9, 13, 16, 20, 23, 26, 27, 30, 31, 33, 34, 46, 47, 50, 53, 54, 57, 60, 61, 64, 67, 68, 71, 75, 78, 82, 85, 86, 89, 92, 93, 96, 99, 100, 103, 106, 110, 114, 115, 118, 121, 125, 128, 132, 135, 139, 142, 146, 147]

DHD_29
[2, 5, 6, 8, 9, 10, 12, 13, 16, 19, 20, 22, 23, 26, 27, 30, 33, 34, 39, 42, 45, 46, 49, 53, 56, 60, 63, 66, 67, 70, 71, 74, 77, 78, 81, 84, 85, 88, 91, 92, 95, 98, 99, 102, 106, 112, 115, 116, 119, 120, 122, 123, 126, 129, 130, 133, 137, 140, 141, 144, 145]

DHD_31
[2, 5, 6, 9, 10, 12, 13, 16, 17, 19, 20, 23, 24, 26, 27, 30, 31, 33, 34, 37, 38, 39, 43, 46, 50, 54, 57, 60, 61, 64, 65, 68, 71, 75, 78, 81, 82, 85, 88, 89, 92, 95, 96, 99, 102, 103, 106, 109, 110, 119, 123, 126, 130, 133, 134, 137, 140, 141, 144, 147, 148, 151, 152]

DHD_32
[5, 6, 9, 12, 16, 19, 23, 26, 27, 30, 33, 34, 37, 44, 48, 49, 52, 55, 56, 58, 59, 62, 63, 65, 66, 69, 70, 73, 76, 77, 79, 80, 82, 83, 86, 87, 90, 93, 94, 97, 100, 101, 104, 107, 108, 111, 114, 115, 118, 123, 124, 127, 130, 133, 134, 137, 138, 140, 141, 144, 145, 147, 148, 151, 152]

DHD_38
[42, 43, 46, 49, 50, 52, 53, 56, 57, 60, 63, 64, 67, 70, 71, 74, 77, 79, 80, 84, 87, 88, 91, 94, 95, 98, 101, 102, 105, 109, 116, 117, 120, 123, 124, 127, 131, 134, 137, 138, 141, 144, 145, 149, 153, 158, 161, 162, 165, 168, 169, 172, 175, 176, 179, 182, 183, 185, 186, 187, 189]

DHD_39
[2, 6, 9, 13, 16, 20, 23, 27, 29, 30, 34, 40, 43, 46, 47, 50, 51, 54, 57, 58, 60, 61, 64, 110, 114, 117, 121, 124, 128, 131, 132, 135, 138, 145, 149, 152, 156, 159, 160, 163, 164, 166, 167, 170, 173, 174, 176, 177, 178]

DHD_40
[5, 9, 11, 12, 15, 16, 19, 23, 26, 29, 30, 33, 43, 46, 49, 50, 53, 56, 57, 59, 60, 63, 64, 67, 71, 108, 112, 116, 119, 123, 127, 130, 133, 134, 137, 138, 148, 151, 154, 158, 161, 165, 168, 169, 172, 175]

DHD_43
[3, 4, 7, 11, 14, 18, 22, 25, 29, 34, 35, 39, 43, 46, 47, 50, 51, 54, 57, 58, 61, 62, 65, 71, 72, 75, 76, 79, 82, 83, 86, 87, 90, 93, 94, 97, 98, 100, 101, 104, 111, 114, 115, 117, 118, 122, 125, 126, 129, 133, 136, 137, 140, 144]

TABLE 2-continued

Interface residues by position number across both chains 'a' and 'b'

DHD_60
[6, 7, 9, 10, 13, 16, 17, 20, 23, 24, 27, 30, 31, 34, 35, 51, 54, 55, 58, 61, 62, 65, 68, 72, 75, 76, 77, 83, 87, 90, 91, 93, 94, 97, 100, 101, 104, 105, 108, 111, 115, 116, 121, 122, 124, 125, 128, 131, 132, 135, 136, 138, 139, 142, 143, 149]
DHD_63
[6, 10, 13, 17, 20, 24, 27, 30, 31, 34, 41, 44, 45, 48, 51, 52, 55, 56, 58, 59, 62, 65, 66, 68, 69, 70, 72, 73, 74, 80, 83, 84, 87, 90, 93, 94, 97, 104, 105, 118, 122, 125, 126, 129, 132, 136, 139, 140, 143, 146, 150]
DHD_65
[2, 5, 6, 8, 9, 12, 13, 16, 19, 20, 23, 26, 27, 29, 30, 33, 34, 37, 43, 47, 50, 54, 57, 61, 64, 68, 71, 72, 75, 82, 85, 86, 89, 92, 93, 96, 99, 100, 103, 106, 107, 110, 118, 120, 121, 123, 127, 128, 131, 134, 135, 138, 139, 141, 142, 145, 148]
DHD_66
[6, 10, 13, 16, 17, 20, 24, 27, 31, 34, 42, 43, 46, 49, 50, 53, 54, 56, 57, 60, 63, 64, 67, 68, 71, 78, 81, 82, 85, 88, 89, 92, 95, 99, 102, 103, 107, 112, 113, 115, 116, 119, 123, 126, 127, 130, 133, 137, 140, 141]
DHD_67
[6, 9, 10, 13, 16, 17, 20, 21, 23, 24, 27, 28, 30, 31, 34, 36, 42, 46, 49, 52, 53, 56, 60, 63, 67, 70, 74, 77, 80, 81, 84, 87, 88, 91, 94, 95, 98, 101, 102, 105, 110, 114, 123, 130, 131, 133, 134, 140, 144, 147, 151]
DHD_69
[2, 5, 6, 9, 10, 12, 13, 16, 17, 19, 20, 23, 26, 27, 30, 33, 35, 44, 47, 51, 54, 58, 61, 65, 68, 72, 75, 76, 78, 82, 85, 86, 89, 92, 96, 99, 100, 102, 103, 106, 107, 111, 117, 118, 120, 121, 124, 127, 128, 131, 134, 135, 138, 139, 141, 142, 146]
DHD_70
[6, 9, 10, 13, 16, 17, 20, 23, 24, 26, 27, 30, 31, 34, 37, 38, 41, 43, 44, 47, 50, 51, 54, 57, 58, 61, 64, 65, 68, 71, 72, 73, 74, 78, 81, 82, 85, 88, 89, 92, 95, 96, 99, 102, 103, 106, 107, 109, 110, 111, 119, 120, 123, 124, 127, 130, 131, 134, 137, 138, 141, 144, 145, 148]
DHD_71
[9, 16, 19, 23, 30, 34, 40, 43, 44, 46, 47, 50, 51, 54, 57, 58, 61, 64, 65, 69, 72, 75, 78, 79, 82, 85, 86, 89, 92, 93, 96, 97, 99, 100, 103, 106, 111, 115, 118, 119, 121, 122, 125, 128, 129, 132, 136, 139, 140]
DHD_72
[1, 2, 5, 6, 8, 9, 12, 16, 19, 23, 26, 27, 30, 33, 34, 40, 43, 46, 47, 50, 54, 57, 63, 64, 67, 68, 75, 78, 79, 82, 85, 86, 89, 92, 93, 96, 99, 102, 103, 106, 108, 112, 115, 116, 119, 120, 123, 126, 130, 133, 137, 140, 143]
DHD_73
[2, 6, 9, 10, 12, 16, 17, 23, 24, 27, 30, 31, 34, 36, 37, 40, 43, 44, 47, 51, 54, 57, 58, 61, 65, 69, 79, 82, 86, 89, 92, 93, 96, 99, 100, 103, 104, 107, 117, 120, 124, 127, 131, 134, 137, 138, 141, 142, 145, 148, 149]
DHD_88
[2, 3, 6, 9, 13, 16, 20, 23, 27, 30, 34, 37, 48, 51, 52, 55, 56, 58, 59, 62, 63, 65, 66, 69, 70, 72, 73, 76, 79, 80, 81, 83, 87, 90, 91, 94, 97, 98, 101, 104, 105, 108, 111, 112, 115, 116, 121, 125, 128, 132, 135, 136, 139, 140, 142, 143, 146, 149, 150, 153, 154]
DHD_89
[1, 2, 5, 8, 9, 12, 15, 16, 19, 22, 23, 26, 29, 30, 33, 34, 36, 37, 38, 48, 51, 55, 58, 62, 65, 69, 72, 79, 82, 83, 86, 87, 89, 90, 93, 94, 97, 100, 101, 103, 104, 107, 108, 109, 110, 111, 114, 117, 118, 121, 124, 128, 131, 135, 138, 139, 142, 145, 146]
DHD_90
[1, 2, 5, 6, 8, 9, 12, 13, 16, 19, 20, 23, 26, 27, 29, 30, 33, 34, 37, 39, 43, 46, 47, 50, 54, 57, 61, 64, 68, 71, 75, 77, 78, 81, 82, 85, 88, 89, 91, 92, 95, 96, 99, 102, 103, 106, 109, 110, 113, 116, 119, 122, 125, 126, 129, 132, 133, 136, 139, 140, 143, 146, 147, 150, 151]
DHD_91
[2, 5, 9, 12, 16, 17, 19, 23, 26, 27, 30, 33, 39, 40, 43, 46, 50, 53, 57, 60, 64, 67, 70, 74, 77, 78, 81, 84, 85, 88, 91, 92, 95, 96, 98, 99, 101, 109, 112, 116, 119, 123, 126, 130, 133, 137, 138]
DHD_92
[5, 6, 8, 9, 12, 13, 15, 16, 19, 20, 22, 23, 26, 27, 29, 30, 33, 36, 37, 38, 42, 46, 49, 50, 53, 56, 57, 59, 60, 63, 67, 70, 71, 74, 77, 80, 81, 84, 87, 88, 91, 94, 95, 98, 101, 102, 105, 109, 110, 114, 118, 121, 125, 128, 129, 132, 135, 136, 139, 142, 143]
DHD_93
[2, 5, 6, 9, 10, 12, 13, 16, 19, 20, 23, 26, 27, 30, 34, 35, 37, 40, 44, 47, 51, 54, 58, 61, 65, 76, 79, 83, 86, 87, 90, 93, 94, 97, 100, 104, 107, 109, 113, 116, 117, 120, 123, 124, 127, 130, 131, 134, 137, 138, 141, 144, 145]
DHD_94
[1, 5, 8, 9, 12, 15, 16, 19, 22, 23, 26, 29, 30, 33, 37, 45, 48, 51, 52, 55, 59, 62, 66, 69, 73, 75, 76, 84, 87, 88, 91, 94, 98, 101, 102, 105, 108, 109, 111, 112, 115, 117, 118, 122, 126, 129, 130, 133, 136, 140, 143, 147, 150, 151, 154]
DHD_95
[2, 6, 9, 13, 16, 20, 23, 26, 27, 30, 34, 37, 39, 41, 42, 45, 48, 49, 52, 55, 56, 59, 62, 63, 66, 69, 70, 72, 73, 75, 81, 85, 88, 91, 92, 95, 96, 98, 99, 102, 105, 106, 109, 110, 113, 114, 120, 123, 124, 127, 130, 131, 134, 137, 138, 141, 145, 148, 151]
DHD_96
[1, 5, 6, 9, 10, 12, 13, 16, 19, 20, 23, 26, 27, 30, 33, 34, 42, 45, 46, 49, 52, 53, 56, 59, 60, 63, 66, 67, 70, 74, 75, 77, 81, 84, 88, 91, 95, 98, 102, 105, 114, 118, 119, 122, 123, 126, 129, 130, 132, 133, 136, 137, 139, 140, 143, 144, 146, 147, 150]
DHD_97
[1, 2, 5, 6, 8, 9, 12, 15, 16, 19, 20, 22, 23, 26, 27, 29, 30, 32, 33, 37, 39, 41, 44, 47, 51, 54, 58, 61, 65, 68, 71, 72, 79, 82, 83, 86, 89, 90, 93, 96, 97, 100, 103, 104, 107, 110, 115, 116, 119, 120, 121, 123, 126, 127, 130, 133, 134, 136, 137, 140, 141, 144, 147]
DHD_98
[6, 7, 9, 13, 16, 20, 23, 27, 30, 34, 35, 38, 43, 44, 50, 51, 53, 54, 57, 60, 61, 64, 67, 68, 71, 72, 74, 75, 78, 82, 85, 86, 89, 92, 93, 96, 99, 100, 103, 106, 110, 119, 123, 127, 130, 133, 134, 137, 141, 144, 148, 151, 152]
DHD_99
[2, 5, 6, 9, 12, 16, 19, 20, 23, 26, 30, 33, 34, 46, 50, 53, 57, 60, 64, 67, 70, 71, 74, 78, 82, 85, 89, 92, 96, 99, 103, 106, 110, 113, 123, 126, 130, 133, 137, 140, 141, 144, 147, 148, 151, 154, 155]

TABLE 2-continued

Interface residues by position number across both chains 'a' and 'b'

DHD_100
[1, 5, 8, 9, 12, 15, 16, 19, 22, 23, 26, 29, 30, 33, 38, 41, 42, 45, 49, 52, 55, 56, 59, 63, 66, 70, 73, 74, 77, 80, 81, 84, 87, 88, 91, 94, 95, 98, 101, 102, 104, 105, 106, 108, 109, 112, 115, 119, 122, 123, 126, 129, 130, 133, 136, 137]
DHD_101
[5, 6, 9, 12, 13, 16, 20, 23, 27, 30, 34, 39, 43, 46, 47, 50, 53, 54, 57, 60, 64, 67, 68, 71, 74, 75, 78, 79, 81, 84, 85, 88, 92, 95, 99, 102, 106, 109, 119, 120, 123, 126, 130, 133, 134, 137, 138, 140, 144, 147, 151]
DHD_102
[6, 9, 13, 16, 20, 22, 23, 27, 30, 34, 38, 44, 47, 51, 54, 55, 57, 58, 61, 65, 68, 69, 72, 75, 80, 83, 86, 90, 93, 97, 100, 104, 107, 108, 112, 113, 117, 121, 124, 128, 131, 132, 135, 138, 142, 145]
DHD_103
[1, 2, 5, 6, 8, 9, 13, 16, 17, 19, 20, 23, 27, 30, 34, 39, 43, 46, 47, 50, 53, 54, 57, 61, 64, 68, 70, 71, 79, 80, 82, 86, 89, 93, 94, 96, 100, 103, 106, 112, 116, 119, 123, 126, 130, 133, 134, 137, 140]
DHD_104
[6, 9, 10, 13, 16, 17, 19, 20, 23, 24, 27, 30, 31, 34, 45, 48, 52, 55, 59, 62, 66, 69, 80, 83, 84, 87, 90, 94, 97, 98, 101, 104, 113, 114, 117, 120, 124, 127, 131, 134, 138, 141, 144, 145]
DHD_105
[9, 12, 16, 19, 23, 26, 30, 33, 37, 41, 43, 44, 47, 50, 51, 54, 57, 58, 61, 64, 65, 68, 71, 72, 79, 82, 83, 86, 89, 90, 93, 97, 100, 101, 103, 104, 107, 118, 121, 122, 125, 128, 129, 132, 135, 136, 139, 142, 143, 146, 147]
DHD_106
[2, 3, 6, 9, 10, 12, 13, 16, 17, 20, 23, 24, 27, 30, 34, 43, 46, 50, 53, 57, 60, 64, 67, 71, 74, 78, 81, 85, 88, 92, 93, 95, 99, 102, 103, 106, 109, 110, 113, 120, 121, 123, 127, 128, 130, 134, 135, 137, 141, 144, 148, 151, 155]
DHD_107
[2, 6, 9, 10, 13, 16, 20, 23, 24, 27, 30, 31, 34, 40, 43, 46, 50, 53, 56, 57, 60, 63, 64, 67, 71, 73, 75, 81, 84, 85, 88, 91, 92, 95, 98, 99, 102, 106, 109, 114, 115, 116, 119, 122, 123, 125, 126, 129, 130, 133, 136, 137, 140, 143, 144, 146]
DHD_108
[2, 6, 7, 10, 17, 20, 21, 24, 25, 28, 35, 42, 43, 46, 50, 53, 57, 60, 61, 64, 68, 71, 75, 82, 86, 89, 93, 97, 100, 104, 111, 115, 116, 123, 124, 127, 128, 130, 131, 134, 135, 138, 141, 142, 145, 146, 149, 152, 153, 156]
DHD_109
[6, 7, 10, 14, 17, 21, 25, 28, 32, 35, 41, 42, 44, 45, 48, 49, 52, 55, 56, 59, 60, 62, 63, 66, 70, 77, 81, 84, 85, 88, 92, 95, 99, 102, 106, 109, 111, 116, 117, 120, 123, 124, 127, 130, 131, 134, 135, 138, 141, 142]
DHD_110
[5, 6, 9, 13, 17, 20, 24, 27, 31, 35, 38, 48, 49, 52, 53, 56, 59, 60, 63, 66, 67, 70, 74, 77, 78, 81, 84, 85, 88, 91, 92, 95, 96, 99, 102, 103, 106, 109, 110, 113, 114, 117, 128, 129, 132, 136, 139, 143, 147, 150, 154, 157, 161]
DHD_111
[5, 6, 9, 10, 13, 16, 17, 20, 23, 24, 27, 28, 31, 34, 35, 47, 51, 54, 58, 62, 65, 69, 72, 76, 80, 84, 87, 90, 91, 94, 95, 98, 101, 102, 105, 109, 112, 113, 116, 122, 125, 129, 132, 136, 140, 143, 147, 154, 158]
DHD_112
[6, 13, 16, 17, 20, 24, 27, 31, 35, 38, 48, 51, 52, 55, 58, 59, 62, 63, 66, 69, 70, 73, 76, 77, 80, 81, 88, 91, 92, 95, 99, 102, 106, 109, 113, 120, 121, 123, 124, 126, 127, 130, 133, 134, 137, 138, 141, 144, 145, 148, 151, 152, 155, 156]
DHD_113
[6, 9, 13, 14, 16, 20, 23, 27, 30, 31, 34, 39, 43, 44, 47, 48, 51, 54, 55, 58, 61, 62, 65, 66, 68, 69, 72, 73, 76, 80, 83, 84, 87, 90, 91, 94, 97, 98, 101, 102, 105, 108, 109, 112, 117, 122, 125, 129, 133, 136, 140, 143, 147, 151]
DHD_114
[5, 6, 9, 10, 13, 16, 17, 20, 23, 24, 27, 30, 31, 34, 35, 38, 39, 41, 44, 47, 51, 55, 58, 62, 65, 69, 72, 76, 81, 84, 87, 88, 91, 95, 98, 99, 102, 105, 106, 108, 109, 113, 117, 122, 126, 129, 130, 133, 137, 140, 144, 147, 151, 155]
DHD_115
[5, 6, 9, 12, 13, 16, 17, 20, 23, 24, 27, 30, 31, 34, 37, 43, 47, 50, 54, 57, 58, 61, 65, 68, 69, 72, 74, 75, 76, 78, 79, 82, 85, 86, 89, 90, 93, 96, 97, 100, 103, 104, 107, 108, 121, 125, 128, 132, 135, 139, 143, 146, 150, 153]
DHD_116
[3, 6, 7, 10, 14, 17, 21, 24, 25, 28, 32, 35, 36, 48, 49, 52, 56, 59, 60, 63, 66, 67, 70, 71, 74, 77, 78, 81, 87, 88, 91, 95, 98, 99, 102, 103, 105, 106, 109, 110, 113, 116, 129, 133, 136, 140, 144, 147, 151, 154, 158, 161, 162]
DHD_117
[6, 10, 13, 17, 20, 21, 24, 27, 28, 31, 35, 38, 40, 44, 47, 48, 51, 55, 58, 59, 62, 65, 66, 69, 72, 73, 76, 77, 79, 83, 84, 87, 90, 91, 94, 98, 101, 102, 105, 108, 109, 112, 116, 125, 126, 129, 133, 136, 140, 141, 143, 144, 147, 151, 154, 155]
DHD_118
[6, 10, 13, 14, 17, 20, 24, 28, 31, 35, 38, 49, 52, 53, 56, 59, 60, 63, 66, 67, 70, 74, 77, 81, 82, 85, 88, 92, 95, 99, 102, 106, 109, 110, 113, 116, 118, 119, 123, 127, 130, 131, 134, 137, 138, 141, 145, 148, 149, 152, 153]
DHD_119
[2, 6, 10, 13, 14, 17, 20, 21, 24, 25, 28, 31, 32, 35, 40, 41, 45, 46, 49, 52, 56, 60, 63, 67, 71, 74, 75, 78, 82, 84, 85, 88, 89, 92, 95, 96, 99, 103, 106, 107, 110, 113, 114, 117, 120, 122, 127, 131, 134, 138, 141, 142, 145, 148, 149, 152, 156]
DHD_120
[7, 10, 13, 14, 17, 21, 25, 28, 31, 32, 35, 41, 44, 45, 48, 49, 51, 52, 55, 56, 59, 62, 63, 66, 69, 70, 73, 74, 79, 83, 84, 87, 91, 94, 95, 98, 101, 102, 105, 109, 112, 113, 122, 126, 129, 133, 136, 137, 140, 144, 147, 148, 151]
DHD_121
[5, 6, 9, 13, 16, 20, 23, 27, 30, 37, 43, 46, 47, 50, 53, 54, 57, 60, 61, 64, 67, 68, 71, 74, 75, 82, 85, 86, 89, 92, 93, 96, 99, 100, 103, 106, 107, 110, 113, 115, 120, 123, 127, 130, 134, 137, 141, 144, 148]
DHD_122
[6, 10, 13, 14, 17, 21, 24, 25, 28, 31, 32, 35, 41, 44, 45, 48, 51, 52, 55, 59, 62, 63, 66, 69, 70, 73, 74, 75, 81, 82, 85, 88, 92, 95, 96, 99, 100, 102, 103, 106, 107, 110, 113, 123, 127, 131, 134, 138, 141, 145, 152, 156, 157]
DHD_123
[1, 3, 6, 10, 13, 14, 17, 20, 21, 24, 28, 31, 32, 35, 38, 39, 40, 42, 44, 48, 51, 52, 55, 59, 62, 66, 69, 70, 73, 74, 80, 83, 84, 87, 91, 94, 95, 98, 102, 105, 109, 110, 115, 118, 119, 122, 123, 126, 129, 130, 133, 134, 136, 137, 140, 144, 145, 147, 148]

TABLE 2-continued

Interface residues by position number across both chains 'a' and 'b'

DHD_124
[6, 9, 10, 13, 16, 17, 20, 24, 27, 28, 31, 34, 35, 38, 43, 44, 47, 50, 51, 54, 58, 61, 62, 65, 68, 69, 72, 79, 83, 86, 87, 90, 91, 94, 97, 98, 101, 104, 105, 108, 112, 121, 125, 128, 129, 132, 136, 139, 143, 146, 147, 150, 154, 155]
DHD_125
[2, 6, 9, 10, 13, 16, 17, 20, 24, 27, 28, 31, 35, 38, 43, 46, 47, 50, 54, 57, 58, 61, 65, 68, 69, 72, 73, 75, 79, 82, 83, 86, 90, 93, 97, 100, 101, 104, 107, 108, 111, 121, 122, 125, 129, 132, 133, 136, 139, 140, 143, 147, 150]
DHD_126
[1, 2, 5, 6, 9, 10, 12, 13, 16, 20, 23, 24, 27, 28, 30, 31, 34, 43, 47, 50, 51, 54, 58, 61, 62, 65, 68, 69, 72, 83, 86, 87, 90, 94, 97, 98, 101, 105, 108, 109, 112, 115, 121, 122, 125, 128, 132, 136, 139, 140, 143, 146, 147, 150, 151]
DHD_127
[3, 6, 9, 10, 13, 14, 16, 17, 20, 23, 24, 27, 31, 34, 39, 44, 47, 51, 54, 58, 61, 65, 68, 72, 79, 83, 86, 90, 93, 96, 97, 100, 103, 104, 107, 111, 114, 117, 121, 124, 128, 131, 135, 139, 142, 145, 146]
DHD_128
[6, 9, 10, 13, 16, 17, 20, 23, 24, 27, 30, 31, 32, 40, 44, 47, 51, 54, 58, 61, 65, 68, 72, 79, 83, 86, 87, 90, 93, 97, 100, 104, 118, 121, 125, 128, 132, 135, 139, 142, 146]
DHD_129
[2, 5, 6, 9, 12, 13, 16, 19, 20, 23, 24, 26, 27, 30, 34, 42, 46, 49, 53, 56, 60, 63, 64, 67, 70, 74, 80, 81, 84, 88, 91, 94, 95, 98, 101, 102, 105, 109, 112, 122, 125, 126, 129, 132, 133, 135, 136, 139, 143, 146, 147, 150, 153]
DHD_130
[3, 6, 10, 13, 17, 20, 24, 27, 31, 34, 37, 41, 44, 45, 48, 51, 52, 55, 58, 59, 62, 65, 66, 69, 70, 72, 73, 79, 83, 86, 90, 93, 97, 100, 104, 107, 111, 116, 121, 122, 125, 128, 129, 132, 135, 136, 139, 142, 143, 146, 149, 150, 153]
DHD_131
[3, 6, 9, 10, 13, 16, 17, 20, 24, 27, 31, 34, 44, 48, 51, 52, 54, 55, 58, 59, 61, 62, 65, 66, 69, 72, 73, 76, 83, 87, 90, 91, 94, 97, 101, 104, 108, 111, 121, 124, 125, 128, 131, 132, 135, 138, 139, 142, 145, 146, 149, 150, 152, 153]
DHD_132
[5, 6, 9, 12, 13, 16, 19, 20, 23, 26, 27, 30, 33, 34, 37, 39, 43, 46, 47, 50, 54, 57, 64, 68, 71, 74, 75, 85, 86, 89, 92, 93, 95, 99, 100, 103, 105, 106, 107, 110, 114, 120, 123, 127, 130, 134, 137, 141, 144, 148]
DHD_133
[6, 10, 13, 17, 20, 21, 24, 27, 31, 34, 39, 44, 45, 48, 51, 52, 55, 58, 59, 62, 65, 66, 69, 72, 73, 76, 83, 87, 90, 94, 97, 101, 104, 108, 111, 112, 121, 122, 125, 126, 129, 132, 136, 139, 143, 146, 149, 150, 153]
DHD_134
[6, 9, 10, 13, 16, 17, 20, 23, 24, 27, 30, 31, 34, 38, 43, 47, 50, 54, 57, 61, 64, 68, 71, 75, 82, 85, 89, 92, 96, 99, 103, 106, 110, 111, 118, 122, 125, 129, 132, 133, 136, 139, 140, 143, 146]
DHD_135
[2, 5, 6, 9, 12, 13, 16, 19, 20, 23, 26, 27, 30, 33, 34, 37, 38, 46, 50, 53, 57, 60, 64, 67, 71, 80, 81, 84, 87, 91, 94, 95, 98, 101, 102, 105, 108, 115, 119, 122, 126, 129, 130, 133, 136, 140, 143]
DHD_136
[5, 6, 8, 9, 12, 15, 16, 19, 22, 23, 26, 29, 30, 33, 36, 37, 41, 45, 48, 52, 55, 59, 62, 66, 69, 70, 72, 73, 79, 82, 83, 86, 89, 90, 93, 97, 100, 104, 107, 117, 120, 121, 124, 127, 128, 131, 134, 135, 138, 141, 142]
DHD_137
[2, 6, 9, 13, 16, 17, 20, 23, 24, 27, 30, 31, 34, 43, 46, 47, 50, 54, 57, 61, 64, 68, 71, 72, 74, 78, 81, 85, 89, 92, 96, 99, 102, 103, 107, 113, 116, 117, 120, 123, 124, 127, 130, 131, 134, 137, 138, 141]
DHD_138
[6, 10, 13, 17, 20, 24, 27, 31, 34, 43, 47, 50, 54, 57, 61, 64, 68, 71, 82, 86, 89, 93, 96, 100, 103, 107, 110, 119, 120, 123, 126, 127, 130, 133, 134, 137, 140, 143, 144, 147, 148, 150, 151]
DHD_139
[2, 5, 6, 9, 12, 13, 16, 19, 20, 23, 26, 27, 30, 34, 37, 38, 39, 45, 49, 52, 56, 59, 63, 66, 76, 79, 80, 83, 86, 87, 90, 93, 94, 97, 100, 101, 104, 107, 108, 113, 115, 118, 121, 125, 128, 132, 135, 139, 142, 143, 145, 146]
DHD_140
[5, 6, 9, 12, 13, 16, 19, 20, 23, 26, 27, 30, 33, 36, 38, 43, 47, 50, 51, 54, 57, 61, 64, 68, 71, 78, 81, 85, 88, 89, 92, 95, 96, 99, 102, 103, 120, 124, 127, 131, 134, 135, 138, 141, 145, 148]
DHD_141
[6, 10, 13, 17, 20, 24, 27, 28, 31, 34, 37, 40, 43, 44, 47, 48, 51, 54, 57, 58, 61, 62, 64, 65, 68, 71, 72, 81, 85, 88, 92, 95, 99, 102, 106, 109, 113, 118, 120, 123, 124, 127, 130, 131, 134, 137, 138, 141, 144, 145, 148, 151, 152]
DHD_142
[1, 2, 5, 6, 9, 12, 13, 15, 16, 19, 20, 23, 24, 26, 27, 30, 33, 40, 44, 47, 51, 54, 58, 61, 68, 69, 72, 75, 78, 79, 82, 85, 86, 89, 92, 95, 96, 99, 100, 103, 106, 107, 110, 120, 121, 124, 127, 131, 134, 138, 141, 145, 148, 152]
DHD_143
[2, 6, 9, 13, 16, 17, 20, 23, 27, 30, 34, 39, 44, 48, 51, 55, 58, 62, 65, 66, 69, 72, 73, 83, 87, 90, 94, 97, 101, 104, 108, 111, 121, 124, 125, 128, 131, 132, 135, 136, 138, 139, 142, 145, 146, 149, 150, 152, 153]
DHD_144
[1, 5, 6, 9, 12, 13, 16, 19, 20, 23, 26, 27, 30, 33, 42, 46, 49, 53, 56, 60, 63, 67, 70, 73, 74, 76, 77, 80, 81, 83, 84, 87, 88, 90, 91, 94, 95, 98, 99, 101, 102, 105, 108, 109, 117, 120, 121, 124, 128, 131, 135, 138, 142, 145, 149, 150]
DHD_145
[5, 6, 9, 12, 13, 16, 19, 20, 23, 26, 30, 33, 34, 47, 50, 54, 57, 61, 64, 68, 71, 75, 78, 85, 86, 88, 89, 92, 95, 96, 99, 102, 103, 106, 109, 110, 113, 123, 127, 130, 134, 137, 141, 144, 145, 148, 151, 155]
DHD_146
[2, 5, 6, 9, 10, 12, 13, 16, 19, 23, 26, 27, 30, 33, 34, 40, 43, 46, 50, 53, 54, 57, 60, 61, 64, 67, 71, 78, 81, 82, 85, 88, 89, 92, 95, 96, 99, 100, 102, 103, 106, 126, 129, 133, 136, 140, 143, 147, 150, 151]
DHD_147
[6, 7, 10, 13, 14, 17, 20, 24, 27, 31, 34, 37, 38, 42, 43, 46, 49, 50, 53, 54, 56, 57, 60, 63, 64, 67, 70, 71, 74, 81, 84, 88, 91, 95, 98, 102, 105, 109, 116, 119, 123, 126, 127, 130, 133, 137, 140, 141, 144, 147, 148]
DHD_149
[1, 5, 6, 9, 12, 13, 16, 17, 19, 23, 26, 27, 30, 33, 34, 42, 46, 49, 53, 56, 60, 63, 67, 70, 74, 75, 77, 81, 84, 85, 88, 91, 92, 95, 98, 102, 105, 106, 116, 120, 123, 124, 127, 130, 131, 134, 137, 138, 141, 144, 145, 148]

TABLE 2-continued

Interface residues by position number across both chains 'a' and 'b'

DHD_150
[1, 2, 5, 6, 9, 12, 13, 16, 19, 20, 23, 26, 27, 30, 33, 34, 42, 46, 49, 50, 53, 56, 60, 63, 67, 70, 74, 75, 77, 81, 88, 91, 95, 98, 102, 105, 108, 116, 120, 123, 124, 127, 130, 131, 134, 137, 138, 141, 144, 145, 148]

DHD_151
[5, 9, 12, 13, 16, 19, 20, 23, 26, 27, 30, 33, 34, 36, 43, 46, 47, 50, 54, 57, 61, 64, 68, 71, 74, 78, 81, 82, 85, 88, 89, 92, 95, 96, 99, 102, 103, 106, 111, 116, 120, 123, 127, 130, 134, 137, 141, 144, 148]

DHD_152
[5, 6, 9, 12, 13, 19, 20, 23, 26, 27, 30, 33, 34, 36, 40, 43, 46, 47, 50, 54, 57, 61, 64, 68, 71, 74, 78, 81, 82, 85, 88, 89, 92, 95, 96, 99, 102, 103, 106, 111, 116, 120, 123, 127, 134, 137, 141, 144, 148]

DHD_153
[6, 10, 13, 14, 17, 20, 21, 24, 27, 31, 34, 44, 45, 48, 51, 52, 58, 59, 62, 65, 66, 69, 73, 74, 76, 80, 83, 84, 87, 90, 91, 94, 97, 101, 104, 105, 107, 115, 118, 122, 125, 126, 129, 132, 136, 139, 143]

DHD_154
[2, 5, 6, 9, 12, 16, 19, 20, 23, 26, 27, 30, 33, 34, 40, 43, 47, 50, 54, 57, 61, 64, 68, 71, 72, 74, 78, 81, 85, 88, 92, 95, 99, 102, 106, 109, 115, 116, 119, 122, 123, 126, 129, 133, 136, 137, 140, 143, 144, 147]

DHD_155
[5, 6, 9, 13, 16, 19, 20, 23, 27, 30, 34, 43, 47, 50, 53, 54, 57, 61, 64, 68, 75, 78, 79, 81, 82, 85, 88, 89, 92, 95, 96, 99, 102, 109, 113, 116, 120, 123, 127, 130, 134, 137]

DHD_156
[5, 6, 9, 12, 13, 16, 19, 20, 23, 26, 27, 30, 37, 40, 44, 47, 51, 54, 58, 61, 65, 68, 75, 76, 79, 82, 83, 89, 90, 93, 96, 97, 100, 104, 124, 128, 131, 132, 135, 138, 142, 145, 146]

DHD_157
[5, 6, 9, 13, 16, 20, 23, 27, 30, 33, 34, 37, 39, 43, 44, 47, 48, 51, 54, 55, 58, 61, 62, 65, 68, 69, 72, 75, 76, 79, 83, 86, 87, 90, 93, 94, 97, 100, 101, 104, 107, 118, 122, 125, 129, 132, 136, 139, 143, 146, 150]

DHD13_2341
[4, 5, 8, 11, 12, 15, 18, 19, 22, 25, 29, 32, 33, 36, 39, 41, 71, 91, 95, 98, 102, 105, 106, 109, 112, 113, 116, 117, 119, 121, 125, 126, 129, 132, 133, 136, 137, 139, 140, 143, 144, 146, 147, 150, 153, 154]

DHD13_AAAA
[6, 9, 13, 16, 17, 20, 23, 24, 27, 30, 34, 39, 44, 47, 48, 51, 54, 55, 58, 61, 62, 65, 68, 69, 72, 75, 82, 85, 89, 92, 96, 99, 100, 103, 106, 107, 109, 110, 111, 115, 123, 124, 127, 128, 130, 134, 137, 138, 141, 144, 145, 148, 149, 151]

DHD13_B AAA
[6, 9, 12, 13, 16, 17, 20, 23, 24, 27, 30, 34, 37, 38, 39, 44, 47, 51, 54, 55, 58, 61, 62, 65, 68, 69, 72, 75, 82, 85, 89, 92, 95, 96, 99, 100, 103, 106, 110, 115, 123, 127, 130, 134, 137, 138, 141, 144, 145, 148, 149, 151]

DHD13_XAAA
[6, 9, 13, 16, 17, 20, 23, 24, 27, 30, 34, 37, 38, 39, 44, 47, 48, 51, 54, 55, 58, 61, 62, 65, 68, 69, 72, 75, 82, 85, 89, 92, 96, 99, 100, 103, 106, 109, 110, 115, 123, 127, 130, 134, 137, 138, 141, 144, 145, 148, 149, 151]

DHD13_XAAX
[6, 9, 12, 13, 16, 17, 20, 23, 24, 27, 30, 34, 37, 38, 39, 44, 47, 48, 51, 54, 55, 58, 61, 62, 65, 68, 69, 72, 75, 82, 85, 89, 92, 96, 99, 100, 103, 106, 109, 110, 115, 123, 127, 130, 134, 137, 138, 141, 144, 145, 148, 149, 151]

DHD13_XAXA
[6, 9, 13, 16, 17, 20, 23, 24, 27, 30, 34, 37, 38, 39, 44, 47, 48, 51, 54, 55, 58, 61, 62, 65, 68, 69, 72, 75, 82, 85, 89, 92, 96, 99, 100, 103, 106, 109, 110, 115, 123, 127, 130, 134, 137, 138, 141, 144, 145, 148, 149, 151]

DHD15
[5, 6, 9, 12, 13, 16, 19, 20, 23, 26, 27, 30, 33, 34, 37, 39, 40, 44, 47, 48, 51, 52, 55, 58, 59, 62, 65, 69, 72, 78, 82, 83, 86, 89, 90, 93, 96, 97, 100, 103, 104, 107, 110, 111, 114, 116, 117, 121, 125, 128, 129, 132, 135, 136, 139, 142, 143, 146, 149]

DHD17
[6, 9, 10, 13, 16, 17, 20, 23, 24, 27, 30, 31, 34, 38, 42, 43, 46, 50, 53, 57, 60, 64, 67, 71, 75, 81, 84, 88, 91, 95, 98, 102, 105, 106, 109, 118, 121, 125, 128, 132, 135, 136, 139, 142, 146]

DHD20
[3, 6, 9, 10, 13, 16, 17, 20, 23, 24, 27, 30, 31, 34, 38, 42, 43, 46, 50, 53, 57, 60, 61, 64, 67, 68, 71, 75, 78, 81, 85, 88, 91, 92, 95, 98, 99, 102, 105, 109, 118, 121, 125, 128, 132, 135, 139, 142, 146, 150]

DHD21
[6, 9, 10, 13, 16, 20, 23, 24, 27, 30, 31, 34, 38, 43, 44, 46, 47, 50, 51, 53, 54, 57, 58, 60, 61, 63, 64, 65, 68, 71, 72, 75, 78, 79, 82, 85, 89, 92, 93, 96, 99, 100, 103, 107, 108, 112, 113, 116, 119, 120, 123, 126, 127, 130, 133, 134, 137, 141, 142]

DHD25
[2, 5, 6, 9, 12, 13, 16, 19, 23, 26, 27, 30, 44, 47, 48, 51, 54, 55, 58, 61, 62, 65, 68, 69, 72, 75, 76, 83, 86, 87, 90, 93, 94, 97, 100, 101, 104, 107, 114, 115, 117, 118, 121, 124, 128, 131, 132, 135, 138, 142, 145]

DHD27
[5, 6, 9, 12, 15, 16, 19, 22, 23, 26, 29, 30, 33, 37, 41, 42, 45, 49, 52, 56, 59, 63, 66, 70, 73, 74, 77, 81, 84, 88, 91, 95, 98, 102, 105, 108, 115, 116, 119, 122, 123, 126, 129, 130, 133, 136, 137, 140, 141, 143, 144, 147, 148]

DHD30
[5, 6, 8, 9, 12, 15, 16, 19, 22, 23, 26, 29, 30, 33, 34, 37, 39, 42, 45, 49, 52, 56, 59, 63, 66, 70, 75, 78, 82, 85, 89, 92, 96, 99, 103, 106, 113, 116, 117, 120, 124, 127, 131, 134, 138, 141, 144, 145]

DHD33
[1, 5, 6, 9, 12, 13, 16, 19, 20, 23, 26, 27, 30, 33, 34, 39, 40, 43, 46, 47, 50, 57, 60, 61, 64, 68, 71, 75, 78, 82, 85, 86, 89, 92, 93, 96, 99, 100, 103, 112, 113, 116, 119, 120, 123, 126, 127, 130, 133, 134, 137, 140, 141, 144]

DHD34_XAAAA
[1, 5, 8, 9, 12, 16, 19, 23, 26, 29, 30, 33, 37, 45, 48, 49, 52, 55, 56, 59, 62, 63, 66, 69, 70, 73, 76, 77, 86, 90, 93, 97, 100, 104, 105, 107, 111, 114, 124, 125, 128, 131, 132, 135, 138, 142, 145, 149, 152, 153, 156, 157]

DHD34_XAAXA
[1, 5, 8, 9, 12, 16, 19, 23, 26, 29, 30, 33, 37, 45, 48, 49, 52, 55, 56, 59, 62, 63, 66, 69, 70, 73, 76, 77, 86, 90, 93, 97, 100, 104, 105, 107, 108, 111, 114, 124, 125, 128, 131, 132, 135, 138, 142, 145, 149, 152, 153, 156, 157]

TABLE 2-continued

Interface residues by position number across both chains 'a' and 'b'

DHD34_XAXXA
[1, 5, 8, 9, 12, 16, 19, 22, 23, 26, 29, 30, 33, 37, 45, 48, 49, 52, 55, 56, 59, 62, 63, 66, 69, 70, 73, 76, 77, 86, 90, 93, 97, 100, 104, 105, 107, 108, 111, 114, 117, 124, 125, 128, 131, 132, 135, 138, 142, 145, 149, 152, 153, 156, 157]
DHD36
[2, 6, 9, 13, 16, 20, 23, 27, 30, 33, 34, 39, 40, 42, 43, 46, 47, 50, 51, 53, 54, 57, 58, 61, 64, 75, 79, 82, 86, 89, 93, 96, 97, 100, 103, 110, 114, 117, 118, 121, 124, 125, 128, 131, 132, 135, 138, 139, 142, 143]
DHD37_ABXB
[2, 5, 9, 11, 12, 15, 16, 19, 23, 26, 29, 30, 33, 37, 43, 46, 49, 50, 53, 56, 57, 59, 60, 63, 64, 67, 77, 81, 84, 88, 91, 92, 95, 98, 99, 102, 105, 113, 116, 119, 120, 123, 126, 130, 133, 134, 137, 140, 141, 144]
DHD37_AXBB
[2, 5, 9, 12, 16, 18, 19, 22, 23, 26, 29, 30, 33, 37, 43, 46, 49, 50, 52, 53, 56, 57, 60, 67, 70, 71, 77, 78, 81, 84, 88, 91, 95, 96, 99, 102, 105, 113, 116, 119, 120, 123, 126, 127, 130, 133, 134, 137, 140, 144]
DHD37_AXXB
[2, 5, 9, 11, 12, 15, 16, 19, 22, 23, 26, 29, 30, 33, 37, 43, 46, 49, 50, 53, 56, 57, 59, 60, 63, 64, 67, 77, 81, 84, 88, 89, 92, 95, 98, 99, 102, 105, 113, 116, 119, 120, 123, 126, 130, 133, 134, 137, 140, 141, 144]
DFID37_BBBB
[5, 9, 12, 16, 19, 22, 23, 26, 30, 33, 42, 43, 46, 50, 53, 56, 57, 60, 63, 64, 66, 67, 74, 77, 78, 81, 84, 85, 88, 92, 95, 98, 99, 102, 105, 108, 111, 113, 116, 119, 123, 126, 130, 133, 137, 140, 141, 144]
DHD37_XBBA
[2, 5, 8, 9, 12, 16, 19, 23, 25, 26, 29, 30, 33, 37, 43, 45, 46, 49, 50, 53, 60, 63, 64, 67, 70, 71, 77, 78, 81, 84, 85, 88, 91, 95, 98, 102, 103, 105, 113, 116, 119, 120, 123, 126, 127, 130, 133, 137, 140, 141, 144]
DHD37_XBXB
[2, 5, 9, 11, 12, 15, 16, 19, 23, 26, 30, 33, 37, 43, 46, 50, 53, 56, 57, 59, 60, 63, 64, 67, 77, 81, 84, 88, 92, 95, 98, 99, 102, 105, 113, 116, 119, 120, 123, 126, 130, 133, 134, 137, 140, 141, 144]
XAAX
[3, 6, 9, 13, 16, 20, 23, 27, 30, 34, 43, 47, 50, 54, 57, 61, 64, 68, 71, 72, 3, 6, 9, 13, 16, 20, 23, 27, 30, 34, 43, 47, 50, 54, 57, 61, 64, 68, 71, 72]
XAXA
[3, 6, 9, 13, 16, 20, 23, 27, 30, 34, 43, 47, 50, 54, 57, 61, 64, 68, 71, 72, 3, 6, 9, 13, 16, 20, 23, 27, 30, 34, 43, 47, 50, 54, 57, 61, 64, 68, 71, 72]

In one embodiment, the monomer A polypeptide and the monomer B polypeptide have their interaction specificity determined by at least one designed hydrogen bond network at the interface between the monomer A and the monomer B. In some aspects, (i) monomer A comprises 1 helix, and monomer B comprises 1 helix; (ii) monomer A comprises 1 helix and monomer B comprises 2 helices; (iii) monomer A comprises 1 helix and monomer B comprises 3 helices, (iv) monomer A comprises 1 helix and monomer B comprises 4 helices; or (v) monomer A comprises 1 helix and monomer B comprises 5 helices, wherein the monomer A and the monomer B comprise a hydrogen bond network, e.g., hydrogen bonds that are capable of being formed by the interface residues according to Table 2. In some aspects, (i) monomer A comprises 2 helices, and monomer B comprises 1 helix; (ii) monomer A comprises 2 helices and monomer B comprises 2 helices; (iii) monomer A comprises 2 helices and monomer B comprises 3 helices, (iv) monomer A comprises 2 helices and monomer B comprises 4 helices; or (v) monomer A comprises 2 helices and monomer B comprises 5 helices, wherein the monomer A and the monomer B comprise a hydrogen bond network, e.g., hydrogen bonds that are capable of being formed by the interface residues according to Table 2. In some aspects, (i) monomer A comprises 3 helices, and monomer B comprises 1 helix; (ii) monomer A comprises 3 helices and monomer B comprises 2 helices; (iii) monomer A comprises 3 helices and monomer B comprises 3 helices, (iv) monomer A comprises 3 helices and monomer B comprises 4 helices; or (v) monomer A comprises 3 helices and monomer B comprises 5 helices, wherein the monomer A and the monomer B comprise a hydrogen bond network, e.g., hydrogen bonds that are capable of being formed by the interface residues according to Table 2. In some aspects, (i) monomer A comprises 4 helices, and monomer B comprises 1 helix; (ii) monomer A comprises 4 helices and monomer B comprises 2 helices; (iii) monomer A comprises 4 helices and monomer B comprises 3 helices, (iv) monomer A comprises 4 helices and monomer B comprises 4 helices; or (v) monomer A comprises 4 helices and monomer B comprises 5 helices, wherein the monomer A and the monomer B comprise a hydrogen bond network, e.g., hydrogen bonds that are capable of being formed by the interface residues according to Table 2. In some aspects, (i) monomer A comprises 5 helices, and monomer B comprises 1 helix; (ii) monomer A comprises 5 helices and monomer B comprises 2 helices; (iii) monomer A comprises 5 helices and monomer B comprises 3 helices, (iv) monomer A comprises 5 helices and monomer B comprises 4 helices; or (v) monomer A comprises 5 helices and monomer B comprises 5 helices, wherein the monomer A and the monomer B comprise a hydrogen bond network, e.g., hydrogen bonds that are capable of being formed by the interface residues according to Table 2.

In a second aspect, the disclosure provides non-naturally occurring polypeptides comprising a polypeptide having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 1-290, or the group consisting of SEQ ID NOS:1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494. The amino acid sequences of SEQ ID NOS: 1-290 are provided in Table 1A, and the amino acid sequences of SEQ ID NOS: 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 are provided in Table 1B, and can be used, for example, to generate the heterodimers of the disclosure.

In some aspects, the disclosure provides non-naturally occurring polypeptides comprising a polypeptide having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 1-290, wherein GlySer at amino acid positions 1 and 2 of SEQ ID NO: 1, 55, 81, 83, 101, 105, 115, 117, 119, 121, 123, 125, 127, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, or 193 are optional, e.g., not present. The amino acid sequences of SEQ ID NOS: 1-290 are provided in Table 1A, and can be used, for example, to generate the heterodimers of the disclosure.

In some aspects, the disclosure provides non-naturally occurring polypeptides comprising a polypeptide having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 1-290, wherein GlySer at amino acid positions 1 and 2 of SEQ ID NO: 6, 8, 14, 16, 26, 30, 32, 34, 36, 38, 40, 42, 46, 48, 54, 56, 58, 60, 62, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 128, 130, 132, 134, 136, 138, 140, 142, 144, 146, 148, 150, 152, 154, 156, 158, 160, 162, 164, 166, 168, 170, 172, 176, 178, 180, 182, 184, 186, 188, 190, 192, or 194 are optional, e.g., not present.

In some aspects, the disclosure provides non-naturally occurring polypeptides comprising a polypeptide having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494. The amino acid sequences of SEQ ID NOS: 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 are provided in Table 1B, and can be used, for example, to generate the heterodimers of the disclosure.

In some aspects, the disclosure provides non-naturally occurring polypeptides comprising a polypeptide having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, wherein the SEQ ID NOs: 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 is not linked to GlySer at the immediate N terminus or the polypeptide does not comprise GlySer at the N terminus.

In some aspects, the disclosure provides non-naturally occurring polypeptides comprising a polypeptide consisting of an amino acid sequence at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494. In some aspects, the disclosure provides non-naturally occurring polypeptides comprising a polypeptide consisting of the sequence of SEQ ID NOs: 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494.

In one embodiment, the amino acid changes from the reference amino acid sequence are conservative amino acid substitutions. In another embodiment, amino acid residues at 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of defined interface positions are invariant compared to the reference amino acid sequence. The defined interface residues are as provided in Table 2.

In a second aspect, the disclosure provides proteins comprising 2, 3, 4, or more non-naturally occurring polypeptides having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 1-290, wherein the 2, 3, 4, or more naturally occurring polypeptides are covalently linked. In some aspects, the disclosure provides proteins comprising 2, 3, 4, or more non-naturally occurring polypeptides having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS: 1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, wherein the 2, 3, 4, or more naturally occurring polypeptides are covalently linked. In some aspects, the sequences of monomer A and monomer B listed herein can be modified (substituted) such that the resulting amino acid sequence maintains a hydrogen bond network of the original amino acid sequence as described in Tables 1A and 1B.

In this aspect, the proteins can be used to generate scaffolds that can be used for any suitable purpose including but not limited to those disclosed herein. In one embodiment, each of the 2, 3, 4, or more non-naturally occurring polypeptides are different. In another embodiment, the 2, 3, 4, or more non-naturally occurring polypeptides may include 2, 3, 4, or more identical polypeptides. In all embodiments, the 2, 3, 4, or more non-naturally occurring polypeptides may, for example, be covalently linked as part of a fusion protein. The 2, 3, 4, or more non-naturally occurring polypeptides may each be separated by an amino acid linker. Any suitable amino acid linker may be used.

In some aspects, the linker is a flexible linker. In some aspects, the linker is a GS linker. In other aspects, the GS linker comprises (GGS)n, (GSEGS)n (SEQ ID NO:423) or (GGGS)n (SEQ ID NO:425), wherein n is an integer between 1 and 100. In some aspects, the linker comprises an amino acid sequence having at least 70%, 75%, 80%, 85%, 90%, 91%, 92%, 93%, 94%, 95%, 96%, 97%, 98%, 99%, or 100% sequence identity along the length of the amino acid sequence as set forth in GSEGSGSEGSGS (SEQ ID NO:427) or GSEGSGSEGSGGS (SEQ ID NO:461). In some aspects, the linker comprises an amino acid sequence having at least 70%, 75%, 80%, 85%, 90%, 91%, 92%, 93%, 94%, 95%, 96%, 97%, 98%, 99%, or 100% sequence identity along the length of the amino acid sequence as set forth in GSEGSGSEGS (SEQ ID NO:429). In some aspects, the linker comprises an amino acid sequence having at least 70%, 75%, 80%, 85%, 90%, 91%, 92%, 93%, 94%, 95%, 96%, 97%, 98%, 99%, or 100% sequence identity along the length of the amino acid sequence as set forth in (GSEGS)n, wherein n is 1 to 10, e.g., 1, 2, 3, 4, 5, 6, 7, 8, 9, or 10 (SEQ ID NO:423).

In one embodiment, each of the 2, 3, 4, or more non-naturally occurring polypeptides have at least 70%, 75%, 80%, 85%, 90%, 91%, 92%, 93%, 94%, 95%, 96%, 97%, 98%, 99%, or 100% sequence identity along the length of the amino acid sequence of an odd-numbered SEQ ID NO: selected from the group consisting of SEQ ID NOS:1-290. In one embodiment, each of the 2, 3, 4, or more non-naturally occurring polypeptides have at least 70%, 75%, 80%, 85%, 90%, 91%, 92%, 93%, 94%, 95%, 96%, 97%, 98%, 99%, or 100% sequence identity along the length of the amino acid sequence of an odd-numbered SEQ ID NO: selected from the group consisting of SEQ ID NOS:1-290, wherein GlySer at amino acid positions 1 and 2 of SEQ ID NO: 1, 55, 81, 83, 101, 105, 115, 117, 119, 121, 123, 125, 127, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, or 193 are optional, e.g., not present. In another embodiment, each of the 2, 3, 4, or more non-naturally occurring polypeptides have at least 70%, 75%, 80%, 85%, 90%, 91%, 92%, 93%, 94%, 95%, 96%, 97%, 98%, 99%, or 100% sequence identity along the length of the amino acid sequence of an even-numbered SEQ ID NO: selected from the group consisting of SEQ ID NOS:1-290. In another embodiment, each of the 2, 3, 4, or more non-naturally occurring polypeptides have at least 70%, 75%, 80%, 85%, 90%, 91%, 92%, 93%, 94%, 95%, 96%, 97%, 98%, 99%, or 100% sequence identity along the length of the amino acid sequence of an even-numbered SEQ ID NO: selected from the group consisting of SEQ ID NOS:1-290, wherein GlySer at amino acid positions 1 and 2 of SEQ ID NO: 6, 8, 14, 16, 26, 30, 32, 34, 36, 38, 40, 42, 46, 48, 54, 56, 58, 60, 62, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 128, 130, 132, 134, 136, 138, 140, 142, 144, 146, 148, 150, 152, 154, 156, 158, 160, 162, 164, 166, 168, 170, 172, 176, 178, 180, 182, 184, 186, 188, 190, 192, or 194 are optional, e.g., not present. In a further embodiment, the 2, 3, 4, or more non-naturally occurring polypeptides include:
  (a) polypeptides having at least 70%, 75%, 80%, 85%, 90%, 91%, 92%, 93%, 94%, 95%, 96%, 97%, 98%, 99%, or 100% sequence identity along the length of the amino acid sequence of an odd-numbered SEQ ID NO: selected from the group consisting of SEQ ID NOS:1-290, or selected from the group consisting of SEQ ID NOS: 1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494; and
  (b) polypeptides having at least 70%, 75%, 80%, 85%, 90%, 91%, 92%, 93%, 94%, 95%, 96%, 97%, 98%, 99%, or 100% sequence identity along the length of the amino acid sequence of an even-numbered SEQ ID NO: selected from the group consisting of SEQ ID NOS:1-290, or selected from the group consisting of SEQ ID NOS: 1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494.

In some aspects, the 2, 3, 4, or more non-naturally occurring polypeptides include:
  (a) a polypeptide having at least 70%, 75%, 80%, 85%, 90%, 91%, 92%, 93%, 94%, 95%, 96%, 97%, 98%, 99%, or 100% sequence identity along the length of the amino acid sequence of chain a in Table 1A and/or 1B; and
  (b) a polypeptide having at least 70%, 75%, 80%, 85%, 90%, 91%, 92%, 93%, 94%, 95%, 96%, 97%, 98%, 99%, or 100% sequence identity along the length of the amino acid sequence of chain b in Table 1A and/or 1B.

In some aspects, the protein of the present disclosure comprises a heterotrimer. In some aspects, the heterotrimer comprises a monomer having an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 1A and 1B, wherein the amino acid sequence forms a hydrogen bond network, e.g., hydrogen bond network formed by the interface residues according to Table 2. In some aspects, the heterotrimer of the present disclosure comprises at least two monomers, wherein each of the monomers comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 1A and 1B, wherein the amino acid sequence forms a hydrogen bond network, e.g., hydrogen bond network formed by the interface residues according to Table 2.

In some aspects, the heterotrimer of the present disclosure comprises at least three monomers, wherein each of the monomers comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 1A and 1B, wherein the amino acid sequence forms a hydrogen bond network, e.g., hydrogen bond network formed by the interface residues according to Table 2.

In some aspects, the heterotrimer of the present disclosure comprises at least one heterodimer, wherein the heterodimer comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 3 and 4, wherein the amino acid sequence forms a hydrogen bond network, e.g., hydrogen bond network formed by the interface residues according to Table 2.

In some aspects, the heterotrimer of the present disclosure comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 3 and 4, wherein the amino acid sequence forms a hydrogen bond network.

In some aspects, the protein of the present disclosure comprises a heterotetramer. In some aspects, the heterotetramer comprises a monomer having an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 1A and 1B, wherein the amino acid sequence forms a hydrogen bond network, e.g., hydrogen bond network formed by the interface residues according to Table 2. In some aspects, the heterotetramer of the present disclosure comprises at least two monomers, wherein each of the monomers comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 1A and 1B, wherein the amino acid sequence forms a hydrogen bond network, e.g., hydrogen bond network formed by the interface residues according to Table 2.

In some aspects, the heterotetramer of the present disclosure comprises at least three monomers, wherein each of the monomers comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 1A and 1B, wherein the amino acid sequence forms a hydrogen bond network, e.g., hydrogen bond network formed by the interface residues according to Table 2.

In some aspects, the heterotetramer of the present disclosure comprises at least four monomers, wherein each of the monomers comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 1A and 1B, wherein the amino acid sequence forms a hydrogen bond network, e.g., hydrogen bond network formed by the interface residues according to Table 2.

In some aspects, the heterotetramer of the present disclosure comprises at least one heterodimer, wherein the heterodimer comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 1A and 1B, wherein the amino acid sequence forms a hydrogen bond network, e.g., hydrogen bond network formed by the interface residues according to Table 2.

In some aspects, the heterotetramer of the present disclosure comprises at least two heterodimers, wherein each of the two heterodimers comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 1A and 1B, wherein the amino acid sequence forms a hydrogen bond network, e.g., hydrogen bond network formed by the interface residues according to Table 2.

In some aspects, the heterotetramer of the present disclosure comprises at least one heterotrimer, wherein the heterotrimer comprises an amino acid sequence at least 70%, 75%, 80%, 85%, 90%, 91%, 92%, 93%, 94%, 95%, 96%, 97%, 98%, 99%, or 100% sequence identity along the length of the amino acid sequence described in Tables 3 and 4, wherein the amino acid sequence forms a hydrogen bond network.

In another embodiment, the protein comprises the amino acid sequence having at least 70%, 75%, 80%, 85%, 90%, 91%, 92%, 93%, 94%, 95%, 96%, 97%, 98%, 99%, or 100% sequence identity along the length of the amino acid sequence selected from the group consisting of SEQ ID NOS:291, 294, 296, 299, and 302-305. The amino acid sequence of SEQ ID NOS:291, 294, 296, 299, and 302-305 is provided in Table 3. These are merely exemplary such proteins of this aspect of the disclosure, and those of skill in the art will understand that any suitable combination of the monomers of the disclosure can be used in generating the proteins of this aspect.

TABLE 3

| Design name | Oligomerization State | Chain | Design Sequence |
|---|---|---|---|
| DHDSC_9-13-37 | Heterotetramer (linker italicized and underlined) | 9a-13a-37a | PKEEARELIRKQKELIKE QKKLIKEAKQKSDSRDAE RIWKRSREINRESKKINK RIKELIKS*GSEGSGSEGS GS*TKEDILERQRKIIERA QEIHRRQQEILEELERII RKPGSSEEAMKRMLKLLE ESLRLLKELLELSEESAQ LLYEQR*GSEGSGSEGSGS* DSDEHLKKLKTFLENLRR HLDRLDKHIKQLRDILSE NPEDERVKDVIDLSERSV RIVKTVIKIFEDSVRKKE SEQ ID NO: 291 |
| DHD9-13 | Heterotrimer | 9a-13a | PKEEARELIRKQKELIKE QKKLIKEAKQKSDSRDAE RIWKRSREINRESKKINK RIKELIKSGSEGSGSEGS GSTKEDILERQRKIIERA QEIHRRQQEILEELERII RKPGSSEEAMKRMLKLLE ESLRLLKELLELSEESAQ LLYEQR SEQ ID NO: 294 |
| DHD15-37 | Heterotrimer | 15b-37a | TERKLLERSRRLQEESKR LLDEMAEIMRRIKKLLDD PDSEDIAREIKELLRRLK EIIERNQRIAKEHEYIAR ERSGPGSGSEGSDSDEHL KKLKTFLENLRRHLDRLD KHIKQLRDILSENPEDER VKDVIDLSERSVRIVKTV IKIFEDSVRKKE SEQ ID NO: 296 |
| DHD13-37 | Heterotrimer | 13b-37b | TEKRLLEEAERAHREQKE IIKKAQELHRRLEEIVRQ SGSSEEAKKEAKKILEEI RELSKRSLELLREILYLS QEQKGSEGSGSEGSGSDD KELDKLLDTLEKILQTAT KIIDDANKLLEKLRRSER KDPKWETYVELLKRHEKA VKELLEIAKTHAKKVE SEQ ID NO: 299 |
| OPHD_15-9 | Heterotrimer | 15b-9a | TERKLLERSRRLQEESKR LLDEMAEIMRRIKKLLDD PDSEDIAREIKELLRRLK EIIERNQRIAKEHEYIAR ERSGSEGSGSEGSGSPKE EARELIRKQKELIKEQKK LIKEAKQKSDSRDAERIW KRSREINRESKKINKRIK ELIKS SEQ ID NO: 302 |
| OPHD_37-9 | Heterotrimer | 37a-9a | PKKEAEELAEESEELHDR SEKLHERAEQSSNSEEAR KILEDIERISERIEEISD RIERLLRSGSEGSGSEGS GSDDKELDKLLDTLEKIL QTATKIIDDANKLLEKLR RSERKDPKWETYVELLKR HEKAVKELLEIAKTHAKK VE SEQ ID NO: 303 |
| OPHD_13-9 | Heterotrimer | 13a-9a | TKEDILERQRKIIERAQE IHRRQQEILEELERIIRK PGSSEEAMKRMLKLLEES LRLLKELLELSEESAQLL YEQRGSEGSGSEGSGSPK EEARELIRKQKELIKEQK |

TABLE 3-continued

| Design name | Oligomer-ization State | Chain | Design Sequence |
|---|---|---|---|
| | | | KLIKEAKQKSDSRDAERI WKRSREIKRESKKINKRI KELIKS SEQ ID NO: 304 |
| OPHD_9-37 | Heterotrimer | 9b-37a | PKKEAEELAEESEELHDR SEKLHERAEQSSNSEEAR KILEDIERISERIEEISD RIERLLRSGSEGSGSEGS DSDEHLKKLKTFLENLRR HLDRLDKHIKQLRDILSE NPEDERVKDVIDLSERSV RIVKTVIKIFEDSVRKKE SEQ ID NO: 305 |

In a third aspect, the disclosure provides protein scaffolds, comprising
a) a first designed component comprised of any number of monomer A polypeptides and/or monomer B polypeptides, each from different heterodimers, connected into a single component by amino acid linkers.
b) a second designed component, comprising corresponding monomers for each monomer A and/or monomer B in the first designed component one;
wherein the first and second designed components interact to form the protein scaffold, and wherein each monomer A only interacts in the scaffold with its monomer B binding partner. In one embodiment, the first designed component may comprise the protein of any embodiment or combination of embodiments disclosed herein, and/or the second designed component may comprise a plurality of individual polypeptides of embodiment or combination of embodiments disclosed herein. In non-limiting embodiments, the first designed component and the second designed component may comprise a set of three (Heterotrimer) or four (Heterotetramer) binding partners as shown in Table 4. As will be understood by those of skill in the art based on the teachings herein, heterotrimers of the disclosure (including but not limited to the exemplary heterotrimers shown in Table 4) include a first component fusion protein of two polypeptides of the disclosure, and the second component comprises two separate polypeptides that are binding partners of the two polypeptides in the fusion protein. For example, the DHD9-13 scaffold comprises a first designed component comprising the DHD9 A monomer covalently linked to the DHD13 A monomer, and the second designed component comprises individual DHD9 B and DHD13 B monomers. Different scaffolds are separated in the Table by a blank row. As will be understood by those of skill I the art, these are merely exemplary; the monomers in the first designed component may be linked in any order, and any monomers may be included in the designed components. As will be further understood by those of skill based on the teachings herein, heterotetramers (including but not limited to the exemplary heterotetramer shown in Table 4) include a first component fusion protein of three polypeptides of the disclosure, and the second component comprises three separate polypeptides that are binding partners of the three polypeptides in the fusion protein.

TABLE 4

| | | | |
|---|---|---|---|
| DHD9-13 | Heterotrimer | 9a-13a | PKEEARELIRKQKELIKEQKKLIKEAKQKSDSRDAERIWKRSREINRESKK INKRIKELIKSGSEGSGSEGSGSTKEDILERQRKIIERAQEIHRRQQEILE ELERIIRKPGSSEEAMKRMLKLLEESLRLLKELLELSEESAQLLYEQR SEQ ID NO: 294 |
| DHD9-13 | Heterotrimer | 9b | PKKEAEELAEESEELHDRSEKLHERAEQSSNSEEARKILEDIERISERIEE ISDRIERLLRS SEQ ID NO: 2 |
| DHD9-13 | Heterotrimer | 13b | GSHHHHHHGSGSENLYFQGSTEKRLLEEAERAHREQKEIIKKAQELHRRLE EIVRQSGSSEEAKKEAKKILEEIRELSKRSLELLREILYLSQEQK SEQ ID NO: 295 |
| DHD9-13 | Heterotrimer | 13b | HHHHHHGSGSENLYFQGSTEKRLLEEAERAHREQKEIIKKAQELHRRLEEI VRQSGSSEEAKKEAKKILEEIRELSKRSLELLREILYLSQEQK SEQ ID NO: 431 |
| DHD15-37 | Heterotrimer | 15b-37a | TERKLLERSRRLQEESKRLLDEMAEIMRRIKKLLDDPDSEDIAREIKELLR RLKEIIERNQRIAKEHEYIARERSGPGSGSEGSDSDEHLKKLKTFLENLRR HLDRLDKHIKQLRDILSENPEDERVKDVIDLSERSVRIVKTVIKIFEDSVR KKE SEQ ID NO: 296 |
| DHD15-37 | Heterotrimer | 15a | TREELLRENIELAKEHIEIMREILELLQKMEELLERQSSEDILEELRKIIE RIRELLDRSRKIHERSEEIAYKEE SEQ ID NO: 297 |
| DHD15-37 | Heterotrimer | 37b | GSHHHHHHGSGSENLYFQGSDDKELDKLLDTLEKILQTATKIIDDANKLLE KLRRSERKDPKVVETYVELLKREEKAVKELLEIAKTHAKKVE SEQ ID NO: 298 |
| DHD15-37 | Heterotrimer | 37b | HHHHHHGSGSENLYFQGSDDKELDKLLDTLEKILQTATKIIDDANKLLEKL RRSERKDPKVVETYVELLKRHEKAVKELLEIAKTHAKKVE SEQ ID NO: 433 |
| DHD13-37 | Heterotrimer | 13b-37b | TEKRLLEEAERAHREQKEIIKKAQELHRRLEEIVRQSGSSEEAKKEAKKIL EEIRELSKRSLELLREILYLSQEQKGSEGSGSEGSGSDDKELDKLLDTLEK ILQTATKIIDDANKLLEKLRRSERKDPKVVETYVELLKRHEKAVKELLEIA KTHAKKVE SEQ ID NO: 299 |

TABLE 4-continued

| | | | |
|---|---|---|---|
| DHD13-37 | Heterotrimer | 13a | TKEDILERQRKIIERAQEIHRRQQEILEELERIIRKPGSSEEAMKRMLKLL EESLRLLKELLELSEESAQLLYEQR SEQ ID NO: 300 |
| DHD13-37 | Heterotrimer | 37a | GSSHHHHHHSSGENLYFQGSDSDEHLKKLKTFLENLRRHLDRLDKHIKQLR DILSENPEDERVKDVIDLSERSVRIVKTVIKIFEDSVRKKE SEQ ID NO: 301 |
| DHD13-37 | Heterotrimer | 37a | SHHHHHHSSGENLYFQGSDSDEHLKKLKTFLENLRRHLDRLDKHIKQLRDI LSENPEDERVKDVIDLSERSVRIVKTVIKIFEDSVRKKE SEQ ID NO: 435 |
| OPHD_15-9 | Heterotrimer | 15b-9a | TERKLLERSRRLQEESKRLLDEMAEIMRRIKKLLDDPDSEDIAREIKELLR RLKEIIERNQRIAKEHEYIARERSGSEGSGSEGSGSPKEEARELIRKQKEL IKEQKKLIKEAKQKSDSRDAERIWKRSREINRESKKINKRIKELIKS SEQ ID NO: 302 |
| OPHD_15-9 | Heterotrimer | 15a | TREELLRENIELAKEHIEIMREILELLQKMEELLEKARGADEDVAKTIKEL LRRLKEIIERNQRIAKEHEYIARERS SEQ ID NO: 19 |
| OPHD_15-9 | Heterotrimer | 9b | PKKEAEELAEESEELHDRSEKLHERAEQSSNSEEARKILEDIERISERIEE ISDRIERLLRS SEQ ID NO: 2 |
| OPHD_37-9 | Heterotrimer | 37a-9a | PKKEAEELAEESEELHDRSEKLHERAEQSSNSEEARKILEDIERISERIEE ISDRIERLLRSGSEGSGSEGSGSDDKELDKLLDTLEKILQTATKIIDDANK LLEKLRRSERKDPKVVETYVELLKRHEKAVKELLEIAKTHAKKVE SEQ ID NO: 303 |
| OPHD_37-9 | Heterotrimer | 37b | GSDDKELDKLLDTLEKILQTATKIIDDANKLLEKLRRSERKDPKVVETYVE LLKRHEKAVKELLEIAKTHAKKVE SEQ ID NO: 42 |
| OPHD_37-9 | Heterotrimer | 37b | DDKELDKLLDTLEKILQTATKIIDDANKLLEKLRRSERKDPKVVETYVELL KRHEKAVKELLEIAKTHAKKVE SEQ ID NO: 352 |
| OPHD_37-9 | Heterotrimer | 9b | PKKEAEELAEESEELHDRSEKLHERAEQSSNSEEARKILEDIERISERIEE ISDRIERLLRS SEQ ID NO: 2 |
| OPHD_13-9 | Heterotrimer | 13a-9a | TKEDILERQRKIIERAQEIHRRQQEILEELERIIRKPGSSEEAMKRMLKLL EESLRLLKELLELSEESAQLLYEQRGSEGSGSEGSGSPKEEARELIRKQKE LIKEQKKLIKEAKQKSDSRDAERIWKRSREINRESKKINKRIKELIKS SEQ ID NO: 304 |
| OPHD_13-9 | Heterotrimer | 13b | GTEKRLLEEAERAHREQKEIIKKAQELHRRLEEIVRQSGSSEEAKKEAKKI LEEIRELSKRSLELLREILYLSQEQKGSLVPR SEQ ID NO: 4 |
| OPHD_13-9 | Heterotrimer | 9b | PKKEAEELAEESEELHDRSEKLHERAEQSSNSEEARKILEDIERISERIEE ISDRIERLLRS SEQ ID NO: 2 |
| OPHD_9-37 | Heterotrimer | 9b-37a | PKKEAEELAEESEELHDRSEKLHERAEQSSNSEEARKILEDIERISERIEE ISDRIERLLRSGSEGSGSEGSGSDSDEHLKKLKTFLENLRRHLDRLDKHIQL RDILSENPEDERVKDVIDLSERSVRIVKTVIKIFEDSVRKKE SEQ ID NO: 305 |
| OPHD_9-37 | Heterotrimer | 9a | GSPKEEARELIRKQKELIKEQKKLIKEAKQKSDSRDAERIWKRSREINRES KKINKRIKELIKS SEQ ID NO: 1 |
| OPHD_9-37 | Heterotrimer | 9a | PKEEARELIRKQKELIKEQKKLIKEAKQKSDSRDAERIWKRSREINRESKK INKRIKELIKS SEQ ID NO: 331 |
| OPHD_9-37 | Heterotrimer | 37b | GSDDKELDKLLDTLEKILQTATKIIDDANKLLEKLRRSERKDPKVVETYVE LLKRHEKAVKELLEIAKTHAKKVE SEQ ID NO: 42 |
| OPHD_9-37 | Heterotrimer | 37b | DDKELDKLLDTLEKILQTATKIIDDANKLLEKLRRSERKDPKVVETYVELL KRHEKAVKELLEIAKTHAKKVE SEQ ID NO: 352 |
| DHDSC_9-13-37 | Heterotetramer | 9a-13a-37a | PKEEARELIRKQKELIKEQKKLIKEAKQKSDSRDAERIWKRSREINRESKK INKRIKELIKSGSEGSGSEGSGSTKEDILERQRKIIERAQEIHRRQQEILE ELERIIRKPGSSEEAMKRMLKLLEESLRLLKELLELSEESAQLLYEQRGSE GSGSEGSGSDSDEHLKKLKTFLENLRRHLDRLDKHIQLRDILSENPEDER VKDVIDLSERSVRIVKTVIKIFEDSVRKKE SEQ ID NO: 291 |
| DHDSC_9-13-37 | Heterotetramer | 9b | PKKEAEELAEESEELEDRSEKLHERAEQSSNSEEARKILEDIERISERIEE ISDRIERLLRS SEQ ID NO: 2 |
| DHDSC_9-13-37 | Heterotetramer | 13b | TEKRLLEEAERAHREQKEIIKKAQELHRRLEEIVRQSGSSEEAKKEAKKIL EEIRELSKRSLELLREILYLSQEQK SEQ ID NO: 292 |
| DHDSC_9-13-37 | Heterotetramer | 37b | GSSHHHHHHSSGENLYFQGSDDKELDKLLDTLEKILQTATKIIDDANKLLE KLRRSERKDPKVVETYVELLKRHEKAVKELLEIAKTHAKKVE SEQ ID NO: 293 |

TABLE 4-continued

| | | | |
|---|---|---|---|
| DHDSC_9-<br>13-37 | Heterotetramer | 37b | SHHHHHHSSGENLYFQGSDDKELDKLLDTLEKILQTATKIIDDANKLLEKL<br>RRSERKDPKVVETYVELLKRHEKAVKELLEIAKTHAKKVE SEQ ID<br>NO: 437 |

In these embodiments, the scaffold may be stable up to 95° C. and has a guanidine denaturation midpoint of 4 M, as described in the examples that follow.

In some aspects, the heterotrimer or heterotetramer of the present disclosure does not comprise a His tag.

In another aspect, the disclosure provides protein scaffolds, comprising
  (a) a fusion protein comprising of 2, 3, 4, or more polypeptides, wherein each polypeptide present in the fusion protein is a non-naturally occurring polypeptide comprises 1-5 alpha helices, wherein adjacent alpha helices may optionally be connected by an amino acid linker;
  wherein each polypeptide in the fusion protein is capable of non-covalently interacting with a binding partner, and wherein the fusion protein does not comprise a binding partner for any polypeptide present in the fusion protein; and
  (b) a binding partner for at least one of the polypeptides present in the fusion protein;
  wherein the fusion protein and the binding partner non-covalently interact to form the protein scaffold, wherein an interaction specificity between the binding partner and the at least polypeptide in the fusion protein are determined by at least one hydrogen bond network at the interface between the binding partner and the at least one polypeptide.

Binding partners are polypeptides capable of forming heterodimers with a polypeptide present in the fusion protein, and are exemplified above with respect to SEQ ID NO:1-290. The binding partner for at least one polypeptide in the fusion protein may comprise a binding partner for 2, 3, 4, or all polypeptides in the fusion protein. As will be understood, when more than one binding partner is present, they are present as individual binding partner polypeptides, and not linked together.

The fusion protein may comprise 2, 3, 4, or more polypeptides. In certain embodiments, the fusion protein comprises at least 3 or 4 polypeptides in total. Exemplary embodiments of such fusion proteins are provided herein, for example in describing heterotrimer and heterotetramer embodiments in Table 4. The polypeptides in the fusion protein may all be the same, may all be different, or may include both identical and distinct polypeptides. In one specific embodiment, each polypeptide in the fusion protein is a different polypeptide.

In one embodiment,
  (i) the fusion protein comprises 2, 3, 4, or more polypeptide having at least 70%, 75%, 80%, 85%, 90%, 91%, 92%, 93%, 94%, 95%, 96%, 97%, 98%, 99%, or 100% sequence identity along the length of the amino acid sequence of SEQ ID NOS: 1-290, or SEQ ID NOS: 1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494; and
  (ii) the binding partner comprises a binding partner as defined herein for each polypeptide in (i), wherein each binding partner has at least 70%, 75%, 80%, 85%, 90%, 91%, 92%, 93%, 94%, 95%, 96%, 97%, 98%, 99%, or 100% sequence identity along the length of the amino acid sequence selected from the group SEQ ID NOS: 1-290, or selected from the group consisting of SEQ ID NOS: 1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494. As described herein, the odd-numbered SEQ ID NOS: between SEQ ID NO:1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 are noted as "A" monomers and the even-numbered SEQ ID NOS between SEQ ID NO:1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 are the "B" monomers, with adjacent A and B monomers in Tables 1A and 1B capable of forming heterodimers as described in detail herein. Thus, for example, if the fusion protein included the polypeptide of SEQ ID NO:1, then binding partner may include SEQ ID NO:2, while if the fusion protein included the polypeptide of SEQ ID NO:2, then binding partner may include SEQ ID NO:1. The numerous combinations of fusion protein polypeptides and binding partners will be clear to those of skill in the art based on the teachings herein.

In one embodiment, amino acid changes in the fusion protein and the binding partner from the reference amino acid sequence are conservative amino acid substitutions. In another embodiment amino acid residues at 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of defined interface positions in the polypeptides in the fusion protein and the binding partner are invariant compared to the reference amino acid sequence. In a further embodiment, the at least one hydrogen bond network is asymmetric. In a further embodiment, the binding interface comprises at least 25% hydrophobic residues. In another embodiment, the scaffold is stable up to 95° C. and has a guanidine denaturation midpoint of 4 M.

In another embodiment, the disclosure provides methods of forming the designed heterodimer disclosed herein, comprising:
  a) providing two of the monomers as unlinked monomers;
  b) providing the other two monomers as linked monomers whereby the unlinked monomers associate with their respective monomer of the same heterodimer, and not with any of the other monomers. Further details of this aspect are provided in the examples that follow.

In another embodiment, the disclosure provides a designed heterodimer protein comprising:
  a) asymmetric buried hydrogen bond networks incorporated into regularly repeating backbone structures; and
  b) helix hairpin helix monomers wherein the supercoil phases of the helices are fixed at 0, 90, 180, or 270 degrees and the supercoil twist ($\omega 0$) and helical twist ($\omega 1$) are held constant for either a two layer left handed super coil ($\omega 0=-2.85$ and ($\omega 1=102.85$), or a 5 layer untwisted bundle ($\omega 0=0$ and $\omega 1=100$) 27. Further details of this aspect are provided in the examples that follow.

In another embodiment, the disclosure provides uses of the polypeptide, protein, heterodimer protein, protein scaffold, nucleic acid, expression vector, and/or cell of any embodiment or combination of embodiments for any suitable purposed, including but not limited to those disclosed herein such as designing protein logic gates In a fourth aspect, the disclosure provides fusion proteins comprising a polypeptide of the formula X-B-Z, wherein:
(a) the X domain is a non-naturally occurring polypeptide comprising 1, 2, or 3 alpha helices, wherein the X domain is capable of non-covalently binding to a first target;
(b) the Z domain is a non-naturally occurring polypeptide comprising 1, 2, or 3 alpha helices, wherein the Z domain is capable of non-covalently binding to either (i) a second target that differs from the first target, or (ii) a different non-naturally occurring polypeptide comprising 1, 2, or 3 alpha helices; and
(c) the B domain is an amino acid linker;
wherein a combined number of alpha helices from the X domain and the Z domain is 4, 5, or 6; and
wherein the X domain and the Z domain interact at a binding interface, wherein the binding interface comprises a hydrogen bond network in which at least one side chain in each alpha helix hydrogen of the X domain bonds with a side chain in an alpha helix in the Z domain, and wherein the binding interface comprises a plurality of hydrophobic residues. Each helix in the X domain H-bonds with at least one helix in the Z domain and each helix in the Z domain H-bonds with at least one helix in the X domain.

In a fifth aspect, the disclosure provides kits or compositions, comprising at least two fusion proteins comprising the formula X-B-Z, wherein
the B domain in each fusion protein is independently a polypeptide linker;
the X domain in each fusion protein comprises a first non-naturally occurring polypeptide comprising 1, 2, or 3 alpha helices;
the Z domain in each fusion protein comprises a second non-naturally occurring polypeptide comprising 1, 2, or 3 alpha helices, wherein a combined number of alpha helices from the X domain and the Z domain in each individual fusion protein is 4, 5, or 6; wherein
the X domain and the Z domain interact at a binding interface, wherein the binding interface comprises a hydrogen bond network in which at least one side chain in each X domain alpha helix bonds with a side chain in an alpha helix in the Z domain; wherein the X domain in a first fusion protein is capable of non-covalently binding to a first target;
the Z domain in a second fusion protein is capable of non-covalently binding to a second target; and
the X domains and Z domains in each individual fusion protein that are not capable of non-covalently binding to the first target or the second target are capable of non-covalently binding to an X or a Z domain of a different fusion protein in the plurality of fusion proteins.

The fusion proteins and kits can be used, for example, in the methods disclosed herein such as for logic gate construction, and for any other suitable use as will be appreciated by those of skill in the art based on the teachings herein.

Specifically, fusion proteins can be used for designing 2-input AND and OR logic gates built from de novo designed proteins that regulate the association of arbitrary protein units ranging from split enzymes to transcriptional machinery in vitro, and in living cells. Binding interaction cooperativity makes the gates largely insensitive to stoichiometric imbalances in the inputs, and the modularity of the approach enables ready extension to 3-input OR, AND, and disjunctive normal form gates. The modularity and cooperativity of the control elements, coupled with the ability to de novo design an essentially unlimited number of protein components, enables design of sophisticated post-translational control logic over a wide range of biological functions.

In one embodiment, the Z domain is a non-naturally occurring polypeptide comprising 1, 2, or 3 alpha helices, wherein the Z domain is capable of non-covalently binding to a second target that differs from the first target, This embodiment is useful, for example, for generating single component dimerizers for use in AND/NOR gates. In another embodiment, the Z domain is a non-naturally occurring polypeptide comprising 1, 2, or 3 alpha helices, wherein the Z domain is capable of non-covalently binding to a different non-naturally occurring polypeptide comprising 1, 2, or 3 alpha helices. This embodiment is useful, for example, for generating 2 or 3-component dimerizers for use in AND/NOR gates.

The first targets and second targets may be any target suitable for an intended use. In non-limiting embodiments, the first target and/or the second target may comprise polypeptides or nucleic acids.

In one embodiment of the kit or composition,
(i) the first fusion protein has the formula X1-B1-Z1, wherein the X1 domain is capable of non-covalently binding to the first target; and
(ii) the second fusion protein has the formula X2-B2-Z2, wherein the Z2 domain is capable of non-covalently binding to the second target; and wherein the Z1 and X2 domains are capable of non-covalently binding to each other.

In another embodiment of the kit or composition,
(i) the first fusion protein has the formula X1-B1-Z1, wherein the X1 domain is capable of non-covalently binding to the first target; and
(ii) the second fusion protein has the formula X2-B2-Z2,
(iii) the at least two fusion proteins comprise a third fusion protein of formula X3-B3-Z3, wherein the Z3 domain is capable of non-covalently binding to the second target; wherein
(A) the Z1 and X2 domains are capable of non-covalently binding to each other; and
(B) the Z2 and X3 domains are capable of non-covalently binding to each other.

In one embodiment of the fusion protein or the kits or compositions, the binding interface comprises at least 25%, 30%, 35%, 40%, 45%, 50%, 55%, 60% or greater hydrophobic residues. The B domain linker may be any suitable amino acid sequence, including but not limited to those described herein. In one embodiment, the B domain for each fusion protein is independently between 6-12, 6-11, 6-10, 7-12, 7-11, 7-10, 8-12, 8-11, 8-10, 9-12, 9-11, 9-10, 10-12, 10-11, 11-12, 6, 7, 8, 9, 10, 11, or 12 amino acids in length.

In another embodiment, the combined number of alpha helices from the X and Z domains in an individual fusion protein is 4. In a further embodiment, the X domain of each fusion protein has 2 alpha helices and the Z domain of each fusion protein has 2 alpha helices. In one embodiment, either the X domain or the Z domain of each fusion protein has 1 alpha helix and the other has 3 alpha helices.

In one embodiment, each X domain and each Z domain comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to SEQ ID NOS:1-290, or selected from the group consisting of SEQ ID NOS: 1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, with the proviso that the X domain and the Z domain do not form a heterodimer (a-b) pair. In one embodiment, each X domain and each Z domain comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to SEQ ID NOS:1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, with the proviso that the X domain and the Z domain do not form a heterodimer (a-b) pair. In one non-limiting embodiment, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of amino acid residues at defined interface positions as defined in Table 2 are invariant in the polypeptides relative to the reference polypeptide.

A different nomenclature is used in the examples that follow. Table 5 provides correspondence between the names used in the examples and in Tables 1A and 1B. The first column is the numbering used in the examples, while the second column lists the corresponding name in Tables 1A and 1B. For example, polypeptide 1 in the examples is DHD37_ABXB (a), 1' is DHD37_ABXB (b). Polypeptide 2 is DHD15 (a), 2' is DHD15 (b), and so on.

TABLE 5

| | |
|---|---|
| 1: | DHD 37_ABXB |
| 2: | DHD 15 |
| 3: | DHD 131 |
| 4: | DHD 101 |
| 5: | DHD 9 |
| 6: | DHD 150 |
| 7: | DHD 154 |
| 8: | DHD 17 |
| 9: | DHD 13_XAAA |
| 10: | DHD 39 |
| 11: | DHD 155 |

In one embodiment, each fusion protein independently comprises a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide having the amino acid sequence of a sequence selected from the group consisting of SEQ ID NO: 302, 303, 306-326, 439, 441, 443, 445, 447, 449, 451, 453, 455, and 457:

```
2'-1'_2-residue_linker
                                                         (SEQ ID NO: 306)
GSTERKLLERSRRLQEESKRLLDEMAEIMRRIKKLLDDPDSEDIAREIKELLRRLKEIIERNQRIAKEHEYIARE

RSAADDKELDKLLDTLEKILQTATKIIDDANKLLEKLRRSERKDPKVVETYVELLKRHEKAVKELLEIAKTHAKK

VE

2'-1'_2-residue_linker
                                                         (SEQ ID NO: 439)
TERKLLERSRRLQEESKRLLDEMAEIMRRIKKLLDDPDSEDIAREIKELLRRLKEIIERNQRIAKEHEYIARERS

AADDKELDKLLDTLEKILQTATKIIDDANKLLEKLRRSERKDPKVVETYVELLKRHEKAVKELLEIAKTHAKKVE

2'-1'_6-residue_linker
                                                         (SEQ ID NO: 307)
GSTERKLLERSRRLQEESKRLLDEMAEIMRRIKKLLDDPDSEDIAREIKELLRRLKEIIERNQRIAKEHEYIARE

RSGGSGSPDDKELDKLLDTLEKILQTATKIIDDANKLLEKLRRSERKDPKVVETYVELLKRHEKAVKELLEIAKT

HAKKVE

2'-1'_6-residue_linker
                                                         (SEQ ID NO: 441)
TERKLLERSRRLQEESKRLLDEMAEIMRRIKKLLDDPDSEDIAREIKELLRRLKEIIERNQRIAKEHEYIARERS

GGSGSPDDKELDKLLDTLEKILQTATKIIDDANKLLEKLRRSERKDPKVVETYVELLKRHEKAVKELLEIAKTHA

KKVE

2'-1'_12-residue_linker
                                                         (SEQ ID NO: 308)
GSTERKLLERSRRLQEESKRLLDEMAEIMRRIKKLLDDPDSEDIAREIKELLRRLKEIIERNQRIAKEHEYIARE

RSGGSGSPGGSGSPDDKELDKLLDTLEKILQTATKIIDDANKLLEKLRRSERKDPKVVETYVELLKRHEKAVKEL

LEIAKTHAKKVE
```

```
2'-1'_12-residue_linker
                                                     (SEQ ID NO: 443)
TERKLLERSRRLQEESKRLLDEMAEIMRRIKKLLDDPDSEDIAREIKELLRRLKEIIERNQRIAKEHEYIARERS

GGSGSPGGSGSPDDKELDKLLDTLEKILQTATKIIDDANKLLEKLRRSERKDPKVVETYVELLKRHEKAVKELLE

IAKTHAKKVE

2'-1'_24-residue_linker
                                                     (SEQ ID NO: 309)
GSTERKLLERSRRLQEESKRLLDEMAEIMRRIKKLLDDPDSEDIAREIKELLRRLKEIIERNQRIAKEHEYIARE

RSGGSGSPGGSGSPGGSGSPGGSGSPDDKELDKLLDTLEKILQTATKIIDDANKLLEKLRRSERKDPKVVETYVE

LLKRHEKAVKELLEIAKTHAKKVE

2'-1'_24-residue_linker
                                                     (SEQ ID NO: 445)
TERKLLERSRRLQEESKRLLDEMAEIMRRIKKLLDDPDSEDIAREIKELLRRLKEIIERNQRIAKEHEYIARERS

GGSGSPGGSGSPGGSGSPGGSGSPDDKELDKLLDTLEKILQTATKIIDDANKLLEKLRRSERKDPKVVETYVELL

KRHEKAVKELLEIAKTHAKKVE 11-7'
                                                     (SEQ ID NO: 310)
PEDDVVRIIKEDLESNREVLREQKEIHRILELVTRGEVSEEAIDRVLKRQEDLLKKQKESTDKARKVVEERRGSE

GSGSEGSDLEDLLRRLRRLVDEQRRLVEELERVSRRLEKAVRDNEDERELARLSREHSDIQDKHDKLAREILEVL

KRLLERTE

1'-4'
                                                     (SEQ ID NO: 311)
GSDAYDLDRIVKEHRRLVEEQRELVEELEKLVRRQEDHRVDKKESHEILERLERIIRRSTRILTELEKLTDEFER

RTRGSEGSGSEGSGSDDKELDKLLDTLEKILQTATKIIDDANKLLEKLRRSERKDPKVVETYVELLKRHEKAVKE

LLEIAKTHAKKVE

1'-4'
                                                     (SEQ ID NO: 447)
DAYDLDRIVKEHRRLVEEQRELVEELEKLVRRQEDHRVDKKESHEILERLERIIRRSTRILTELEKLTDEFERRT

RGSEGSGSEGSGSDDKELDKLLDTLEKILQTATKIIDDANKLLEKLRRSERKDPKVVETYVELLKRHEKAVKELL

EIAKTHAKKVE 4-3'
                                                     (SEQ ID NO: 312)
GSDEDDELERLLREYHRVLREYEKLLEELRRLYEEYKRGEVSEEESDRILREIKEILDKSERLWDLSEEVWRTLL

YQAEGSEGSGSEGSDEKDYHRRLIEHLEDLVRRHEELIKRQKKVVEELERRGLDERLRRVVDRFRRSSERWEEVI

ERFRQVVDKLRKSVE 4-3'
                                                     (SEQ ID NO: 449)
DEDDELERLLREYHRVLREYEKLLEELRRLYEEYKRGEVSEEESDRILREIKEILDKSERLWDLSEEVWRTLLYQ

AEGSEGSGSEGSDEKDYHRRLIEHLEDLVRRHEELIKRQKKVVEELERRGLDERLRRVVDRFRRSSERWEEVIER

FRQVVDKLRKSVE 3-2'*
                                                     (SEQ ID NO: 313)
GSTERKLLERSRRLQEESKRLLDEMAEIMRRIKKLLKKARGADEKVLDELRKIIERIRELLDRSRKIHERSEEIA

YKEEGSEGSGSEGSGSDESDRIRKIVEESDEIVKESRKLAERARELIKESEDKRVSEERNERLLEELLRILDENA

ELLKRNLELLKEVLYRTR 3-2'*
                                                     (SEQ ID NO: 451)
TERKLLERSRRLQEESKRLLDEMAEIMRRIKKLLKKARGADEKVLDELRKIIERIRELLDRSRKIHERSEEIAYK

EEGSEGSGSEGSGSDESDRIRKIVEESDEIVKESRKLAERARELIKESEDKRVSEERNERLLEELLRILDENAEL

LKRNLELLKEVLYRTR
```

-continued

1'-3'
(SEQ ID NO: 314)
GSDEDDELERLLREYHRVLREYEKLLEELRRLYEEYKRGEVSEEESDRILREIKEILDKSERLWDLSEEVWRTLL

YQAEGSEGSGSEGSGSDDKELDKLLDTLEKILQTATKIIDDANKLLEKLRRSERKDPKVVETYVELLKRHEKAVK

ELLEIAKTHAKKVE

1'-3'
(SEQ ID NO: 453)
DEDDELERLLREYHRVLREYEKLLEELRRLYEEYKRGEVSEEESDRILREIKEILDKSERLWDLSEEVWRTLLYQ

AEGSEGSGSEGSGSDDKELDKLLDTLEKILQTATKIIDDANKLLEKLRRSERKDPKVVETYVELLKRHEKAVKEL

LEIAKTHAKKVE

1'-5
(SEQ ID NO: 303)
PKKEAEELAEESEELHDRSEKLHERAEQSSNSEEARKILEDIERISERIEEISDRIERLLRSGSEGSGSEGSGSD

DKELDKLLDTLEKILQTATKIIDDANKLLEKLRRSERKDPKVVETYVELLKRHEKAVKELLEIAKTHAKKVE

5'-2'
(SEQ ID NO: 302)
TERKLLERSRRLQEESKRLLDEMAEIMRRIKKLLDDPDSEDIAREIKELLRRLKEIIERNQRIAKEHEYIARERS

GSEGSGSEGSGSPKEEARELIRKQKELIKEQKKLIKEAKQKSDSRDAERIWKRSREINRESKKINKRIKELIKS 1-6
(SEQ ID NO: 315)
DSDEHLKKLKTFLENLRRHLDRLDKHIKQLRDILSENPEDERVKDVIDLSERSVRIVKTVIKIFEDSVRKKEGSE

GSGSEGSGSEGSGSEGSGSEGSGSEGSPTDEVIEVLKELLRIHRENLRVNEEIVEVNERASRVTDREELERLLRR

SNELIKRSRELNEESKKLIEKLERLAT

1'-7
(SEQ ID NO: 316)
DDKELDKLLDTLEKILQTATKIIDDANKLLEKLRRSERKDPKVVETYVELLKRHEKAVKELLEIAKTHAKKVEGS

EGSGSEGSTAEELLEVHKKSDRVTKEHLRVSEEILKVVEVLTRGEVSSEVLKRVLRKLEELTDKLRRVTEEQRRV

VEKLN

6'-7
(SEQ ID NO: 317)
DNEEIIKEARRVVEEYKKAVDRLEELVRRAENAKHASEKELKDIVREILRISKELNKVSERLIELWERSQERARG

SEGSGSEGSTAEELLEVHKKSDRVTKEHLRVSEEILKVVEVLTRGEVSSEVLKRVLRKLEELTDKLRRVTEEQRR

VVEKLN

1'-6-7
(SEQ ID NO: 318)
DDKELDKLLDTLEKILQTATKIIDDANKLLEKLRRSERKDPKVVETYVELLKRHEKAVKELLEIAKTHAKKVEGS

EGSGSEGSGSEGSGSEGSGSEGSPTDEVIEVLKELLRIHRENLRVNEEIVEVNERASRVTDREELERLLR

RSNELIKRSRELNEESKKLIEKLERLATGSEGSGSEGSGSEGSGSEGSGSEGSGSEGSTAEELLEVHKKSDRVTK

EHLRVSEEILKVVEVLTRGEVSSEVLKRVLRKLEELTDKLRRVTEEQRRVVEKLN 11-1
(SEQ ID NO: 319)
DSDEHLKKLKTFLENLRRHLDRLDKHIKQLRDILSENPEDERVKDVIDLSERSVRIVKTVIKIFEDSVRKKEGSE

GSGSEGSPEDDVVRIIKEDLESNREVLREQKEIHRILELVTRGEVSEEAIDRVLKRQEDLLKKQKESTDKARKVV

EERR 11-6'
(SEQ ID NO: 320)
DNEEIIKEARRVVEEYKKAVDRLEELVRRAENAKHASEKELKDIVREILRISKELNKVSERLIELWERSQERARG

SEGSGSEGSPEDDVVRIIKEDLESNREVLREQKEIHRILELVTRGEVSEEAIDRVLKRQEDLLKKQKESTDKARK

VVEERR

-continued 11-7'
(SEQ ID NO: 321)
DLEDLLRRLRRLVDEQRRLVEELERVSRRLEKAVRDNEDERELARLSREHSDIQDKHDKLAREILEVLKRLLERT

EGSEGSGSEGSGSEGSGSEGSGSEGSGSEGSPEDDVVRIIKEDLESNREVLREQKEIHRILELVTRGEVSEEAID

RVLKRQEDLLKKQKESTDKARKVVEERR

1'-6
(SEQ ID NO: 322)
GSDDKELDKLLDTLEKILQTATKIIDDANKLLEKLRRSERKDPKVVETYVELLKRHEKAVKELLEIAKTHAKKVE

GSEGSGSEGSPTDEVIEVLKELLRIHRENLRVNEEIVEVNERASRVTDREELERLLRRSNELIKRSRELNEESKK

LIEKLERLAT

1'-6
(SEQ ID NO: 455)
DDKELDKLLDTLEKILQTATKIIDDANKLLEKLRRSERKDPKVVETYVELLKRHEKAVKELLEIAKTHAKKVEGS

EGSGSEGSPTDEVIEVLKELLRIHRENLRVNEEIVEVNERASRVTDREELERLLRRSNELIKRSRELNEESKKLI

EKLERLAT 7-1
(SEQ ID NO: 323)
DSDEHLKKLKTFLENLRRHLDRLDKHIKQLRDILSENPEDERVKDVIDLSERSVRIVKTVIKIFEDSVRKKEGSE

GSGSEGSTAEELLEVHKKSDRVTKEHLRVSEEILKVVEVLTRGEVSSEVLKRVLRKLEELTDKLRRVTEEQRRVV

EKLN

4'-2'*
(SEQ ID NO: 324)
GTERKLLERSRRLQEESKRLLDEMAEIMRRIKKLLKKARGADEKVLDELRKIIERIRELLDRSRKIHERSEEIAY

KEEGSEGSGSEGSGSDAYDLDRIVKEHRRLVEEQRELVEELEKLVRRQEDHRVDKKESHEILERLERIIRRSTRI

LTELEKLTDEFERRTR

2*-1'
(SEQ ID NO: 325)
TREELLRENIELAKEHIEIMREILELLQKMEELLEKARGADEDVAKTIKELLRRLKEIIERNQRIAKEHEYIARE

RSGSEGSGSEGSGSDDKELDKLLDTLEKILQTATKIIDDANKLLEKLRRSERKDPKVVETYVELLKRHEKAVKEL

LEIAKTHAKKVE

1'-9
(SEQ ID NO: 326)
GSDDKELDKLLDTLEKILQTATKIIDDANKLLEKLRRSERKDPKVVETYVELLKRHEKAVKELLEIAKTHAKKVE

GSEGSGSEGSGTKEDILERQRKIIERAQEIHRRQQEILEELERIIRKPGSSEEAMKRMLKLLEESLRLLKELLEL

SEESAQLLYEQR

1'-9
(SEQ ID NO: 457)
DDKELDKLLDTLEKILQTATKIIDDANKLLEKLRRSERKDPKVVETYVELLKRHEKAVKELLEIAKTHAKKVEGS

EGSGSEGSGTKEDILERQRKIIERAQEIHRRQQEILEELERIIRKPGSSEEAMKRMLKLLEESLRLLKELLELSE

ESAQLLYEQR

In some aspects, each fusion protein independently comprises a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to, a polypeptide having the amino acid sequence of SEQ ID NO: 302, 303, 306-326, 439, 441, 443, 445, 447, 449, 451, 453, 455, and 457, wherein GlySer at amino acid residues 1 and 2 of any of 302, 303, 306-326, 439, 441, 443, 445, 447, 449, 451, 453, 455, and 457 are optional, e.g., not present.

In another embodiment, the kits or compositions further comprising the first target and the second target. In one embodiment, the first target and the second target each independently comprise a polypeptide of the formula X10-B10-Z10, wherein
(a) the X10 domain is a non-naturally occurring polypeptide comprising 1, 2, or 3 alpha helices;
(b) the Z10 domain is a non-naturally occurring polypeptide comprising 1, 2, or 3 alpha helices; and
(c) the B10 domain is an amino acid linker;
wherein the X domain and the Z domain interact at a target binding interface, wherein the target binding interface comprises a hydrogen bond network in which at least one side chain in each alpha helix of the X domain hydrogen bonds with a side chain in a different alpha helix in the Z domain, and wherein the target binding interface comprises a plurality of hydrophobic residues. In one embodiment, the target binding interface comprises at least 25% hydrophobic residues. In another embodiment, the B10 domain for the first target and the second target is independently between 6-12, 6-11, 6-10, 7-12, 7-11, 7-10, 8-12, 8-11, 8-10, 9-12, 9-11, 9-10, 10-12, 10-11, 11-12, 6, 7, 8, 9, 10, 11, or 12 amino acids in length. In another embodiment, the combined number of alpha helices from the X and Z domains in the first target and the second target protein is 4. In a further embodiment, (a) the X10 domain of each of the first target and the second target has 2 alpha helices and the Z10 domain of each of the first target and the second target has 2 alpha helices; or
(b) either the X10 domain or the Z10 domain of each of the first target and the second target has 1 alpha helix and the other has 3 alpha helices. In one embodiment, each X10 domain and each Z10 domain comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide having the amino acid sequence selected from SEQ ID NOS:1-290, 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, with the proviso that the X10 domain forms a heterodimer (a-b) pair with the X domain of the fusion protein, and the Z10 domain forms a heterodimer (a-b) pair with the Z domain of the fusion protein. In one embodiment, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of amino acid residues at defined interface positions of the first target and/or the second target are invariant compared to the reference polypeptide amino acid sequence (interface residues shown in Table 2).

In another embodiment, the first target and/or the second target further comprise one or more effector polypeptide domains linked to one or more of the X10 and/or Z10 domains, for example, wherein the one or more effector polypeptide domains may comprise a polypeptide including, but not limited to, nucleic acid binding proteins, transcription factors, receptor binding proteins, split enzymes, effectors of membrane receptors, etc.

In a sixth aspect, the disclosure provides methods, comprising:
(i) contacting the fusion protein of embodiment or combination of embodiments of the fifth or sixth aspects disclosed herein with a biological sample under conditions to promote non-covalent binding of the fusion protein with first target and second target present in the sample, and
(ii) detecting non-covalent binding of the one or more fusion proteins to the first target and/or the second target in the biological sample.

The detecting may comprise any suitable means for detecting binding, including but not limited to mass spectrometry, yeast-2-hybrid detection, functional assays, or any other suitable assay as will be clear to those of skill in the art based on the current disclosure. In one embodiment, the method comprises detecting cooperative non-covalent binding of the one or more fusion proteins to the first target and the second target in the biological sample. This embodiment comprises use of the fusion proteins in AND gate logic, as described in more detail in the examples that follow. As used herein, "cooperative" binding means binding the fusion protein cannot bind to the first target without also binding to the second target, and the fusion protein cannot bind to the second target without binding to the first target.

In another embodiment, the method comprises detecting non-covalent binding of the one or more fusion proteins to the first target or the second target in the biological sample. This embodiment comprises use of the fusion proteins in OR gate logic, as described in more detail in the examples that follow.

In another embodiment, the disclosure provides methods comprising:
(a) contacting a biological sample with at least two fusion proteins, wherein each of the at least two fusion proteins comprises the formula X-B-Z, wherein
each B is independently a polypeptide linker;
each X domain comprises a first non-naturally occurring polypeptide comprising 1, 2, or 3 alpha helices;
each Z domain comprises a second non-naturally occurring polypeptide comprising 1, 2, or 3 alpha helices, wherein a combined number of alpha helices from the X domain and the Z domain in each individual fusion protein is 4, 5, or 6; wherein the X domain and the Z domain interact at a binding interface, wherein the binding interface comprises a hydrogen bond network in which at least one side chain in each X domain alpha helix bonds with a side chain in an alpha helix in the Z domain; wherein the X domain in a first fusion protein is capable of non-covalently binding to a first target;
the Z domain in a second fusion protein is capable of non-covalently binding to a second target; and
the X domains and Z domains in each individual fusion protein that are not capable of non-covalently binding to the first target or the second target are capable of non-covalently binding to an X or a Z domain of a different fusion protein in the plurality of fusion proteins;
(b) detecting non-covalent binding of the two or more fusion proteins to the first target and/or the second target in the biological sample. This embodiment comprises use of the fusion proteins in 2 component AND or OR gate logic, as described in more detail in the examples that follow.

In one embodiment of the AND or OR gate logic, the detecting comprises detecting cooperative non-covalent binding of the two or more fusion proteins to the first target and the second target in the biological sample. In another embodiment,
(i) the first fusion protein has the formula X1-B1-Z1, wherein the X1 domain is capable of non-covalently binding to the first target; and
(ii) the second fusion protein has the formula X2-B2-Z2, wherein the Z2 domain is capable of non-covalently binding to the first target; and wherein the Z1 and X2 domains are capable of non-covalently binding to each other.

In a further embodiment,
(i) the first fusion protein has the formula X1-B1-Z1, wherein the X1 domain is capable of non-covalently binding to the first target; and
(ii) the second fusion protein has the formula X2-B2-Z2,
(iii) the at least two fusion proteins comprise a third fusion protein of formula X3-B3-Z3, wherein the Z3 domain is capable of non-covalently binding to the second target; wherein (A) the Z1 and X2 domains are capable of non-covalently binding to each other; and
(B) the Z2 and X3 domains are capable of non-covalently binding to each other.

In another embodiment, the X domains, Y domains, B domains, and or fusion proteins are as recited in any embodiment or combination of embodiments disclosed herein, such as in the fourth and fifth aspects. In one embodiment, at least one of the fusion proteins comprises one or more effector polypeptide domains linked to one or more of the X and/or Z domains, and wherein the detecting step comprises detecting an output signal caused by binding the first target and/or the second target. In another embodiment, the detecting step comprises detecting an output signal from the one or more effector polypeptide caused by cooperative non-covalently binding of the first target and the second target. Such detection may be by any suitable means dependent in part on the output signal to be detected, including but not limited to those disclosed herein. The output signal to be detected may be any suitable output signal including but not limited to fluorescence activity, functional activity, etc.

Any suitable effector polypeptide domain may be employed as suitable for an intended use. In one embodiment, the one or more effector polypeptide domains may comprise a polypeptide including, but not limited to, nucleic acid binding proteins, transcription factors, receptor binding proteins, nucleic acid binding proteins, transcription factors, receptor binding proteins, split enzymes, effectors of membrane receptors, etc.

In a seventh aspect, the disclosure provides compositions comprising
(a) a first polypeptide comprising 2 alpha helices, wherein the first polypeptide is capable of non-covalently binding a first target; and
(b) a second polypeptide comprising 2 alpha helices, wherein the first polypeptide is capable of non-covalently binding to the second polypeptide, and wherein the second polypeptide is capable of non-covalently binding a second target that differs from the first target; wherein:
(i) a binding affinity of the first polypeptide for the first target is approximately equal to a binding affinity of the second polypeptide for the second target; and
(ii) the binding affinity of the first polypeptide for the first target and the binding affinity of the second polypeptide for the second target are greater than the binding affinity of the first target and the second target for each other.

Compositions of this seventh aspect can be used, for example, as NOR gates as described in detail in the examples that follow.

In one embodiment, the composition further comprises the first target and the second target. The first targets and second targets may be any target suitable for an intended use. In non-limiting embodiments, the first target and/or the second target may comprise polypeptides or nucleic acids. In another embodiment, the first target and/or the second target further comprise one or more effector polypeptide domains. Any effector polypeptide domains may be used as suitable for an intended use. In one embodiment, the one or more effector polypeptide domains may comprise a polypeptide including, but not limited to, nucleic acid binding proteins, transcription factors, receptor binding proteins, split enzymes, effectors of membrane receptors, etc. In another embodiment, the first polypeptide and/or the second polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide having the amino acid sequence selected from the group consisting of SEQ ID NOS:1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, as listed in Tables 1A and 1B. In one embodiment, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of amino acid residues at defined interface positions of the first polypeptide and/or the second polypeptide are invariant compared to the reference polypeptide amino acid sequence (interface residues shown in Table 2).

In one non-limiting and exemplary embodiment,
(a) the first polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO:3

9
(SEQ ID NO: 3)
GTKEDILERQRKIIERAQEIHRRQQEILEELERIIRKPGSSEEAMKRM

LKLLEESLRLLKELLELSEESAQLLYEQR;

and
(b) the second polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO:58.

10'
(SEQ ID NO: 58)
GSSADDVLEDILKIIRELIEILDQILSLLNQLLKLLRHGVPNAKKVVE

KYKEILELYLQLVSLFLKIVKTHADAVSGKIDKKAEEEIKKEEEKIKE

KLRQAKDILKKLQEEIDKTR

In one non-limiting and exemplary embodiment,
(a) the first polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO:3

9
(SEQ ID NO: 3)
GTKEDILERQRKIIERAQEIHRRQQEILEELERIIRKPGSSEEAMKRM

LKLLEESLRLLKELLELSEESAQLLYEQR;

and
(b) the second polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO:362.

10'

(SEQ ID NO: 362)
SADDVLEDILKIIRELIEILDQILSLLNQLLKLLRHGVPNAKKVVEKY

KEILELYLQLVSLFLKIVKTHADAVSGKIDKKAEEEIKKEEEKIKEKL

RQAKDILKKLQEEIDKTR

In another embodiment, the first target and/or the second target each comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide having the amino acid sequence selected from the group consisting of SEQ ID NO:1-290, with the proviso that the first target forms a heterodimer (a-b) pair with the first polypeptide, and the second target forms a heterodimer (a-b) pair with the second polypeptide. In another embodiment, the first target and/or the second target each comprises a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide having the amino acid sequence selected from the group consisting of SEQ ID NO:1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, with the proviso that the first target forms a heterodimer (a-b) pair with the first polypeptide, and the second target forms a heterodimer (a-b) pair with the second polypeptide. Heterodimer A-B pairs among the polypeptides of SEQ ID NOS:1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 are described at length above (See also FIG. 16). In one embodiment, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of amino acid residues at defined interface positions of the first target and/or the second target are invariant compared to the reference polypeptide amino acid sequence (interface residues shown in Table 2).

The compositions of this seventh aspect can be used for any suitable purpose, including in designing NOR logic gates. In one embodiment, the disclosure provides methods comprising
(a) contacting a biological sample with the composition of any embodiment or combination of embodiments of the seventh aspect of the disclosure; and
(b) detecting binding, of the first polypeptide to the first target and binding of the second polypeptide to the second target in the sample, such as detecting an output signal caused by actions of effector polypeptides upon binding. Additional details of the use of the compositions of the seventh aspect of the disclosure in NOR logic gates re described in detail in the examples that follow.

In an eighth aspect, the disclosure provides compositions comprising:
(a) a first polypeptide comprising 2 alpha helices, wherein the first polypeptide is capable of non-covalently binding a first target; and
(b) a second polypeptide comprising 2 alpha helices, wherein the polypeptide is capable of non-covalently binding to the second polypeptide, and wherein the second polypeptide is capable of non-covalently binding a second target that differs from the first target; wherein:
  (i) a binding affinity of the first polypeptide for the second polypeptide is greater than a binding affinity of the second polypeptide for the second target;
  (ii) a binding affinity of the first polypeptide for the first target is approximately equal to a binding affinity of the second polypeptide for the second target; and
  (iii) the binding affinity of the first polypeptide for the first target and the binding affinity of the second polypeptide for the second target are greater than the binding affinity of the first target and the second target for each other.

Compositions of this eighth aspect can be used, for example, as XNOR gates as described in detail in the examples that follow. In one embodiment, the composition further comprises the first target and the second target. The first targets and second targets may be any target suitable for an intended use. In non-limiting embodiments, the first target and/or the second target may comprise polypeptides or nucleic acids. In another embodiment, the first target and/or the second target further comprise one or more effector polypeptide domains. Any effector polypeptide domains may be used as suitable for an intended use. In one embodiment, the one or more effector polypeptide domains may comprise a polypeptide including, but not limited to, nucleic acid binding proteins, transcription factors, receptor binding proteins, split enzymes, effectors of membrane receptors, etc. In another embodiment, the first polypeptide and/or the second polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide having the amino acid sequence selected from the group consisting of SEQ ID NOS:1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, as listed in Tables 1A and 1B. In one embodiment, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of amino acid residues at defined interface positions of the first polypeptide and/or the second polypeptide are compared to the reference polypeptide amino acid sequence (interface residues shown in Table 2).

In one non-limiting and exemplary embodiment,
(a) the first polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO:3

9
(SEQ ID NO: 3)
GTKEDILERQRKIIERAQEIHRRQQEILEELERIIRKPGSSEEAMKRM

LKLLEESLRLLKELLELSEESAQLLYEQR;

and
(b) the second polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO:42.

1' (b)
(SEQ ID NO: 42)
GSDDKELDKLLDTLEKILQTATKIIDDANKLLEKLRRSERKDPKVVET

YVELLKRHEKAVKELLEIAKTHAKKVE

In one non-limiting and exemplary embodiment,
(a) the first polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO:3

9
(SEQ ID NO: 3)
GTKEDILERQRKIIERAQEIHRRQQEILEELERIIRKPGSSEEAMKRM

LKLLEESLRLLKELLELSEESAQLLYEQR;

and
(b) the second polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO:352.

1' (b)
(SEQ ID NO: 352)
DDKELDELLDTLEKILQTATKIIDDANKLLEKLRRSERKDPKVVETYV

ELLERHEKAVKELLEIAKTHAKKVE

In another embodiment, the first target and/or the second target each comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide having the amino acid sequence selected from the group consisting of SEQ ID NO:1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, with the proviso that the first target forms a heterodimer (a-b) pair with the first polypeptide, and the second target forms a heterodimer (a-b) pair with the second polypeptide. Heterodimer A-B pairs among the polypeptides of SEQ ID NOS:1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 are described at length above (See also FIG. 16). In one embodiment, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of amino acid residues at defined interface positions of the first target and/or the second target are invariant compared to the reference polypeptide amino acid sequence (interface residues shown in Table 2).

The compositions of this eighth aspect can be used for any suitable purpose, including in designing XNOR logic gates. In one embodiment, the disclosure provides methods comprising (a) contacting a biological sample with the composition of any embodiment of the eighth aspect of the disclosure; and
(b) detecting binding interactions between the first polypeptide and the first target. the second polypeptide and the second target, the first polypeptide and the second polypeptide, and the first target and the second target in the sample, such as detecting an output signal caused by actions of effector polypeptides upon binding. Additional details of the use of the compositions of the eighth aspect of the disclosure in XNOR logic gates re described in detail in the examples that follow.

In a ninth aspect, the disclosure provides compositions comprising:
(a) a first polypeptide comprising 4 alpha helices, wherein the first polypeptide is capable of non-covalently binding a first target; and
(b) a second polypeptide comprising 4 alpha helices, wherein the second polypeptide is capable of non-covalently binding a second target that differs from the first target; wherein:
(i) a binding affinity of the first target for the second target is greater than a binding affinity of the first polypeptide for the first target;
(ii) a binding affinity of the first polypeptide for the first target is approximately equal to a binding affinity of the second polypeptide for the second target; and
(iii) the sum of the binding affinity of (A) the first polypeptide for the first target and (B) the binding affinity of the second polypeptide for the second target, is greater than the binding affinity of the first target and the second target.

Compositions of this ninth aspect can be used, for example, as NAND gates as described in detail in the examples that follow. In one embodiment, the composition further comprises the first target and the second target. The first targets and second targets may be any target suitable for an intended use. In non-limiting embodiments, the first target and/or the second target may comprise polypeptides or nucleic acids. In another embodiment, the first target and/or the second target further comprise one or more effector polypeptide domains. Any effector polypeptide domains may be used as suitable for an intended use. In one embodiment, the one or more effector polypeptide domains may comprise a polypeptide including, but not limited to, nucleic acid binding proteins, transcription factors, receptor binding proteins, split enzymes, effectors of membrane receptors, etc. In another embodiment, the first polypeptide and/or the second polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide having the amino acid sequence selected from the group consisting of SEQ ID NOS:1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, as listed in Tables 1A and 1B. In one embodiment, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of amino acid residues at defined interface positions of the first polypeptide and/or the second polypeptide are invariant compared to the reference polypeptide amino acid sequence (interface residues shown in Table 2).

In one non-limiting and exemplary embodiment,
(a) the first polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO:42

1' (b)
(SEQ ID NO: 42)
GSDDKELDKLLDTLEKILQTATKIIDDANKLLEKLRRSERKDPKVVET

YVELLKRHEKAVKELLEIAKTHAKKVE (b) the second polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO: 57.

10
(SEQ ID NO: 57)
DHSRKLEEILDRLRKHVKRLLEHLRELLSLVKENPEDKDLVEVLELSL

AILRRSLEAVEAFLKSVTKKDPDDEDLRRKADEIRKEVEEIKKSLAEV

EKEIYKLK

In one non-limiting and exemplary embodiment,
(a) the first polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO:352

1' (b)
(SEQ ID NO: 352)
DDKELDELLLDTLEKILQTATKIIDDANKLLEKLRRSERKDPKVVETYV

ELLKRHEKAVKELLEIAKTHAKKVE (b) the second polypeptide comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to one having the amino acid sequence of SEQ ID NO: 57.

10
(SEQ ID NO: 57)
DHSRKLEEILDRLRKHVKRLLEHLRELLSLVKENPEDKDLVEVLELSL

AILRRSLEAVEAFLKSVTKKDPDDEDLRRKADEIRKEVEEIKKSLAEV

EKEIYKLK

In another embodiment, the first target and/or the second target each comprise a polypeptide that is 50%, 55%, 60%, 65%, 70%, 75%, 80%, 85%, 90%, 91%, 92%, 93%, 94%, 95%, 96%, 97%, 98%, 99%, or 100% identical to the full length of a polypeptide selected from the group including, but not limited to a polypeptide having the amino acid sequence selected from the group consisting of SEQ ID NO:1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494, with the proviso that the first target forms a heterodimer (a-b) pair with the first polypeptide, and the second target forms a heterodimer (a-b) pair with the second polypeptide. Heterodimer A-B pairs among the polypeptides of SEQ ID NOS:1-290 and 331, 332, 334, 336-422, 424, 426, 428, 430, 432, 434, 436, 438, 440, 442, 444, 446, 448, 450, 452, 454, 456, 458-460, 462, 464, 466, 468, 470, 472, 474, 476, 478, 480, 482, 484, 486, 488, 490, 493, and 494 are described at length above (See also FIG. 16). In one embodiment, at least 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of amino acid residues at defined interface positions of the first target and/or the second target are compared to the reference polypeptide amino acid sequence (interface residues shown in Table 2).

The compositions of this ninth aspect can be used for any suitable purpose, including in designing NAND logic gates. In one embodiment, the disclosure provides methods comprising
(a) contacting a biological sample with the composition of any embodiment of the ninth aspect of the disclosure; and
(b) detecting binding interactions between the first polypeptide and the first target. the second polypeptide and the second target, and the first target and the second target in the sample, such as detecting an output signal caused by actions of effector polypeptides upon binding.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

As will be understood by those of skill in the art, the polypeptides of the invention may include additional residues at the N-terminus, C-terminus, or both that are not present in the polypeptides of the invention; these additional residues are not included in determining the percent identity of the polypeptides of the invention relative to the reference polypeptide.

As noted above, the polypeptides of the invention may include additional residues at the N-terminus, C-terminus, or both. Such residues may be any residues suitable for an intended use, including but not limited to detection tags (i.e.: fluorescent proteins, antibody epitope tags, etc.), linkers, therapeutic agents, ligands suitable for purposes of purification (His tags, etc.), ligands to drive localization, and peptide domains that add functionality to the polypeptides.

In a tenth aspect, the disclosure provides nucleic acids encoding the polypeptide, protein, fusion protein, scaffold, or design component of any embodiment or combination of embodiments disclosed herein. The nucleic acid sequence may comprise single stranded or double stranded RNA or DNA in genomic or cDNA form, or DNA-RNA hybrids, each of which may include chemically or biochemically modified, non-natural, or derivatized nucleotide bases. Such nucleic acid sequences may comprise additional sequences useful for promoting expression and/or purification of the encoded polypeptide, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the disclosure.

In an eleventh aspect, the disclosure provides expression vector comprising one or more nucleic acids of the disclosure operatively linked to a control sequence. "Expression vector" includes vectors that operatively link a nucleic acid coding region or gene to any control sequences capable of effecting expression of the gene product. "Control sequences" operably linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In various embodiments, the expression vector may comprise a plasmid, viral-based vector, or any other suitable expression vector.

In a twelfth aspect, the disclosure provides cells comprising one or more nucleic acid, expression vector, polypeptide, protein, heterodimer protein, and/or protein scaffold of any embodiment or combination of embodiments disclosed herein. Nucleic acids or expression vectors may be episomal or chromosomally integrated. Any suitable cell type may be used, such prokaryotic or eukaryotic cells. The cells can be transiently or stably engineered to incorporate the expression vector of the disclosure, using techniques including but not limited to bacterial transformations, calcium phosphate co-precipitation, electroporation, or liposome mediated-, DEAE dextran mediated-, polycationic mediated-, or viral mediated transfection In addition, the disclosure provides methods of producing a polypeptide, fusion protein, protein, heterodimer, etc. (collectively referred to as polypeptide) disclosed herein. In one embodiment, the method comprises the steps of (a) culturing a host according to this aspect of the disclosure under conditions conducive to the expression of the polypeptide, and (b) optionally, recovering the expressed polypeptide. The expressed polypeptide can be recovered from the cell free extract or recovered from the culture medium. In another embodiment, the method comprises chemically synthesizing the polypeptides.

Example 1 Design of Orthogonal Protein Heterodimers

Abstract: Here we demonstrate that heterodimeric interaction specificity can be achieved using extensive and modular buried hydrogen bond networks. We used the Crick generating equations to produce millions of four helix backbones with varying degrees of supercoiling around a central axis, identified those accommodating extensive hydrogen bond networks, and designed connected pairs of helices with short loops and optimize the remainder of the sequence. 65 of 97 such designs expressed in E. coli formed constitutive heterodimers, and crystal structures of four designs were in close agreement with the computational models and confirmed the designed hydrogen bond networks. In cells, a set of six heterodimers were found to be fully orthogonal, and in vitro, following mixing of 32 chains from sixteen heterodimer designs, denaturation in 5M GdnHCl and reannealing, the vast majority of the interactions were between the designed cognate pairs. The ability to design orthogonal protein heterodimers enables sophisticated protein based control logic for synthetic biology, and illustrates that nature has not fully explored the possibilities for programmable biomolecular interaction modalities. Hydrogen bond networks, including modular hydrogen bond networks are described in published patent application number WO2017173356, incorporated by reference herein.

Figure 5A:
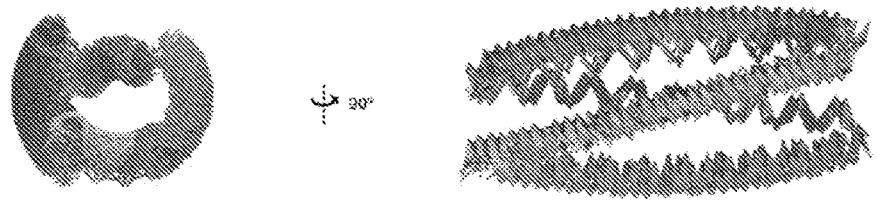
FIGS. 5A to 5B show example HBNets resulting from the systematic search.
Figure 5B:
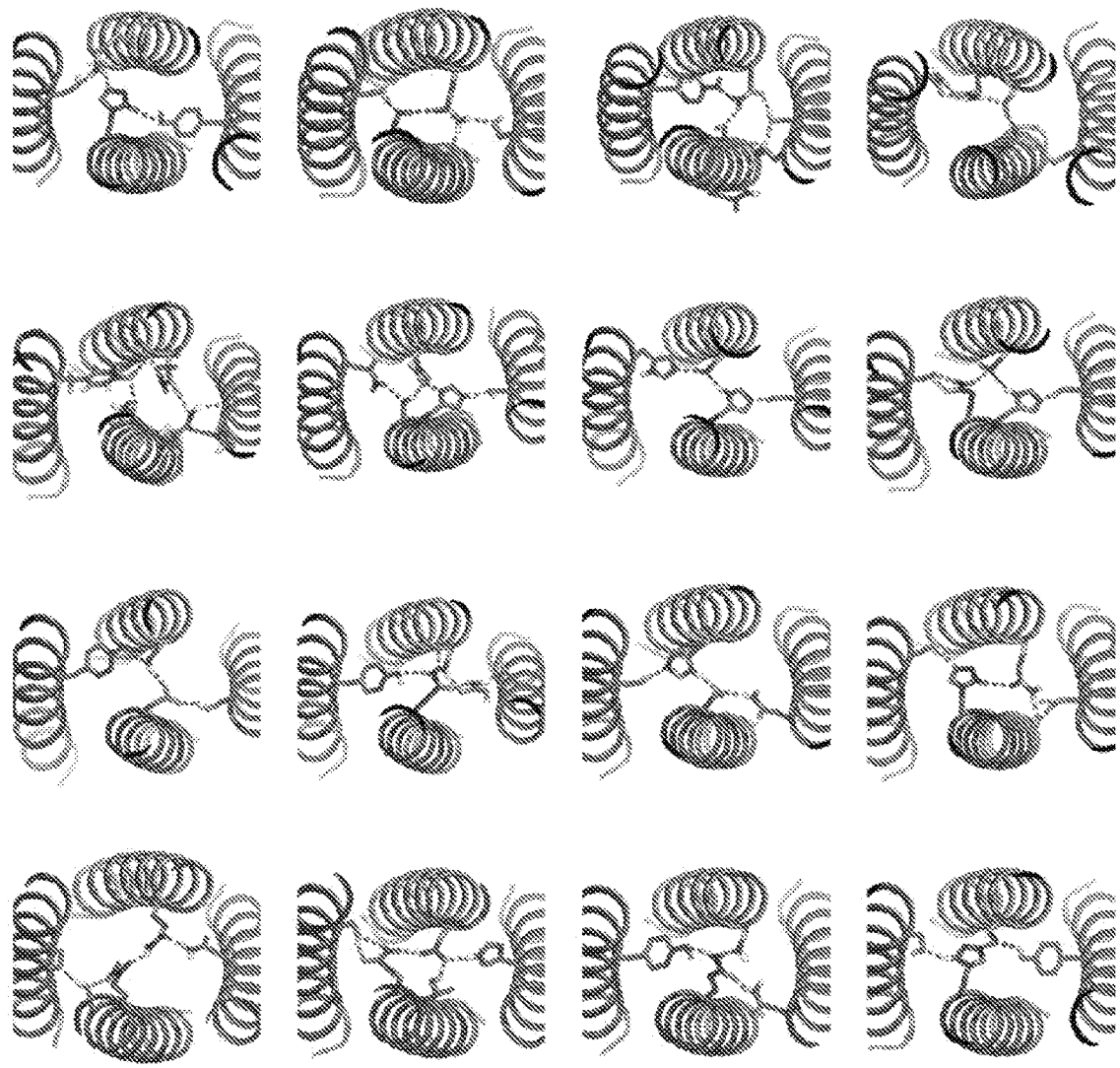

Orthogonal sets of protein-protein and protein-peptide interactions play important roles in biological systems. Creation of new specificities by sequence redesign has been difficult, often resulting in promiscuous binding We hypothesized that large sets of designed heterodimers could be generated by incorporating asymmetric buried hydrogen bond networks into regularly repeating backbone structures. We generated helical bundle heterodimers in which each monomer is a helix-turn-helix starting from four-helix backbones. For each of the four helices, we exhaustively sampled the helical phase ($\Delta\Phi_1$), supercoil radius (R) and offset along the Z-axis (Z offset) (FIG. 1A), restricting the supercoil phases of the helices to 0, 90, 180 and 270 degrees, and the supercoil twist ($\omega_0$) and helical twist ($\omega_1$) to the ideal values for either a two layer left handed super coil ($\omega_0$=−2.85 and $\omega_1$=102.85), or a 5 layer untwisted bundle ($\omega_0$=0 and $\omega_1$=100) (FIG. 5A-B). This yielded 27 million untwisted and 60 million left-handed supercoiled backbones for both parallel and antiparallel orientations of opposing helices (FIG. 1B).

Figures 6A, 6B, 6C:
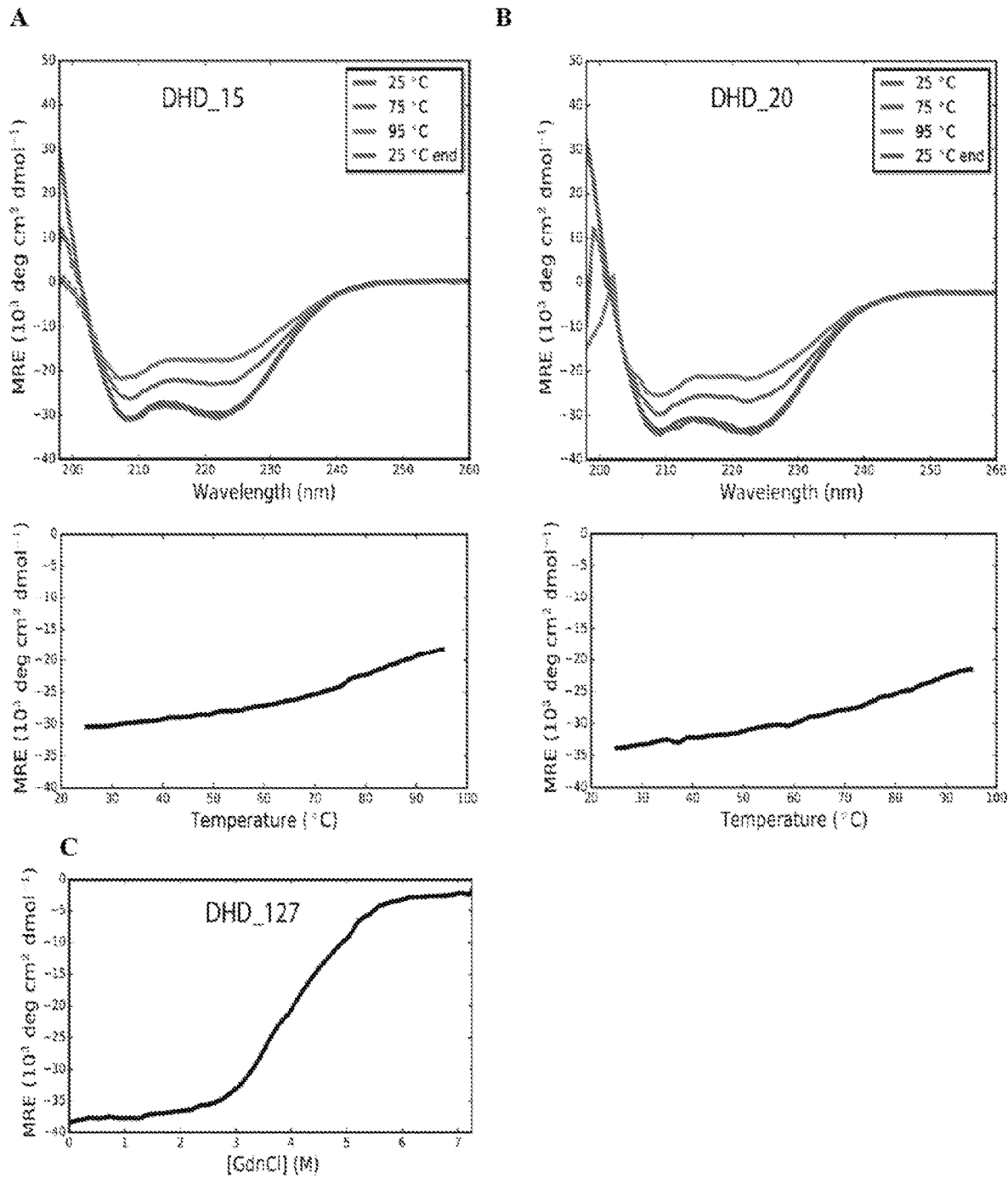
FIGS. 6A to 6C show thermal and chemical denaturation of DHDs.

To identify the modular hydrogen bond network equivalents to DNA base pairs, we used ROSETTA™ HBNET[21] to design buried hydrogen bond networks in the central repeat units of each backbone, and obtained 2251 hydrogen bond networks involving at least 4 side chain residues with all heavy-atom donors and acceptors participating in hydrogen bonds, and connecting all 4 helices (FIG. 1c; FIG. 6, Table 6). We then identified all of the geometrically compatible placements of these hydrogen bond networks in each backbone (FIG. 1d), selected backbones accommodating at least two networks, and connected pairs of helices with short loops (FIG. 1e). Low energy sequences were identified using ROSETTADESIGN™[22] calculations in which the hydrogen bond networks were held fixed. Designs with fully satisfied hydrogen bond networks and tight hydrophobic packing were selected for experimental characterization, excluding those with networks with C2 symmetry to disfavor homodimerization of monomers. Designed heterodimers (DHDs) are referred to by numbers with monomers labeled a orb; for example, DHD15_a refers to monomer "a" of design DHD15.

TABLE 6

The frequency of observing each hydrogen bond networks during the systematic search.

| HBNet composition | Frequency | Percentage (%) |
|---|---|---|
| (S/T) 2Q1Y1 | 13954 | 3.87071362 |
| (S/T) 3Q1 | 9959 | 2.76253669 |
| (S/T) 2D1H1 | 8452 | 2.34450849 |
| (S/T) 1Q2Y1 | 7603 | 2.10900356 |
| (S/T) 1D1Q1Y1 | 7359 | 2.04132016 |
| (S/T) 3D1 | 6332 | 1.75643963 |
| (S/T) 3D1Q1 | 5525 | 1.53258512 |
| (S/T) 1D1Q3 | 5071 | 1.40664962 |
| (S/T) 1D1Q2 | 5062 | 1.4041531 |
| (S/T) 2N1Y1 | 5046 | 1.39971484 |
| (S/T) 1N1Q1Y1 | 4921 | 1.36504097 |
| (S/T) 2H2 | 4683 | 1.29902192 |
| (S/T) 2H1Q1 | 4572 | 1.26823152 |
| (S/T) 3H1 | 3955 | 1.09708129 |
| (S/T) 2D1Q2 | 3946 | 1.09458477 |
| (S/T) 1D1N1Q2 | 3862 | 1.07128393 |
| (S/T) 3N1 | 3783 | 1.04937005 |
| (S/T) 2D1Y1 | 3762 | 1.04354484 |
| (S/T) 2D1Q1 | 3669 | 1.01774747 |
| (S/T) 1D1H1Q1 | 3653 | 1.01330922 |
| (S/T) 1D1Q1W1 | 3409 | 0.94562582 |
| (S/T) 1D1Q2Y1 | 3342 | 0.92704063 |
| (S/T) 2Q3 | 3111 | 0.86296331 |
| (S/T) 2D1N1Q1 | 2999 | 0.83189552 |
| (S/T) 2Q2Y1 | 2850 | 0.79056427 |
| (S/T) 1D1W1Y1 | 2849 | 0.79028688 |
| (S/T) 2N1Q2 | 2741 | 0.76032865 |
| (S/T) 2D1Q1Y1 | 2723 | 0.75533562 |
| (S/T) 1D1N1Q1Y1 | 2684 | 0.74451737 |
| (S/T) 2Q1W1 | 2641 | 0.73258956 |
| (S/T) 2H1N1Q1 | 2591 | 0.71872001 |
| (S/T) 2Q2 | 2582 | 0.71622349 |
| (S/T) 2N1Q1 | 2554 | 0.70845654 |
| (S/T) 2D1W1 | 2467 | 0.68432353 |
| (S/T) 2H1N1 | 2377 | 0.65935834 |
| (S/T) 4Q1 | 2305 | 0.63938619 |
| (S/T) 1N1Q2Y1 | 2296 | 0.63688967 |
| (S/T) 1D2Q2 | 2285 | 0.63383837 |
| (S/T) 2D1H1Q1 | 2276 | 0.63134185 |
| (S/T) 2D1Q1W1 | 2267 | 0.62884533 |
| (S/T) 1H1Q1Y1 | 2222 | 0.61636274 |
| (S/T) 1D1N1Q1 | 2207 | 0.61220187 |
| (S/T) 2H1Y1 | 2150 | 0.59639059 |
| (S/T) 1D1N1Y1 | 2109 | 0.58501756 |
| (S/T) 1Q1Y2 | 1962 | 0.54424109 |
| (S/T) 1H1Q2 | 1957 | 0.54285413 |
| (S/T) 1Q1W1Y1 | 1954 | 0.54202196 |
| (S/T) 2N1Q1Y1 | 1935 | 0.53675153 |
| (S/T) 3H1Q1 | 1901 | 0.52732024 |
| (S/T) 1D1H1W1 | 1879 | 0.52121764 |

Figure 10:
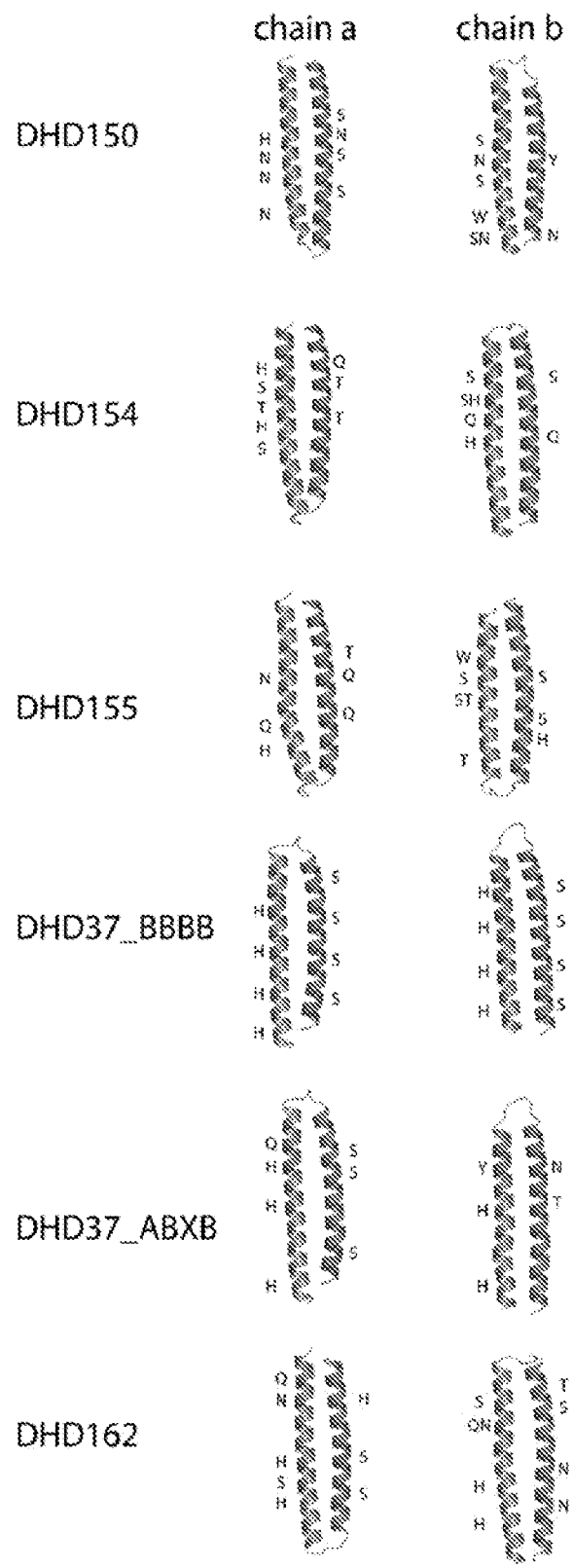
FIG. 10 shows hydrogen bond network sequence motifs of the set of 6 orthogonal pairs in Y2H experiments. Letters patches mark the location of hydrogen bond network forming residues on the backbones, and indicate residue identities.

94 of the 97 selected designs were well-expressed in *E. coli* with both monomers co-purifying by Ni-affinity chromatography (only one monomer contains a hexahistidine tag). For 85/94, the dominant species observed in size exclusion chromatography (SEC) had the expected size (FIG. 10. Three designs characterized by CD spectroscopy were found to be all alpha helical and stable at 95° C. (FIG. 1g, FIG. 6). Sequences and other information on the designs are provided in Tables 1A-B (above).

Figures 7A, 7B:
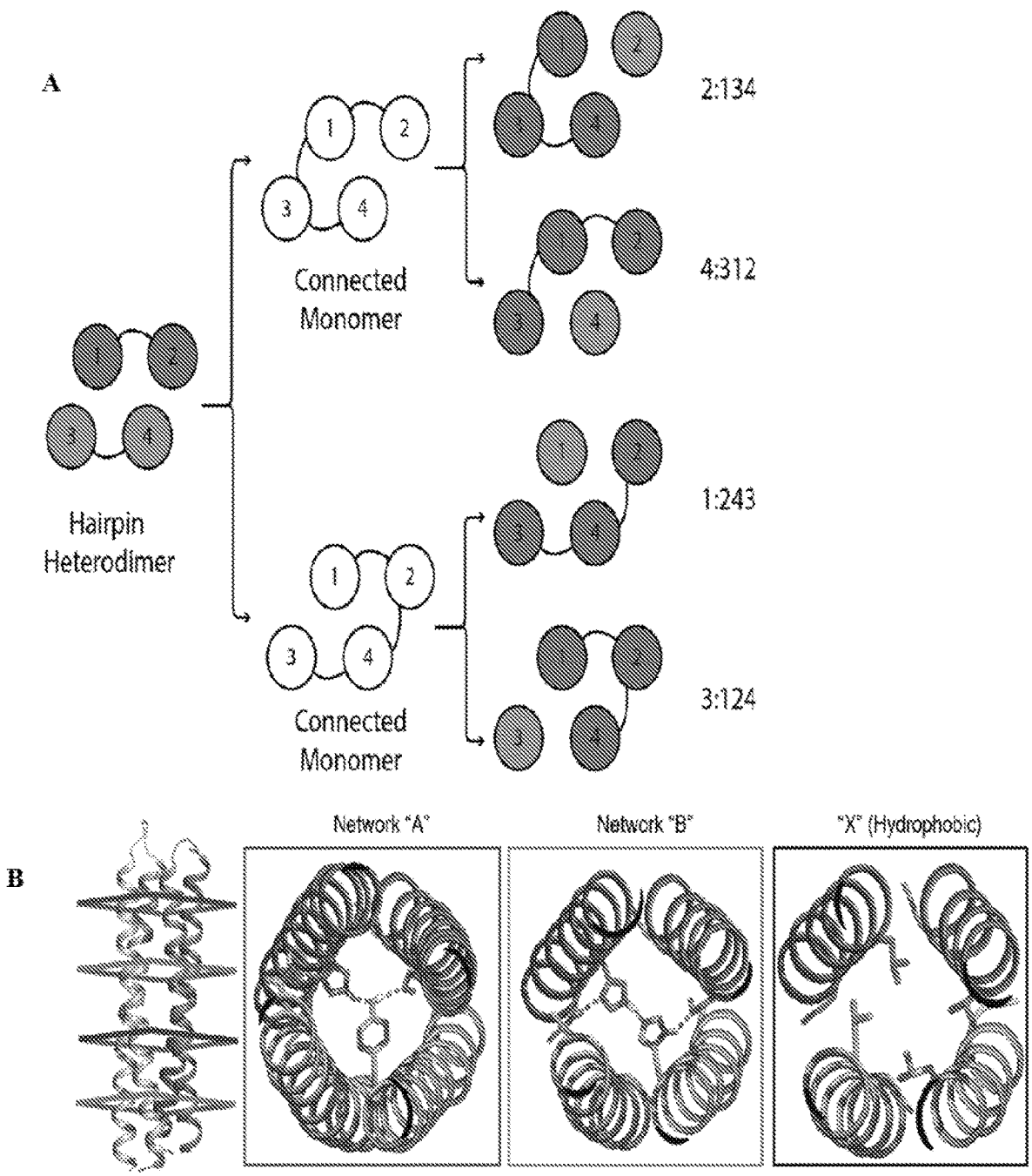
FIG. 7A to 7B show backbone and hydrogen bond network permutations.
Figures 8A, 8B, 8C, 8D, 8E, 8F, 8G, 8H:
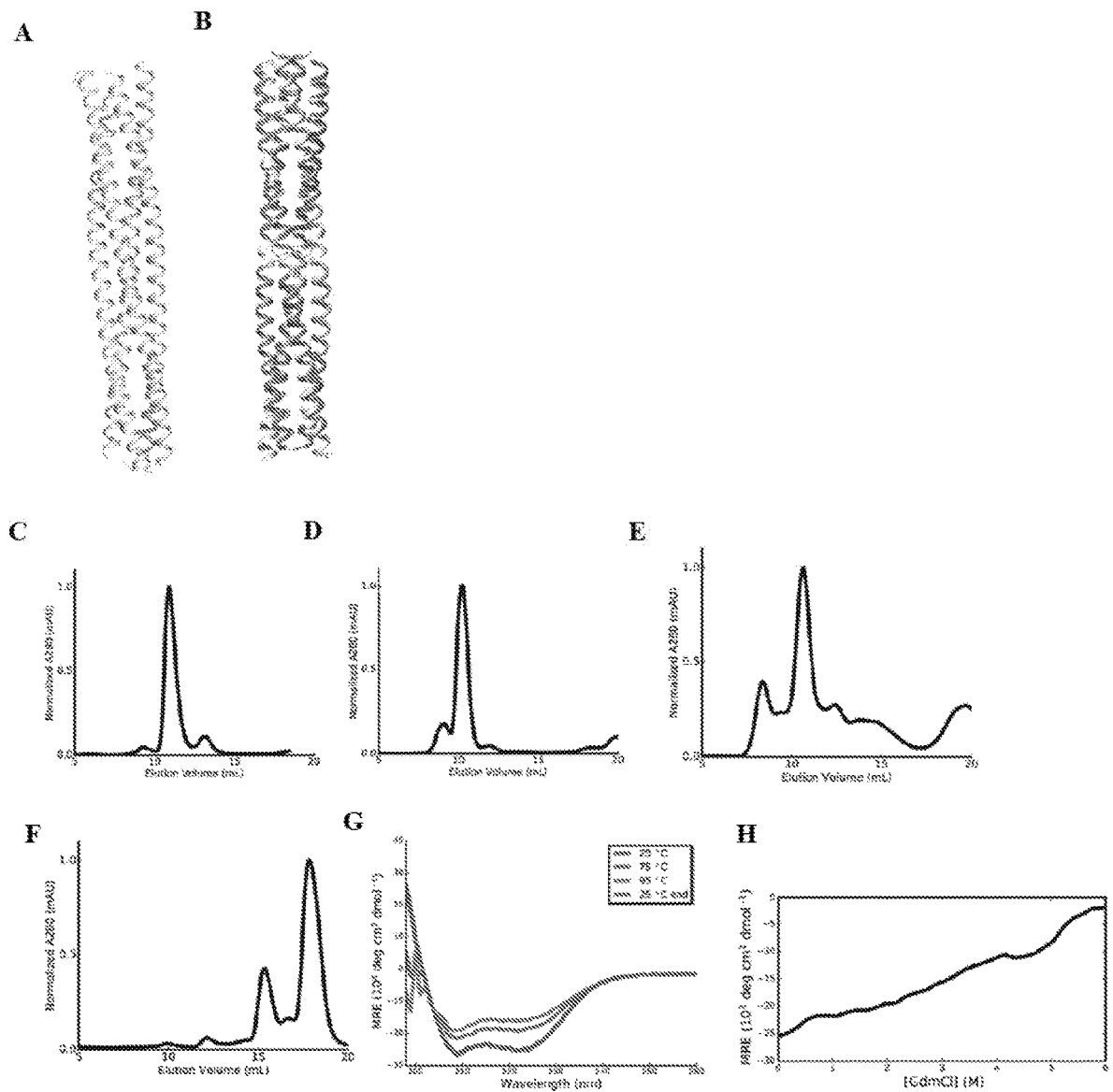
FIGS. 8A to 8H show crystal structure of the domain swapped DHD_15 and biophysical characterization of higher order oligomers.

We explored the extent to which the heterodimer set could be expanded by permuting the hydrogen bond networks in the different helical repeat units, and by permuting the backbone connectivity. Assigning each unique network a letter, DHD37_XBBA indicates a variant where the second, third and fourth repeat units have hydrogen bond networks B, B, and A, and the first heptad has exclusively hydrophobic residues in the core, while DHD103_1:423 indicates a heterodimer where one monomer consists of the first helix of DHD103 and the other monomer consists of helices 2 through 4 (FIG. 7). 13 of 14 hydrogen bond network permuted variants and 9 of 10 "3+1" backbone-permuted heterodimers (generated from five starting "2+2" heterodimers) ran as single peaks on SEC.

SAXS spectra collected for 44 designs were consistent with the design models (FIG. 1h, FIG. 2f-h,). The X-ray crystal structures of DHD131, DHD37_1:234, DHD127 and DHD15 had backbone Cα atom RMSDs to the design models ranging from 0.95 to 1.7 Å. The extensive five-residue buried hydrogen bond network of DHD131 (involving two serines, an asparagine, a tyrosine, and a tryptophan) is nearly identical in the crystal structure, with an additional water molecule bridging the interactions (FIG. 2a). The two designed hydrogen bond networks in DHD37_1:234, which contain buried histidine and tyrosine aromatic side chains sterically disfavoring homodimers, are in close agreement with the crystal structure (FIG. 2b). In DHD127, the histidines in the two hydrogen bond networks adopt a rotamer different from the design model (FIG. 2c), making a hydrogen bond with a water molecule. A crystal structure of DHD15 at pH 7.0 is similar to the design model (FIG. 2d), while a structure at pH 6.5 is of a domain-swapped, heterotetramer conformation.

Figures 3A, 3B, 3C:
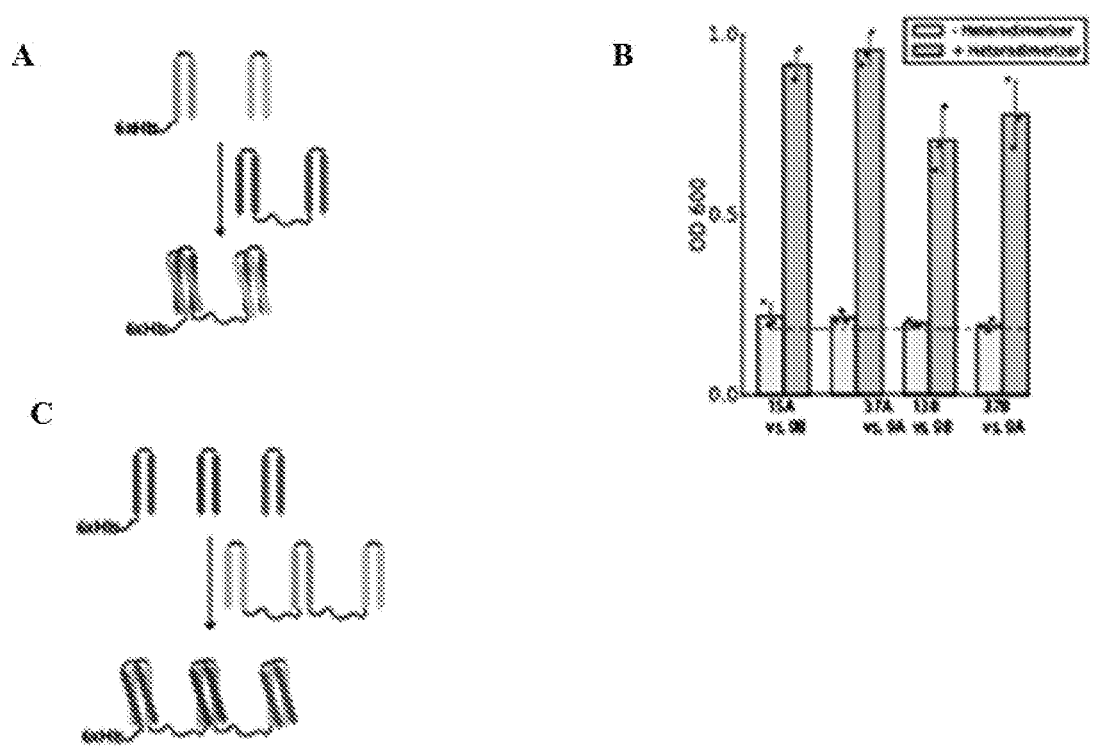
FIGS. 3A to 3C shows new functionality from DHD combinations.

We built three induced dimerization systems by fusing one monomer each from two different heterodimers via a flexible linker, and testing whether the remaining two monomers from each pair could be brought together by the fusion (FIG. 3a). In each case, the three components co-purified by Ni-NTA chromatography (one monomer has a hexahistidine tag); In yeast two-hybrid assays (Y2H) with monomers from two different heterodimers fused to the DNA binding domain (DBD) and transcriptional activation domain (AD), expression of the heterodimerizer fusion as a separate polypeptide chain increased signal significantly over background (FIG. 3b).

Figures 9A, 9B, 9C, 9D, 9E, 9F, 9G:
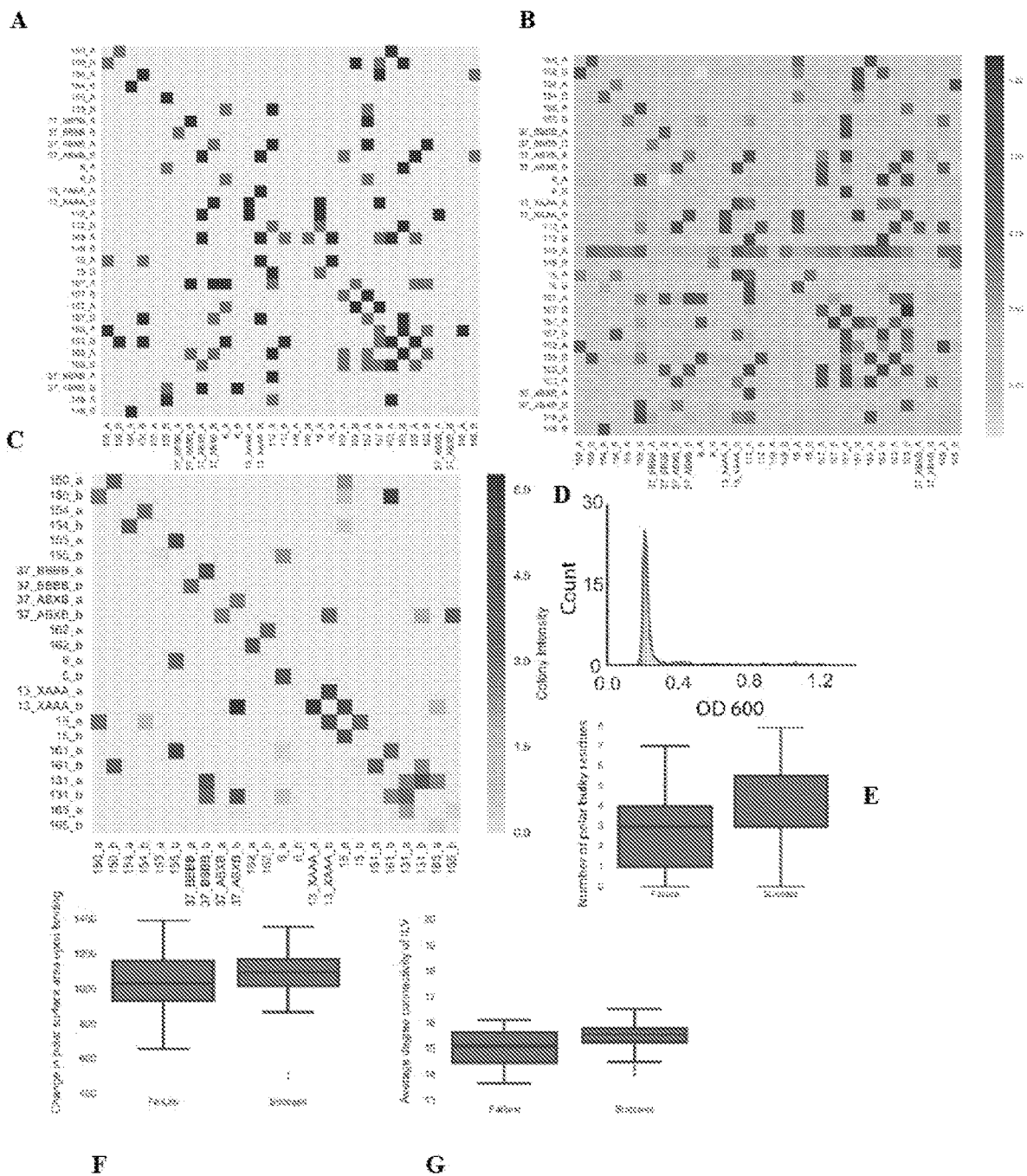
FIGS. 9A to 9G show Y2H all-against-all assay of 16 DHDs.

We covalently linked the monomer chain "a" subunits of 3 DHDs via flexible linkers (FIG. 3C), and co-expressed this "scaffold" and the 3 separate chain "b" monomers, one with a hexahistidine tag, in *E. coli*. The scaffold plus monomer assembly is stable at 95° C. and has a guanidine denaturation midpoint of 4 M (FIG. 9).

Figures 4A, 4B, 4C:
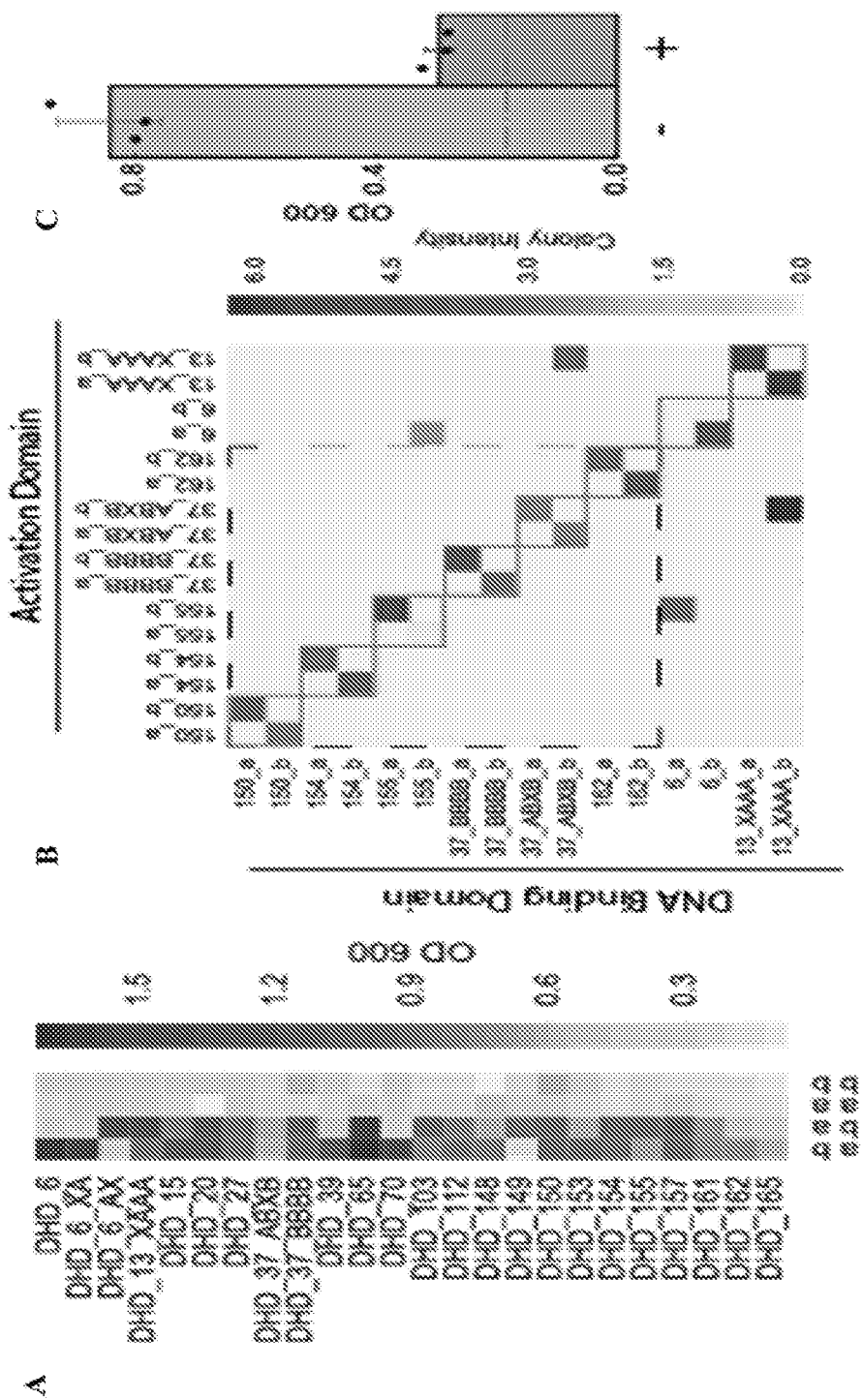
FIGS. 4A to 4C show all-against-all orthogonality assessment.

By generating interfaces with many polar groups which are energetically costly to bury without geometrically matched hydrogen bonding interactions, our design protocol implicitly disfavors non-cognate interactions (explicit negative design to disfavor non-cognate interactions is computationally intractable given the very large number of possible off-target binding modes). For 24 designs, strong interactions were observed by Y2H with the two partners fused to DBD and AD, but not when either partner was fused to both domains; the designed heterodimers, but not the homodimers, form in cells (FIG. 4A). The 24 monomers in 12 of these designs were crossed in an all-by-all Y2H experiment; interactions were observed for all cognate pairs, and 27 of the 552 possible non-cognate interactions (FIG. 9). Orthogonality was higher for an 8 DHD subset: of 240 possible non-cognate interactions, only 4 were observed (FIG. 4B; the interacting polar residues are depicted schematically in FIG. 10). Co-expression of unfused monomers eliminated off-target interactions (FIG. 4C); the cognate interactions are evidently stronger than the non-cognate interactions.

Our results demonstrate that the domain of unbounded sets of orthogonal heterodimeric biomolecules constructed from a single repeating backbone is not limited to nucleic acids. Interaction specificity arises from extensive buried hydrogen bond networks such as the fully connected TYR- SER-TRP-ASN-SER (SEQ ID NO:333) crystallographically confirmed network in FIG. 2a, and heterogeneity in the size of the residues at the designed interface (FIG. 9d-i), analogous to the contribution of steric effects to Watson-Crick base pairing specificity. Our large set of orthogonal interactions, together with the retention of specificity in the fused monomer systems (the induced dimerizer and scaffold of FIG. 3), and the interaction strength hierarchy illustrated by the cognate interaction competition experiment (FIG. 4c), can be used, by way of non-limiting example, to prepare protein based cellular control circuits with faster response times and better integration with signaling inputs and outputs than current nucleic acid based circuitry.

Methods for Example 1

Computational Design
1. Systematic Sampling of Parametric Helical Backbones

We used a generalization of the Crick coiled-coil parameters[5] to independently sample all four helices of the heterodimers supercoiled around the same axis. The supercoil twist (coo) and helical twist (col) were coupled and ideal values were used[20] with coo and cot held constant among the helices. A left-handed supercoil results from $\omega_0=-2.85$ and $\omega_1=102.85$, and a straight bundle with no supercoiling from $\omega_0=0$ and $\omega_1=100$. The supercoil phases ($\Delta\Phi_0$) for the helices were fixed at 0°, 90°, 180° and 270°, respectively. The offset along the Z-axis (Z offset) for the first helix was fixed to 0 as a reference point, with the rest of the helices independently sampling from −1.51 Å to 1.51 Å, with a step size of 1.51 Å. All helices sampled helical phases ($\Delta\Phi_1$) independently, from 0° to 90°, with a step size of 10°. Two of the helices with a $\Delta\Phi_0$ separation of 180° sampled the radius from Z-axis (R) from 5 Å to 8 Å, while the other two sampled from 7 Å to 10 Å, all with a step size of 1 Å. Each helix is set to have 35 residues to accommodate 5 heptad repeats. After removing redundant sample points from the overlapping regions of radii sampling, the supercoiled helical bundles contained more than 60 million unique backbones, and the straight helical bundles contained more than 27 million unique backbones.

2. HBNet Search

For each parametrically generated backbone, HBNet™[21] was used to search the middle heptad for hydrogen bond networks that connect all four helices, contain at least four side chains contributing hydrogen bonds, have all heavy atom donors and acceptors satisfied, and span the intermolecular interface. Symmetry was not enforced during the HBNet™ search. For buried interface positions, only non-charged polar amino acids were considered; for residues that were at the boundary between protein core and surface, all polar amino acids were considered. A subsequent Rosetta™ design calculation was performed to optimize hydrophobic packing, with atom pair restraints from HBNet™ being put on the newly identified hydrogen bond networks. Finally, a minimization step and side chain repacking step was performed without atom pair restraints on hydrogen bonding residues to evaluate how well the networks remained intact in the absence of the constraints. Designs with at most alanines in the middle heptad and no buried unsatisfied polar heavy atoms were selected for downstream design.

3. Generating Combinations of HBNets™ with Heptad Stacking

The purpose of this step is to identify five-heptad backbones (full backbones) that can accommodate at least 2 HBNets™. Instead of generating one-heptad backbones and full backbones separately, searching for HBNets™ in the one-heptad backbones and aligning them to all full backbones, we reasoned the heptad stacking method remains the same if one simply searches for HBNets™ in the middle heptad on all full backbones, extracts the middle heptads, and aligns them to all full backbones. We therefore extracted the middle heptads containing HBNets™, generated all variants of chain ordering, and did pairwise alignment of middle heptads to full backbones using TMalign[30]. All alignments with root mean square deviation (RMSD) less than 0.3 were identified and full backbones that can accommodate at least 2 middle heptads were selected for final design.

4. Connecting Parametric Helical Backbones

Helical backbones are connected with short 2-5 residue loops such that the RMSD of each loop is less than 0.4 RMSD to a nine residues stretch in a native protein. Distance and directionality between helices limit what loops can connect, as such, our closure extends and shrinks helices by up to 3 residues. We then superimpose all short loops from the PDB onto the first and last two helical residues. The loops with the lowest stub-RMSD are minimized using the Rosetta™ score function onto the helical endpoints to ensure a near perfect closure. Loop quality is assessed by measuring the distance in RMSD to the closest nine stretch in the PDB. The loop with the lowest RMSD is returned as the solution. We repeat this procedure to connect all helices and report the solution with the lowest RMSD.

5. Design Calculations

Backbones were regularized using Cartesian space minimization in Rosetta™ to alleviate any torsional strain introduced by heptad stacking. Two consecutive Rosetta™ packing rounds were performed with increasing weight on the repulsive energy to optimize hydrophobic packing, while constraining the hydrogen bond network residues. A Fast-Design step was subsequently used within a generic Monte Carlo mover to optimize secondary structure shape complementarity, while allowing at most 8% alanine, 3 methionine and 3 phenylalanine in the protein core. The last step of minimization and side chain repacking to identify the movement of HBNets without atom pair constraints is the same as what was described in Step 2.

6. Selection Criteria and Metrics Used to Evaluate Designs

Designs were selected based on the following criteria: change in polar surface area upon binding (dSASA_polar) greater than 800 Å; secondary structure shape complementarity (ss_sc) score greater than 0.65; holes score around HBNets less than −1.4; no buried unsatisfied heavy atoms; at least one buried bulky polar side chains per monomer. Selected designs were then visually inspected for good packing of hydrophobic side chains, especially the interdigitation of isoleucine, leucine and valine. Surface tyrosines were added at non-interfering positions to aid protein concentration measurement by recording OD280. Surface charge residues for a few of the designs were redesigned to shift the theoretical isoelectric point away from buffer pH.

RMSD Calculations

Crystal structures and the corresponding design models were superimposed with TMalign using all heavy atoms. From this alignment, RMSD was calculated across all alpha-carbon atoms, and also across heavy atoms of the hydrogen bond network residues.

Logistic Regression

Designs were first scored with various filters in Rosetta™ with the filter values reported. Experimental results and Rosetta™ filter values were used as input to a logistic regression method 31 to find correlations between computational metrics and experimental observations.

Visualization and Figures

All structural images for figures were generated using PyMOL 32.

Buffer and Media Recipe

TBM-5052: 1.2% [wt/vol] tryptone, 2.4% [wt/vol] yeast extract, 0.5% [wt/vol] glycerol, 0.05% [wt/vol] D-glucose, 0.2% [wt/vol] D-lactose, 25 mM Na2HPO4, 25 mM KH2PO4, 50 mM NH4Cl, 5 mM Na2SO4, 2 mM MgSO4, 10 µM FeCl3, 4 µM CaCl2, 2 µM MnCl2, 2 µM ZnSO4, 400 nM CoCl2, 400 nM NiCl2, 400 nM CuCl2, 400 nM Na2MoO4, 400 nM Na2SeO3, 400 nM H3BO3

Lysis buffer: 20 mM Tris, 300 mM NaCl, 20 mM Imidazole, pH 8.0 at room temperature Wash buffer: 20 mM Tris, 300 mM NaCl, 30 mM Imidazole, pH 8.0 at room temperature Elution buffer: 20 mM Tris, 300 mM NaCl, 250 mM Imidazole, pH 8.0 at room temperature Buffer W: 100 mM Tris-HCl pH 8.0, 150 mM NaCl and 1 mM EDTA Buffer E: Buffer W containing 2.5 mM D-desthiobiotin TBS buffer: 20 mM Tris pH 8.0, 100 mM NaCl Construction of Synthetic Genes For the expression of heterodimers, both monomers were encoded in the same plasmid, separated by a ribosome binding sequence (GAAGGAGATATCATC; SEQ ID NO:327). Synthetic genes were ordered from Genscript Inc. (Piscataway, N.J., USA) and delivered in pET21-NESG E. coli expression vector, inserted between the NdeI and XhoI sites. For the pET21-NESG constructs, a hexahistidine tag and a tobacco etch virus (TEV) protease cleavage site (GSSHHHHHHSSGENLYFQGS; SEQ ID NO:328) were added in frame at the N-terminus of the second monomer. A stop codon was introduced at the 3' end of the second monomer to stop expression of the C-terminal hexahistidine tag in the vector. For purification with Strep-tactin resin, a streptavidin tag (SAWSHPQFEKGGGSGGGSGG-SAWSHPQFEKSGENLYFQGS; SEQ ID NO:329) coding sequence was cloned in frame 5' of the first monomer sequence.

For the co-expression of 3 and 4 proteins from the same plasmid (induced dimerization and synthetic scaffold designs), synthetic genes were cloned in the pRSFDuet-1 expression vector. The first (in the case of 3 proteins) or first two (in the case of 4 proteins) genes were cloned between NcoI and HindIII sites, with a ribosome binding site separating the 2 proteins in the latter case. The last two genes were cloned between NdeI and XhoI sites, separated by a ribosome binding site. A hexahistidine tag and a TEV protease cleavage site coding sequence were cloned in frame 5' of the last gene.

Genes for yeast-two-hybrid (Y2H) studies were cloned into plasmids bearing the GAL4 transcription activation domain (poAD) and the GAL4 DNA-binding domain (poDBD).

Protein Expression

Plasmids were transformed into chemically competent E. coli expression strains BL21(DE3)Star (Invitrogen) or Lemo21™ (DE3) (New England Biolabs) for protein expression. Single colonies were picked from agar plates following transformation and growth overnight, and 5 ml starter cultures were grown at 37° C. in Luria-Bertani (LB) medium containing 100 µg/mL carbenicillin (for pET21-NESG vectors) or kanamycin (for pRSFDuet-1 vectors) with shaking at 225 rpm for 18 hours at 37° C. Starter cultures were diluted into 500 ml TBM-5052 containing 100 µg/mL carbenicillin or kanamycin, and incubated with shaking at 225 rpm for 24 hours at 37° C.

For expression of $^{13}C^{15}N$- or $^{15}N$-labeled protein, the plasmids were transformed into the Lemo21™ (DE3) E. coli expression strain and plated on M9/glucose plates containing 50 µg/mL carbenicillin. For the starter culture, a single colony was used for inoculation of 50 mL LB medium with 50 µg/mL carbenicillin in a 250 mL baffled flask, and incubated with shaking at 225 rpm for 18 hours at 37° C. 10 mL of the starter culture was then transferred to a 2 L baffled flask containing 500 mL of Terrific Broth™ (Difco), with 25 mM Na2HPO4, 25 mM KH2PO4, 50 mM NH4Cl, 5 mM Na2SO4, and 100 µg/mL carbenicillin. The culture was grown at 37° C. to an OD600 of approximately 1.0, then centrifuged at 5000 rcf for 15 minutes to pellet the cells. The Terrific Broth™ medium was removed, and the cells were washed briefly with 30 mL of phosphate buffered saline (PBS). The cells were then transferred to a fresh 2 L baffled flask containing 500 mL of labeled media (25 mM Na2HPO4, 25 mM KH2PO4, 50 mM 15NH4Cl, 5 mM Na2SO4, 0.2% (w/v) 13C glucose), and 100 µg/mL carbenicillin. The cells were allowed to grow at 37° C. for 2 hours, before IPTG (Carbosynth) was added to 1 mM and the temperature was reduced to 18° C. The labeled glucose and NH4Cl were obtained from Cambridge Isotopes.

Affinity Purification

Cells were harvested by centrifugation for 15 minutes at 5000 rcf at 4° C. and resuspended in 20 ml lysis buffer. Lysozyme, DNAse, and EDTA-free cocktail protease inhibitor (Roche) were added to the resuspended cell pellet before sonication at 70% power for 5 minutes. For Immobilized metal affinity chromatography (IMAC), lysates were clarified by centrifugation at 4° C. and 18,000 rpm for at least 30 minutes and applied to Ni-NTA (Qiagen) columns pre-equilibrated with lysis buffer. The column was washed two times with column volumes (CV) of wash buffer, followed by 5 CV of elution buffer. For Strep tag purification, elution fractions from IMAC were applied to Strep-Tactin® Superflow resin (IBA) pre-equilibrated in Buffer W. The column was washed with 5 CV Buffer W, before applying 3 CV Buffer E to elute proteins off the column. Mass and purity of eluted proteins were confirmed using electrospray ionization mass spectrometry (ESI-MS) on a Thermo Scientific TSQ Quantum Access mass spectrometer.

Size-Exclusion Chromatography (SEC)

N-terminal hexahistidine tags and streptavidin tags were cleaved with TEV protease overnight at room temperature, at a ratio of 1 mg TEV for 100 mg of protein. Prior to addition of TEV, buffer was exchanged into lysis buffer. After TEV cleavage, sample was passed over an additional Ni-NTA column and washed with 1.5 CV of lysis buffer, flow through were collected and further purified by SEC using a Superdex™ 75 10/300 increase column (GE Healthcare) in TBS buffer.

Circular Dichroism (CD) Measurements

CD wavelength scans (260 to 195 nm) and temperature melts (25 to 95° C.) were performed using an AVIV model 420 CD spectrometer. Temperature melts were carried out at a heating rate of 4° C./min and monitored by the change in ellipticity at 222 nm; protein samples were diluted to 0.25 mg/mL in PBS pH 7.4 in a 0.1 cm cuvette. Guanidinium chloride (GdmCl) titrations were performed on the same spectrometer with automated titration apparatus in PBS pH 7.4 at 25° C., with a protein concentration of 0.025 mg/mL in a 1 cm cuvette with stir bar. Each titration consisted of at least 40 evenly distributed GdmCl concentration points with one minute mixing time for each step. Titrant solution consisted of the same concentration of protein in PBS+GdmCl.

Crystallization of Protein Samples

Purified protein samples were concentrated to approximately 20 mg/ml in 25 mM Tris pH 8.0 and 150 mM NaCl. Samples were screened with a 5-position deck Mosquito™ crystal (ttplabtech) with an active humidity chamber, utilizing the following crystallization screens: JCSG+™ (Qiagen), Crystal Screen™ (Hampton Research), PEG/Ion™ (Hampton Research), PEGRx HT™ (Hampton Research), Index™ (Hampton Research) and Morpheus™ (Molecular Dimensions). The optimal conditions for crystallization of the different designs were found as follows: OPHD_37_N3Cl, 0.15 M potassium bromide and 30% w/v polyethylene glycol monomethyl ether 2000; OPHD_127, 0.12 M ethylene glycols, 0.1 M buffer system 3 pH 8,5, and 50% v/v precipitate mix 1 from the Morpheus screen; OPHD_15, 0.2 M Ammonium sulfate, 0.1 M BIS-TRIS pH 6.5, 18% v/v Polyethylene glycol 400; OPHD_15, 0.1 M Imidazole pH 7.0, and 25% v/v Polyethylene glycol monomethyl ether 550; OPHD_131, 0.2 M Ammonium acetate, 0.1 M HEPES pH 7.5, 25% w/v Polyethylene glycol 3,350. Crystals were obtained after 1 to 14 days by the hanging drop vapor diffusion method with the drops consisting of a 1:1, 2:1 and 1:2 mixture of protein solution and reservoir solution.

X-Ray Data Collection and Structure Determination

The crystals of the designed proteins were looped and placed in the corresponding reservoir solution, containing 20% (v/v) glycerol if the reservoir solution did not contain cryoprotectant, and flash-frozen in liquid nitrogen. The X-ray data sets were collected at the Advanced Light Source at Lawrence Berkeley National Laboratory with beamlines 8.2.1 and 8.2.2. Data sets were indexed and scaled using either XDS[33] or HKL2000[34]. Initial models were generated by the molecular-replacement method with the program PHASER 35 within the Phenix™ software suite[36], using the design models as the initial search models. Efforts were made to reduce model bias through refinement with simulated annealing using Phenix.refine™[37], or, if the resolution was sufficient, by using Phenix.autobuild™[38] with rebuild-in-place set to false, simulated annealing and prime-and-switch phasing. Iterative rounds of manual building in COOT[39] and refinement in Phenix™ were used to produce the final models. Due to the high degree of self-similarity inherit in coiled-coil-like proteins, datasets for the reported structures suffered from a high degree of pseudo translational non-crystallographic symmetry, as report by Phenix.Xtriage™, which complicated structure refinement and may explain the higher than expected R values reported. RMSDs of bond lengths, angles and dihedrals from ideal geometries were calculated with Phenix™[36]. The overall quality of all final models was assessed using the program MOLPROBITY™[40].

Small Angle X-Ray Scattering (SAXS)

Samples were purified by SEC in 25 mM Tris pH 8.0, 150 mM NaCl and 2% glycerol; fractions preceding the void volume of the column were used as blanks for buffer subtraction. Scattering measurements were performed at the SIBYLS™ 12.3.1 beamline at the Advanced Light Source. The X-ray wavelength ($\lambda$) was 1.27 Å, and the sample-to-detector distance was 1.5 m, corresponding to a scattering vector q ($q=4\pi \sin \theta/\lambda$, where $2\theta$ is the scattering angle) range of 0.01 to 0.3 Å$^{-1}$. A series of exposures, in equal sub-second time slices, were taken of each well: 0.3 second exposures for 10 seconds resulting in 32 frames per sample. For each sample, data was collected for two different concentrations to test for concentration-dependent effects; "low" concentration samples ranged from 2-3 mg/mL and "high" concentration samples ranged from 5-7 mg/mL. Data was processed using the SAXS FrameSlice™ online serve and analyzed using the ScÅtter™ software package[41,42] FoXS™[43, 44] was used to compare design models to experimental scattering profiles and calculate quality of fit ($\chi$) values.

Yeast Two-Hybrid Assay

For each pair of binders tested, chemically competent cells of yeast strain PJ69-4a (MATa trp1-901 leu2-3,112 ura3-52 his3-200 gal4(deleted) gal80(deleted) LYS2:: GAL1-HIS3 GAL2-ADE2 met2::GAL7-lacZ) were transformed with the appropriate pair of plasmids containing DNA binding domain or activation domains, using the LiAc/SS carrier DNA/PEG method[45]. In the case of induced dimerization, the heterodimerizer was cloned downstream of one of the "monomer proteins", separated by a p2a and nuclear locolization sequence (GSGATNFSLLKQAGD-VEENPGPGDKAELIPEPPKKKRKVELGTA; SEQ ID NO:330). The p2a sequence ensures translational cleavage to make the heterodimerizer a separate protein from the "monomer protein". The selection of transformed yeast cells was performed in synthetic dropout (SDO) media lacking tryptophan and leucine for 48 hours with shaking at 1000 rpm at 30° C. The resulting culture was diluted 1:100 and grown for 16 hours in fresh SDO media lacking tryptophan and leucine, before transferring to a 96 well plate and diluted 1:100 into SDO media containing 100 mM 3-Amino-1,2,4-triazole (3-AT), lacking tryptophan, leucine and histidine (5 mM 3-AT in the case of induced dimerization). The culture was incubated with shaking at 1000 rpm at 30° C. Since bringing the DNA binding domain and the transcription activation domain into proximity is necessary for the growth of yeast cells in media lacking histidine, binding of two proteins was indicated by the growth of yeast cells[46,47]. The optical density of yeast cells was recorded after 48 hours. For Y2H assay on agar plates, the 1:100 diluted overnight culture was transferred onto Nunc™ OmniTray™ (Thermo Fisher) using a 96 Solid Pin Multi-Blot Replicator (V&P Scientific), with the agar lacking tryptophan, leucine and histidine, and containing 100 mM 3-AT. The plates were imaged daily until Day 5 to monitor the sizes of colonies. Images were analyzed by the ColonyArea[48] package on ImageJ.

References for Example 1

1. Jones, S. & Thornton, J. M. Principles of protein-protein interactions. *Proc. Natl. Acad. Sci. U.S.A* 93, 13-20 (1996).
2. Harbury, P. B., Zhang, T., Kim, P. S. & Alber, T. A switch between two-, three-, and four-stranded coiled coils in GCN4 leucine zipper mutants. *Science* 262, 1401-1407 (1993).
3. Diss, M. L. & Kennan, A. J. Orthogonal recognition in dimeric coiled coils via buried polar-group modulation. *J. Am. Chem. Soc.* 130, 1321-1327 (2008).
4. Thomas, F., Boyle, A. L., Burton, A. J. & Woolfson, D. N. A set of de novo designed parallel heterodimeric coiled coils with quantified dissociation constants in the micromolar to sub-nanomolar regime. *J. Am. Chem. Soc.* 135, 5161-5166 (2013).
5. Crick, F. H. C. The Fourier transform of a coiled-coil. *Acta Cryst* (1953). Q6, 685-689 [doi:10.1107/S0365110X53001952] 6, 1-5 (1953).
6. Zarrinpar, A., Park, S.-H. & Lim, W. A. Optimization of specificity in a cellular protein interaction network by negative selection. *Nature* 426, 676-680 (2003).

7. Aakre, C. D. et al. Evolving new protein-protein interaction specificity through promiscuous intermediates. *Cell* 163, 594-606 (2015).
8. Joachimiak, L. A., Kortemme, T., Stoddard, B. L. & Baker, D. Computational design of a new hydrogen bond network and at least a 300-fold specificity switch at a protein-protein interface. *J. Mol. Biol.* 361, 195-208 (2006).
9. Skerker, J. M. et al. Rewiring the specificity of two-component signal transduction systems. *Cell* 133, 1043-1054 (2008).
10. Crooks, R. O., Baxter, D., Panek, A. S., Lubben, A. T. & Mason, J. M. Deriving Heterospecific Self-Assembling Protein-Protein Interactions Using a Computational Interactome Screen. *J. Mol. Biol.* 428, 385-398 (2016).
11. Gradišar, H. & Jerala, R. De novo design of orthogonal peptide pairs forming parallel coiled-coil heterodimers. *J Pept. Sci.* 17, 100-106 (2011).
12. Thompson, K. E., Bashor, C. J., Lim, W. A. & Keating, A. E. SYNZIP protein interaction toolbox: in vitro and in vivo specifications of heterospecific coiled-coil interaction domains. *ACS Synth. Biol.* 1, 118-129 (2012).
13. Reinke, A. W., Grant, R. A. & Keating, A. E. A synthetic coiled-coil interactome provides heterospecific modules for molecular engineering. *J. Am. Chem. Soc.* 132, 6025-6031 (2010).
14. Acharya, A., Rishi, V. & Vinson, C. Stability of 100 homo and heterotypic coiled-coil a-a' pairs for ten amino acids (A, L, I, V, N, K, S, T, E, and R). *Biochemistry* 45, 11324-11332 (2006).
15. Grigoryan, G. & Keating, A. E. Structure-based prediction of bZIP partnering specificity. *J. Mol. Biol.* 355, 1125-1142 (2006).
16. Gonzalez, L., Jr, Woolfson, D. N. & Alber, T. Buried polar residues and structural specificity in the GCN4 leucine zipper. *Nat. Struct. Biol.* 3, 1011-1018 (1996).
17. Lumb, K. J. & Kim, P. S. A buried polar interaction imparts structural uniqueness in a designed heterodimeric coiled coil. *Biochemistry* 34, 8642-8648 (1995).
18. Tatko, C. D., Nanda, V., Lear, J. D. & DeGrado, W. F. Polar Networks Control Oligomeric Assembly in Membranes. *J. Am. Chem. Soc.* 128, 4170-4171 (2006).
19. Grigoryan, G. & DeGrado, W. F. Probing Designability via a Generalized Model of Helical Bundle Geometry. *J. Mol. Biol.* 405, 1079-1100 (2011).
20. Huang, P.-S. et al. High thermodynamic stability of parametrically designed helical bundles. *Science* 346, 481-485 (2014).
21. Boyken, S. E. et al. De novo design of protein homo-oligomers with modular hydrogen-bond network-mediated specificity. *Science* 352, 680-687 (2016).
22. Leaver-Fay, A. et al. ROSETTA™3: an object-oriented software suite for the simulation and design of macromolecules. *Methods Enzymol.* 487, 545-574 (2011).
23. Ruotolo, B. T. & Robinson, C. V. Aspects of native proteins are retained in vacuum. *Curr. Opin. Chem. Biol.* 10, 402-408 (2006).
24. Sahasrabuddhe, A. et al. Confirmation of intersubunit connectivity and topology of designed protein complexes by native MS. *Proc. Natl. Acad. Sci. U.S.A* 115, 1268-1273 (2018).
25. Zhou, M., Huang, C. & Wysocki, V. H. Surface-induced dissociation of ion mobility-separated noncovalent complexes in a quadrupole/time-of-flight mass spectrometer. *Anal. Chem.* 84, 6016-6023 (2012).
26. Zhou, M. & Wysocki, V. H. Surface induced dissociation: dissecting noncovalent protein complexes in the gas phase. *Acc. Chem. Res.* 47, 1010-1018 (2014).
27. Anderson, G. P., Shriver-Lake, L. C., Liu, J. L. & Goldman, E. R. Orthogonal Synthetic Zippers as Protein Scaffolds. *ACS Omega* 3, 4810-4815 (2018).
28. Rothemund, P. W. K. Folding DNA to create nanoscale shapes and patterns. *Nature* 440, 297-302 (2006).
29. Qian, L. & Winfree, E. Scaling up digital circuit computation with DNA strand displacement cascades. *Science* 332, 1196-1201 (2011).
30. Zhang, Y. & Skolnick, J. TM-align: a protein structure alignment algorithm based on the TM-score. Nucleic Acids Res. 33, 2302-2309 (2005).
31. Rocklin, G. J. et al. Global analysis of protein folding using massively parallel design, synthesis, and testing. *Science* 357, 168-175 (2017).
32. Schrödinger, LLC. The PyMOL Molecular Graphics System, Version 1.8. (2015).
33. Kabsch, W. XDS. Acta Crystallogr. D Biol. Crystallogr. 66, 125-132 (2010).
34. Otwinowski, Z. & Minor, W. Processing of X-ray diffraction data collected in oscillation mode. Methods Enzymol. 276, 307-326 (1997).
35. McCoy, A. J. et al. Phaser crystallographic software. J. Appl. Crystallogr. 40, 658-674 (2007).
36. Adams, P. D. et al. PHENIX: a comprehensive Python-based system for macromolecular structure solution. Acta Crystallogr. D Biol. Crystallogr. 66, 213-221 (2010).
37. Afonine, P. V. et al. Joint X-ray and neutron refinement with phenix.refine. Acta Crystallogr. D Biol. Crystallogr. 66, 1153-1163 (2010).
38. Terwilliger, T. C. et al. Iterative model building, structure refinement and density modification with the PHENIX AutoBuild wizard. Acta Crystallogr. D Biol. Crystallogr. 64, 61-69 (2008).
39. Emsley, P. & Cowtan, K. Coot: model-building tools for molecular graphics. Acta Crystallogr. D Biol. Crystallogr. 60, 2126-2132 (2004).
40. Davis, I. W. et al. MolProbity: all-atom contacts and structure validation for proteins and nucleic acids. Nucleic Acids Res. 35, W375-83 (2007).
41. Dyer, K. N. et al. High-throughput SAXS for the characterization of biomolecules in solution: a practical approach. Methods Mol. Biol. 1091, 245-258 (2014).
42. Rambo, R. P. & Tainer, J. A. Characterizing flexible and intrinsically unstructured biological macromolecules by SAS using the Porod-Debye law. Biopolymers 95, 559-571 (2011).
43. Schneidman-Duhovny, D., Hammel, M. & Sali, A. FoXS: a web server for rapid computation and fitting of SAXS profiles. Nucleic Acids Res. 38, W540-4 (2010).
44. Schneidman-Duhovny, D., Hammel, M., Tainer, J. A. & Sali, A. Accurate SAXS profile computation and its assessment by contrast variation experiments. Biophys. J. 105, 962-974 (2013).
45. Schiestl, R. H. & Gietz, R. D. High efficiency transformation of intact yeast cells using single stranded nucleic acids as a carrier. Curr. Genet. 16, 339-346 (1989).
46. Chien, C. T., Bartel, P. L., Sternglanz, R. & Fields, S. The two-hybrid system: a method to identify and clone genes for proteins that interact with a protein of interest. Proc. Natl. Acad. Sci. U.S.A 88, 9578-9582 (1991).
47. Bartel, P. L., Roecklein, J. A., SenGupta, D. & Fields, S. A protein linkage map of *Escherichia coli* bacteriophage T7. Nat. Genet. 12, 72-77 (1996).

48. Guzman, C., Bagga, M., Kaur, A., Westermarck, J. & Abankwa, D. ColonyArea: an ImageJ plugin to automatically quantify colony formation in clonogenic assays. PLoS One 9, e92444 (2014).
49. Dyachenko, A. et al. Tandem Native Mass-Spectrometry on Antibody-Drug Conjugates and Submillion Da Antibody-Antigen Protein Assemblies on an Orbitrap EMR Equipped with a High-Mass Quadrupole Mass Selector. Anal. Chem. 87, 6095-6102 (2015).
50. Waitt, G. M., Xu, R., Wisely, G. B. & Williams, J. D. Automated in-line gel filtration for native state mass spectrometry. J. Am. Soc. Mass Spectrom. 19, 239-245 (2008).
51. Marty, M. T. et al. Bayesian deconvolution of mass and ion mobility spectra: from binary interactions to polydisperse ensembles. Anal. Chem. 87, 4370-4376 (2015).
52. Bern, M. et al. Parsimonious Charge Deconvolution for Native Mass Spectrometry. J. Proteome Res. 17, 1216-1226 (2018).
53. Jones, D. T. Protein secondary structure prediction based on position-specific scoring matrices. *J. Mol. Biol.* 292, 195-202 (1999).

Example 2. Orthogonal Protein Heterodimers for Designing Modular Protein Logic Gates Abstract: The de novo design of modular protein logic for regulating protein function at the post-transcriptional level is a challenge for computational protein design and could have wide ranging applications in synthetic biology. Here we describe the design of 2-input AND, OR, NAND, NOR, XNOR, and NOT gates built from de novo designed proteins that regulate the association of arbitrary protein units ranging from split enzymes to transcriptional machinery in vitro, and in living cells. Binding interaction cooperativity makes the gates largely insensitive to stoichiometric imbalances in the inputs, and the modularity of the approach enables ready extension to 3-input OR, AND, and disjunctive normal form gates. The modularity and cooperativity of the control elements, coupled with the ability to de novo design an essentially unlimited number of protein components, should enable design of sophisticated post-translational control logic over a wide range of biological functions.
Introduction The ability to de novo design protein-based logic gates with modular control of arbitrary protein-protein interactions could open the door to the tunable design of novel bio-orthogonal functionalities.

In principle, it should be possible to design a wide range of logic gates de novo using a set of orthogonal heterodimeric molecules. For example, given hypothetical heterodimer pairs A:A', B:B', and C: C', an AND gate modulating the association of A with C' can be constructed by genetically fusing A' and B, and B' and C: association occurs only in the presence of both A'-B, and B'-C (here and below ":" denotes noncovalent interaction, and "-", genetic fusion via flexible linkers). Several building block properties are desirable for constructing such associative logic gates. First, there should be many mutually orthogonal heterodimeric pairs, so that gate complexity is not limited by the number of individual elements. Second, the building blocks should be modular and similar in structure so that differences in building block shape and other properties do not have to be considered when constructing the gates. Third, single building blocks should be able to bind to multiple partners with different, tunable affinities, allowing inputs to perform negation operations by disrupting pre-existing lower affinity interactions. Fourth, the interactions should be cooperative so gate activation is not sensitive to stoichiometric imbalances in the inputs. In the above AND gate, for example, if the interactions are not cooperative, a large excess of A'-B will pull the equilibrium towards partially assembled complexes (A'-B with either A or B'-C but not both), which will disrupt gate activation.

Figures 11A, 11B, 11C, 11D, 11E, 11F, 11G, 11H:
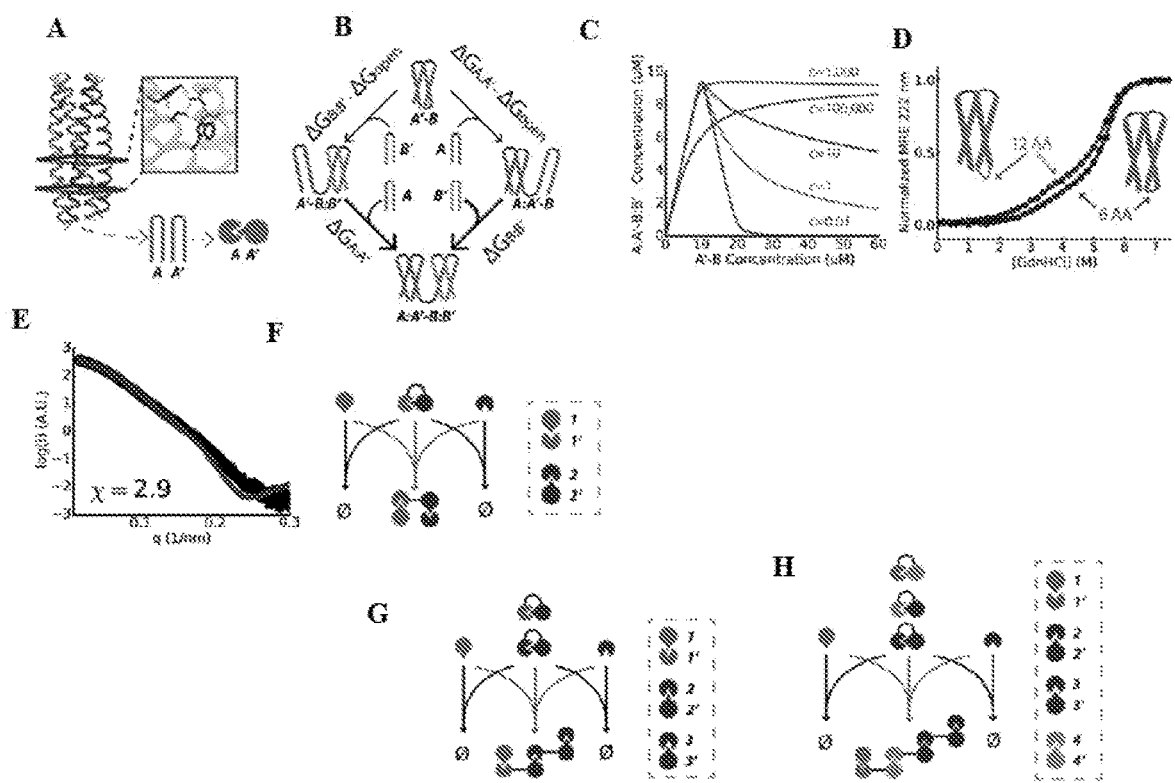
FIGS. 11A to 11H show cooperativity of CIPHR logic gates.

Here, we explored the possibility of designing logic gates satisfying all four of the above criteria using de novo designed protein heterodimers with hydrogen bond network-mediated specificity (34). Sets of 6 (in vivo) and 15 (in vitro) mutually orthogonal designed heterodimers (DHDs, hereafter referred to by numbers, e.g. 1 and 1' form one cognate pair. with hydrogen bond network (see FIG. 11A inset for example) mediated specificity are available for logic gate construction, satisfying condition 1 (orthogonality). The heterodimeric interfaces all share the same four helix bundle topology (FIG. 11A), satisfying condition 2 (modularity). The shared interaction interface allows a limited amount of cross talk between pairs, leading to a hierarchy of binding affinities, satisfying condition 3 (multiple binding specificities). Inspired by cooperatively activatable systems in nature (35, 36), we sought to achieve condition 4 (cooperativity) by constructing the monomer fusions (A'-B and B'-C in the above example) in such a way that the interaction surfaces (with A and C') are buried within the fusions. The free energy required to expose these buried interfaces would oppose gate activation, and we reasoned that the system could be tuned so that only the binding energy provided by both interactions would be sufficient to overcome this barrier, thus ensuring cooperative gate activation (FIG. 11B). If condition 2 (modularity) holds, then a single scheme for ensuring cooperativity could in principle work for a wide range of gate configurations.
Design of Cooperativity To explore the design of cooperative building blocks, we focused on the simple system A+A'-B+B' (we refer to this as induced dimerization below, A and B' as the monomers, and A'-B as the dimerizer). If binding is not cooperative, the amount of the trimeric complex decreases when A'-B is in stoichiometric excess relative to A and B': the formation of intermediate dimeric species of the linker protein binding to either of the monomers competes with formation of trimeric complexes. On the contrary, if binding is cooperative such that no binding to either monomer occurs in the absence of the other, the amount of trimeric complex formed becomes insensitive to an excess of the dimerizer. A simple thermodynamic model of the effect of binding cooperativity on the stoichiometric response of such induced dimerization systems (FIG. 11B, supplemental materials modeling section) shows that as the binding cooperativity decreases, there is a corresponding decrease in the final concentration of full trimeric complexes at high dimerizer concentrations (FIG. 11C).

Figures 14A, 14B:
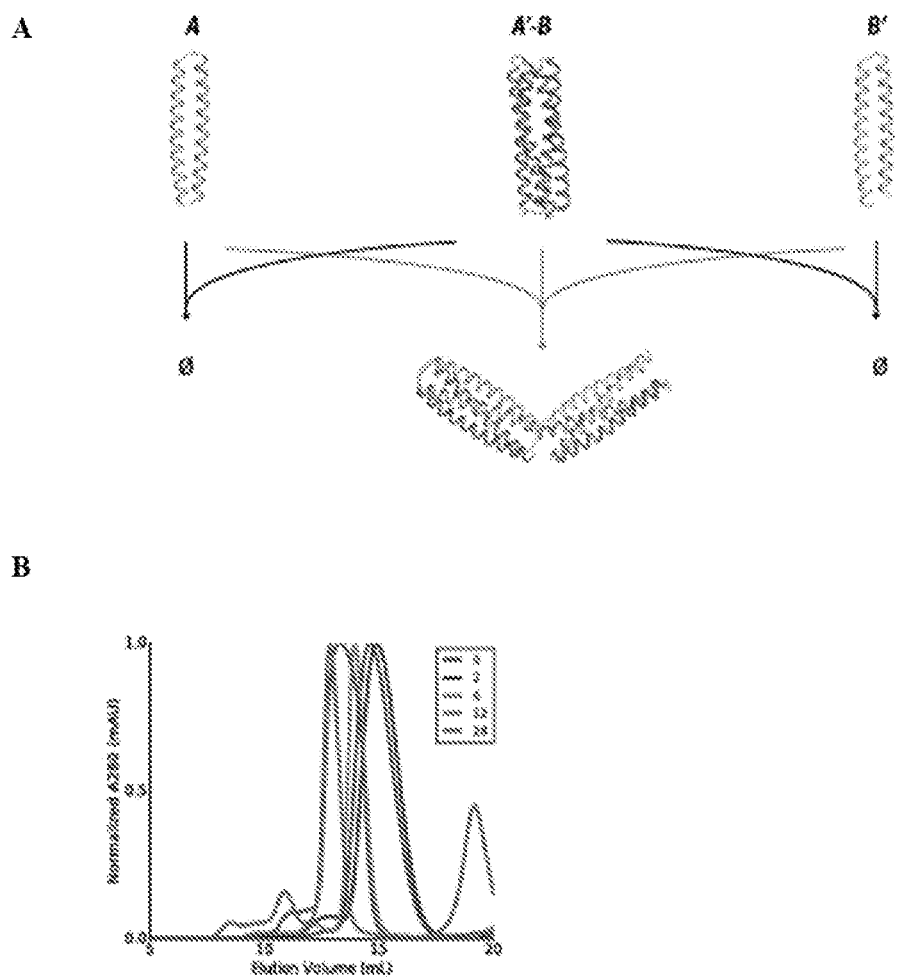
FIG. 14A shows molecular implementation of the cooperative induced dimerization system, binding only occurs when all three components are present.
FIG. 14B shows size exclusion chromatography profiles of 1'-2' variants with 0, 2, 6, 12, and 24 amino acids in the flexible linker connecting 1' and 2.

We hypothesized that a folded four helix bundle like state of the A'-B dimerizer could oppose binding to either A or B', as the relatively hydrophobic interacting surfaces would likely be sequestered within the folded structure (FIG. 14A). We tested different flexible linker lengths connecting A' with B using heterodimers 1:1' and 2:2' as a model system. All designs were found to be folded and stable in circular dichroism (CD) guanidine hydrochloride (GdnHCl) denaturation experiments, with unfolding free energies greater than 13 kcal/mol (FIG. 11D, Table 10). Although 1'-2' dimerizer constructs with short linkers of 0 and 2 residues, or with a very long 24 residue linker could be purified as monomers (FIG. 14B), they were prone to aggregation. In contrast, designs with 6 and 12 residue linkers remained largely monomeric (data not shown). Small angle x-ray scattering (SAXS) experiments (37) indicate their hydrodynamic radii are close to those of folded four-helix bundle DHDs (FIG. 11E). Linkers in this length range likely allow the two monomers (1' and 2') to fold back on each other such that the largely hydrophobic interaction surfaces are buried against each other; such a structure would have to partially unfold for 1'-2' to interact with either 1 or 2 with free energy cost $\Delta G_{open}$ (FIG. 11B), the magnitude of which determines the extent of cooperativity for the gate. We selected a linker length of 6- or 12-residues for all of the following experiments.

We studied the cooperativity of the induced dimerizer system in vitro using native mass spectrometry (FIG. 11F). 1, 2 and 1'-2' were separately expressed in *E. coli* and purified. We first measured the extent to which 1 activates the binding of 2 to 1'-2'. At 10 μM each of 2 and 1'-2', the fraction of 2 in complex with 1'-2' increased from 3% to 100% upon addition of 20 μM 1 (data not shown); a fold increase comparable with naturally occurring allosteric systems (35). To assess how this activation of binding influences the sensitivity of binding to stoichiometric imbalance, 10 μM 1 and 2 were titrated with increasing concentrations of 1'-2' (FIG. 11F), and the species formed determined by nMS. The heterotrimeric 1:1'-2':2 complex was observed over a wide range of 1'-2' concentrations (data not shown). Even in the presence of a 6 fold excess of 1'-2', there was no decrease in the amount of 1:1'-2':2 formed, and neither 1:1'-2' or 1'-2':2 were observed (data not shown). We define cooperativity as the ratio of the affinities in the presence and absence of the other monomer, which in our model directly relates to the free energy of opening of the dimerizer ($c = e^{\Delta G_{open}/RT}$, see supplementary materials). Matching the thermodynamic model to native MS data (data not shown) produces an estimated c value of 991,000, which corresponds to $\Delta G_{open}$ of 7 kcal/mol. This is about half the measured unfolding free energy of 1'-2', suggesting that binding may not require complete unfolding of the four helix bundle state of the dimerizer.

With linker units displaying cooperative binding, we reasoned that the lack of dependence on stoichiometric excesses of one of the components should extend to more complex gates. Using nMS, we investigated the cooperativity of a 2-input AND gate constructed from the two inputs 1'-3' and 3-2', and monomers 1 and 2 brought together by the two inputs (FIG. 11G). As the concentration of the 2 inputs was increased, the amount of heterotetrameric complex plateaued at a stoichiometry of 2:1, and then remained constant up to a molar ratio of 6:1. Very little partial complexes (heterotrimers and heterodimers) were observed, further indicating high cooperativity (data not shown). We constructed a 3-input AND gate from 1'-4', 4-3', and 3-2', which together should control the association of 1 and 2 (FIG. 11H). Similar to the 2-input AND gate, the amount of full, pentameric complexes only decreased slightly at greater than stoichiometric concentrations of inputs with no detectable competing tetrameric complexes (data not shown).

Modular Logic Gate Construction

Figures 12A, 12B, 12C, 12D, 12E, 12F, 12G:
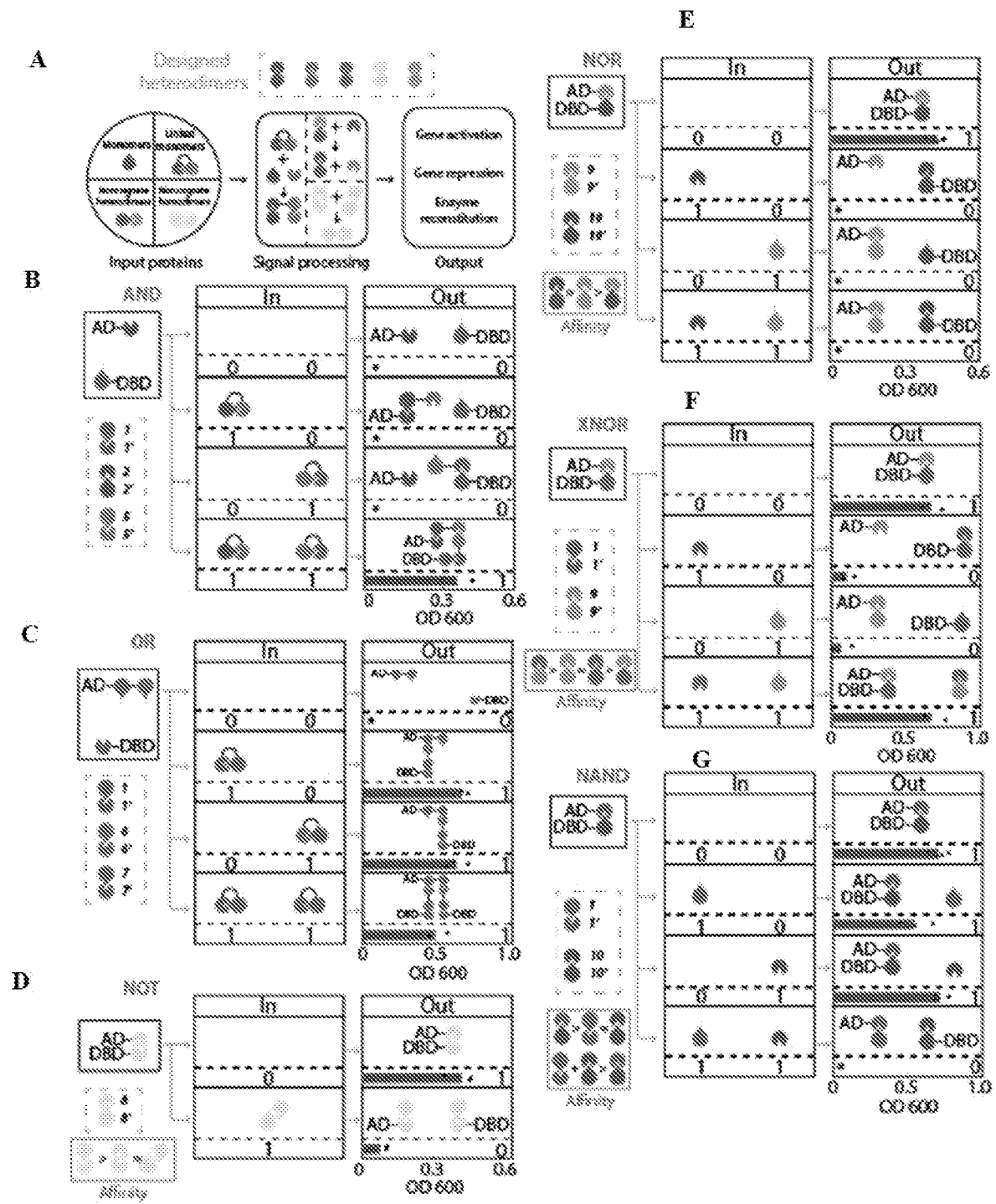
FIGS. 12A to 12G show CIPHR two input logic gates.

We explored the modular combination of DHDs to generate a range of 2-input Cooperatively Inducible Protein HeterodimeR (CIPHR) logic gates. Monomers from individual DHDs were linked to effector proteins of interest via genetic fusion, whose colocalization or dissociation is dependent upon the inputs. Taking advantage of previously measured all-by-all specificity matrices (34), two modes of interactions were explored: cognate binding between designed protein pairs, or competitive binding involving multispecific interactions. The choice of effector proteins is independent from the input proteins, allowing diverse functional outputs (FIG. 12A).

We used a variant of the yeast-two-hybrid (Y2H) assay to characterize the behavior of the designed logic gates, using a setup similar to previously described yeast-four-hybrid systems (38, 39). To construct an AND gate, we fused 2 to the Gal4 activation domain (AD), and 1 to the Gal4 DNA binding domain (DBD). The colocalization of AD and DBD, and resulting induction of transcription of the His3 gene, is dependent upon the expression of both input proteins (1'-5, 5'-2'). Growth in media lacking histidine required expression of both inputs (FIG. 12B). An OR gate was similarly constructed by linking the 1-6 fusion to the AD and 7' to the DBD. Expression of either of the inputs 1'-7 or 6'-7 results in growth by driving association of AD with DBD (FIG. 12C).

Figures 15A, 15B:
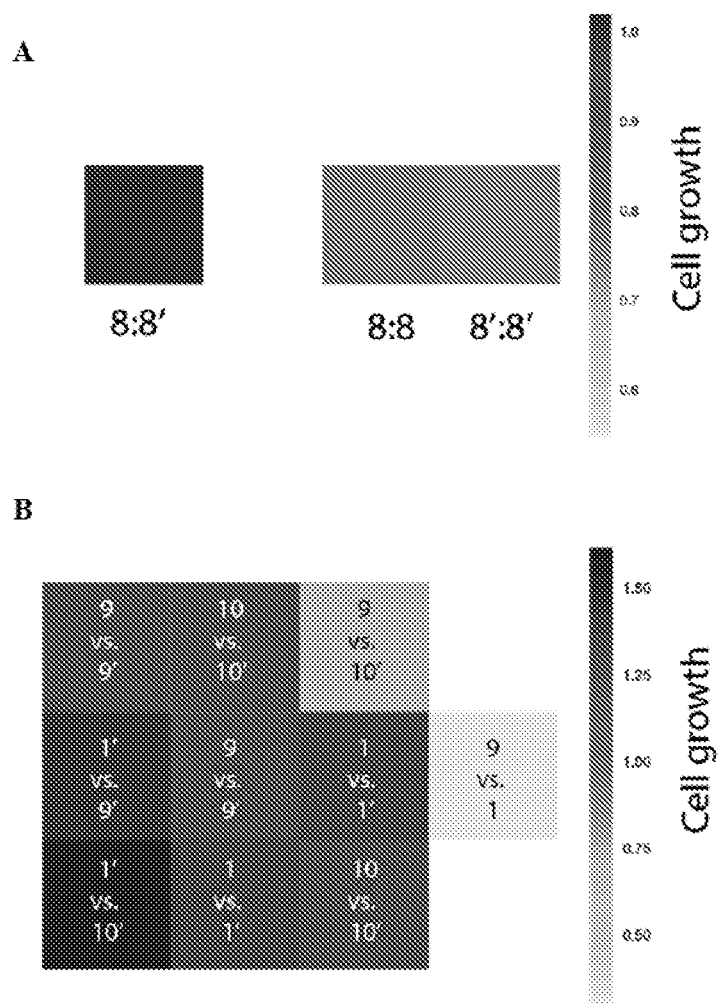
FIGS. 15A and 15B show binding affinity gradient from individual Y2H experiments.

We explored the construction of additional boolean logic gates by exploiting binding affinity hierarchies identified in all by all Y2H experiments (34). 8 not only interacts with 8' but also forms homodimers (FIG. 15A); hence 8' must outcompete 8 homodimers to form the heterodimer. We constructed a NOT gate by fusing 8 to both AD or DBD; yeast cells stopped growing in the presence of co-expressed 8' input protein (FIG. 12D). Based on the affinity hierarchy 9:9' 10:10'>9:10' (FIG. 15B), we constructed a NOR gate in which 9 was fused to the AD, 10' to the DBD, with 9' and 10 the two inputs. Either or both of the inputs outcompete the 9:10' interaction and hinder yeast growth (FIG. 12E). Based on the affinity hierarchy 9':1'>9:9'≈1:1'>9:1 (FIG. 15B), an XNOR gate was constructed by fusing 9 to AD, 1 to DBD, and using 9' and 1' as the two inputs: the presence of either outcompetes the 9:1 binding and blocks growth, but when both are expressed they instead interact with each other and growth is observed (FIG. 12F). Similarly, a NAND gate was designed based on the interaction hierarchy 1':10'>1:1'≈10:10'>1:10 (FIG. 15B). Neither 1 nor 10 alone can outcompete the 1':10' binding and hence growth occurs, but when both are expressed, the free energy of formation of both 1:1' and 10:10' outweighs that of 1':10' and growth is blocked (FIG. 12G).

3 Input CIPHR Logic Gates

We constructed a 3-input AND gate (FIG. 10M) in which monomers 1 and 2 are brought into proximity by the three inputs 1'-4', 4-3', and 3-2'. We experimentally tested all eight possible input combinations (FIG. 13A), quantifying all complexes using nMS with both 1 and 2 present. Consistent with proper function of a 3-input AND gate, 1 and 2 only showed significant co-assembly when all three inputs are present (data not shown).

Figures 13A, 13B, 13C, 13D, 13E:
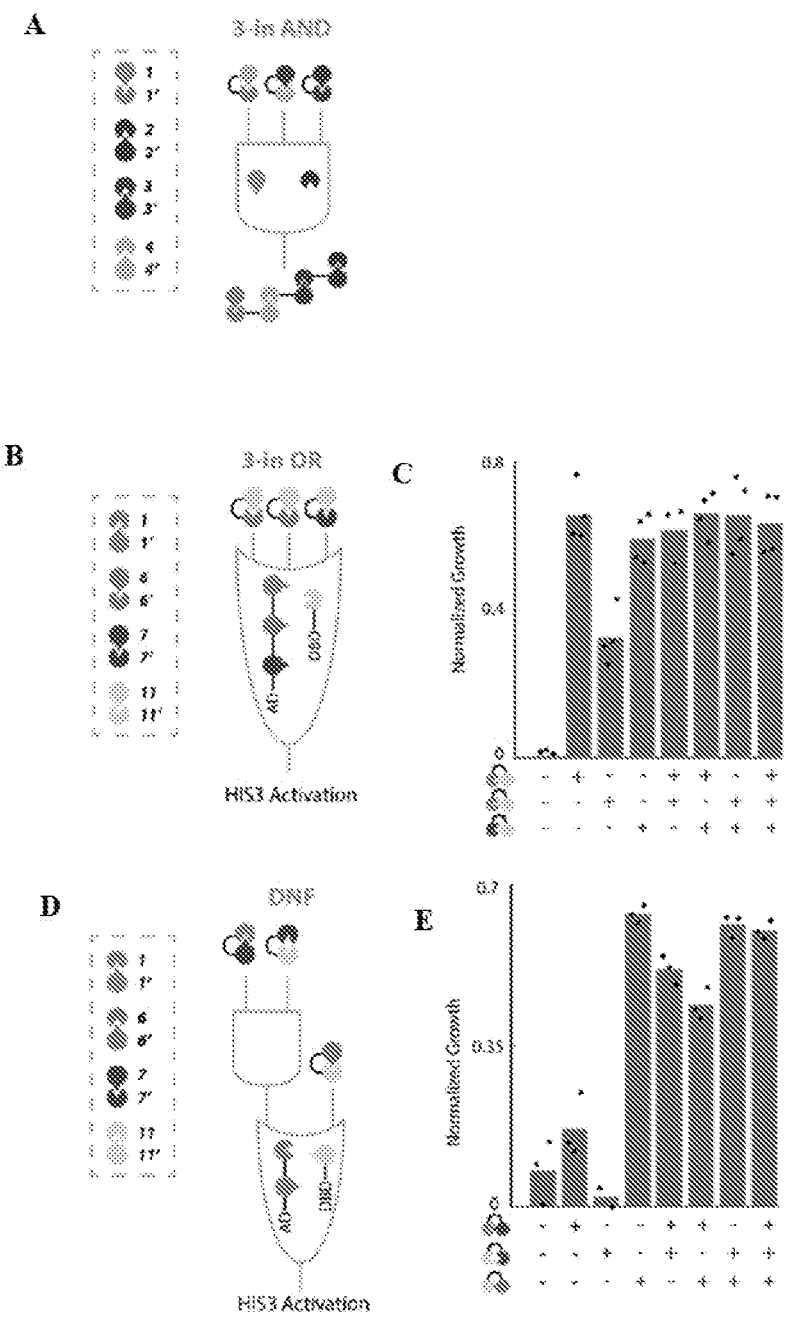
FIGS. 13A to 13E show three-input CIPHR logic gates.

To test the modularity of CIPHR logic gates, we designed two different 3-input CIPHR logic gates using the same 4 pairs of DHDs and tested them via Y2H. To make a 3-input OR gate, 1'-6-7 was fused to AD, and 11' to DBD. Either one of the 3 inputs (11-1, 11-6', 11-7') is able to bring AD to DBD via their linked proteins (FIG. 13B). Y2H results confirmed the correct behavior of this logic gate in cells: any of the input proteins induces cell growth (FIG. 13C). We constructed a CIPHR disjunctive normal form (DNF, [A AND B] OR C) gate by fusing 1'-6 to AD, 11' to DBD with inputs 11-7', 7-1, or 11-6' (FIG. 13D). In Y2H experiments, the DNF gate functioned as designed, with low yeast growth levels when no input or only one of the 11-7' and 7-1 input proteins are present, and high yeast growth levels otherwise (FIG. 13E).

References for Example 2

1. R. Nussinov, How do dynamic cellular signals travel long distances? *Mol. Biosyst.* 8, 22-26 (2012).
2. A. W. Reinke, J. Baek, O. Ashenberg, A. E. Keating, Networks of bZIP protein-protein interactions diversified over a billion years of evolution. *Science.* 340, 730-734 (2013).
3. Y. E. Antebi, J. M. Linton, H. Klumpe, B. Bintu, M. Gong, C. Su, R. McCardell, M. B. Elowitz, Combinatorial Signal Perception in the BMP Pathway. *Cell.* 170, 1184-1196.e24 (2017).
4. B. Z. Harris, W. A. Lim, Mechanism and role of PDZ domains in signaling complex assembly. *J. Cell Sci.* 114, 3219-3231 (2001).
5. G. Seelig, D. Soloveichik, D. Y. Zhang, E. Winfree, Enzyme-free nucleic acid logic circuits. *Science.* 314, 1585-1588 (2006).
6. L. Qian, E. Winfree, Scaling up digital circuit computation with DNA strand displacement cascades. *Science.* 332, 1196-1201 (2011).
7. M. B. Elowitz, S. Leibler, A synthetic oscillatory network of transcriptional regulators. *Nature.* 403, 335-338 (2000).
8. T. S. Gardner, C. R. Cantor, J. J. Collins, Construction of a genetic toggle switch in *Escherichia coli*. *Nature.* 403, 339-342 (2000).
9. A. Tamsir, J. J. Tabor, C. A. Voigt, Robust multicellular computing using genetically encoded NOR gates and chemical "wires." *Nature.* 469, 212-215 (2011).
10. P. Siuti, J. Yazbek, T. K. Lu, Synthetic circuits integrating logic and memory in living cells. *Nat. Biotechnol.* 31, 448-452 (2013).
11. J. Bonnet, P. Yin, M. E. Ortiz, P. Subsoontorn, D. Endy, Amplifying genetic logic gates. *Science.* 340, 599-603 (2013).
12. B. H. Weinberg, N. T. H. Pham, L. D. Caraballo, T. Lozanoski, A. Engel, S. Bhatia, W. W. Wong, Large-scale design of robust genetic circuits with multiple inputs and outputs for mammalian cells. *Nat. Biotechnol.* 35, 453-462 (2017).
13. S. Auslander, D. Auslander, M. Muller, M. Wieland, M. Fussenegger, Programmable single-cell mammalian biocomputers. *Nature.* 487, 123-127 (2012).
14. A. S. Khalil, T. K. Lu, C. J. Bashor, C. L. Ramirez, N. C. Pyenson, J. K. Joung, J. J. Collins, A synthetic biology framework for programming eukaryotic transcription functions. *Cell.* 150, 647-658 (2012).
15. N. Roquet, A. P. Soleimany, A. C. Ferris, S. Aaronson, T. K. Lu, Synthetic recombinase-based state machines in living cells. *Science.* 353, aad8559 (2016).
16. L. B. Andrews, A. A. K. Nielsen, C. A. Voigt, Cellular checkpoint control using programmable sequential logic. *Science.* 361, eaap8987 (2018).
17. B. Angelici, E. Mailand, B. Haefliger, Y. Benenson, Synthetic Biology Platform for Sensing and Integrating Endogenous Transcriptional Inputs in Mammalian Cells. *Cell Rep.* 16, 2525-2537 (2016).
18. J. J. Lohmueller, T. Z. Armel, P. A. Silver, A tunable zinc finger-based framework for Boolean logic computation in mammalian cells. *Nucleic Acids Res.* 40, 5180-5187 (2012).
19. A. A. Green, P. A. Silver, J. J. Collins, P. Yin, Toehold switches: de-novo-designed regulators of gene expression. *Cell.* 159, 925-939 (2014).
20. A. A. Green, J. Kim, D. Ma, P. A. Silver, J. J. Collins, P. Yin, Complex cellular logic computation using ribocomputing devices. *Nature.* 548, 117-121 (2017).
21. K. Rinaudo, L. Bleris, R. Maddamsetti, S. Subramanian, R. Weiss, Y. Benenson, A universal RNAi-based logic evaluator that operates in mammalian cells. *Nat. Biotechnol.* 25, 795-801 (2007).
22. L. Wroblewska, T. Kitada, K. Endo, V. Siciliano, B. Stillo, H. Saito, R. Weiss, Mammalian synthetic circuits with RNA binding proteins for RNA-only delivery. *Nat. Biotechnol.* 33, 839-841 (2015).
23. S.-H. Park, A. Zarrinpar, W. A. Lim, Rewiring MAP kinase pathways using alternative scaffold assembly mechanisms. *Science.* 299, 1061-1064 (2003).
24. P. L. Howard, M. C. Chia, S. Del Rizzo, F.-F. Liu, T. Pawson, Redirecting tyrosine kinase signaling to an apoptotic caspase pathway through chimeric adaptor proteins. *Proc. Natl. Acad. Sci. U.S.A* 100, 11267-11272 (2003).
25. B. J. Yeh, R. J. Rutigliano, A. Deb, D. Bar-Sagi, W. A. Lim, Rewiring cellular morphology pathways with synthetic guanine nucleotide exchange factors. *Nature.* 447, 596-600 (2007).
26. L. Morsut, K. T. Roybal, X. Xiong, R. M. Gordley, S. M. Coyle, M. Thomson, W. A. Lim, Engineering Customized Cell Sensing and Response Behaviors Using Synthetic Notch Receptors. *Cell.* 164, 780-791 (2016).
27. K. T. Roybal, L. J. Rupp, L. Morsut, W. J. Walker, K. A. McNally, J. S. Park, W. A. Lim, Precision Tumor Recognition by T Cells With Combinatorial Antigen-Sensing Circuits. *Cell.* 164, 770-779 (2016).
28. J. E. Dueber, B. J. Yeh, K. Chak, W. A. Lim, Reprogramming Control of an Allosteric Signaling Switch Through Modular Recombination. *Science.* 301, 1904-1908 (2003).
29. R. M. Gordley, R. E. Williams, C. J. Bashor, J. E. Toettcher, S. Yan, W. A. Lim, Engineering dynamical control of cell fate switching using synthetic phosphoregulons. *Proc. Natl. Acad. Sci. U.S.A* 113, 13528-13533 (2016).
30. J. E. Dueber, E. A. Mirsky, W. A. Lim, Engineering synthetic signaling proteins with ultrasensitive input/output control. *Nat. Biotechnol.* 25, 660-662 (2007).
31. X. J. Gao, L. S. Chong, M. S. Kim, M. B. Elowitz, Programmable protein circuits in living cells. *Science.* 361, 1252-1258 (2018).
32. T. Fink, J. Lonzarić, A. Praznik, T. Plaper, E. Merljak, K. Leben, N. Jerala, T. Lebar, . Strmšek, F. Lapenta, M. Benčina, R. Jerala, Design of fast proteolysis-based signaling and logic circuits in mammalian cells. *Nat. Chem. Biol.* 15, 115-122 (2019).
33. A. J. Smith, F. Thomas, D. Shoemark, D. N. Woolfson, N. J. Savery, Guiding Biomolecular Interactions in Cells Using de Novo Protein-Protein Interfaces. *ACS Synth. Biol.* 8, 1284-1293 (2019).
34. Z. Chen, S. E. Boyken, M. Jia, F. Busch, D. Flores-Solis, M. J. Bick, P. Lu, Z. L. VanAernum, A. Sahasrabuddhe, R. A. Langan, S. Bermeo, T. J. Brunette, V. K. Mulligan, L. P. Carter, F. DiMaio, N. G. Sgourakis, V. H. Wysocki, D. Baker, Programmable design of orthogonal protein heterodimers. *Nature.* 565, 106-111 (2019).
35. K. E. Prehoda, J. A. Scott, R. D. Mullins, W. A. Lim, Integration of multiple signals through cooperative regulation of the N-WASP-Arp2/3 complex. *Science.* 290, 801-806 (2000).
36. B. Yu, I. R. S. Martins, P. Li, G. K. Amarasinghe, J. Umetani, M. E. Fernandez-Zapico, D. D. Billadeau, M. Machius, D. R. Tomchick, M. K. Rosen, Structural and energetic mechanisms of cooperative autoinhibition and activation of Vav1. *Cell.* 140, 246-256 (2010).
37. K. N. Dyer, M. Hammel, R. P. Rambo, S. E. Tsutakawa, I. Rodic, S. Classen, J. A. Tainer, G. L. Hura, High-throughput SAXS for the characterization of biomolecules in solution: a practical approach. *Methods Mol. Biol.* 1091, 245-258 (2014).
38. A. Pause, B. Peterson, G. Schaffar, R. Stearman, R. D. Klausner, Studying interactions of four proteins in the yeast two-hybrid system: structural resemblance of the pVHL/elongin BC/hCUL-2 complex with the ubiquitin ligase complex SKP1/cullin/F-box protein. *Proc. Natl. Acad. Sci. U.S.A* 96, 9533-9538 (1999).
39. B. Sandrock, J. M. Egly, A yeast four-hybrid system identifies Cdk-activating kinase as a regulator of the XPD helicase, a subunit of transcription factor IIH. *J. Biol. Chem.* 276, 35328-35333 (2001).
40. A. S. Dixon, M. K. Schwinn, M. P. Hall, K. Zimmerman, P. Otto, T. H. Lubben, B. L. Butler, B. F. Binkowski, T. Machleidt, T. A. Kirkland, M. G. Wood, C. T. Eggers, L. P. Encell, K. V. Wood, NanoLuc Complementation Reporter Optimized for Accurate Measurement of Protein Interactions in Cells. *ACS Chem. Biol.* 11, 400-408 (2016).
41. Y.-C. Kwon, M. C. Jewett, High-throughput preparation methods of crude extract for robust cell-free protein synthesis. *Sci. Rep.* 5, 8663 (2015).
42. J. R. Porter, C. I. Stains, B. W. Jester, I. Ghosh, A general and rapid cell-free approach for the interrogation of protein-protein, protein-DNA, and protein-RNA interactions and their antagonists utilizing split-protein reporters. *J. Am. Chem. Soc.* 130, 6488-6497 (2008).
43. S. L. Maude, T. W. Laetsch, J. Buechner, S. Rives, M. Boyer, H. Bittencourt, P. Bader, M. R. Verneris, H. E. Stefanski, G. D. Myers, M. Qayed, B. De Moerloose, H. Hiramatsu, K. Schlis, K. L. Davis, P. L. Martin, E. R. Nemecek, G. A. Yanik, C. Peters, A. Baruchel, N. Boissel, F. Mechinaud, A. Balduzzi, J. Krueger, C. H. June, B. L. Levine, P. Wood, T. Taran, M. Leung, K. T. Mueller, Y. Zhang, K. Sen, D. Lebwohl, M. A. Pulsipher, S. A. Grupp, Tisagenlecleucel in Children and Young Adults with B-Cell Lymphoblastic Leukemia. *N. Engl. J. Med.* 378, 439-448 (2018).
44. S. S. Neelapu, F. L. Locke, N. L. Bartlett, L. J. Lekakis, D. B. Miklos, C. A. Jacobson, I. Braunschweig, O. O. Oluwole, T. Siddiqi, Y. Lin, J. M. Timmerman, P. J. Stiff, J. W. Friedberg, I. W. Flinn, A. Goy, B. T. Hill, M. R. Smith, A. Deol, U. Farooq, P. McSweeney, J. Munoz, I. Avivi, J. E. Castro, J. R. Westin, J. C. Chavez, A. Ghobadi, K. V. Komanduri, R. Levy, E. D. Jacobsen, T. E. Witzig, P. Reagan, A. Bot, J. Rossi, L. Navale, Y. Jiang, J. Aycock, M. Elias, D. Chang, J. Wiezorek, W. Y. Go, Axicabtagene Ciloleucel CAR T-Cell Therapy in Refractory Large B-Cell Lymphoma. *N. Engl. J. Med.* 377, 2531-2544 (2017).
45. J. A. Fraietta, S. F. Lacey, E. J. Orlando, I. Pruteanu-Malinici, M. Gohil, S. Lundh, A. C. Boesteanu, Y. Wang, R. S. O'Connor, W.-T. Hwang, E. Pequignot, D. E. Ambrose, C. Zhang, N. Wilcox, F. Bedoya, C. Dorfmeier, F. Chen, L. Tian, H. Parakandi, M. Gupta, R. M. Young, F. B. Johnson, I. Kulikovskaya, L. Liu, J. Xu, S. H. Kassim, M. M. Davis, B. L. Levine, N. V. Frey, D. L. Siegel, A. C. Huang, E. J. Wherry, H. Bitter, J. L. Brogdon, D. L. Porter, C. H. June, J. J. Melenhorst, Determinants of response and resistance to CD19 chimeric antigen receptor (CAR) T cell therapy of chronic lymphocytic leukemia. *Nat. Med.* 24, 563-571 (2018).
46. C. H. June, R. S. O'Connor, O. U. Kawalekar, S. Ghassemi, M. C. Milone, CAR T cell immunotherapy for human cancer. *Science.* 359, 1361-1365 (2018).
47. A. H. Long, W. M. Haso, J. Shern, K. M. Wanhainen, M. Murgai, M. Ingaramo, J. P. Smith, A. J. Walker, M. E. Kohler, V. R. Venkateshwara, R. N. Kaplan, G. H. Patterson, T. J. Fry, R. J. Orentas, C. L. Mackall, 4-1BB costimulation ameliorates T cell exhaustion induced by tonic signaling of chimeric antigen receptors. *Nat. Med.* 21, 581-590 (2015).
48. E. J. Wherry, M. Kurachi, Molecular and cellular insights into T cell exhaustion. *Nat. Rev. Immunol.* 15, 486-499 (2015).
49. E. John Wherry, S. J. Ha, S. M. Kaech, W. Nicholas Haining, S. Sarkar, V. Kalia, S. Subramaniam, J. Blattman, D. L. Barber, R. Ahmed, Molecular Signature of CD8+ T Cell Exhaustion during Chronic Viral Infection. *Immunity.* 27 (2007), doi:10.1016/j.immuni.2007.11.006.
50. K. E. Pauken, M. A. Sammons, P. M. Odorizzi, S. Manne, J. Godec, O. Khan, A. M. Drake, Z. Chen, D. R. Sen, M. Kurachi, R. A. Barnitz, C. Bartman, B. Bengsch, A. C. Huang, J. M. Schenkel, G. Vahedi, W. N. Haining, S. L. Berger, E. J. Wherry, Epigenetic stability of exhausted T cells limits durability of reinvigoration by PD-1 blockade. *Science.* 354, 1160-1165 (2016).
51. K. E. Prehoda, W. A. Lim, How signaling proteins integrate multiple inputs: a comparison of N-WASP and Cdk2. *Curr. Opin. Cell Biol.* 14, 149-154 (2002).

Figure 17:
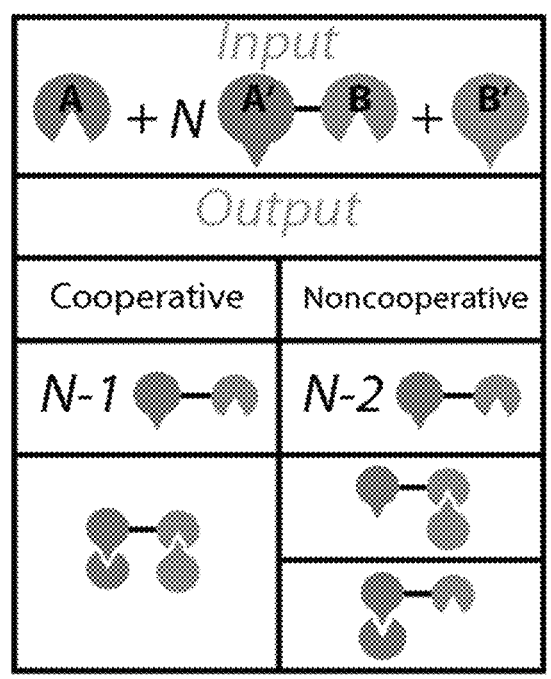
FIG. 17 shows a thermodynamic modeling of cooperativity for an induced dimerization system involving proteins A, A'-B, and B'.

Referring to FIG. 17, for an induced dimerization system involving proteins A, A'-B, and B', a stoichiometric excess (N) of the A'-B protein results in partially assembled dimeric complexes if the binding is non-cooperative, but fully assembled trimeric complexes if the binding is cooperative.

Figure 18:
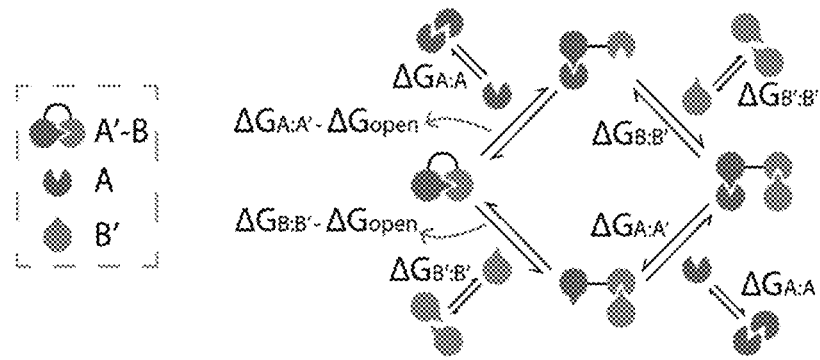
FIG. 18 shows a model of a cooperatively induced dimerization system at thermodynamic equilibrium, assuming a 'closed' state for A'-B, where the binding interfaces are buried within the four-helix bundle, and the binding of A'-B to either A or B' helix hairpins needs to overcome an energy barrier of transitioning from the 'closed' to 'open' state.

We model the cooperatively induced dimerization system at thermodynamic equilibrium. Shown in FIG. 18, assuming a 'closed' state for A'-B, where the binding interfaces are buried within the four-helix bundle, the binding of A'-B to either A or B' helix hairpins needs to overcome an energy barrier of transitioning from the 'closed' to 'open' state ($\Delta G_{open}$). Therefore the free energy of binding between A'-B to A or B' can be expressed as $\Delta G_{A:A'}$-$\Delta G_{open}$ and $\Delta G_{B:B'}$-$\Delta G_{open}$, respectively, where $\Delta G_{A:A'}$ and $\Delta G_{B:B'}$ represent the free energy of binding between the cognate pairs in the absence of the fusion. Once the A:A'-B or A-B':B complexes form, subsequent binding can be simply represented by the binding between cognate heterodimers: $\Delta G_{A:A'}$ or $\Delta G_{B:B'}$. We also observed the presence of $(A)_2$ and $(B')_2$ homodimers, therefore added free energy terms describing such processes into the model ($\Delta G_{A:A}$ or $\Delta G_{B':B'}$).

$\Delta G$ relates to equilibrium constants by $\Delta G$=$-RT\ln K$, and we further consider the system in terms of K. We make the simplifying assumption that the affinity of A'-B to either A or B' is identical ($K_1$=[A:A'-B]/([A][A'-B])=[A'-B:B']/([B][A'-B])). Finally, we define the cooperativity of the system, c, as the ratio between the equilibrium constants in the presence or absence of the other partner (c=$K_{B:B'}$/$K_1$=$K_{A:A'}$/$K_1$). For an entirely non-cooperative process (c=1), $K_{B:B'}$=$K_1$ and $K_{A:A'}$=$K_1$ i.e., the first binding event does not affect the affinity of the subsequent binding event.

Since $K_1$=exp($-(\Delta G_{A:A'}-\Delta G_{open})$/RT), rewriting the equation for c in terms of free energies leads to c=exp($\Delta G_{open}$)/RT. Therefore, the extent of cooperativity is solely determined by the magnitude of the free energy required to partially unfold/expose the buried binding interfaces of the dimerizer A'-B.

Figure 19:
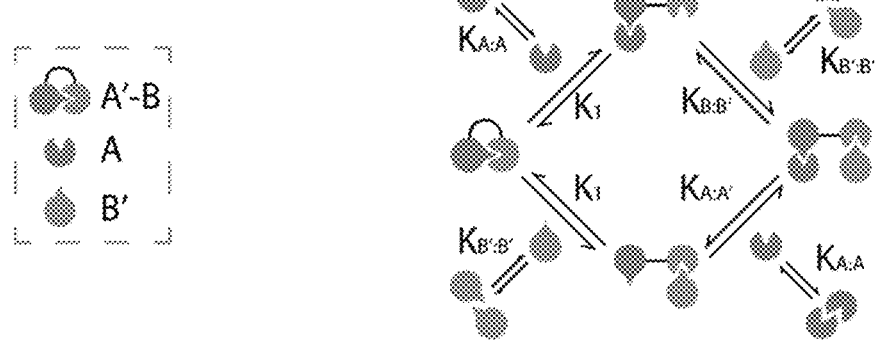
FIG. 19 shows that explicitly incorporating the equilibrium constants for homodimerization ($K_{A:A}$ and $K_{B':B'}$) of the model exemplified in FIG. 18 only affects the absolute position of each equilibrium, but does not affect the magnitude of the cooperativity.

We note that explicitly incorporating the equilibrium constants for homodimerization ($K_{A:A}$ and $K_{B':B'}$) only affect the absolute position of each equilibrium, but does not affect the magnitude of the cooperativity (see FIG. 19). Indeed, taking A as an example, the binding to the closed state becomes $K_1 * K_{A:A}$, and the binding to the open state becomes $K_{A:A'} * K_{A:A}$. Because $K_{A:A}$ is present in both the numerator and the denominator, they cancel out, and c remains purely defined by the relative magnitudes of $K_1$ and $K_{A:A'}$.

We solved the following system of equations in Mathematica to simulate the amount of A:A'-B:B' at equilibrium as a function of the initial concentration of A'-B:

$$K_{A:A} = \frac{[A_2]}{[A][A]}$$

$$K_{B':B'} = \frac{[B'_2]}{[B'][B']}$$

$$K_1 = \frac{[A:A'-B]}{[A][A'-B]}$$

$$K_1 = \frac{[B':A'-B]}{[B'][A'-B]}$$

$$K_{A:A'} = \frac{[A:A'-B:B']}{[A][A'-B:B']}$$

$$K_{B:B'} = \frac{[A:A'-B:B']}{[B'][A:A'-B]}$$

$$[A]_{tot} = 2*[A_2] + [A] + [A:A'-B] + [A:A'-B:B']$$

$$[B']_{tot} = 2*[B'_2] + [A'-B:B'] + [A:A'-B:B']$$

$$[A'-B]_{tot} = [A'-B:B'] + [A:A'-B'] + [A:A'-B:B']$$

We knew from previous native MS titration experiments that the equilibrium dissociation constants of cognate designed heterodimers (DHDs) is in the ~10 nM range (1), therefore $K_{A:A}=K_{B:B}=0.1$ nM$^{-1}$. Varying values of $K_1$ (and hence the cooperativity factor, $c=K_{A:A}/K_1$) showed different responses of the amount of A:A'-B:B' at equilibrium as a function of the initial concentration of A'-B, as shown in FIG. 12C.

We experimentally estimated $K_1$ using native MS experiments. Mixing 10 μM of 1 and 1'-2' resulted in no detectable amount of the 1:1'-2' complex, suggesting very weak binding. The sensitivity of native MS places a lower-bound on the concentration of species that can be detected (0.0375 μM). Using this value, a lower-bound for the affinity of 1:1'-2' can be estimated (1/$K_1$≥2.65 mM). This is close to the value of 9.91 mM obtained by calculating the affinity based on the c value of 991,000 reported in FIG. 13H.

This thermodynamic modeling demonstrates that binding cooperativity can be achieved for an induced dimerization system through occlusion of the binding interfaces. We achieved this by fusing hairpins via a flexible linker, rationalizing that the spontaneous folding of these constructs would bury the interaction interfaces on the inside of a four helical bundle like topology. Formation of these structures is corroborated by: i) SAXS profiles that are consistent with DHDs structures, m-values from chemical denaturation experiments consistent with ΔSASA for the unfolding of DHD topologies, and iii) $\Delta G_{open} < \Delta G_{folding}$, suggesting that exposing the binding interfaces requires partial unfolding of these fused constructs, but does not exceed the folding free energy of these proteins (a physically unrealistic scenario).

Materials and Methods
Buffer and Media Recipe
TBM-5052: 1.2% [wt/vol] tryptone, 2.4% [wt/vol] yeast extract, 0.5% [wt/vol] glycerol, 0.05% [wt/vol] D-glucose, 0.2% [wt/vol] D-lactose, 25 mM Na2HPO4, 25 mM KH2PO4, 50 mM NH4Cl, 5 mM Na2SO4, 2 mM MgSO4, 10 μM FeCl3, 4 μM CaCl2, 2 μM MnCl2, 2 μM ZnSO4, 400 nM CoCl2, 400 nM NiCl2, 400 nM CuCl2, 400 nM Na2MoO4, 400 nM Na2SeO3, 400 nM H3BO3.

Lysis buffer: 20 mM Tris, 300 mM NaCl, 20 mM Imidazole, pH 8.0 at room temperature.

Wash buffer: 20 mM Tris, 300 mM NaCl, 30 mM Imidazole, pH 8.0 at room temperature.

Elution buffer: 20 mM Tris, 300 mM NaCl, 250 mM Imidazole, pH 8.0 at room temperature.

TBS buffer: 20 mM Tris pH 8.0, 100 mM NaCl.

YPAD buffer: Peptone 20 g/L, yeast extract 10 g/L, Adenine hemisulfate 10 μg/L, dextrose (20 g/L).

C-Trp-Ura-Leu-His+Adenine: hemisulfate+Glucose.

Yeast nitrogen base w/o amino acids (6.7 g/L), synthetic DO media (–Leu/–His/–Trp/–Ura) (1.4 g/L), dextrose (20 g/L), adenine hemisulfate (10 μg/L).

Construction of Synthetic Genes
For the expression of proteins in *E. coli*, synthetic genes were ordered from Genscript Inc. (Piscataway, N.J., USA) and delivered in pET21-NESG *E. coli* expression vector, inserted between the NdeI and XhoI sites. For each expression construct, a hexahistidine tag followed by a tobacco etch virus (TEV) protease cleavage site (GSSHHHHHHSS-GENLYFQGS) (SEQ ID NO:328) were added in frame at the N-terminus of the protein. A stop codon was introduced at the 3' end of the protein coding sequence to prevent expression of the C-terminal hexahistidine tag in the vector.

Genes for yeast-two-hybrid (Y2H) studies were cloned into plasmids bearing the GAL4 DNA-binding domain (poDBD) and the GAL4 transcription activation domain (poAD) (2). Input proteins were cloned into plasmids V510 (uracil auxotrophic selection marker) and MX1 (bleomycin selection marker). Genes were expressed under the control of ADH1 promoters.

Protein Expression
Plasmids were transformed into chemically competent *E. coli* expression strain Lemo21™(DE3) (New England Biolabs) for protein expression. Following transformation and overnight growth, single colonies were picked from agar plates into 5 ml Luria-Bertani (LB) medium containing 100 μg/mL carbenicillin (for pET21-NESG vectors) with shaking at 225 rpm for 18 hours at 37° C. Proteins were expressed using the auto induction method (7): starter cultures were further diluted into 500 ml TBM-5052 containing 100 μg/mL carbenicillin, and incubated with shaking at 225 rpm for 24 hours at 37° C.

Affinity Purification
*E. coli* cells were harvested by centrifugation at 5000 rcf for 15 minutes at 4° C. and the pellet resuspended in 18 ml lysis buffer. EDTA-free cocktail protease inhibitor (Roche), lysozyme, and DNAse were added to the resuspended cell pellet, followed by cell lysis via sonication at 70% power for 5 minutes. Lysates were clarified by centrifugation at 4° C. and 18,000 rpm for 45 minutes and applied to columns containing Ni-NTA (Qiagen) resin pre-equilibrated with lysis buffer. The column was washed two times with 5 column volumes (CV) of wash buffer, followed by 5 CV of elution buffer for protein elution.

Size-Exclusion Chromatography (SEC)
Eluted proteins were buffer exchanged into lysis buffer. N-terminal hexahistidine tags were removed with TEV protease cleavage overnight at room temperature, at a ratio of 1 mg TEV for 100 mg of protein. After TEV cleavage, sample was passed over a fresh Ni-NTA column and washed with 1.5 CV of lysis buffer, collecting flow through. The resulting proteins were purified by SEC using a Superdex™ 75 10/300 increase column (GE Healthcare) in TBS buffer.

Circular Dichroism (CD) Measurements

Circular dichroism (CD) wavelength scans (260-195 nm) and temperature melts (25-95° C.) were performed using an AVIV™ model 420 CD spectrometer, with protein samples diluted to 0.25 mg/ml in PBS pH 7.4 in a 0.1-cm cuvette. Temperature melts were carried out at a heating rate of 4° C./min and monitored by the change in ellipticity at 222 nm.

GdmCl titrations were performed on a JASCO™ model J-1500 with automated titration apparatus in PBS pH 7.4 at 25° C., with protein concentrations between 0.08 mg/ml to 0.025 mg/ml in a 1-cm cuvette with stir bar. Each titration consisted of at least 34 evenly distributed GdmCl concentration points up to 7.4 M with 30 seconds mixing time for each step. Titrant solution consisted of the same concentration of protein in PBS and GdmCl.

CD Data Analysis and Model Fitting

Folding free energies were obtained by fitting equilibrium denaturation data. Fused hairpin constructs had biphasic unfolding transitions, indicating the existence of an intermediate on their respective energy landscapes. Since native MS showed that Linker 0, Linker 2, Linker 6, and Linker 12 were almost exclusively monomeric in buffer (data not shown), it was concluded that these intermediates were partially folded monomeric species. Thus, the chemical denaturation data of these proteins was fitted to a unimolecular 3-state model:

$$N \Leftrightarrow I \Leftrightarrow D$$

where N represents the fully folded state, I a partially folded intermediate, and D the denatured state. The fraction of each species can be written as a function of $K_1=[I]/[N]$ and $K_2=[D]/[I]$, the equilibrium constants for the first and second transitions respectively:

$$f_N = (1 + K_1 + K_1 \cdot K_2)^{-1}$$

$$f_I = \left(1 + K_2 + \frac{1}{K_1}\right)^{-1}$$

$$f_D = \left(1 + \frac{1}{K_2} + \frac{1}{K_1 \cdot K_2}\right)^{-1}$$

In the context of equilibrium chemical denaturation experiments, the free energy of unfolding is a linear function of denaturant concentration:

$$\Delta G_{[den]} = \Delta G_{buffer} - m \cdot [den]$$

where $\Delta G_{[den]}$ represents the free energy of the system at a given concentration of denaturant, $\Delta G_{buffer}$ is the corresponding free energy change in the absence of denaturant, and m is a constant of proportionality that relates to the change in solvent-accessible surface area upon unfolding ($\Delta SASA$). Thus, the effect of denaturant on the equilibrium constant relating to each transition can be written as a function of its free energy difference in buffer, and a specific m-value:

$$K_1 = \exp\left(\frac{m_1 \cdot [den] - \Delta G_1}{R \cdot T}\right)$$

$$K_2 = \exp\left(\frac{m_2 \cdot [den] - \Delta G_2}{R \cdot T}\right)$$

By combining these expressions with the definitions for $f_N$, $f_I$, $f_D$, the fractional distribution of each species can be expressed as a function of denaturant concentration, and the free energy change corresponding to each transition (in buffer). Finally, for an ensemble spectroscopic technique such as CD, the observed signal (the dependent variable) as a function of denaturant concentration (the independent variable) can be expressed as a linear combination of the spectroscopic signals corresponding to each species, weighed by their fractional contribution to the ensemble:

$$MRE_{222\ nm} = f_N \cdot MRE_N + f_I \cdot MRE_I + f_D \cdot MRE_D$$

Where $MRE_N$, $MRE_I$, $MRE_D$ represent the spectroscopic signatures (baselines) for the native, intermediate, and denatured states respectively. This equation was used to fit chemical denaturation data for the different linker proteins, and the fitted parameters are reported in Table 10. For Linker 24 in buffer, native MS revealed a significant proportion of dimer (data not shown). Therefore, this model is not entirely appropriate for describing the unfolding, and the fitted values for this construct should be interpreted with care. Nevertheless, denaturation performed at different concentrations of protein revealed that the position of the second transition was concentration-independent, and thus unimolecular. For this event, the model holds.

The total m-values for these linked hairpins were found to be around 3 kcal mol-1 It has been shown that m-values correlate with $\Delta SASA$ of unfolding (8). For the folded state, SASA was estimated from the structures of DHDs (I) using PyMOL™ to be 8800 Å$^2$. For the unfolded state, SASA was estimated using ProtSA™ (9, 10), and is about 20,000 Å$^2$. Thus, $\Delta SASA$ for the unimolecular unfolding of a fused hairpin should be around 11,000 Å$^2$, which would have a predicted m-value of 3.3. This number is in close agreement with the fitted parameters reported here, in line with the notion that the folded state for these linker proteins has a four helix bundle topology.

Small Angle X-Ray Scattering (SAXS)

Protein samples were purified by SEC in 25 mM Tris pH 8.0, 150 mM NaCl and 2% glycerol; elution fractions preceding the void volume of the column were used as blanks for buffer subtraction. Scattering measurements were performed at the SIBYLS™ 12.3.1 beamline at the Advanced Light Source. The sample-to-detector distance was 1.5 m, and the X-ray wavelength ($\lambda$) was 1.27 Å, corresponding to a scattering vector q ($q=4\pi \sin \theta/\lambda$, where $2\theta$ is the scattering angle) range of 0.01 to 0.3 Å$^{-1}$. A series of exposures were taken of each well, in equal sub-second time slices: 0.3-s exposures for 10 s resulting in 32 frames per sample. For each sample, data were collected for two different concentrations to test for concentration-dependent effects; 'low' concentration samples ranged at 2.5 mg/ml and 'high' concentration samples at 5 mg/ml. Data were processed using the SAXS FrameSlice™ online serve and analyzed using the ScÅtter™ software package (11, 12). The FoXS™ online server (13, 14) was used to compare experimental scattering profiles to design models and calculate quality of fit ($\chi$) values.

Yeast Two-Hybrid Assay for Logic Gates

Chemically competent cells of yeast strain PJ69-4a (MATa trp1-901 leu2-3,112 ura3-52 his3-200 gal4(deleted) gal80(deleted) LYS2::GAL1-HIS3 GAL2-ADE2 met2::GAL7-lacZ) were transformed with the appropriate pair of plasmids containing DNA binding domains (DBD) or activation domains (AD), using the LiAc/SS carrier DNA/PEG method (15). For two input CIPHR logic gates, genes encoding the input proteins (together with selection markers) were genetically integrated into either or both of the Ura3 locus (uracil auxotrophic selection marker) or the YCR043 locus (bleomycin selection marker). In the case of three input CIPHR logic gates, genes encoding two input proteins were genetically integrated as described, with the additional input cloned downstream of either the AD or DBD plasmid, separated by a p2a and nuclear localization sequence (GSGATNFSLLKQAGDVEENPGPGDKAELI-PEPPKKKRKVELGTA; SEQ ID NO:330). The p2a sequence ensures translational cleavage to make the additional input protein a separate protein. The selection of transformed yeast cells was performed in synthetic dropout (SDO) medium lacking tryptophan and leucine for 48 h with shaking at 1,000 r.p.m. at 30° C. The resulting culture was diluted 1:100 and grown for 16 h in fresh SDO medium lacking tryptophan and leucine, before being diluted 1:100 in fresh SDO medium lacking tryptophan, leucine and histidine. The culture was incubated with shaking at 1,000 r.p.m. at 30° C. As it is necessary to bring the DBD and the transcription activation domain into proximity for the growth of yeast cells in medium lacking histidine, successful activation of logic gates was indicated by the growth of yeast cells (16, 17). The optical density of yeast cells was recorded at 24 h, 48 h, and 72 h.

TABLE 10

Fitted parameters for equilibrium chemical denaturation. Errors represent fitting errors.

| | Linker 0 | Linker 2 | Linker 6 | Linker 12 | Linker 24 |
|---|---|---|---|---|---|
| $\Delta G_1^{(N \Leftrightarrow I)}$ (kcal mol$^{-1}$) | 3.6 (±0.4) | 3.5 (±0.2) | 3.5 (±0.2) | 2.7 (±0.1) | 3.7 (±0.3) |
| $\Delta G_2^{(I \Leftrightarrow D)}$ (kcal mol$^{-1}$) | 9.8 (±0.6) | 10.7 (±0.4) | 12.2 (±0.4) | 10.6 (±0.5) | 10.4 (±0.8) |
| $\Delta G_{tot}^{(N \Leftrightarrow D)}$ (kcal mol$^{-1}$) | 13.5 (±0.7) | 14.1 (±0.4) | 15.7 (±0.5) | 13.3 (±0.5) | 14.1 (±0.8) |
| $m_1$ (kcal mol$^{-1}$ M$^{-1}$) | 1.1 (±0.2) | 1.0 (±0.1) | 0.9 (±0.1) | 0.75 (±0.05) | 1.1 (±0.1) |
| $m_2$ (kcal mol$^{-1}$ M$^{-1}$) | 1.8 (±0.1) | 1.97 (±0.07) | 2.22 (±0.08) | 1.96 (±0.08) | 2.0 (±0.1) |
| $m_{tot}$ (kcal mol$^{-1}$ M$^{-1}$) | 2.9 (±0.2) | 3.0 (±0.1) | 3.1 (±0.1) | 2.71 (±0.09) | 3.1 (±0.2) |
| MRE$_N$ (deg cm$^2$ dmol$^{-1}$) | −23,574 (±114) | −27,561 (±84) | −24,712 (±63) | −33,849 (±131) | −26,438 (±123) |
| MRE$_I$ (deg cm$^2$ dmol$^{-1}$) | −16,330 (±749) | −18,139 (±540) | −14,779 (±710) | −17,362 (±1,158) | −15,567 (±914) |
| MRE$_D$ (deg cm$^2$ dmol$^{-1}$) | −525 (±107) | −785 (±82) | −937 (±68) | −1,104 (±99) | −1,125 (±133) |

REFERENCES

1. Z. Chen, S. E. Boyken, M. Jia, F. Busch, D. Flores-Solis, M. J. Bick, P. Lu, Z. L. VanAernum, A. Sahasrabuddhe, R. A. Langan, S. Bermeo, T. J. Brunette, V. K. Mulligan, L. P. Carter, F. DiMaio, N. G. Sgourakis, V. H. Wysocki, D. Baker, Programmable design of orthogonal protein heterodimers. *Nature.* 565, 106-111 (2019).

2. S. E. Boyken, Z. Chen, B. Groves, R. A. Langan, G. Oberdorfer, A. Ford, J. M. Gilmore, C. Xu, F. DiMaio, J. H. Pereira, B. Sankaran, G. Seelig, P. H. Zwart, D. Baker, De novo design of protein homo-oligomers with modular hydrogen-bond network-mediated specificity. *Science.* 352, 680-687 (2016).

3. A. S. Dixon, M. K. Schwinn, M. P. Hall, K. Zimmerman, P. Otto, T. H. Lubben, B. L. Butler, B. F. Binkowski, T. Machleidt, T. A. Kirkland, M. G. Wood, C. T. Eggers, L. P. Encell, K. V. Wood, NanoLuc Complementation Reporter Optimized for Accurate Measurement of Protein Interactions in Cells. *ACS Chem. Biol.* 11, 400-408 (2016).

4. M. E. Lee, W. C. DeLoache, B. Cervantes, J. E. Dueber, A Highly Characterized Yeast Toolkit for Modular, Multipart Assembly. *ACS Synth. Biol.* 4, 975-986 (2015).

5. A. S. Khalil, T. K. Lu, C. J. Bashor, C. L. Ramirez, N. C. Pyenson, J. K. Joung, J. J. Collins, A synthetic biology framework for programming eukaryotic transcription functions. *Cell.* 150, 647-658 (2012).

6. A. Aranda-Diaz, K. Mace, I. Zuleta, P. Harrigan, H. El-Samad, Robust Synthetic Circuits for Two-Dimensional Control of Gene Expression in Yeast. *ACS Synth. Biol.* 6, 545-554 (2017).

7. F. W. Studier, Protein production by auto-induction in high density shaking cultures. *Protein Expr. Purif.* 41, 207-234 (2005).

8. J. K. Myers, C. N. Pace, J. M. Scholtz, Denaturant m values and heat capacity changes: relation to changes in accessible surface areas of protein unfolding. *Protein Sci.* 4, 2138-2148 (1995).

9. P. Bernado, M. Blackledge, J. Sancho, Sequence-specific solvent accessibilities of protein residues in unfolded protein ensembles. *Biophys. J.* 91, 4536-4543 (2006).

10. J. Estrada, P. Bernado, M. Blackledge, J. Sancho, ProtSA: a web application for calculating sequence specific protein solvent accessibilities in the unfolded ensemble. *BMC Bioinformatics.* 10, 104 (2009).

11. K. N. Dyer, M. Hammel, R. P. Rambo, S. E. Tsutakawa, I. Rodic, S. Classen, J. A. Tainer, G. L. Hura, High-throughput SAXS for the characterization of biomolecules in solution: a practical approach. *Methods Mol. Biol.* 1091, 245-258 (2014).

12. R. P. Rambo, J. A. Tainer, Characterizing flexible and intrinsically unstructured biological macromolecules by SAS using the Porod-Debye law. *Biopolymers.* 95, 559-571 (2011).

13. D. Schneidman-Duhovny, M. Hammel, A. Sali, FoXS: a web server for rapid computation and fitting of SAXS profiles. *Nucleic Acids Res.* 38, W540-4 (2010).

14. D. Schneidman-Duhovny, M. Hammel, J. A. Tainer, A. Sali, Accurate SAXS profile computation and its assessment by contrast variation experiments. *Biophys. J.* 105, 962-974 (2013).

15. R. H. Schiestl, R. D. Gietz, High efficiency transformation of intact yeast cells using single stranded nucleic acids as a carrier. *Curr. Genet.* 16, 339-346 (1989).
16. C. T. Chien, P. L. Bartel, R. Sternglanz, S. Fields, The two-hybrid system: a method to identify and clone genes for proteins that interact with a protein of interest. *Proc. Natl. Acad. Sci. U.S.A* 88, 9578-9582 (1991).
17. P. L. Bartel, J. A. Roecklcin, D. SenGupta, S. Fields, A protein linkage map of *Escherichia coli* bacteriophage T7. *Nat. Genet.* 12, 72-77 (1996).
18. Z. L. VanAernum, J. D. Gilbert, M. E. Belov, A. A. Makarov, S. R. Horning, V. H. Wysocki, Surface-Induced Dissociation of Noncovalent Protein Complexes in an Extended Mass Range Orbitrap Mass Spectrometer. *Anal. Chem.* 91, 3611-3618 (2019).
19. M. T. Marty, A. J. Baldwin, E. G. Marklund, G. K. A. Hochberg, J. L. P. Benesch, C. V. Robinson, Bayesian deconvolution of mass and ion mobility spectra: from binary interactions to polydisperse ensembles. *Anal. Chem.* 87, 4370-4376 (2015).
20. Y.-C. Kwon, M. C. Jewett, High-throughput preparation methods of crude extract for robust cell-free protein synthesis. *Sci. Rep.* 5, 8663 (2015).
21. M. C. Jewett, J. R. Swartz, Mimicking the *Escherichia coli* cytoplasmic environment activates long-lived and efficient cell-free protein synthesis. *Biotechnol. Bioeng.* 86, 19-26 (2004).
22. A. D. Silverman, N. Kelley-Loughnane, J. B. Lucks, M. C. Jewett, Deconstructing Cell-Free Extract Preparation for in Vitro Activation of Transcriptional Genetic Circuitry. *ACS Synth. Biol.* 8, 403-414 (2019).
23. J. R. Swartz, M. C. Jewett, K. A. Woodrow, in *Recombinant Gene Expression: Reviews and Protocols*, P. Balbás, A. Lorence, Eds. (Humana Press, Totowa, N J, 2004), pp. 169-182.
24. V. Muñoz, L. Serrano, Elucidating the folding problem of helical peptides using empirical parameters. III. Temperature and pH dependence. *J. Mol. Biol.* 245, 297-308 (1995).
23. V. Muñoz, L. Serrano, Elucidating the folding problem of helical peptides using empirical parameters. III. Temperature and pH dependence. *J. Mol. Biol.* 245, 297-308 (1995).

We claim:

1. A designed heterodimer protein, comprising:
   (a) a monomer A polypeptide, comprising an amino acid sequence having at least 95% identity to the amino acid sequence of SEQ ID NO: 263; and
   (b) a monomer B polypeptide, comprising an amino acid sequence having at least 95% identity to the amino acid sequence of SEQ ID NO: 264,
   wherein the monomer A polypeptide and the monomer B polypeptide non-covalently interact to form the designed heterodimer protein.

2. The designed heterodimer protein of claim 1, wherein the monomer A polypeptide and the monomer B polypeptide have their interaction specificity determined by at least one designed hydrogen bond network at the interface between the monomer A polypeptide and the monomer B polypeptide.

3. The designed heterodimer protein of claim 1, wherein at least 20%, of defined interface positions are invariant compared to the monomer A polypeptide or the monomer B polypeptide amino acid sequence.

4. A kit comprising the designed heterodimer protein of claim 1.

5. The designed heterodimer protein of claim 1, wherein the monomer A polypeptide is linked to an additional polypeptide sequence at the N-terminus, the C-terminus, or both.

6. The designed heterodimer protein of claim 1, wherein the monomer B polypeptide is linked to an additional polypeptide sequence at the N-terminus, the C-terminus, or both.

7. A non-naturally occurring polypeptide comprising an amino acid sequence having at least 95% sequence identity to the amino acid sequence selected from the group consisting of SEQ ID NOS: 263-264.

8. A nucleic acid encoding the polypeptide of claim 7.

9. An expression vector comprising the nucleic acid of claim 8 operatively linked to a promoter.

10. A cell comprising the nucleic acid of claim 8.

* * * * *

```
                        SEQUENCE LISTING

<160> NUMBER OF SEQ ID NOS: 494

<210> SEQ ID NO 1
<211> LENGTH: 64
<212> TYPE: PRT
<213> ORGANISM: Artificial Sequence
<220> FEATURE:
<223> OTHER INFORMATION: Synthetic peptide

<400> SEQUENCE: 1

Gly Ser Pro Lys Glu Glu Ala Arg Glu Leu Ile Arg Lys Gln Lys Glu
1               5                   10                  15

Leu Ile Lys Glu Gln Lys Lys Leu Ile Lys Glu Ala Lys Gln Lys Ser
            20                  25                  30

Asp Ser Arg Asp Ala Glu Arg Ile Trp Lys Arg Ser Arg Glu Ile Asn
        35                  40                  45

Arg Glu Ser Lys Lys Ile Asn Lys Arg Ile Lys Glu Leu Ile Lys Ser
    50                  55                  60

<210> SEQ ID NO 2
<211> LENGTH: 62
<212> TYPE: PRT
<213> ORGANISM: Artificial Sequence
<220> FEATURE:
<223> OTHER INFORMATION: Synthetic peptide

<400> SEQUENCE: 2

Pro Lys Lys Glu Ala Glu Glu Leu Ala Glu Glu Ser Glu Glu Leu His
1               5                   10                  15

Asp Arg Ser Glu Lys Leu His Glu Arg Ala Glu Gln Ser Ser Asn Ser
            20                  25                  30

Glu Glu Ala Arg Lys Ile Leu Glu Asp Ile Glu Arg Ile Ser Glu Arg
        35                  40                  45

Ile Glu Glu Ile Ser Asp Arg Ile Glu Arg Leu Leu Arg Ser
    50                  55                  60
```

```
<210> SEQ ID NO 3
<211> LENGTH: 77
<212> TYPE: PRT
<213> ORGANISM: Artificial Sequence
<220> FEATURE:
<223> OTHER INFORMATION: Synthetic peptide

<400> SEQUENCE: 3

Gly Thr Lys Glu Asp Ile Leu Glu Arg Gln Arg Lys Ile Ile Glu Arg
1               5                   10                  15

Ala Gln Glu Ile His Arg Arg Gln Glu Ile Leu Glu Glu Leu Glu
            20                  25                  30

Arg Ile Ile Arg Lys Pro Gly Ser Ser Glu Glu Ala Met Lys Arg Met
        35                  40                  45

Leu Lys Leu Leu Glu Glu Ser Leu Arg Leu Leu Lys Glu Leu Leu Glu
    50                  55                  60

Leu Ser Glu Glu Ser Ala Gln Leu Leu Tyr Glu Gln Arg
65                  70                  75

<210> SEQ ID NO 4
<211> LENGTH: 83
<212> TYPE: PRT
<213> ORGANISM: Artificial Sequence
<220> FEATURE:
<223> OTHER INFORMATION: Synthetic peptide

<400> SEQUENCE: 4

Gly Thr Glu Lys Arg Leu Leu Glu Glu Ala Glu Arg Ala His Arg Glu
1               5                   10                  15

Gln Lys Glu Ile Ile Lys Lys Ala Gln Glu Leu His Arg Arg Leu Glu
            20                  25                  30

Glu Ile Val Arg Gln Ser Gly Ser Ser Glu Glu Ala Lys Lys Glu Ala
        35                  40                  45

Lys Lys Ile Leu Glu Glu Ile Arg Glu Leu Ser Lys Arg Ser Leu Glu
    50                  55                  60

Leu Leu Arg Glu Ile Leu Tyr Leu Ser Gln Glu Gln Lys Gly Ser Leu
65                  70                  75                  80

Val Pro Arg

<210> SEQ ID NO 5
<211> LENGTH: 76
<212> TYPE: PRT
<213> ORGANISM: Artificial Sequence
<220> FEATURE:
<223> OTHER INFORMATION: Synthetic peptide

<400> SEQUENCE: 5

Thr Lys Glu Asp Ile Leu Glu Arg Gln Arg Lys Ile Ile Glu Arg Ala
1               5                   10                  15

Gln Glu Ile Ile Arg Arg Gln Gln Glu Ile Leu Glu Glu Leu Glu Arg
            20                  25                  30

Ile Ile Arg Lys Pro Gly Ser Ser Glu Glu Ala Met Lys Arg Met Leu
        35                  40                  45

Lys Leu Leu Glu Glu Ser Leu Arg Leu Leu Lys Glu Leu Leu Glu Leu
    50                  55                  60

Leu Glu Glu Ser Ala Gln Leu Leu Tyr Glu Gln Arg
65                  70                  75

<210> SEQ ID NO 6
<211> LENGTH: 78
```

-continued

```
<212> TYPE: PRT
<213> ORGANISM: Artificial Sequence
<220> FEATURE:
<223> OTHER INFORMATION: Synthetic peptide

<400> SEQUENCE: 6

Gly Ser Thr Glu Lys Arg Leu Leu Glu Glu Ala Glu Arg Ala His Arg
1               5                   10                  15

Glu Ala Lys Glu Ile Ile Lys Lys Ala Gln Glu Leu His Arg Arg Leu
            20                  25                  30

Glu Glu Ile Val Arg Gln Ser Gly Ser Ser Glu Glu Ala Lys Lys Glu
        35                  40                  45

Ala Lys Lys Ile Leu Glu Glu Ile Arg Glu Leu Ser Lys Arg Leu Leu
    50                  55                  60

Glu Leu Leu Arg Glu Ile Leu Tyr Leu Ser Gln Glu Gln Lys
65                  70                  75

<210> SEQ ID NO 7
<211> LENGTH: 76
<212> TYPE: PRT
<213> ORGANISM: Artificial Sequence
<220> FEATURE:
<223> OTHER INFORMATION: Synthetic peptide

<400> SEQUENCE: 7

Thr Lys Glu Asp Ile Leu Glu Arg Ala Arg Lys Ile Ile Glu Arg Ala
1               5                   10                  15

Gln Glu Ile His Arg Arg Gln Gln Ile Leu Glu Glu Leu Glu Arg
            20                  25                  30

Ile Ile Arg Lys Pro Gly Ser Ser Glu Glu Ala Met Lys Arg Met Leu
        35                  40                  45

Lys Leu Leu Glu Glu Ser Leu Arg Leu Lys Glu Leu Leu Glu Leu
    50                  55                  60

Ser Glu Glu Leu Ala Gln Leu Leu Tyr Glu Gln Arg
65                  70                  75

<210> SEQ ID NO 8
<211> LENGTH: 78
<212> TYPE: PRT
<213> ORGANISM: Artificial Sequence
<220> FEATURE:
<223> OTHER INFORMATION: Synthetic peptide

<400> SEQUENCE: 8

Gly Ser Thr Glu Lys Arg Leu Leu Glu Glu Ala Glu Arg Ala Ile Arg
1               5                   10                  15

Glu Gln Lys Glu Ile Ile Lys Lys Ala Gln Glu Leu His Arg Arg Leu
            20                  25                  30

Glu Glu Ile Val Arg Gln Ser Gly Ser Ser Glu Glu Ala Lys Lys Glu
        35                  40                  45

Ala Lys Lys Ile Leu Glu Glu Ile Arg Glu Leu Ser Lys Arg Ser Leu
    50                  55                  60

Glu Leu Leu Arg Glu Ile Leu Tyr Leu Leu Gln Glu Gln Lys
65                  70                  75

<210> SEQ ID NO 9
<211> LENGTH: 35
<212> TYPE: PRT
<213> ORGANISM: Artificial Sequence
<220> FEATURE:
<223> OTHER INFORMATION: Synthetic peptide
```

<400> SEQUENCE: 9

Thr Lys Glu Asp Ile Leu Glu Arg Gln Arg Lys Ile Ile Glu Arg Ala
1               5                   10                  15

Gln Glu Ile His Arg Arg Gln Gln Glu Ile Leu Glu Glu Leu Glu Tyr
            20                  25                  30

Ile Ile Arg
        35

<210> SEQ ID NO 10
<211> LENGTH: 121
<212> TYPE: PRT
<213> ORGANISM: Artificial Sequence
<220> FEATURE:
<223> OTHER INFORMATION: Synthetic peptide

<400> SEQUENCE: 10

Met Ser Glu Glu Ala Met Lys Arg Met Leu Lys Leu Leu Glu Glu Ser
1               5                   10                  15

Leu Arg Leu Leu Lys Glu Leu Leu Glu Leu Ser Glu Glu Ser Ala Gln
            20                  25                  30

Leu Leu Tyr Glu Gln Arg Lys Ala Asn Asn Gly Ser Glu Thr Glu Lys
        35                  40                  45

Arg Leu Leu Glu Glu Ala Glu Arg Ala His Arg Glu Gln Lys Glu Ile
    50                  55                  60

Ile Lys Lys Ala Gln Glu Leu His Arg Arg Leu Glu Glu Ile Val Arg
65                  70                  75                  80

Gln Ser Gly Ser Ser Glu Ala Lys Lys Glu Ala Lys Lys Ile Leu
                85                  90                  95

Glu Glu Ile Arg Glu Leu Ser Lys Arg Ser Leu Glu Leu Leu Arg Glu
            100                 105                 110

Ile Leu Tyr Leu Ser Gln Glu Gln Lys
        115                 120

<210> SEQ ID NO 11
<211> LENGTH: 77
<212> TYPE: PRT
<213> ORGANISM: Artificial Sequence
<220> FEATURE:
<223> OTHER INFORMATION: Synthetic peptide

<400> SEQUENCE: 11

Met Thr Lys Glu Asp Ile Leu Glu Arg Gln Arg Lys Ile Ile Glu Arg
1               5                   10                  15

Ala Gln Glu Ile His Arg Arg Gln Gln Glu Ile Leu Lys Glu Gln Glu
            20                  25                  30

Lys Ile Ile Arg Lys Pro Gly Ser Ser Glu Glu Ala Met Lys Arg Ser
        35                  40                  45

Leu Lys Leu Ile Glu Glu Ser Leu Arg Leu Leu Lys Glu Leu Leu Glu
    50                  55                  60

Leu Ser Glu Glu Ser Ala Gln Leu Leu Tyr Glu Gln Arg
65                  70                  75

<210> SEQ ID NO 12
<211> LENGTH: 77
<212> TYPE: PRT
<213> ORGANISM: Artificial Sequence
<220> FEATURE:
<223> OTHER INFORMATION: Synthetic peptide

```
<400> SEQUENCE: 12

Gly Thr Glu Lys Arg Leu Leu Glu Glu Ala Glu Arg Ala His Arg Glu
1               5                  10                  15

Gln Lys Glu Ile Ile Lys Lys Ala Gln Glu Leu His Lys Glu Leu Thr
            20                  25                  30

Lys Ile His Gln Gln Ser Gly Ser Glu Glu Ala Lys Lys Arg Ala
        35                  40                  45

Leu Lys Ile Ser Gln Glu Ile Arg Glu Leu Ser Lys Arg Ser Leu Glu
    50                  55                  60

Leu Leu Arg Glu Ile Leu Tyr Leu Ser Gln Glu Gln Lys
65                  70                  75

<210> SEQ ID NO 13
<211> LENGTH: 76
<212> TYPE: PRT
<213> ORGANISM: Artificial Sequence
<220> FEATURE:
<223> OTHER INFORMATION: Synthetic peptide

<400> SEQUENCE: 13

Thr Lys Glu Asp Ile Leu Glu Arg Gln Arg Lys Ile Ile Glu Arg Ala
1               5                  10                  15

Gln Glu Ile His Arg Arg Gln Gln Glu Ile Leu Lys Arg Ser Glu Glu
            20                  25                  30

Ile Ile Arg Lys Pro Gly Ser Ser Glu Ala Leu Glu Thr Leu Arg
        35                  40                  45

Glu Leu Gln Glu Glu Ser Leu Arg Leu Lys Glu Leu Leu Glu Leu
    50                  55                  60

Ser Glu Glu Ser Ala Gln Leu Leu Tyr Glu Gln Arg
65                  70                  75

<210> SEQ ID NO 14
<211> LENGTH: 78
<212> TYPE: PRT
<213> ORGANISM: Artificial Sequence
<220> FEATURE:
<223> OTHER INFORMATION: Synthetic peptide

<400> SEQUENCE: 14

Gly Ser Thr Glu Lys Arg Leu Leu Glu Glu Ala Glu Arg Ala His Arg
1               5                  10                  15

Glu Gln Lys Glu Ile Ile Lys Lys Ala Gln Glu Leu His Arg Arg Thr
            20                  25                  30

Glu Glu Ile Ile Arg Gln Ser Gly Ser Ser Glu Glu Ala Lys Asp Glu
        35                  40                  45

Leu Arg Arg Ile Gln Glu Glu Ile Arg Glu Leu Ser Lys Arg Ser Leu
    50                  55                  60

Glu Leu Leu Arg Glu Ile Leu Tyr Leu Ser Gln Glu Gln Lys
65                  70                  75

<210> SEQ ID NO 15
<211> LENGTH: 36
<212> TYPE: PRT
<213> ORGANISM: Artificial Sequence
<220> FEATURE:
<223> OTHER INFORMATION: Synthetic peptide

<400> SEQUENCE: 15

Thr Thr Lys Arg Tyr Leu Glu Glu Ala Glu Arg Ala His Arg Glu Gln
1               5                  10                  15
```

```
Lys Glu Ile Ile Lys Lys Ala Gln Glu Leu His Arg Arg Leu Glu Glu
            20                  25                  30

Ile Val Arg Gln
        35

<210> SEQ ID NO 16
<211> LENGTH: 116
<212> TYPE: PRT
<213> ORGANISM: Artificial Sequence
<220> FEATURE:
<223> OTHER INFORMATION: Synthetic peptide

<400> SEQUENCE: 16

Gly Ser Ser Glu Glu Ala Lys Lys Glu Ala Lys Lys Ile Leu Glu Glu
1               5                   10                  15

Ile Arg Glu Leu Ser Lys Arg Ser Leu Glu Leu Leu Arg Glu Ile Leu
            20                  25                  30

Tyr Leu Ser Gln Gln Val Asn Asp Val Asp Glu Lys Ala Leu Glu Arg
        35                  40                  45

Gln Arg Lys Ile Ile Glu Arg Ala Gln Glu Ile His Arg Arg Gln Gln
    50                  55                  60

Glu Ile Leu Glu Glu Leu Arg Ile Ile Arg Lys Pro Gly Ser Ser
65                  70                  75                  80

Glu Glu Ala Met Lys Arg Met Leu Lys Leu Glu Glu Ser Leu Arg
                85                  90                  95

Leu Leu Lys Glu Leu Leu Glu Leu Ser Glu Ser Ala Gln Leu Leu
            100                 105                 110

Tyr Glu Ala Arg
        115

<210> SEQ ID NO 17
<211> LENGTH: 35
<212> TYPE: PRT
<213> ORGANISM: Artificial Sequence
<220> FEATURE:
<223> OTHER INFORMATION: Synthetic peptide

<400> SEQUENCE: 17

Glu Ala Met Lys Arg Met Leu Lys Leu Leu Glu Glu Ser Leu Arg Leu
1               5                   10                  15

Leu Lys Glu Leu Leu Glu Leu Ser Glu Ser Ala Gln Leu Leu Tyr
            20                  25                  30

Glu Ala Arg
        35

<210> SEQ ID NO 18
<211> LENGTH: 116
<212> TYPE: PRT
<213> ORGANISM: Artificial Sequence
<220> FEATURE:
<223> OTHER INFORMATION: Synthetic peptide

<400> SEQUENCE: 18

Thr Thr Lys Arg Tyr Leu Glu Glu Ala Glu Arg Ala His Arg Glu Gln
1               5                   10                  15

Lys Glu Ile Ile Lys Lys Ala Gln Glu Leu His Arg Arg Leu Glu Glu
            20                  25                  30

Ile Val Arg Gln Ser Gly Ser Ser Glu Glu Ala Lys Lys Glu Ala Lys
        35                  40                  45
```

```
Lys Ile Leu Glu Glu Ile Arg Glu Leu Ser Lys Arg Ser Leu Glu Leu
 50                  55                  60

Leu Arg Glu Ile Leu Tyr Leu Ser Gln Gln Val Asn Asp Val Asp Glu
 65                  70                  75                  80

Lys Ala Leu Glu Arg Gln Arg Lys Ile Ile Glu Arg Ala Gln Glu Ile
                 85                  90                  95

His Arg Arg Gln Gln Glu Ile Leu Glu Leu Glu Arg Ile Ile Arg
            100                 105                 110

Lys Pro Gly Ser
        115

<210> SEQ ID NO 19
<211> LENGTH: 77
<212> TYPE: PRT
<213> ORGANISM: Artificial Sequence
<220> FEATURE:
<223> OTHER INFORMATION: Synthetic peptide

<400> SEQUENCE: 19

Thr Arg Glu Glu Leu Leu Arg Glu Asn Ile Glu Leu Ala Lys Glu His
 1               5                  10                  15

Ile Glu Ile Met Arg Glu Ile Leu Glu Leu Leu Gln Lys Met Glu Glu
                20                  25                  30

Leu Leu Glu Lys Ala Arg Gly Ala Asp Glu Asp Val Ala Lys Thr Ile
            35                  40                  45

Lys Glu Leu Leu Arg Arg Leu Lys Glu Ile Ile Glu Arg Asn Gln Arg
 50                  55                  60

Ile Ala Lys Glu His Glu Tyr Ile Ala Arg Glu Arg Ser
 65                  70                  75

<210> SEQ ID NO 20
<211> LENGTH: 78
<212> TYPE: PRT
<213> ORGANISM: Artificial Sequence
<220> FEATURE:
<223> OTHER INFORMATION: Synthetic peptide

<400> SEQUENCE: 20

Gly Thr Glu Arg Lys Leu Leu Glu Arg Ser Arg Arg Leu Gln Glu Glu
 1               5                  10                  15

Ser Lys Arg Leu Leu Asp Glu Met Ala Glu Ile Met Arg Arg Ile Lys
                20                  25                  30

Lys Leu Leu Lys Lys Ala Arg Gly Ala Asp Glu Lys Val Leu Asp Glu
            35                  40                  45

Leu Arg Lys Ile Ile Glu Arg Ile Arg Glu Leu Leu Asp Arg Ser Arg
 50                  55                  60

Lys Ile His Glu Arg Ser Glu Glu Ile Ala Tyr Lys Glu Glu
 65                  70                  75

<210> SEQ ID NO 21
<211> LENGTH: 76
<212> TYPE: PRT
<213> ORGANISM: Artificial Sequence
<220> FEATURE:
<223> OTHER INFORMATION: Synthetic peptide

<400> SEQUENCE: 21

Gly Asp Arg Gln Glu Leu Ile Arg Arg Asn Ile Glu Leu Leu Lys Glu
 1               5                  10                  15

His Ile Lys Ile Leu Glu Glu Ile Ser Gln Leu Ile Glu Glu Leu Ser
```

```
                    20                  25                  30

Glu Leu Leu Asp Lys Ser Ser Glu Glu Val Val Lys Arg Tyr Lys
                35                  40                  45

Lys Ile Leu Glu Arg Tyr Lys Gln Leu Leu Arg Lys Ser Gln Glu Ile
 50                  55                  60

His Lys Glu Ser Ser Glu Ile Ala Lys Lys Glu Ser
 65                  70                  75

<210> SEQ ID NO 22
<211> LENGTH: 82
<212> TYPE: PRT
<213> ORGANISM: Artificial Sequence
<220> FEATURE:
<223> OTHER INFORMATION: Synthetic peptide

<400> SEQUENCE: 22

Gly Asp Glu Gln Lys Leu Ile Glu Arg Ser Gln Arg Met Gln Lys Glu
 1               5                  10                  15

Ser Leu Glu Leu Leu Lys Glu Ile Ile Lys Ile Leu Asp Thr Ile Glu
                20                  25                  30

Lys Leu Leu Asp Lys Pro Asp Ser Glu Glu Leu Leu Asp Thr Ile Lys
                35                  40                  45

Lys Leu His Asp Thr Leu Lys Lys Ile His Asp Arg Asn Lys Lys Leu
 50                  55                  60

Leu Lys Glu His Glu Glu Ile Leu Arg Gln Arg Ser Gly Ser Leu Val
 65                  70                  75                  80

Pro Arg

<210> SEQ ID NO 23
<211> LENGTH: 73
<212> TYPE: PRT
<213> ORGANISM: Artificial Sequence
<220> FEATURE:
<223> OTHER INFORMATION: Synthetic peptide

<400> SEQUENCE: 23

Asp Lys Glu Glu Glu Tyr Lys Arg Leu Leu Asp Glu Ile Lys Glu Ile
 1               5                  10                  15

Leu Lys Glu Ser Lys Glu Val Leu Lys Asp Ser Lys Arg Val Leu Glu
                20                  25                  30

Asp Ile Lys Arg Lys Val Pro Asp Asp Leu Val Lys Leu Leu Glu
                35                  40                  45

Lys His Val Arg Leu Leu Glu Glu His Val Lys Leu Leu Gln Leu
 50                  55                  60

Ile Arg Glu Ala Glu Lys Ser Ser Lys
 65                  70

<210> SEQ ID NO 24
<211> LENGTH: 72
<212> TYPE: PRT
<213> ORGANISM: Artificial Sequence
<220> FEATURE:
<223> OTHER INFORMATION: Synthetic peptide

<400> SEQUENCE: 24

Gln Gly Ser Ser Ala Glu Glu Leu Leu Lys Lys Ile Lys Glu Ser Glu
 1               5                  10                  15

Lys Lys Ile Arg Asp Ser Leu Arg Lys Ile Lys Glu Ile Lys Lys
                20                  25                  30
```

-continued

```
Ser Arg Lys Glu Gly Val Asp Asp Lys Gln Leu Asp Leu Ile Arg Lys
         35                  40                  45

Val Val Glu Ser His Arg Asp Leu Leu Arg Leu His Arg Asp Leu Leu
 50                  55                  60

Arg Leu Leu Arg Glu Glu Thr Ser
 65                  70
```

<210> SEQ ID NO 25
<211> LENGTH: 77
<212> TYPE: PRT
<213> ORGANISM: Artificial Sequence
<220> FEATURE:
<223> OTHER INFORMATION: Synthetic peptide

<400> SEQUENCE: 25

```
Asp Ile Asp Glu Ser Ile Lys Glu Val Glu Lys Leu Leu Glu Val
 1               5                  10                  15

Glu Gln Ser Leu Gln Lys Leu Asp Asp Ser Leu Lys Lys Leu Leu Glu
             20                  25                  30

Lys Val Asn Gln Asp Pro Asp Val Asp Asp Ser Val Arg Lys Ile Val
         35                  40                  45

Lys Arg His Val Glu Ile Leu Lys Arg His Glu Val Leu Lys Arg
 50                  55                  60

Leu Ile Glu Val Val Lys Glu His Thr Lys Thr Val Lys
 65                  70                  75
```

<210> SEQ ID NO 26
<211> LENGTH: 72
<212> TYPE: PRT
<213> ORGANISM: Artificial Sequence
<220> FEATURE:
<223> OTHER INFORMATION: Synthetic peptide

<400> SEQUENCE: 26

```
Gly Ser Asp Arg Glu Glu Val His Lys Glu Ile Val Lys Leu Ile Arg
 1               5                  10                  15

Glu Ile Ile Lys Ile His Lys Lys Ile Leu Lys Ile His Glu Lys Ile
             20                  25                  30

Lys Asn Gly Glu Ile Asp Pro Ser Glu Ile Leu Lys Leu Ser Glu Glu
         35                  40                  45

Ile Lys Lys Leu Thr Asp Thr Ile Ile Lys Ile Glu Asp Leu Glu
 50                  55                  60

Gln Leu Thr Arg Asp Leu Arg Arg
 65                  70
```

<210> SEQ ID NO 27
<211> LENGTH: 71
<212> TYPE: PRT
<213> ORGANISM: Artificial Sequence
<220> FEATURE:
<223> OTHER INFORMATION: Synthetic peptide

<400> SEQUENCE: 27

```
Asp Arg Lys Glu Ile Val Lys Arg His Gln Lys Val Val Glu Leu Leu
 1               5                  10                  15

Lys Glu Ser Ser Lys Leu Leu Arg Glu Ser Ser Lys Leu Leu Gln Arg
             20                  25                  30

Leu Leu Asp Lys Thr Gly Asp Glu Asn Leu Gln Lys Ala Val Asp Asp
         35                  40                  45

Gln Asp Lys Ala Ile Lys Arg Gln Glu Thr Ala Ile Arg Lys Ser Gln
```

```
                50                  55                  60
Glu Ala Ser Lys Lys Leu Asp
 65                  70

<210> SEQ ID NO 28
<211> LENGTH: 77
<212> TYPE: PRT
<213> ORGANISM: Artificial Sequence
<220> FEATURE:
<223> OTHER INFORMATION: Synthetic peptide

<400> SEQUENCE: 28

Asp Asn Ser Glu Glu Ile Lys Lys Val Ala Lys Thr Ser Arg Glu Val
  1               5                  10                  15

Ala Glu Tyr Ser Glu Arg Val Ala Lys Glu Asn Asp Lys Val Val Lys
                 20                  25                  30

Thr Leu Glu Glu Gly Lys Ile Asp Glu Ser Glu Leu Leu Arg Leu Leu
             35                  40                  45

Glu Glu Ser Ile Lys Ile Phe Asp Thr Ala Leu Lys Leu His Glu Glu
         50                  55                  60

Ala Tyr Lys Leu His Gln Asp Leu Val Arg Lys Val Ser
 65                  70                  75

<210> SEQ ID NO 29
<211> LENGTH: 72
<212> TYPE: PRT
<213> ORGANISM: Artificial Sequence
<220> FEATURE:
<223> OTHER INFORMATION: Synthetic peptide

<400> SEQUENCE: 29

Asp Glu Ser Glu Ala Ala Ser Val Ala Ile Glu Ser Val Gln Ile Leu
  1               5                  10                  15

Val Glu Ser Val Lys Leu Leu Glu Gly Ser Val Arg Ile Leu Leu Asp
                 20                  25                  30

Ala Val Lys Lys Asn Gly Val Glu Asp Leu Leu Arg Val Ala Gln Arg
             35                  40                  45

Trp Glu Lys Leu Val Asp Glu Trp Leu Lys Val Lys Arg Trp Leu
         50                  55                  60

Asp Asn Val Arg Asp Ile Gln Arg
 65                  70

<210> SEQ ID NO 30
<211> LENGTH: 76
<212> TYPE: PRT
<213> ORGANISM: Artificial Sequence
<220> FEATURE:
<223> OTHER INFORMATION: Synthetic peptide

<400> SEQUENCE: 30

Gly Ser Asp Lys Ala Glu Glu Val Glu Lys Ser Val Arg Lys Ile Glu
  1               5                  10                  15

Glu Ser Ile Lys Lys Ile Arg Lys Ser Ile Lys Lys Ala Glu Asp Ala
                 20                  25                  30

Val Gln Leu Leu Lys Glu Gly Lys Ile Asp Ala Lys Asp Phe Leu Arg
             35                  40                  45

Ile Val Arg Glu Asp Leu Glu Val Val Lys Glu Asp Val Glu Ile Val
         50                  55                  60

Lys Glu Asp Val Glu Asn Val Arg Glu Phe Ser Ser
 65                  70                  75
```

-continued

```
<210> SEQ ID NO 31
<211> LENGTH: 69
<212> TYPE: PRT
<213> ORGANISM: Artificial Sequence
<220> FEATURE:
<223> OTHER INFORMATION: Synthetic peptide

<400> SEQUENCE: 31

Ser Asp Lys Glu Val Ser Asp Lys Leu Leu Lys Ala Ser Lys Lys Leu
1               5                   10                  15

Leu Lys Val Ser Glu Glu Leu Leu Glu Val Val Arg Arg Leu Leu Lys
                20                  25                  30

Ala Leu Lys Asp Asp Glu Leu Ile Lys Lys Ile Ala Asp Leu Leu Arg
            35                  40                  45

Lys Ile Ile Asp Lys Asp Lys Lys Phe Ile Arg Thr Ser Glu Glu Ile
        50                  55                  60

Val Lys Glu Ser Arg
65

<210> SEQ ID NO 32
<211> LENGTH: 78
<212> TYPE: PRT
<213> ORGANISM: Artificial Sequence
<220> FEATURE:
<223> OTHER INFORMATION: Synthetic peptide

<400> SEQUENCE: 32

Gly Ser Asp Leu Lys Glu Val Leu Lys Thr Val Glu Glu Ala Val Lys
1               5                   10                  15

Glu Ile Ile Lys Ser Ser Glu Glu Leu Leu Gln Ile Ser Arg Lys Ile
                20                  25                  30

Leu Glu Ile Ser Arg Val Gly Val Asp Glu His Glu Tyr Ile Ser Ala
            35                  40                  45

Ile Arg Glu Tyr Leu Lys Ala Leu Glu Lys His Ile Gln Ile Leu Lys
        50                  55                  60

Lys Phe Ile Glu Ile Leu Lys Glu Leu Ile Arg Ala Val Ser
65                  70                  75

<210> SEQ ID NO 33
<211> LENGTH: 81
<212> TYPE: PRT
<213> ORGANISM: Artificial Sequence
<220> FEATURE:
<223> OTHER INFORMATION: Synthetic peptide

<400> SEQUENCE: 33

Ser Lys Glu Glu Ile Asp Lys Ile Val Lys Lys His Lys Lys Lys Ile
1               5                   10                  15

Glu Glu His Lys Lys Lys Val Asp Glu Leu Lys Lys Leu Val Glu Glu
                20                  25                  30

His Asp Lys Arg Val Ser Gln Asp Lys Asp Lys Val Lys Lys Lys Leu
            35                  40                  45

Ser Glu Glu Val Lys Lys Ile Ile Lys Arg Leu Glu Glu Val Ser Lys
        50                  55                  60

Arg Leu Glu Glu Val Ser Lys Lys Leu Leu Lys Val Ile Ser Asp Lys
65                  70                  75                  80

Arg
```

<210> SEQ ID NO 34
<211> LENGTH: 78
<212> TYPE: PRT
<213> ORGANISM: Artificial Sequence
<220> FEATURE:
<223> OTHER INFORMATION: Synthetic peptide

<400> SEQUENCE: 34

```
Gly Ser Asn Asp Glu Glu Leu Lys Lys Ile Leu Glu Thr Leu Asp Arg
1               5                   10                  15

Ile Leu Lys Lys Leu Asp Lys Ile Leu Thr Arg Leu Ile Glu Val Leu
            20                  25                  30

Lys Lys Ser Glu Asp Pro Asn Leu Asp Asp Lys Asp Tyr Thr Glu Leu
        35                  40                  45

Val Lys Gln Phe Ile Glu Leu Ile Lys Lys Tyr Glu Glu Val Val Lys
    50                  55                  60

Glu Tyr Glu Glu Val Val Arg Gln Leu Ile Arg Leu Phe Ser
65                  70                  75
```

<210> SEQ ID NO 35
<211> LENGTH: 81
<212> TYPE: PRT
<213> ORGANISM: Artificial Sequence
<220> FEATURE:
<223> OTHER INFORMATION: Synthetic peptide

<400> SEQUENCE: 35

```
Ser Lys Glu Glu Ile Asp Lys Ile Val Lys Lys His Lys Lys Lys Ile
1               5                   10                  15

Glu Glu Leu Lys Lys Leu Val Asp Glu Leu Lys Lys Leu Val Glu Glu
            20                  25                  30

His Asp Lys Arg Val Ser Gln Asp Lys Asp Asp Lys Val Lys Lys Leu
        35                  40                  45

Ser Glu Glu Val Lys Lys Ile Ile Lys Arg Val Glu Glu Val Ala Lys
    50                  55                  60

Arg Leu Glu Glu Val Ser Lys Lys Leu Leu Lys Val Ile Ser Asp Lys
65                  70                  75                  80

Arg
```

<210> SEQ ID NO 36
<211> LENGTH: 78
<212> TYPE: PRT
<213> ORGANISM: Artificial Sequence
<220> FEATURE:
<223> OTHER INFORMATION: Synthetic peptide

<400> SEQUENCE: 36

```
Gly Ser Asn Asp Glu Glu Leu Lys Lys Ile Leu Glu Thr Leu Asp Arg
1               5                   10                  15

Ile Leu Lys Lys Leu Gly Lys Ile Leu Thr Arg Leu Ile Glu Val Leu
            20                  25                  30

Lys Lys Ser Glu Asp Pro Asn Leu Asp Asp Lys Asp Tyr Thr Glu Leu
        35                  40                  45

Val Lys Gln Phe Ile Glu Leu Ile Lys Lys Phe Glu Glu Val Ile Lys
    50                  55                  60

Glu Tyr Glu Glu Val Val Arg Gln Leu Ile Arg Leu Phe Ser
65                  70                  75
```

<210> SEQ ID NO 37
<211> LENGTH: 81

```
<212> TYPE: PRT
<213> ORGANISM: Artificial Sequence
<220> FEATURE:
<223> OTHER INFORMATION: Synthetic peptide

<400> SEQUENCE: 37

Ser Lys Glu Glu Ile Asp Lys Ile Val Lys His Lys Lys Lys Ile
1               5                   10                  15

Glu Glu His Lys Lys Lys Val Asp Glu His Lys Lys Leu Val Glu Glu
                20                  25                  30

His Asp Lys Arg Val Ser Gln Asp Lys Asp Lys Val Lys Lys Leu
                35                  40                  45

Ser Glu Glu Leu Lys Lys Ile Ser Lys Arg Leu Glu Glu Val Ser Lys
    50                  55                  60

Arg Leu Glu Glu Val Ser Lys Lys Leu Lys Val Ile Ser Asp Lys
65                  70                  75                  80

Arg

<210> SEQ ID NO 38
<211> LENGTH: 78
<212> TYPE: PRT
<213> ORGANISM: Artificial Sequence
<220> FEATURE:
<223> OTHER INFORMATION: Synthetic peptide

<400> SEQUENCE: 38

Gly Ser Asn Asp Glu Glu Leu Lys Lys Ile Leu Glu Thr Leu Asp Arg
1               5                   10                  15

Ile Leu Lys Lys Leu Asp Lys Ile Leu Thr Arg Leu Asp Glu Val Leu
                20                  25                  30

Lys Lys Ser Glu Asp Pro Asn Leu Asp Lys Asp Tyr Thr Glu Leu
                35                  40                  45

Val Lys Gln Tyr Ile Glu Leu Val Lys Tyr Glu Glu Val Val Lys
    50                  55                  60

Glu Tyr Glu Glu Val Val Arg Gln Leu Ile Arg Leu Phe Ser
65                  70                  75

<210> SEQ ID NO 39
<211> LENGTH: 69
<212> TYPE: PRT
<213> ORGANISM: Artificial Sequence
<220> FEATURE:
<223> OTHER INFORMATION: Synthetic peptide

<400> SEQUENCE: 39

Asp His Ser Arg Lys Leu Lys Glu Ile Leu Asp Arg Leu Arg Lys His
1               5                   10                  15

Val Lys Arg Leu Lys Glu His Leu Asp Glu Leu Arg Asp Leu Val Arg
                20                  25                  30

Gln Val Pro Glu Asp Lys Leu Leu Glu His Val Lys Leu Ser Asp
                35                  40                  45

Lys Ile Leu Gln Ile Ser Glu Arg Ala Val Arg Glu Phe Thr Lys Ser
    50                  55                  60

Val Asp Lys Asp Ser
65

<210> SEQ ID NO 40
<211> LENGTH: 76
<212> TYPE: PRT
<213> ORGANISM: Artificial Sequence
```

<220> FEATURE:
<223> OTHER INFORMATION: Synthetic peptide

<400> SEQUENCE: 40

Gly Ser Asp Lys Lys Asp Glu Leu Glu Arg Ile Leu Asp Glu Ile Arg
1               5                   10                  15

Arg Leu Ile Glu Arg Leu Asp Glu Ile Leu Ser Arg Leu Asn Lys Leu
                20                  25                  30

Leu Glu Leu Leu Lys His Gly Val Pro Asn Ala Lys Glu Val Val Lys
            35                  40                  45

Asp Tyr Ile Arg Leu Leu Lys Glu Tyr Leu Glu Leu Val Lys Glu Phe
        50                  55                  60

Leu Lys Leu Val Lys Arg His Ala Asp Leu Val Ser
65                  70                  75

<210> SEQ ID NO 41
<211> LENGTH: 72
<212> TYPE: PRT
<213> ORGANISM: Artificial Sequence
<220> FEATURE:
<223> OTHER INFORMATION: Synthetic peptide

<400> SEQUENCE: 41

Asp Ser Asp Glu His Leu Lys Lys Leu Lys Thr Phe Leu Glu Asn Leu
1               5                   10                  15

Arg Arg His Leu Asp Arg Leu Asp Lys His Ile Lys Gln Leu Arg Asp
                20                  25                  30

Ile Leu Ser Glu Asn Pro Glu Asp Glu Arg Val Lys Asp Val Ile Asp
            35                  40                  45

Leu Ser Glu Arg Ser Val Arg Ile Val Lys Thr Val Ile Lys Ile Phe
        50                  55                  60

Glu Asp Ser Val Arg Lys Lys Glu
65                  70

<210> SEQ ID NO 42
<211> LENGTH: 75
<212> TYPE: PRT
<213> ORGANISM: Artificial Sequence
<220> FEATURE:
<223> OTHER INFORMATION: Synthetic peptide

<400> SEQUENCE: 42

Gly Ser Asp Asp Lys Glu Leu Asp Lys Leu Leu Asp Thr Leu Glu Lys
1               5                   10                  15

Ile Leu Gln Thr Ala Thr Lys Ile Ile Asp Asp Ala Asn Lys Leu Leu
                20                  25                  30

Glu Lys Leu Arg Arg Ser Glu Arg Lys Asp Pro Lys Val Val Glu Thr
            35                  40                  45

Tyr Val Glu Leu Leu Lys Arg His Glu Lys Ala Val Lys Glu Leu Leu
        50                  55                  60

Glu Ile Ala Lys Thr His Ala Lys Lys Val Glu
65                  70                  75

<210> SEQ ID NO 43
<211> LENGTH: 73
<212> TYPE: PRT
<213> ORGANISM: Artificial Sequence
<220> FEATURE:
<223> OTHER INFORMATION: Synthetic peptide

<400> SEQUENCE: 43

```
Met Asp Glu Asp His Leu Lys Lys Leu Lys Thr His Leu Glu Lys
1               5                   10                  15

Leu Glu Arg His Leu Lys Leu Leu Glu Asp His Ala Lys Lys Leu Glu
            20                  25                  30

Asp Ile Leu Lys Glu Arg Pro Glu Asp Ser Ala Val Lys Glu Ser Ile
        35                  40                  45

Asp Glu Leu Arg Arg Ser Ile Glu Leu Val Arg Glu Ser Ile Glu Ile
    50                  55                  60

Phe Arg Gln Ser Val Glu Glu Glu
65              70
```

<210> SEQ ID NO 44
<211> LENGTH: 74
<212> TYPE: PRT
<213> ORGANISM: Artificial Sequence
<220> FEATURE:
<223> OTHER INFORMATION: Synthetic peptide

<400> SEQUENCE: 44

```
Gly Asp Val Lys Glu Leu Thr Lys Ile Leu Asp Thr Leu Thr Lys Ile
1               5                   10                  15

Leu Glu Thr Ala Thr Lys Val Ile Lys Asp Ala Thr Lys Leu Leu Glu
            20                  25                  30

Glu His Arg Lys Ser Asp Lys Pro Asp Pro Arg Leu Ile Glu Thr His
        35                  40                  45

Lys Lys Leu Val Glu Glu His Glu Thr Leu Val Arg Gln His Lys Glu
    50                  55                  60

Leu Ala Glu Glu His Leu Lys Arg Thr Arg
65              70
```

<210> SEQ ID NO 45
<211> LENGTH: 72
<212> TYPE: PRT
<213> ORGANISM: Artificial Sequence
<220> FEATURE:
<223> OTHER INFORMATION: Synthetic peptide

<400> SEQUENCE: 45

```
Asp Ser Asp Glu His Leu Lys Lys Leu Lys Thr Phe Leu Glu Asn Leu
1               5                   10                  15

Arg Arg His Leu Asp Arg Leu Asp Lys Leu Leu Lys Glu Leu Arg Asp
            20                  25                  30

Ile Leu Ser Glu Asn Pro Glu Asp Glu Arg Val Lys Asp Val Ile Asp
        35                  40                  45

Glu Leu Glu Arg Val Ile Arg Ile Val Lys Thr Val Ile Lys Ile Phe
    50                  55                  60

Glu Asp Ser Val Arg Lys Lys Glu
65              70
```

<210> SEQ ID NO 46
<211> LENGTH: 75
<212> TYPE: PRT
<213> ORGANISM: Artificial Sequence
<220> FEATURE:
<223> OTHER INFORMATION: Synthetic peptide

<400> SEQUENCE: 46

```
Gly Ser Asp Asp Lys Glu Leu Asp Lys Leu Leu Asp Thr Leu Glu Lys
1               5                   10                  15
```

```
Ile Leu Gln Thr Ala Thr Lys Ile Ile Asp Asp Leu Asn Lys Val Leu
            20                  25                  30

Glu Lys Leu Arg Arg Ser Glu Arg Lys Asp Pro Lys Val Ile Glu Thr
            35                  40                  45

Val Val Glu Leu Leu Lys Arg His Gly Lys Ala Val Lys Glu Leu Leu
50                  55                  60

Glu Ile Ala Lys Thr His Ala Lys Lys Val Glu
65                  70                  75
```

<210> SEQ ID NO 47
<211> LENGTH: 72
<212> TYPE: PRT
<213> ORGANISM: Artificial Sequence
<220> FEATURE:
<223> OTHER INFORMATION: Synthetic peptide

<400> SEQUENCE: 47

```
Asp Ser Asp Glu His Leu Lys Lys Leu Lys Thr Phe Leu Glu Asn Leu
1               5                   10                  15

Arg Arg Leu Glu Asp Leu Leu Asp Lys His Ile Lys Gln Leu Arg Asp
            20                  25                  30

Ile Leu Ser Glu Asn Pro Glu Asp Glu Arg Val Lys Asp Val Ile Asp
            35                  40                  45

Leu Ser Glu Arg Val Val Arg Thr Val Lys Thr Val Ile Lys Ile Phe
50                  55                  60

Glu Asp Ser Val Arg Lys Lys Glu
65                  70
```

<210> SEQ ID NO 48
<211> LENGTH: 75
<212> TYPE: PRT
<213> ORGANISM: Artificial Sequence
<220> FEATURE:
<223> OTHER INFORMATION: Synthetic peptide

<400> SEQUENCE: 48

```
Gly Ser Asp Asp Lys Glu Leu Asp Lys Leu Leu Asp Thr Leu Glu Lys
1               5                   10                  15

Ile Leu Gln Thr Ala Thr Lys Val Val Asp Asp Ala Asn Lys Leu Leu
            20                  25                  30

Glu Lys Leu Arg Arg Ser Glu Arg Lys Asp Pro Lys Val Val Glu Thr
            35                  40                  45

Tyr Val Glu Leu Leu Lys Arg Leu Gly Lys Leu Ile Lys Glu Leu Leu
50                  55                  60

Glu Ile Ala Lys Thr His Ala Lys Lys Val Glu
65                  70                  75
```

<210> SEQ ID NO 49
<211> LENGTH: 37
<212> TYPE: PRT
<213> ORGANISM: Artificial Sequence
<220> FEATURE:
<223> OTHER INFORMATION: Synthetic peptide

<400> SEQUENCE: 49

```
Asp Ser Asp Glu His Leu Lys Lys Leu Lys Thr Phe Leu Glu Asn Leu
1               5                   10                  15

Arg Arg His Leu Asp Arg Leu Asp Lys His Ile Lys Gln Leu Arg Asp
            20                  25                  30

Ile Leu Ser Glu Asn
```

-continued

```
                35

<210> SEQ ID NO 50
<211> LENGTH: 114
<212> TYPE: PRT
<213> ORGANISM: Artificial Sequence
<220> FEATURE:
<223> OTHER INFORMATION: Synthetic peptide

<400> SEQUENCE: 50

Glu Asp Glu Arg Val Lys Asp Val Ile Asp Leu Ser Glu Arg Ser Val
1               5                   10                  15

Arg Ile Val Lys Thr Val Ile Lys Ile Phe Glu Asp Ser Val Arg Lys
            20                  25                  30

Leu Glu Lys Thr Lys Pro Asp Ser Lys Thr Ala Lys Glu Leu Asp Lys
        35                  40                  45

Leu Leu Asp Thr Leu Glu Lys Ile Leu Gln Thr Ala Thr Lys Ile Ile
    50                  55                  60

Asp Asp Ala Asn Lys Leu Leu Glu Lys Leu Arg Arg Ser Glu Arg Lys
65                  70                  75                  80

Asp Pro Lys Val Val Glu Thr Tyr Val Glu Leu Leu Lys Arg His Glu
                85                  90                  95

Lys Ala Val Lys Glu Leu Leu Glu Ile Ala Lys Thr His Ala Lys Lys
            100                 105                 110

Val Glu

<210> SEQ ID NO 51
<211> LENGTH: 114
<212> TYPE: PRT
<213> ORGANISM: Artificial Sequence
<220> FEATURE:
<223> OTHER INFORMATION: Synthetic peptide

<400> SEQUENCE: 51

Asp Ser Asp Glu His Leu Tyr Lys Leu Lys Thr Phe Leu Glu Asn Leu
1               5                   10                  15

Arg Arg His Leu Asp Arg Leu Asp Lys His Ile Lys Gln Leu Arg Asp
            20                  25                  30

Ile Leu Ser Glu Asn Pro Glu Asp Glu Arg Val Lys Asp Ala Ile Asp
        35                  40                  45

Leu Ser Glu Arg Ser Val Arg Ile Val Lys Thr Val Ile Lys Ile Phe
    50                  55                  60

Glu Asp Ser Val Arg Lys Glu Lys Arg Pro Ile Asp Lys Arg Asp
65                  70                  75                  80

Asp Lys Glu Leu Asp Lys Leu Leu Asp Thr Leu Glu Lys Ile Leu Gln
                85                  90                  95

Thr Ala Thr Lys Ile Ile Asp Asp Ala Asn Lys Leu Leu Glu Tyr Leu
            100                 105                 110

Arg Arg

<210> SEQ ID NO 52
<211> LENGTH: 35
<212> TYPE: PRT
<213> ORGANISM: Artificial Sequence
<220> FEATURE:
<223> OTHER INFORMATION: Synthetic peptide

<400> SEQUENCE: 52

Gly Asp Pro Lys Val Val Glu Thr Tyr Val Glu Leu Leu Lys Arg His
```

```
                1               5                  10                  15
            Glu Lys Ala Val Lys Glu Leu Leu Glu Ile Ala Lys Thr His Ala Lys
                               20                  25                  30

Lys Val Glu
                    35

<210> SEQ ID NO 53
<211> LENGTH: 72
<212> TYPE: PRT
<213> ORGANISM: Artificial Sequence
<220> FEATURE:
<223> OTHER INFORMATION: Synthetic peptide

<400> SEQUENCE: 53

Asp Ser Asp Glu His Leu Asp Arg Leu Asp Lys His Leu Lys Lys Leu
1               5                   10                  15

Lys Thr Phe Leu Glu Asn Leu Arg Arg His Ile Lys Gln Leu Arg Asp
                20                  25                  30

Ile Leu Ser Glu Asn Pro Glu Asp Glu Arg Val Lys Asp Val Ile Asp
                35                  40                  45

Leu Ser Lys Thr Val Ile Lys Ile Phe Glu Asp Ser Val Arg Lys Lys
            50                  55                  60

Glu Arg Ser Val Arg Ile Val Glu
65                  70

<210> SEQ ID NO 54
<211> LENGTH: 75
<212> TYPE: PRT
<213> ORGANISM: Artificial Sequence
<220> FEATURE:
<223> OTHER INFORMATION: Synthetic peptide

<400> SEQUENCE: 54

Gly Ser Asp Asp Lys Glu Ala Thr Lys Ile Ile Asp Asp Leu Asp Lys
1               5                   10                  15

Leu Leu Asp Thr Leu Glu Lys Ile Leu Gln Thr Ala Asn Lys Leu Leu
                20                  25                  30

Glu Lys Leu Arg Arg Ser Glu Arg Lys Asp Pro Lys Val Val Glu Thr
                35                  40                  45

Tyr Val Lys Ala Val Lys Glu Leu Leu Glu Ile Ala Lys Thr His Ala
            50                  55                  60

Glu Leu Leu Lys Arg His Glu Lys Lys Val Glu
65                  70                  75

<210> SEQ ID NO 55
<211> LENGTH: 72
<212> TYPE: PRT
<213> ORGANISM: Artificial Sequence
<220> FEATURE:
<223> OTHER INFORMATION: Synthetic peptide

<400> SEQUENCE: 55

Asp Ser Asp Glu His Ile Lys Gln Leu Arg Asp His Leu Asp Arg Leu
1               5                   10                  15

Asp Lys His Leu Lys Lys Leu Lys Thr Phe Leu Glu Asn Leu Arg Arg
                20                  25                  30

Ile Leu Ser Glu Asn Pro Glu Asp Glu Arg Val Lys Thr Val Ile Lys
                35                  40                  45

Ile Phe Glu Asp Ser Val Arg Lys Lys Glu Arg Ser Val Arg Ile Val
            50                  55                  60
```

```
Lys Asp Val Ile Asp Leu Ser Glu
 65                  70
```

<210> SEQ ID NO 56
<211> LENGTH: 75
<212> TYPE: PRT
<213> ORGANISM: Artificial Sequence
<220> FEATURE:
<223> OTHER INFORMATION: Synthetic peptide

<400> SEQUENCE: 56

```
Gly Ser Asp Asp Lys Glu Ala Asn Lys Leu Leu Glu Lys Ala Thr Lys
 1               5                  10                  15

Ile Ile Asp Asp Leu Asp Lys Leu Leu Asp Thr Leu Glu Lys Ile Leu
                20                  25                  30

Gln Thr Leu Arg Arg Ser Glu Arg Lys Asp Pro Lys Ala Val Lys Glu
            35                  40                  45

Leu Leu Glu Ile Ala Lys Thr His Ala Glu Leu Leu Lys Arg His Glu
 50                  55                  60

Lys Val Val Glu Thr Tyr Val Lys Lys Val Glu
 65                  70                  75
```

<210> SEQ ID NO 57
<211> LENGTH: 104
<212> TYPE: PRT
<213> ORGANISM: Artificial Sequence
<220> FEATURE:
<223> OTHER INFORMATION: Synthetic peptide

<400> SEQUENCE: 57

```
Asp His Ser Arg Lys Leu Glu Glu Ile Leu Asp Arg Leu Arg Lys His
 1               5                  10                  15

Val Lys Arg Leu Leu Glu His Leu Arg Glu Leu Leu Ser Leu Val Lys
                20                  25                  30

Glu Asn Pro Glu Asp Lys Asp Leu Val Glu Val Leu Glu Leu Ser Leu
            35                  40                  45

Ala Ile Leu Arg Arg Ser Leu Glu Ala Val Glu Ala Phe Leu Lys Ser
 50                  55                  60

Val Thr Lys Lys Asp Pro Asp Glu Asp Leu Arg Arg Lys Ala Asp
 65                  70                  75                  80

Glu Ile Arg Lys Glu Val Glu Glu Ile Lys Lys Ser Leu Ala Glu Val
                85                  90                  95

Glu Lys Glu Ile Tyr Lys Leu Lys
            100
```

<210> SEQ ID NO 58
<211> LENGTH: 116
<212> TYPE: PRT
<213> ORGANISM: Artificial Sequence
<220> FEATURE:
<223> OTHER INFORMATION: Synthetic peptide

<400> SEQUENCE: 58

```
Gly Ser Ser Ala Asp Asp Val Leu Glu Asp Ile Leu Lys Ile Ile Arg
 1               5                  10                  15

Glu Leu Ile Glu Ile Leu Asp Gln Ile Leu Ser Leu Leu Asn Gln Leu
                20                  25                  30

Leu Lys Leu Leu Arg His Gly Val Pro Asn Ala Lys Lys Val Val Glu
            35                  40                  45
```

```
Lys Tyr Lys Glu Ile Leu Glu Leu Tyr Leu Gln Leu Val Ser Leu Phe
 50                  55                  60

Leu Lys Ile Val Lys Thr His Ala Asp Ala Val Ser Gly Lys Ile Asp
 65                  70                  75                  80

Lys Lys Ala Glu Glu Ile Lys Lys Glu Glu Lys Ile Lys Glu
                 85                  90                  95

Lys Leu Arg Gln Ala Lys Asp Ile Leu Lys Lys Leu Gln Glu Ile
            100                 105                 110

Asp Lys Thr Arg
        115
```

<210> SEQ ID NO 59
<211> LENGTH: 107
<212> TYPE: PRT
<213> ORGANISM: Artificial Sequence
<220> FEATURE:
<223> OTHER INFORMATION: Synthetic peptide

<400> SEQUENCE: 59

```
Asp Arg Asp Ala His Leu Tyr Lys Leu Leu Thr Phe Leu Glu Gln Leu
 1                   5                  10                  15

Val Arg His Leu Asp Arg Leu Val Lys His Ile Thr Gln Leu Arg Asp
                20                  25                  30

Ile Val Lys Lys Asp Pro Glu Asp Glu Arg Ala Val Asp Val Ile Arg
            35                  40                  45

Gln Ser Val Arg Ser Leu Glu Ile Val Ile Thr Val Leu Lys Ile Phe
 50                  55                  60

Val Asp Ser Val Ser Asp Ala Ala Arg Ser Lys Glu Ala Glu Lys Ile
 65                  70                  75                  80

Val Arg Lys Ile Arg Lys Glu Ile Asp Glu Ile Arg Gln Lys Leu Arg
                85                  90                  95

Glu Ile Asp Lys Glu Val Lys Lys Thr Thr Ser
            100                 105
```

<210> SEQ ID NO 60
<211> LENGTH: 114
<212> TYPE: PRT
<213> ORGANISM: Artificial Sequence
<220> FEATURE:
<223> OTHER INFORMATION: Synthetic peptide

<400> SEQUENCE: 60

```
Gly Ser Asn Asp Lys Val Leu Asp Lys Ile Leu Asp Ile Leu Asp Arg
 1                   5                  10                  15

Ile Leu Arg Leu Ala Thr Arg Val Ile Asp Leu Ala Asn Lys Leu Leu
                20                  25                  30

Gln Val Lys Lys Ser Thr His Lys Asp Pro Arg Ile Val Glu Thr
            35                  40                  45

Tyr Lys Glu Leu Leu Lys Ile His Glu Thr Ala Val Arg Leu Leu
 50                  55                  60

Glu Leu Ala Asp Leu His Arg Arg Leu Lys Ser Lys Asp Glu Glu Ala
 65                  70                  75                  80

Asn Lys Arg Val Glu Thr Glu Leu Asp Arg Ile Arg Lys Lys Val Lys
                85                  90                  95

Asp Ile Glu Asp Lys Val Arg Lys Leu Glu Asp Lys Val Arg Lys Thr
            100                 105                 110

Ala Ser
```

<210> SEQ ID NO 61
<211> LENGTH: 68
<212> TYPE: PRT
<213> ORGANISM: Artificial Sequence
<220> FEATURE:
<223> OTHER INFORMATION: Synthetic peptide

<400> SEQUENCE: 61

```
Asn Asp Leu Ser Lys Glu Val Leu Lys Lys Leu Glu Lys Ser Val Glu
1               5                   10                  15

Glu Leu Leu Arg Arg Val Gln Lys Ser Val Lys Glu Ala Gln Lys Arg
            20                  25                  30

Gly Leu Leu Ser Asp Glu Leu Val Asp Arg His Leu Lys Ile Leu Asn
        35                  40                  45

Gln Leu Val Lys Arg His Leu Glu Leu Gln Glu Val Ile Lys Arg
    50                  55                  60

Ser Asp Lys Lys
65
```

<210> SEQ ID NO 62
<211> LENGTH: 78
<212> TYPE: PRT
<213> ORGANISM: Artificial Sequence
<220> FEATURE:
<223> OTHER INFORMATION: Synthetic peptide

<400> SEQUENCE: 62

```
Gly Ser Asp Glu Ala Val Lys Arg Val Glu Lys Ser Leu Lys Ile
1               5                   10                  15

Leu Asp Glu Val Ile Lys Lys Ser Leu Asp Ile Leu Arg Glu Leu Ile
            20                  25                  30

Glu Leu Gln Ile Arg His Ala Lys Asp Asp Glu Ser Val Ile Arg Ala
        35                  40                  45

Ser Lys Ser Ala Leu Lys Asp Ala Ile Glu Ala Leu Lys Lys Ser Leu
    50                  55                  60

Asp Glu Ile Lys Lys Ala Leu Lys Arg Ser Ala Asp Glu Gly
65                  70                  75
```

<210> SEQ ID NO 63
<211> LENGTH: 76
<212> TYPE: PRT
<213> ORGANISM: Artificial Sequence
<220> FEATURE:
<223> OTHER INFORMATION: Synthetic peptide

<400> SEQUENCE: 63

```
Ser Ser Glu Glu Val Val Lys Val His Glu Lys Val Val Lys Leu His
1               5                   10                  15

Lys Glu Ile Leu Glu Leu Leu Lys Lys Ile Ile Lys Ile His Glu Thr
            20                  25                  30

Ala Ala Arg Asp Pro Asp Asp Lys Asp Ser Ile Lys Lys Leu Ser Asp
        35                  40                  45

Glu Ile Lys Lys Ile Val Lys Arg Ile Glu Asp Ile Ser Asp Gln Ala
    50                  55                  60

Lys Arg Glu Ser Ser Asp Ala Gln Arg Lys Gln Ser
65                  70                  75
```

<210> SEQ ID NO 64
<211> LENGTH: 74
<212> TYPE: PRT

<213> ORGANISM: Artificial Sequence
<220> FEATURE:
<223> OTHER INFORMATION: Synthetic peptide

<400> SEQUENCE: 64

Asp Lys Glu Glu Ser Lys Glu Leu Leu Lys Lys Leu Lys Glu Ile
1               5                   10                  15

Leu Lys Arg Ser Glu Leu Leu Glu Glu Ser Lys Glu Leu Leu Lys
                20                  25                  30

Leu Ala Lys Asn Gly Glu Ile Asp Glu Ser Glu Leu Ala Asp Ala Asp
            35                  40                  45

Arg Lys Leu Asn Lys Lys His Glu Lys Leu Val Gln Asp Ile Gln Asp
        50                  55                  60

Leu Leu Arg Glu His Glu Arg Gln Asp Arg
65                  70

<210> SEQ ID NO 65
<211> LENGTH: 73
<212> TYPE: PRT
<213> ORGANISM: Artificial Sequence
<220> FEATURE:
<223> OTHER INFORMATION: Synthetic peptide

<400> SEQUENCE: 65

Asp Glu Lys Lys Ile Asp Lys Ile Val Lys Glu Thr Glu Asp Leu
1               5                   10                  15

Leu Gln Lys Ser Glu Lys Leu Leu Gln Gln Ser Lys Glu Ala Val Lys
                20                  25                  30

Arg Ile Arg Ser Gln Val Lys Glu Asn Glu Ile Val Asp Arg Leu Leu
            35                  40                  45

Arg Ile Ser Glu Glu Leu Leu Lys Ile Ser Arg Arg Leu Val Glu Ile
        50                  55                  60

Ser Arg Arg Ile Ala Ser Thr Leu Ser
65                  70

<210> SEQ ID NO 66
<211> LENGTH: 78
<212> TYPE: PRT
<213> ORGANISM: Artificial Sequence
<220> FEATURE:
<223> OTHER INFORMATION: Synthetic peptide

<400> SEQUENCE: 66

Gly Ser Ser Lys Glu Glu Val Ile Arg Leu Leu Lys Glu Asn Val Arg
1               5                   10                  15

Leu Ile Lys Glu Asn Leu Glu Leu Leu Thr Arg Asn Leu Lys Leu Ile
                20                  25                  30

Thr Asp Leu Val Arg Gly Ser Asn Gly Ser Glu Glu Lys Ile Lys Thr
            35                  40                  45

Leu Lys Glu Leu Leu Lys Glu Tyr Arg Glu Leu Leu Lys Arg Tyr Arg
        50                  55                  60

Lys Leu Val Glu Asp Tyr Lys Arg Leu Val Asp Lys His Asp
65                  70                  75

<210> SEQ ID NO 67
<211> LENGTH: 81
<212> TYPE: PRT
<213> ORGANISM: Artificial Sequence
<220> FEATURE:
<223> OTHER INFORMATION: Synthetic peptide

```
<400> SEQUENCE: 67

Glu Ile Gln Glu Leu Ile Lys Ser Ser Arg Arg Ile Ile Glu Ser
1               5                   10                  15

Lys Glu Leu Ile Lys Glu Ser Glu Glu Val Leu Arg Arg Ile Lys Glu
                20                  25                  30

Ile Leu Asp Arg Ile Arg Asn Gly Val Asp Asn Gln Glu Asp Leu Leu
            35                  40                  45

Arg Glu Ile Leu Lys Leu Leu Thr Lys Asn Leu Lys Ile Ile Gln Arg
    50                  55                  60

Asn Leu Lys Leu Leu Gln Asp Asn Ala Glu Ile Leu Lys Arg Leu Val
65                  70                  75                  80

Ser

<210> SEQ ID NO 68
<211> LENGTH: 75
<212> TYPE: PRT
<213> ORGANISM: Artificial Sequence
<220> FEATURE:
<223> OTHER INFORMATION: Synthetic peptide

<400> SEQUENCE: 68

Gly Ser Tyr Ile Glu Asp Val Ile Lys Lys Ile Leu Asp Val Ser Arg
1               5                   10                  15

Glu Leu Ile Lys Leu Ser Arg Thr Ile Ile Lys Ile Ser Glu Glu Ile
                20                  25                  30

Asn Lys Gln Leu Gln Gln Gly Arg Asp Thr Lys Asp Leu Val Lys Lys
            35                  40                  45

Tyr Asp Glu Ile Ile Lys Lys Tyr Thr Arg Ile Val Gln His Tyr Thr
    50                  55                  60

Glu Leu Ile Lys Glu Leu Gln Lys Leu Leu Ser
65                  70                  75

<210> SEQ ID NO 69
<211> LENGTH: 75
<212> TYPE: PRT
<213> ORGANISM: Artificial Sequence
<220> FEATURE:
<223> OTHER INFORMATION: Synthetic peptide

<400> SEQUENCE: 69

Ser Pro Thr Glu Glu Ala Ile Gln Leu Ser Gln Arg Val Ile Glu Leu
1               5                   10                  15

Ser Lys Arg Val Ile Glu Leu Ser Lys Glu Ile Leu Lys Leu Leu Lys
                20                  25                  30

Arg Val Leu Asp Leu Leu Pro Asp Leu Asp Lys Asn Glu Glu Lys Arg
            35                  40                  45

Leu Asp Asp Tyr Asp Lys Glu Leu Lys Glu Tyr Asp Lys Glu Leu Lys
    50                  55                  60

Lys Tyr Glu Lys Arg Leu Lys Asp Leu Ala Ser
65                  70                  75

<210> SEQ ID NO 70
<211> LENGTH: 75
<212> TYPE: PRT
<213> ORGANISM: Artificial Sequence
<220> FEATURE:
<223> OTHER INFORMATION: Synthetic peptide

<400> SEQUENCE: 70
```

Gly Ser Glu Glu Glu Ile Leu Lys Ile Gln Lys Glu Leu Leu Arg
1               5                   10                  15

Ile Gln Ser Glu Ile Leu Asp Lys Gln Lys Ile Leu Asp Thr Leu
            20                  25                  30

Arg Ser Asn Gly Ala Val Thr Glu Glu Val Arg Ser Ile Leu Glu Lys
            35                  40                  45

Val Glu Arg Leu Ser Glu Glu Ala Lys Glu Leu Ser Lys Glu Ala Lys
    50                  55                  60

Glu Leu Thr Lys Glu Val Ser Lys Leu Ile Ser
65                  70                  75

<210> SEQ ID NO 71
<211> LENGTH: 77
<212> TYPE: PRT
<213> ORGANISM: Artificial Sequence
<220> FEATURE:
<223> OTHER INFORMATION: Synthetic peptide

<400> SEQUENCE: 71

Ser Pro Leu Lys Glu Leu Asn Asn Gln Leu Leu Arg Leu Leu Arg Glu
1               5                   10                  15

Leu Val Lys Val Ser Lys Lys Ile Val Asp Leu Ser Lys Thr Ile Ile
            20                  25                  30

Glu Val Leu Lys His Thr Asp Leu Asp Pro Arg Leu Leu Asp Ser Leu
            35                  40                  45

Glu Lys Ser Gln Gln Glu Leu Asp Lys Ser Gln Lys Glu Leu Asp Lys
    50                  55                  60

Val Val Lys Glu Leu Thr Lys Val Asn Lys Lys Leu Gln
65                  70                  75

<210> SEQ ID NO 72
<211> LENGTH: 78
<212> TYPE: PRT
<213> ORGANISM: Artificial Sequence
<220> FEATURE:
<223> OTHER INFORMATION: Synthetic peptide

<400> SEQUENCE: 72

Gly Ser Pro Leu Glu Asp Leu Val Arg Lys Tyr Asp Glu Leu Val Lys
1               5                   10                  15

Thr Tyr Glu Lys Leu Val Glu Glu Phe Lys Lys Ala Val Asp Lys Tyr
            20                  25                  30

Asp Lys Ala Val Lys Lys Ala Pro Val Ser Lys Glu Ala Thr Asp Ser
            35                  40                  45

Leu Asp Leu Ile Arg Lys Val Leu Glu Leu Leu Asp Arg Asn Leu Lys
    50                  55                  60

Leu Ile Lys Glu Asn Ala Lys Leu Ile Lys Glu Leu Leu Lys
65                  70                  75

<210> SEQ ID NO 73
<211> LENGTH: 69
<212> TYPE: PRT
<213> ORGANISM: Artificial Sequence
<220> FEATURE:
<223> OTHER INFORMATION: Synthetic peptide

<400> SEQUENCE: 73

Ser Pro Thr Arg Glu Asn Glu Lys Val Ile Lys Glu Asn Glu Lys Val
1               5                   10                  15

Ile Ser Asp Asn Glu Arg Val Leu Glu Glu Val Val Lys Val Val Glu

-continued

```
                20                  25                  30

Thr Ala Thr Asp Arg Lys Glu Ile Gln Asp Ala Val Asp Glu Val Arg
            35                  40                  45

Lys Ser Val Asp Lys Leu Arg Asp Ser Val Arg Lys Leu Glu Glu Ser
        50                  55                  60

Val Arg Thr Leu Asp
65

<210> SEQ ID NO 74
<211> LENGTH: 72
<212> TYPE: PRT
<213> ORGANISM: Artificial Sequence
<220> FEATURE:
<223> OTHER INFORMATION: Synthetic peptide

<400> SEQUENCE: 74

Gly Ser Pro Ile Lys Asp Ile Ser Lys Arg Leu Leu Glu Ile Ser Lys
1               5                   10                  15

Arg Leu Val Glu Ile Ser Asp Arg Ile Val Glu Leu Leu Gln Arg Ile
            20                  25                  30

Ala Asp Ser Lys Asp Pro Asn Lys Asp Leu Gln Lys Glu Val Lys Asp
        35                  40                  45

Val Leu Glu Glu Tyr Lys Arg Leu Val Arg Glu Tyr Arg Glu Val Val
    50                  55                  60

Lys Glu Tyr Glu Lys Val Val Ser
65                  70

<210> SEQ ID NO 75
<211> LENGTH: 75
<212> TYPE: PRT
<213> ORGANISM: Artificial Sequence
<220> FEATURE:
<223> OTHER INFORMATION: Synthetic peptide

<400> SEQUENCE: 75

Asp Glu Asp Glu His Val Lys Gln Leu Ile Lys Asn Ala Asp Leu Leu
1               5                   10                  15

Arg Lys His Ala Glu Leu Leu Lys Glu Leu Val Lys Leu Phe Gln Glu
            20                  25                  30

Ile Ala Ser Gln Ile Pro Asp Asp Arg Val Ala Lys Lys Val Thr Asp
        35                  40                  45

Val Val Asp Arg Ile Asp Lys Ile Leu Lys Gln Thr Glu Lys Leu Val
    50                  55                  60

Arg Arg Thr Lys Gln Ile Leu Asp Tyr Ser Arg
65                  70                  75

<210> SEQ ID NO 76
<211> LENGTH: 71
<212> TYPE: PRT
<213> ORGANISM: Artificial Sequence
<220> FEATURE:
<223> OTHER INFORMATION: Synthetic peptide

<400> SEQUENCE: 76

Gly Ser Asn Leu Glu Glu Leu Val Lys Leu Lys Glu Val Leu Glu
1               5                   10                  15

Met His Glu Arg Leu Leu Arg Ile His Glu Asp Leu Val Glu Ala His
            20                  25                  30

Lys Ser Asn Ala Ser Asp Lys Glu Ser Glu Arg Lys Leu Lys Lys Ser
        35                  40                  45
```

```
Asp Lys Asp Ile Lys Glu Ser Leu Lys Lys Ile Lys Ser Ile Ile Asp
         50                  55                  60

Gln Val Arg Tyr Ile Gln Ser
 65                  70

<210> SEQ ID NO 77
<211> LENGTH: 70
<212> TYPE: PRT
<213> ORGANISM: Artificial Sequence
<220> FEATURE:
<223> OTHER INFORMATION: Synthetic peptide

<400> SEQUENCE: 77

Pro Val Glu Asp Ile Ile Glu Glu Ser Leu Arg Leu Leu Glu Glu Ser
  1               5                  10                  15

Leu Lys Leu Leu Asn Arg Ile Leu Lys Leu Leu Glu Asp Ser Leu Arg
                 20                  25                  30

Lys Leu Pro Arg Ser Glu Glu Trp Arg Gln Arg Leu Asp Glu Phe Arg
             35                  40                  45

Lys Lys Leu Glu Asp Trp Lys Glu Glu Leu Glu Arg Trp Ile Glu Asp
         50                  55                  60

Val Arg Tyr Lys Lys Thr
 65                  70

<210> SEQ ID NO 78
<211> LENGTH: 78
<212> TYPE: PRT
<213> ORGANISM: Artificial Sequence
<220> FEATURE:
<223> OTHER INFORMATION: Synthetic peptide

<400> SEQUENCE: 78

Gly Ser Asp Glu Asp Tyr Glu Ser Arg Glu Ile Ile Asp Glu Ile Arg
  1               5                  10                  15

Lys Leu Leu Asp Arg Ser Lys Lys Ile Val His Arg Ser Gln Arg Leu
                 20                  25                  30

Val Glu Arg Val Lys Ser Thr Pro Leu Ser Glu Asp Gln Glu Asp Leu
             35                  40                  45

Ile Arg Arg His Glu Glu Thr Ile Asn Arg His Arg Glu Leu Val Lys
         50                  55                  60

Glu Leu Glu Lys Val Leu Glu Asp His Glu His Ile Arg
 65                  70                  75

<210> SEQ ID NO 79
<211> LENGTH: 78
<212> TYPE: PRT
<213> ORGANISM: Artificial Sequence
<220> FEATURE:
<223> OTHER INFORMATION: Synthetic peptide

<400> SEQUENCE: 79

Pro Glu Glu Asp Ser Arg Arg Val Leu Glu Arg Phe Val Arg Val Ser
  1               5                  10                  15

Arg Glu Val Leu Lys Val Leu Glu Glu Phe Leu Arg Val Ser Glu Glu
                 20                  25                  30

Leu Leu Arg Glu Ala Asp Arg Asp Arg Asp Arg Leu Glu Glu Tyr
             35                  40                  45

Glu Arg Gln Val Asp Glu Leu Arg Glu Glu Ile Arg Arg Tyr Lys Glu
         50                  55                  60
```

-continued

Glu Val Asp Lys Phe Asp Lys Glu Val Lys Tyr Tyr Lys Lys
65                  70                  75

<210> SEQ ID NO 80
<211> LENGTH: 79
<212> TYPE: PRT
<213> ORGANISM: Artificial Sequence
<220> FEATURE:
<223> OTHER INFORMATION: Synthetic peptide

<400> SEQUENCE: 80

Gly Ser Pro Glu Lys Asp Glu Asn Arg Lys Leu Leu Asp Lys Val Arg
1               5                   10                  15

Lys Leu Val Glu Lys Ser Arg Arg Leu Val Glu Glu Leu Arg Lys Leu
            20                  25                  30

Val Asp Gln Ser Thr Lys Asn Gly Leu Ile Asp Glu Lys Ala Leu Arg
        35                  40                  45

Lys Gln Gln Glu Val Leu Arg Lys Val Glu Glu Val Leu Glu Lys Gln
    50                  55                  60

Glu Arg Val Leu Arg Glu Leu Glu Glu Ile Ser Tyr Arg Val Ile
65                  70                  75

<210> SEQ ID NO 81
<211> LENGTH: 39
<212> TYPE: PRT
<213> ORGANISM: Artificial Sequence
<220> FEATURE:
<223> OTHER INFORMATION: Synthetic peptide

<400> SEQUENCE: 81

Gly Ser Pro Glu Arg Asp Glu Asn Arg Lys Leu Leu Asp Lys Val Arg
1               5                   10                  15

Lys Leu Val Glu Lys Ser Arg Arg Leu Val Glu Glu Leu Arg Lys Leu
            20                  25                  30

Val Asp Gln Ser Thr Lys Asn
        35

<210> SEQ ID NO 82
<211> LENGTH: 124
<212> TYPE: PRT
<213> ORGANISM: Artificial Sequence
<220> FEATURE:
<223> OTHER INFORMATION: Synthetic peptide

<400> SEQUENCE: 82

Gly Ser Asp Glu Lys Ala Leu Arg Lys Gln Gln Glu Val Leu Arg Lys
1               5                   10                  15

Val Glu Glu Val Leu Glu Lys Gln Glu Arg Val Leu Arg Glu Leu Glu
            20                  25                  30

Glu Ile Ser Tyr Arg Val Ile Thr Arg Gly Glu Asp His Lys Ala Glu
        35                  40                  45

Glu Asp Ser Arg Arg Val Leu Glu Arg Phe Val Arg Val Ser Arg Glu
    50                  55                  60

Val Leu Lys Val Leu Glu Glu Phe Leu Arg Val Ser Glu Glu Leu Leu
65                  70                  75                  80

Arg Glu Ala Asp Arg Asp Arg Asp Arg Leu Glu Glu Tyr Glu Arg
                85                  90                  95

Gln Val Asp Glu Leu Arg Glu Glu Ile Arg Arg Tyr Lys Glu Glu Val
                100                 105                 110

Asp Lys Phe Asp Lys Glu Val Lys Tyr Tyr Lys Lys

```
                115                 120

<210> SEQ ID NO 83
<211> LENGTH: 39
<212> TYPE: PRT
<213> ORGANISM: Artificial Sequence
<220> FEATURE:
<223> OTHER INFORMATION: Synthetic peptide

<400> SEQUENCE: 83

Gly Ser Asp Arg Arg Leu Glu Glu Tyr Glu Arg Gln Val Asp Glu Leu
1               5                   10                  15

Arg Glu Glu Ile Arg Arg Tyr Lys Glu Val Asp Lys Phe Asp Lys
            20                  25                  30

Glu Val Lys Tyr Tyr Lys Lys
        35

<210> SEQ ID NO 84
<211> LENGTH: 125
<212> TYPE: PRT
<213> ORGANISM: Artificial Sequence
<220> FEATURE:
<223> OTHER INFORMATION: Synthetic peptide

<400> SEQUENCE: 84

Gly Ser Pro Glu Arg Asp Glu Asn Arg Lys Leu Leu Asp Lys Val Arg
1               5                   10                  15

Lys Leu Val Glu Lys Ser Arg Arg Leu Val Glu Glu Leu Arg Lys Leu
            20                  25                  30

Val Asp Gln Ser Thr Lys Asn Gly Leu Ile Asp Glu Lys Ala Leu Arg
        35                  40                  45

Lys Gln Gln Glu Val Leu Arg Lys Val Glu Glu Val Leu Glu Lys Gln
    50                  55                  60

Glu Arg Val Leu Arg Glu Leu Glu Glu Ile Ser Tyr Arg Val Ile Thr
65                  70                  75                  80

Arg Gly Glu Asp His Lys Ala Glu Glu Asp Ser Arg Arg Val Leu Glu
                85                  90                  95

Arg Phe Val Arg Val Ser Arg Glu Val Leu Lys Val Leu Glu Glu Phe
            100                 105                 110

Leu Arg Val Ser Glu Glu Leu Leu Arg Glu Ala Asp Arg
        115                 120                 125

<210> SEQ ID NO 85
<211> LENGTH: 75
<212> TYPE: PRT
<213> ORGANISM: Artificial Sequence
<220> FEATURE:
<223> OTHER INFORMATION: Synthetic peptide

<400> SEQUENCE: 85

Asp Leu Ser Glu Glu Ser Lys Lys Phe Val Glu Lys Val Lys Lys Leu
1               5                   10                  15

Glu Lys Glu Ser Arg Glu Leu Glu Lys Gln Val Lys Lys Ile Glu Glu
            20                  25                  30

Asp Ser Arg Ser Val Glu Asn Asp Val Gln Lys Glu Phe Leu Glu Leu
        35                  40                  45

Leu Lys Arg Leu Leu Asp Ile Gln Lys Val Val Glu Val Leu Arg
    50                  55                  60

Glu Val Val Lys Val Gln Gln Tyr Val Asp Ser
65                  70                  75
```

<210> SEQ ID NO 86
<211> LENGTH: 80
<212> TYPE: PRT
<213> ORGANISM: Artificial Sequence
<220> FEATURE:
<223> OTHER INFORMATION: Synthetic peptide

<400> SEQUENCE: 86

Gly Ser Asp Ser Glu Tyr Glu Ser Arg Gln Val Leu Arg Glu Leu Asp
1               5                   10                  15

Thr Val Leu Lys Asp Ser His Thr Val Leu Glu Ala Leu Arg Gln Val
            20                  25                  30

Ile Arg Asp Ser Gln Asp Val Val Ser Lys Ser Asp Glu Glu Ser Arg
        35                  40                  45

Arg Val Ile Asp Asp Leu Glu Lys Val Ile Gln Asp Ser Lys Lys Val
    50                  55                  60

Leu Asp Asp Ile Lys Arg Leu Ile Asp Lys Ser Lys Ser Ile Lys Ser
65                  70                  75                  80

<210> SEQ ID NO 87
<211> LENGTH: 75
<212> TYPE: PRT
<213> ORGANISM: Artificial Sequence
<220> FEATURE:
<223> OTHER INFORMATION: Synthetic peptide

<400> SEQUENCE: 87

Asn Glu Asp Glu Leu Leu Lys Leu Leu Thr Glu Asn Leu Lys Leu Leu
1               5                   10                  15

Asp Glu Asn Leu Lys Leu Leu Arg Glu Asn Leu Ser Leu Leu Arg Gln
            20                  25                  30

Ala Asn Asn Ile Thr Asp Lys Asn Arg Ile Arg Glu Ile Val Lys Gln
        35                  40                  45

Ser Lys Glu Ile Val Lys Gln Ser Arg Glu Ile Leu Lys Gln Ser Lys
    50                  55                  60

Glu Ile Val Glu Arg Ile Lys Tyr Ile Val Ser
65                  70                  75

<210> SEQ ID NO 88
<211> LENGTH: 78
<212> TYPE: PRT
<213> ORGANISM: Artificial Sequence
<220> FEATURE:
<223> OTHER INFORMATION: Synthetic peptide

<400> SEQUENCE: 88

Gly Ser Ser Leu Tyr Glu Leu Thr Gln Arg Tyr Glu Lys Leu Val Gln
1               5                   10                  15

Gln Tyr Glu Glu Leu Val Lys Asp Tyr Arg Arg Leu Val Lys Lys Leu
            20                  25                  30

Glu Lys Leu Lys Arg Asp Asn Lys Pro Asp Lys Arg Leu Leu Lys Glu
        35                  40                  45

Ile Val Asp Val Ile Lys Lys Ser Val Glu Ile Asp Arg Ser Leu
    50                  55                  60

Lys Leu Leu Glu Glu Ser Ile Lys Ile Leu Glu Glu Thr Asp
65                  70                  75

<210> SEQ ID NO 89
<211> LENGTH: 73

```
<212> TYPE: PRT
<213> ORGANISM: Artificial Sequence
<220> FEATURE:
<223> OTHER INFORMATION: Synthetic peptide

<400> SEQUENCE: 89

Ser Gln Glu Arg Ser Leu Glu Ile Leu Lys Arg Ile Leu Asp Val Leu
1               5                   10                  15

Lys Glu Ser Leu Glu Ile Leu Lys Glu Ser Leu Ser Ile Leu Arg Gln
            20                  25                  30

Leu Ala Ser Arg Ile Lys Asn Pro Asn Arg Lys Ile Glu Glu Ile Leu
        35                  40                  45

Lys Glu Ser Asp Lys Ile Ile Lys Glu Ser Asp Lys Val Leu Lys Glu
    50                  55                  60

Ile Glu Glu Val Ile Arg Tyr Ser Ser
65                  70

<210> SEQ ID NO 90
<211> LENGTH: 78
<212> TYPE: PRT
<213> ORGANISM: Artificial Sequence
<220> FEATURE:
<223> OTHER INFORMATION: Synthetic peptide

<400> SEQUENCE: 90

Gly Ser Asp Ile Glu Tyr Glu Ser Lys Glu Ile Leu Glu Leu Ile Lys
1               5                   10                  15

Glu Leu Leu Lys Leu Ser Arg Glu Leu Leu Lys Glu Ser Arg Arg Ala
            20                  25                  30

Leu Glu Leu Val Arg Lys Ser Arg Asp Asp Ser Ile Val Glu Glu Val
        35                  40                  45

Ile Gln Val His Lys Lys Val Leu Asp Ile His Lys Glu Val Leu Lys
    50                  55                  60

Ile Val Arg Lys Val Val Glu Val His Arg Arg Val Lys Ser
65                  70                  75

<210> SEQ ID NO 91
<211> LENGTH: 76
<212> TYPE: PRT
<213> ORGANISM: Artificial Sequence
<220> FEATURE:
<223> OTHER INFORMATION: Synthetic peptide

<400> SEQUENCE: 91

Ser Lys Lys Asp Glu Ser Thr Lys Leu Glu Arg Leu Ala Glu Lys Ile
1               5                   10                  15

Asp Glu Ile Thr Lys Arg Ile Glu Glu Leu Val Lys Asp Val Lys Arg
            20                  25                  30

Lys Ser Ser Glu Gly Val Asp Lys Asp Gln Gln Lys Ile Asp Glu
        35                  40                  45

Val Phe Gln Lys Leu Leu Asp Leu Gln Arg Glu Ile Leu Glu Ile Leu
    50                  55                  60

Asp Arg Ile Leu Lys Val Gln Gln Tyr Ile Leu Asp
65                  70                  75

<210> SEQ ID NO 92
<211> LENGTH: 78
<212> TYPE: PRT
<213> ORGANISM: Artificial Sequence
<220> FEATURE:
<223> OTHER INFORMATION: Synthetic peptide
```

<400> SEQUENCE: 92

Gly Ser Asp Leu Glu Tyr Leu Asn Arg Arg Leu Leu Gln Leu Ile Lys
1               5                   10                  15

Thr Leu Ile Asp Leu Asn Arg His Leu Leu Lys Leu Ile Asp Lys Leu
            20                  25                  30

Lys Lys Leu Asn Ser Arg Glu Gly Asp Glu Lys Ile Lys Glu Glu
        35                  40                  45

Ser Lys Gln Ile Gln Glu Gln Phe Lys Glu Ile Val Glu Arg Ser Lys
50                  55                  60

Glu Ile Ile Lys Gln Ile Lys Glu Ile Ile Lys Arg Ser Gln
65                  70                  75

<210> SEQ ID NO 93
<211> LENGTH: 79
<212> TYPE: PRT
<213> ORGANISM: Artificial Sequence
<220> FEATURE:
<223> OTHER INFORMATION: Synthetic peptide

<400> SEQUENCE: 93

Asp Phe Glu Arg Ser Ser Arg Arg Leu Glu Lys Val Val Glu Asp Leu
1               5                   10                  15

Arg Arg Ser Ser Asp Arg Leu Arg Glu Val Ile Asp Glu Leu Arg Lys
            20                  25                  30

Ser Ala Asp Glu Lys Asp Glu Asp Leu Arg Arg Ala Arg Lys
        35                  40                  45

Glu His Arg Asp Leu Ile Glu Glu Leu Lys Arg Ala Leu Glu Lys Gln
50                  55                  60

Glu Glu Ile Ile Lys His Leu Gln Glu Leu Val Tyr Arg Gln Leu
65                  70                  75

<210> SEQ ID NO 94
<211> LENGTH: 78
<212> TYPE: PRT
<213> ORGANISM: Artificial Sequence
<220> FEATURE:
<223> OTHER INFORMATION: Synthetic peptide

<400> SEQUENCE: 94

Gly Ser Glu Glu Ser Glu Glu Val Arg Lys Val Val Glu Arg Ile Lys
1               5                   10                  15

Lys Ile Ser Arg Glu Leu Glu Glu Val Val Lys Glu Leu Asp Arg Val
            20                  25                  30

Ser Lys Glu Phe Asp Arg His Gly Glu Thr Asp Glu Ile Val Arg Glu
        35                  40                  45

His Glu Arg Ile Val Glu Lys Leu Glu Glu Ile Val Lys Lys His Thr
50                  55                  60

Lys Ile Val Glu Glu Leu Ala Glu Ile Val Tyr Lys Gln Gln
65                  70                  75

<210> SEQ ID NO 95
<211> LENGTH: 71
<212> TYPE: PRT
<213> ORGANISM: Artificial Sequence
<220> FEATURE:
<223> OTHER INFORMATION: Synthetic peptide

<400> SEQUENCE: 95

Ser Asp Asp Asp Ser Val Arg Val Leu Asp Glu Ile Val Lys Ile Leu

```
                1               5                   10                  15
Asp Glu Ser Val Lys Leu Leu Lys Glu Ser Leu Lys Leu Leu Asp Asp
                    20                  25                  30

Phe Leu Arg Thr Lys Pro Asp Asp His Leu Lys Glu Val Val Lys Glu
            35                  40                  45

Ser Lys Lys Val Val Glu Gln Ser Lys Lys Val Leu Asp Arg Ile Lys
    50                  55                  60

Lys Ile Ile Tyr Glu Ser Lys
65                  70

<210> SEQ ID NO 96
<211> LENGTH: 72
<212> TYPE: PRT
<213> ORGANISM: Artificial Sequence
<220> FEATURE:
<223> OTHER INFORMATION: Synthetic peptide

<400> SEQUENCE: 96

Gly Ser Asp Leu Leu Tyr Leu Ser Lys Glu Leu Lys Leu Val Arg
1               5                   10                  15

Glu Leu Leu Lys Leu Ser Arg Glu Leu Val Glu Leu Ser Arg Arg Leu
                20                  25                  30

Val Asn Ser Thr His Lys Ser Pro Glu Leu Val Lys Lys Tyr Asp Lys
            35                  40                  45

Leu Val Lys Lys Tyr Gln Asp Leu Leu Lys Lys Leu Ala Asp Val Ala
    50                  55                  60

Asp Glu Tyr Leu Arg Gln Arg Ser
65                  70

<210> SEQ ID NO 97
<211> LENGTH: 76
<212> TYPE: PRT
<213> ORGANISM: Artificial Sequence
<220> FEATURE:
<223> OTHER INFORMATION: Synthetic peptide

<400> SEQUENCE: 97

Asp Glu Lys Asp Tyr His Arg Arg Leu Ile Glu His Leu Glu Asp Leu
1               5                   10                  15

Val Arg Arg His Glu Glu Leu Ile Lys Arg Gln Lys Lys Val Val Glu
                20                  25                  30

Glu Leu Glu Arg Arg Gly Leu Asp Glu Arg Leu Arg Arg Val Val Asp
            35                  40                  45

Arg Phe Arg Arg Ser Ser Glu Arg Trp Glu Glu Val Ile Glu Arg Phe
    50                  55                  60

Arg Gln Val Val Asp Lys Leu Arg Lys Ser Val Glu
65                  70                  75

<210> SEQ ID NO 98
<211> LENGTH: 78
<212> TYPE: PRT
<213> ORGANISM: Artificial Sequence
<220> FEATURE:
<223> OTHER INFORMATION: Synthetic peptide

<400> SEQUENCE: 98

Gly Ser Asp Ala Tyr Asp Leu Asp Arg Ile Val Lys Glu His Arg Arg
1               5                   10                  15

Leu Val Glu Glu Gln Arg Glu Leu Val Glu Glu Leu Glu Lys Leu Val
                20                  25                  30
```

```
Arg Arg Gln Glu Asp His Arg Val Asp Lys Lys Glu Ser His Glu Ile
        35                  40                  45

Leu Glu Arg Leu Glu Arg Ile Ile Arg Arg Ser Thr Arg Ile Leu Thr
 50                  55                  60

Glu Leu Glu Lys Leu Thr Asp Glu Phe Glu Arg Arg Thr Arg
 65                  70                  75
```

<210> SEQ ID NO 99
<211> LENGTH: 77
<212> TYPE: PRT
<213> ORGANISM: Artificial Sequence
<220> FEATURE:
<223> OTHER INFORMATION: Synthetic peptide

<400> SEQUENCE: 99

```
Asp Glu Arg Tyr Arg Ala Arg Glu His Ile Arg Val Glu Glu His
 1               5                  10                  15

Thr Lys Arg Leu Arg His Ile Leu Lys Arg Leu Arg Glu His Glu Glu
                20                  25                  30

Lys Leu Arg Arg Glu Leu Lys Pro Gly Asp Glu Ile Thr Glu Ser Val
        35                  40                  45

Asp Arg Phe Lys Lys Ile Val Asp Gln Phe Glu Glu Ser Ile Lys Lys
 50                  55                  60

Phe Glu Thr Val Ser Glu Glu Leu Arg Lys Ser Asp Ser
 65                  70                  75
```

<210> SEQ ID NO 100
<211> LENGTH: 71
<212> TYPE: PRT
<213> ORGANISM: Artificial Sequence
<220> FEATURE:
<223> OTHER INFORMATION: Synthetic peptide

<400> SEQUENCE: 100

```
Gly Ser Asp Arg Gln Arg Ile Leu Asp Arg Leu Asp Lys Ile Leu Glu
 1               5                  10                  15

Lys Leu Asp Asp Ile Leu Lys Lys Leu Lys Asp Ile Leu Glu Thr Leu
                20                  25                  30

Ser Lys Asp Asp Val Ser Asp Arg Arg His Lys Asp Leu Val Glu Lys
        35                  40                  45

Phe Arg Glu Leu Val Asp Thr His His Lys Leu Val Glu Arg Tyr Arg
 50                  55                  60

Glu Leu Val Tyr Gln Asn Arg
 65                  70
```

<210> SEQ ID NO 101
<211> LENGTH: 38
<212> TYPE: PRT
<213> ORGANISM: Artificial Sequence
<220> FEATURE:
<223> OTHER INFORMATION: Synthetic peptide

<400> SEQUENCE: 101

```
Gly Ser Asp Glu Ile Thr Glu Ser Val Asp Arg Phe Lys Lys Ile Val
 1               5                  10                  15

Asp Gln Phe Glu Glu Ser Ile Lys Lys Phe Glu Thr Val Ser Glu Glu
                20                  25                  30

Leu Arg Lys Ser Ile Ser
        35
```

```
<210> SEQ ID NO 102
<211> LENGTH: 107
<212> TYPE: PRT
<213> ORGANISM: Artificial Sequence
<220> FEATURE:
<223> OTHER INFORMATION: Synthetic peptide

<400> SEQUENCE: 102

Gly Ser Asp Pro Gln Arg Ala Ala Asp Arg Leu Asp Lys Ile Leu Glu
1               5                   10                  15

Lys Leu Asp Asp Ile Leu Lys Lys Leu Lys Asp Ile Leu Glu Thr Leu
            20                  25                  30

Ser Lys Asp Asp Val Lys Asp Arg Arg Ala Lys Asp Leu Val Glu Lys
        35                  40                  45

Phe Arg Glu Leu Val Asp Thr His His Lys Leu Val Glu Arg Tyr Arg
50                  55                  60

Glu Leu Val Tyr Thr Ala Thr Ala Gly Ser Asp Leu Ala Arg Glu Leu
65                  70                  75                  80

Ile Arg Arg Val Glu Glu His Thr Lys Arg Leu Arg His Ile Leu Lys
                85                  90                  95

Arg Leu Arg Glu His Glu Glu Lys Leu Arg Arg
            100                 105

<210> SEQ ID NO 103
<211> LENGTH: 73
<212> TYPE: PRT
<213> ORGANISM: Artificial Sequence
<220> FEATURE:
<223> OTHER INFORMATION: Synthetic peptide

<400> SEQUENCE: 103

Asn Ala Asp Asp Gln Leu Ala Thr Ser Ile Lys Lys Leu Glu Asp Ser
1               5                   10                  15

Ile Asp Gln Leu Ile Lys Ile Val Arg Lys Phe Glu Glu Ser Val Lys
            20                  25                  30

Lys Leu Gln Lys His Gly Val Asp Gln His His Val Glu Ile Leu Arg
        35                  40                  45

Lys Ile Val Glu Ile Phe Arg Gln His Ile Glu Lys Leu Lys Lys His
50                  55                  60

Leu Glu Lys Leu Arg Tyr Thr Ser Ser
65                  70

<210> SEQ ID NO 104
<211> LENGTH: 70
<212> TYPE: PRT
<213> ORGANISM: Artificial Sequence
<220> FEATURE:
<223> OTHER INFORMATION: Synthetic peptide

<400> SEQUENCE: 104

Gly Ser Asp Lys Glu Tyr Leu Val Thr Glu His Glu Lys Leu Val Arg
1               5                   10                  15

Glu His Glu Lys Ile Val Ser Glu Ile Glu Lys Leu Val Lys Lys His
            20                  25                  30

Glu Ala Gly Val Asp Glu Ser Leu Glu Glu Ile Leu Lys Lys Val
        35                  40                  45

Glu Lys Leu Leu Arg Lys Leu Asp Glu Ile Leu Glu Gln Leu Thr Gln
50                  55                  60

Leu Leu Arg Lys Thr Glu
```

```
65                  70

<210> SEQ ID NO 105
<211> LENGTH: 36
<212> TYPE: PRT
<213> ORGANISM: Artificial Sequence
<220> FEATURE:
<223> OTHER INFORMATION: Synthetic peptide

<400> SEQUENCE: 105

Gly Ser Asp Gln His Val Val Glu Ile Leu Arg Lys Ile Val Glu Ile
1               5                   10                  15

Phe Arg Gln His Ile Glu Lys Leu Lys Lys His Leu Glu Lys Leu Arg
            20                  25                  30

Tyr Thr Ser Ser
        35

<210> SEQ ID NO 106
<211> LENGTH: 114
<212> TYPE: PRT
<213> ORGANISM: Artificial Sequence
<220> FEATURE:
<223> OTHER INFORMATION: Synthetic peptide

<400> SEQUENCE: 106

Gly Ser Asp Ala Glu Tyr Leu Val Thr Glu His Glu Lys Leu Val Arg
1               5                   10                  15

Glu His Glu Lys Ile Val Ser Glu Ile Glu Lys Leu Val Lys Lys His
            20                  25                  30

Glu Lys Gly Val Asp Glu Ser Glu Leu Glu Glu Ile Leu Lys Lys Val
        35                  40                  45

Glu Lys Leu Leu Arg Lys Leu Asp Glu Ile Leu Glu Gln Leu Thr Gln
    50                  55                  60

Leu Leu Arg Lys Ala Glu Lys His Ile Asp Lys His Ser Lys Ala Ala
65                  70                  75                  80

Asp Gln Leu Ala Thr Ser Ile Lys Lys Leu Glu Asp Ser Ile Asp Gln
                85                  90                  95

Leu Ile Lys Ile Val Arg Lys Phe Glu Glu Ser Val Lys Lys Leu Gln
            100                 105                 110

Lys His

<210> SEQ ID NO 107
<211> LENGTH: 74
<212> TYPE: PRT
<213> ORGANISM: Artificial Sequence
<220> FEATURE:
<223> OTHER INFORMATION: Synthetic peptide

<400> SEQUENCE: 107

Asp Glu Asp Asp Ile Arg Arg Val Leu Asp Glu Ser Arg Arg Val
1               5                   10                  15

Leu Glu His Ser Arg Arg Val Leu Lys Arg Ser Glu Glu Val Leu Glu
            20                  25                  30

Lys Ala Ser Arg Lys Lys Glu Lys Asp Thr Glu Glu Ile Glu Lys His
        35                  40                  45

Leu Lys Arg Leu Arg Glu His Ala Lys Lys Leu Glu Lys His Arg Arg
    50                  55                  60

Glu Leu Asp Asp Phe Leu Tyr Lys Glu Ile
65                  70
```

<210> SEQ ID NO 108
<211> LENGTH: 74
<212> TYPE: PRT
<213> ORGANISM: Artificial Sequence
<220> FEATURE:
<223> OTHER INFORMATION: Synthetic peptide

<400> SEQUENCE: 108

Gly Ser Arg Asp Lys Tyr Leu Leu Glu Arg Leu Asn Asp Ile Leu Lys
1               5                   10                  15

Lys Leu Asp Glu Ile Val Asp Lys Leu Ser Asp Ile Leu Lys Arg Leu
                20                  25                  30

Lys Asp Val Arg His Asp Arg Leu Gln Glu Leu Val Glu Arg Tyr
                35                  40                  45

Lys Glu Ile Val Lys Glu Tyr Lys Arg Ile Val Glu Glu Tyr Glu Lys
        50                  55                  60

Leu Val Arg Glu Phe Glu Glu Gln Gln Arg
65                  70

<210> SEQ ID NO 109
<211> LENGTH: 73
<212> TYPE: PRT
<213> ORGANISM: Artificial Sequence
<220> FEATURE:
<223> OTHER INFORMATION: Synthetic peptide

<400> SEQUENCE: 109

Asp Arg Asp Tyr Glu Asp Lys Glu Phe Lys Lys Ile Ile Lys Glu Leu
1               5                   10                  15

Glu Asp Val Gln Glu Glu Leu Lys Lys Leu Gln Glu Lys Ile Lys Arg
                20                  25                  30

Phe Ser Ser Glu Leu Glu Glu Pro Asn Glu Leu Leu Lys Glu Gln Leu
                35                  40                  45

Lys Val Asn Glu Glu Gln Leu Glu Val Asn Lys Lys Ile Leu Lys Ile
        50                  55                  60

Leu Arg Asp Gln Leu Lys Gln Asn Glu
65                  70

<210> SEQ ID NO 110
<211> LENGTH: 76
<212> TYPE: PRT
<213> ORGANISM: Artificial Sequence
<220> FEATURE:
<223> OTHER INFORMATION: Synthetic peptide

<400> SEQUENCE: 110

Gly Ser Asp Ala Glu Tyr Lys Val Arg Glu Ser Val Lys Arg Ser Lys
1               5                   10                  15

Glu Ser Val Lys His Ser Glu Asp Val Val Asp Lys Leu Asn Lys Ser
                20                  25                  30

Val Lys Leu Ser Glu Ser Gly His Ser Asp Ala Glu Lys Ala Ser Arg
                35                  40                  45

Glu Leu Val Lys Leu Val Arg Glu Val Val Leu Ser Arg Glu Val
        50                  55                  60

Ile Lys Leu Ser Glu Lys Val Leu Arg Val Ile Ser
65                  70                  75

<210> SEQ ID NO 111
<211> LENGTH: 79
<212> TYPE: PRT

<213> ORGANISM: Artificial Sequence
<220> FEATURE:
<223> OTHER INFORMATION: Synthetic peptide

<400> SEQUENCE: 111

```
Asp Leu Gln Tyr Lys Gln Glu Lys Leu Ile Arg His Phe Asp Arg Val
1               5                   10                  15
Val Arg Glu Trp Asp Lys Leu Val Arg Lys Phe Ser Lys Val Leu Glu
                20                  25                  30
Lys Gln Lys His Glu Ser Lys Asp Lys Glu Leu Glu Ala Ser Arg
        35                  40                  45
Arg Val Asp Glu Leu Ile Lys Arg Leu Arg Gln Leu Lys Arg Ser
    50                  55                  60
Lys Glu Ile Leu Arg Arg Leu Lys Glu Leu Ser Arg Lys Ser Ser
65                  70                  75
```

<210> SEQ ID NO 112
<211> LENGTH: 79
<212> TYPE: PRT
<213> ORGANISM: Artificial Sequence
<220> FEATURE:
<223> OTHER INFORMATION: Synthetic peptide

<400> SEQUENCE: 112

```
Gly Ser Asp Trp Glu Glu Leu Arg Arg Leu Glu Lys Val Leu Gln
1               5                   10                  15
Glu Tyr Glu Glu Ile Val Lys Glu Leu Ile Asp Leu Ile Glu Arg Leu
                20                  25                  30
Ile Lys Val Ser Glu Asp Lys Ser Lys Asp Ala Ser Glu Tyr Lys Lys
        35                  40                  45
Leu Val Thr Glu Leu Glu Lys Leu Ile Ser Lys Leu Glu Glu Ile Ser
    50                  55                  60
Lys Lys Leu Glu Glu Leu Val Lys Glu Tyr Glu Tyr Lys Thr Glu
65                  70                  75
```

<210> SEQ ID NO 113
<211> LENGTH: 76
<212> TYPE: PRT
<213> ORGANISM: Artificial Sequence
<220> FEATURE:
<223> OTHER INFORMATION: Synthetic peptide

<400> SEQUENCE: 113

```
Asp Ala Lys Asp Glu Leu Glu Lys Ser Leu Gln Glu Ile Glu Ser
1               5                   10                  15
Leu Lys Glu Leu Lys Lys Leu Leu Glu Glu Leu Asp Lys Ser Leu Arg
                20                  25                  30
Glu Leu Thr Ser Gln Gly Arg Asn Lys Lys Leu Glu Glu His Ile Lys
        35                  40                  45
Lys Val Gln Lys Phe Ile Glu Leu Val Lys Lys Tyr Ile Lys Ala Val
    50                  55                  60
Gln Asp Tyr Leu Lys Glu Val Arg Tyr Asp Asn Ser
65                  70                  75
```

<210> SEQ ID NO 114
<211> LENGTH: 75
<212> TYPE: PRT
<213> ORGANISM: Artificial Sequence
<220> FEATURE:
<223> OTHER INFORMATION: Synthetic peptide

<400> SEQUENCE: 114

Gly Ser Asp Lys Glu Arg Ala Ala Arg Ala Thr Glu Glu Met Val Lys
1               5                   10                  15

Leu Thr Lys Lys Leu Leu Lys Ala Val Glu Asp Leu Val Arg Asp Val
                20                  25                  30

Arg Arg Leu Leu Lys Glu Gly Leu Ile Ser Glu Lys His Ala Arg Ile
            35                  40                  45

Ala Glu Thr Ile Leu Glu Val Phe Lys Lys His Ala Lys Ile Ile Lys
        50                  55                  60

Lys His Val Asp Ile Val Lys Tyr Asp Glu Ser
65                  70                  75

<210> SEQ ID NO 115
<211> LENGTH: 78
<212> TYPE: PRT
<213> ORGANISM: Artificial Sequence
<220> FEATURE:
<223> OTHER INFORMATION: Synthetic peptide

<400> SEQUENCE: 115

Gly Ser Pro Leu Lys Glu Arg Leu Leu Glu Ile Gln Arg Asp Leu Asp
1               5                   10                  15

Arg Val Leu Glu Glu Val Val Glu Arg Leu Leu Arg Ile Gln Glu Arg
                20                  25                  30

Leu Asp Ser Val Val Glu Arg Lys Pro Pro Asp Val His Glu Glu Tyr
            35                  40                  45

Lys Tyr Ile Val Asp Glu Ile Arg Glu Ile Val Glu Arg Val Val Arg
        50                  55                  60

Glu Tyr Glu Glu Ile Val Lys Arg Ile Asp Glu Glu Val Arg
65                  70                  75

<210> SEQ ID NO 116
<211> LENGTH: 83
<212> TYPE: PRT
<213> ORGANISM: Artificial Sequence
<220> FEATURE:
<223> OTHER INFORMATION: Synthetic peptide

<400> SEQUENCE: 116

Gly Ser Glu Glu Asp Glu Arg Ile Arg Tyr Asp Leu Asp Arg Ile Arg
1               5                   10                  15

Lys Asp Val Arg Arg Lys Leu Glu Glu Ile Arg Gln Arg Val Arg Glu
                20                  25                  30

Leu Glu Lys Lys Leu Arg Asp Ala Gly His Arg Arg Asp Glu Lys Glu
            35                  40                  45

Leu Leu Arg Glu Leu Ile Glu Thr Ser Lys Asp Ile Leu Arg Leu Val
        50                  55                  60

Glu Glu Leu Leu Lys Lys Ile Ile Asp Lys Ser Glu Asp Leu Leu Arg
65                  70                  75                  80

Lys Thr Glu

<210> SEQ ID NO 117
<211> LENGTH: 73
<212> TYPE: PRT
<213> ORGANISM: Artificial Sequence
<220> FEATURE:
<223> OTHER INFORMATION: Synthetic peptide

<400> SEQUENCE: 117

Gly Ser Asp Glu Glu Asp Tyr Ile Asn Glu Asn Val Glu Lys Asp Val
1               5                   10                  15

Arg Asp Ile Glu Asp Val Arg Arg Ile Asn Glu Arg Ile Arg Glu
            20                  25                  30

Leu Leu Glu Lys Ile Arg Thr Glu Glu Val Leu Gln Arg Val Leu Glu
        35                  40                  45

Glu His His Glu Leu Val Arg Val Leu Arg Lys Leu Val Glu Ile
    50                  55                  60

Leu Arg Lys His Glu Glu Glu Asn Arg
65                  70

<210> SEQ ID NO 118
<211> LENGTH: 77
<212> TYPE: PRT
<213> ORGANISM: Artificial Sequence
<220> FEATURE:
<223> OTHER INFORMATION: Synthetic peptide

<400> SEQUENCE: 118

Gly Ser Asp Glu Glu Glu Tyr Tyr Lys Glu Lys Leu His Lys Leu Leu
1               5                   10                  15

Arg Glu Ile Glu Glu Leu Leu Lys His Tyr Arg Glu Leu Val Arg Arg
            20                  25                  30

Leu Glu Glu Leu Val Lys Arg Gly Leu Asp Lys Asp Thr Ala Ala
        35                  40                  45

His Ile Leu Glu Arg Leu Ser Glu Leu Leu Glu Arg Ile Ile Arg Arg
    50                  55                  60

Val Ala His Thr Leu Arg Arg Leu Ser Glu Glu Arg Arg
65                  70                  75

<210> SEQ ID NO 119
<211> LENGTH: 84
<212> TYPE: PRT
<213> ORGANISM: Artificial Sequence
<220> FEATURE:
<223> OTHER INFORMATION: Synthetic peptide

<400> SEQUENCE: 119

Gly Ser Asp Glu Asp Glu Ile Ser Tyr Asp Ser Lys Arg Arg Val Glu
1               5                   10                  15

Glu Ile Val Arg Gln Ala Arg Glu Lys Ser Lys Ser Arg Lys Asp
            20                  25                  30

Ile Glu Asp Val Ala Glu Val Leu Arg Lys Gly Asp Val Ser Glu Lys
        35                  40                  45

Glu Val Val Asp Glu Leu Val Lys Val Leu Glu Gln Val Lys Val
    50                  55                  60

Leu Arg Glu Ala Val Glu Arg Leu Arg Glu Val Leu Lys Lys Gln Val
65                  70                  75                  80

Asp Asp Val Arg

<210> SEQ ID NO 120
<211> LENGTH: 82
<212> TYPE: PRT
<213> ORGANISM: Artificial Sequence
<220> FEATURE:
<223> OTHER INFORMATION: Synthetic peptide

<400> SEQUENCE: 120

Gly Ser Asp Ile Val Glu Leu Val Asp His Leu Leu Lys Arg Ser Leu
1               5                   10                  15

Lys Leu Leu Glu Glu Leu Ala Glu Leu Val Arg Arg Leu Leu Glu Lys
            20                  25                  30

Ser Thr Glu Leu Leu Lys Arg Arg Thr Glu Glu His Lys Glu Glu Val
        35                  40                  45

Val Glu Glu Ser Glu Tyr Met Val Arg Glu Leu Glu Gly Arg Leu Arg
    50                  55                  60

Arg Val Val Asp Glu Ser Glu Lys Leu Val Arg Asp Ala Asp Lys His
65                  70                  75                  80

Ile Arg

<210> SEQ ID NO 121
<211> LENGTH: 83
<212> TYPE: PRT
<213> ORGANISM: Artificial Sequence
<220> FEATURE:
<223> OTHER INFORMATION: Synthetic peptide

<400> SEQUENCE: 121

Gly Ser Lys Glu Lys Asp Ile Val Lys Thr Leu Val Asp Leu Leu Arg
1               5                   10                  15

Glu Asn Leu Glu Thr Leu Glu Arg Leu Ile Glu Val Val Arg Leu
            20                  25                  30

Leu Lys Glu Asn Val Asp Val Arg Asp Glu Gly Arg Asp Asp Lys Asp
        35                  40                  45

Ser Glu Arg Ile Leu Arg Asp Ile Lys Arg Arg Ile Asp Glu Ala Ala
    50                  55                  60

Lys Glu Ser Arg Glu Ile Ile Glu Arg Ile Glu Lys Glu Val Glu Tyr
65                  70                  75                  80

Arg Ser Arg

<210> SEQ ID NO 122
<211> LENGTH: 80
<212> TYPE: PRT
<213> ORGANISM: Artificial Sequence
<220> FEATURE:
<223> OTHER INFORMATION: Synthetic peptide

<400> SEQUENCE: 122

Gly Ser Pro Glu Val Asp Val Leu Arg Arg Ile Val Arg Glu Ile Leu
1               5                   10                  15

Lys Ala Ser Glu Glu Leu Leu Arg Leu Leu Arg Lys Leu Ile Asp Glu
            20                  25                  30

Ala Leu Lys Leu Ser Glu Arg Lys Arg Asp Ser Gln Glu Tyr Arg Glu
        35                  40                  45

Val Val Asp Arg Val Lys Lys Glu Leu Glu Arg Leu Leu Asp Glu Tyr
    50                  55                  60

Arg Lys Leu Val Glu Glu Leu Lys Glu Lys Leu Arg Tyr Asp Thr Arg
65                  70                  75                  80

<210> SEQ ID NO 123
<211> LENGTH: 84
<212> TYPE: PRT
<213> ORGANISM: Artificial Sequence
<220> FEATURE:
<223> OTHER INFORMATION: Synthetic peptide

<400> SEQUENCE: 123

Gly Ser Asp Lys Arg Tyr Glu Ser Glu Lys Leu Lys Arg Arg Leu Asp
1               5                   10                  15

```
Glu Ala Val Glu Lys Val Arg Glu Val Val Glu Arg Val Glu Arg Glu
            20                  25                  30

Ser Asp Arg Val Leu Glu Val Arg Arg Arg Glu Ser Lys Glu
        35                  40                  45

Val Val Asp Lys Val Ile Glu Asp Asn Asp Lys Ala Leu Glu Asp Val
 50                  55                  60

Leu Arg Val Val Asp Glu Val Ala Lys Val Val Arg Asp Val Val Arg
65                  70                  75                  80

Glu Asn Thr Arg
```

<210> SEQ ID NO 124
<211> LENGTH: 77
<212> TYPE: PRT
<213> ORGANISM: Artificial Sequence
<220> FEATURE:
<223> OTHER INFORMATION: Synthetic peptide

<400> SEQUENCE: 124

```
Gly Ser Pro Arg Glu Tyr His Ser Lys Asp Ile Leu Arg Lys Val Asp
 1               5                  10                  15

Glu Ile Leu Glu Arg Ile Arg Arg His Ala Asp Arg Val Lys Lys Lys
            20                  25                  30

Ser Glu Arg Leu Lys Arg Glu Asn Val Asp Val Asn Glu His Ser Lys
        35                  40                  45

Asp Val Lys Arg Val Ile Arg Glu Leu Leu Glu Leu Val Lys Glu Leu
 50                  55                  60

Leu Arg Leu Ala Lys Lys His Ser Asp Asp Gln Gln Glu
65                  70                  75
```

<210> SEQ ID NO 125
<211> LENGTH: 79
<212> TYPE: PRT
<213> ORGANISM: Artificial Sequence
<220> FEATURE:
<223> OTHER INFORMATION: Synthetic peptide

<400> SEQUENCE: 125

```
Gly Ser Asp Glu Asp Glu Ile Leu Tyr His Ser Glu Arg Leu Leu Gln
 1               5                  10                  15

Lys Leu Lys Lys Glu Leu Asp Asp Leu Lys Gly Lys Ser Arg Glu Leu
            20                  25                  30

Leu Glu Glu Leu Lys Lys Glu Asp Pro Asp Asp Arg Leu Ile Glu Arg
        35                  40                  45

Ile Ile Arg Leu His Asp Glu Val Leu Lys Asp Leu Asp Glu Val Leu
 50                  55                  60

Lys Asn Ile Leu Glu Val His Arg Glu Val Leu Glu Arg Leu Arg
65                  70                  75
```

<210> SEQ ID NO 126
<211> LENGTH: 75
<212> TYPE: PRT
<213> ORGANISM: Artificial Sequence
<220> FEATURE:
<223> OTHER INFORMATION: Synthetic peptide

<400> SEQUENCE: 126

```
Asp Lys Leu Asp Arg Leu Leu Lys Ile His Glu Glu Ala Leu Arg Arg
 1               5                  10                  15

Ala Glu Glu Leu Ile Lys Arg Leu Leu Asp Ile His Arg Arg Ala Leu
```

```
                    20                  25                  30

Asp Leu Ala Arg Arg Gly Glu Leu Asp Asp Tyr Leu Leu Lys Glu Ser
                35                  40                  45

Glu Arg Glu Leu Arg Glu Ile Ile Arg Arg Ala Arg Glu Glu Leu Lys
            50                  55                  60

Glu Ser Arg Asp Arg Leu Glu Glu Ile Ser Arg
65                  70                  75

<210> SEQ ID NO 127
<211> LENGTH: 80
<212> TYPE: PRT
<213> ORGANISM: Artificial Sequence
<220> FEATURE:
<223> OTHER INFORMATION: Synthetic peptide

<400> SEQUENCE: 127

Gly Ser Pro Lys Glu Glu Leu Ile Arg Arg Val Leu Glu Glu Val Lys
1               5                   10                  15

Arg Leu Asn Glu Lys Leu Leu Glu Ile Ile Arg Arg Ala Ala Glu Leu
                20                  25                  30

Val Lys Arg Ala Asn Asp Glu Leu Pro Glu Thr Glu Lys Leu Arg Glu
            35                  40                  45

Ile Asp Arg Glu Leu Gly Lys Lys Leu Lys Glu Ile Glu Asp Glu Leu
        50                  55                  60

Arg Arg Ile Asp Lys Glu Leu Asp Ala Leu Tyr Glu Ile Glu Asp
65                  70                  75                  80

<210> SEQ ID NO 128
<211> LENGTH: 80
<212> TYPE: PRT
<213> ORGANISM: Artificial Sequence
<220> FEATURE:
<223> OTHER INFORMATION: Synthetic peptide

<400> SEQUENCE: 128

Gly Ser Pro Lys Leu Asp Lys Leu Arg Glu Leu Leu Glu Arg Asn Leu
1               5                   10                  15

Glu Lys Leu Arg Glu Ile Leu Glu Glu Val Leu Lys Ile Leu Arg Thr
                20                  25                  30

Asn Leu Glu Arg Val Arg Glu Asp Ile Arg Asp Glu Asp Val Leu Gln
            35                  40                  45

Glu Tyr Glu Arg Leu Ile Arg Lys Ala Glu Glu Asp Leu Arg Arg Val
        50                  55                  60

Leu Lys Glu Tyr Asp Asp Leu Leu Lys Lys Leu Val Tyr Glu Leu Arg
65                  70                  75                  80

<210> SEQ ID NO 129
<211> LENGTH: 75
<212> TYPE: PRT
<213> ORGANISM: Artificial Sequence
<220> FEATURE:
<223> OTHER INFORMATION: Synthetic peptide

<400> SEQUENCE: 129

Gly Ser Lys Glu Asp Glu Ser Val Lys Arg Ala Glu Glu Ile Val Arg
1               5                   10                  15

Thr Leu Leu Lys Leu Leu Glu Asp Ser Leu Arg Glu Ala Glu Arg Ser
                20                  25                  30

Leu Arg Asp Ile Lys Asn Gly Glu Asp Glu His Asn Leu Arg Arg Ile
            35                  40                  45
```

```
Ser Glu Lys Leu Glu Glu Leu Ser Lys Arg Ile Thr Glu Thr Ile Glu
        50                  55                  60

Arg Leu Leu Arg Glu Leu Gln Tyr Thr Ser Arg
65                  70                  75

<210> SEQ ID NO 130
<211> LENGTH: 84
<212> TYPE: PRT
<213> ORGANISM: Artificial Sequence
<220> FEATURE:
<223> OTHER INFORMATION: Synthetic peptide

<400> SEQUENCE: 130

Gly Ser Pro Asn Gln Glu Leu Leu Asp Arg Val Arg Lys Ile Leu Glu
1               5                   10                  15

Asp Leu Leu Arg Leu Asn Glu Glu Leu Val Arg Leu Asn Lys Glu Leu
            20                  25                  30

Leu Lys Arg Ala Leu Glu Met Arg Arg Lys Asn Arg Asp Ser Glu Glu
        35                  40                  45

Val Leu Glu Arg Leu Ala Glu Glu Tyr Arg Lys Arg Leu Glu Glu Tyr
    50                  55                  60

Arg Arg Glu Leu Glu Lys Leu Leu Glu Glu Leu Glu Thr Ile Tyr
65                  70                  75                  80

Arg Tyr Lys Arg

<210> SEQ ID NO 131
<211> LENGTH: 84
<212> TYPE: PRT
<213> ORGANISM: Artificial Sequence
<220> FEATURE:
<223> OTHER INFORMATION: Synthetic peptide

<400> SEQUENCE: 131

Gly Ser Asp Glu Ser Glu Glu Ala Gln His Glu Val Glu Lys Val Leu
1               5                   10                  15

Asp Asp Ile Arg Arg Leu Ser Glu His Leu Gln Lys Arg Leu Glu Glu
            20                  25                  30

Val Leu Glu Glu Val Tyr Glu Leu Arg Arg Glu Gly Ser Asp Arg Thr
        35                  40                  45

Glu Val Val Glu Leu Leu Lys Glu Val Ile Arg Glu Ile Val Arg Val
    50                  55                  60

Asn Arg Glu Ala Leu Glu Arg Leu Leu Arg Val Val Glu Glu Ala Val
65                  70                  75                  80

Lys Arg Asn Glu

<210> SEQ ID NO 132
<211> LENGTH: 83
<212> TYPE: PRT
<213> ORGANISM: Artificial Sequence
<220> FEATURE:
<223> OTHER INFORMATION: Synthetic peptide

<400> SEQUENCE: 132

Gly Ser Asp Glu Glu Glu Leu Val Glu Thr Val Lys Arg Ile Gln Lys
1               5                   10                  15

Glu Ile Leu Asp Arg Leu Thr Glu Leu Ala Lys Leu Leu Val Glu Ile
            20                  25                  30

Gln Arg Glu Ile Lys Lys Leu Lys Asp Glu Gly Glu Asp Asp Lys Glu
        35                  40                  45
```

```
Leu Lys Arg Leu Ser Asp Glu Leu Glu Glu Lys Val Arg Gln Val Val
    50                  55                  60

Glu Glu Ile Lys Arg Leu Ser Asp Glu Leu Glu Thr Val Glu Tyr
65                  70                  75                  80

Val Ser Arg
```

<210> SEQ ID NO 133
<211> LENGTH: 80
<212> TYPE: PRT
<213> ORGANISM: Artificial Sequence
<220> FEATURE:
<223> OTHER INFORMATION: Synthetic peptide

<400> SEQUENCE: 133

```
Gly Ser Asp Glu Glu Glu Val Val Arg Arg Ala Glu Glu Leu Val
1               5                   10                  15

Lys Glu His Glu Glu Leu Ile Glu Arg Val Ile Arg Thr His Glu Glu
                20                  25                  30

Leu Val Tyr Lys Leu Glu Asp Gln Gly Ala Asp Lys Lys Leu Val Asp
                35                  40                  45

Val Leu Lys Arg Val Val Glu Glu Ser Glu Arg Val Ala Arg Glu Ile
    50                  55                  60

Val Lys Val Ser Arg Glu Leu Ile Arg Leu Glu Glu Ala Ser Arg
65                  70                  75                  80
```

<210> SEQ ID NO 134
<211> LENGTH: 80
<212> TYPE: PRT
<213> ORGANISM: Artificial Sequence
<220> FEATURE:
<223> OTHER INFORMATION: Synthetic peptide

<400> SEQUENCE: 134

```
Gly Ser Ser Lys Glu Glu Ile Leu Lys Glu Leu Glu Asp Leu Gln Arg
1               5                   10                  15

Arg Leu Ile Glu Glu Leu Lys Lys Leu Gln Glu Arg Val Val Glu Leu
                20                  25                  30

Leu Glu Glu Leu Ile Lys Arg Leu Arg Asp Arg Gly Arg Asp Asp Lys
                35                  40                  45

His Leu Lys Arg Leu Val Lys Glu Val Arg Arg Leu Ser Glu Glu Val
    50                  55                  60

Leu Arg Ser Ile Lys Glu Val Ser Asp Arg Val Arg Tyr Gln Leu Arg
65                  70                  75                  80
```

<210> SEQ ID NO 135
<211> LENGTH: 81
<212> TYPE: PRT
<213> ORGANISM: Artificial Sequence
<220> FEATURE:
<223> OTHER INFORMATION: Synthetic peptide

<400> SEQUENCE: 135

```
Gly Ser Asp Lys Glu Glu Glu Ser Glu Tyr Leu Leu Arg Asp Leu Val
1               5                   10                  15

Arg Leu Leu Glu Lys Val Lys Glu Lys Ile Glu Glu Val Asn Arg Glu
                20                  25                  30

Val Glu Lys Leu Leu Lys Lys Val Lys Asp Gly Arg Leu Asp Arg Arg
                35                  40                  45

Glu Val Leu Arg Glu Ile Leu Arg Leu Asn Arg Glu Leu Ala Glu Ile
```

```
                 50                  55                  60
Ile Lys Glu Val Val Asp Arg Ile Arg His Val Val Glu Arg Ser Glu
 65                  70                  75                  80

Arg

<210> SEQ ID NO 136
<211> LENGTH: 76
<212> TYPE: PRT
<213> ORGANISM: Artificial Sequence
<220> FEATURE:
<223> OTHER INFORMATION: Synthetic peptide

<400> SEQUENCE: 136

Gly Ser Asp Leu His Glu Val Val Tyr Glu Thr Lys Glu Leu Leu Lys
 1               5                  10                  15

Arg Ile Glu Glu Val Val Glu Glu Leu Arg Lys Lys Ser Glu Asp Ile
                 20                  25                  30

Ile Arg Lys Ala Glu Arg Gly Glu Ile Ser Glu Asp Glu Leu Lys Arg
             35                  40                  45

Leu Gln Glu Glu Ile Ala Arg Glu Ala Lys Lys Leu Leu Asp Glu Ile
         50                  55                  60

Lys Arg Val Leu Glu Arg His Leu Glu Gln Thr Leu
 65                  70                  75

<210> SEQ ID NO 137
<211> LENGTH: 81
<212> TYPE: PRT
<213> ORGANISM: Artificial Sequence
<220> FEATURE:
<223> OTHER INFORMATION: Synthetic peptide

<400> SEQUENCE: 137

Gly Ser Pro Val Glu Glu Ile Ile Lys Glu Val Val Lys Arg Val Ile
 1               5                  10                  15

Glu Val Gln Glu Lys Val Leu Arg Ile Ile Ser His Ala Val Lys Arg
                 20                  25                  30

Val Val Glu Val Gln Lys Lys Tyr Asp Pro Gly Ser Glu Glu Ser Asn
             35                  40                  45

Arg Val Val Glu Glu Val Lys Lys Thr Ile Glu Asp Ala Ile Arg Glu
         50                  55                  60

Ser Asp Glu Val Val Asp Glu Val Val Lys Arg Ile Gln Tyr Thr Val
 65                  70                  75                  80

Arg

<210> SEQ ID NO 138
<211> LENGTH: 80
<212> TYPE: PRT
<213> ORGANISM: Artificial Sequence
<220> FEATURE:
<223> OTHER INFORMATION: Synthetic peptide

<400> SEQUENCE: 138

Gly Ser Pro Glu Gln Glu Ile Ala Asp Arg Ile Leu Thr Glu Ile Arg
 1               5                  10                  15

Glu Ser Gln Lys Glu Leu Glu Arg Leu Ala Arg Lys Ile Leu Lys Leu
                 20                  25                  30

Leu Asp Glu Ser Gln Glu Lys Ala Lys Arg Gly Arg Leu Ser Glu Glu
             35                  40                  45

Glu Ser Asp Glu Leu Leu Glu Arg Ile Lys Lys Glu Leu Asp Glu Leu
```

```
                50                  55                  60
Leu Glu Arg Ser Lys Glu Leu Lys Lys Ile Glu Tyr Glu Leu Arg
 65                  70                  75                  80

<210> SEQ ID NO 139
<211> LENGTH: 80
<212> TYPE: PRT
<213> ORGANISM: Artificial Sequence
<220> FEATURE:
<223> OTHER INFORMATION: Synthetic peptide

<400> SEQUENCE: 139

Gly Ser Asp Glu Asp Lys Glu Ala Asn Arg Val Leu Asp Glu Val Leu
 1               5                  10                  15

Lys Thr Val Arg Asp Leu Leu Glu Thr Ala Asn Glu Val Leu Lys Glu
                20                  25                  30

Val Leu Tyr Arg Leu Lys Arg Thr Asp Asp Gln Glu Lys Val Val Arg
            35                  40                  45

Thr Leu Thr Glu Val Leu Lys Glu His Leu Lys Leu Val Glu Glu Ile
        50                  55                  60

Val Arg Ile Leu Asp Lys Val Leu Lys Glu His Leu Glu Thr Glu Lys
 65                  70                  75                  80

<210> SEQ ID NO 140
<211> LENGTH: 76
<212> TYPE: PRT
<213> ORGANISM: Artificial Sequence
<220> FEATURE:
<223> OTHER INFORMATION: Synthetic peptide

<400> SEQUENCE: 140

Gly Ser Pro Glu Asp Val Leu Arg Arg Leu Glu Glu Val Ser Glu
 1               5                  10                  15

Lys Ile Leu Arg Val Ala Glu Asp Val Ala Arg Gln Leu Arg Glu Val
                20                  25                  30

Ser Glu Lys Ile Thr Gln Gly Lys Val Asp Arg Lys Glu Trp Glu Glu
            35                  40                  45

Asp Ile Lys Arg Leu Lys Arg Glu Leu Glu Glu Leu Leu Arg Glu Trp
        50                  55                  60

Lys Glu Glu Ile Glu Arg Leu Thr Tyr Glu Leu Arg
 65                  70                  75

<210> SEQ ID NO 141
<211> LENGTH: 78
<212> TYPE: PRT
<213> ORGANISM: Artificial Sequence
<220> FEATURE:
<223> OTHER INFORMATION: Synthetic peptide

<400> SEQUENCE: 141

Gly Ser Arg Arg Glu Glu Val Val Lys Arg Ile Arg Glu Leu Leu Lys
 1               5                  10                  15

Arg Asn Lys Glu Leu Ile Asp Arg Ile Arg Glu Leu Leu Glu Glu Asn
                20                  25                  30

Glu Tyr Leu Asp Lys Asp Ala Arg Asp Lys Asp Val Leu Arg Arg Ser
            35                  40                  45

Val Glu Leu Leu Glu Glu Leu Val Arg Ile Leu Glu Glu Ser Val Glu
        50                  55                  60

Leu Ala Lys Glu Ile Ile Lys Leu Leu Arg Glu Val Val Glu
 65                  70                  75
```

```
<210> SEQ ID NO 142
<211> LENGTH: 75
<212> TYPE: PRT
<213> ORGANISM: Artificial Sequence
<220> FEATURE:
<223> OTHER INFORMATION: Synthetic peptide

<400> SEQUENCE: 142

Gly Ser Asp Glu Lys Glu Asp Asn Arg Arg Leu Gln His Lys Ile Glu
1               5                   10                  15

Arg Ile Leu Glu Lys Asn Glu Asp Leu Gln Arg Lys Leu Glu Glu Ile
                20                  25                  30

Leu Glu Leu Leu Glu Arg Gly Glu Ala Asp Glu Lys Ile Asp Arg
            35                  40                  45

Leu Arg Lys Ala Val Glu Asp Tyr Arg Arg Val Glu Glu Ile Lys
        50                  55                  60

Glu Asp Val Lys Arg His Lys Tyr Thr Val Arg
65                  70                  75

<210> SEQ ID NO 143
<211> LENGTH: 77
<212> TYPE: PRT
<213> ORGANISM: Artificial Sequence
<220> FEATURE:
<223> OTHER INFORMATION: Synthetic peptide

<400> SEQUENCE: 143

Gly Ser Asp Glu Lys Glu Glu Ala Lys Lys Ala Ser Glu Glu Ser Val
1               5                   10                  15

Arg Thr Val Glu Arg Ile Leu Glu Glu Leu Leu Lys Ala Ser Glu Glu
                20                  25                  30

Ser Val Glu Leu Leu Arg Arg Gly Glu Asp Ala Lys Asp Val Val Glu
            35                  40                  45

Arg Ser Lys Glu Ala Leu Lys Arg Val Lys Glu Leu Leu Asp Glu Val
        50                  55                  60

Val Lys Arg Ser Asp Glu Ile Leu Lys Tyr Ile His Asn
65                  70                  75

<210> SEQ ID NO 144
<211> LENGTH: 84
<212> TYPE: PRT
<213> ORGANISM: Artificial Sequence
<220> FEATURE:
<223> OTHER INFORMATION: Synthetic peptide

<400> SEQUENCE: 144

Gly Ser Asp Glu Lys Lys Leu Ile Asn Glu Val Val Glu Thr Gln Lys
1               5                   10                  15

Arg Leu Ile Lys Glu Ala Ala Lys Arg Leu Ser Glu Val Val Arg His
                20                  25                  30

Gln Thr Glu Leu Ile Arg Glu Leu Arg Glu Lys Asn Val Asp Asp Lys
            35                  40                  45

Asp Val Glu Lys Leu Leu Lys Glu Ser Leu Asp Leu Ala Glu Glu Ile
        50                  55                  60

Val Arg Arg Ile Lys Glu Leu Leu Asp Glu Ser Lys Lys Leu Val Glu
65                  70                  75                  80

Tyr Val Ser Asn
```

-continued

<210> SEQ ID NO 145
<211> LENGTH: 76
<212> TYPE: PRT
<213> ORGANISM: Artificial Sequence
<220> FEATURE:
<223> OTHER INFORMATION: Synthetic peptide

<400> SEQUENCE: 145

Gly Ser Pro Asp Met Asp Glu Val Lys Arg Val Leu Asp Glu Leu Ile
1               5                   10                  15

Glu Ile Gln Glu Glu Ile Leu Arg Glu Ile Lys Arg Val Leu Glu Lys
            20                  25                  30

Leu Ile Lys Ile Gln Glu Asp Asn Gly Ser Gly Tyr Glu Ser Arg Glu
        35                  40                  45

Val Val Arg Glu Ile Val Glu Ile Ala Arg Lys Leu Val Glu Arg Ser
    50                  55                  60

Arg Arg Val Val Lys Lys Ile Thr Glu Thr Leu Gln
65                  70                  75

<210> SEQ ID NO 146
<211> LENGTH: 80
<212> TYPE: PRT
<213> ORGANISM: Artificial Sequence
<220> FEATURE:
<223> OTHER INFORMATION: Synthetic peptide

<400> SEQUENCE: 146

Gly Ser Asp Glu Arg Tyr Ala Thr Arg Glu Ile Val Glu Arg Ile Glu
1               5                   10                  15

Arg Ile Ala Arg Glu Ile Leu Lys Arg Thr Glu Ile Val Arg Glu
            20                  25                  30

Val Arg Glu Val Leu Ser Arg Asp Val Asp Gln Glu Glu Val Val Arg
        35                  40                  45

Arg Leu Ala Asp Leu Leu Arg Glu Ser Val Glu Leu Val Gln His Leu
    50                  55                  60

Val Arg Arg Val Glu Glu Leu Leu Gln Glu Ser Val Glu Arg Lys Lys
65                  70                  75                  80

<210> SEQ ID NO 147
<211> LENGTH: 79
<212> TYPE: PRT
<213> ORGANISM: Artificial Sequence
<220> FEATURE:
<223> OTHER INFORMATION: Synthetic peptide

<400> SEQUENCE: 147

Gly Ser Pro Glu Arg Glu Ala Leu Arg Glu Val Leu Glu Asp Leu Lys
1               5                   10                  15

Arg Val Thr Asp Arg Leu Arg Glu Leu Val Glu Arg Val Leu Glu Glu
            20                  25                  30

Leu Lys Lys Val Thr Asp His Val Asp Ser Gly Arg Ile Leu Arg Glu
        35                  40                  45

Ser Arg Arg Val Leu Lys Glu Leu Lys Asp Ile Ile Glu Glu Ile Leu
    50                  55                  60

Arg Glu Ser Glu Lys Val Leu Glu Lys Leu Lys Tyr Thr Glu Asp
65                  70                  75

<210> SEQ ID NO 148
<211> LENGTH: 80
<212> TYPE: PRT
<213> ORGANISM: Artificial Sequence

```
<220> FEATURE:
<223> OTHER INFORMATION: Synthetic peptide

<400> SEQUENCE: 148

Gly Ser Pro Ala Arg Glu Ile Leu Glu Glu Val Val Lys Lys His Leu
1               5                   10                  15

Glu Val Val Glu Asp Ala Ala Arg Ile Leu Glu Ile Ile Arg Glu
            20                  25                  30

His Glu Lys Ala Val Arg Glu Asp Arg Asp Lys Glu Leu Glu Glu
        35                  40                  45

Ile Ser Arg Asp Leu Leu Arg Lys Ala Arg Glu Ala Leu Lys Val
    50                  55                  60

Lys Asp Ile Ser Asp Asp Leu Ser Arg Glu Ile Glu Tyr Val Ala Ser
65                  70                  75                  80

<210> SEQ ID NO 149
<211> LENGTH: 75
<212> TYPE: PRT
<213> ORGANISM: Artificial Sequence
<220> FEATURE:
<223> OTHER INFORMATION: Synthetic peptide

<400> SEQUENCE: 149

Gly Ser Pro Val Glu Glu Ala Ile Lys Lys Val Ile Asp Asp Leu Arg
1               5                   10                  15

Asp Val Gln Arg Lys Ile Arg Glu Leu Val Glu Glu Leu Ile Arg Leu
            20                  25                  30

Leu Glu Glu Val Gln Arg Asp Asn Asp Lys Arg Glu Ser Glu Tyr Val
        35                  40                  45

Val Glu Arg Val Glu Glu Ile Leu Arg Arg Ile Thr Glu Thr Ser Arg
    50                  55                  60

Glu Val Val Arg Lys Ala Val Glu Asp Leu Ser
65                  70                  75

<210> SEQ ID NO 150
<211> LENGTH: 81
<212> TYPE: PRT
<213> ORGANISM: Artificial Sequence
<220> FEATURE:
<223> OTHER INFORMATION: Synthetic peptide

<400> SEQUENCE: 150

Gly Ser Asp Ser Asp Glu Lys Ala Glu Tyr Leu Leu Lys Glu Met Glu
1               5                   10                  15

Arg Val Val Arg Glu Ser Asp Glu Val Val Lys Lys Ile Leu Arg Asp
            20                  25                  30

Leu Glu Glu Val Leu Glu Arg Leu Arg Arg Gly Glu Ile Ser Glu Asp
        35                  40                  45

Asp Val Thr Glu Ile Leu Lys Glu Leu Ala Glu Arg His Ile Arg Ala
    50                  55                  60

Ile Glu Glu Leu Val Arg Arg Leu Arg Glu Leu Leu Glu Arg His Lys
65                  70                  75                  80

Arg

<210> SEQ ID NO 151
<211> LENGTH: 79
<212> TYPE: PRT
<213> ORGANISM: Artificial Sequence
<220> FEATURE:
<223> OTHER INFORMATION: Synthetic peptide
```

<400> SEQUENCE: 151

Gly Ser Pro Val Glu Val Leu Lys Glu Leu Ser Glu Val Asn Glu
1               5                   10                  15

Arg Val Arg Asp Ile Ala Arg Glu Ile Ile Glu Arg Leu Ser Glu Val
                20                  25                  30

Asn Glu Glu Val Lys Glu Thr Asp Asp Glu Asp Leu Lys Lys Ile
            35                  40                  45

Ser Lys Lys Val Val Asp Glu Val Asp Leu Leu Arg Lys Ile Leu
    50                  55                  60

Glu Val Ser Glu Glu Val Val Arg Arg Val Glu Tyr His Asp Arg
65                  70                  75

<210> SEQ ID NO 152
<211> LENGTH: 76
<212> TYPE: PRT
<213> ORGANISM: Artificial Sequence
<220> FEATURE:
<223> OTHER INFORMATION: Synthetic peptide

<400> SEQUENCE: 152

Gly Ser Pro Lys Glu Asp Ile Leu Arg Glu Val Leu Arg Arg His Lys
1               5                   10                  15

Glu Ile Val Arg Glu Ile Val Arg Leu Val Arg Glu Ala Val Glu Thr
                20                  25                  30

His Leu Glu Leu Val Lys Arg Asn Ser Asp Asp Arg Asp Ala Gln Asp
            35                  40                  45

Val Ile Arg Lys Leu Glu Glu Asp Leu Glu Arg Leu Val Arg His Ala
    50                  55                  60

Gln Glu Val Ile Glu Glu Ile Phe Tyr Arg Leu His
65                  70                  75

<210> SEQ ID NO 153
<211> LENGTH: 75
<212> TYPE: PRT
<213> ORGANISM: Artificial Sequence
<220> FEATURE:
<223> OTHER INFORMATION: Synthetic peptide

<400> SEQUENCE: 153

Gly Ser Pro Arg Ser Tyr Leu Leu Lys Glu Leu Ala Asp Leu Ser Gln
1               5                   10                  15

His Leu Val Arg Leu Leu Glu Arg Leu Val Arg Glu Ser Glu Arg Val
                20                  25                  30

Val Glu Val Leu Glu Arg Gly Glu Val Asp Glu Glu Glu Leu Lys Arg
            35                  40                  45

Leu Glu Asp Leu His Arg Glu Leu Glu Lys Ala Val Arg Glu Val Arg
    50                  55                  60

Glu Thr His Arg Glu Ile Arg Glu Arg Ser Arg
65                  70                  75

<210> SEQ ID NO 154
<211> LENGTH: 76
<212> TYPE: PRT
<213> ORGANISM: Artificial Sequence
<220> FEATURE:
<223> OTHER INFORMATION: Synthetic peptide

<400> SEQUENCE: 154

Gly Ser Asp Arg Glu Tyr Ile Ile Lys Asp Ile Leu Asp Ser Gln Glu

```
                1               5                  10                  15
His Leu Leu Arg Leu Ile Glu Glu Leu Leu Glu Thr Gln Lys Glu Leu
                20                  25                  30

Leu Glu Ile Leu Lys Arg Arg Pro Asp Ser Val Glu Arg Val Arg Glu
                35                  40                  45

Leu Val Arg Arg Ser Lys Glu Ile Ala Asp Glu Ile Arg Arg Gln Ser
        50                  55                  60

Asp Arg Asn Val Arg Leu Leu Glu Glu Val Ser Lys
65                  70                  75
```

<210> SEQ ID NO 155
<211> LENGTH: 75
<212> TYPE: PRT
<213> ORGANISM: Artificial Sequence
<220> FEATURE:
<223> OTHER INFORMATION: Synthetic peptide

<400> SEQUENCE: 155

```
Gly Ser Asp Glu Lys Asp Glu Ile Arg His Val Ile Glu Ser Val Glu
1               5                  10                  15

Arg Leu Ile Glu Asp Ile Lys Arg Leu Leu Lys Thr Leu Arg Glu Leu
                20                  25                  30

Ala His Asp Asp Ser Asp Lys Lys Thr Val Lys Glu Val Leu Asp Arg
                35                  40                  45

Val Lys Glu Met Ile Glu Arg His Arg Arg Glu Leu Glu Glu His Arg
        50                  55                  60

Lys Glu Leu Glu Arg Ala Glu Tyr Glu Val Arg
65                  70                  75
```

<210> SEQ ID NO 156
<211> LENGTH: 76
<212> TYPE: PRT
<213> ORGANISM: Artificial Sequence
<220> FEATURE:
<223> OTHER INFORMATION: Synthetic peptide

<400> SEQUENCE: 156

```
Gly Ser Glu Ser Glu Asp Arg Ile Lys Glu Leu Leu Lys Arg His Ile
1               5                  10                  15

Glu Leu Val Glu Arg His Glu Glu Leu Leu His Glu Ile Lys Lys Leu
                20                  25                  30

Ile Asp Leu Glu Glu Lys Asp Asp Lys Asp Arg Glu Glu Ala Val Lys
                35                  40                  45

Arg Ile Asp Asp Ala Ile Lys Glu Ser Glu Glu Met Leu Glu Glu Ser
        50                  55                  60

Lys Glu Ile Leu Glu Glu Ile Glu Tyr Leu Asn Arg
65                  70                  75
```

<210> SEQ ID NO 157
<211> LENGTH: 77
<212> TYPE: PRT
<213> ORGANISM: Artificial Sequence
<220> FEATURE:
<223> OTHER INFORMATION: Synthetic peptide

<400> SEQUENCE: 157

```
Gly Ser Ser Leu Glu Asp Ser Val Arg Leu Asn Asp Glu Val Val Lys
1               5                  10                  15

Val Val Glu Arg Val Val Arg Leu Asn Gln Glu Val Val Arg Leu Ile
                20                  25                  30
```

```
Lys His Ala Thr Asp Val Glu Asp Glu Glu Thr Val Lys Tyr Val Leu
        35                  40                  45

Glu Arg Val Arg Glu Val Leu Asp Glu Ser Arg Glu Val Leu Lys Arg
    50                  55                  60

Val His Glu Leu Leu Glu Glu Ser Glu Arg Arg Leu Glu
65                  70                  75
```

<210> SEQ ID NO 158
<211> LENGTH: 82
<212> TYPE: PRT
<213> ORGANISM: Artificial Sequence
<220> FEATURE:
<223> OTHER INFORMATION: Synthetic peptide

<400> SEQUENCE: 158

```
Gly Ser His Glu Lys Asp Ile Val Tyr Lys Val Glu Asp Leu Val Arg
1               5                   10                  15

Lys Ser Asp Arg Ile Ala Glu Arg Ala Arg Glu Ile Val Lys Arg Ser
            20                  25                  30

Arg Asp Ile Met Arg Glu Ile Arg Lys Asp Lys Asp Asn Lys Lys Leu
        35                  40                  45

Ser Asp Asp Leu Leu Lys Val Thr Arg Asp Leu Gln Arg Val Val Asp
    50                  55                  60

Glu Leu Glu Glu Leu Ser Arg Glu Leu Leu Arg Val Ala Glu Glu Ser
65                  70                  75                  80

Arg Lys
```

<210> SEQ ID NO 159
<211> LENGTH: 76
<212> TYPE: PRT
<213> ORGANISM: Artificial Sequence
<220> FEATURE:
<223> OTHER INFORMATION: Synthetic peptide

<400> SEQUENCE: 159

```
Gly Ser Pro Glu Leu Asp Glu Val Lys Lys Leu Ile Asp Glu Leu Lys
1               5                   10                  15

Lys Ser Val Glu Arg Leu Glu Glu Ser Ile Arg Glu Val Lys Glu Ser
            20                  25                  30

Ile Lys Lys Leu Arg Lys Gly Asp Ile Asp Ala Glu Glu Asn Ile Lys
        35                  40                  45

Leu Leu Lys Glu Asn Ile Lys Ile Val Arg Glu Asn Ile Lys Ile Ile
    50                  55                  60

Lys Glu Ile Ile Asp Val Val Gln Tyr Val Leu Arg
65                  70                  75
```

<210> SEQ ID NO 160
<211> LENGTH: 82
<212> TYPE: PRT
<213> ORGANISM: Artificial Sequence
<220> FEATURE:
<223> OTHER INFORMATION: Synthetic peptide

<400> SEQUENCE: 160

```
Gly Ser Asp Glu Glu Glu Ile Glu Glu Leu Leu Arg Glu Leu Glu Lys
1               5                   10                  15

Leu Leu Lys Lys Ser Glu Glu Ala Leu Glu Glu Ser Lys Lys Leu Ile
            20                  25                  30

Asp Glu Ser Glu Glu Leu Leu Arg Arg Asp Arg Leu Asp Lys Glu Lys
```

```
                35                  40                  45
His Val Arg Ala Ser Glu Glu His Val Lys Leu Ser Glu Glu His Leu
 50                  55                  60

Arg Ile Ser Arg Glu Ile Val Lys Ile Leu Glu Lys Ala Val Tyr Ser
 65                  70                  75                  80

Thr Arg

<210> SEQ ID NO 161
<211> LENGTH: 79
<212> TYPE: PRT
<213> ORGANISM: Artificial Sequence
<220> FEATURE:
<223> OTHER INFORMATION: Synthetic peptide

<400> SEQUENCE: 161

Gly Ser Asp Glu Ser Asp Arg Ile Arg Lys Ile Val Glu Glu Ser Asp
  1               5                  10                  15

Glu Ile Val Lys Glu Ser Arg Lys Leu Ala Glu Arg Ala Arg Glu Leu
                 20                  25                  30

Ile Lys Glu Ser Glu Asp Lys Arg Val Ser Glu Glu Arg Asn Glu Arg
             35                  40                  45

Leu Leu Glu Glu Leu Leu Arg Ile Leu Asp Glu Asn Ala Glu Leu Leu
 50                  55                  60

Lys Arg Asn Leu Glu Leu Leu Lys Glu Val Leu Tyr Arg Thr Arg
 65                  70                  75

<210> SEQ ID NO 162
<211> LENGTH: 79
<212> TYPE: PRT
<213> ORGANISM: Artificial Sequence
<220> FEATURE:
<223> OTHER INFORMATION: Synthetic peptide

<400> SEQUENCE: 162

Gly Ser Asp Glu Asp Glu Leu Glu Arg Leu Leu Arg Glu Tyr His
  1               5                  10                  15

Arg Val Leu Arg Glu Tyr Glu Lys Leu Leu Glu Glu Leu Arg Arg Leu
                 20                  25                  30

Tyr Glu Glu Tyr Lys Arg Gly Glu Val Ser Glu Glu Ser Asp Arg
             35                  40                  45

Ile Leu Arg Glu Ile Lys Glu Ile Leu Asp Lys Ser Glu Arg Leu Trp
 50                  55                  60

Asp Leu Ser Glu Glu Val Trp Arg Thr Leu Leu Tyr Gln Ala Glu
 65                  70                  75

<210> SEQ ID NO 163
<211> LENGTH: 78
<212> TYPE: PRT
<213> ORGANISM: Artificial Sequence
<220> FEATURE:
<223> OTHER INFORMATION: Synthetic peptide

<400> SEQUENCE: 163

Gly Ser Asp Lys Lys Asp Ala Ser Arg Arg Ala Ile Arg Val Leu His
  1               5                  10                  15

Glu Phe Val Arg Val Ser Glu Glu Val Leu Glu Val Leu Arg Lys Ser
                 20                  25                  30

Val Glu Ser Leu Lys Arg Leu Asp Val Asp Glu Lys Ile Lys Arg Thr
             35                  40                  45
```

-continued

His Asp Arg Ile Glu Glu Leu Arg Arg Trp Lys Arg Glu Leu Glu
    50                  55                  60

Glu Leu Ile Glu Arg Leu Arg Glu Trp Glu Tyr His Gln Asp
65                  70                  75

<210> SEQ ID NO 164
<211> LENGTH: 75
<212> TYPE: PRT
<213> ORGANISM: Artificial Sequence
<220> FEATURE:
<223> OTHER INFORMATION: Synthetic peptide

<400> SEQUENCE: 164

Gly Ser Asp Asp Glu Glu Glu Asp Lys Arg Leu Leu Glu Glu Val Lys
1               5                   10                  15

Arg Ser Leu Asp Thr Asp Glu Arg Ile Leu Glu Lys Leu Arg His Ser
            20                  25                  30

Leu Glu Arg Gln Leu Glu Asp Val Asp Lys Asp Glu Asp Ser Arg Arg
        35                  40                  45

Val Leu Arg Glu Leu Asp Glu Ile Thr Lys Arg Ser Arg Glu Val Val
    50                  55                  60

Lys Arg Leu Arg Lys Leu Ala Tyr Glu Ser Lys
65                  70                  75

<210> SEQ ID NO 165
<211> LENGTH: 79
<212> TYPE: PRT
<213> ORGANISM: Artificial Sequence
<220> FEATURE:
<223> OTHER INFORMATION: Synthetic peptide

<400> SEQUENCE: 165

Gly Ser Asp Lys Glu Tyr Lys Leu Asp Arg Ile Leu Arg Arg Leu Asp
1               5                   10                  15

Glu Leu Ile Lys Gln Leu Ser Arg Ile Leu Glu Glu Ile Glu Arg Leu
            20                  25                  30

Val Asp Glu Leu Glu Arg Glu Pro Leu Asp Asp Lys Glu Val Gln Asp
        35                  40                  45

Val Ile Glu Arg Ile Val Glu Leu Ile Asp Glu His Leu Glu Leu Leu
    50                  55                  60

Lys Glu Tyr Ile Lys Leu Leu Glu Glu Tyr Ile Lys Thr Thr Lys
65                  70                  75

<210> SEQ ID NO 166
<211> LENGTH: 79
<212> TYPE: PRT
<213> ORGANISM: Artificial Sequence
<220> FEATURE:
<223> OTHER INFORMATION: Synthetic peptide

<400> SEQUENCE: 166

Gly Ser Pro Ser Lys Glu Tyr Gln Glu Lys Ser Ala Glu Arg Gln Lys
1               5                   10                  15

Glu Leu Leu His Glu Tyr Glu Lys Leu Val Arg His Leu Arg Glu Leu
            20                  25                  30

Val Glu Lys Leu Gln Arg Arg Glu Leu Asp Lys Glu Val Leu Arg
        35                  40                  45

Arg Leu Val Glu Ile Leu Glu Arg Leu Lys Asp Leu His Lys Lys Ile
    50                  55                  60

Glu Asp Ala His Arg Lys Asn Glu Glu Ala His Lys Glu Asn Lys

```
65                  70                  75

<210> SEQ ID NO 167
<211> LENGTH: 78
<212> TYPE: PRT
<213> ORGANISM: Artificial Sequence
<220> FEATURE:
<223> OTHER INFORMATION: Synthetic peptide

<400> SEQUENCE: 167

Gly Ser Arg Asp Arg Lys Ile Ser Glu Glu Leu Ile Lys Ala Leu Glu
1               5                   10                  15

Asp His Ile Arg Met Leu Glu Glu Leu Ile Arg Ala Ile Glu Glu His
                20                  25                  30

Ile Lys Leu Ala Glu Arg Gly Val Asp Glu Lys Glu Leu Arg Glu Ser
            35                  40                  45

Leu Glu Glu Leu Lys Lys Ile Val Asp Glu Leu Glu Lys Ser Leu Glu
        50                  55                  60

Glu Leu Arg Lys Leu Ala Glu Arg Tyr Lys Tyr Glu Thr Arg
65                  70                  75

<210> SEQ ID NO 168
<211> LENGTH: 77
<212> TYPE: PRT
<213> ORGANISM: Artificial Sequence
<220> FEATURE:
<223> OTHER INFORMATION: Synthetic peptide

<400> SEQUENCE: 168

Gly Ser Pro Lys Glu Glu Ser Val Glu Glu Leu Lys Arg Val Ile Asp
1               5                   10                  15

Lys His Glu Glu Ile Leu Arg Glu Leu Lys Arg Val Leu Glu Glu His
                20                  25                  30

Glu Arg Val Ser His Asp Glu Asp Asn Glu Leu Arg Arg Ser Leu
            35                  40                  45

Glu Arg Leu Lys His Ile Leu Asp Arg Leu His Glu Ser Leu Lys Glu
        50                  55                  60

Leu His Glu Leu Leu Lys Lys Asn Glu Tyr Thr Glu Arg
65                  70                  75

<210> SEQ ID NO 169
<211> LENGTH: 77
<212> TYPE: PRT
<213> ORGANISM: Artificial Sequence
<220> FEATURE:
<223> OTHER INFORMATION: Synthetic peptide

<400> SEQUENCE: 169

Gly Ser Asp His Glu Tyr Trp Val Lys Ile Val Glu Arg Ile Leu Arg
1               5                   10                  15

Val Met Glu Lys His Ala Glu Ile Val Lys Lys His Leu Glu Ile Val
                20                  25                  30

Glu Arg Val Val Arg Glu Gly Pro Ser Glu Asp Leu Arg Arg Lys Leu
            35                  40                  45

Lys Glu Ser Leu Arg Glu Ile Glu Glu Ser Leu Arg Glu Leu Lys Glu
        50                  55                  60

Leu Leu Asp Glu Leu Asp Glu Leu Ser Glu Lys Thr Arg
65                  70                  75

<210> SEQ ID NO 170
```

<211> LENGTH: 72
<212> TYPE: PRT
<213> ORGANISM: Artificial Sequence
<220> FEATURE:
<223> OTHER INFORMATION: Synthetic peptide

<400> SEQUENCE: 170

Gly Ser Asp Glu Glu Tyr Val Thr Arg Ser Gln Arg Arg Leu Lys Arg
1               5                   10                  15

Leu Leu Glu Glu Tyr Ile Lys Val Val Glu Glu His Ala Arg Leu Val
            20                  25                  30

Glu Arg Asn Glu Arg Asp Asp Lys Glu Leu Lys Arg Ser Ile Asp Glu
        35                  40                  45

Leu Asp Lys Leu Thr Lys Glu Leu Leu Glu Leu Val Lys Arg Tyr Lys
    50                  55                  60

Glu Leu Val Asp Lys Thr Glu Thr
65                  70

<210> SEQ ID NO 171
<211> LENGTH: 76
<212> TYPE: PRT
<213> ORGANISM: Artificial Sequence
<220> FEATURE:
<223> OTHER INFORMATION: Synthetic peptide

<400> SEQUENCE: 171

Gly Ser Asp Lys Glu Glu Ile Val Lys Leu Gln Asp Glu Val Ile Lys
1               5                   10                  15

Thr Leu Glu Arg His Leu Asp Ile Leu Arg Lys His Ile Asp Leu Leu
            20                  25                  30

Glu Lys Leu Lys Asp His Leu Ser Glu Glu Leu Lys Glu Arg Val Asp
        35                  40                  45

Arg Ser Ile Lys Lys Leu Glu Glu Ser Ile Lys Arg Leu Glu Arg Ile
    50                  55                  60

Ile Glu Glu Leu Gln Glu Leu Ala Glu Tyr Ser Leu
65                  70                  75

<210> SEQ ID NO 172
<211> LENGTH: 75
<212> TYPE: PRT
<213> ORGANISM: Artificial Sequence
<220> FEATURE:
<223> OTHER INFORMATION: Synthetic peptide

<400> SEQUENCE: 172

Gly Ser Arg Glu Glu Leu Lys Glu Ser Ala Glu Glu Leu Glu Arg
1               5                   10                  15

Ser Val Arg Glu Leu Lys Lys Glu Ala Asp Lys Tyr Lys Glu Glu Val
            20                  25                  30

Asp Arg Leu His Tyr Arg Gly Lys Val Asp Lys Asp Trp Val Arg Val
        35                  40                  45

Val Glu Lys Leu Ile Lys Leu Val Glu Glu His Leu Glu Leu Ile Arg
    50                  55                  60

Glu His Leu Glu Leu Leu Lys Glu Glu Arg Arg
65                  70                  75

<210> SEQ ID NO 173
<211> LENGTH: 75
<212> TYPE: PRT
<213> ORGANISM: Artificial Sequence
<220> FEATURE:

<223> OTHER INFORMATION: Synthetic peptide

<400> SEQUENCE: 173

Gly Ser Asp Met Glu Tyr Glu Leu Lys Lys Ser Ala Glu Glu Leu Arg
1               5                   10                  15

Lys Ser Leu Glu Glu Leu Lys Arg Ile Leu Asp Glu Leu His Lys Ser
            20                  25                  30

Leu Arg Glu Leu Arg Arg His Gly Asp Asp Glu Glu Tyr Val Gln Thr
        35                  40                  45

Val Glu Glu Leu Arg Lys Glu Leu Glu Glu His Ala Lys Lys Leu Glu
    50                  55                  60

Glu His Leu Lys Glu Leu Glu Arg Val Ala Thr
65                  70                  75

<210> SEQ ID NO 174
<211> LENGTH: 70
<212> TYPE: PRT
<213> ORGANISM: Artificial Sequence
<220> FEATURE:
<223> OTHER INFORMATION: Synthetic peptide

<400> SEQUENCE: 174

Pro Glu Tyr Glu Leu Lys Lys Ser Val Asp Asp Leu Lys Arg Asp Val
1               5                   10                  15

Asp Arg Leu Val Glu Glu Val Glu Glu Val Phe Glu Leu Ser Lys Glu
            20                  25                  30

Arg Leu Arg Glu Asp Arg Lys His Leu Glu Leu Val Glu Glu Met Val
        35                  40                  45

Arg Leu Ile Glu Lys His Leu Glu Leu Ile Lys Glu His Leu Lys Leu
    50                  55                  60

Ala Asp Asp His Val Arg
65                  70

<210> SEQ ID NO 175
<211> LENGTH: 78
<212> TYPE: PRT
<213> ORGANISM: Artificial Sequence
<220> FEATURE:
<223> OTHER INFORMATION: Synthetic peptide

<400> SEQUENCE: 175

Gly Ser Arg Glu Lys Asp Glu Ser Lys Glu Leu Asn Asp Glu Tyr Lys
1               5                   10                  15

Lys Leu Leu Glu Glu Tyr Glu Arg Leu Leu Arg Arg Ser Glu Glu Leu
            20                  25                  30

Val Lys Arg Ala Lys Gly Pro Arg Asp Glu Lys Glu Leu Lys Arg Ile
        35                  40                  45

Leu Glu Glu Asn Glu Asp Ile Leu Arg Arg Thr Lys Glu Ile Leu Glu
    50                  55                  60

Arg Thr Lys Glu Ile Ser Glu Glu Gln Lys Tyr Arg Arg Arg
65                  70                  75

<210> SEQ ID NO 176
<211> LENGTH: 78
<212> TYPE: PRT
<213> ORGANISM: Artificial Sequence
<220> FEATURE:
<223> OTHER INFORMATION: Synthetic peptide

<400> SEQUENCE: 176

Gly Ser Asp Lys Asp Glu Arg Gln Glu Arg Leu Asn Glu Glu Ser Asp
1               5                   10                  15

Lys Ser Asn Glu Glu Ser Glu Arg Ser Asn Arg Glu Ser Glu Glu Leu
                20                  25                  30

Asn Arg Arg Ala Arg Gly Pro Asn Asp Glu Lys Glu Leu Gln Glu Ile
            35                  40                  45

Leu Asp Arg His Leu Glu Leu Leu Glu Arg Asn Gln Arg Leu Leu Asp
        50                  55                  60

Glu Asn Lys Glu Ile Leu Arg Glu Ser Gln Tyr Leu Asn Asp
65                  70                  75

<210> SEQ ID NO 177
<211> LENGTH: 76
<212> TYPE: PRT
<213> ORGANISM: Artificial Sequence
<220> FEATURE:
<223> OTHER INFORMATION: Synthetic peptide

<400> SEQUENCE: 177

Gly Ser Glu Asn Lys Tyr Ile Leu Lys Glu Ile Leu Lys Leu Leu Arg
1               5                   10                  15

Glu Asn Leu Lys Leu Leu His Asp Ile Leu Arg Leu Leu Asp Glu Asn
                20                  25                  30

Leu Glu Glu Leu Glu Lys His Gly Ala Lys Asp Leu Asp Asp Tyr Arg
            35                  40                  45

Arg Lys Ile Glu Glu Ile Arg Lys Lys Val Glu Asp Tyr Arg Glu Lys
        50                  55                  60

Ile Glu Glu Ile Glu Lys Lys Val Glu Arg Asp Arg
65                  70                  75

<210> SEQ ID NO 178
<211> LENGTH: 75
<212> TYPE: PRT
<213> ORGANISM: Artificial Sequence
<220> FEATURE:
<223> OTHER INFORMATION: Synthetic peptide

<400> SEQUENCE: 178

Gly Ser Glu Ser Glu Tyr Thr Gln Glu Glu Ile Leu Glu Leu Leu Lys
1               5                   10                  15

Glu Ser Ile Lys Leu Leu Arg Glu Ile Leu Arg Leu Leu Glu Glu Ser
                20                  25                  30

Glu Glu Leu Trp Arg Arg Glu Asn Thr Lys Ser Glu Arg Ser Glu Glu
            35                  40                  45

Ile Lys Glu Arg Ala Lys Glu Ala Ile Lys Arg Ser Glu Glu Ile Leu
        50                  55                  60

Glu Arg Val Lys Arg Leu Ser Asp His Ser Arg
65                  70                  75

<210> SEQ ID NO 179
<211> LENGTH: 74
<212> TYPE: PRT
<213> ORGANISM: Artificial Sequence
<220> FEATURE:
<223> OTHER INFORMATION: Synthetic peptide

<400> SEQUENCE: 179

Gly Ser Asp Glu Glu Glu Ala Asn Tyr Val Ser Asp Lys Ala Val Lys
1               5                   10                  15

Ile Ala Glu Asp Val Gln Glu Leu Leu Lys Glu Leu Leu Glu Leu Ser

```
                20                  25                  30

Glu Val Val Arg Arg Gly Glu Val Asp Glu Asp Glu Tyr Asp Arg Val
            35                  40                  45

Leu Arg Lys Leu Gln Glu Val Met Lys Glu Tyr Glu Val Leu Lys
        50                  55                  60

Glu Tyr Glu Glu Val Ser Arg Lys His Glu
65                  70

<210> SEQ ID NO 180
<211> LENGTH: 80
<212> TYPE: PRT
<213> ORGANISM: Artificial Sequence
<220> FEATURE:
<223> OTHER INFORMATION: Synthetic peptide

<400> SEQUENCE: 180

Gly Ser Pro Glu Lys Tyr Leu Ile Lys Thr Gln Glu Glu Leu Leu Arg
1               5                   10                  15

Arg His Ala Glu Ile Leu Glu Asp Leu Ile Arg Lys Val Glu Arg Gln
            20                  25                  30

Val Asp Leu Arg Arg Lys Val Asp Glu Arg Asp Glu Asp Leu Lys Arg
        35                  40                  45

Glu Leu Glu Arg Ser Leu Arg Glu Leu Glu Arg Leu Val Arg Glu Ser
    50                  55                  60

Ser Arg Leu Val Glu Glu Ile Arg Glu Leu Ser Lys Glu Ile Lys Arg
65                  70                  75                  80

<210> SEQ ID NO 181
<211> LENGTH: 78
<212> TYPE: PRT
<213> ORGANISM: Artificial Sequence
<220> FEATURE:
<223> OTHER INFORMATION: Synthetic peptide

<400> SEQUENCE: 181

Gly Ser Asp Glu Glu Tyr Glu Leu Glu Arg Ile Ser Arg Glu Ser Lys
1               5                   10                  15

Glu Leu Leu Glu Arg Tyr Lys Arg Leu Leu Arg Glu Tyr Gln Glu Leu
            20                  25                  30

Leu Lys Glu Leu Arg His Val Lys Asp Leu Asp Arg Ala Val Lys Ile
        35                  40                  45

Ile His Glu Leu Met Arg Val Ser Lys Glu Leu Val Glu Ile Ser His
    50                  55                  60

Arg Leu Leu Glu Leu His Glu Arg Leu Val Arg Arg Lys
65                  70                  75

<210> SEQ ID NO 182
<211> LENGTH: 79
<212> TYPE: PRT
<213> ORGANISM: Artificial Sequence
<220> FEATURE:
<223> OTHER INFORMATION: Synthetic peptide

<400> SEQUENCE: 182

Gly Ser Glu Lys Glu Tyr Ile Glu Lys Leu Ser Arg Lys Ile Glu Glu
1               5                   10                  15

Asp Ile Arg Arg Ser Glu Glu Arg Ala Lys Asp Ser Glu Arg Leu Val
            20                  25                  30

Arg Arg Leu Glu Glu Leu Ala Lys Arg Lys Arg Leu Asp Leu Asp Asp
        35                  40                  45
```

Val Leu Arg Val Ala Glu Glu Asn Leu Glu Ile Leu Glu Asp Asn Leu
            50                  55                  60

Arg Ile Leu Glu Glu Ile Leu Lys Glu Gln Asp Lys Ser Asn Arg
65                  70                  75

<210> SEQ ID NO 183
<211> LENGTH: 75
<212> TYPE: PRT
<213> ORGANISM: Artificial Sequence
<220> FEATURE:
<223> OTHER INFORMATION: Synthetic peptide

<400> SEQUENCE: 183

Gly Ser Pro His Glu Val Val Glu Leu His Glu Arg Val Met Glu
1               5                   10                  15

Ile Ser Glu Arg Ala Val Glu Leu Ile Gln Arg Ile Ile Asp Ile Ile
            20                  25                  30

Arg Arg Ile Arg Glu Asp Asp Lys Asp Ile Glu Lys Leu Val Lys Thr
            35                  40                  45

Ile Arg Asp Leu Val Arg Glu Tyr Glu Glu Leu His Arg Glu Leu Glu
            50                  55                  60

Glu Ile Asp Glu Glu Ile Tyr Lys Lys Ser Glu
65                  70                  75

<210> SEQ ID NO 184
<211> LENGTH: 82
<212> TYPE: PRT
<213> ORGANISM: Artificial Sequence
<220> FEATURE:
<223> OTHER INFORMATION: Synthetic peptide

<400> SEQUENCE: 184

Gly Ser Asp His Glu Asp Val Val Arg Leu His Glu Asp Leu Val Arg
1               5                   10                  15

Lys Gln Glu Asp Ala Arg Arg Val Leu Glu Glu Ile Val Arg Leu Ala
            20                  25                  30

Glu Glu Ile Val Glu Val Ile Lys Lys Asp Lys Asp Lys Asp Lys Asp Arg
            35                  40                  45

Val Thr Arg Leu Val Glu Glu Ile Glu Lys Leu Val Glu Glu Tyr Lys
            50                  55                  60

Lys Lys Val Asp Glu Met Arg Lys Ile Ser Asp Ile Lys Tyr Arg
65                  70                  75                  80

Ser Arg

<210> SEQ ID NO 185
<211> LENGTH: 79
<212> TYPE: PRT
<213> ORGANISM: Artificial Sequence
<220> FEATURE:
<223> OTHER INFORMATION: Synthetic peptide

<400> SEQUENCE: 185

Gly Ser Arg Ala Arg Glu Val Val Lys Arg Ala Lys Arg Ile Ile Glu
1               5                   10                  15

Glu Trp Gln Lys Ile Leu Glu Glu Trp Arg Arg Ile Leu Glu Glu Trp
            20                  25                  30

Arg Arg Leu Leu Glu Asp Glu Arg Val Asp Asp Arg Asp Asn Glu Arg
            35                  40                  45

Ile Ile Arg Glu Asn Glu Arg Val Ile Arg Glu Asn Glu Lys Ile Ile

```
                    50                  55                  60
Arg Asp Val Ile Arg Leu Leu Glu Glu Leu Leu Tyr Glu Arg Arg
 65                  70                  75

<210> SEQ ID NO 186
<211> LENGTH: 79
<212> TYPE: PRT
<213> ORGANISM: Artificial Sequence
<220> FEATURE:
<223> OTHER INFORMATION: Synthetic peptide

<400> SEQUENCE: 186

Gly Ser Arg Glu Asp Glu Glu Leu Glu Glu Ile Asp Arg Ile Arg
 1               5                  10                  15

Gln Met Val Glu Glu Tyr Glu Glu Leu Val Lys Glu Tyr Glu Glu Leu
                20                  25                  30

Thr Glu Lys Tyr Lys Gln Gly Lys Val Asp Lys Glu Glu Ser Lys Lys
                35                  40                  45

Ile Ile Glu Lys Ser Glu Arg Leu Leu Asp Leu Ser Gln Asp Ala Val
                50                  55                  60

Arg Lys Val Lys Glu Ile Ile Arg Arg Ile Leu Tyr Thr Asn Arg
 65                  70                  75

<210> SEQ ID NO 187
<211> LENGTH: 77
<212> TYPE: PRT
<213> ORGANISM: Artificial Sequence
<220> FEATURE:
<223> OTHER INFORMATION: Synthetic peptide

<400> SEQUENCE: 187

Gly Ser Pro Lys Glu Glu Ile Val Lys Leu His Asp Glu Ser Ala Glu
 1               5                  10                  15

Leu His Arg Arg Ser Val Glu Val Ala Asp Glu Ile Leu Lys Met His
                20                  25                  30

Glu Arg Ser Lys Asp Val Asp Asp Glu Arg Glu Ser Arg Glu Leu Ser
                35                  40                  45

Lys Glu Ile Glu Arg Leu Ile Arg Glu Val Glu Val Ser Lys Arg
                50                  55                  60

Ile Lys Arg Leu Ser Glu Glu Val Glu Tyr Leu Val Arg
 65                  70                  75

<210> SEQ ID NO 188
<211> LENGTH: 77
<212> TYPE: PRT
<213> ORGANISM: Artificial Sequence
<220> FEATURE:
<223> OTHER INFORMATION: Synthetic peptide

<400> SEQUENCE: 188

Gly Ser Pro Leu Glu Glu Ile Leu Lys Ile Gln Arg Arg Ile Asn Lys
 1               5                  10                  15

Ile Gln Asp Asp Ile Asn Lys Ile Leu His Glu Ile Leu Arg Met Gln
                20                  25                  30

Glu Lys Leu Asn Arg Ser Ser Asp Lys Asp Glu Val Glu Glu Ser Leu
                35                  40                  45

Arg Arg Ile Arg Glu Leu Ile Lys Arg Ile Lys Asp Leu Ser Lys Glu
                50                  55                  60

Ile Glu Asp Leu Ser Arg Glu Val Lys Tyr Arg Thr Thr
 65                  70                  75
```

<210> SEQ ID NO 189
<211> LENGTH: 81
<212> TYPE: PRT
<213> ORGANISM: Artificial Sequence
<220> FEATURE:
<223> OTHER INFORMATION: Synthetic peptide

<400> SEQUENCE: 189

Gly Ser Pro Glu Asp Glu His Val Tyr Val Arg Glu Ile Tyr Glu
1               5                   10                  15

Val Leu Arg Glu His Ala Glu Val Leu Glu Glu Asn Arg Glu Val Ile
            20                  25                  30

Glu Arg Leu Leu Glu Ala Lys Lys Arg Gly Asp Lys Ser Glu Glu Leu
        35                  40                  45

Val Lys Glu Leu Lys Lys Ser Ile Asp Lys Leu Lys Glu Ile Ser Arg
50                  55                  60

Lys Leu Glu Glu Ile Val Lys Glu Leu Glu Lys Val Ser Glu Lys Leu
65                  70                  75                  80

Lys

<210> SEQ ID NO 190
<211> LENGTH: 79
<212> TYPE: PRT
<213> ORGANISM: Artificial Sequence
<220> FEATURE:
<223> OTHER INFORMATION: Synthetic peptide

<400> SEQUENCE: 190

Gly Ser Asp Glu Asp Glu Thr Ser Tyr Arg Ile Leu Glu Leu Leu Arg
1               5                   10                  15

Glu Ile Val Arg Ala Ser Arg Glu Leu Ile Arg Leu Ser Glu Glu Leu
            20                  25                  30

Leu Glu Val Ala Arg Arg Asp Asp Lys Asp Glu Thr Val Leu Glu Thr
        35                  40                  45

Leu Ile Arg Glu Tyr Lys Glu Leu Leu Asp Arg Tyr Arg Arg Leu Ile
50                  55                  60

Glu Glu Leu Thr Arg Leu Val Glu Glu Tyr Glu Arg Ser Arg
65                  70                  75

<210> SEQ ID NO 191
<211> LENGTH: 74
<212> TYPE: PRT
<213> ORGANISM: Artificial Sequence
<220> FEATURE:
<223> OTHER INFORMATION: Synthetic peptide

<400> SEQUENCE: 191

Gly Ser Thr Gln Glu Glu Ile Asn Arg Ile Gln His Glu Val Leu Arg
1               5                   10                  15

Ile Gln Glu Glu Ile Asp Glu Ile Leu Arg Asp Ile Val Glu Lys Leu
            20                  25                  30

Lys Ala Ile Ser Arg Gly Glu Leu Asp His Glu Val Val Lys Asp Val
        35                  40                  45

Glu Asp Lys Val Arg Glu Ala Leu Glu Lys Ser Glu Glu Leu Leu Asp
50                  55                  60

Lys Ser Arg Lys Val Glu Tyr Lys Ser Glu
65                  70

```
<210> SEQ ID NO 192
<211> LENGTH: 82
<212> TYPE: PRT
<213> ORGANISM: Artificial Sequence
<220> FEATURE:
<223> OTHER INFORMATION: Synthetic peptide

<400> SEQUENCE: 192

Gly Ser Asp Glu Glu Leu Asn Arg Glu Leu Leu Glu Lys Ser Lys
1               5                   10                  15

Arg Leu Val Asp Ile Asn Arg Asp Ile Ile Arg Thr Ala Gln Glu Leu
            20                  25                  30

Ile Glu Met Leu Lys Asp Ser Lys Asp Gly Arg Val Asp Glu Asp Thr
        35                  40                  45

Lys Arg Glu Leu Arg Asp Lys Leu Arg Lys Leu Glu Glu Lys Leu Glu
    50                  55                  60

Arg Val Arg Glu Glu Leu Arg Lys Tyr Glu Glu Leu Leu Arg Tyr Val
65                  70                  75                  80

Gln Arg

<210> SEQ ID NO 193
<211> LENGTH: 77
<212> TYPE: PRT
<213> ORGANISM: Artificial Sequence
<220> FEATURE:
<223> OTHER INFORMATION: Synthetic peptide

<400> SEQUENCE: 193

Gly Ser Asp Glu Lys Asp Arg Val Tyr Glu Ile Leu Lys Glu Val Gln
1               5                   10                  15

Arg Leu Val Lys Glu Tyr Arg Asp Ile Ser Lys Glu Ile Glu Asp Leu
            20                  25                  30

Val Lys His Tyr Glu His Ile Thr Asp Asp Glu Ala Gln Glu Val Ser
        35                  40                  45

Lys Glu Leu Ile Asp Lys Ser Leu Arg Ala Ser Glu Ile Val Arg Glu
    50                  55                  60

Leu Ile Arg Leu Ile Lys Glu Leu Leu Asp Glu Leu Glu
65                  70                  75

<210> SEQ ID NO 194
<211> LENGTH: 79
<212> TYPE: PRT
<213> ORGANISM: Artificial Sequence
<220> FEATURE:
<223> OTHER INFORMATION: Synthetic peptide

<400> SEQUENCE: 194

Gly Ser Asp Glu Glu Asp Val Leu Tyr His Leu Arg Glu Leu Leu Glu
1               5                   10                  15

Glu Leu Lys Arg Val Ser Asp Asp Tyr Glu Arg Leu Val Arg Glu Ile
            20                  25                  30

Lys Glu Thr Ser Glu Arg Lys Asp Arg Asp Thr Lys Glu Asn Lys Asp
        35                  40                  45

Met Leu Asp Glu Leu Val Lys Ala His Arg Gln Glu Lys Leu Leu
    50                  55                  60

Glu Arg Leu Val Arg Leu Leu Glu Glu Leu Phe Glu Arg Lys Arg
65                  70                  75

<210> SEQ ID NO 195
<211> LENGTH: 54
```

```
<212> TYPE: PRT
<213> ORGANISM: Artificial Sequence
<220> FEATURE:
<223> OTHER INFORMATION: Synthetic peptide

<400> SEQUENCE: 195

Pro Arg Glu Gln Ala Ile Arg Ile Ser Glu Glu Ile Ile Arg Ile Ser
1               5                   10                  15

Lys Lys Ile Ile Glu Ile Leu Glu Arg Thr Arg Ser Ser Thr Ala Arg
            20                  25                  30

Glu Ala Met Lys Trp Ala Lys Asp Ser Ile Arg Leu Ala Glu Glu Ser
        35                  40                  45

Lys Tyr Leu Leu Asp Lys
        50

<210> SEQ ID NO 196
<211> LENGTH: 54
<212> TYPE: PRT
<213> ORGANISM: Artificial Sequence
<220> FEATURE:
<223> OTHER INFORMATION: Synthetic peptide

<400> SEQUENCE: 196

Ile Glu Asp Asp Val Lys Lys Ile Gln Asp Ser Thr Lys Lys Ala Gln
1               5                   10                  15

Lys Glu Thr Ile Glu Ala Leu Glu Arg Ser Thr Ser Ser Thr Ala Arg
            20                  25                  30

Lys Gln Met Glu Glu Gln Lys Glu Gln Ile Arg Leu Gln Lys Glu Ala
        35                  40                  45

Met Tyr Leu Leu Lys Lys
        50

<210> SEQ ID NO 197
<211> LENGTH: 76
<212> TYPE: PRT
<213> ORGANISM: Artificial Sequence
<220> FEATURE:
<223> OTHER INFORMATION: Synthetic peptide

<400> SEQUENCE: 197

Ser Arg Glu Glu Ile Ala Lys Leu Gln Glu Glu Val Ile Lys Leu Gln
1               5                   10                  15

Arg Arg Val Ile Glu Leu Gln Lys Glu Val Ile Glu Leu Gln Arg Arg
            20                  25                  30

Ala Lys Glu Leu Thr Ser Ser Tyr Thr Lys Gly Ile Leu Glu Ile Gln
        35                  40                  45

Arg Arg Ile Glu Glu Ile Gln Arg Glu Ile Glu Glu Ile Gln Lys Arg
    50                  55                  60

Ile Glu Glu Ile Gln Glu Glu Ile Gln Arg Arg Thr
65                  70                  75

<210> SEQ ID NO 198
<211> LENGTH: 76
<212> TYPE: PRT
<213> ORGANISM: Artificial Sequence
<220> FEATURE:
<223> OTHER INFORMATION: Synthetic peptide

<400> SEQUENCE: 198

Ser Asp Glu Glu Ile Lys Arg Leu Ser Glu Glu Val Ile Gln Leu Ser
1               5                   10                  15
```

```
Arg Arg Val Ile Lys Met Ser Arg Glu Ala Ile Lys Leu Ser Arg Glu
            20                  25                  30

Val Gln Lys Leu Thr Pro Ser Tyr Gln Lys Arg Ile Lys Glu Ile Ala
        35                  40                  45

Asp Arg Ser Ile Glu Leu Ala Arg Glu Ser Ile Glu Ile Ala Lys Arg
    50                  55                  60

Ser Glu Lys Ile Ala Glu Glu Ser Gln Arg Arg Thr
65                  70                  75
```

<210> SEQ ID NO 199
<211> LENGTH: 56
<212> TYPE: PRT
<213> ORGANISM: Artificial Sequence
<220> FEATURE:
<223> OTHER INFORMATION: Synthetic peptide

<400> SEQUENCE: 199

```
Pro Ala Lys Asp Glu Ala Leu Lys Met Ala Asn Glu Ser Leu Glu Leu
1               5                   10                  15

Ala Lys Lys Ser Ala Arg Leu Ile Gln Glu Ser Ser Lys Glu Ile
            20                  25                  30

Leu Glu Arg Ile Glu Lys Ile Gln Arg Arg Ile Ala Glu Leu Gln Asp
        35                  40                  45

Arg Ile Ala Tyr Leu Ile Lys Lys
    50                  55
```

<210> SEQ ID NO 200
<211> LENGTH: 56
<212> TYPE: PRT
<213> ORGANISM: Artificial Sequence
<220> FEATURE:
<223> OTHER INFORMATION: Synthetic peptide

<400> SEQUENCE: 200

```
Pro Ala Lys Asp Glu Ala Leu Arg Met Ile Asp Glu Ser Arg Glu Leu
1               5                   10                  15

Ile Lys Lys Ser Asn Glu Leu Ile Gln Arg Ser Ser Ser Lys Glu Ile
            20                  25                  30

Leu Glu Arg Ile Leu Glu Ile Gln Arg Lys Ile Ala Glu Leu Gln Lys
        35                  40                  45

Arg Ile Gln Tyr Leu Leu Lys Ser
    50                  55
```

<210> SEQ ID NO 201
<211> LENGTH: 75
<212> TYPE: PRT
<213> ORGANISM: Artificial Sequence
<220> FEATURE:
<223> OTHER INFORMATION: Synthetic peptide

<400> SEQUENCE: 201

```
Thr Asp Glu Ala Arg Tyr Arg Ser Glu Arg Ile Val Lys Glu Ala Lys
1               5                   10                  15

Arg Leu Leu Asp Glu Ala Arg Arg Arg Ser Glu Lys Ile Val Arg Glu
            20                  25                  30

Ala Lys Gln Arg Ser Asn Ser Glu Asp Ala Lys Arg Ile Met Glu Glu
        35                  40                  45

Asn Leu Arg Glu Ser Glu Glu Ala Ala Arg Arg Leu Arg Glu Ile Ile
    50                  55                  60

Arg Arg Asn Leu Glu Glu Ser Arg Glu Thr Gly
```

65                  70                 75

<210> SEQ ID NO 202
<211> LENGTH: 75
<212> TYPE: PRT
<213> ORGANISM: Artificial Sequence
<220> FEATURE:
<223> OTHER INFORMATION: Synthetic peptide

<400> SEQUENCE: 202

Thr Arg Glu Ala Leu Glu Tyr Gln Arg Lys Met Ala Glu Glu Ile Glu
1                5                 10                15

Asp Leu Leu Arg Glu Ala Leu Arg Arg Gln Glu Glu Met Val Arg Glu
            20                25                30

Ala Lys Gln Arg Ser Leu Ser Glu Glu Phe Lys Arg Ile Met Glu Arg
            35                40                45

Ile Leu Glu Glu Gln Glu Arg Val Met Arg Leu Ala Lys Glu Ala Leu
     50                55                60

Glu Arg Ile Leu Glu Glu Gln Lys Arg Thr Gly
65                 70                 75

<210> SEQ ID NO 203
<211> LENGTH: 76
<212> TYPE: PRT
<213> ORGANISM: Artificial Sequence
<220> FEATURE:
<223> OTHER INFORMATION: Synthetic peptide

<400> SEQUENCE: 203

Ser Glu Arg Thr Lys Arg Glu Ala Lys Arg Ser Gln Glu Glu Ile Leu
1                5                 10                15

Arg Glu Ala Lys Glu Ala Met Arg Arg Ala Lys Glu Ser Gln Asp His
            20                25                30

Arg Gln Asn Arg Asp Gly Ser Asn Ser Glu Asp Leu Glu Arg Leu Ser
            35                40                45

Gln Glu Gln Lys Arg Glu Leu Glu Val Glu Arg Arg Leu Lys Glu
     50                55                60

Leu Ala Arg Glu Gln Lys Tyr Lys Leu Glu Asp Ser
65                 70                 75

<210> SEQ ID NO 204
<211> LENGTH: 76
<212> TYPE: PRT
<213> ORGANISM: Artificial Sequence
<220> FEATURE:
<223> OTHER INFORMATION: Synthetic peptide

<400> SEQUENCE: 204

Ser Glu Asp Leu Lys Arg Ile Leu Lys Glu Ile Thr Glu Arg Glu Leu
1                5                 10                15

Lys Leu Met Gln Asp Leu Met Glu Ile Leu Lys Lys Ile Thr Glu Asp
            20                25                30

Glu Asn Asn Leu Asp Ser Asn Asn Ser Glu Asp Leu Lys Arg Ser Ile
            35                40                45

Glu Lys Ala Arg Arg Ile Leu Asp Glu Ala Leu Arg Lys Leu Glu Glu
     50                55                60

Ser Ala Arg Arg Ala Lys Tyr Ile Gln Glu Asp Asn
65                 70                 75

<210> SEQ ID NO 205

```
<211> LENGTH: 76
<212> TYPE: PRT
<213> ORGANISM: Artificial Sequence
<220> FEATURE:
<223> OTHER INFORMATION: Synthetic peptide

<400> SEQUENCE: 205

Thr Glu Asp Glu Ile Arg Glu Ser Leu Lys Trp Leu Asp Glu Val Leu
1               5                   10                  15

Gln Glu Leu Arg Glu Ile Ala Arg Glu Ser Asn Glu Val Leu Glu Arg
            20                  25                  30

Asn Arg Gln Lys Ser Arg Ser Asp Lys Leu Arg Glu Asp Ile Glu Arg
        35                  40                  45

Tyr Lys Lys Arg Met Glu Ala Arg Lys Lys Leu Asp Asp Gln Leu
    50                  55                  60

Asn Lys Tyr Lys Lys Arg Met Asp Glu Asn Arg Ser
65                  70                  75

<210> SEQ ID NO 206
<211> LENGTH: 76
<212> TYPE: PRT
<213> ORGANISM: Artificial Sequence
<220> FEATURE:
<223> OTHER INFORMATION: Synthetic peptide

<400> SEQUENCE: 206

Thr Glu Glu Glu Leu Lys Glu Ser Lys Lys Phe Ala Glu Asp Leu Ala
1               5                   10                  15

Arg Ser Ala Arg Arg Ala Leu Lys Glu Ser Lys Arg Val Leu Glu Glu
            20                  25                  30

Ile Ser Gln Ala Ser Arg Ser Lys Lys Leu Glu Glu Ile Val Arg Arg
        35                  40                  45

Tyr Lys Glu Gln Val Lys Arg Trp Gln Asp Glu Trp Asp Glu Arg Ala
    50                  55                  60

Arg Glu Tyr Arg Lys Arg Met Lys Glu Asn Arg Ser
65                  70                  75

<210> SEQ ID NO 207
<211> LENGTH: 76
<212> TYPE: PRT
<213> ORGANISM: Artificial Sequence
<220> FEATURE:
<223> OTHER INFORMATION: Synthetic peptide

<400> SEQUENCE: 207

Thr Lys Thr Glu Glu Ile Glu Arg Leu Ala Arg Glu Ile Lys Lys Leu
1               5                   10                  15

Ser Glu Lys Val Glu Arg Leu Ala Gln Glu Ile Glu Glu Leu Ser Arg
            20                  25                  30

Arg Val Lys Glu Glu Asn Ser Thr Asp Arg Glu Leu Lys Glu Ala Asn
        35                  40                  45

Arg Glu Ile Glu Arg Ala Ile Arg Glu Ile Lys Ala Asn Lys Arg
    50                  55                  60

Met Glu Glu Ala Leu Arg Arg Met Lys Tyr Asn Gly
65                  70                  75

<210> SEQ ID NO 208
<211> LENGTH: 76
<212> TYPE: PRT
<213> ORGANISM: Artificial Sequence
<220> FEATURE:
```

<223> OTHER INFORMATION: Synthetic peptide

<400> SEQUENCE: 208

Thr Lys Thr Glu Glu His Glu Arg Leu Ala Arg Glu Ile Ser Lys Leu
1               5                   10                  15

Ala Asp Glu His Arg Lys Leu Ala Lys Ile Ile Glu Glu Leu Ala Arg
            20                  25                  30

Arg Ile Lys Glu Glu Asn Leu Thr Asp Asp Glu Leu Arg Glu Ala Ile
        35                  40                  45

Arg Lys Ile Glu Asp Ala Leu Arg Lys Asn Lys Glu Ala Leu Lys Ile
    50                  55                  60

Met Lys Glu Ala Ala Glu Arg Asn Arg Tyr Asn Thr
65                  70                  75

<210> SEQ ID NO 209
<211> LENGTH: 76
<212> TYPE: PRT
<213> ORGANISM: Artificial Sequence
<220> FEATURE:
<223> OTHER INFORMATION: Synthetic peptide

<400> SEQUENCE: 209

Thr Lys Lys Glu Glu Ser Arg Glu Leu Ala Arg Glu Ser Glu Glu Leu
1               5                   10                  15

Ala Arg Glu Ser Glu Lys Leu Ala Arg Lys Ser Leu Glu Leu Ala Arg
            20                  25                  30

Arg Ala Glu Ser Ser Gly Ser Glu Glu Glu Lys Arg Arg Ile Ile Asp
        35                  40                  45

Glu Asn Arg Lys Ile Ile Glu Arg Asn Arg Glu Ile Ile Glu Arg Asn
    50                  55                  60

Lys Glu Ile Ile Glu Tyr Asn Lys Glu Leu Ile Ser
65                  70                  75

<210> SEQ ID NO 210
<211> LENGTH: 76
<212> TYPE: PRT
<213> ORGANISM: Artificial Sequence
<220> FEATURE:
<223> OTHER INFORMATION: Synthetic peptide

<400> SEQUENCE: 210

Thr Lys Asp Glu Glu Ser Leu Glu Leu Asn Arg Glu Ser Glu Glu Leu
1               5                   10                  15

Asn Arg Lys Ser Glu Glu Leu Asn Arg Lys Ser Lys Glu Leu Asn Asp
            20                  25                  30

Arg Ala Glu Ser Ser Asn Ser Glu Glu Glu Lys Glu Ile Leu Arg
        35                  40                  45

Glu His Lys Glu Ile Leu Arg Glu His Leu Glu Ile Leu Arg Arg His
    50                  55                  60

Lys Glu Ile Leu Arg Arg His Lys Tyr Leu Thr Ser
65                  70                  75

<210> SEQ ID NO 211
<211> LENGTH: 75
<212> TYPE: PRT
<213> ORGANISM: Artificial Sequence
<220> FEATURE:
<223> OTHER INFORMATION: Synthetic peptide

<400> SEQUENCE: 211

-continued

Thr Arg Glu Glu Leu Arg Glu Asn Ile Glu Leu Ala Lys Glu His
1               5                   10                  15

Ile Glu Ile Met Arg Glu Ile Leu Glu Leu Leu Gln Lys Met Glu Glu
                20                  25                  30

Leu Leu Glu Arg Gln Ser Ser Glu Asp Ile Leu Glu Glu Leu Arg Lys
            35                  40                  45

Ile Ile Glu Arg Ile Arg Glu Leu Leu Asp Arg Ser Arg Lys Ile His
        50                  55                  60

Glu Arg Ser Glu Glu Ile Ala Tyr Lys Glu Glu
65                  70                  75

<210> SEQ ID NO 212
<211> LENGTH: 79
<212> TYPE: PRT
<213> ORGANISM: Artificial Sequence
<220> FEATURE:
<223> OTHER INFORMATION: Synthetic peptide

<400> SEQUENCE: 212

Ser Glu Asp Ile Ala Arg Glu Ile Lys Glu Leu Leu Arg Arg Leu Lys
1               5                   10                  15

Glu Ile Ile Glu Arg Asn Gln Arg Ile Ala Lys Glu His Glu Tyr Ile
                20                  25                  30

Ala Arg Glu Arg Lys Lys Leu Asp Pro Ser Asn Glu Lys Glu Arg Lys
            35                  40                  45

Leu Leu Glu Arg Ser Arg Arg Leu Gln Glu Glu Ser Lys Arg Leu Leu
        50                  55                  60

Asp Glu Met Ala Glu Ile Met Arg Arg Ile Lys Lys Leu Leu Asp
65                  70                  75

<210> SEQ ID NO 213
<211> LENGTH: 75
<212> TYPE: PRT
<213> ORGANISM: Artificial Sequence
<220> FEATURE:
<223> OTHER INFORMATION: Synthetic peptide

<400> SEQUENCE: 213

Asp Arg Gln Lys Leu Ile Glu Glu Asn Ile Lys Leu Leu Asp Lys His
1               5                   10                  15

Ile Lys Ile Leu Glu Glu Ile Leu Arg Leu Leu Lys Lys Asp Ile Asp
                20                  25                  30

Leu Leu Lys Lys Ser Ser Ser Glu Glu Val Leu Glu Glu Leu Lys Lys
            35                  40                  45

Ile His Arg Arg Ile Asp Lys Leu Leu Asp Glu Ser Lys Lys Ile His
        50                  55                  60

Lys Arg Ser Ser Glu Ile Val Lys Lys Arg Ser
65                  70                  75

<210> SEQ ID NO 214
<211> LENGTH: 75
<212> TYPE: PRT
<213> ORGANISM: Artificial Sequence
<220> FEATURE:
<223> OTHER INFORMATION: Synthetic peptide

<400> SEQUENCE: 214

Asp Glu Gln Lys Leu Ile Glu Thr Ser Gln Arg Leu Gln Glu Lys Ser
1               5                   10                  15

Glu Arg Leu Leu Glu Lys Phe Glu Gln Ile Leu Arg Glu Ala Ser Asp

```
            20                  25                  30

Leu Tyr Arg Lys Pro Asp Ser Glu Glu Leu Arg Arg Val Glu Lys
        35                  40                  45

Leu Leu Arg Glu Leu Glu Lys Leu Ile Arg Glu Asn Gln Asp Leu Ala
    50                  55                  60

Arg Lys His Glu Lys Ile Leu Arg Asp Gln Ser
65                  70                  75

<210> SEQ ID NO 215
<211> LENGTH: 75
<212> TYPE: PRT
<213> ORGANISM: Artificial Sequence
<220> FEATURE:
<223> OTHER INFORMATION: Synthetic peptide

<400> SEQUENCE: 215

Asp Arg Gln Glu Leu Ile Arg Glu Asn Ile Glu Leu Leu Lys Lys His
1               5                   10                  15

Ile Lys Ile Val Lys Glu Ile Gln Lys Leu Ile Glu Thr Phe Ile Glu
                20                  25                  30

Leu Leu Lys Lys Ser Ser Glu Glu Ile Leu Arg Arg Leu Lys Lys
        35                  40                  45

Ile Leu Lys Arg Ile Glu Lys Leu Tyr Arg Glu Ser Gln Glu Ile His
    50                  55                  60

Lys Arg Ser Glu Glu Ile Ala Lys Lys Arg Gln
65                  70                  75

<210> SEQ ID NO 216
<211> LENGTH: 75
<212> TYPE: PRT
<213> ORGANISM: Artificial Sequence
<220> FEATURE:
<223> OTHER INFORMATION: Synthetic peptide

<400> SEQUENCE: 216

Asp Glu Glu Arg Leu Ile Asp Lys Ser Arg Glu Leu Gln Lys Glu Ser
1               5                   10                  15

Glu Glu Leu Leu Lys Glu Leu Leu Lys Ile Phe Lys Arg Ile Glu Glu
                20                  25                  30

Leu Leu Glu Lys Pro Asp Ser Glu Glu Leu Ile Arg Glu Ile Lys Lys
        35                  40                  45

Leu Leu Glu Thr Leu Ser Glu Ile His Lys Arg Asn Glu Lys Leu Ala
    50                  55                  60

Arg Thr His Glu Glu Ile Leu Arg Gln Gln Ser
65                  70                  75

<210> SEQ ID NO 217
<211> LENGTH: 74
<212> TYPE: PRT
<213> ORGANISM: Artificial Sequence
<220> FEATURE:
<223> OTHER INFORMATION: Synthetic peptide

<400> SEQUENCE: 217

Ser Thr Arg Asp Val Gln Arg Glu Ile Ala Lys Ala Phe Lys Lys Met
1               5                   10                  15

Ala Asp Val Gln Lys Lys Leu Ala Glu Glu Ile Lys Arg His Val Lys
                20                  25                  30

Asn Val Glu Lys Lys Asn Lys Asp Asn Asp Glu Tyr Arg Lys Ile Ala
        35                  40                  45
```

Thr Glu Leu Leu Lys Lys Ala Thr Glu Ser Gln Lys Lys Leu Lys Glu
                50                  55                  60

Leu Leu Asp Arg Ile Arg Lys Ser Asp Ser
 65                  70

<210> SEQ ID NO 218
<211> LENGTH: 74
<212> TYPE: PRT
<213> ORGANISM: Artificial Sequence
<220> FEATURE:
<223> OTHER INFORMATION: Synthetic peptide

<400> SEQUENCE: 218

Asp Lys Asp Asp Arg Ser Thr Ser Leu Leu Lys Arg Val Glu Lys Leu
 1               5                  10                  15

Ile Asp Glu Ser Asp Arg Ile Ile Asp Lys Phe Thr Thr Leu Ile Glu
                20                  25                  30

Leu Ser Arg Asn Gly Lys Ile Asp Asp Gln Tyr Lys Lys Glu Leu
             35                  40                  45

Lys Glu Ile Leu Glu Leu Leu Lys Lys Tyr Asp Lys His Val Lys Glu
 50                  55                  60

Val Glu Glu Leu Leu Lys Arg Leu Asn Ser
 65                  70

<210> SEQ ID NO 219
<211> LENGTH: 70
<212> TYPE: PRT
<213> ORGANISM: Artificial Sequence
<220> FEATURE:
<223> OTHER INFORMATION: Synthetic peptide

<400> SEQUENCE: 219

Ser Lys Arg Lys Ala Leu Glu Val Ser Glu Arg Val Val Arg Ile Ser
 1               5                  10                  15

Glu Lys Val Val Arg Val Leu Asp Glu Ser Ser Asp Leu Leu Lys Lys
                20                  25                  30

Ser Tyr Asp Asp Ser Asp Lys Phe Ala Glu Leu Ile Asp Arg His Glu
             35                  40                  45

Glu Lys Ile Lys Lys Trp Lys Lys Leu Ile Lys Glu Trp Leu Glu Ile
 50                  55                  60

Ile Gln Arg His Lys Ser
 65                  70

<210> SEQ ID NO 220
<211> LENGTH: 68
<212> TYPE: PRT
<213> ORGANISM: Artificial Sequence
<220> FEATURE:
<223> OTHER INFORMATION: Synthetic peptide

<400> SEQUENCE: 220

Ser Ala Glu Glu Phe Val Lys Leu Ser Glu Glu Ala Val Lys Arg Ser
 1               5                  10                  15

Lys Glu Ile Leu Asp Ile Val Arg Lys Gln Val Lys Leu Val Lys Ala
                20                  25                  30

Gly Val Asp Lys His Glu Ile Thr Asp Ser Leu Arg Lys Ser Glu Lys
             35                  40                  45

Leu Ile Glu Glu His Lys Glu Leu Ile Lys Thr His Arg Asp Leu Leu
 50                  55                  60

```
Arg Arg Glu Asn
65

<210> SEQ ID NO 221
<211> LENGTH: 74
<212> TYPE: PRT
<213> ORGANISM: Artificial Sequence
<220> FEATURE:
<223> OTHER INFORMATION: Synthetic peptide

<400> SEQUENCE: 221

Ser Ser Thr Glu Ile Leu Lys Arg Phe Lys Arg Ala Leu Arg Glu Ser
1               5                   10                  15

Glu Lys Ile Val Lys His Ser Arg Arg Val Leu Lys Ile Ile Arg Glu
            20                  25                  30

Val Leu Lys Gln Lys Pro Thr Gln Ala Val His Asp Leu Val Arg Ile
        35                  40                  45

Ile Glu Thr Gln Val Lys Ala Leu Glu Glu Gln Leu Lys Val Leu Lys
    50                  55                  60

Arg Ile Val Glu Ala Leu Glu Arg Gln Ser
65                  70

<210> SEQ ID NO 222
<211> LENGTH: 73
<212> TYPE: PRT
<213> ORGANISM: Artificial Sequence
<220> FEATURE:
<223> OTHER INFORMATION: Synthetic peptide

<400> SEQUENCE: 222

Asp Lys Gln Lys Glu Ile Lys Asp Ile Leu Glu Lys Thr Arg Arg Ile
1               5                   10                  15

Ala Glu Glu Ser Arg Lys Ile Ala Glu Lys Phe Asp Glu Ile Ile Lys
            20                  25                  30

Arg Ser Thr Glu Gly Lys Ile Asp Glu Ser Leu Thr Lys Glu Leu Glu
        35                  40                  45

Glu Leu Val Lys Glu Val Ile Lys Leu Ser Gly Asp Asp Ala Arg Thr
    50                  55                  60

Ser Asp Asp Leu Val Arg Lys Glu Ser
65                  70

<210> SEQ ID NO 223
<211> LENGTH: 74
<212> TYPE: PRT
<213> ORGANISM: Artificial Sequence
<220> FEATURE:
<223> OTHER INFORMATION: Synthetic peptide

<400> SEQUENCE: 223

Asp Glu Asp Glu Ser Ile Lys Leu Thr Arg Lys Ser Ile Glu Glu Thr
1               5                   10                  15

Arg Lys Ser Leu Lys Ile Ile Lys Glu Val Val Glu Leu Ile Arg Glu
            20                  25                  30

Val Leu Lys His Ile Lys Asp Leu Asp Lys Glu Ile Phe Glu Arg Ile
        35                  40                  45

Asp Lys Ile Leu Asp Lys Tyr Lys Lys Gln Val Asp Thr Tyr Asp Glu
    50                  55                  60

Ile Leu Lys Glu Tyr Glu Lys Lys Gln Arg
65                  70
```

-continued

<210> SEQ ID NO 224
<211> LENGTH: 70
<212> TYPE: PRT
<213> ORGANISM: Artificial Sequence
<220> FEATURE:
<223> OTHER INFORMATION: Synthetic peptide

<400> SEQUENCE: 224

Ser Glu Leu Asp Glu Gln Lys Glu Leu Ile Lys Lys Gln Glu Lys Leu
1               5                   10                  15

Ile Glu Glu Gln Gln Arg Leu Leu Ser Lys Ile Arg Arg Met Phe Lys
            20                  25                  30

Glu Arg Val Lys Asp Gln Glu Leu Leu Arg Glu Ile Gln Lys Val Leu
        35                  40                  45

Lys Arg Ser Gln Glu Ile Val Glu Thr Ser Lys Ile Leu Asp Arg
    50                  55                  60

Ser Asp Lys Thr Thr Glu
65                  70

<210> SEQ ID NO 225
<211> LENGTH: 76
<212> TYPE: PRT
<213> ORGANISM: Artificial Sequence
<220> FEATURE:
<223> OTHER INFORMATION: Synthetic peptide

<400> SEQUENCE: 225

Asp Gln Lys Glu Ile Asn Thr Arg Ile Val Glu Lys Leu Glu Arg Ile
1               5                   10                  15

Phe Lys Lys Ser Lys Glu Ile Val Arg Gln Ser Glu Arg Val Ile Ser
            20                  25                  30

Thr Ile Glu Lys Lys Thr Glu Asp Glu Arg Glu Leu Asp Leu Leu Arg
        35                  40                  45

Arg His Val Lys Ile Val Arg Glu His Leu Lys Leu Leu Glu Glu Leu
    50                  55                  60

Leu Lys Ile Ile Lys Glu Val Gln Lys Glu Ser Glu
65                  70                  75

<210> SEQ ID NO 226
<211> LENGTH: 71
<212> TYPE: PRT
<213> ORGANISM: Artificial Sequence
<220> FEATURE:
<223> OTHER INFORMATION: Synthetic peptide

<400> SEQUENCE: 226

Asp Thr Glu Glu Leu Val Lys Arg Leu Asn Glu Leu Leu Lys Glu Leu
1               5                   10                  15

Ser Lys Leu Val Lys Glu Phe Ile Lys Ile Leu Glu Thr Tyr Arg Lys
            20                  25                  30

Asp Gln Thr Lys Asp Thr Ser Lys Ile Ser Arg Val Asp Arg Ile
        35                  40                  45

Leu Lys Thr Tyr Glu Asp Leu Leu Gln Lys Tyr Lys Glu Ile Leu Glu
    50                  55                  60

Lys Ile Glu Lys Gln Leu Ser
65                  70

<210> SEQ ID NO 227
<211> LENGTH: 68
<212> TYPE: PRT
<213> ORGANISM: Artificial Sequence

```
<220> FEATURE:
<223> OTHER INFORMATION: Synthetic peptide

<400> SEQUENCE: 227

Asp Tyr Ala Arg Leu Ile Asp Gln Ala Val Glu Val Thr Arg Lys Val
1               5                   10                  15

Val Glu Val Asn Val Thr Val Ala Arg Val Asn Asp Lys Phe Ala Lys
            20                  25                  30

His Leu Gly Asp Glu Glu Leu Arg Arg Val Ser Glu His Leu Lys Glu
        35                  40                  45

Val Ser Lys Asp Leu Gln Glu Val Ala Lys Lys Ser Lys Asp Ala Ala
    50                  55                  60

Arg Gln Val Lys
65

<210> SEQ ID NO 228
<211> LENGTH: 77
<212> TYPE: PRT
<213> ORGANISM: Artificial Sequence
<220> FEATURE:
<223> OTHER INFORMATION: Synthetic peptide

<400> SEQUENCE: 228

Asp Val Ser Lys Val Ala Glu Glu Tyr Leu Gln Ile Ser Lys Thr Leu
1               5                   10                  15

Val Asp Ile Ser Arg Thr Leu Leu Glu Ile Ser Glu Arg Leu Val Arg
            20                  25                  30

Leu Val Arg Thr Val Ala Asp Asp Arg Ser Glu Val Lys Lys Ala Ile
        35                  40                  45

Glu Asp Ser Ile Glu Val Leu Lys Thr Ser Glu Glu Val Val Arg Gln
    50                  55                  60

Ile Lys Arg Ala Ser Asp Lys Leu Val Lys Ala Ile Ser
65                  70                  75

<210> SEQ ID NO 229
<211> LENGTH: 76
<212> TYPE: PRT
<213> ORGANISM: Artificial Sequence
<220> FEATURE:
<223> OTHER INFORMATION: Synthetic peptide

<400> SEQUENCE: 229

Asp Ala Lys Glu Ile Gln Arg Arg Val Glu Ile Gln Thr Glu Val
1               5                   10                  15

Val Lys Leu Gln Lys Lys Ala Val Asp Ile Ile Arg Lys Ile Ile Glu
            20                  25                  30

Ala Phe Asn Asn Ser Asn Ile Asp Gln Ser Leu Leu Glu Ala Ala Lys
        35                  40                  45

Glu Ile Val Lys Glu Ile Asp Lys Leu Glu Lys Leu Thr Glu Ser Leu
    50                  55                  60

Leu Glu Glu Ser Lys Lys Leu Leu Lys Arg Ser Ser
65                  70                  75

<210> SEQ ID NO 230
<211> LENGTH: 76
<212> TYPE: PRT
<213> ORGANISM: Artificial Sequence
<220> FEATURE:
<223> OTHER INFORMATION: Synthetic peptide

<400> SEQUENCE: 230
```

Ser Ala Glu Glu Val Val Lys Leu Ala Lys Ile Phe Leu Glu Leu Leu
1               5                   10                  15

Arg Glu Ser Ile Lys Leu Leu Lys Arg Ser Val Asp Leu Leu Arg Lys
                20                  25                  30

Ser Ser Asp Pro Ser Leu Asp Lys Ser Glu Ala Glu Lys Val Ser Arg
            35                  40                  45

Glu Ile Glu Lys Val Ser Asp Thr Ser Leu Lys Leu Ser Lys Lys Ala
    50                  55                  60

Leu Asp Val Val Lys Arg Ala Leu Lys Val Ala Ser
65                  70                  75

<210> SEQ ID NO 231
<211> LENGTH: 81
<212> TYPE: PRT
<213> ORGANISM: Artificial Sequence
<220> FEATURE:
<223> OTHER INFORMATION: Synthetic peptide

<400> SEQUENCE: 231

Asp Glu Lys Asp Ala Ala Arg Lys Ala Arg Lys Val Ser Glu Glu Ala
1               5                   10                  15

Lys Glu Ala Ser Lys Lys Ile Glu Lys Ala Leu Glu Ser Lys Arg
                20                  25                  30

Ile Leu Asn Thr Leu Lys Gln Lys Lys Asp Glu Gln Val Lys Val
            35                  40                  45

Ile Lys Glu His Glu Asp Val Leu Arg Gln Ile Glu Lys Ile Gln Lys
    50                  55                  60

Gln Val Leu Glu Ile Gln Lys Glu Val Ala Lys Leu Leu Glu Ser Leu
65                  70                  75                  80

Asp

<210> SEQ ID NO 232
<211> LENGTH: 71
<212> TYPE: PRT
<213> ORGANISM: Artificial Sequence
<220> FEATURE:
<223> OTHER INFORMATION: Synthetic peptide

<400> SEQUENCE: 232

Ser Ala Asp Asp Val Ala Arg Ala Ser Glu Lys Val Leu Arg Val Ala
1               5                   10                  15

Arg Glu Ser Ala Lys Ala Ala Asp Lys Ser Leu Glu Val Phe Lys Glu
                20                  25                  30

Val Val Lys Arg Gly Asp Lys Glu Ala Phe Leu Gln Val Val Lys Ile
            35                  40                  45

Asn Glu Val Val Lys Ile Asn Ile Thr Val Ile Arg Ile Leu Ile
    50                  55                  60

Glu Val Ser Lys Thr Ala Thr
65                  70

<210> SEQ ID NO 233
<211> LENGTH: 112
<212> TYPE: PRT
<213> ORGANISM: Artificial Sequence
<220> FEATURE:
<223> OTHER INFORMATION: Synthetic peptide

<400> SEQUENCE: 233

Asp Glu Tyr Val Lys Glu Thr Leu Lys Gln Leu Arg Glu Ala Leu Ala

```
                1               5                  10                 15
        Ser Leu Arg Glu Ala Asp Lys Arg Ile Thr Glu Leu Val Lys Glu Ala
                        20                  25                 30

Arg Lys Lys Pro Leu Ser Glu Ala Ala Arg Lys Phe Ala Glu Ala Ile
                        35                  40                 45

Val Thr His Val Lys Val Val Val Glu His Val Glu Val Val Leu Arg
                        50                  55                 60

His Val Glu Val Leu Val Glu Ala Lys Lys Asn Gly Val Ile Asp Lys
        65                      70                  75                 80

Ser Ile Leu Asp Asn Ala Leu Arg Ile Ile Glu Asn Val Ile Arg Leu
                        85                  90                 95

Leu Ser Asn Val Ile Arg Val Val Asp Glu Val Leu Gln Asp Leu Asp
                        100                 105                110

<210> SEQ ID NO 234
<211> LENGTH: 113
<212> TYPE: PRT
<213> ORGANISM: Artificial Sequence
<220> FEATURE:
<223> OTHER INFORMATION: Synthetic peptide

<400> SEQUENCE: 234

Asp Ala Ser Asp Val Ile Arg Arg Ile His Glu Leu Phe Glu Glu Val
        1               5                  10                 15

His Arg Leu Ile Glu Ala Val His Arg Ala Ile Glu Asp Val Ala Lys
                        20                  25                 30

Ala Ala Gln Lys Lys Gly Leu Asp Glu Ser Ala Val Glu Ile Leu Ala
                        35                  40                 45

Glu Leu Ser Lys Glu Leu Ala Lys Leu Ser Arg Arg Leu Ala Glu Ile
                        50                  55                 60

Ser Arg Glu Ile Gln Lys Val Val Thr Asp Pro Asp Lys Glu Ala
        65                      70                  75                 80

Val Glu Arg Leu Lys Glu Ile Ile Lys Glu Ile Lys Lys Gln Leu Asp
                        85                  90                 95

Glu Leu Arg Asp Arg Leu Arg Lys Leu Gln Asp Leu Leu Tyr Lys Leu
                        100                 105                110

Lys

<210> SEQ ID NO 235
<211> LENGTH: 77
<212> TYPE: PRT
<213> ORGANISM: Artificial Sequence
<220> FEATURE:
<223> OTHER INFORMATION: Synthetic peptide

<400> SEQUENCE: 235

Ser Glu Asp Lys Ala His His Asp Ile Val Arg Val Leu Glu Glu Leu
        1               5                  10                 15

Ile Lys Ile His Asp Glu Leu Met Lys Ile Ser Glu Glu Ile Leu Lys
                        20                  25                 30

Ala Thr Ser Asp Ser Thr Ala Thr Asp Glu Thr Lys Glu Glu Leu Lys
                        35                  40                 45

Arg Arg Ser Lys Glu Ala Gln Lys Lys Ser Asp Thr Leu Val Lys Ile
                        50                  55                 60

Val Lys Glu Leu Glu Lys Glu Ser Arg Lys Ala Gln Ser
        65                      70                  75
```

```
<210> SEQ ID NO 236
<211> LENGTH: 73
<212> TYPE: PRT
<213> ORGANISM: Artificial Sequence
<220> FEATURE:
<223> OTHER INFORMATION: Synthetic peptide

<400> SEQUENCE: 236

Asp Asp Glu Glu Lys Tyr Arg Gln Ile Ile Arg Glu Ala Gln Glu Ile
1               5                   10                  15

Ser Lys Thr Ala Lys Arg Ile Leu Arg Asp Ala Gln Glu Ile Ser Lys
            20                  25                  30

Arg Ile Arg His Gln Gly Val Asp Arg Ser Glu His Gln Arg Leu Val
        35                  40                  45

Asp Leu Leu Arg Glu Leu Ile Lys Glu His His Lys Leu Leu Arg Arg
    50                  55                  60

Gln Gln Glu Ala Asp Thr Arg Asn Asp
65                  70

<210> SEQ ID NO 237
<211> LENGTH: 74
<212> TYPE: PRT
<213> ORGANISM: Artificial Sequence
<220> FEATURE:
<223> OTHER INFORMATION: Synthetic peptide

<400> SEQUENCE: 237

Asp Arg Lys Asp Lys Ala Arg Lys Ala Ser Glu Lys Leu Glu Glu Val
1               5                   10                  15

Ile Gln Arg Trp Lys Thr Val Ala Asp Lys Trp Lys Lys Met Val Asp
            20                  25                  30

Leu Val Ser Asn Gly Lys Leu Ser Gln Glu Glu Val Ala Arg Val Thr
        35                  40                  45

Glu Glu Leu Leu Lys Ile Gln Thr Glu Leu Ala Lys Leu Leu Glu Glu
    50                  55                  60

His Ala Lys Val Leu Gln Glu Ser Ala Ser
65                  70

<210> SEQ ID NO 238
<211> LENGTH: 77
<212> TYPE: PRT
<213> ORGANISM: Artificial Sequence
<220> FEATURE:
<223> OTHER INFORMATION: Synthetic peptide

<400> SEQUENCE: 238

Ser Asp Glu Glu Ser Ile Lys Thr Gln Ser Glu Leu Ile Lys Thr Ser
1               5                   10                  15

Glu Glu Leu Leu Lys Asp Val Lys Arg Ile Asp Glu Glu Leu Gln Lys
            20                  25                  30

Leu Arg Asp Asp Pro Thr Leu Asp Glu Ser Glu Leu Lys Lys Arg Val
        35                  40                  45

Lys Glu Trp Ser Asp Arg Val Arg Lys Ala Lys Glu Ile Ser Arg Lys
    50                  55                  60

Ile Gln Glu Ile Val Lys Glu Ser Lys Lys Arg Ser Ser
65                  70                  75

<210> SEQ ID NO 239
<211> LENGTH: 72
<212> TYPE: PRT
<213> ORGANISM: Artificial Sequence
```

<220> FEATURE:
<223> OTHER INFORMATION: Synthetic peptide

<400> SEQUENCE: 239

```
Asp Lys Asp Glu Glu Leu Arg Lys Val Ile Glu Lys Tyr Arg Glu Met
1               5                   10                  15

Val Lys Glu Tyr Arg Lys Val Ile Arg Glu Tyr Glu Glu Val Ile Lys
                20                  25                  30

Ser Ser Lys Thr Ile Asp Lys Ser Ser Leu Ile Ser Leu Ser Arg Lys
            35                  40                  45

Met Val Glu Leu Ser Gln Arg Val Ile Asp Val Ser Asp Glu Val Ala
    50                  55                  60

Lys Val Leu Ser Arg Lys Gln Ser
65                  70
```

<210> SEQ ID NO 240
<211> LENGTH: 69
<212> TYPE: PRT
<213> ORGANISM: Artificial Sequence
<220> FEATURE:
<223> OTHER INFORMATION: Synthetic peptide

<400> SEQUENCE: 240

```
Thr Asp Glu Glu Arg Leu Lys Lys Gln Thr Lys Glu Leu Lys Glu Gln
1               5                   10                  15

Thr Lys Gln Leu Glu Lys Gln Lys Asp Leu Leu Glu Lys Ile Ser Asn
                20                  25                  30

Gly Glu Ile Ser Lys Asp Glu Ile Gln Glu Ile Lys Glu Ser Lys
            35                  40                  45

Lys Ile Ala Lys Glu Ser Gln Lys Ala Leu Asp Ser Ser Arg Lys Ala
    50                  55                  60

Leu Glu Glu Val Ser
65
```

<210> SEQ ID NO 241
<211> LENGTH: 75
<212> TYPE: PRT
<213> ORGANISM: Artificial Sequence
<220> FEATURE:
<223> OTHER INFORMATION: Synthetic peptide

<400> SEQUENCE: 241

```
Asp Glu Lys Glu Val Ser Lys Glu Ile Ile Lys Val Leu Lys Asp Ile
1               5                   10                  15

Ala Lys Val Gln Gln Lys Val Ile Glu Val Ser Gln Arg Leu Ala Ser
                20                  25                  30

Val Leu Arg Ala Asp Asp Asn Val Val Lys Arg Ala Leu Glu Glu
            35                  40                  45

Tyr Glu Lys Ile Leu Glu Glu Leu Arg Glu Leu Asn Lys Glu Ile Glu
    50                  55                  60

Lys Leu Thr Asp Lys Tyr Arg Lys Val Thr Ser
65                  70                  75
```

<210> SEQ ID NO 242
<211> LENGTH: 77
<212> TYPE: PRT
<213> ORGANISM: Artificial Sequence
<220> FEATURE:
<223> OTHER INFORMATION: Synthetic peptide

<400> SEQUENCE: 242

```
Asp Ser Asp Glu Gln Thr Lys Glu Leu Glu Lys Leu Thr Glu Leu His
1               5                   10                  15

Lys Arg His Val Glu Lys Leu Lys Ser Gln Thr Lys Glu Ser Arg Glu
                20                  25                  30

Val Asp Ser Asn Lys Leu Trp Lys Ser Lys Val Lys Asp Lys Leu
            35                  40                  45

Ser Glu Ser Glu Lys Glu Leu Gln Lys Leu Ser Asp Gln Asp Lys Lys
        50                  55                  60

Ala Lys Asp Ala Leu Glu Ser Ser Arg Arg Lys Asn Asp
65                  70                  75
```

<210> SEQ ID NO 243
<211> LENGTH: 76
<212> TYPE: PRT
<213> ORGANISM: Artificial Sequence
<220> FEATURE:
<223> OTHER INFORMATION: Synthetic peptide

<400> SEQUENCE: 243

```
Asp Ala Glu Gln Leu Lys Leu Leu Thr Lys Leu Leu Arg His Gln
1               5                   10                  15

Gln Arg Leu Leu Gln Leu Ile Lys Glu Ser Leu Lys Leu Ile Glu Lys
                20                  25                  30

Ile Asp Gln Ser Ser Gln Glu Asn Gln Asp Ile Arg Lys Trp Arg
            35                  40                  45

Glu Val Thr Lys Lys Leu Arg Glu Leu Ile Lys Thr Ser Glu Lys Leu
        50                  55                  60

Val Arg Glu Leu Glu Lys Ser Tyr Lys Lys Ser Ser
65                  70                  75
```

<210> SEQ ID NO 244
<211> LENGTH: 70
<212> TYPE: PRT
<213> ORGANISM: Artificial Sequence
<220> FEATURE:
<223> OTHER INFORMATION: Synthetic peptide

<400> SEQUENCE: 244

```
Ser Leu Arg Asp Val Val Arg Arg Tyr Gln Glu Leu Val Arg Tyr
1               5                   10                  15

Asp Glu Leu Ile Lys Thr Leu Thr Glu Ile Leu Lys Lys Tyr Gln Lys
                20                  25                  30

Lys Gly Ala Glu Asp Lys Asp Ala Ser Thr Leu Val Lys Ala Val
            35                  40                  45

Arg Thr Ser Leu Lys Leu Ser Lys Glu Leu Leu Lys Leu Asn Ser Glu
        50                  55                  60

Leu Leu Lys Glu Asp Ser
65                  70
```

<210> SEQ ID NO 245
<211> LENGTH: 69
<212> TYPE: PRT
<213> ORGANISM: Artificial Sequence
<220> FEATURE:
<223> OTHER INFORMATION: Synthetic peptide

<400> SEQUENCE: 245

```
Ser Lys Glu Glu Leu Lys Arg Lys Leu Asp Glu Leu Lys Lys Arg Ser
1               5                   10                  15
```

```
Asp Thr Leu Lys Glu Leu Ser Lys Lys Leu Lys Glu Ile Ser Glu Arg
            20                  25                  30

Asn Pro Asp Asp Lys Ser Val His Arg Thr Ile Ile Arg Ile His Arg
        35                  40                  45

Glu Phe Val Lys Asn His Lys Glu Ile Val Arg Val Ile Glu Glu Ile
    50                  55                  60

Val Ser Asp Lys Ser
65

<210> SEQ ID NO 246
<211> LENGTH: 71
<212> TYPE: PRT
<213> ORGANISM: Artificial Sequence
<220> FEATURE:
<223> OTHER INFORMATION: Synthetic peptide

<400> SEQUENCE: 246

Ser Lys Gln Asp Glu His Asp Arg Leu Leu Lys Ile His Asp Lys Leu
1               5                  10                  15

Val Lys Gln His Asp Glu Leu Leu Lys Leu Leu Thr Lys Leu Ser Arg
            20                  25                  30

Ala Gly Asp Ser Val Thr Lys Lys Leu Glu Glu Ile Leu Arg Lys
        35                  40                  45

Leu Gln Glu Val Ser Lys Gln Leu Glu Ser Leu Lys Asp Ala Asp
    50                  55                  60

Lys Val Ser Lys Asp Ile Asn
65                  70

<210> SEQ ID NO 247
<211> LENGTH: 69
<212> TYPE: PRT
<213> ORGANISM: Artificial Sequence
<220> FEATURE:
<223> OTHER INFORMATION: Synthetic peptide

<400> SEQUENCE: 247

Thr Val Gln Ser Leu Leu Glu Gln His Val Lys Ile Val Lys Arg Ser
1               5                  10                  15

Ile Glu Ile Leu Glu Arg His Thr Gln Ile Leu Gln Asp Ile Ala Arg
            20                  25                  30

Ser Gln Gly Val Ser Lys Glu Leu Glu Asp Val Glu Arg Gln Val Lys
        35                  40                  45

Glu Tyr Arg Lys Glu Val Lys Lys Leu Glu Glu Asp Leu Arg Gln Leu
    50                  55                  60

Ser Arg Asn Ser Lys
65

<210> SEQ ID NO 248
<211> LENGTH: 76
<212> TYPE: PRT
<213> ORGANISM: Artificial Sequence
<220> FEATURE:
<223> OTHER INFORMATION: Synthetic peptide

<400> SEQUENCE: 248

Ser Asp Ser Asp Arg Ile Glu Lys Leu Ile Arg Glu Ser Thr Glu Leu
1               5                  10                  15

Leu Lys Glu Gln Gln Lys Leu Ala Lys Arg Ser Arg Glu Leu Ala Glu
            20                  25                  30

Thr Val Glu Ser Leu Pro Leu Thr Glu Glu Tyr Leu Lys Gln Gln Arg
```

```
                35                  40                  45
Glu His Gln Lys Lys Ile Glu Lys Leu Leu Lys Asp Ser Glu Lys His
        50                  55                  60

Leu Glu Glu Leu Lys Arg Leu Val Lys Ser Glu Lys
65                  70                  75
```

<210> SEQ ID NO 249
<211> LENGTH: 70
<212> TYPE: PRT
<213> ORGANISM: Artificial Sequence
<220> FEATURE:
<223> OTHER INFORMATION: Synthetic peptide

<400> SEQUENCE: 249

```
Asp Ser Glu Lys Arg Ile Glu Asp Ile Leu Arg Thr Asp Leu Glu Leu
1               5                   10                  15

Ala Lys Arg Asp Ala Glu Leu Val Lys Glu His Ile Lys Leu Val Lys
                20                  25                  30

Arg Ile Asp Leu Ser Glu Leu Lys Lys Gln Val Glu Asp Val Glu
            35                  40                  45

Lys Glu Ser Lys Lys Leu Glu Asp Ser Ser Gly Lys Leu Val Gln Lys
        50                  55                  60

Val Arg Lys Arg Ser Ser
65                  70
```

<210> SEQ ID NO 250
<211> LENGTH: 80
<212> TYPE: PRT
<213> ORGANISM: Artificial Sequence
<220> FEATURE:
<223> OTHER INFORMATION: Synthetic peptide

<400> SEQUENCE: 250

```
Asp Glu Glu Glu Arg Ala Lys Asp Leu Arg Lys Tyr Leu Glu Glu Gln
1               5                   10                  15

Thr Gln Tyr Tyr Arg Thr Val Thr Glu His Leu Arg Asn Leu Glu Lys
                20                  25                  30

Val Val Glu Glu Leu Glu Arg Arg Gly Lys Pro Ser Ser Glu Leu Gln
            35                  40                  45

Gln Ile Leu Glu Arg Ser Gln Arg Ile Tyr Lys Glu Thr Thr Glu Ile
        50                  55                  60

Tyr Asp Thr Ser Lys Lys Leu Ile Glu Glu Leu Asp Lys His His Arg
65                  70                  75                  80
```

<210> SEQ ID NO 251
<211> LENGTH: 77
<212> TYPE: PRT
<213> ORGANISM: Artificial Sequence
<220> FEATURE:
<223> OTHER INFORMATION: Synthetic peptide

<400> SEQUENCE: 251

```
Pro Leu Glu Asp Ile Leu Lys Arg His Leu Asp Lys Val Arg Glu Leu
1               5                   10                  15

Val Arg Leu Ser Glu Glu Val Asn Lys Leu Ala Lys Glu Val Leu Asp
                20                  25                  30

Ile Leu Lys Asp Lys Arg Val Asp Glu Lys Glu Leu Asp Lys Val Leu
            35                  40                  45

Lys Glu Leu Glu Lys Val Val Glu Glu Tyr Glu Arg Ala Val Lys Glu
        50                  55                  60
```

```
Ser Arg Asp Leu Leu Arg Glu Leu Arg Glu Thr Thr Arg
65                  70                  75

<210> SEQ ID NO 252
<211> LENGTH: 75
<212> TYPE: PRT
<213> ORGANISM: Artificial Sequence
<220> FEATURE:
<223> OTHER INFORMATION: Synthetic peptide

<400> SEQUENCE: 252

Asp Lys Glu Arg Leu Leu Glu Ile His Glu Arg Ile Gln Lys Leu Leu
1               5                   10                  15

Asp Arg Asn Leu Glu Ile Ile Glu Arg Leu Leu Arg Leu Leu Arg Glu
                20                  25                  30

Ala Arg Asp Ile Lys Asp Asp Lys Leu Asp Lys Val Ile Lys Arg
            35                  40                  45

Leu Lys Glu Leu Ser Glu Glu Ser Lys Asp Ile Leu Asp Lys Ile Lys
        50                  55                  60

Glu Leu Leu Lys Glu Ser Glu Lys Glu Leu Thr
65                  70                  75

<210> SEQ ID NO 253
<211> LENGTH: 75
<212> TYPE: PRT
<213> ORGANISM: Artificial Sequence
<220> FEATURE:
<223> OTHER INFORMATION: Synthetic peptide

<400> SEQUENCE: 253

Pro Glu Asp Glu Val Ile Arg Val Ile Glu Glu Leu Leu Arg Ile Ala
1               5                   10                  15

Ala Glu Val Asp Glu Val His Arg Arg Asn Val Glu Val Gln Glu Glu
                20                  25                  30

Ala Ser Arg Val Thr Asp Arg Glu Arg Leu Glu Arg Leu Asn Arg Glu
            35                  40                  45

Ser Glu Glu Leu Ile Lys Arg Ser Arg Glu Leu Ile Glu Glu Gln Arg
        50                  55                  60

Lys Leu Ile Glu Arg Leu Glu Arg Leu Ala Thr
65                  70                  75

<210> SEQ ID NO 254
<211> LENGTH: 74
<212> TYPE: PRT
<213> ORGANISM: Artificial Sequence
<220> FEATURE:
<223> OTHER INFORMATION: Synthetic peptide

<400> SEQUENCE: 254

Asp Leu Glu Glu Leu Ile Lys Glu Tyr Ala Glu Val Val Arg Arg His
1               5                   10                  15

His Lys Ala Val Arg Asp Leu Glu Arg Leu Val Arg Glu Leu Ala Asn
                20                  25                  30

Ala Lys His Ala Ser Glu Glu Glu Leu Lys Arg Ile Ala Thr Glu Ile
            35                  40                  45

Leu Arg Ile Val Lys Glu Leu Ile Arg Val Gln Glu Arg Leu Ile Lys
        50                  55                  60

Leu Ser Glu Asp Ser Asn Glu Glu Ser Arg
65                  70
```

<210> SEQ ID NO 255
<211> LENGTH: 75
<212> TYPE: PRT
<213> ORGANISM: Artificial Sequence
<220> FEATURE:
<223> OTHER INFORMATION: Synthetic peptide

<400> SEQUENCE: 255

```
Pro Thr Asp Glu Val Ile Glu Val Leu Lys Glu Leu Leu Arg Ile His
1               5                   10                  15

Arg Glu Asn Leu Arg Val Asn Glu Glu Ile Val Glu Val Asn Glu Arg
                20                  25                  30

Ala Ser Arg Val Thr Asp Arg Glu Leu Glu Arg Leu Leu Arg Arg
            35                  40                  45

Ser Asn Glu Leu Ile Lys Arg Ser Arg Glu Leu Asn Glu Glu Ser Lys
        50                  55                  60

Lys Leu Ile Glu Lys Leu Glu Arg Leu Ala Thr
65                  70                  75
```

<210> SEQ ID NO 256
<211> LENGTH: 74
<212> TYPE: PRT
<213> ORGANISM: Artificial Sequence
<220> FEATURE:
<223> OTHER INFORMATION: Synthetic peptide

<400> SEQUENCE: 256

```
Asp Asn Glu Glu Ile Ile Lys Glu Ala Arg Arg Val Val Glu Glu Tyr
1               5                   10                  15

Lys Lys Ala Val Asp Arg Leu Glu Glu Leu Val Arg Arg Ala Glu Asn
                20                  25                  30

Ala Lys His Ala Ser Glu Lys Glu Leu Lys Asp Ile Val Arg Glu Ile
            35                  40                  45

Leu Arg Ile Ser Lys Glu Leu Asn Lys Val Ser Glu Arg Leu Ile Glu
        50                  55                  60

Leu Trp Glu Arg Ser Gln Glu Arg Ala Arg
65                  70
```

<210> SEQ ID NO 257
<211> LENGTH: 72
<212> TYPE: PRT
<213> ORGANISM: Artificial Sequence
<220> FEATURE:
<223> OTHER INFORMATION: Synthetic peptide

<400> SEQUENCE: 257

```
Pro Lys Glu Asp Ile Asp Arg Val Ser Arg Glu Leu Val Arg Val His
1               5                   10                  15

Lys Glu Leu Leu Glu Val Leu Arg Lys Ser Thr Glu Ile Val Glu Ala
                20                  25                  30

Val Ala Arg Asn Glu Lys Asp Glu Arg Thr Ile Glu Val Leu Glu
            35                  40                  45

Glu Gln Glu Arg Ala Val Arg Lys Leu Glu Glu Val Ser Lys Lys His
        50                  55                  60

Lys Glu Ala Val Lys Arg Leu Lys
65                  70
```

<210> SEQ ID NO 258
<211> LENGTH: 77
<212> TYPE: PRT

<213> ORGANISM: Artificial Sequence
<220> FEATURE:
<223> OTHER INFORMATION: Synthetic peptide

<400> SEQUENCE: 258

Glu Leu Glu Arg Leu Ser Glu Glu Ile Gln Lys Leu Ser Asp Arg Leu
1               5                   10                  15

Ile Glu Leu Ile Arg Arg His Ser Lys Val Leu Glu Glu Ile Val Arg
            20                  25                  30

Leu Leu Lys His Lys Asp Asn Asp Glu Arg Glu Val Arg Leu Leu
        35                  40                  45

Lys Leu Leu Arg Asp Leu Thr Arg Arg Tyr Glu Glu Val Leu Arg Lys
    50                  55                  60

Val Glu Glu Ile Val Lys Arg Gln Glu Asp Glu Ser Arg
65                  70                  75

<210> SEQ ID NO 259
<211> LENGTH: 72
<212> TYPE: PRT
<213> ORGANISM: Artificial Sequence
<220> FEATURE:
<223> OTHER INFORMATION: Synthetic peptide

<400> SEQUENCE: 259

Pro Glu Glu Asp Ile Leu Arg Leu Leu Arg Lys Leu Val Glu Val Asp
1               5                   10                  15

Lys Glu Leu Leu Glu Val Val Arg Glu Ser Thr Glu Val Val Arg Leu
            20                  25                  30

Val Ala Arg Asn Glu Lys Asp Val Glu Thr Val Glu Val Leu Arg
        35                  40                  45

Lys Gln Glu Glu Val Val Arg Lys Tyr Glu Arg Val Ser Arg Glu Leu
    50                  55                  60

Glu Glu Ala Val Arg Arg Leu Lys
65                  70

<210> SEQ ID NO 260
<211> LENGTH: 77
<212> TYPE: PRT
<213> ORGANISM: Artificial Sequence
<220> FEATURE:
<223> OTHER INFORMATION: Synthetic peptide

<400> SEQUENCE: 260

Glu Leu Lys Asp Leu Val Glu Glu Ile Val Lys Leu Ser Lys Glu Asn
1               5                   10                  15

Leu Lys Leu Trp Glu Asp His Ser Arg Val Leu Glu Glu Ile Val Arg
            20                  25                  30

Leu Leu Lys His Lys Asp Asn Asp Glu Arg Glu Val Arg Leu Leu
        35                  40                  45

Lys Leu Leu Glu Asp Leu Thr Arg Arg Ala Glu Glu Thr Ser Arg Arg
    50                  55                  60

Ile Glu Glu Ile Val Lys Glu Ala Glu Asp Arg Ala Arg
65                  70                  75

<210> SEQ ID NO 261
<211> LENGTH: 74
<212> TYPE: PRT
<213> ORGANISM: Artificial Sequence
<220> FEATURE:
<223> OTHER INFORMATION: Synthetic peptide -continued

<400> SEQUENCE: 261

Asp Glu Glu Arg Glu Leu Arg Glu Val Leu Arg Lys His His Arg Val
1               5                   10                  15

Val Arg Glu Trp Thr Lys Val Val Glu Glu Leu Lys Arg Val Val Glu
                20                  25                  30

Leu Leu Lys Arg Gly Glu Thr Ser Glu Glu Asp Leu Leu Arg Val Leu
            35                  40                  45

Lys Lys Leu Leu Glu Met Asp Lys Arg Ile Leu Glu Val Asn Arg Glu
50                  55                  60

Val Leu Arg Val Leu Glu Lys Arg Leu Thr
65                  70

<210> SEQ ID NO 262
<211> LENGTH: 70
<212> TYPE: PRT
<213> ORGANISM: Artificial Sequence
<220> FEATURE:
<223> OTHER INFORMATION: Synthetic peptide

<400> SEQUENCE: 262

Ser Leu Glu Glu Ile Ile Glu Glu Leu Val Glu Leu Val Arg Arg Ser
1               5                   10                  15

Val Glu Ile Ala Lys Glu Ser Asp Glu Val Ala Arg Arg Ile Val Glu
                20                  25                  30

Ser Glu Asp Lys Lys Glu Leu Ile Asp Thr Leu Arg Asp Leu His
            35                  40                  45

Arg Glu Trp Gln Glu Val Thr Lys Arg Ala Glu Leu Val Arg Glu
50                  55                  60

Ala Glu Lys Glu Val Arg
65                  70

<210> SEQ ID NO 263
<211> LENGTH: 72
<212> TYPE: PRT
<213> ORGANISM: Artificial Sequence
<220> FEATURE:
<223> OTHER INFORMATION: Synthetic peptide

<400> SEQUENCE: 263

Thr Ala Glu Glu Leu Leu Glu Val His Lys Lys Ser Asp Arg Val Thr
1               5                   10                  15

Lys Glu His Leu Arg Val Ser Glu Glu Ile Leu Lys Val Val Glu Val
                20                  25                  30

Leu Thr Arg Gly Glu Val Ser Ser Glu Val Leu Lys Arg Val Leu Arg
            35                  40                  45

Lys Leu Glu Glu Leu Thr Asp Lys Leu Arg Arg Val Thr Glu Glu Gln
50                  55                  60

Arg Arg Val Val Glu Lys Leu Asn
65                  70

<210> SEQ ID NO 264
<211> LENGTH: 76
<212> TYPE: PRT
<213> ORGANISM: Artificial Sequence
<220> FEATURE:
<223> OTHER INFORMATION: Synthetic peptide

<400> SEQUENCE: 264

Asp Leu Glu Asp Leu Leu Arg Arg Leu Arg Arg Leu Val Asp Glu Gln
1               5                   10                  15

```
Arg Arg Leu Val Glu Glu Leu Glu Arg Val Ser Arg Arg Leu Glu Lys
        20                  25                  30

Ala Val Arg Asp Asn Glu Asp Glu Arg Glu Leu Ala Arg Leu Ser Arg
            35                  40                  45

Glu His Ser Asp Ile Gln Asp Lys His Asp Lys Leu Ala Arg Glu Ile
50                  55                  60

Leu Glu Val Leu Lys Arg Leu Leu Glu Arg Thr Glu
65                  70                  75
```

<210> SEQ ID NO 265
<211> LENGTH: 72
<212> TYPE: PRT
<213> ORGANISM: Artificial Sequence
<220> FEATURE:
<223> OTHER INFORMATION: Synthetic peptide

<400> SEQUENCE: 265

```
Pro Glu Asp Asp Val Val Arg Ile Ile Lys Glu Asp Leu Glu Ser Asn
1               5                   10                  15

Arg Glu Val Leu Arg Glu Gln Lys Glu Ile His Arg Ile Leu Glu Leu
            20                  25                  30

Val Thr Arg Gly Glu Val Ser Glu Glu Ala Ile Asp Arg Val Leu Lys
            35                  40                  45

Arg Gln Glu Asp Leu Leu Lys Lys Gln Lys Glu Ser Thr Asp Lys Ala
50                  55                  60

Arg Lys Val Val Glu Glu Arg Arg
65                  70
```

<210> SEQ ID NO 266
<211> LENGTH: 70
<212> TYPE: PRT
<213> ORGANISM: Artificial Sequence
<220> FEATURE:
<223> OTHER INFORMATION: Synthetic peptide

<400> SEQUENCE: 266

```
Asp Glu Val Arg Leu Ile Thr Glu Trp Leu Lys Leu Ser Glu Glu Ser
1               5                   10                  15

Thr Arg Leu Leu Lys Glu Leu Val Glu Leu Thr Arg Leu Leu Arg Asn
            20                  25                  30

Asn Val Pro Asn Val Glu Glu Ile Leu Arg Glu His Glu Arg Ile Ser
            35                  40                  45

Arg Glu Leu Glu Arg Leu Ser Arg Arg Leu Lys Asp Leu Ala Asp Lys
50                  55                  60

Leu Glu Arg Thr Arg Arg
65                  70
```

<210> SEQ ID NO 267
<211> LENGTH: 70
<212> TYPE: PRT
<213> ORGANISM: Artificial Sequence
<220> FEATURE:
<223> OTHER INFORMATION: Synthetic peptide

<400> SEQUENCE: 267

```
Asp Glu Asp Glu Val Val Lys Val His Glu Glu His Val Lys Ser His
1               5                   10                  15

Glu Glu Ile His Arg Ser His Glu Glu Val Val Arg Ala Ala Glu Glu
            20                  25                  30
```

```
Asp Lys Arg Asp Ser Arg Glu Leu Arg Thr Leu Met Glu Glu His Arg
            35                  40                  45

Lys Leu Leu Glu Glu Asn Glu Lys Ser Ile Glu Val Lys Lys Ile
 50                  55                  60

His Glu Arg Val Lys Arg
 65                  70

<210> SEQ ID NO 268
<211> LENGTH: 80
<212> TYPE: PRT
<213> ORGANISM: Artificial Sequence
<220> FEATURE:
<223> OTHER INFORMATION: Synthetic peptide

<400> SEQUENCE: 268

Lys Lys Glu Glu Leu Ile Asp Ile Ser Lys Glu Val Leu Asp Leu Asp
 1               5                  10                  15

Asp Glu Ile Asn Lys Ile Ser Lys Glu Ile Leu Glu Leu Ile Lys Lys
                20                  25                  30

Leu Leu Arg Leu Lys Glu Glu Gly Arg Glu Asp Lys Asp Lys Ala Arg
            35                  40                  45

Glu Val Lys Arg Arg Ile Arg Glu Leu His Arg Ile Gln Glu Leu
 50                  55                  60

Asn Lys Arg Leu Arg Glu Leu His Lys Arg Val Gln Glu Thr Lys Arg
 65                  70                  75                  80

<210> SEQ ID NO 269
<211> LENGTH: 77
<212> TYPE: PRT
<213> ORGANISM: Artificial Sequence
<220> FEATURE:
<223> OTHER INFORMATION: Synthetic peptide

<400> SEQUENCE: 269

Pro Glu Glu Asp Ile Ala Arg Arg Val Glu Asp Leu Leu Arg Lys Ser
 1               5                  10                  15

Glu Glu Leu Ile Lys Glu Ser Glu Lys Ile Leu Lys Glu Ser Lys Arg
                20                  25                  30

Leu Leu Asp Arg Asn Asp Ser Asp Lys Arg Val Leu Glu Thr Asn Leu
            35                  40                  45

Arg Leu Ile Asp Lys His Thr Lys Leu Leu Glu Arg Asn Leu Glu Leu
 50                  55                  60

Leu Glu Glu Leu Leu Lys Leu Ala Glu Asp Val Ala Lys
 65                  70                  75

<210> SEQ ID NO 270
<211> LENGTH: 74
<212> TYPE: PRT
<213> ORGANISM: Artificial Sequence
<220> FEATURE:
<223> OTHER INFORMATION: Synthetic peptide

<400> SEQUENCE: 270

Arg Phe Lys Asp Leu Ser Arg Glu Tyr Ile Glu Val Val Lys Arg Leu
 1               5                  10                  15

Leu Glu Leu Ser Arg Glu Ala Leu Glu Val Leu Arg Glu Ile Lys Asp
                20                  25                  30

Thr Asp Lys Thr Asp Lys Lys Arg Ile Lys Glu Leu Ile Asp Arg Leu
            35                  40                  45

Arg Lys Leu Ile Glu Glu Tyr Lys Arg Ile Ile Asp Arg Leu Arg Lys
```

```
                        50                  55                  60

Leu Ser Lys Asp Leu Glu Glu Glu His Arg
 65                  70

<210> SEQ ID NO 271
<211> LENGTH: 73
<212> TYPE: PRT
<213> ORGANISM: Artificial Sequence
<220> FEATURE:
<223> OTHER INFORMATION: Synthetic peptide

<400> SEQUENCE: 271

Asp Glu Glu Glu Leu Val Lys Ile Leu Lys Glu Leu Gln Arg Leu Ser
  1               5                  10                  15

Glu Glu Ser Leu Glu Ile Asn Lys Arg Leu Val Glu Ile Leu Arg Leu
                 20                  25                  30

Leu Arg Arg Gly Glu Val Pro Lys Glu Val Glu Lys Lys Leu Arg
             35                  40                  45

Glu Ile Lys Lys Glu Gln Glu Lys Leu Asp Arg Glu His Glu Lys Ile
         50                  55                  60

Lys Lys Arg Ile Glu Glu Ile Thr Lys
 65                  70

<210> SEQ ID NO 272
<211> LENGTH: 74
<212> TYPE: PRT
<213> ORGANISM: Artificial Sequence
<220> FEATURE:
<223> OTHER INFORMATION: Synthetic peptide

<400> SEQUENCE: 272

Ser Leu Lys Glu Lys Ile Leu Glu Ile Ile Glu Arg Asn Met Lys Leu
  1               5                  10                  15

Val Glu Leu Ser Asn Arg Ser Val Glu Ile Val Ala Arg Ile Leu Lys
                 20                  25                  30

Gly Glu Lys Asp Asp Glu Glu Thr Leu Glu Arg Leu Leu Arg Glu Trp
             35                  40                  45

Asp Lys Ile Thr Arg Asp Tyr Glu Glu Ile Ile Lys Glu Ser Arg Lys
         50                  55                  60

Leu Val Lys Glu Leu Glu Glu Glu Ala Lys
 65                  70

<210> SEQ ID NO 273
<211> LENGTH: 74
<212> TYPE: PRT
<213> ORGANISM: Artificial Sequence
<220> FEATURE:
<223> OTHER INFORMATION: Synthetic peptide

<400> SEQUENCE: 273

Ser Lys Thr Glu Ile Leu Arg Lys Ala Leu Glu Ile His Lys Glu Gln
  1               5                  10                  15

Ile Asp Ile Val Arg Lys Leu Ile Glu Leu Ser Glu Glu Val Leu Lys
                 20                  25                  30

Leu Val Glu Glu Ser Lys Glu Lys Asn Leu Glu Lys Leu Lys Arg Ile
             35                  40                  45

Asp Glu Glu Thr Asp Arg Leu Leu Glu Arg Leu Asp Glu Leu His Lys
         50                  55                  60

Arg Leu Thr Glu Leu Ala Glu Arg Leu Lys
 65                  70
```

<210> SEQ ID NO 274
<211> LENGTH: 80
<212> TYPE: PRT
<213> ORGANISM: Artificial Sequence
<220> FEATURE:
<223> OTHER INFORMATION: Synthetic peptide

<400> SEQUENCE: 274

```
Ser Asp Asp Glu Ala Arg Lys Gln Leu Glu Glu Met Lys Arg Arg Leu
1               5                   10                  15

Arg Glu Val Glu Lys Lys Ser Lys Arg Val Glu Glu Arg Val Arg Glu
                20                  25                  30

Leu Glu Arg Leu Val Arg Glu Asn Arg Glu Asp Glu Asp Arg Val Leu
            35                  40                  45

Lys Thr Leu Glu Asp Leu Leu Arg Glu Asn Glu Lys Leu Val Arg Thr
        50                  55                  60

Ile Glu Arg His Val Arg Glu Gln Arg Glu Leu Ser Lys Glu Val Lys
65                  70                  75                  80
```

<210> SEQ ID NO 275
<211> LENGTH: 73
<212> TYPE: PRT
<213> ORGANISM: Artificial Sequence
<220> FEATURE:
<223> OTHER INFORMATION: Synthetic peptide

<400> SEQUENCE: 275

```
Ser Glu Glu Leu Glu Lys Lys Ala Asp Glu Leu Arg Lys Leu Ser
1               5                   10                  15

Glu Glu Trp Arg Lys Leu Gln Glu Glu Asp Lys Arg Leu Ser Glu Met
                20                  25                  30

Val Glu Lys Gly Glu Leu Asp Leu Gln Glu Val Asp Glu His Ser Leu
            35                  40                  45

Arg Val Leu Glu Arg Ala Thr Glu Val His Arg Thr Val Asp Lys Val
        50                  55                  60

Ile Glu Glu Ile Leu Arg Thr Thr Asn
65                  70
```

<210> SEQ ID NO 276
<211> LENGTH: 77
<212> TYPE: PRT
<213> ORGANISM: Artificial Sequence
<220> FEATURE:
<223> OTHER INFORMATION: Synthetic peptide

<400> SEQUENCE: 276

```
Ser Glu Lys Glu Arg His Arg Glu Ser Gln Glu Thr Gln Glu Ile
1               5                   10                  15

Arg Arg Thr His Glu Glu Ile Ile Arg Lys Leu Glu Glu Ile Leu Arg
                20                  25                  30

Arg Ala Lys Ala Gly Glu Leu Pro Glu Glu Thr Leu Asp Arg Leu Arg
            35                  40                  45

Arg Ile Met Glu Arg Leu Lys Glu Leu Ser Glu Arg Leu Asp Asp Leu
        50                  55                  60

Val Arg Lys Leu Arg Asp Asp His Arg Arg Glu Gln Lys
65                  70                  75
```

<210> SEQ ID NO 277
<211> LENGTH: 76

```
<212> TYPE: PRT
<213> ORGANISM: Artificial Sequence
<220> FEATURE:
<223> OTHER INFORMATION: Synthetic peptide

<400> SEQUENCE: 277

Ser Glu Lys Glu Ile Leu Glu Glu Leu Lys Arg Ile Leu Lys Arg Val
1               5                   10                  15

Lys Asp Ile Ser Asp Arg Leu Glu Glu Leu Asp Lys Arg Thr Glu Glu
            20                  25                  30

Ile Ala Arg Arg Glu Pro Thr Lys Glu Leu Val Asp Glu Leu Val Lys
        35                  40                  45

Ile His Arg Asp Trp Leu Arg Leu His Glu Glu Ile Leu Lys Leu Val
    50                  55                  60

Asp Asp Ala Leu Lys Lys Val Glu Asp Ala Thr Lys
65                  70                  75

<210> SEQ ID NO 278
<211> LENGTH: 73
<212> TYPE: PRT
<213> ORGANISM: Artificial Sequence
<220> FEATURE:
<223> OTHER INFORMATION: Synthetic peptide

<400> SEQUENCE: 278

Asp Leu Arg Glu Leu Leu Glu Leu Gln Arg Glu Ala Ser Arg Leu His
1               5                   10                  15

Arg Glu Leu Val Lys Leu Leu Thr Glu Leu Val Lys Lys Leu Glu Leu
            20                  25                  30

Ile Ala Lys Gly Glu Asp Ile Arg Glu Glu Asp Leu Lys Arg Ile Lys
        35                  40                  45

Glu Arg Leu Glu Glu Ile Lys Lys Arg Ser Lys Arg Ile Lys Glu Glu
    50                  55                  60

Ser Asp Glu Ile Asp Lys Lys Thr Lys
65                  70

<210> SEQ ID NO 279
<211> LENGTH: 72
<212> TYPE: PRT
<213> ORGANISM: Artificial Sequence
<220> FEATURE:
<223> OTHER INFORMATION: Synthetic peptide

<400> SEQUENCE: 279

Ser Glu Arg Glu Leu Gln Arg Glu Leu Asn Lys Ile Val Arg Arg Ile
1               5                   10                  15

Leu Glu Ile His Arg Glu Val Ser Glu Leu His Gln Arg Ala Val Lys
            20                  25                  30

Leu Ile Arg Glu Asn Asp Asn Ser Glu Glu Leu Glu Glu Ile Ser Arg
        35                  40                  45

Arg Ile Glu Glu Leu Ser Lys Gly Leu Glu Lys Leu Val Arg Glu His
    50                  55                  60

Asp Glu Ile Val Lys Thr Ile Glu
65                  70

<210> SEQ ID NO 280
<211> LENGTH: 77
<212> TYPE: PRT
<213> ORGANISM: Artificial Sequence
<220> FEATURE:
<223> OTHER INFORMATION: Synthetic peptide
```

<400> SEQUENCE: 280

Ser Glu Arg Glu Lys Leu Asp Arg Asn Asp Glu Glu Leu Lys Glu Ile
1               5                   10                  15

Asn Lys Arg Val Glu Glu Ile Lys Glu Arg Ser Asp Arg Ile Thr Glu
            20                  25                  30

Ala Ile Glu Lys Asn Glu Arg Ser Glu Glu Ile Arg Arg Leu Ser
        35                  40                  45

Arg Glu Gln Asn Glu Ala Leu Gln Arg Leu Leu Leu His Lys Lys
    50                  55                  60

Leu Val Lys Leu His Arg Glu Leu Leu Glu Asp Thr Arg
65                  70                  75

<210> SEQ ID NO 281
<211> LENGTH: 76
<212> TYPE: PRT
<213> ORGANISM: Artificial Sequence
<220> FEATURE:
<223> OTHER INFORMATION: Synthetic peptide

<400> SEQUENCE: 281

Asp Lys Glu Asp Val Ile Arg Val His Asp Glu Gln His Lys Leu Ile
1               5                   10                  15

Glu Glu Gln Leu Glu Leu Thr Arg Arg Ile Ala Glu Leu Val Arg Glu
            20                  25                  30

Ile Ala Lys Asn Thr Ala Ser Glu Glu Ile Lys Glu Met Leu Lys
        35                  40                  45

Glu Ile Lys Arg Leu Asp Asp Arg Ser Arg Glu Ile Gln Asp Arg Leu
    50                  55                  60

Gln Lys Leu Leu Glu Glu Ile Arg Arg Lys Thr Lys
65                  70                  75

<210> SEQ ID NO 282
<211> LENGTH: 73
<212> TYPE: PRT
<213> ORGANISM: Artificial Sequence
<220> FEATURE:
<223> OTHER INFORMATION: Synthetic peptide

<400> SEQUENCE: 282

Thr Glu Glu Glu Ile Val Glu Leu Asn Lys Asp Ile Gln Arg Lys Ser
1               5                   10                  15

Lys Glu His Ile Asp Leu Gln Asn Glu Leu Val Lys Lys Ile Glu Arg
            20                  25                  30

Ala Ile Arg Glu Asn Asn Ile Thr Glu Glu Leu Leu Glu Glu Leu Glu
        35                  40                  45

Arg Leu Leu Arg Glu Ser Glu Lys Ile Val Glu Ile Arg Arg Ile
    50                  55                  60

Thr Asp Lys Ile Arg Lys Asp Ala Lys
65                  70

<210> SEQ ID NO 283
<211> LENGTH: 72
<212> TYPE: PRT
<213> ORGANISM: Artificial Sequence
<220> FEATURE:
<223> OTHER INFORMATION: Synthetic peptide

<400> SEQUENCE: 283

Ser Glu Lys Glu Ile Leu Glu Arg Leu Leu Arg Leu Ser Lys Glu Gln

```
                1               5                   10                  15
Asn Glu Ile Ser Glu Glu Ile His Arg Leu Thr Glu Arg Leu Val Glu
                20                  25                  30

Leu Lys Arg Arg Lys Asp Asp Glu Arg Leu Lys Arg Ile Leu Asp
            35                  40                  45

Arg Gln Lys Arg Leu Val Glu Arg Ala Arg Glu Ile Ser Lys Glu Tyr
    50                  55                  60

Glu Asp Leu Leu Arg Lys Leu Glu
65                  70

<210> SEQ ID NO 284
<211> LENGTH: 69
<212> TYPE: PRT
<213> ORGANISM: Artificial Sequence
<220> FEATURE:
<223> OTHER INFORMATION: Synthetic peptide

<400> SEQUENCE: 284

Ser Met Glu Glu Leu Leu Arg Lys Asn Ala Arg Leu Ser Arg Lys Gln
1               5                   10                  15

Leu Lys Ile Ile Asp Glu His Leu Glu Leu Ser Thr Lys Leu Thr Arg
            20                  25                  30

Gly Glu Ala Gly Asp Glu Thr Leu Glu Glu Ile Glu Arg Arg Ser Arg
        35                  40                  45

Glu Met Leu Glu Glu Gln Arg Val Asp Glu Ser Lys Arg Ile
    50                  55                  60

Arg Glu Lys Leu Lys
65

<210> SEQ ID NO 285
<211> LENGTH: 76
<212> TYPE: PRT
<213> ORGANISM: Artificial Sequence
<220> FEATURE:
<223> OTHER INFORMATION: Synthetic peptide

<400> SEQUENCE: 285

Ser Glu Glu Glu Ile Arg Asp Ile Val Glu Lys Leu Leu Arg Thr His
1               5                   10                  15

Glu Glu Val Leu Lys Glu Ile Lys Lys Leu Leu Asp Asp Ser Glu Arg
            20                  25                  30

Val Arg Arg Arg Glu Leu Asp Lys Lys Asp Leu Asp Arg Ile Gln Lys
        35                  40                  45

Glu Gln Arg Asp Ile Gln Glu Glu Asn Lys Glu Lys Ala Lys Arg Phe
    50                  55                  60

Asp Glu Leu Val Lys Glu Leu Lys Lys Ala Ala Lys
65                  70                  75

<210> SEQ ID NO 286
<211> LENGTH: 70
<212> TYPE: PRT
<213> ORGANISM: Artificial Sequence
<220> FEATURE:
<223> OTHER INFORMATION: Synthetic peptide

<400> SEQUENCE: 286

Ser Glu Glu Glu His Arg Arg Thr Met Glu Lys Val Glu Lys Glu Val
1               5                   10                  15

Arg Asp Ile Lys Arg Arg Ser Glu Glu Val Lys Lys Val Lys Ala
            20                  25                  30
```

-continued

Asn Thr Leu Ser Glu Glu Asp Leu Val Arg Leu Leu Glu Arg Leu Val
                35                  40                  45

Glu Asp His Lys Arg Leu Gln Asp Leu Ser Gln Ile Ile Glu Arg
     50                  55                  60

Asp Glu Lys Ala Thr Lys
 65                  70

<210> SEQ ID NO 287
<211> LENGTH: 72
<212> TYPE: PRT
<213> ORGANISM: Artificial Sequence
<220> FEATURE:
<223> OTHER INFORMATION: Synthetic peptide

<400> SEQUENCE: 287

Asp Glu Asp Glu Leu Ala Lys Glu Ile Glu Asp Val Gln Arg Arg Asn
  1               5                  10                  15

Lys Glu Ser Gln Glu Glu His Asp Lys Ser Val Lys Lys Leu Glu Ala
                 20                  25                  30

Ala Glu Arg Gly Glu Ile Asp Glu Asp Ser Leu Leu Arg Val Leu Glu
                35                  40                  45

Glu Asp Ile Lys Val Leu Glu Lys Asp Ile Glu Val Leu Glu Arg Ser
     50                  55                  60

Ile Glu Val Ile Glu Lys Ala Glu
 65                  70

<210> SEQ ID NO 288
<211> LENGTH: 73
<212> TYPE: PRT
<213> ORGANISM: Artificial Sequence
<220> FEATURE:
<223> OTHER INFORMATION: Synthetic peptide

<400> SEQUENCE: 288

Ser Glu Lys Glu Leu Ile Arg Arg Leu Leu Glu Gln Gln Arg Gln His
  1               5                  10                  15

Leu Arg Leu Ser Glu Arg Leu Ile Glu Leu Ser Arg Arg Leu Val Glu
                 20                  25                  30

Val Val Arg Lys Gly Lys Asp Asn Arg Asp Leu Leu Arg Glu Leu Lys
                35                  40                  45

Lys Leu Ser Glu Glu His Lys Lys His Ser Lys Asp His Glu Lys
     50                  55                  60

Val Arg Glu Ile Arg Glu Arg Glu Lys
 65                  70

<210> SEQ ID NO 289
<211> LENGTH: 75
<212> TYPE: PRT
<213> ORGANISM: Artificial Sequence
<220> FEATURE:
<223> OTHER INFORMATION: Synthetic peptide

<400> SEQUENCE: 289

Asp Arg Lys Asp Leu Leu Lys Arg Asn Ile Lys Leu Leu Asp Arg His
  1               5                  10                  15

Leu Lys Ile Leu Asp Thr Ile Leu Lys Leu Leu Glu Lys Leu Ser Glu
                 20                  25                  30

Leu Leu Lys Lys Ser Ser Glu Glu Val Val Lys Glu Tyr Lys Lys
                35                  40                  45

Ile Leu Asp Glu Ile Arg Lys Leu Leu Glu Glu Ser Lys Glu Ile His
    50                  55                  60

Lys Glu Ser Lys Glu Ile Leu Glu Arg Glu Ser
65                  70                  75

<210> SEQ ID NO 290
<211> LENGTH: 75
<212> TYPE: PRT
<213> ORGANISM: Artificial Sequence
<220> FEATURE:
<223> OTHER INFORMATION: Synthetic peptide

<400> SEQUENCE: 290

Asp Glu Glu Lys Leu Ile Glu Arg Ser Lys Arg Leu Gln Glu Glu Ser
1               5                   10                  15

Glu Gln Leu Leu Glu Lys Phe Glu Gln Ile Leu Arg Glu Leu Thr Glu
            20                  25                  30

Leu Leu Glu Lys Pro Asp Ser Glu Glu Leu Ala Arg Lys Ile Lys Lys
        35                  40                  45

Leu His Asp Glu Leu Arg Lys Ile Ile Lys Arg Asn Gln Glu Leu Ile
    50                  55                  60

Arg Glu His Glu Glu Ile Leu Arg Lys Arg Asp
65                  70                  75

<210> SEQ ID NO 291
<211> LENGTH: 234
<212> TYPE: PRT
<213> ORGANISM: Artificial Sequence
<220> FEATURE:
<223> OTHER INFORMATION: Synthetic peptide

<400> SEQUENCE: 291

Pro Lys Glu Glu Ala Arg Glu Leu Ile Arg Lys Gln Lys Glu Leu Ile
1               5                   10                  15

Lys Glu Gln Lys Lys Leu Ile Lys Glu Ala Lys Gln Lys Ser Asp Ser
            20                  25                  30

Arg Asp Ala Glu Arg Ile Trp Lys Arg Ser Arg Glu Ile Asn Arg Glu
        35                  40                  45

Ser Lys Lys Ile Asn Lys Arg Ile Lys Glu Leu Ile Lys Ser Gly Ser
    50                  55                  60

Glu Gly Ser Gly Ser Gly Ser Gly Ser Thr Lys Glu Asp Ile Leu
65                  70                  75                  80

Glu Arg Gln Arg Lys Ile Ile Glu Arg Ala Gln Glu Ile His Arg Arg
            85                  90                  95

Gln Gln Glu Ile Leu Glu Glu Leu Arg Ile Ile Arg Lys Pro Gly
            100                 105                 110

Ser Ser Glu Glu Ala Met Lys Arg Met Leu Lys Leu Leu Glu Glu Ser
        115                 120                 125

Leu Arg Leu Leu Lys Glu Leu Leu Glu Leu Ser Glu Glu Ser Ala Gln
    130                 135                 140

Leu Leu Tyr Glu Gln Arg Gly Ser Glu Gly Ser Gly Ser Glu Gly Ser
145                 150                 155                 160

Gly Ser Asp Ser Asp Glu His Leu Lys Lys Leu Lys Thr Phe Leu Glu
                165                 170                 175

Asn Leu Arg Arg His Leu Asp Arg Leu Asp Lys His Ile Lys Gln Leu
            180                 185                 190

Arg Asp Ile Leu Ser Glu Asn Pro Glu Asp Glu Arg Val Lys Asp Val
        195                 200                 205

```
Ile Asp Leu Ser Glu Arg Ser Val Arg Ile Val Lys Thr Val Ile Lys
    210                 215                 220

Ile Phe Glu Asp Ser Val Arg Lys Lys Glu
225                 230
```

<210> SEQ ID NO 292
<211> LENGTH: 76
<212> TYPE: PRT
<213> ORGANISM: Artificial Sequence
<220> FEATURE:
<223> OTHER INFORMATION: Synthetic peptide

<400> SEQUENCE: 292

```
Thr Glu Lys Arg Leu Leu Glu Glu Ala Glu Arg Ala His Arg Glu Gln
1               5                   10                  15

Lys Glu Ile Ile Lys Lys Ala Gln Glu Leu His Arg Arg Leu Glu Glu
            20                  25                  30

Ile Val Arg Gln Ser Gly Ser Ser Glu Glu Ala Lys Lys Glu Ala Lys
        35                  40                  45

Lys Ile Leu Glu Glu Ile Arg Glu Leu Ser Lys Arg Ser Leu Glu Leu
    50                  55                  60

Leu Arg Glu Ile Leu Tyr Leu Ser Gln Glu Gln Lys
65                  70                  75
```

<210> SEQ ID NO 293
<211> LENGTH: 93
<212> TYPE: PRT
<213> ORGANISM: Artificial Sequence
<220> FEATURE:
<223> OTHER INFORMATION: Synthetic peptide

<400> SEQUENCE: 293

```
Gly Ser Ser His His His His His His Ser Ser Gly Glu Asn Leu Tyr
1               5                   10                  15

Phe Gln Gly Ser Asp Asp Lys Glu Leu Asp Lys Leu Leu Asp Thr Leu
            20                  25                  30

Glu Lys Ile Leu Gln Thr Ala Thr Lys Ile Ile Asp Asp Ala Asn Lys
        35                  40                  45

Leu Leu Glu Lys Leu Arg Arg Ser Glu Arg Lys Asp Pro Lys Val Val
    50                  55                  60

Glu Thr Tyr Val Glu Leu Leu Lys Arg His Glu Lys Ala Val Lys Glu
65                  70                  75                  80

Leu Leu Glu Ile Ala Lys Thr His Ala Lys Lys Val Glu
                85                  90
```

<210> SEQ ID NO 294
<211> LENGTH: 150
<212> TYPE: PRT
<213> ORGANISM: Artificial Sequence
<220> FEATURE:
<223> OTHER INFORMATION: Synthetic peptide

<400> SEQUENCE: 294

```
Pro Lys Glu Glu Ala Arg Glu Leu Ile Arg Lys Gln Lys Glu Leu Ile
1               5                   10                  15

Lys Glu Gln Lys Lys Leu Ile Lys Glu Ala Lys Gln Lys Ser Asp Ser
            20                  25                  30

Arg Asp Ala Glu Arg Ile Trp Lys Arg Ser Arg Glu Ile Asn Arg Glu
        35                  40                  45
```

```
Ser Lys Lys Ile Asn Lys Arg Ile Lys Glu Leu Ile Lys Ser Gly Ser
 50                  55                  60

Glu Gly Ser Gly Ser Glu Gly Ser Gly Ser Thr Lys Glu Asp Ile Leu
 65                  70                  75                  80

Glu Arg Gln Arg Lys Ile Ile Glu Arg Ala Gln Glu Ile His Arg Arg
                 85                  90                  95

Gln Gln Glu Ile Leu Glu Glu Leu Glu Arg Ile Ile Arg Lys Pro Gly
            100                 105                 110

Ser Ser Glu Glu Ala Met Lys Arg Met Leu Lys Leu Leu Glu Glu Ser
            115                 120                 125

Leu Arg Leu Leu Lys Glu Leu Leu Glu Leu Ser Glu Glu Ser Ala Gln
            130                 135                 140

Leu Leu Tyr Glu Gln Arg
145                 150

<210> SEQ ID NO 295
<211> LENGTH: 96
<212> TYPE: PRT
<213> ORGANISM: Artificial Sequence
<220> FEATURE:
<223> OTHER INFORMATION: Synthetic peptide

<400> SEQUENCE: 295

Gly Ser His His His His His His Gly Ser Gly Ser Glu Asn Leu Tyr
 1               5                  10                  15

Phe Gln Gly Ser Thr Glu Lys Arg Leu Leu Glu Glu Ala Glu Arg Ala
                 20                  25                  30

His Arg Glu Gln Lys Glu Ile Lys Lys Ala Gln Glu Leu His Arg
             35                  40                  45

Arg Leu Glu Glu Ile Val Arg Gln Ser Gly Ser Ser Glu Glu Ala Lys
 50                  55                  60

Lys Glu Ala Lys Lys Ile Leu Glu Glu Ile Arg Glu Leu Ser Lys Arg
 65                  70                  75                  80

Ser Leu Glu Leu Leu Arg Glu Ile Leu Tyr Leu Ser Gln Glu Gln Lys
                 85                  90                  95

<210> SEQ ID NO 296
<211> LENGTH: 156
<212> TYPE: PRT
<213> ORGANISM: Artificial Sequence
<220> FEATURE:
<223> OTHER INFORMATION: Synthetic peptide

<400> SEQUENCE: 296

Thr Glu Arg Lys Leu Leu Glu Arg Ser Arg Arg Leu Gln Glu Glu Ser
 1               5                  10                  15

Lys Arg Leu Leu Asp Glu Met Ala Glu Ile Met Arg Ile Lys Lys
                 20                  25                  30

Leu Leu Asp Asp Pro Asp Ser Glu Asp Ile Ala Arg Glu Ile Lys Glu
             35                  40                  45

Leu Leu Arg Arg Leu Lys Glu Ile Ile Glu Arg Asn Gln Arg Ile Ala
 50                  55                  60

Lys Glu His Glu Tyr Ile Ala Arg Glu Arg Ser Gly Pro Gly Ser Gly
 65                  70                  75                  80

Ser Glu Gly Ser Asp Ser Asp Glu His Leu Lys Lys Leu Lys Thr Phe
                 85                  90                  95

Leu Glu Asn Leu Arg Arg His Leu Asp Arg Leu Asp Lys His Ile Lys
            100                 105                 110
```

```
Gln Leu Arg Asp Ile Leu Ser Glu Asn Pro Glu Asp Glu Arg Val Lys
        115                 120                 125

Asp Val Ile Asp Leu Ser Glu Arg Ser Val Arg Ile Val Lys Thr Val
    130                 135                 140

Ile Lys Ile Phe Glu Asp Ser Val Arg Lys Lys Glu
145                 150                 155

<210> SEQ ID NO 297
<211> LENGTH: 75
<212> TYPE: PRT
<213> ORGANISM: Artificial Sequence
<220> FEATURE:
<223> OTHER INFORMATION: Synthetic peptide

<400> SEQUENCE: 297

Thr Arg Glu Glu Leu Leu Arg Glu Asn Ile Glu Leu Ala Lys Glu His
1               5                   10                  15

Ile Glu Ile Met Arg Glu Ile Leu Glu Leu Leu Gln Lys Met Glu Glu
            20                  25                  30

Leu Leu Glu Arg Gln Ser Ser Glu Asp Ile Leu Glu Glu Leu Arg Lys
        35                  40                  45

Ile Ile Glu Arg Ile Arg Glu Leu Leu Asp Arg Ser Arg Lys Ile His
    50                  55                  60

Glu Arg Ser Glu Glu Ile Ala Tyr Lys Glu Glu
65                  70                  75

<210> SEQ ID NO 298
<211> LENGTH: 93
<212> TYPE: PRT
<213> ORGANISM: Artificial Sequence
<220> FEATURE:
<223> OTHER INFORMATION: Synthetic peptide

<400> SEQUENCE: 298

Gly Ser His His His His His His Gly Ser Gly Ser Glu Asn Leu Tyr
1               5                   10                  15

Phe Gln Gly Ser Asp Asp Lys Glu Leu Asp Lys Leu Leu Asp Thr Leu
            20                  25                  30

Glu Lys Ile Leu Gln Thr Ala Thr Lys Ile Ile Asp Asp Ala Asn Lys
        35                  40                  45

Leu Leu Glu Lys Leu Arg Arg Ser Glu Arg Lys Asp Pro Lys Val Val
    50                  55                  60

Glu Thr Tyr Val Glu Leu Leu Lys Arg His Glu Lys Ala Val Lys Glu
65                  70                  75                  80

Leu Leu Glu Ile Ala Lys Thr His Ala Lys Lys Val Glu
            85                  90

<210> SEQ ID NO 299
<211> LENGTH: 161
<212> TYPE: PRT
<213> ORGANISM: Artificial Sequence
<220> FEATURE:
<223> OTHER INFORMATION: Synthetic peptide

<400> SEQUENCE: 299

Thr Glu Lys Arg Leu Leu Glu Glu Ala Glu Arg Ala His Arg Glu Gln
1               5                   10                  15

Lys Glu Ile Ile Lys Lys Ala Gln Glu Leu His Arg Arg Leu Glu Glu
            20                  25                  30
```

```
Ile Val Arg Gln Ser Gly Ser Glu Glu Ala Lys Lys Glu Ala Lys
         35                  40                  45

Lys Ile Leu Glu Glu Ile Arg Glu Leu Ser Lys Arg Ser Leu Glu Leu
 50                  55                  60

Leu Arg Glu Ile Leu Tyr Leu Ser Gln Glu Gln Lys Gly Ser Glu Gly
 65                  70                  75                  80

Ser Gly Ser Glu Gly Ser Gly Ser Asp Asp Lys Glu Leu Asp Lys Leu
                 85                  90                  95

Leu Asp Thr Leu Glu Lys Ile Leu Gln Thr Ala Thr Lys Ile Ile Asp
             100                 105                 110

Asp Ala Asn Lys Leu Leu Glu Lys Leu Arg Arg Ser Glu Arg Lys Asp
             115                 120                 125

Pro Lys Val Val Glu Thr Tyr Val Glu Leu Leu Lys Arg His Glu Lys
         130                 135                 140

Ala Val Lys Glu Leu Leu Glu Ile Ala Lys Thr His Ala Lys Lys Val
145                 150                 155                 160

Glu

<210> SEQ ID NO 300
<211> LENGTH: 76
<212> TYPE: PRT
<213> ORGANISM: Artificial Sequence
<220> FEATURE:
<223> OTHER INFORMATION: Synthetic peptide

<400> SEQUENCE: 300

Thr Lys Glu Asp Ile Leu Glu Arg Gln Arg Lys Ile Ile Glu Arg Ala
 1               5                  10                  15

Gln Glu Ile His Arg Arg Gln Gln Glu Ile Leu Glu Glu Leu Glu Arg
                 20                  25                  30

Ile Ile Arg Lys Pro Gly Ser Ser Glu Glu Ala Met Lys Arg Met Leu
             35                  40                  45

Lys Leu Leu Glu Glu Ser Leu Arg Leu Leu Lys Glu Leu Leu Glu Leu
 50                  55                  60

Ser Glu Glu Ser Ala Gln Leu Leu Tyr Glu Gln Arg
 65                  70                  75

<210> SEQ ID NO 301
<211> LENGTH: 92
<212> TYPE: PRT
<213> ORGANISM: Artificial Sequence
<220> FEATURE:
<223> OTHER INFORMATION: Synthetic peptide

<400> SEQUENCE: 301

Gly Ser Ser His His His His His Ser Ser Gly Glu Asn Leu Tyr
 1               5                  10                  15

Phe Gln Gly Ser Asp Ser Asp Glu His Leu Lys Lys Leu Lys Thr Phe
                 20                  25                  30

Leu Glu Asn Leu Arg Arg His Leu Asp Arg Leu Asp Lys His Ile Lys
             35                  40                  45

Gln Leu Arg Asp Ile Leu Ser Glu Asn Pro Glu Asp Glu Arg Val Lys
 50                  55                  60

Asp Val Ile Asp Leu Ser Glu Arg Ser Val Arg Ile Val Lys Thr Val
 65                  70                  75                  80

Ile Lys Ile Phe Glu Asp Ser Val Arg Lys Lys Glu
             85                  90
```

```
<210> SEQ ID NO 302
<211> LENGTH: 149
<212> TYPE: PRT
<213> ORGANISM: Artificial Sequence
<220> FEATURE:
<223> OTHER INFORMATION: Synthetic peptide

<400> SEQUENCE: 302

Thr Glu Arg Lys Leu Leu Glu Arg Ser Arg Leu Gln Glu Ser
1               5                   10                  15

Lys Arg Leu Leu Asp Glu Met Ala Glu Ile Met Arg Arg Ile Lys Lys
            20                  25                  30

Leu Leu Asp Asp Pro Asp Ser Glu Asp Ile Ala Arg Glu Ile Lys Glu
        35                  40                  45

Leu Leu Arg Arg Leu Lys Glu Ile Ile Glu Arg Asn Gln Arg Ile Ala
    50                  55                  60

Lys Glu His Glu Tyr Ile Ala Arg Glu Arg Ser Gly Ser Glu Gly Ser
65                  70                  75                  80

Gly Ser Glu Gly Ser Gly Ser Pro Lys Glu Glu Ala Arg Glu Leu Ile
                85                  90                  95

Arg Lys Gln Lys Glu Leu Ile Lys Glu Gln Lys Lys Leu Ile Lys Glu
            100                 105                 110

Ala Lys Gln Lys Ser Asp Ser Arg Asp Ala Glu Arg Ile Trp Lys Arg
        115                 120                 125

Ser Arg Glu Ile Asn Arg Glu Ser Lys Lys Ile Asn Lys Arg Ile Lys
    130                 135                 140

Glu Leu Ile Lys Ser
145

<210> SEQ ID NO 303
<211> LENGTH: 147
<212> TYPE: PRT
<213> ORGANISM: Artificial Sequence
<220> FEATURE:
<223> OTHER INFORMATION: Synthetic peptide

<400> SEQUENCE: 303

Pro Lys Lys Glu Ala Glu Leu Ala Glu Glu Ser Glu Glu Leu His
1               5                   10                  15

Asp Arg Ser Glu Lys Leu His Glu Arg Ala Glu Gln Ser Ser Asn Ser
            20                  25                  30

Glu Glu Ala Arg Lys Ile Leu Glu Asp Ile Glu Arg Ile Ser Glu Arg
        35                  40                  45

Ile Glu Glu Ile Ser Asp Arg Ile Glu Arg Leu Leu Arg Ser Gly Ser
    50                  55                  60

Glu Gly Ser Gly Ser Glu Gly Ser Gly Ser Asp Lys Glu Leu Asp
65                  70                  75                  80

Lys Leu Leu Asp Thr Leu Glu Lys Ile Leu Gln Thr Ala Thr Lys Ile
            85                  90                  95

Ile Asp Asp Ala Asn Lys Leu Leu Lys Leu Arg Arg Ser Glu Arg
        100                 105                 110

Lys Asp Pro Lys Val Val Glu Thr Tyr Val Glu Leu Leu Lys Arg His
        115                 120                 125

Glu Lys Ala Val Lys Glu Leu Leu Glu Ile Ala Lys Thr His Ala Lys
    130                 135                 140

Lys Val Glu
145
```

```
<210> SEQ ID NO 304
<211> LENGTH: 150
<212> TYPE: PRT
<213> ORGANISM: Artificial Sequence
<220> FEATURE:
<223> OTHER INFORMATION: Synthetic peptide

<400> SEQUENCE: 304

Thr Lys Glu Asp Ile Leu Glu Arg Gln Arg Lys Ile Ile Glu Arg Ala
1               5                   10                  15

Gln Glu Ile His Arg Arg Gln Gln Glu Ile Leu Glu Glu Leu Glu Arg
            20                  25                  30

Ile Ile Arg Lys Pro Gly Ser Ser Glu Glu Ala Met Lys Arg Met Leu
        35                  40                  45

Lys Leu Leu Glu Glu Ser Leu Arg Leu Leu Lys Glu Leu Leu Glu Leu
    50                  55                  60

Ser Glu Glu Ser Ala Gln Leu Leu Tyr Glu Gln Arg Gly Ser Glu Gly
65                  70                  75                  80

Ser Gly Ser Glu Gly Ser Gly Ser Pro Lys Glu Glu Ala Arg Glu Leu
                85                  90                  95

Ile Arg Lys Gln Lys Glu Leu Ile Lys Glu Gln Lys Lys Leu Ile Lys
            100                 105                 110

Glu Ala Lys Gln Lys Ser Asp Ser Arg Asp Ala Glu Arg Ile Trp Lys
        115                 120                 125

Arg Ser Arg Glu Ile Asn Arg Glu Ser Lys Lys Ile Asn Lys Arg Ile
    130                 135                 140

Lys Glu Leu Ile Lys Ser
145                 150

<210> SEQ ID NO 305
<211> LENGTH: 144
<212> TYPE: PRT
<213> ORGANISM: Artificial Sequence
<220> FEATURE:
<223> OTHER INFORMATION: Synthetic peptide

<400> SEQUENCE: 305

Pro Lys Lys Glu Ala Glu Glu Leu Ala Glu Glu Ser Glu Glu Leu His
1               5                   10                  15

Asp Arg Ser Glu Lys Leu His Glu Arg Ala Glu Gln Ser Ser Asn Ser
            20                  25                  30

Glu Glu Ala Arg Lys Ile Leu Glu Asp Ile Glu Arg Ile Ser Glu Arg
        35                  40                  45

Ile Glu Glu Ile Ser Asp Arg Ile Glu Arg Leu Leu Arg Ser Gly Ser
    50                  55                  60

Glu Gly Ser Gly Ser Glu Gly Ser Asp Ser Asp Glu His Leu Lys Lys
65                  70                  75                  80

Leu Lys Thr Phe Leu Glu Asn Leu Arg Arg His Leu Asp Arg Leu Asp
                85                  90                  95

Lys His Ile Lys Gln Leu Arg Asp Ile Leu Ser Glu Asn Pro Glu Asp
            100                 105                 110

Glu Arg Val Lys Asp Val Ile Asp Leu Ser Glu Arg Ser Val Arg Ile
        115                 120                 125

Val Lys Thr Val Ile Lys Ile Phe Glu Asp Ser Val Arg Lys Lys Glu
    130                 135                 140
```

```
<210> SEQ ID NO 306
<211> LENGTH: 152
<212> TYPE: PRT
<213> ORGANISM: Artificial Sequence
<220> FEATURE:
<223> OTHER INFORMATION: Synthetic peptide

<400> SEQUENCE: 306

Gly Ser Thr Glu Arg Lys Leu Leu Glu Arg Ser Arg Arg Leu Gln Glu
1               5                   10                  15

Glu Ser Lys Arg Leu Leu Asp Glu Met Ala Glu Ile Met Arg Arg Ile
            20                  25                  30

Lys Lys Leu Leu Asp Asp Pro Asp Ser Glu Asp Ile Ala Arg Glu Ile
        35                  40                  45

Lys Glu Leu Leu Arg Arg Leu Lys Glu Ile Ile Glu Arg Asn Gln Arg
    50                  55                  60

Ile Ala Lys Glu His Glu Tyr Ile Ala Arg Glu Arg Ser Ala Ala Asp
65                  70                  75                  80

Asp Lys Glu Leu Asp Lys Leu Leu Asp Thr Leu Glu Lys Ile Leu Gln
                85                  90                  95

Thr Ala Thr Lys Ile Ile Asp Asp Ala Asn Lys Leu Leu Glu Lys Leu
            100                 105                 110

Arg Arg Ser Glu Arg Lys Asp Pro Lys Val Val Glu Thr Tyr Val Glu
        115                 120                 125

Leu Leu Lys Arg His Glu Lys Ala Val Lys Glu Leu Glu Ile Ala
    130                 135                 140

Lys Thr His Ala Lys Lys Val Glu
145                 150

<210> SEQ ID NO 307
<211> LENGTH: 156
<212> TYPE: PRT
<213> ORGANISM: Artificial Sequence
<220> FEATURE:
<223> OTHER INFORMATION: Synthetic peptide

<400> SEQUENCE: 307

Gly Ser Thr Glu Arg Lys Leu Leu Glu Arg Ser Arg Arg Leu Gln Glu
1               5                   10                  15

Glu Ser Lys Arg Leu Leu Asp Glu Met Ala Glu Ile Met Arg Arg Ile
            20                  25                  30

Lys Lys Leu Leu Asp Asp Pro Asp Ser Glu Asp Ile Ala Arg Glu Ile
        35                  40                  45

Lys Glu Leu Leu Arg Arg Leu Lys Glu Ile Ile Glu Arg Asn Gln Arg
    50                  55                  60

Ile Ala Lys Glu His Glu Tyr Ile Ala Arg Glu Arg Ser Gly Gly Ser
65                  70                  75                  80

Gly Ser Pro Asp Asp Lys Glu Leu Asp Lys Leu Leu Asp Thr Leu Glu
                85                  90                  95

Lys Ile Leu Gln Thr Ala Thr Lys Ile Ile Asp Asp Ala Asn Lys Leu
            100                 105                 110

Leu Glu Lys Leu Arg Arg Ser Glu Arg Lys Asp Pro Lys Val Val Glu
        115                 120                 125

Thr Tyr Val Glu Leu Leu Lys Arg His Glu Lys Ala Val Lys Glu Leu
    130                 135                 140

Leu Glu Ile Ala Lys Thr His Ala Lys Lys Val Glu
145                 150                 155
```

<210> SEQ ID NO 308
<211> LENGTH: 162
<212> TYPE: PRT
<213> ORGANISM: Artificial Sequence
<220> FEATURE:
<223> OTHER INFORMATION: Synthetic peptide

<400> SEQUENCE: 308

```
Gly Ser Thr Glu Arg Lys Leu Leu Glu Arg Ser Arg Arg Leu Gln Glu
1               5                   10                  15

Glu Ser Lys Arg Leu Leu Asp Glu Met Ala Glu Ile Met Arg Arg Ile
            20                  25                  30

Lys Lys Leu Leu Asp Asp Pro Asp Ser Glu Asp Ile Ala Arg Glu Ile
        35                  40                  45

Lys Glu Leu Leu Arg Arg Leu Lys Glu Ile Ile Glu Arg Asn Gln Arg
    50                  55                  60

Ile Ala Lys Glu His Glu Tyr Ile Ala Arg Glu Arg Ser Gly Gly Ser
65                  70                  75                  80

Gly Ser Pro Gly Gly Ser Gly Ser Pro Asp Asp Lys Glu Leu Asp Lys
                85                  90                  95

Leu Leu Asp Thr Leu Glu Lys Ile Leu Gln Thr Ala Thr Lys Ile Ile
            100                 105                 110

Asp Asp Ala Asn Lys Leu Leu Glu Lys Leu Arg Arg Ser Glu Arg Lys
        115                 120                 125

Asp Pro Lys Val Val Glu Thr Tyr Val Glu Leu Leu Lys Arg His Glu
    130                 135                 140

Lys Ala Val Lys Glu Leu Leu Glu Ile Ala Lys Thr His Ala Lys Lys
145                 150                 155                 160

Val Glu
```

<210> SEQ ID NO 309
<211> LENGTH: 174
<212> TYPE: PRT
<213> ORGANISM: Artificial Sequence
<220> FEATURE:
<223> OTHER INFORMATION: Synthetic peptide

<400> SEQUENCE: 309

```
Gly Ser Thr Glu Arg Lys Leu Leu Glu Arg Ser Arg Arg Leu Gln Glu
1               5                   10                  15

Glu Ser Lys Arg Leu Leu Asp Glu Met Ala Glu Ile Met Arg Arg Ile
            20                  25                  30

Lys Lys Leu Leu Asp Asp Pro Asp Ser Glu Asp Ile Ala Arg Glu Ile
        35                  40                  45

Lys Glu Leu Leu Arg Arg Leu Lys Glu Ile Ile Glu Arg Asn Gln Arg
    50                  55                  60

Ile Ala Lys Glu His Glu Tyr Ile Ala Arg Glu Arg Ser Gly Gly Ser
65                  70                  75                  80

Gly Ser Pro Gly Gly Ser Gly Ser Pro Gly Gly Ser Gly Ser Pro Gly
                85                  90                  95

Gly Ser Gly Ser Pro Asp Asp Lys Glu Leu Asp Lys Leu Leu Asp Thr
            100                 105                 110

Leu Glu Lys Ile Leu Gln Thr Ala Thr Lys Ile Ile Asp Asp Ala Asn
        115                 120                 125

Lys Leu Leu Glu Lys Leu Arg Arg Ser Glu Arg Lys Asp Pro Lys Val
    130                 135                 140
```

```
Val Glu Thr Tyr Val Glu Leu Leu Lys Arg His Glu Lys Ala Val Lys
145                 150                 155                 160

Glu Leu Leu Glu Ile Ala Lys Thr His Ala Lys Lys Val Glu
                165                 170
```

<210> SEQ ID NO 310
<211> LENGTH: 158
<212> TYPE: PRT
<213> ORGANISM: Artificial Sequence
<220> FEATURE:
<223> OTHER INFORMATION: Synthetic peptide

<400> SEQUENCE: 310

```
Pro Glu Asp Val Val Arg Ile Ile Lys Glu Asp Leu Glu Ser Asn
1               5                   10                  15

Arg Glu Val Leu Arg Glu Gln Lys Glu Ile His Arg Ile Leu Glu Leu
                20                  25                  30

Val Thr Arg Gly Glu Val Ser Glu Glu Ala Ile Asp Arg Val Leu Lys
            35                  40                  45

Arg Gln Glu Asp Leu Leu Lys Lys Gln Lys Glu Ser Thr Asp Lys Ala
50                  55                  60

Arg Lys Val Val Glu Glu Arg Gly Ser Gly Ser Gly Ser Glu
65                  70                  75                  80

Gly Ser Asp Leu Glu Asp Leu Leu Arg Arg Leu Arg Arg Leu Val Asp
                85                  90                  95

Glu Gln Arg Arg Leu Val Glu Glu Leu Glu Arg Val Ser Arg Arg Leu
                100                 105                 110

Glu Lys Ala Val Arg Asp Asn Glu Asp Glu Arg Glu Leu Ala Arg Leu
                115                 120                 125

Ser Arg Glu His Ser Asp Ile Gln Asp Lys His Asp Lys Leu Ala Arg
130                 135                 140

Glu Ile Leu Glu Val Leu Lys Arg Leu Leu Glu Arg Thr Glu
145                 150                 155
```

<210> SEQ ID NO 311
<211> LENGTH: 163
<212> TYPE: PRT
<213> ORGANISM: Artificial Sequence
<220> FEATURE:
<223> OTHER INFORMATION: Synthetic peptide

<400> SEQUENCE: 311

```
Gly Ser Asp Ala Tyr Asp Leu Asp Arg Ile Val Lys Glu His Arg Arg
1               5                   10                  15

Leu Val Glu Glu Gln Arg Glu Leu Val Glu Glu Leu Glu Lys Leu Val
                20                  25                  30

Arg Arg Gln Glu Asp His Arg Val Asp Lys Lys Glu Ser His Glu Ile
            35                  40                  45

Leu Glu Arg Leu Glu Arg Ile Ile Arg Arg Ser Thr Arg Ile Leu Thr
50                  55                  60

Glu Leu Glu Lys Leu Thr Asp Glu Phe Glu Arg Arg Thr Arg Gly Ser
65                  70                  75                  80

Glu Gly Ser Gly Ser Glu Gly Ser Gly Ser Asp Asp Lys Glu Leu Asp
                85                  90                  95

Lys Leu Leu Asp Thr Leu Glu Lys Ile Leu Gln Thr Ala Thr Lys Ile
                100                 105                 110

Ile Asp Asp Ala Asn Lys Leu Leu Glu Lys Leu Arg Arg Ser Glu Arg
115                 120                 125
```

```
Lys Asp Pro Lys Val Val Glu Thr Tyr Val Glu Leu Leu Lys Arg His
            130                 135                 140

Glu Lys Ala Val Lys Glu Leu Leu Glu Ile Ala Lys Thr His Ala Lys
145                 150                 155                 160

Lys Val Glu

<210> SEQ ID NO 312
<211> LENGTH: 165
<212> TYPE: PRT
<213> ORGANISM: Artificial Sequence
<220> FEATURE:
<223> OTHER INFORMATION: Synthetic peptide

<400> SEQUENCE: 312

Gly Ser Asp Glu Asp Glu Leu Glu Arg Leu Leu Arg Glu Tyr His
1               5                   10                  15

Arg Val Leu Arg Glu Tyr Glu Lys Leu Leu Glu Glu Leu Arg Arg Leu
                20                  25                  30

Tyr Glu Glu Tyr Lys Arg Gly Glu Val Ser Glu Glu Ser Asp Arg
                35                  40                  45

Ile Leu Arg Glu Ile Lys Glu Ile Leu Asp Lys Ser Glu Arg Leu Trp
50                  55                  60

Asp Leu Ser Glu Glu Val Trp Arg Thr Leu Leu Tyr Gln Ala Glu Gly
65                  70                  75                  80

Ser Glu Gly Ser Gly Ser Gly Ser Asp Glu Lys Asp Tyr His Arg
                85                  90                  95

Arg Leu Ile Glu His Leu Glu Asp Val Arg Arg His Glu Glu Leu
                100                 105                 110

Ile Lys Arg Gln Lys Lys Val Val Glu Glu Leu Glu Arg Arg Gly Leu
                115                 120                 125

Asp Glu Arg Leu Arg Arg Val Val Asp Arg Phe Arg Arg Ser Ser Glu
130                 135                 140

Arg Trp Glu Glu Val Ile Glu Arg Phe Arg Gln Val Val Asp Lys Leu
145                 150                 155                 160

Arg Lys Ser Val Glu
                165

<210> SEQ ID NO 313
<211> LENGTH: 168
<212> TYPE: PRT
<213> ORGANISM: Artificial Sequence
<220> FEATURE:
<223> OTHER INFORMATION: Synthetic peptide

<400> SEQUENCE: 313

Gly Ser Thr Glu Arg Lys Leu Leu Glu Arg Ser Arg Arg Leu Gln Glu
1               5                   10                  15

Glu Ser Lys Arg Leu Leu Asp Glu Met Ala Glu Ile Met Arg Arg Ile
                20                  25                  30

Lys Lys Leu Leu Lys Lys Ala Arg Gly Ala Asp Glu Lys Val Leu Asp
                35                  40                  45

Glu Leu Arg Lys Ile Ile Glu Arg Ile Arg Glu Leu Leu Asp Arg Ser
    50                  55                  60

Arg Lys Ile His Glu Arg Ser Glu Glu Ile Ala Tyr Lys Glu Gly
65                  70                  75                  80

Ser Glu Gly Ser Gly Ser Glu Gly Ser Gly Ser Asp Glu Ser Asp Arg
                85                  90                  95
```

```
Ile Arg Lys Ile Val Glu Glu Ser Asp Glu Ile Val Lys Glu Ser Arg
                100                 105                 110

Lys Leu Ala Glu Arg Ala Arg Glu Leu Ile Lys Glu Ser Glu Asp Lys
            115                 120                 125

Arg Val Ser Glu Glu Arg Asn Glu Arg Leu Leu Glu Glu Leu Leu Arg
        130                 135                 140

Ile Leu Asp Glu Asn Ala Glu Leu Leu Lys Arg Asn Leu Glu Leu Leu
145                 150                 155                 160

Lys Glu Val Leu Tyr Arg Thr Arg
                165

<210> SEQ ID NO 314
<211> LENGTH: 164
<212> TYPE: PRT
<213> ORGANISM: Artificial Sequence
<220> FEATURE:
<223> OTHER INFORMATION: Synthetic peptide

<400> SEQUENCE: 314

Gly Ser Asp Glu Asp Glu Leu Glu Arg Leu Leu Arg Glu Tyr His
1               5                   10                  15

Arg Val Leu Arg Glu Tyr Glu Lys Leu Leu Glu Glu Leu Arg Arg Leu
            20                  25                  30

Tyr Glu Glu Tyr Lys Arg Gly Glu Val Ser Glu Glu Ser Asp Arg
        35                  40                  45

Ile Leu Arg Glu Ile Lys Glu Ile Leu Asp Lys Ser Glu Arg Leu Trp
50                  55                  60

Asp Leu Ser Glu Glu Val Trp Arg Thr Leu Leu Tyr Gln Ala Glu Gly
65                  70                  75                  80

Ser Glu Gly Ser Gly Ser Glu Gly Ser Gly Ser Asp Asp Lys Glu Leu
                85                  90                  95

Asp Lys Leu Leu Asp Thr Leu Glu Lys Ile Leu Gln Thr Ala Thr Lys
            100                 105                 110

Ile Ile Asp Asp Ala Asn Lys Leu Leu Glu Lys Leu Arg Arg Ser Glu
        115                 120                 125

Arg Lys Asp Pro Lys Val Val Glu Thr Tyr Val Glu Leu Leu Lys Arg
    130                 135                 140

His Glu Lys Ala Val Lys Glu Leu Leu Glu Ile Ala Lys Thr His Ala
145                 150                 155                 160

Lys Lys Val Glu

<210> SEQ ID NO 315
<211> LENGTH: 177
<212> TYPE: PRT
<213> ORGANISM: Artificial Sequence
<220> FEATURE:
<223> OTHER INFORMATION: Synthetic peptide

<400> SEQUENCE: 315

Asp Ser Asp Glu His Leu Lys Lys Leu Lys Thr Phe Leu Glu Asn Leu
1               5                   10                  15

Arg Arg His Leu Asp Arg Leu Asp Lys His Ile Lys Gln Leu Arg Asp
            20                  25                  30

Ile Leu Ser Glu Asn Pro Glu Asp Glu Arg Val Lys Asp Val Ile Asp
        35                  40                  45

Leu Ser Glu Arg Ser Val Arg Ile Val Lys Thr Val Ile Lys Ile Phe
    50                  55                  60
```

```
Glu Asp Ser Val Arg Lys Lys Glu Gly Ser Glu Ser Gly Ser Glu
 65                  70                  75                  80

Gly Ser Gly Ser Glu Gly Ser Gly Ser Glu Gly Ser Gly Ser Glu Gly
                 85                  90                  95

Ser Gly Ser Glu Gly Ser Pro Thr Asp Glu Val Ile Glu Val Leu Lys
                100                 105                 110

Glu Leu Leu Arg Ile His Arg Glu Asn Leu Arg Val Asn Glu Glu Ile
            115                 120                 125

Val Glu Val Asn Glu Arg Ala Ser Arg Val Thr Asp Arg Glu Glu Leu
130                 135                 140

Glu Arg Leu Leu Arg Arg Ser Asn Glu Leu Ile Lys Arg Ser Arg Glu
145                 150                 155                 160

Leu Asn Glu Glu Ser Lys Lys Leu Ile Glu Lys Leu Glu Arg Leu Ala
                165                 170                 175

Thr

<210> SEQ ID NO 316
<211> LENGTH: 155
<212> TYPE: PRT
<213> ORGANISM: Artificial Sequence
<220> FEATURE:
<223> OTHER INFORMATION: Synthetic peptide

<400> SEQUENCE: 316

Asp Asp Lys Glu Leu Asp Lys Leu Leu Asp Thr Leu Glu Lys Ile Leu
1               5                   10                  15

Gln Thr Ala Thr Lys Ile Ile Asp Asp Ala Asn Lys Leu Leu Glu Lys
                20                  25                  30

Leu Arg Arg Ser Glu Arg Lys Asp Pro Lys Val Val Glu Thr Tyr Val
            35                  40                  45

Glu Leu Leu Lys Arg His Glu Lys Ala Val Lys Glu Leu Leu Glu Ile
 50                  55                  60

Ala Lys Thr His Ala Lys Lys Val Glu Gly Ser Gly Ser Gly Ser
 65                  70                  75                  80

Glu Gly Ser Thr Ala Glu Glu Leu Leu Glu Val His Lys Lys Ser Asp
                 85                  90                  95

Arg Val Thr Lys Glu His Leu Arg Val Ser Glu Glu Ile Leu Lys Val
                100                 105                 110

Val Glu Val Leu Thr Arg Gly Glu Val Ser Ser Glu Val Leu Lys Arg
            115                 120                 125

Val Leu Arg Lys Leu Glu Gly Leu Thr Asp Lys Leu Arg Arg Val Thr
130                 135                 140

Glu Glu Gln Arg Arg Val Val Glu Lys Leu Asn
145                 150                 155

<210> SEQ ID NO 317
<211> LENGTH: 156
<212> TYPE: PRT
<213> ORGANISM: Artificial Sequence
<220> FEATURE:
<223> OTHER INFORMATION: Synthetic peptide

<400> SEQUENCE: 317

Asp Asn Glu Glu Ile Ile Lys Glu Ala Arg Arg Val Val Glu Glu Tyr
1               5                   10                  15

Lys Lys Ala Val Asp Arg Leu Glu Glu Leu Val Arg Arg Ala Glu Asn
                20                  25                  30
```

```
Ala Lys His Ala Ser Glu Lys Glu Leu Lys Asp Ile Val Arg Glu Ile
        35                  40                  45

Leu Arg Ile Ser Lys Glu Leu Asn Lys Val Ser Glu Arg Leu Ile Glu
 50                  55                  60

Leu Trp Glu Arg Ser Gln Glu Arg Ala Arg Gly Ser Glu Gly Ser Gly
 65                  70                  75                  80

Ser Glu Gly Ser Thr Ala Glu Glu Leu Glu Val His Lys Lys Ser
                 85                  90                  95

Asp Arg Val Thr Lys Glu His Leu Arg Val Ser Glu Glu Ile Leu Lys
                100                 105                 110

Val Val Glu Val Leu Thr Arg Gly Glu Val Ser Ser Glu Val Leu Lys
                115                 120                 125

Arg Val Leu Arg Lys Leu Glu Glu Leu Thr Asp Lys Leu Arg Arg Val
130                 135                 140

Thr Glu Glu Gln Arg Arg Val Val Glu Lys Leu Asn
145                 150                 155
```

<210> SEQ ID NO 318
<211> LENGTH: 280
<212> TYPE: PRT
<213> ORGANISM: Artificial Sequence
<220> FEATURE:
<223> OTHER INFORMATION: Synthetic peptide

<400> SEQUENCE: 318

```
Asp Asp Lys Glu Leu Asp Lys Leu Leu Asp Thr Leu Glu Lys Ile Leu
 1               5                  10                  15

Gln Thr Ala Thr Lys Ile Ile Asp Asp Ala Asn Lys Leu Leu Glu Lys
                 20                  25                  30

Leu Arg Arg Ser Glu Arg Lys Asp Pro Lys Val Val Glu Thr Tyr Val
                 35                  40                  45

Glu Leu Leu Lys Arg His Glu Lys Ala Val Lys Glu Leu Leu Glu Ile
 50                  55                  60

Ala Lys Thr His Ala Lys Lys Val Glu Gly Ser Glu Gly Ser Gly Ser
 65                  70                  75                  80

Glu Gly Ser Gly Ser Glu Gly Ser Gly Ser Glu Gly Ser Gly Ser Glu
                 85                  90                  95

Gly Ser Gly Ser Glu Gly Ser Pro Thr Asp Glu Val Ile Glu Val Leu
                100                 105                 110

Lys Glu Leu Leu Arg Ile His Arg Glu Asn Leu Arg Val Asn Glu Glu
                115                 120                 125

Ile Val Glu Val Asn Glu Arg Ala Ser Arg Val Thr Asp Arg Glu Glu
                130                 135                 140

Leu Glu Arg Leu Leu Arg Arg Ser Asn Glu Leu Ile Lys Arg Ser Arg
145                 150                 155                 160

Glu Leu Asn Glu Glu Ser Lys Lys Leu Ile Glu Lys Leu Glu Arg Leu
                165                 170                 175

Ala Thr Gly Ser Glu Gly Ser Gly Ser Glu Gly Ser Gly Ser Glu Gly
                180                 185                 190

Ser Gly Ser Glu Gly Ser Gly Ser Glu Gly Ser Gly Ser Glu Gly Ser
                195                 200                 205

Thr Ala Glu Glu Leu Leu Glu Val His Lys Lys Ser Asp Arg Val Thr
210                 215                 220

Lys Glu His Leu Arg Val Ser Glu Glu Ile Leu Lys Val Val Glu Val
225                 230                 235                 240
```

```
Leu Thr Arg Gly Glu Val Ser Glu Val Leu Lys Arg Val Leu Arg
                245                 250                 255

Lys Leu Glu Glu Leu Thr Asp Lys Leu Arg Arg Val Thr Glu Gln
            260                 265                 270

Arg Arg Val Val Glu Lys Leu Asn
        275                 280

<210> SEQ ID NO 319
<211> LENGTH: 154
<212> TYPE: PRT
<213> ORGANISM: Artificial Sequence
<220> FEATURE:
<223> OTHER INFORMATION: Synthetic peptide

<400> SEQUENCE: 319

Asp Ser Asp Glu His Leu Lys Lys Leu Lys Thr Phe Leu Glu Asn Leu
1               5                   10                  15

Arg Arg His Leu Asp Arg Leu Asp Lys His Ile Lys Gln Leu Arg Asp
            20                  25                  30

Ile Leu Ser Glu Asn Pro Glu Asp Glu Arg Val Lys Asp Val Ile Asp
        35                  40                  45

Leu Ser Glu Arg Ser Val Arg Ile Val Lys Thr Val Ile Lys Ile Phe
    50                  55                  60

Glu Asp Ser Val Arg Lys Lys Glu Gly Ser Glu Gly Ser Gly Ser Glu
65                  70                  75                  80

Gly Ser Pro Glu Asp Asp Val Val Arg Ile Ile Lys Glu Asp Leu Glu
                85                  90                  95

Ser Asn Arg Glu Val Leu Arg Glu Gln Lys Glu Ile His Arg Ile Leu
            100                 105                 110

Glu Leu Val Thr Arg Gly Glu Val Ser Glu Glu Ala Ile Asp Arg Val
        115                 120                 125

Leu Lys Arg Gln Glu Asp Leu Leu Lys Lys Gln Lys Glu Ser Thr Asp
    130                 135                 140

Lys Ala Arg Lys Val Val Glu Glu Arg Arg
145                 150

<210> SEQ ID NO 320
<211> LENGTH: 156
<212> TYPE: PRT
<213> ORGANISM: Artificial Sequence
<220> FEATURE:
<223> OTHER INFORMATION: Synthetic peptide

<400> SEQUENCE: 320

Asp Asn Glu Glu Ile Ile Lys Glu Ala Arg Arg Val Val Glu Glu Tyr
1               5                   10                  15

Lys Lys Ala Val Asp Arg Leu Glu Glu Leu Val Arg Arg Ala Glu Asn
            20                  25                  30

Ala Lys His Ala Ser Glu Lys Glu Leu Lys Asp Ile Val Arg Glu Ile
        35                  40                  45

Leu Arg Ile Ser Lys Glu Leu Asn Lys Val Ser Glu Arg Leu Ile Glu
    50                  55                  60

Leu Trp Glu Arg Ser Gln Glu Arg Ala Arg Gly Ser Glu Gly Ser Gly
65                  70                  75                  80

Ser Glu Gly Ser Pro Glu Asp Asp Val Val Arg Ile Ile Lys Glu Asp
                85                  90                  95

Leu Glu Ser Asn Arg Glu Val Leu Arg Glu Gln Lys Glu Ile His Arg
```

```
                    100                 105                 110
Ile Leu Glu Leu Val Thr Arg Gly Glu Val Ser Glu Glu Ala Ile Asp
            115                 120                 125

Arg Val Leu Lys Arg Gln Glu Asp Leu Leu Lys Lys Gln Lys Glu Ser
        130                 135                 140

Thr Asp Lys Ala Arg Lys Val Val Glu Glu Arg Arg
145                 150                 155

<210> SEQ ID NO 321
<211> LENGTH: 178
<212> TYPE: PRT
<213> ORGANISM: Artificial Sequence
<220> FEATURE:
<223> OTHER INFORMATION: Synthetic peptide

<400> SEQUENCE: 321

Asp Leu Glu Asp Leu Leu Arg Arg Leu Arg Arg Leu Val Asp Glu Gln
1               5                   10                  15

Arg Arg Leu Val Glu Glu Leu Glu Arg Val Ser Arg Arg Leu Glu Lys
            20                  25                  30

Ala Val Arg Asp Asn Glu Asp Glu Arg Glu Leu Ala Arg Leu Ser Arg
        35                  40                  45

Glu His Ser Asp Ile Gln Asp Lys His Asp Lys Leu Ala Arg Glu Ile
    50                  55                  60

Leu Glu Val Leu Lys Arg Leu Leu Glu Arg Thr Glu Gly Ser Glu Gly
65                  70                  75                  80

Ser Gly Ser Glu Gly Ser Gly Ser Glu Gly Ser Gly Ser Glu Gly Ser
                85                  90                  95

Gly Ser Glu Gly Ser Gly Ser Glu Gly Ser Pro Glu Asp Asp Val Val
            100                 105                 110

Arg Ile Ile Lys Glu Asp Leu Glu Ser Asn Arg Glu Val Leu Arg Glu
        115                 120                 125

Gln Lys Glu Ile His Arg Ile Leu Glu Leu Val Thr Arg Gly Glu Val
    130                 135                 140

Ser Glu Glu Ala Ile Asp Arg Val Leu Lys Arg Gln Glu Asp Leu Leu
145                 150                 155                 160

Lys Lys Gln Lys Glu Ser Thr Asp Lys Ala Arg Lys Val Val Glu Glu
                165                 170                 175

Arg Arg

<210> SEQ ID NO 322
<211> LENGTH: 160
<212> TYPE: PRT
<213> ORGANISM: Artificial Sequence
<220> FEATURE:
<223> OTHER INFORMATION: Synthetic peptide

<400> SEQUENCE: 322

Gly Ser Asp Asp Lys Glu Leu Asp Lys Leu Leu Asp Thr Leu Glu Lys
1               5                   10                  15

Ile Leu Gln Thr Ala Thr Lys Ile Ile Asp Asp Ala Asn Lys Leu Leu
            20                  25                  30

Glu Lys Leu Arg Arg Ser Glu Arg Lys Asp Pro Lys Val Glu Glu Thr
        35                  40                  45

Tyr Val Glu Leu Leu Lys Arg His Glu Lys Ala Val Lys Glu Leu Leu
    50                  55                  60

Glu Ile Ala Lys Thr His Ala Lys Lys Val Glu Gly Ser Glu Gly Ser
```

```
                65                  70                  75                  80

Gly Ser Glu Gly Ser Pro Thr Asp Glu Val Ile Glu Val Leu Lys Glu
                85                  90                  95

Leu Leu Arg Ile His Arg Glu Asn Leu Arg Val Asn Glu Glu Ile Val
                100                 105                 110

Glu Val Asn Glu Arg Ala Ser Arg Val Thr Asp Arg Glu Glu Leu Glu
                115                 120                 125

Arg Leu Leu Arg Arg Ser Asn Glu Leu Ile Lys Arg Ser Arg Glu Leu
                130                 135                 140

Asn Glu Glu Ser Lys Lys Leu Ile Glu Lys Leu Glu Arg Leu Ala Thr
145                 150                 155                 160

<210> SEQ ID NO 323
<211> LENGTH: 154
<212> TYPE: PRT
<213> ORGANISM: Artificial Sequence
<220> FEATURE:
<223> OTHER INFORMATION: Synthetic peptide

<400> SEQUENCE: 323

Asp Ser Asp Glu His Leu Lys Lys Leu Lys Thr Phe Leu Glu Asn Leu
1               5                   10                  15

Arg Arg His Leu Asp Arg Leu Asp Lys His Ile Lys Gln Leu Arg Asp
                20                  25                  30

Ile Leu Ser Glu Asn Pro Glu Asp Glu Arg Val Lys Asp Val Ile Asp
                35                  40                  45

Leu Ser Glu Arg Ser Val Arg Ile Val Lys Thr Val Ile Lys Ile Phe
            50                  55                  60

Glu Asp Ser Val Arg Lys Lys Glu Gly Ser Glu Gly Ser Gly Ser Glu
65              70                  75                  80

Gly Ser Thr Ala Glu Glu Leu Leu Glu Val His Lys Lys Ser Asp Arg
                85                  90                  95

Val Thr Lys Glu His Leu Arg Val Ser Glu Glu Ile Leu Lys Val Val
                100                 105                 110

Glu Val Leu Thr Arg Gly Glu Val Ser Ser Glu Val Leu Lys Arg Val
                115                 120                 125

Leu Arg Lys Leu Glu Glu Leu Thr Asp Lys Leu Arg Arg Val Thr Glu
            130                 135                 140

Glu Gln Arg Arg Val Val Glu Lys Leu Asn
145                 150

<210> SEQ ID NO 324
<211> LENGTH: 166
<212> TYPE: PRT
<213> ORGANISM: Artificial Sequence
<220> FEATURE:
<223> OTHER INFORMATION: Synthetic peptide

<400> SEQUENCE: 324

Gly Thr Glu Arg Lys Leu Leu Glu Arg Ser Arg Arg Leu Gln Glu Glu
1               5                   10                  15

Ser Lys Arg Leu Leu Asp Glu Met Ala Glu Ile Met Arg Arg Ile Lys
                20                  25                  30

Lys Leu Leu Lys Lys Ala Arg Gly Ala Asp Glu Lys Val Leu Asp Glu
            35                  40                  45

Leu Arg Lys Ile Ile Glu Arg Ile Arg Glu Leu Leu Asp Arg Ser Arg
            50                  55                  60
```

Lys Ile His Glu Arg Ser Glu Glu Ile Ala Tyr Lys Glu Glu Gly Ser
65                  70                  75                  80

Glu Gly Ser Gly Ser Gly Ser Gly Ser Asp Ala Tyr Asp Leu Asp
            85                  90                  95

Arg Ile Val Lys Glu His Arg Arg Leu Val Glu Glu Gln Arg Glu Leu
            100                 105                 110

Val Glu Glu Leu Glu Lys Leu Val Arg Arg Gln Glu Asp His Arg Val
            115                 120                 125

Asp Lys Lys Glu Ser His Glu Ile Leu Glu Arg Leu Glu Arg Ile Ile
    130                 135                 140

Arg Arg Ser Thr Arg Ile Leu Thr Glu Leu Glu Lys Leu Thr Asp Glu
145                 150                 155                 160

Phe Glu Arg Arg Thr Arg
                165

<210> SEQ ID NO 325
<211> LENGTH: 162
<212> TYPE: PRT
<213> ORGANISM: Artificial Sequence
<220> FEATURE:
<223> OTHER INFORMATION: Synthetic peptide

<400> SEQUENCE: 325

Thr Arg Glu Glu Leu Leu Arg Glu Asn Ile Glu Leu Ala Lys Glu His
1               5                   10                  15

Ile Glu Ile Met Arg Glu Ile Leu Glu Leu Leu Gln Lys Met Glu Glu
            20                  25                  30

Leu Leu Glu Lys Ala Arg Gly Ala Asp Glu Asp Val Ala Lys Thr Ile
            35                  40                  45

Lys Glu Leu Leu Arg Arg Leu Lys Glu Ile Ile Glu Arg Asn Gln Arg
    50                  55                  60

Ile Ala Lys Glu His Glu Tyr Ile Ala Arg Arg Ser Gly Ser Glu
65                  70                  75                  80

Gly Ser Gly Ser Glu Gly Ser Gly Ser Asp Asp Lys Glu Leu Asp Lys
            85                  90                  95

Leu Leu Asp Thr Leu Glu Lys Ile Leu Gln Thr Ala Thr Lys Ile Ile
            100                 105                 110

Asp Asp Ala Asn Lys Leu Leu Glu Lys Leu Arg Arg Ser Glu Arg Lys
            115                 120                 125

Asp Pro Lys Val Val Glu Thr Tyr Val Glu Leu Leu Lys Arg His Glu
    130                 135                 140

Lys Ala Val Lys Glu Leu Leu Glu Ile Ala Lys Thr His Ala Lys Lys
145                 150                 155                 160

Val Glu

<210> SEQ ID NO 326
<211> LENGTH: 162
<212> TYPE: PRT
<213> ORGANISM: Artificial Sequence
<220> FEATURE:
<223> OTHER INFORMATION: Synthetic peptide

<400> SEQUENCE: 326

Gly Ser Asp Asp Lys Glu Leu Asp Lys Leu Leu Asp Thr Leu Glu Lys
1               5                   10                  15

Ile Leu Gln Thr Ala Thr Lys Ile Ile Asp Asp Ala Asn Lys Leu Leu
            20                  25                  30

```
Glu Lys Leu Arg Arg Ser Glu Arg Lys Asp Pro Lys Val Glu Thr
             35                  40                  45

Tyr Val Glu Leu Leu Lys Arg His Glu Lys Ala Val Lys Glu Leu Leu
 50                  55                  60

Glu Ile Ala Lys Thr His Ala Lys Lys Val Glu Gly Ser Gly Ser
 65                  70                  75                  80

Gly Ser Glu Gly Ser Gly Thr Lys Glu Asp Ile Leu Glu Arg Gln Arg
                 85                  90                  95

Lys Ile Ile Glu Arg Ala Gln Glu Ile His Arg Arg Gln Gln Glu Ile
                100                 105                 110

Leu Glu Glu Leu Glu Arg Ile Ile Arg Lys Pro Gly Ser Ser Glu Glu
                115                 120                 125

Ala Met Lys Arg Met Leu Lys Leu Leu Glu Glu Ser Leu Arg Leu Leu
130                 135                 140

Lys Glu Leu Leu Glu Leu Ser Glu Glu Ser Ala Gln Leu Leu Tyr Glu
145                 150                 155                 160

Gln Arg

<210> SEQ ID NO 327
<211> LENGTH: 15
<212> TYPE: PRT
<213> ORGANISM: Artificial Sequence
<220> FEATURE:
<223> OTHER INFORMATION: Synthetic peptide

<400> SEQUENCE: 327

Gly Ala Ala Gly Gly Ala Gly Ala Thr Ala Thr Cys Ala Thr Cys
 1               5                  10                  15

<210> SEQ ID NO 328
<211> LENGTH: 20
<212> TYPE: PRT
<213> ORGANISM: Artificial Sequence
<220> FEATURE:
<223> OTHER INFORMATION: Synthetic peptide

<400> SEQUENCE: 328

Gly Ser Ser His His His His His His Ser Ser Gly Glu Asn Leu Tyr
 1               5                  10                  15

Phe Gln Gly Ser
         20

<210> SEQ ID NO 329
<211> LENGTH: 40
<212> TYPE: PRT
<213> ORGANISM: Artificial Sequence
<220> FEATURE:
<223> OTHER INFORMATION: Synthetic peptide

<400> SEQUENCE: 329

Ser Ala Trp Ser His Pro Gln Phe Glu Lys Gly Gly Gly Ser Gly Gly
 1               5                  10                  15

Gly Ser Gly Gly Ser Ala Trp Ser His Pro Gln Phe Glu Lys Ser Gly
                 20                  25                  30

Glu Asn Leu Tyr Phe Gln Gly Ser
                 35                  40

<210> SEQ ID NO 330
<211> LENGTH: 44
<212> TYPE: PRT
<213> ORGANISM: Artificial Sequence
```

<220> FEATURE:
<223> OTHER INFORMATION: Synthetic peptide

<400> SEQUENCE: 330

Gly Ser Gly Ala Thr Asn Phe Ser Leu Leu Lys Gln Ala Gly Asp Val
1               5                   10                  15

Glu Glu Asn Pro Gly Pro Gly Asp Lys Ala Glu Leu Ile Pro Glu Pro
            20                  25                  30

Pro Lys Lys Lys Arg Lys Val Glu Leu Gly Thr Ala
        35                  40

<210> SEQ ID NO 331
<211> LENGTH: 62
<212> TYPE: PRT
<213> ORGANISM: Artificial Sequence
<220> FEATURE:
<223> OTHER INFORMATION: Synthetic peptide

<400> SEQUENCE: 331

Pro Lys Glu Glu Ala Arg Glu Leu Ile Arg Lys Gln Lys Glu Leu Ile
1               5                   10                  15

Lys Glu Gln Lys Lys Leu Ile Lys Glu Ala Lys Gln Lys Ser Asp Ser
            20                  25                  30

Arg Asp Ala Glu Arg Ile Trp Lys Arg Ser Arg Glu Ile Asn Arg Glu
        35                  40                  45

Ser Lys Lys Ile Asn Lys Arg Ile Lys Glu Leu Ile Lys Ser
    50                  55                  60

<210> SEQ ID NO 332
<211> LENGTH: 76
<212> TYPE: PRT
<213> ORGANISM: Artificial Sequence
<220> FEATURE:
<223> OTHER INFORMATION: Synthetic peptide

<400> SEQUENCE: 332

Thr Glu Lys Arg Leu Leu Glu Glu Ala Glu Arg Ala His Arg Glu Ala
1               5                   10                  15

Lys Glu Ile Ile Lys Lys Ala Gln Glu Leu His Arg Arg Leu Glu Glu
            20                  25                  30

Ile Val Arg Gln Ser Gly Ser Ser Glu Glu Ala Lys Lys Glu Ala Lys
        35                  40                  45

Lys Ile Leu Glu Glu Ile Arg Glu Leu Ser Arg Leu Leu Glu Leu
    50                  55                  60

Leu Arg Glu Ile Leu Tyr Leu Ser Gln Glu Gln Lys
65                  70                  75

<210> SEQ ID NO 333
<211> LENGTH: 5
<212> TYPE: PRT
<213> ORGANISM: Artificial Sequence
<220> FEATURE:
<223> OTHER INFORMATION: Synthetic peptide

<400> SEQUENCE: 333

Tyr Ser Trp Asn Ser
1               5

<210> SEQ ID NO 334
<211> LENGTH: 76
<212> TYPE: PRT
<213> ORGANISM: Artificial Sequence
<220> FEATURE:
<223> OTHER INFORMATION: Synthetic peptide

<400> SEQUENCE: 334

Thr Glu Lys Arg Leu Leu Glu Glu Ala Glu Arg Ala His Arg Glu Gln
1               5                   10                  15

Lys Glu Ile Ile Lys Lys Ala Gln Glu Leu His Arg Arg Thr Glu Glu
            20                  25                  30

Ile Ile Arg Gln Ser Gly Ser Ser Glu Glu Ala Lys Asp Glu Leu Arg
        35                  40                  45

Arg Ile Gln Glu Glu Ile Arg Glu Leu Ser Lys Arg Ser Leu Glu Leu
    50                  55                  60

Leu Arg Glu Ile Leu Tyr Leu Ser Gln Glu Gln Lys
65                  70                  75

<210> SEQ ID NO 335

<400> SEQUENCE: 335

000

<210> SEQ ID NO 336
<211> LENGTH: 76
<212> TYPE: PRT
<213> ORGANISM: Artificial Sequence
<220> FEATURE:
<223> OTHER INFORMATION: Synthetic peptide

<400> SEQUENCE: 336

Thr Glu Lys Arg Leu Leu Glu Glu Ala Glu Arg Ala His Arg Glu Gln
1               5                   10                  15

Lys Glu Ile Ile Lys Lys Ala Gln Glu Leu His Arg Arg Thr Glu Glu
            20                  25                  30

Ile Ile Arg Gln Ser Gly Ser Ser Glu Glu Ala Lys Asp Glu Leu Arg
        35                  40                  45

Arg Ile Gln Glu Glu Ile Arg Glu Leu Ser Lys Arg Ser Leu Glu Leu
    50                  55                  60

Leu Arg Glu Ile Leu Tyr Leu Ser Gln Glu Gln Lys
65                  70                  75

<210> SEQ ID NO 337
<211> LENGTH: 37
<212> TYPE: PRT
<213> ORGANISM: Artificial Sequence
<220> FEATURE:
<223> OTHER INFORMATION: Synthetic peptide

<400> SEQUENCE: 337

Pro Glu Arg Asp Glu Asn Arg Lys Leu Leu Asp Lys Val Arg Lys Leu
1               5                   10                  15

Val Glu Lys Ser Arg Arg Leu Val Glu Glu Leu Arg Lys Leu Val Asp
            20                  25                  30

Gln Ser Thr Lys Asn
        35

<210> SEQ ID NO 338
<211> LENGTH: 114
<212> TYPE: PRT
<213> ORGANISM: Artificial Sequence
<220> FEATURE:
<223> OTHER INFORMATION: Synthetic peptide

```
<400> SEQUENCE: 338

Ser Glu Glu Ala Lys Lys Glu Ala Lys Lys Ile Leu Glu Glu Ile Arg
1               5                   10                  15

Glu Leu Ser Lys Arg Ser Leu Glu Leu Leu Arg Glu Ile Leu Tyr Leu
            20                  25                  30

Ser Gln Gln Val Asn Asp Val Asp Glu Lys Ala Leu Glu Arg Gln Arg
        35                  40                  45

Lys Ile Ile Glu Arg Ala Gln Glu Ile His Arg Gln Gln Glu Ile
50                  55                  60

Leu Glu Glu Leu Glu Arg Ile Ile Arg Lys Pro Gly Ser Ser Glu Glu
65                  70                  75                  80

Ala Met Lys Arg Met Leu Lys Leu Leu Glu Glu Ser Leu Arg Leu Leu
                85                  90                  95

Lys Glu Leu Leu Glu Leu Ser Glu Glu Ser Ala Gln Leu Leu Tyr Glu
            100                 105                 110

Ala Arg

<210> SEQ ID NO 339
<211> LENGTH: 37
<212> TYPE: PRT
<213> ORGANISM: Artificial Sequence
<220> FEATURE:
<223> OTHER INFORMATION: Synthetic peptide

<400> SEQUENCE: 339

Asp Arg Arg Leu Glu Glu Tyr Glu Arg Gln Val Asp Glu Leu Arg Glu
1               5                   10                  15

Glu Ile Arg Arg Tyr Lys Glu Glu Val Asp Lys Phe Asp Lys Glu Val
            20                  25                  30

Lys Tyr Tyr Lys Lys
        35

<210> SEQ ID NO 340
<211> LENGTH: 70
<212> TYPE: PRT
<213> ORGANISM: Artificial Sequence
<220> FEATURE:
<223> OTHER INFORMATION: Synthetic peptide

<400> SEQUENCE: 340

Asp Arg Glu Glu Val His Lys Glu Ile Val Lys Leu Ile Arg Glu Ile
1               5                   10                  15

Ile Lys Ile His Lys Lys Ile Leu Lys Ile His Glu Lys Ile Lys Asn
            20                  25                  30

Gly Glu Ile Asp Pro Ser Glu Ile Leu Lys Leu Ser Glu Glu Ile Lys
        35                  40                  45

Lys Leu Thr Asp Thr Ile Ile Lys Ile Ile Glu Asp Leu Glu Gln Leu
50                  55                  60

Thr Arg Asp Leu Arg Arg
65                  70

<210> SEQ ID NO 341
<211> LENGTH: 36
<212> TYPE: PRT
<213> ORGANISM: Artificial Sequence
<220> FEATURE:
<223> OTHER INFORMATION: Synthetic peptide

<400> SEQUENCE: 341
```

```
Asp Glu Ile Thr Glu Ser Val Asp Arg Phe Lys Lys Ile Val Asp Gln
1               5                   10                  15

Phe Glu Glu Ser Ile Lys Lys Phe Glu Thr Val Ser Glu Glu Leu Arg
            20                  25                  30

Lys Ser Ile Ser
        35

<210> SEQ ID NO 342
<211> LENGTH: 74
<212> TYPE: PRT
<213> ORGANISM: Artificial Sequence
<220> FEATURE:
<223> OTHER INFORMATION: Synthetic peptide

<400> SEQUENCE: 342

Asp Lys Ala Glu Glu Val Glu Lys Ser Val Arg Lys Ile Glu Glu Ser
1               5                   10                  15

Ile Lys Lys Ile Arg Lys Ser Ile Lys Ala Glu Asp Ala Val Gln
            20                  25                  30

Leu Leu Lys Glu Gly Lys Ile Asp Ala Lys Asp Phe Leu Arg Ile Val
            35                  40                  45

Arg Glu Asp Leu Glu Val Val Lys Glu Asp Val Glu Ile Val Lys Glu
        50                  55                  60

Asp Val Glu Asn Val Arg Glu Phe Ser Ser
65                  70

<210> SEQ ID NO 343
<211> LENGTH: 34
<212> TYPE: PRT
<213> ORGANISM: Artificial Sequence
<220> FEATURE:
<223> OTHER INFORMATION: Synthetic peptide

<400> SEQUENCE: 343

Asp Gln His Val Val Glu Ile Leu Arg Lys Ile Val Glu Ile Phe Arg
1               5                   10                  15

Gln His Ile Glu Lys Leu Lys Lys His Leu Glu Lys Leu Arg Tyr Thr
            20                  25                  30

Ser Ser

<210> SEQ ID NO 344
<211> LENGTH: 76
<212> TYPE: PRT
<213> ORGANISM: Artificial Sequence
<220> FEATURE:
<223> OTHER INFORMATION: Synthetic peptide

<400> SEQUENCE: 344

Asp Leu Lys Glu Val Leu Lys Thr Val Glu Glu Ala Val Lys Glu Ile
1               5                   10                  15

Ile Lys Ser Ser Glu Glu Leu Leu Gln Ile Ser Arg Lys Ile Leu Glu
            20                  25                  30

Ile Ser Arg Val Gly Val Asp Glu His Glu Tyr Ile Ser Ala Ile Arg
        35                  40                  45

Glu Tyr Leu Lys Ala Leu Glu Lys His Ile Gln Ile Leu Lys Lys Phe
    50                  55                  60

Ile Glu Ile Leu Lys Glu Leu Ile Arg Ala Val Ser
65                  70                  75

<210> SEQ ID NO 345
```

-continued

```
<211> LENGTH: 71
<212> TYPE: PRT
<213> ORGANISM: Artificial Sequence
<220> FEATURE:
<223> OTHER INFORMATION: Synthetic peptide

<400> SEQUENCE: 345

Asp Glu Glu Asp Tyr Ile Asn Glu Asn Val Lys Asp Val Arg Asp
1               5                   10                  15

Ile Glu Asp Asp Val Arg Arg Ile Asn Glu Arg Ile Arg Glu Leu Leu
            20                  25                  30

Glu Lys Ile Arg Thr Glu Glu Val Leu Gln Arg Val Leu Glu Glu His
        35                  40                  45

His Glu Leu Val Glu Arg Val Leu Arg Lys Leu Val Glu Ile Leu Arg
    50                  55                  60

Lys His Glu Glu Glu Asn Arg
65                  70

<210> SEQ ID NO 346
<211> LENGTH: 76
<212> TYPE: PRT
<213> ORGANISM: Artificial Sequence
<220> FEATURE:
<223> OTHER INFORMATION: Synthetic peptide

<400> SEQUENCE: 346

Asn Asp Glu Glu Leu Lys Lys Ile Leu Glu Thr Leu Asp Arg Ile Leu
1               5                   10                  15

Lys Lys Leu Asp Lys Ile Leu Thr Arg Leu Ile Glu Val Leu Lys Lys
            20                  25                  30

Ser Glu Asp Pro Asn Leu Asp Asp Lys Asp Tyr Thr Glu Leu Val Lys
        35                  40                  45

Gln Phe Ile Glu Leu Ile Lys Lys Tyr Glu Glu Val Val Lys Glu Tyr
    50                  55                  60

Glu Glu Val Val Arg Gln Leu Ile Arg Leu Phe Ser
65                  70                  75

<210> SEQ ID NO 347
<211> LENGTH: 82
<212> TYPE: PRT
<213> ORGANISM: Artificial Sequence
<220> FEATURE:
<223> OTHER INFORMATION: Synthetic peptide

<400> SEQUENCE: 347

Asp Glu Asp Glu Ile Ser Tyr Asp Ser Lys Arg Arg Val Glu Glu Ile
1               5                   10                  15

Val Arg Gln Ala Arg Glu Lys Ser Glu Lys Ser Arg Lys Asp Ile Glu
            20                  25                  30

Asp Val Ala Glu Val Leu Arg Lys Gly Asp Val Ser Glu Lys Glu Val
        35                  40                  45

Val Asp Glu Leu Val Lys Val Leu Glu Glu Gln Lys Val Leu Arg
    50                  55                  60

Glu Ala Val Glu Arg Leu Arg Glu Val Leu Lys Lys Gln Val Asp Asp
65                  70                  75                  80

Val Arg

<210> SEQ ID NO 348
<211> LENGTH: 76
<212> TYPE: PRT
```

```
<213> ORGANISM: Artificial Sequence
<220> FEATURE:
<223> OTHER INFORMATION: Synthetic peptide

<400> SEQUENCE: 348

Asn Asp Glu Glu Leu Lys Lys Ile Leu Glu Thr Leu Asp Arg Ile Leu
1               5                   10                  15

Lys Lys Leu Glu Lys Ile Leu Thr Arg Leu Ile Glu Val Leu Lys Lys
                20                  25                  30

Ser Glu Asp Pro Asn Leu Asp Asp Lys Asp Tyr Thr Glu Leu Val Lys
            35                  40                  45

Gln Phe Ile Glu Leu Ile Lys Lys Phe Glu Val Ile Lys Glu Tyr
    50                  55                  60

Glu Glu Val Val Arg Gln Leu Ile Arg Leu Phe Ser
65                  70                  75

<210> SEQ ID NO 349
<211> LENGTH: 81
<212> TYPE: PRT
<213> ORGANISM: Artificial Sequence
<220> FEATURE:
<223> OTHER INFORMATION: Synthetic peptide

<400> SEQUENCE: 349

Lys Glu Lys Asp Ile Val Lys Thr Leu Val Asp Leu Leu Arg Glu Asn
1               5                   10                  15

Leu Glu Thr Leu Glu Arg Leu Ile Glu Val Val Arg Leu Leu Lys
                20                  25                  30

Glu Asn Val Asp Val Arg Asp Glu Gly Arg Asp Asp Lys Asp Ser Glu
            35                  40                  45

Arg Ile Leu Arg Asp Ile Lys Arg Arg Ile Asp Glu Ala Ala Lys Glu
        50                  55                  60

Ser Arg Glu Ile Ile Glu Arg Ile Glu Lys Glu Val Glu Tyr Arg Ser
65                  70                  75                  80

Arg

<210> SEQ ID NO 350
<211> LENGTH: 74
<212> TYPE: PRT
<213> ORGANISM: Artificial Sequence
<220> FEATURE:
<223> OTHER INFORMATION: Synthetic peptide

<400> SEQUENCE: 350

Asp Lys Lys Asp Glu Leu Glu Arg Ile Leu Asp Glu Ile Arg Arg Leu
1               5                   10                  15

Ile Glu Arg Leu Asp Glu Ile Leu Ser Arg Leu Asn Lys Leu Leu Glu
                20                  25                  30

Leu Leu Lys His Gly Val Pro Asn Ala Lys Glu Val Val Lys Asp Tyr
            35                  40                  45

Ile Arg Leu Leu Lys Glu Tyr Leu Glu Leu Val Lys Glu Phe Leu Lys
        50                  55                  60

Leu Val Lys Arg His Ala Asp Leu Val Ser
65                  70

<210> SEQ ID NO 351
<211> LENGTH: 82
<212> TYPE: PRT
<213> ORGANISM: Artificial Sequence
<220> FEATURE:
```

<223> OTHER INFORMATION: Synthetic peptide

<400> SEQUENCE: 351

Asp Lys Arg Tyr Glu Ser Glu Lys Leu Lys Arg Leu Asp Glu Ala
1               5                   10                  15

Val Glu Lys Val Arg Glu Val Val Arg Val Glu Arg Glu Ser Asp
                20                  25                  30

Arg Val Leu Glu Glu Val Arg Arg Arg Glu Ser Lys Glu Val Val
            35                  40                  45

Asp Lys Val Ile Glu Asp Asn Asp Lys Ala Leu Glu Asp Val Leu Arg
        50                  55                  60

Val Val Asp Glu Val Ala Lys Val Val Asp Val Val Arg Glu Asn
65                  70                  75                  80

Thr Arg

<210> SEQ ID NO 352
<211> LENGTH: 73
<212> TYPE: PRT
<213> ORGANISM: Artificial Sequence
<220> FEATURE:
<223> OTHER INFORMATION: Synthetic peptide

<400> SEQUENCE: 352

Asp Asp Lys Glu Leu Asp Lys Leu Leu Asp Thr Leu Glu Lys Ile Leu
1               5                   10                  15

Gln Thr Ala Thr Lys Ile Ile Asp Asp Ala Asn Lys Leu Leu Glu Lys
                20                  25                  30

Leu Arg Arg Ser Glu Arg Lys Asp Pro Lys Val Val Glu Thr Tyr Val
            35                  40                  45

Glu Leu Leu Lys Arg His Glu Lys Ala Val Lys Glu Leu Leu Glu Ile
        50                  55                  60

Ala Lys Thr His Ala Lys Lys Val Glu
65                  70

<210> SEQ ID NO 353
<211> LENGTH: 77
<212> TYPE: PRT
<213> ORGANISM: Artificial Sequence
<220> FEATURE:
<223> OTHER INFORMATION: Synthetic peptide

<400> SEQUENCE: 353

Asp Glu Asp Glu Ile Leu Tyr His Ser Glu Arg Leu Leu Gln Lys Leu
1               5                   10                  15

Lys Lys Glu Leu Asp Asp Leu Lys Glu Lys Ser Arg Glu Leu Leu Glu
                20                  25                  30

Glu Leu Lys Lys Glu Asp Pro Asp Asp Arg Leu Ile Glu Arg Ile Ile
            35                  40                  45

Arg Leu His Asp Glu Val Leu Lys Asp Leu Asp Glu Val Leu Lys Asn
        50                  55                  60

Ile Leu Glu Val His Arg Glu Val Leu Glu Arg Leu Arg
65                  70                  75

<210> SEQ ID NO 354
<211> LENGTH: 73
<212> TYPE: PRT
<213> ORGANISM: Artificial Sequence
<220> FEATURE:
<223> OTHER INFORMATION: Synthetic peptide

```
<400> SEQUENCE: 354

Asp Asp Lys Glu Leu Asp Lys Leu Leu Asp Thr Leu Glu Lys Ile Leu
1               5                   10                  15

Gln Thr Ala Thr Lys Ile Ile Asp Asp Leu Asn Lys Val Leu Glu Lys
            20                  25                  30

Leu Arg Arg Ser Glu Arg Lys Asp Pro Lys Val Ile Glu Thr Val Val
        35                  40                  45

Glu Leu Leu Lys Arg His Glu Lys Ala Val Lys Glu Leu Leu Glu Ile
50                  55                  60

Ala Lys Thr His Ala Lys Lys Val Glu
65                  70

<210> SEQ ID NO 355
<211> LENGTH: 78
<212> TYPE: PRT
<213> ORGANISM: Artificial Sequence
<220> FEATURE:
<223> OTHER INFORMATION: Synthetic peptide

<400> SEQUENCE: 355

Pro Lys Glu Glu Leu Ile Arg Arg Val Leu Glu Glu Val Lys Arg Leu
1               5                   10                  15

Asn Glu Lys Leu Leu Glu Ile Ile Arg Arg Ala Ala Glu Leu Val Lys
            20                  25                  30

Arg Ala Asn Asp Glu Leu Pro Glu Thr Glu Lys Leu Arg Glu Ile Asp
        35                  40                  45

Arg Glu Leu Glu Lys Lys Leu Lys Glu Ile Glu Asp Glu Leu Arg Arg
50                  55                  60

Ile Asp Lys Glu Leu Asp Asp Ala Leu Tyr Glu Ile Glu Asp
65                  70                  75

<210> SEQ ID NO 356
<211> LENGTH: 73
<212> TYPE: PRT
<213> ORGANISM: Artificial Sequence
<220> FEATURE:
<223> OTHER INFORMATION: Synthetic peptide

<400> SEQUENCE: 356

Asp Asp Lys Glu Leu Asp Lys Leu Leu Asp Thr Leu Glu Lys Ile Leu
1               5                   10                  15

Gln Thr Ala Thr Lys Val Val Asp Asp Ala Asn Lys Leu Leu Glu Lys
            20                  25                  30

Leu Arg Arg Ser Glu Arg Lys Asp Pro Lys Val Val Glu Thr Tyr Val
        35                  40                  45

Glu Leu Leu Lys Arg Leu Glu Lys Leu Ile Lys Glu Leu Leu Glu Ile
50                  55                  60

Ala Lys Thr His Ala Lys Lys Val Glu
65                  70

<210> SEQ ID NO 357
<211> LENGTH: 73
<212> TYPE: PRT
<213> ORGANISM: Artificial Sequence
<220> FEATURE:
<223> OTHER INFORMATION: Synthetic peptide

<400> SEQUENCE: 357

Lys Glu Asp Glu Ser Val Lys Arg Ala Glu Glu Ile Val Arg Thr Leu
1               5                   10                  15
```

Leu Lys Leu Leu Glu Asp Ser Leu Arg Glu Ala Glu Arg Ser Leu Arg
            20                  25                  30

Asp Ile Lys Asn Gly Glu Asp Glu His Asn Leu Arg Arg Ile Ser Glu
            35                  40                  45

Lys Leu Glu Glu Leu Ser Lys Arg Ile Thr Glu Thr Ile Glu Arg Leu
50                      55                  60

Leu Arg Glu Leu Gln Tyr Thr Ser Arg
65                  70

<210> SEQ ID NO 358
<211> LENGTH: 73
<212> TYPE: PRT
<213> ORGANISM: Artificial Sequence
<220> FEATURE:
<223> OTHER INFORMATION: Synthetic peptide

<400> SEQUENCE: 358

Asp Asp Lys Glu Ala Thr Lys Ile Ile Asp Asp Leu Asp Lys Leu Leu
1               5                   10                  15

Asp Thr Leu Glu Lys Ile Leu Gln Thr Ala Asn Lys Leu Leu Glu Lys
            20                  25                  30

Leu Arg Arg Ser Glu Arg Lys Asp Pro Lys Val Val Glu Thr Tyr Val
            35                  40                  45

Lys Ala Val Lys Glu Leu Leu Glu Ile Ala Lys Thr His Ala Glu Leu
50                      55                  60

Leu Lys Arg His Glu Lys Lys Val Glu
65                  70

<210> SEQ ID NO 359
<211> LENGTH: 82
<212> TYPE: PRT
<213> ORGANISM: Artificial Sequence
<220> FEATURE:
<223> OTHER INFORMATION: Synthetic peptide

<400> SEQUENCE: 359

Asp Glu Ser Glu Glu Ala Gln His Glu Val Glu Lys Val Leu Asp Asp
1               5                   10                  15

Ile Arg Arg Leu Ser Glu His Leu Gln Lys Arg Leu Glu Glu Val Leu
            20                  25                  30

Glu Glu Val Tyr Glu Leu Arg Arg Glu Gly Ser Asp Arg Thr Glu Val
            35                  40                  45

Val Glu Leu Leu Lys Glu Val Ile Arg Glu Ile Val Arg Val Asn Arg
50                      55                  60

Glu Ala Leu Glu Arg Leu Leu Arg Val Val Glu Ala Val Lys Arg
65                  70                  75                  80

Asn Glu

<210> SEQ ID NO 360
<211> LENGTH: 73
<212> TYPE: PRT
<213> ORGANISM: Artificial Sequence
<220> FEATURE:
<223> OTHER INFORMATION: Synthetic peptide

<400> SEQUENCE: 360

Asp Asp Lys Glu Ala Asn Lys Leu Leu Glu Lys Ala Thr Lys Ile Ile
1               5                   10                  15

Asp Asp Leu Asp Lys Leu Leu Asp Thr Leu Glu Lys Ile Leu Gln Thr

```
                20                  25                  30
Leu Arg Arg Ser Glu Arg Lys Asp Pro Lys Ala Val Lys Glu Leu Leu
            35                  40                  45

Glu Ile Ala Lys Thr His Ala Glu Leu Leu Lys Arg His Glu Lys Val
        50                  55                  60

Val Glu Thr Tyr Val Lys Lys Val Glu
65                  70

<210> SEQ ID NO 361
<211> LENGTH: 78
<212> TYPE: PRT
<213> ORGANISM: Artificial Sequence
<220> FEATURE:
<223> OTHER INFORMATION: Synthetic peptide

<400> SEQUENCE: 361

Asp Glu Glu Glu Val Val Arg Arg Ala Glu Leu Val Lys Glu
1               5                   10                  15

His Glu Glu Leu Ile Glu Arg Val Ile Arg Thr His Glu Glu Leu Val
            20                  25                  30

Tyr Lys Leu Glu Asp Gln Gly Ala Asp Lys Lys Leu Val Asp Val Leu
        35                  40                  45

Lys Arg Val Val Glu Glu Ser Glu Arg Val Ala Arg Glu Ile Val Lys
    50                  55                  60

Val Ser Arg Glu Leu Ile Arg Leu Leu Glu Glu Ala Ser Arg
65                  70                  75

<210> SEQ ID NO 362
<211> LENGTH: 114
<212> TYPE: PRT
<213> ORGANISM: Artificial Sequence
<220> FEATURE:
<223> OTHER INFORMATION: Synthetic peptide

<400> SEQUENCE: 362

Ser Ala Asp Asp Val Leu Glu Asp Ile Leu Lys Ile Ile Arg Glu Leu
1               5                   10                  15

Ile Glu Ile Leu Asp Gln Ile Leu Ser Leu Leu Asn Gln Leu Leu Lys
            20                  25                  30

Leu Leu Arg His Gly Val Pro Asn Ala Lys Lys Val Val Glu Lys Tyr
        35                  40                  45

Lys Glu Ile Leu Glu Leu Tyr Leu Gln Leu Val Ser Leu Phe Leu Lys
    50                  55                  60

Ile Val Lys Thr His Ala Asp Ala Val Ser Gly Lys Ile Asp Lys Lys
65                  70                  75                  80

Ala Glu Glu Glu Ile Lys Lys Glu Glu Lys Ile Lys Glu Lys Leu
                85                  90                  95

Arg Gln Ala Lys Asp Ile Leu Lys Lys Leu Gln Glu Glu Ile Asp Lys
            100                 105                 110

Thr Arg

<210> SEQ ID NO 363
<211> LENGTH: 79
<212> TYPE: PRT
<213> ORGANISM: Artificial Sequence
<220> FEATURE:
<223> OTHER INFORMATION: Synthetic peptide

<400> SEQUENCE: 363
```

```
Asp Lys Glu Glu Ser Glu Tyr Leu Leu Arg Asp Leu Val Arg Leu
1               5                   10                  15

Leu Glu Lys Val Lys Glu Lys Ile Glu Glu Val Asn Arg Glu Val Glu
            20                  25                  30

Lys Leu Leu Lys Lys Val Lys Asp Gly Arg Leu Asp Arg Arg Glu Val
            35                  40                  45

Leu Arg Glu Ile Leu Arg Leu Asn Arg Glu Leu Ala Glu Ile Ile Lys
        50                  55                  60

Glu Val Val Asp Arg Ile Arg His Val Val Glu Arg Ser Glu Arg
65                  70                  75
```

<210> SEQ ID NO 364
<211> LENGTH: 112
<212> TYPE: PRT
<213> ORGANISM: Artificial Sequence
<220> FEATURE:
<223> OTHER INFORMATION: Synthetic peptide

<400> SEQUENCE: 364

```
Asn Asp Lys Val Leu Asp Lys Ile Leu Asp Ile Leu Asp Arg Ile Leu
1               5                   10                  15

Arg Leu Ala Thr Arg Val Ile Asp Leu Ala Asn Lys Leu Leu Gln Val
            20                  25                  30

Lys Lys Lys Ser Thr His Lys Asp Pro Arg Ile Val Glu Thr Tyr Lys
            35                  40                  45

Glu Leu Leu Lys Ile His Glu Thr Ala Val Arg Leu Leu Glu Leu
        50                  55                  60

Ala Asp Leu His Arg Arg Leu Lys Ser Lys Asp Glu Glu Ala Asn Lys
65                  70                  75                  80

Arg Val Glu Thr Glu Leu Asp Arg Ile Arg Lys Lys Val Lys Asp Ile
                85                  90                  95

Glu Asp Lys Val Arg Lys Leu Glu Asp Lys Val Arg Lys Thr Ala Ser
                100                 105                 110
```

<210> SEQ ID NO 365
<211> LENGTH: 79
<212> TYPE: PRT
<213> ORGANISM: Artificial Sequence
<220> FEATURE:
<223> OTHER INFORMATION: Synthetic peptide

<400> SEQUENCE: 365

```
Pro Val Glu Glu Ile Ile Lys Glu Val Val Lys Arg Val Ile Glu Val
1               5                   10                  15

Gln Glu Lys Val Leu Arg Ile Ile Ser His Ala Val Lys Arg Val Val
            20                  25                  30

Glu Val Gln Lys Lys Tyr Asp Pro Gly Ser Glu Ser Asn Arg Val
            35                  40                  45

Val Glu Glu Val Lys Lys Thr Ile Glu Asp Ala Ile Arg Glu Ser Asp
        50                  55                  60

Glu Val Val Asp Glu Val Val Lys Arg Ile Gln Tyr Thr Val Arg
65                  70                  75
```

<210> SEQ ID NO 366
<211> LENGTH: 76
<212> TYPE: PRT
<213> ORGANISM: Artificial Sequence
<220> FEATURE:
<223> OTHER INFORMATION: Synthetic peptide

```
<400> SEQUENCE: 366

Asp Glu Ala Val Lys Arg Val Val Glu Lys Ser Leu Lys Ile Leu Asp
1               5                   10                  15

Glu Val Ile Lys Lys Ser Leu Asp Ile Leu Arg Glu Leu Ile Glu Leu
            20                  25                  30

Gln Ile Arg His Ala Lys Asp Asp Glu Ser Val Ile Arg Ala Ser Lys
        35                  40                  45

Ser Ala Leu Lys Asp Ala Ile Glu Ala Leu Lys Lys Ser Leu Asp Glu
    50                  55                  60

Ile Lys Lys Ala Leu Lys Arg Ser Ala Asp Glu Gly
65                  70                  75

<210> SEQ ID NO 367
<211> LENGTH: 78
<212> TYPE: PRT
<213> ORGANISM: Artificial Sequence
<220> FEATURE:
<223> OTHER INFORMATION: Synthetic peptide

<400> SEQUENCE: 367

Asp Glu Asp Lys Glu Ala Asn Arg Val Leu Asp Glu Val Leu Lys Thr
1               5                   10                  15

Val Arg Asp Leu Leu Glu Thr Ala Asn Glu Val Leu Lys Glu Val Leu
            20                  25                  30

Tyr Arg Leu Lys Arg Thr Asp Asp Gln Glu Lys Val Val Arg Thr Leu
        35                  40                  45

Thr Glu Val Leu Lys Glu His Leu Lys Leu Val Glu Glu Ile Val Arg
    50                  55                  60

Ile Leu Asp Lys Val Leu Lys Glu His Leu Glu Thr Glu Lys
65                  70                  75

<210> SEQ ID NO 368
<211> LENGTH: 76
<212> TYPE: PRT
<213> ORGANISM: Artificial Sequence
<220> FEATURE:
<223> OTHER INFORMATION: Synthetic peptide

<400> SEQUENCE: 368

Ser Lys Glu Glu Val Ile Arg Leu Leu Lys Glu Asn Val Arg Leu Ile
1               5                   10                  15

Lys Glu Asn Leu Glu Leu Leu Thr Arg Asn Leu Lys Leu Ile Thr Asp
            20                  25                  30

Leu Val Arg Gly Ser Asn Gly Ser Glu Glu Lys Ile Lys Thr Leu Lys
        35                  40                  45

Glu Leu Leu Lys Glu Tyr Arg Glu Leu Leu Lys Arg Tyr Arg Lys Leu
    50                  55                  60

Val Glu Asp Tyr Lys Arg Leu Val Asp Lys His Asp
65                  70                  75

<210> SEQ ID NO 369
<211> LENGTH: 76
<212> TYPE: PRT
<213> ORGANISM: Artificial Sequence
<220> FEATURE:
<223> OTHER INFORMATION: Synthetic peptide

<400> SEQUENCE: 369

Arg Arg Glu Glu Val Val Lys Arg Ile Arg Glu Leu Leu Lys Arg Asn
1               5                   10                  15
```

```
Lys Glu Leu Ile Asp Arg Ile Arg Glu Leu Glu Glu Asn Glu Tyr
                20                  25                  30

Leu Asp Lys Asp Ala Arg Asp Lys Asp Val Leu Arg Arg Ser Val Glu
            35                  40                  45

Leu Leu Glu Glu Leu Val Arg Ile Leu Glu Ser Val Glu Leu Ala
    50                  55                  60

Lys Glu Ile Ile Lys Leu Leu Arg Glu Val Val Glu
65                  70                  75

<210> SEQ ID NO 370
<211> LENGTH: 73
<212> TYPE: PRT
<213> ORGANISM: Artificial Sequence
<220> FEATURE:
<223> OTHER INFORMATION: Synthetic peptide

<400> SEQUENCE: 370

Tyr Ile Glu Asp Val Ile Lys Lys Ile Leu Asp Val Ser Arg Glu Leu
1               5                   10                  15

Ile Lys Leu Ser Arg Thr Ile Ile Lys Ile Ser Glu Glu Ile Asn Lys
                20                  25                  30

Gln Leu Gln Gln Gly Arg Asp Thr Lys Asp Leu Val Lys Lys Tyr Asp
            35                  40                  45

Glu Ile Ile Lys Lys Tyr Thr Arg Ile Val Gln His Tyr Thr Glu Leu
    50                  55                  60

Ile Lys Glu Leu Gln Lys Leu Leu Ser
65                  70

<210> SEQ ID NO 371
<211> LENGTH: 75
<212> TYPE: PRT
<213> ORGANISM: Artificial Sequence
<220> FEATURE:
<223> OTHER INFORMATION: Synthetic peptide

<400> SEQUENCE: 371

Asp Glu Lys Glu Glu Ala Lys Lys Ala Ser Glu Glu Ser Val Arg Thr
1               5                   10                  15

Val Glu Arg Ile Leu Glu Glu Leu Leu Lys Ala Ser Glu Glu Ser Val
                20                  25                  30

Glu Leu Leu Arg Arg Gly Glu Asp Ala Lys Asp Val Val Glu Arg Ser
            35                  40                  45

Lys Glu Ala Leu Lys Arg Val Lys Glu Leu Leu Asp Glu Val Val Lys
    50                  55                  60

Arg Ser Asp Glu Ile Leu Lys Tyr Ile His Asn
65                  70                  75

<210> SEQ ID NO 372
<211> LENGTH: 73
<212> TYPE: PRT
<213> ORGANISM: Artificial Sequence
<220> FEATURE:
<223> OTHER INFORMATION: Synthetic peptide

<400> SEQUENCE: 372

Glu Glu Glu Glu Ile Leu Lys Ile Gln Lys Glu Leu Leu Arg Ile Gln
1               5                   10                  15

Ser Glu Ile Glu Leu Asp Lys Gln Lys Lys Ile Leu Asp Thr Leu Arg Ser
                20                  25                  30
```

Asn Gly Ala Val Thr Glu Glu Val Arg Ser Ile Leu Glu Lys Val Glu
            35                  40                  45

Arg Leu Ser Glu Glu Ala Lys Glu Leu Ser Lys Glu Ala Lys Glu Leu
 50                  55                  60

Thr Lys Glu Val Ser Lys Leu Ile Ser
 65                  70

<210> SEQ ID NO 373
<211> LENGTH: 74
<212> TYPE: PRT
<213> ORGANISM: Artificial Sequence
<220> FEATURE:
<223> OTHER INFORMATION: Synthetic peptide

<400> SEQUENCE: 373

Pro Asp Met Asp Glu Val Lys Arg Val Leu Asp Glu Leu Ile Glu Ile
 1               5                  10                  15

Gln Glu Glu Ile Leu Arg Glu Ile Lys Arg Val Leu Glu Lys Leu Ile
            20                  25                  30

Lys Ile Gln Glu Asp Asn Gly Ser Glu Tyr Glu Ser Arg Glu Val Val
            35                  40                  45

Arg Glu Ile Val Glu Ile Ala Arg Lys Leu Val Glu Arg Ser Arg Arg
 50                  55                  60

Val Val Lys Lys Ile Thr Glu Thr Leu Gln
 65                  70

<210> SEQ ID NO 374
<211> LENGTH: 76
<212> TYPE: PRT
<213> ORGANISM: Artificial Sequence
<220> FEATURE:
<223> OTHER INFORMATION: Synthetic peptide

<400> SEQUENCE: 374

Pro Leu Glu Asp Leu Val Arg Lys Tyr Asp Glu Leu Val Lys Thr Tyr
 1               5                  10                  15

Glu Lys Leu Val Glu Glu Phe Lys Lys Ala Val Asp Lys Tyr Asp Lys
            20                  25                  30

Ala Val Lys Lys Ala Pro Val Ser Lys Glu Ala Thr Asp Ser Leu Asp
            35                  40                  45

Leu Ile Arg Lys Val Leu Glu Leu Leu Asp Arg Asn Leu Lys Leu Ile
 50                  55                  60

Lys Glu Asn Ala Lys Leu Ile Lys Glu Leu Leu Lys
 65                  70                  75

<210> SEQ ID NO 375
<211> LENGTH: 77
<212> TYPE: PRT
<213> ORGANISM: Artificial Sequence
<220> FEATURE:
<223> OTHER INFORMATION: Synthetic peptide

<400> SEQUENCE: 375

Pro Glu Arg Glu Ala Leu Arg Glu Val Leu Glu Asp Leu Lys Arg Val
 1               5                  10                  15

Thr Asp Arg Leu Arg Glu Leu Val Glu Arg Val Leu Glu Glu Leu Lys
            20                  25                  30

Lys Val Thr Asp His Val Asp Ser Glu Arg Ile Leu Arg Glu Ser Arg
            35                  40                  45

Arg Val Leu Lys Glu Leu Lys Asp Ile Ile Glu Glu Ile Leu Arg Glu

```
                50                  55                  60
Ser Glu Lys Val Leu Glu Lys Leu Lys Tyr Thr Glu Asp
 65                  70                  75
```

<210> SEQ ID NO 376
<211> LENGTH: 70
<212> TYPE: PRT
<213> ORGANISM: Artificial Sequence
<220> FEATURE:
<223> OTHER INFORMATION: Synthetic peptide

<400> SEQUENCE: 376

```
Pro Ile Lys Asp Ile Ser Lys Arg Leu Leu Glu Ile Ser Lys Arg Leu
 1               5                  10                  15

Val Glu Ile Ser Asp Arg Ile Val Glu Leu Leu Gln Arg Ile Ala Asp
                20                  25                  30

Ser Lys Asp Pro Asn Lys Asp Leu Gln Lys Glu Val Lys Asp Val Leu
            35                  40                  45

Glu Glu Tyr Lys Arg Leu Val Arg Glu Tyr Arg Glu Val Val Lys Glu
        50                  55                  60

Tyr Glu Lys Val Val Ser
 65                  70
```

<210> SEQ ID NO 377
<211> LENGTH: 73
<212> TYPE: PRT
<213> ORGANISM: Artificial Sequence
<220> FEATURE:
<223> OTHER INFORMATION: Synthetic peptide

<400> SEQUENCE: 377

```
Pro Val Glu Glu Ala Ile Lys Lys Val Ile Asp Asp Leu Arg Asp Val
 1               5                  10                  15

Gln Arg Lys Ile Arg Glu Leu Val Glu Glu Leu Ile Arg Leu Leu Glu
                20                  25                  30

Glu Val Gln Arg Asp Asn Asp Lys Arg Glu Ser Glu Tyr Val Val Glu
            35                  40                  45

Arg Val Glu Glu Ile Leu Arg Arg Ile Thr Glu Thr Ser Arg Glu Val
        50                  55                  60

Val Arg Lys Ala Val Glu Asp Leu Ser
 65                  70
```

<210> SEQ ID NO 378
<211> LENGTH: 69
<212> TYPE: PRT
<213> ORGANISM: Artificial Sequence
<220> FEATURE:
<223> OTHER INFORMATION: Synthetic peptide

<400> SEQUENCE: 378

```
Asn Leu Glu Glu Leu Val Lys Leu Leu Lys Glu Val Leu Glu Met His
 1               5                  10                  15

Glu Arg Leu Leu Arg Ile His Glu Asp Leu Val Glu Ala His Lys Ser
                20                  25                  30

Asn Ala Ser Asp Lys Glu Ser Glu Arg Lys Leu Lys Lys Ser Asp Lys
            35                  40                  45

Asp Ile Lys Glu Ser Leu Lys Lys Ile Lys Ser Ile Ile Asp Gln Val
        50                  55                  60

Arg Tyr Ile Gln Ser
 65
```

<210> SEQ ID NO 379
<211> LENGTH: 77
<212> TYPE: PRT
<213> ORGANISM: Artificial Sequence
<220> FEATURE:
<223> OTHER INFORMATION: Synthetic peptide

<400> SEQUENCE: 379

```
Pro Val Glu Glu Val Leu Lys Glu Leu Ser Glu Val Asn Glu Arg Val
1               5                   10                  15

Arg Asp Ile Ala Arg Glu Ile Ile Glu Arg Leu Ser Glu Val Asn Glu
            20                  25                  30

Glu Val Lys Glu Thr Asp Asp Glu Asp Glu Leu Lys Lys Ile Ser Lys
        35                  40                  45

Lys Val Val Asp Glu Val Glu Asp Leu Leu Arg Lys Ile Leu Glu Val
    50                  55                  60

Ser Glu Glu Val Val Arg Arg Val Glu Tyr His Asp Arg
65                  70                  75
```

<210> SEQ ID NO 380
<211> LENGTH: 76
<212> TYPE: PRT
<213> ORGANISM: Artificial Sequence
<220> FEATURE:
<223> OTHER INFORMATION: Synthetic peptide

<400> SEQUENCE: 380

```
Asp Glu Asp Tyr Glu Ser Arg Glu Ile Ile Asp Glu Ile Arg Lys Leu
1               5                   10                  15

Leu Asp Arg Ser Lys Lys Ile Val His Arg Ser Gln Arg Leu Val Glu
            20                  25                  30

Arg Val Lys Ser Thr Pro Leu Ser Glu Asp Gln Glu Asp Leu Ile Arg
        35                  40                  45

Arg His Glu Glu Thr Ile Asn Arg His Arg Glu Leu Val Lys Glu Leu
    50                  55                  60

Glu Lys Val Leu Glu Asp His Glu Arg His Ile Arg
65                  70                  75
```

<210> SEQ ID NO 381
<211> LENGTH: 73
<212> TYPE: PRT
<213> ORGANISM: Artificial Sequence
<220> FEATURE:
<223> OTHER INFORMATION: Synthetic peptide

<400> SEQUENCE: 381

```
Pro Arg Ser Tyr Leu Leu Lys Glu Leu Ala Asp Leu Ser Gln His Leu
1               5                   10                  15

Val Arg Leu Leu Glu Arg Leu Val Arg Glu Ser Glu Arg Val Val Glu
            20                  25                  30

Val Leu Glu Arg Gly Glu Val Asp Glu Glu Leu Lys Arg Leu Glu
        35                  40                  45

Asp Leu His Arg Glu Leu Glu Lys Ala Val Arg Glu Val Arg Glu Thr
    50                  55                  60

His Arg Glu Ile Arg Glu Arg Ser Arg
65                  70
```

<210> SEQ ID NO 382
<211> LENGTH: 77

```
<212> TYPE: PRT
<213> ORGANISM: Artificial Sequence
<220> FEATURE:
<223> OTHER INFORMATION: Synthetic peptide

<400> SEQUENCE: 382

Pro Glu Lys Asp Glu Asn Arg Lys Leu Leu Asp Lys Val Arg Lys Leu
1               5                   10                  15

Val Glu Lys Ser Arg Arg Leu Val Glu Glu Leu Arg Lys Leu Val Asp
            20                  25                  30

Gln Ser Thr Lys Asn Gly Leu Ile Asp Glu Lys Ala Leu Arg Lys Gln
        35                  40                  45

Gln Glu Val Leu Arg Lys Val Glu Glu Val Leu Glu Lys Gln Glu Arg
    50                  55                  60

Val Leu Arg Glu Leu Glu Glu Ile Ser Tyr Arg Val Ile
65                  70                  75

<210> SEQ ID NO 383
<211> LENGTH: 73
<212> TYPE: PRT
<213> ORGANISM: Artificial Sequence
<220> FEATURE:
<223> OTHER INFORMATION: Synthetic peptide

<400> SEQUENCE: 383

Asp Glu Lys Asp Glu Ile Arg His Val Ile Glu Ser Val Glu Arg Leu
1               5                   10                  15

Ile Glu Asp Ile Lys Arg Leu Leu Lys Thr Leu Arg Glu Leu Ala His
            20                  25                  30

Asp Asp Ser Asp Lys Lys Thr Val Lys Glu Val Leu Asp Arg Val Lys
        35                  40                  45

Glu Met Ile Glu Arg His Arg Arg Glu Leu Glu His Arg Lys Glu
    50                  55                  60

Leu Glu Arg Ala Glu Tyr Glu Val Arg
65                  70

<210> SEQ ID NO 384
<211> LENGTH: 122
<212> TYPE: PRT
<213> ORGANISM: Artificial Sequence
<220> FEATURE:
<223> OTHER INFORMATION: Synthetic peptide

<400> SEQUENCE: 384

Asp Glu Lys Ala Leu Arg Lys Gln Gln Glu Val Leu Arg Lys Val Glu
1               5                   10                  15

Glu Val Leu Glu Lys Gln Glu Arg Val Leu Arg Glu Leu Glu Glu Ile
            20                  25                  30

Ser Tyr Arg Val Ile Thr Arg Gly Glu Asp His Lys Ala Glu Glu Asp
        35                  40                  45

Ser Arg Arg Val Leu Glu Arg Phe Val Arg Val Ser Glu Val Leu
    50                  55                  60

Lys Val Leu Glu Glu Phe Leu Arg Val Ser Glu Leu Leu Arg Glu
65                  70                  75                  80

Ala Asp Arg Asp Arg Asp Arg Arg Leu Glu Glu Tyr Glu Arg Gln Val
                85                  90                  95

Asp Glu Leu Arg Glu Glu Ile Arg Arg Tyr Lys Glu Glu Val Asp Lys
                100                 105                 110

Phe Asp Lys Glu Val Lys Tyr Tyr Lys Lys
```

-continued

<210> SEQ ID NO 385
<211> LENGTH: 75
<212> TYPE: PRT
<213> ORGANISM: Artificial Sequence
<220> FEATURE:
<223> OTHER INFORMATION: Synthetic peptide

<400> SEQUENCE: 385

Ser Leu Glu Asp Ser Val Arg Leu Asn Asp Glu Val Val Lys Val Val
1               5                   10                  15

Glu Arg Val Val Arg Leu Asn Gln Glu Val Val Arg Leu Ile Lys His
            20                  25                  30

Ala Thr Asp Val Glu Asp Glu Thr Val Lys Tyr Val Leu Glu Arg
        35                  40                  45

Val Arg Glu Val Leu Asp Glu Ser Arg Glu Val Leu Lys Arg Val His
    50                  55                  60

Glu Leu Leu Glu Glu Ser Glu Arg Arg Leu Glu
65                  70                  75

<210> SEQ ID NO 386
<211> LENGTH: 123
<212> TYPE: PRT
<213> ORGANISM: Artificial Sequence
<220> FEATURE:
<223> OTHER INFORMATION: Synthetic peptide

<400> SEQUENCE: 386

Pro Glu Arg Asp Glu Asn Arg Lys Leu Leu Asp Lys Val Arg Lys Leu
1               5                   10                  15

Val Glu Lys Ser Arg Arg Leu Val Glu Glu Leu Arg Lys Leu Val Asp
            20                  25                  30

Gln Ser Thr Lys Asn Gly Leu Ile Asp Glu Lys Ala Leu Arg Lys Gln
        35                  40                  45

Gln Glu Val Leu Arg Lys Val Glu Val Leu Glu Lys Gln Glu Arg
    50                  55                  60

Val Leu Arg Glu Leu Glu Glu Ile Ser Tyr Arg Val Ile Thr Arg Gly
65                  70                  75                  80

Glu Asp His Lys Ala Glu Glu Asp Ser Arg Arg Val Leu Glu Arg Phe
                85                  90                  95

Val Arg Val Ser Arg Glu Val Leu Lys Val Leu Glu Glu Phe Leu Arg
            100                 105                 110

Val Ser Glu Glu Leu Leu Arg Glu Ala Asp Arg
        115                 120

<210> SEQ ID NO 387
<211> LENGTH: 74
<212> TYPE: PRT
<213> ORGANISM: Artificial Sequence
<220> FEATURE:
<223> OTHER INFORMATION: Synthetic peptide

<400> SEQUENCE: 387

Pro Glu Leu Asp Glu Val Lys Lys Leu Ile Asp Glu Leu Lys Lys Ser
1               5                   10                  15

Val Glu Arg Leu Glu Glu Ser Ile Arg Glu Val Lys Glu Ser Ile Lys
            20                  25                  30

Lys Leu Arg Lys Gly Asp Ile Asp Ala Glu Glu Asn Ile Lys Leu Leu
        35                  40                  45

```
Lys Glu Asn Ile Lys Ile Val Arg Glu Asn Ile Lys Ile Ile Lys Glu
        50                  55                  60

Ile Ile Asp Val Val Gln Tyr Val Leu Arg
65                  70
```

<210> SEQ ID NO 388
<211> LENGTH: 78
<212> TYPE: PRT
<213> ORGANISM: Artificial Sequence
<220> FEATURE:
<223> OTHER INFORMATION: Synthetic peptide

<400> SEQUENCE: 388

```
Asp Ser Glu Tyr Glu Ser Arg Gln Val Leu Arg Glu Leu Asp Thr Val
1               5                   10                  15

Leu Lys Asp Ser His Thr Val Leu Glu Ala Leu Arg Gln Val Ile Arg
            20                  25                  30

Asp Ser Gln Asp Val Val Ser Lys Ser Asp Glu Glu Ser Arg Arg Val
        35                  40                  45

Ile Asp Asp Leu Glu Lys Val Ile Gln Asp Ser Lys Lys Val Leu Asp
    50                  55                  60

Asp Ile Lys Arg Leu Ile Asp Lys Ser Lys Ser Ile Lys Ser
65                  70                  75
```

<210> SEQ ID NO 389
<211> LENGTH: 77
<212> TYPE: PRT
<213> ORGANISM: Artificial Sequence
<220> FEATURE:
<223> OTHER INFORMATION: Synthetic peptide

<400> SEQUENCE: 389

```
Asp Glu Ser Asp Arg Ile Arg Lys Ile Val Glu Glu Ser Asp Glu Ile
1               5                   10                  15

Val Lys Glu Ser Arg Lys Leu Ala Glu Arg Ala Arg Glu Leu Ile Lys
            20                  25                  30

Glu Ser Glu Asp Lys Arg Val Ser Glu Glu Arg Asn Glu Arg Leu Leu
        35                  40                  45

Glu Glu Leu Leu Arg Ile Leu Asp Glu Asn Ala Glu Leu Leu Lys Arg
    50                  55                  60

Asn Leu Glu Leu Leu Lys Glu Val Leu Tyr Arg Thr Arg
65                  70                  75
```

<210> SEQ ID NO 390
<211> LENGTH: 76
<212> TYPE: PRT
<213> ORGANISM: Artificial Sequence
<220> FEATURE:
<223> OTHER INFORMATION: Synthetic peptide

<400> SEQUENCE: 390

```
Ser Leu Tyr Glu Leu Thr Gln Arg Tyr Glu Lys Leu Val Gln Gln Tyr
1               5                   10                  15

Glu Glu Leu Val Lys Asp Tyr Arg Arg Leu Val Lys Lys Leu Glu Lys
            20                  25                  30

Leu Lys Arg Asp Asn Lys Pro Asp Lys Arg Leu Leu Lys Glu Ile Val
        35                  40                  45

Asp Val Ile Lys Lys Ser Val Glu Ile Ile Asp Arg Ser Leu Lys Leu
    50                  55                  60
```

```
Leu Glu Glu Ser Ile Lys Ile Leu Glu Glu Thr Asp
 65                  70                  75
```

<210> SEQ ID NO 391
<211> LENGTH: 76
<212> TYPE: PRT
<213> ORGANISM: Artificial Sequence
<220> FEATURE:
<223> OTHER INFORMATION: Synthetic peptide

<400> SEQUENCE: 391

```
Asp Lys Lys Asp Ala Ser Arg Arg Ala Ile Arg Val Leu His Glu Phe
  1               5                  10                  15

Val Arg Val Ser Glu Glu Val Leu Glu Val Leu Arg Lys Ser Val Glu
                 20                  25                  30

Ser Leu Lys Arg Leu Asp Val Asp Glu Lys Ile Lys Arg Thr His Asp
             35                  40                  45

Arg Ile Glu Glu Glu Leu Arg Arg Trp Lys Arg Glu Leu Glu Glu Leu
         50                  55                  60

Ile Glu Arg Leu Arg Glu Trp Glu Tyr His Gln Asp
 65                  70                  75
```

<210> SEQ ID NO 392
<211> LENGTH: 76
<212> TYPE: PRT
<213> ORGANISM: Artificial Sequence
<220> FEATURE:
<223> OTHER INFORMATION: Synthetic peptide

<400> SEQUENCE: 392

```
Asp Ile Glu Tyr Glu Ser Lys Glu Ile Leu Glu Leu Ile Lys Glu Leu
  1               5                  10                  15

Leu Lys Leu Ser Arg Glu Leu Leu Lys Glu Ser Arg Arg Ala Leu Glu
                 20                  25                  30

Leu Val Arg Lys Ser Arg Asp Asp Ser Ile Val Glu Glu Val Ile Gln
             35                  40                  45

Val His Lys Lys Val Leu Asp Ile His Lys Glu Val Leu Lys Ile Val
         50                  55                  60

Arg Lys Val Val Glu Val His Arg Arg Val Lys Ser
 65                  70                  75
```

<210> SEQ ID NO 393
<211> LENGTH: 77
<212> TYPE: PRT
<213> ORGANISM: Artificial Sequence
<220> FEATURE:
<223> OTHER INFORMATION: Synthetic peptide

<400> SEQUENCE: 393

```
Asp Lys Glu Tyr Lys Leu Asp Arg Ile Leu Arg Arg Leu Asp Glu Leu
  1               5                  10                  15

Ile Lys Gln Leu Ser Arg Ile Leu Glu Glu Ile Glu Arg Leu Val Asp
                 20                  25                  30

Glu Leu Glu Arg Glu Pro Leu Asp Asp Lys Glu Val Gln Asp Val Ile
             35                  40                  45

Glu Arg Ile Val Glu Leu Ile Asp Glu His Leu Glu Leu Leu Lys Glu
         50                  55                  60

Tyr Ile Lys Leu Leu Glu Glu Tyr Ile Lys Thr Thr Lys
 65                  70                  75
```

```
<210> SEQ ID NO 394
<211> LENGTH: 76
<212> TYPE: PRT
<213> ORGANISM: Artificial Sequence
<220> FEATURE:
<223> OTHER INFORMATION: Synthetic peptide

<400> SEQUENCE: 394

Asp Leu Glu Tyr Leu Asn Arg Arg Leu Leu Gln Leu Ile Lys Thr Leu
1               5                   10                  15

Ile Asp Leu Asn Arg His Leu Leu Lys Leu Ile Asp Lys Leu Lys Lys
            20                  25                  30

Leu Asn Ser Arg Glu Gly Asp Glu Lys Ile Lys Glu Glu Ser Lys
        35                  40                  45

Gln Ile Gln Glu Gln Phe Lys Glu Ile Val Glu Arg Ser Lys Glu Ile
    50                  55                  60

Ile Lys Gln Ile Lys Glu Ile Ile Lys Arg Ser Gln
65                  70                  75

<210> SEQ ID NO 395
<211> LENGTH: 76
<212> TYPE: PRT
<213> ORGANISM: Artificial Sequence
<220> FEATURE:
<223> OTHER INFORMATION: Synthetic peptide

<400> SEQUENCE: 395

Arg Asp Arg Lys Ile Ser Glu Glu Leu Ile Lys Ala Leu Glu Asp His
1               5                   10                  15

Ile Arg Met Leu Glu Glu Leu Ile Arg Ala Ile Glu Glu His Ile Lys
            20                  25                  30

Leu Ala Glu Arg Gly Val Asp Glu Lys Glu Leu Arg Glu Ser Leu Glu
        35                  40                  45

Glu Leu Lys Lys Ile Val Asp Glu Leu Glu Lys Ser Leu Glu Glu Leu
    50                  55                  60

Arg Lys Leu Ala Glu Arg Tyr Lys Tyr Glu Thr Arg
65                  70                  75

<210> SEQ ID NO 396
<211> LENGTH: 76
<212> TYPE: PRT
<213> ORGANISM: Artificial Sequence
<220> FEATURE:
<223> OTHER INFORMATION: Synthetic peptide

<400> SEQUENCE: 396

Glu Glu Ser Glu Glu Val Arg Lys Val Val Glu Arg Ile Lys Lys Ile
1               5                   10                  15

Ser Arg Glu Leu Glu Glu Val Val Lys Glu Leu Asp Arg Val Ser Lys
            20                  25                  30

Glu Phe Asp Arg His Gly Glu Thr Asp Glu Ile Val Arg Glu His Glu
        35                  40                  45

Arg Ile Val Glu Lys Leu Glu Glu Ile Val Lys Lys His Thr Lys Ile
    50                  55                  60

Val Glu Glu Leu Ala Glu Ile Val Tyr Lys Gln Gln
65                  70                  75

<210> SEQ ID NO 397
<211> LENGTH: 75
<212> TYPE: PRT
<213> ORGANISM: Artificial Sequence
```

-continued

```
<220> FEATURE:
<223> OTHER INFORMATION: Synthetic peptide

<400> SEQUENCE: 397

Asp His Glu Tyr Trp Val Lys Ile Val Glu Arg Ile Leu Arg Val Met
1               5                   10                  15

Glu Lys His Ala Glu Ile Val Lys Lys His Leu Glu Ile Val Glu Arg
            20                  25                  30

Val Val Arg Glu Gly Pro Ser Glu Asp Leu Arg Arg Lys Leu Lys Glu
        35                  40                  45

Ser Leu Arg Glu Ile Glu Glu Ser Leu Arg Glu Leu Lys Glu Leu Leu
    50                  55                  60

Asp Glu Leu Asp Glu Leu Ser Glu Lys Thr Arg
65                  70                  75

<210> SEQ ID NO 398
<211> LENGTH: 70
<212> TYPE: PRT
<213> ORGANISM: Artificial Sequence
<220> FEATURE:
<223> OTHER INFORMATION: Synthetic peptide

<400> SEQUENCE: 398

Asp Leu Leu Tyr Leu Ser Lys Glu Leu Leu Lys Leu Val Arg Glu Leu
1               5                   10                  15

Leu Lys Leu Ser Arg Glu Leu Val Glu Leu Ser Arg Arg Leu Val Asn
            20                  25                  30

Ser Thr His Lys Ser Pro Glu Leu Val Lys Lys Tyr Asp Lys Leu Val
        35                  40                  45

Lys Lys Tyr Gln Asp Leu Leu Lys Lys Leu Ala Asp Val Ala Asp Glu
    50                  55                  60

Tyr Leu Arg Gln Arg Ser
65                  70

<210> SEQ ID NO 399
<211> LENGTH: 74
<212> TYPE: PRT
<213> ORGANISM: Artificial Sequence
<220> FEATURE:
<223> OTHER INFORMATION: Synthetic peptide

<400> SEQUENCE: 399

Asp Lys Glu Glu Ile Val Lys Leu Gln Asp Glu Val Ile Lys Thr Leu
1               5                   10                  15

Glu Arg His Leu Asp Ile Leu Arg Lys His Ile Asp Leu Leu Glu Lys
            20                  25                  30

Leu Lys Asp His Leu Ser Glu Glu Leu Lys Glu Arg Val Asp Arg Ser
        35                  40                  45

Ile Lys Lys Leu Glu Glu Ser Ile Lys Arg Leu Glu Arg Ile Ile Glu
    50                  55                  60

Glu Leu Gln Glu Leu Ala Glu Tyr Ser Leu
65                  70

<210> SEQ ID NO 400
<211> LENGTH: 76
<212> TYPE: PRT
<213> ORGANISM: Artificial Sequence
<220> FEATURE:
<223> OTHER INFORMATION: Synthetic peptide

<400> SEQUENCE: 400
```

```
Asp Ala Tyr Asp Leu Asp Arg Ile Val Lys Glu His Arg Arg Leu Val
1               5                   10                  15

Glu Glu Gln Arg Glu Leu Val Glu Glu Leu Glu Lys Leu Val Arg Arg
                20                  25                  30

Gln Glu Asp His Arg Val Asp Lys Lys Glu Ser His Glu Ile Leu Glu
            35                  40                  45

Arg Leu Glu Arg Ile Ile Arg Arg Ser Thr Arg Ile Leu Thr Glu Leu
        50                  55                  60

Glu Lys Leu Thr Asp Glu Phe Glu Arg Arg Thr Arg
65                  70                  75
```

```
<210> SEQ ID NO 401
<211> LENGTH: 73
<212> TYPE: PRT
<213> ORGANISM: Artificial Sequence
<220> FEATURE:
<223> OTHER INFORMATION: Synthetic peptide

<400> SEQUENCE: 401

Asp Met Glu Tyr Glu Leu Lys Lys Ser Ala Glu Glu Leu Arg Lys Ser
1               5                   10                  15

Leu Glu Glu Leu Lys Arg Ile Leu Asp Glu Leu His Lys Ser Leu Arg
                20                  25                  30

Glu Leu Arg Arg His Gly Asp Asp Glu Glu Tyr Val Gln Thr Val Glu
            35                  40                  45

Glu Leu Arg Lys Glu Leu Glu Glu His Ala Lys Lys Leu Glu Glu His
        50                  55                  60

Leu Lys Glu Leu Glu Arg Val Ala Thr
65                  70
```

```
<210> SEQ ID NO 402
<211> LENGTH: 69
<212> TYPE: PRT
<213> ORGANISM: Artificial Sequence
<220> FEATURE:
<223> OTHER INFORMATION: Synthetic peptide

<400> SEQUENCE: 402

Asp Arg Gln Arg Ile Leu Asp Arg Leu Asp Lys Ile Leu Glu Lys Leu
1               5                   10                  15

Asp Asp Ile Leu Lys Lys Leu Lys Asp Ile Leu Glu Thr Leu Ser Lys
                20                  25                  30

Asp Asp Val Ser Asp Arg Arg His Lys Asp Leu Val Glu Lys Phe Arg
            35                  40                  45

Glu Leu Val Asp Thr His His Lys Leu Val Glu Arg Tyr Arg Glu Leu
        50                  55                  60

Val Tyr Gln Asn Arg
65
```

```
<210> SEQ ID NO 403
<211> LENGTH: 76
<212> TYPE: PRT
<213> ORGANISM: Artificial Sequence
<220> FEATURE:
<223> OTHER INFORMATION: Synthetic peptide

<400> SEQUENCE: 403

Arg Glu Lys Asp Glu Ser Lys Glu Leu Asn Asp Glu Tyr Lys Lys Leu
1               5                   10                  15
```

-continued

```
Leu Glu Glu Tyr Glu Arg Leu Leu Arg Arg Ser Glu Glu Leu Val Lys
            20                  25                  30

Arg Ala Lys Gly Pro Arg Asp Glu Lys Glu Leu Lys Arg Ile Leu Glu
        35                  40                  45

Glu Asn Glu Asp Ile Leu Arg Arg Thr Lys Glu Ile Leu Glu Arg Thr
    50                  55                  60

Lys Glu Ile Ser Glu Glu Gln Lys Tyr Arg Arg Arg
65                  70                  75

<210> SEQ ID NO 404
<211> LENGTH: 105
<212> TYPE: PRT
<213> ORGANISM: Artificial Sequence
<220> FEATURE:
<223> OTHER INFORMATION: Synthetic peptide

<400> SEQUENCE: 404

Asp Pro Gln Arg Ala Ala Asp Arg Leu Asp Lys Ile Leu Glu Lys Leu
1               5                   10                  15

Asp Asp Ile Leu Lys Lys Leu Lys Asp Ile Leu Glu Thr Leu Ser Lys
            20                  25                  30

Asp Asp Val Lys Asp Arg Arg Ala Lys Asp Leu Val Glu Lys Phe Arg
        35                  40                  45

Glu Leu Val Asp Thr His His Lys Leu Val Glu Arg Tyr Arg Glu Leu
    50                  55                  60

Val Tyr Thr Ala Thr Ala Gly Ser Asp Leu Ala Arg Glu Leu Ile Arg
65                  70                  75                  80

Arg Val Glu Glu His Thr Lys Arg Leu Arg His Ile Leu Lys Arg Leu
                85                  90                  95

Arg Glu His Glu Glu Lys Leu Arg Arg
            100                 105

<210> SEQ ID NO 405
<211> LENGTH: 74
<212> TYPE: PRT
<213> ORGANISM: Artificial Sequence
<220> FEATURE:
<223> OTHER INFORMATION: Synthetic peptide

<400> SEQUENCE: 405

Glu Asn Lys Tyr Ile Leu Lys Glu Ile Leu Lys Leu Leu Arg Glu Asn
1               5                   10                  15

Leu Lys Leu Leu His Asp Ile Leu Arg Leu Leu Asp Glu Asn Leu Glu
            20                  25                  30

Glu Leu Glu Lys His Gly Ala Lys Asp Leu Asp Asp Tyr Arg Arg Lys
        35                  40                  45

Ile Glu Glu Ile Arg Lys Lys Val Glu Asp Tyr Arg Glu Lys Ile Glu
    50                  55                  60

Glu Ile Glu Lys Lys Val Glu Arg Asp Arg
65                  70

<210> SEQ ID NO 406
<211> LENGTH: 68
<212> TYPE: PRT
<213> ORGANISM: Artificial Sequence
<220> FEATURE:
<223> OTHER INFORMATION: Synthetic peptide

<400> SEQUENCE: 406

Asp Lys Glu Tyr Leu Val Thr Glu His Glu Lys Leu Val Arg Glu His
```

```
1               5                   10                  15
Glu Lys Ile Val Ser Glu Ile Glu Lys Leu Val Lys Lys His Glu Ala
            20                  25                  30

Gly Val Asp Glu Ser Glu Leu Glu Glu Ile Leu Lys Lys Val Glu Lys
            35                  40                  45

Leu Leu Arg Lys Leu Asp Glu Ile Leu Glu Gln Thr Gln Leu Leu
            50                  55                  60

Arg Lys Thr Glu
65

<210> SEQ ID NO 407
<211> LENGTH: 72
<212> TYPE: PRT
<213> ORGANISM: Artificial Sequence
<220> FEATURE:
<223> OTHER INFORMATION: Synthetic peptide

<400> SEQUENCE: 407

Asp Glu Glu Glu Ala Asn Tyr Val Ser Asp Lys Ala Val Lys Ile Ala
1               5                   10                  15

Glu Asp Val Gln Glu Leu Leu Lys Glu Leu Leu Glu Leu Ser Glu Val
            20                  25                  30

Val Arg Arg Gly Glu Val Asp Glu Asp Glu Tyr Asp Arg Val Leu Arg
            35                  40                  45

Lys Leu Gln Glu Val Met Lys Glu Tyr Glu Glu Val Leu Lys Glu Tyr
            50                  55                  60

Glu Glu Val Ser Arg Lys His Glu
65                  70

<210> SEQ ID NO 408
<211> LENGTH: 112
<212> TYPE: PRT
<213> ORGANISM: Artificial Sequence
<220> FEATURE:
<223> OTHER INFORMATION: Synthetic peptide

<400> SEQUENCE: 408

Asp Ala Glu Tyr Leu Val Thr Glu His Glu Lys Leu Val Arg Glu His
1               5                   10                  15

Glu Lys Ile Val Ser Glu Ile Glu Lys Leu Val Lys Lys His Glu Lys
            20                  25                  30

Gly Val Asp Glu Ser Glu Leu Glu Glu Ile Leu Lys Lys Val Glu Lys
            35                  40                  45

Leu Leu Arg Lys Leu Asp Glu Ile Leu Glu Gln Thr Gln Leu Leu
            50                  55                  60

Arg Lys Ala Glu Lys His Ile Asp Lys His Ser Lys Ala Ala Asp Gln
65                  70                  75                  80

Leu Ala Thr Ser Ile Lys Lys Leu Glu Asp Ser Ile Asp Gln Leu Ile
            85                  90                  95

Lys Ile Val Arg Lys Phe Glu Glu Ser Val Lys Lys Leu Gln Lys His
            100                 105                 110

<210> SEQ ID NO 409
<211> LENGTH: 76
<212> TYPE: PRT
<213> ORGANISM: Artificial Sequence
<220> FEATURE:
<223> OTHER INFORMATION: Synthetic peptide

<400> SEQUENCE: 409
```

Asp Glu Glu Tyr Glu Leu Arg Ile Ser Arg Ser Lys Glu Leu
1               5                   10                  15

Leu Glu Arg Tyr Lys Arg Leu Arg Glu Tyr Gln Glu Leu Leu Lys
            20                  25                  30

Glu Leu Arg His Val Lys Asp Leu Asp Arg Ala Val Lys Ile Ile His
        35                  40                  45

Glu Leu Met Arg Val Ser Lys Glu Leu Val Glu Ile Ser His Arg Leu
    50                  55                  60

Leu Glu Leu His Glu Arg Leu Val Arg Arg Lys
65              70              75

<210> SEQ ID NO 410
<211> LENGTH: 72
<212> TYPE: PRT
<213> ORGANISM: Artificial Sequence
<220> FEATURE:
<223> OTHER INFORMATION: Synthetic peptide

<400> SEQUENCE: 410

Arg Asp Lys Tyr Leu Leu Glu Arg Leu Asn Asp Ile Leu Lys Lys Leu
1               5                   10                  15

Asp Glu Ile Val Asp Lys Leu Ser Asp Ile Leu Lys Arg Leu Lys Asp
            20                  25                  30

Val Arg His Asp Asp Arg Leu Gln Glu Leu Val Glu Arg Tyr Lys Glu
        35                  40                  45

Ile Val Lys Glu Tyr Lys Arg Ile Val Glu Glu Tyr Glu Lys Leu Val
    50                  55                  60

Arg Glu Phe Glu Glu Gln Gln Arg
65              70

<210> SEQ ID NO 411
<211> LENGTH: 73
<212> TYPE: PRT
<213> ORGANISM: Artificial Sequence
<220> FEATURE:
<223> OTHER INFORMATION: Synthetic peptide

<400> SEQUENCE: 411

Pro His Glu Glu Val Val Glu Leu His Glu Arg Val Met Glu Ile Ser
1               5                   10                  15

Glu Arg Ala Val Glu Leu Ile Gln Arg Ile Ile Asp Ile Ile Arg Arg
            20                  25                  30

Ile Arg Glu Asp Asp Lys Asp Ile Glu Lys Leu Val Lys Thr Ile Arg
        35                  40                  45

Asp Leu Val Arg Glu Tyr Glu Glu Leu His Arg Glu Leu Glu Glu Ile
    50                  55                  60

Asp Glu Glu Ile Tyr Lys Lys Ser Glu
65              70

<210> SEQ ID NO 412
<211> LENGTH: 74
<212> TYPE: PRT
<213> ORGANISM: Artificial Sequence
<220> FEATURE:
<223> OTHER INFORMATION: Synthetic peptide

<400> SEQUENCE: 412

Asp Ala Glu Tyr Lys Val Arg Glu Ser Val Lys Arg Ser Lys Glu Ser
1               5                   10                  15

```
Val Lys His Ser Glu Asp Val Val Lys Leu Asn Lys Ser Val Lys
         20                  25                  30

Leu Ser Glu Ser Gly His Ser Asp Ala Glu Lys Ala Ser Arg Glu Leu
             35                  40                  45

Val Lys Leu Val Arg Glu Val Val Glu Leu Ser Arg Glu Val Ile Lys
 50                  55                  60

Leu Ser Glu Lys Val Leu Arg Val Ile Ser
 65                  70
```

<210> SEQ ID NO 413
<211> LENGTH: 77
<212> TYPE: PRT
<213> ORGANISM: Artificial Sequence
<220> FEATURE:
<223> OTHER INFORMATION: Synthetic peptide

<400> SEQUENCE: 413

```
Arg Ala Arg Glu Val Val Lys Arg Ala Lys Arg Ile Ile Glu Glu Trp
 1               5                  10                  15

Gln Lys Ile Leu Glu Glu Trp Arg Arg Ile Leu Glu Glu Trp Arg Arg
             20                  25                  30

Leu Leu Glu Asp Glu Arg Val Asp Asp Arg Asp Asn Glu Arg Ile Ile
             35                  40                  45

Arg Glu Asn Glu Arg Val Ile Arg Glu Asn Glu Lys Ile Ile Arg Asp
 50                  55                  60

Val Ile Arg Leu Leu Glu Glu Leu Leu Tyr Glu Arg Arg
 65                  70                  75
```

<210> SEQ ID NO 414
<211> LENGTH: 77
<212> TYPE: PRT
<213> ORGANISM: Artificial Sequence
<220> FEATURE:
<223> OTHER INFORMATION: Synthetic peptide

<400> SEQUENCE: 414

```
Asp Trp Glu Glu Leu Leu Arg Arg Leu Glu Lys Val Leu Gln Glu Tyr
 1               5                  10                  15

Glu Glu Ile Val Lys Glu Leu Ile Asp Leu Ile Glu Arg Leu Ile Lys
             20                  25                  30

Val Ser Glu Asp Lys Ser Lys Asp Ala Ser Glu Tyr Lys Lys Leu Val
             35                  40                  45

Thr Glu Leu Glu Lys Leu Ile Ser Lys Leu Glu Glu Ile Ser Lys Lys
 50                  55                  60

Leu Glu Glu Leu Val Lys Glu Tyr Glu Tyr Lys Thr Glu
 65                  70                  75
```

<210> SEQ ID NO 415
<211> LENGTH: 75
<212> TYPE: PRT
<213> ORGANISM: Artificial Sequence
<220> FEATURE:
<223> OTHER INFORMATION: Synthetic peptide

<400> SEQUENCE: 415

```
Pro Lys Glu Glu Ile Val Lys Leu His Asp Glu Ser Ala Glu Leu His
 1               5                  10                  15

Arg Arg Ser Val Glu Val Ala Asp Glu Ile Leu Lys Met His Glu Arg
             20                  25                  30

Ser Lys Asp Val Asp Asp Glu Arg Glu Ser Arg Glu Leu Ser Lys Glu
```

```
                35                  40                  45
Ile Glu Arg Leu Ile Arg Glu Val Glu Glu Val Ser Lys Arg Ile Lys
        50                  55                  60

Arg Leu Ser Glu Glu Val Glu Tyr Leu Val Arg
65                  70                  75

<210> SEQ ID NO 416
<211> LENGTH: 73
<212> TYPE: PRT
<213> ORGANISM: Artificial Sequence
<220> FEATURE:
<223> OTHER INFORMATION: Synthetic peptide

<400> SEQUENCE: 416

Asp Lys Glu Arg Ala Ala Arg Ala Thr Glu Glu Met Val Lys Leu Thr
1               5                   10                  15

Lys Lys Leu Leu Lys Ala Val Glu Asp Leu Val Arg Asp Val Arg Arg
                20                  25                  30

Leu Leu Lys Glu Gly Leu Ile Ser Glu Lys His Ala Arg Ile Ala Glu
            35                  40                  45

Thr Ile Leu Glu Val Phe Lys Lys His Ala Lys Ile Ile Lys Lys His
        50                  55                  60

Val Asp Ile Val Lys Tyr Asp Glu Ser
65                  70

<210> SEQ ID NO 417
<211> LENGTH: 79
<212> TYPE: PRT
<213> ORGANISM: Artificial Sequence
<220> FEATURE:
<223> OTHER INFORMATION: Synthetic peptide

<400> SEQUENCE: 417

Pro Glu Asp Glu His Val Tyr Val Val Arg Glu Ile Tyr Glu Val Leu
1               5                   10                  15

Arg Glu His Ala Glu Val Leu Glu Glu Asn Arg Glu Val Ile Glu Arg
                20                  25                  30

Leu Leu Glu Ala Lys Lys Arg Gly Asp Lys Ser Glu Glu Leu Val Lys
            35                  40                  45

Glu Leu Lys Lys Ser Ile Asp Lys Leu Lys Glu Ile Ser Arg Lys Leu
        50                  55                  60

Glu Glu Ile Val Lys Glu Leu Glu Lys Val Ser Glu Lys Leu Lys
65                  70                  75

<210> SEQ ID NO 418
<211> LENGTH: 76
<212> TYPE: PRT
<213> ORGANISM: Artificial Sequence
<220> FEATURE:
<223> OTHER INFORMATION: Synthetic peptide

<400> SEQUENCE: 418

Asn Asp Glu Glu Leu Lys Lys Ile Leu Glu Thr Leu Asp Arg Ile Leu
1               5                   10                  15

Lys Lys Leu Asp Lys Ile Leu Thr Arg Leu Asp Glu Val Leu Lys Lys
                20                  25                  30

Ser Glu Asp Pro Asn Leu Asp Asp Lys Asp Tyr Thr Glu Leu Val Lys
            35                  40                  45

Gln Tyr Ile Glu Leu Val Lys Lys Tyr Glu Glu Val Val Lys Glu Tyr
        50                  55                  60
```

```
Glu Glu Val Val Arg Gln Leu Ile Arg Leu Phe Ser
 65                  70                  75
```

<210> SEQ ID NO 419
<211> LENGTH: 72
<212> TYPE: PRT
<213> ORGANISM: Artificial Sequence
<220> FEATURE:
<223> OTHER INFORMATION: Synthetic peptide

<400> SEQUENCE: 419

```
Thr Gln Glu Glu Ile Asn Arg Ile Gln His Glu Val Leu Arg Ile Gln
 1               5                  10                  15

Glu Glu Ile Asp Glu Ile Leu Arg Asp Ile Val Glu Lys Leu Lys Ala
                20                  25                  30

Ile Ser Arg Gly Glu Leu Asp His Glu Val Val Lys Asp Val Glu Asp
            35                  40                  45

Lys Val Arg Glu Ala Leu Glu Lys Ser Glu Glu Leu Leu Asp Lys Ser
        50                  55                  60

Arg Lys Val Glu Tyr Lys Ser Glu
 65                  70
```

<210> SEQ ID NO 420
<211> LENGTH: 81
<212> TYPE: PRT
<213> ORGANISM: Artificial Sequence
<220> FEATURE:
<223> OTHER INFORMATION: Synthetic peptide

<400> SEQUENCE: 420

```
Glu Glu Asp Glu Arg Ile Arg Tyr Asp Leu Asp Arg Ile Arg Lys Asp
 1               5                  10                  15

Val Arg Arg Lys Leu Glu Glu Ile Arg Gln Arg Val Arg Glu Leu Glu
                20                  25                  30

Lys Lys Leu Arg Asp Ala Gly His Arg Arg Asp Glu Lys Glu Leu Leu
            35                  40                  45

Arg Glu Leu Ile Glu Thr Ser Lys Asp Ile Leu Arg Leu Val Glu Glu
        50                  55                  60

Leu Leu Lys Lys Ile Ile Asp Lys Ser Glu Asp Leu Leu Arg Lys Thr
 65                  70                  75                  80

Glu
```

<210> SEQ ID NO 421
<211> LENGTH: 75
<212> TYPE: PRT
<213> ORGANISM: Artificial Sequence
<220> FEATURE:
<223> OTHER INFORMATION: Synthetic peptide

<400> SEQUENCE: 421

```
Asp Glu Lys Asp Arg Val Tyr Glu Ile Leu Lys Glu Val Gln Arg Leu
 1               5                  10                  15

Val Lys Glu Tyr Arg Asp Ile Ser Lys Glu Ile Glu Asp Leu Val Lys
                20                  25                  30

His Tyr Glu His Ile Thr Asp Asp Glu Ala Gln Glu Val Ser Lys Glu
            35                  40                  45

Leu Ile Asp Lys Ser Leu Arg Ala Ser Glu Ile Val Arg Glu Leu Ile
        50                  55                  60

Arg Leu Ile Lys Glu Leu Leu Asp Glu Leu Glu
 65                  70                  75
```

```
                        65                  70                  75

<210> SEQ ID NO 422
<211> LENGTH: 75
<212> TYPE: PRT
<213> ORGANISM: Artificial Sequence
<220> FEATURE:
<223> OTHER INFORMATION: Synthetic peptide

<400> SEQUENCE: 422

Asp Glu Glu Glu Tyr Tyr Lys Glu Lys Leu His Lys Leu Leu Arg Glu
1               5                   10                  15

Ile Glu Glu Leu Leu Lys His Tyr Arg Glu Leu Val Arg Arg Leu Glu
            20                  25                  30

Glu Leu Val Lys Arg Gly Glu Leu Asp Lys Asp Thr Ala Ala His Ile
        35                  40                  45

Leu Glu Arg Leu Ser Glu Leu Leu Glu Arg Ile Ile Arg Arg Val Ala
    50                  55                  60

His Thr Leu Arg Arg Leu Ser Glu Glu Arg Arg
65                  70                  75

<210> SEQ ID NO 423
<211> LENGTH: 5
<212> TYPE: PRT
<213> ORGANISM: Artificial Sequence
<220> FEATURE:
<223> OTHER INFORMATION: Synthetic peptide

<400> SEQUENCE: 423

Gly Ser Glu Gly Ser
1               5

<210> SEQ ID NO 424
<211> LENGTH: 80
<212> TYPE: PRT
<213> ORGANISM: Artificial Sequence
<220> FEATURE:
<223> OTHER INFORMATION: Synthetic peptide

<400> SEQUENCE: 424

Asp Ile Val Glu Leu Val Asp His Leu Leu Lys Arg Ser Leu Lys Leu
1               5                   10                  15

Leu Glu Glu Leu Ala Glu Leu Val Arg Arg Leu Leu Glu Lys Ser Thr
            20                  25                  30

Glu Leu Leu Lys Arg Arg Thr Glu Glu His Lys Glu Glu Val Val Glu
        35                  40                  45

Glu Ser Glu Tyr Met Val Arg Glu Leu Glu Glu Arg Leu Arg Arg Val
    50                  55                  60

Val Asp Glu Ser Glu Lys Leu Val Arg Asp Ala Asp Lys His Ile Arg
65                  70                  75                  80

<210> SEQ ID NO 425
<211> LENGTH: 4
<212> TYPE: PRT
<213> ORGANISM: Artificial Sequence
<220> FEATURE:
<223> OTHER INFORMATION: Synthetic peptide

<400> SEQUENCE: 425

Gly Gly Gly Ser
1
```

```
<210> SEQ ID NO 426
<211> LENGTH: 78
<212> TYPE: PRT
<213> ORGANISM: Artificial Sequence
<220> FEATURE:
<223> OTHER INFORMATION: Synthetic peptide

<400> SEQUENCE: 426

Pro Glu Val Asp Val Leu Arg Arg Ile Val Arg Glu Ile Leu Lys Ala
1               5                   10                  15

Ser Glu Glu Leu Leu Arg Leu Leu Arg Lys Leu Ile Asp Glu Ala Leu
            20                  25                  30

Lys Leu Ser Glu Arg Lys Arg Asp Ser Gln Glu Tyr Arg Glu Val Val
        35                  40                  45

Asp Arg Val Lys Lys Glu Leu Glu Arg Leu Leu Asp Glu Tyr Arg Lys
    50                  55                  60

Leu Val Glu Glu Leu Lys Glu Lys Leu Arg Tyr Asp Thr Arg
65                  70                  75

<210> SEQ ID NO 427
<211> LENGTH: 12
<212> TYPE: PRT
<213> ORGANISM: Artificial Sequence
<220> FEATURE:
<223> OTHER INFORMATION: Synthetic peptide

<400> SEQUENCE: 427

Gly Ser Glu Gly Ser Gly Ser Glu Gly Ser Gly Ser
1               5                   10

<210> SEQ ID NO 428
<211> LENGTH: 75
<212> TYPE: PRT
<213> ORGANISM: Artificial Sequence
<220> FEATURE:
<223> OTHER INFORMATION: Synthetic peptide

<400> SEQUENCE: 428

Pro Arg Glu Tyr His Ser Lys Asp Ile Leu Arg Lys Val Asp Glu Ile
1               5                   10                  15

Leu Glu Arg Ile Arg Arg His Ala Asp Arg Val Lys Lys Ser Glu
            20                  25                  30

Arg Leu Lys Arg Glu Asn Val Asp Val Asn His Ser Lys Asp Val
        35                  40                  45

Lys Arg Val Ile Arg Glu Leu Leu Glu Leu Val Lys Glu Leu Leu Arg
    50                  55                  60

Leu Ala Lys Lys His Ser Asp Asp Gln Gln Glu
65                  70                  75

<210> SEQ ID NO 429
<211> LENGTH: 10
<212> TYPE: PRT
<213> ORGANISM: Artificial Sequence
<220> FEATURE:
<223> OTHER INFORMATION: Synthetic peptide

<400> SEQUENCE: 429

Gly Ser Glu Gly Ser Gly Ser Glu Gly Ser
1               5                   10

<210> SEQ ID NO 430
<211> LENGTH: 78
<212> TYPE: PRT
```

```
<213> ORGANISM: Artificial Sequence
<220> FEATURE:
<223> OTHER INFORMATION: Synthetic peptide

<400> SEQUENCE: 430

Pro Lys Leu Asp Lys Leu Arg Glu Leu Leu Glu Arg Asn Leu Glu Lys
1               5                   10                  15

Leu Arg Glu Ile Leu Glu Glu Val Leu Lys Ile Leu Arg Thr Asn Leu
                20                  25                  30

Glu Arg Val Arg Glu Asp Ile Arg Asp Glu Asp Val Leu Gln Glu Tyr
            35                  40                  45

Glu Arg Leu Ile Arg Lys Ala Glu Glu Asp Leu Arg Arg Val Leu Lys
        50                  55                  60

Glu Tyr Asp Asp Leu Leu Lys Lys Leu Val Tyr Glu Leu Arg
65                  70                  75

<210> SEQ ID NO 431
<211> LENGTH: 94
<212> TYPE: PRT
<213> ORGANISM: Artificial Sequence
<220> FEATURE:
<223> OTHER INFORMATION: Synthetic peptide

<400> SEQUENCE: 431

His His His His His His Gly Ser Gly Ser Glu Asn Leu Tyr Phe Gln
1               5                   10                  15

Gly Ser Thr Glu Lys Arg Leu Leu Glu Glu Ala Glu Arg Ala His Arg
                20                  25                  30

Glu Gln Lys Glu Ile Ile Lys Lys Ala Gln Glu Leu His Arg Arg Leu
            35                  40                  45

Glu Glu Ile Val Arg Gln Ser Gly Ser Ser Glu Glu Ala Lys Lys Glu
        50                  55                  60

Ala Lys Lys Ile Leu Glu Glu Ile Arg Glu Leu Ser Lys Arg Ser Leu
65                  70                  75                  80

Glu Leu Leu Arg Glu Ile Leu Tyr Leu Ser Gln Glu Gln Lys
                85                  90

<210> SEQ ID NO 432
<211> LENGTH: 82
<212> TYPE: PRT
<213> ORGANISM: Artificial Sequence
<220> FEATURE:
<223> OTHER INFORMATION: Synthetic peptide

<400> SEQUENCE: 432

Pro Asn Gln Glu Leu Leu Asp Arg Val Arg Lys Ile Leu Glu Asp Leu
1               5                   10                  15

Leu Arg Leu Asn Glu Glu Leu Val Arg Leu Asn Lys Glu Leu Leu Lys
                20                  25                  30

Arg Ala Leu Glu Met Arg Arg Lys Asn Arg Asp Ser Glu Glu Val Leu
            35                  40                  45

Glu Arg Leu Ala Glu Glu Tyr Arg Lys Arg Leu Glu Glu Tyr Arg Arg
        50                  55                  60

Glu Leu Glu Lys Leu Leu Glu Glu Leu Glu Glu Thr Ile Tyr Arg Tyr
65                  70                  75                  80

Lys Arg

<210> SEQ ID NO 433
<211> LENGTH: 91
```

```
<212> TYPE: PRT
<213> ORGANISM: Artificial Sequence
<220> FEATURE:
<223> OTHER INFORMATION: Synthetic peptide

<400> SEQUENCE: 433

His His His His His His Gly Ser Gly Ser Glu Asn Leu Tyr Phe Gln
1               5                   10                  15

Gly Ser Asp Asp Lys Glu Leu Asp Lys Leu Leu Asp Thr Leu Glu Lys
            20                  25                  30

Ile Leu Gln Thr Ala Thr Lys Ile Ile Asp Asp Ala Asn Lys Leu Leu
        35                  40                  45

Glu Lys Leu Arg Arg Ser Glu Arg Lys Asp Pro Lys Val Val Glu Thr
50                  55                  60

Tyr Val Glu Leu Leu Lys Arg His Glu Lys Ala Val Lys Glu Leu Leu
65                  70                  75                  80

Glu Ile Ala Lys Thr His Ala Lys Lys Val Glu
            85                  90

<210> SEQ ID NO 434
<211> LENGTH: 81
<212> TYPE: PRT
<213> ORGANISM: Artificial Sequence
<220> FEATURE:
<223> OTHER INFORMATION: Synthetic peptide

<400> SEQUENCE: 434

Asp Glu Glu Glu Leu Val Glu Thr Val Lys Arg Ile Gln Lys Glu Ile
1               5                   10                  15

Leu Asp Arg Leu Thr Glu Leu Ala Lys Leu Leu Val Glu Ile Gln Arg
            20                  25                  30

Glu Ile Lys Lys Leu Lys Asp Glu Gly Glu Asp Lys Glu Leu Lys
        35                  40                  45

Arg Leu Ser Asp Glu Leu Glu Glu Lys Val Arg Gln Val Val Glu Glu
50                  55                  60

Ile Lys Arg Leu Ser Asp Glu Leu Glu Thr Val Glu Tyr Val Ser
65                  70                  75                  80

Arg

<210> SEQ ID NO 435
<211> LENGTH: 90
<212> TYPE: PRT
<213> ORGANISM: Artificial Sequence
<220> FEATURE:
<223> OTHER INFORMATION: Synthetic peptide

<400> SEQUENCE: 435

Ser His His His His His His Ser Ser Gly Glu Asn Leu Tyr Phe Gln
1               5                   10                  15

Gly Ser Asp Ser Asp Glu His Leu Lys Lys Leu Lys Thr Phe Leu Glu
            20                  25                  30

Asn Leu Arg Arg His Leu Asp Arg Leu Asp Lys His Ile Lys Gln Leu
        35                  40                  45

Arg Asp Ile Leu Ser Glu Asn Pro Glu Asp Glu Arg Val Lys Asp Val
50                  55                  60

Ile Asp Leu Ser Glu Arg Ser Val Arg Ile Val Lys Thr Val Ile Lys
65                  70                  75                  80

Ile Phe Glu Asp Ser Val Arg Lys Lys Glu
            85                  90
```

<210> SEQ ID NO 436
<211> LENGTH: 78
<212> TYPE: PRT
<213> ORGANISM: Artificial Sequence
<220> FEATURE:
<223> OTHER INFORMATION: Synthetic peptide

<400> SEQUENCE: 436

```
Ser Lys Glu Glu Ile Leu Lys Glu Leu Glu Asp Leu Gln Arg Arg Leu
1               5                   10                  15

Ile Glu Glu Leu Lys Lys Leu Gln Glu Arg Val Val Glu Leu Leu Glu
            20                  25                  30

Glu Leu Ile Lys Arg Leu Arg Asp Arg Gly Arg Asp Asp Lys His Leu
        35                  40                  45

Lys Arg Leu Val Lys Glu Val Arg Arg Leu Ser Glu Glu Val Leu Arg
    50                  55                  60

Ser Ile Lys Glu Val Ser Asp Arg Val Arg Tyr Gln Leu Arg
65                  70                  75
```

<210> SEQ ID NO 437
<211> LENGTH: 91
<212> TYPE: PRT
<213> ORGANISM: Artificial Sequence
<220> FEATURE:
<223> OTHER INFORMATION: Synthetic peptide

<400> SEQUENCE: 437

```
Ser His His His His His Ser Ser Gly Glu Asn Leu Tyr Phe Gln
1               5                   10                  15

Gly Ser Asp Asp Lys Glu Leu Asp Lys Leu Leu Asp Thr Leu Glu Lys
            20                  25                  30

Ile Leu Gln Thr Ala Thr Lys Ile Ile Asp Asp Ala Asn Lys Leu Leu
        35                  40                  45

Glu Lys Leu Arg Arg Ser Glu Arg Lys Asp Pro Lys Val Val Glu Thr
    50                  55                  60

Tyr Val Glu Leu Leu Lys Arg His Glu Lys Ala Val Lys Glu Leu Leu
65                  70                  75                  80

Glu Ile Ala Lys Thr His Ala Lys Lys Val Glu
                85                  90
```

<210> SEQ ID NO 438
<211> LENGTH: 74
<212> TYPE: PRT
<213> ORGANISM: Artificial Sequence
<220> FEATURE:
<223> OTHER INFORMATION: Synthetic peptide

<400> SEQUENCE: 438

```
Asp Leu His Glu Val Val Tyr Glu Thr Lys Glu Leu Leu Lys Arg Ile
1               5                   10                  15

Glu Glu Val Val Glu Glu Leu Arg Lys Ser Glu Asp Ile Ile Arg
            20                  25                  30

Lys Ala Glu Arg Gly Glu Ile Ser Glu Asp Leu Lys Arg Leu Gln
        35                  40                  45

Glu Glu Ile Ala Arg Glu Ala Lys Lys Leu Leu Asp Glu Ile Lys Arg
    50                  55                  60

Val Leu Glu Arg His Leu Glu Gln Thr Leu
65                  70
```

```
<210> SEQ ID NO 439
<211> LENGTH: 150
<212> TYPE: PRT
<213> ORGANISM: Artificial Sequence
<220> FEATURE:
<223> OTHER INFORMATION: Synthetic peptide

<400> SEQUENCE: 439

Thr Glu Arg Lys Leu Leu Glu Arg Ser Arg Arg Leu Gln Glu Glu Ser
1               5                   10                  15

Lys Arg Leu Leu Asp Glu Met Ala Glu Ile Met Arg Arg Ile Lys Lys
                20                  25                  30

Leu Leu Asp Asp Pro Asp Ser Glu Asp Ile Ala Arg Glu Ile Lys Glu
            35                  40                  45

Leu Leu Arg Arg Leu Lys Glu Ile Ile Glu Arg Asn Gln Arg Ile Ala
    50                  55                  60

Lys Glu His Glu Tyr Ile Ala Arg Glu Arg Ser Ala Ala Asp Asp Lys
65                  70                  75                  80

Glu Leu Asp Lys Leu Leu Asp Thr Leu Glu Lys Ile Leu Gln Thr Ala
                85                  90                  95

Thr Lys Ile Ile Asp Asp Ala Asn Lys Leu Leu Glu Lys Leu Arg Arg
            100                 105                 110

Ser Glu Arg Lys Asp Pro Lys Val Val Glu Thr Tyr Val Glu Leu Leu
        115                 120                 125

Lys Arg His Glu Lys Ala Val Lys Glu Leu Leu Glu Ile Ala Lys Thr
    130                 135                 140

His Ala Lys Lys Val Glu
145                 150

<210> SEQ ID NO 440
<211> LENGTH: 78
<212> TYPE: PRT
<213> ORGANISM: Artificial Sequence
<220> FEATURE:
<223> OTHER INFORMATION: Synthetic peptide

<400> SEQUENCE: 440

Pro Glu Gln Glu Ile Ala Asp Arg Ile Leu Thr Glu Ile Arg Glu Ser
1               5                   10                  15

Gln Lys Glu Leu Glu Arg Leu Ala Arg Lys Ile Leu Lys Leu Leu Asp
                20                  25                  30

Glu Ser Gln Glu Lys Ala Lys Arg Gly Arg Leu Ser Glu Glu Glu Ser
            35                  40                  45

Asp Glu Leu Leu Glu Arg Ile Lys Lys Glu Leu Asp Glu Leu Leu Glu
    50                  55                  60

Arg Ser Lys Glu Leu Leu Lys Lys Ile Glu Tyr Glu Leu Arg
65                  70                  75

<210> SEQ ID NO 441
<211> LENGTH: 154
<212> TYPE: PRT
<213> ORGANISM: Artificial Sequence
<220> FEATURE:
<223> OTHER INFORMATION: Synthetic peptide

<400> SEQUENCE: 441

Thr Glu Arg Lys Leu Leu Glu Arg Ser Arg Arg Leu Gln Glu Glu Ser
1               5                   10                  15

Lys Arg Leu Leu Asp Glu Met Ala Glu Ile Met Arg Arg Ile Lys Lys
```

```
                20                  25                  30

Leu Leu Asp Asp Pro Asp Ser Glu Asp Ile Ala Arg Glu Ile Lys Glu
            35                  40                  45

Leu Leu Arg Arg Leu Lys Glu Ile Ile Glu Arg Asn Gln Arg Ile Ala
        50                  55                  60

Lys Glu His Glu Tyr Ile Ala Arg Glu Arg Ser Gly Gly Ser Gly Ser
65                  70                  75                  80

Pro Asp Asp Lys Glu Leu Asp Lys Leu Leu Asp Thr Leu Glu Lys Ile
                85                  90                  95

Leu Gln Thr Ala Thr Lys Ile Ile Asp Asp Ala Asn Lys Leu Leu Glu
            100                 105                 110

Lys Leu Arg Arg Ser Glu Arg Lys Asp Pro Lys Val Val Glu Thr Tyr
        115                 120                 125

Val Glu Leu Leu Lys Arg His Glu Lys Ala Val Lys Glu Leu Leu Glu
    130                 135                 140

Ile Ala Lys Thr His Ala Lys Lys Val Glu
145                 150

<210> SEQ ID NO 442
<211> LENGTH: 74
<212> TYPE: PRT
<213> ORGANISM: Artificial Sequence
<220> FEATURE:
<223> OTHER INFORMATION: Synthetic peptide

<400> SEQUENCE: 442

Pro Glu Asp Asp Val Leu Arg Arg Leu Glu Glu Val Ser Glu Lys Ile
1               5                   10                  15

Leu Arg Val Ala Glu Asp Val Ala Arg Gln Leu Arg Glu Val Ser Glu
            20                  25                  30

Lys Ile Thr Gln Gly Lys Val Asp Arg Lys Glu Trp Glu Glu Asp Ile
        35                  40                  45

Lys Arg Leu Lys Arg Glu Leu Glu Glu Leu Leu Arg Glu Trp Lys Glu
    50                  55                  60

Glu Ile Glu Arg Leu Thr Tyr Glu Leu Arg
65                  70

<210> SEQ ID NO 443
<211> LENGTH: 160
<212> TYPE: PRT
<213> ORGANISM: Artificial Sequence
<220> FEATURE:
<223> OTHER INFORMATION: Synthetic peptide

<400> SEQUENCE: 443

Thr Glu Arg Lys Leu Leu Glu Arg Ser Arg Arg Leu Gln Glu Glu Ser
1               5                   10                  15

Lys Arg Leu Leu Asp Glu Met Ala Glu Ile Met Arg Arg Ile Lys Lys
            20                  25                  30

Leu Leu Asp Asp Pro Asp Ser Glu Asp Ile Ala Arg Glu Ile Lys Glu
        35                  40                  45

Leu Leu Arg Arg Leu Lys Glu Ile Ile Glu Arg Asn Gln Arg Ile Ala
    50                  55                  60

Lys Glu His Glu Tyr Ile Ala Arg Glu Arg Ser Gly Gly Ser Gly Ser
65                  70                  75                  80

Pro Gly Gly Ser Gly Ser Pro Asp Asp Lys Glu Leu Asp Lys Leu Leu
                85                  90                  95
```

Asp Thr Leu Glu Lys Ile Leu Gln Thr Ala Thr Lys Ile Ile Asp Asp
            100                 105                 110

Ala Asn Lys Leu Leu Glu Lys Leu Arg Arg Ser Glu Arg Lys Asp Pro
        115                 120                 125

Lys Val Val Glu Thr Tyr Val Glu Leu Leu Lys Arg His Glu Lys Ala
    130                 135                 140

Val Lys Glu Leu Leu Glu Ile Ala Lys Thr His Ala Lys Lys Val Glu
145                 150                 155                 160

<210> SEQ ID NO 444
<211> LENGTH: 73
<212> TYPE: PRT
<213> ORGANISM: Artificial Sequence
<220> FEATURE:
<223> OTHER INFORMATION: Synthetic peptide

<400> SEQUENCE: 444

Asp Glu Lys Glu Asp Asn Arg Arg Leu Gln His Lys Ile Glu Arg Ile
1               5                   10                  15

Leu Glu Lys Asn Glu Asp Leu Gln Arg Lys Leu Glu Glu Ile Leu Glu
            20                  25                  30

Leu Leu Glu Arg Gly Glu Ala Asp Glu Glu Lys Ile Asp Arg Leu Arg
        35                  40                  45

Lys Ala Val Glu Asp Tyr Arg Arg Val Val Glu Glu Ile Lys Glu Asp
    50                  55                  60

Val Lys Arg His Lys Tyr Thr Val Arg
65                  70

<210> SEQ ID NO 445
<211> LENGTH: 172
<212> TYPE: PRT
<213> ORGANISM: Artificial Sequence
<220> FEATURE:
<223> OTHER INFORMATION: Synthetic peptide

<400> SEQUENCE: 445

Thr Glu Arg Lys Leu Leu Glu Arg Ser Arg Arg Leu Gln Glu Glu Ser
1               5                   10                  15

Lys Arg Leu Leu Asp Glu Met Ala Glu Ile Met Arg Arg Ile Lys Lys
            20                  25                  30

Leu Leu Asp Asp Pro Asp Ser Glu Asp Ile Ala Arg Glu Ile Lys Glu
        35                  40                  45

Leu Leu Arg Arg Leu Lys Glu Ile Ile Glu Arg Asn Gln Arg Ile Ala
    50                  55                  60

Lys Glu His Glu Tyr Ile Ala Arg Glu Arg Ser Gly Gly Ser Gly Ser
65                  70                  75                  80

Pro Gly Gly Ser Gly Ser Pro Gly Gly Ser Gly Ser Pro Gly Gly Ser
            85                  90                  95

Gly Ser Pro Asp Asp Lys Glu Leu Asp Lys Leu Leu Asp Thr Leu Glu
        100                 105                 110

Lys Ile Leu Gln Thr Ala Thr Lys Ile Ile Asp Asp Ala Asn Lys Leu
    115                 120                 125

Leu Glu Lys Leu Arg Arg Ser Glu Arg Lys Asp Pro Lys Val Val Glu
130                 135                 140

Thr Tyr Val Glu Leu Leu Lys Arg His Glu Lys Ala Val Lys Glu Leu
145                 150                 155                 160

Leu Glu Ile Ala Lys Thr His Ala Lys Lys Val Glu
            165                 170

<210> SEQ ID NO 446
<211> LENGTH: 82
<212> TYPE: PRT
<213> ORGANISM: Artificial Sequence
<220> FEATURE:
<223> OTHER INFORMATION: Synthetic peptide

<400> SEQUENCE: 446

```
Asp Glu Lys Lys Leu Ile Asn Glu Val Val Glu Thr Gln Lys Arg Leu
1               5                   10                  15
Ile Lys Glu Ala Ala Lys Arg Leu Ser Glu Val Val Arg His Gln Thr
            20                  25                  30
Glu Leu Ile Arg Glu Leu Arg Glu Lys Asn Val Asp Asp Lys Asp Val
        35                  40                  45
Glu Lys Leu Leu Lys Glu Ser Leu Asp Leu Ala Glu Glu Ile Val Arg
    50                  55                  60
Arg Ile Lys Glu Leu Leu Asp Glu Ser Lys Lys Leu Val Glu Tyr Val
65                  70                  75                  80
Ser Asn
```

<210> SEQ ID NO 447
<211> LENGTH: 161
<212> TYPE: PRT
<213> ORGANISM: Artificial Sequence
<220> FEATURE:
<223> OTHER INFORMATION: Synthetic peptide

<400> SEQUENCE: 447

```
Asp Ala Tyr Asp Leu Asp Arg Ile Val Lys Glu His Arg Arg Leu Val
1               5                   10                  15
Glu Glu Gln Arg Glu Leu Val Glu Glu Leu Lys Leu Val Arg Arg
            20                  25                  30
Gln Glu Asp His Arg Val Asp Lys Lys Glu Ser His Glu Ile Leu Glu
        35                  40                  45
Arg Leu Glu Arg Ile Ile Arg Arg Ser Thr Arg Ile Leu Thr Glu Leu
    50                  55                  60
Glu Lys Leu Thr Asp Glu Phe Glu Arg Arg Thr Arg Gly Ser Glu Gly
65                  70                  75                  80
Ser Gly Ser Glu Gly Ser Gly Ser Asp Asp Lys Glu Leu Asp Lys Leu
            85                  90                  95
Leu Asp Thr Leu Glu Lys Ile Leu Gln Thr Ala Thr Lys Ile Ile Asp
        100                 105                 110
Asp Ala Asn Lys Leu Leu Glu Lys Leu Arg Arg Ser Glu Arg Lys Asp
    115                 120                 125
Pro Lys Val Val Glu Thr Tyr Val Glu Leu Leu Lys Arg His Glu Lys
130                 135                 140
Ala Val Lys Glu Leu Leu Glu Ile Ala Lys Thr His Ala Lys Lys Val
145                 150                 155                 160
Glu
```

<210> SEQ ID NO 448
<211> LENGTH: 78
<212> TYPE: PRT
<213> ORGANISM: Artificial Sequence
<220> FEATURE:
<223> OTHER INFORMATION: Synthetic peptide

<400> SEQUENCE: 448

```
Asp Glu Arg Tyr Ala Thr Arg Glu Ile Val Glu Arg Ile Glu Arg Ile
1               5                   10                  15

Ala Arg Glu Ile Leu Lys Arg Thr Glu Glu Ile Val Arg Glu Val Arg
                20                  25                  30

Glu Val Leu Ser Arg Asp Val Asp Gln Glu Val Val Arg Arg Leu
            35                  40                  45

Ala Asp Leu Leu Arg Glu Ser Val Glu Leu Val Gln His Leu Val Arg
        50                  55                  60

Arg Val Glu Glu Leu Leu Gln Glu Ser Val Glu Arg Lys Lys
65                  70                  75
```

<210> SEQ ID NO 449
<211> LENGTH: 163
<212> TYPE: PRT
<213> ORGANISM: Artificial Sequence
<220> FEATURE:
<223> OTHER INFORMATION: Synthetic peptide

<400> SEQUENCE: 449

```
Asp Glu Asp Glu Leu Glu Arg Leu Leu Arg Glu Tyr His Arg Val
1               5                   10                  15

Leu Arg Glu Tyr Glu Lys Leu Leu Glu Leu Arg Arg Leu Tyr Glu
                20                  25                  30

Glu Tyr Lys Arg Gly Glu Val Ser Glu Glu Ser Asp Arg Ile Leu
            35                  40                  45

Arg Glu Ile Lys Glu Ile Leu Asp Lys Ser Arg Leu Trp Asp Leu
        50                  55                  60

Ser Glu Glu Val Trp Arg Thr Leu Leu Tyr Gln Ala Glu Gly Ser Glu
65                  70                  75                  80

Gly Ser Gly Ser Glu Gly Ser Glu Lys Asp Tyr His Arg Arg Leu
                85                  90                  95

Ile Glu His Leu Glu Asp Leu Val Arg Arg His Glu Glu Leu Ile Lys
                100                 105                 110

Arg Gln Lys Lys Val Val Glu Glu Leu Glu Arg Gly Leu Asp Glu
            115                 120                 125

Arg Leu Arg Arg Val Val Asp Arg Phe Arg Arg Ser Ser Glu Arg Trp
        130                 135                 140

Glu Glu Val Ile Glu Arg Phe Arg Gln Val Val Asp Lys Leu Arg Lys
145                 150                 155                 160

Ser Val Glu
```

<210> SEQ ID NO 450
<211> LENGTH: 78
<212> TYPE: PRT
<213> ORGANISM: Artificial Sequence
<220> FEATURE:
<223> OTHER INFORMATION: Synthetic peptide

<400> SEQUENCE: 450

```
Pro Ala Arg Glu Ile Leu Glu Glu Val Val Lys Lys His Leu Glu Val
1               5                   10                  15

Val Glu Asp Ala Ala Arg Ile Leu Glu Glu Ile Ile Arg Glu His Glu
                20                  25                  30

Lys Ala Val Arg Glu Asp Arg Asp Lys Lys Glu Leu Glu Glu Ile Ser
            35                  40                  45

Arg Asp Leu Leu Arg Lys Ala Arg Glu Ala Leu Lys Lys Val Lys Asp
        50                  55                  60
```

Ile Ser Asp Asp Leu Ser Arg Glu Ile Glu Tyr Val Ala Ser
65                  70                  75

<210> SEQ ID NO 451
<211> LENGTH: 166
<212> TYPE: PRT
<213> ORGANISM: Artificial Sequence
<220> FEATURE:
<223> OTHER INFORMATION: Synthetic peptide

<400> SEQUENCE: 451

Thr Glu Arg Lys Leu Leu Glu Arg Ser Arg Leu Gln Glu Glu Ser
1               5                   10                  15

Lys Arg Leu Leu Asp Glu Met Ala Glu Ile Met Arg Arg Ile Lys Lys
            20                  25                  30

Leu Leu Lys Lys Ala Arg Gly Ala Asp Glu Lys Val Leu Asp Glu Leu
        35                  40                  45

Arg Lys Ile Ile Glu Arg Ile Arg Glu Leu Leu Asp Arg Ser Arg Lys
50                  55                  60

Ile His Glu Arg Ser Glu Glu Ile Ala Tyr Lys Glu Gly Ser Glu
65              70                  75                  80

Gly Ser Gly Ser Glu Gly Ser Gly Ser Asp Glu Ser Asp Arg Ile Arg
                85                  90                  95

Lys Ile Val Glu Glu Ser Asp Glu Ile Val Lys Glu Ser Arg Lys Leu
            100                 105                 110

Ala Glu Arg Ala Arg Glu Leu Ile Lys Glu Ser Glu Asp Lys Arg Val
        115                 120                 125

Ser Glu Glu Arg Asn Glu Arg Leu Leu Glu Glu Leu Leu Arg Ile Leu
130                 135                 140

Asp Glu Asn Ala Glu Leu Leu Lys Arg Asn Leu Glu Leu Leu Lys Glu
145                 150                 155                 160

Val Leu Tyr Arg Thr Arg
                165

<210> SEQ ID NO 452
<211> LENGTH: 79
<212> TYPE: PRT
<213> ORGANISM: Artificial Sequence
<220> FEATURE:
<223> OTHER INFORMATION: Synthetic peptide

<400> SEQUENCE: 452

Asp Ser Asp Glu Lys Ala Glu Tyr Leu Leu Lys Glu Met Glu Arg Val
1               5                   10                  15

Val Arg Glu Ser Asp Glu Val Val Lys Lys Ile Leu Arg Asp Leu Glu
            20                  25                  30

Glu Val Leu Glu Arg Leu Arg Arg Gly Glu Ile Ser Glu Asp Asp Val
        35                  40                  45

Thr Glu Ile Leu Lys Glu Leu Ala Glu Arg His Ile Arg Ala Ile Glu
    50                  55                  60

Glu Leu Val Arg Arg Leu Arg Glu Leu Leu Glu Arg His Lys Arg
65                  70                  75

<210> SEQ ID NO 453
<211> LENGTH: 162
<212> TYPE: PRT
<213> ORGANISM: Artificial Sequence
<220> FEATURE:
<223> OTHER INFORMATION: Synthetic peptide

<400> SEQUENCE: 453

Asp Glu Asp Asp Glu Leu Glu Arg Leu Leu Arg Glu Tyr His Arg Val
1               5                   10                  15

Leu Arg Glu Tyr Glu Lys Leu Leu Glu Glu Leu Arg Arg Leu Tyr Glu
            20                  25                  30

Glu Tyr Lys Arg Gly Glu Val Ser Glu Glu Ser Asp Arg Ile Leu
        35                  40                  45

Arg Glu Ile Lys Glu Ile Leu Asp Lys Ser Glu Arg Leu Trp Asp Leu
    50                  55                  60

Ser Glu Glu Val Trp Arg Thr Leu Leu Tyr Gln Ala Glu Gly Ser Glu
65              70                  75                  80

Gly Ser Gly Ser Glu Gly Ser Gly Ser Asp Asp Lys Glu Leu Asp Lys
                85                  90                  95

Leu Leu Asp Thr Leu Glu Lys Ile Leu Gln Thr Ala Thr Lys Ile Ile
            100                 105                 110

Asp Asp Ala Asn Lys Leu Leu Glu Lys Leu Arg Arg Ser Glu Arg Lys
        115                 120                 125

Asp Pro Lys Val Val Glu Thr Tyr Val Glu Leu Leu Lys Arg His Glu
    130                 135                 140

Lys Ala Val Lys Glu Leu Leu Glu Ile Ala Lys Thr His Ala Lys Lys
145                 150                 155                 160

Val Glu

<210> SEQ ID NO 454
<211> LENGTH: 74
<212> TYPE: PRT
<213> ORGANISM: Artificial Sequence
<220> FEATURE:
<223> OTHER INFORMATION: Synthetic peptide

<400> SEQUENCE: 454

Pro Lys Glu Asp Ile Leu Arg Glu Val Leu Arg Arg His Lys Glu Ile
1               5                   10                  15

Val Arg Glu Ile Val Arg Leu Val Arg Glu Ala Val Glu Thr His Leu
            20                  25                  30

Glu Leu Val Lys Arg Asn Ser Asp Asp Arg Asp Ala Gln Asp Val Ile
        35                  40                  45

Arg Lys Leu Glu Glu Asp Leu Glu Arg Leu Val Arg His Ala Gln Glu
    50                  55                  60

Val Ile Glu Glu Ile Phe Tyr Arg Leu His
65                  70

<210> SEQ ID NO 455
<211> LENGTH: 158
<212> TYPE: PRT
<213> ORGANISM: Artificial Sequence
<220> FEATURE:
<223> OTHER INFORMATION: Synthetic peptide

<400> SEQUENCE: 455

Asp Asp Lys Glu Leu Asp Lys Leu Leu Asp Thr Leu Glu Lys Ile Leu
1               5                   10                  15

Gln Thr Ala Thr Lys Ile Ile Asp Asp Ala Asn Lys Leu Leu Glu Lys
            20                  25                  30

Leu Arg Arg Ser Glu Arg Lys Asp Pro Lys Val Val Glu Thr Tyr Val
        35                  40                  45

Glu Leu Leu Lys Arg His Glu Lys Ala Val Lys Glu Leu Leu Glu Ile
 50                  55                  60

Ala Lys Thr His Ala Lys Lys Val Glu Gly Ser Glu Gly Ser Gly Ser
 65                  70                  75                  80

Glu Gly Ser Pro Thr Asp Glu Val Ile Glu Val Leu Lys Glu Leu Leu
                 85                  90                  95

Arg Ile His Arg Glu Asn Leu Arg Val Asn Glu Ile Val Glu Val
            100                 105                 110

Asn Glu Arg Ala Ser Arg Val Thr Asp Arg Glu Leu Glu Arg Leu
            115                 120                 125

Leu Arg Arg Ser Asn Glu Leu Ile Lys Arg Ser Arg Glu Leu Asn Glu
130                 135                 140

Glu Ser Lys Lys Leu Ile Glu Lys Leu Glu Arg Leu Ala Thr
145                 150                 155

<210> SEQ ID NO 456
<211> LENGTH: 74
<212> TYPE: PRT
<213> ORGANISM: Artificial Sequence
<220> FEATURE:
<223> OTHER INFORMATION: Synthetic peptide

<400> SEQUENCE: 456

Asp Arg Glu Tyr Ile Ile Lys Asp Ile Leu Asp Ser Gln Glu His Leu
 1               5                  10                  15

Leu Arg Leu Ile Glu Glu Leu Leu Glu Thr Gln Lys Glu Leu Leu Glu
                20                  25                  30

Ile Leu Lys Arg Arg Pro Asp Ser Val Glu Arg Val Arg Glu Leu Val
            35                  40                  45

Arg Arg Ser Lys Glu Ile Ala Asp Glu Ile Arg Gln Ser Asp Arg
        50                  55                  60

Asn Val Arg Leu Leu Glu Glu Val Ser Lys
 65                 70

<210> SEQ ID NO 457
<211> LENGTH: 160
<212> TYPE: PRT
<213> ORGANISM: Artificial Sequence
<220> FEATURE:
<223> OTHER INFORMATION: Synthetic peptide

<400> SEQUENCE: 457

Asp Asp Lys Glu Leu Asp Lys Leu Leu Asp Thr Leu Glu Lys Ile Leu
 1               5                  10                  15

Gln Thr Ala Thr Lys Ile Ile Asp Asp Ala Asn Lys Leu Leu Glu Lys
                20                  25                  30

Leu Arg Ser Glu Arg Lys Asp Pro Lys Val Val Glu Thr Tyr Val
            35                  40                  45

Glu Leu Leu Lys Arg His Glu Lys Ala Val Lys Glu Leu Leu Glu Ile
 50                  55                  60

Ala Lys Thr His Ala Lys Lys Val Glu Gly Ser Glu Gly Ser Gly Ser
 65                  70                  75                  80

Glu Gly Ser Gly Thr Lys Glu Asp Ile Leu Glu Arg Gln Arg Lys Ile
                85                  90                  95

Ile Glu Arg Ala Gln Glu Ile His Arg Gln Gln Glu Ile Leu Glu
            100                 105                 110

Glu Leu Glu Arg Ile Ile Arg Lys Pro Gly Ser Ser Glu Glu Ala Met
115                 120                 125

```
Lys Arg Met Leu Lys Leu Leu Glu Glu Ser Leu Arg Leu Leu Lys Glu
            130                 135                 140

Leu Leu Glu Leu Ser Glu Ser Ala Gln Leu Leu Tyr Glu Gln Arg
145                 150                 155                 160

<210> SEQ ID NO 458
<211> LENGTH: 74
<212> TYPE: PRT
<213> ORGANISM: Artificial Sequence
<220> FEATURE:
<223> OTHER INFORMATION: Synthetic peptide

<400> SEQUENCE: 458

Glu Ser Glu Asp Arg Ile Lys Glu Leu Leu Lys Arg His Ile Glu Leu
1               5                   10                  15

Val Glu Arg His Glu Glu Leu Leu His Glu Ile Lys Lys Leu Ile Asp
            20                  25                  30

Leu Glu Glu Lys Asp Asp Lys Asp Arg Glu Glu Ala Val Lys Arg Ile
        35                  40                  45

Asp Asp Ala Ile Lys Glu Ser Glu Glu Met Leu Glu Glu Ser Lys Glu
    50                  55                  60

Ile Leu Glu Glu Ile Glu Tyr Leu Asn Arg
65                  70

<210> SEQ ID NO 459
<211> LENGTH: 76
<212> TYPE: PRT
<213> ORGANISM: Artificial Sequence
<220> FEATURE:
<223> OTHER INFORMATION: Synthetic peptide

<400> SEQUENCE: 459

Pro Leu Lys Glu Arg Leu Leu Glu Ile Gln Arg Asp Leu Asp Arg Val
1               5                   10                  15

Leu Glu Glu Val Val Glu Arg Leu Leu Arg Ile Gln Glu Arg Leu Asp
            20                  25                  30

Ser Val Val Glu Arg Lys Pro Pro Asp Val His Glu Glu Tyr Lys Tyr
        35                  40                  45

Ile Val Asp Glu Ile Arg Glu Ile Val Glu Arg Val Val Arg Glu Tyr
    50                  55                  60

Glu Glu Ile Val Lys Arg Ile Asp Glu Glu Val Arg
65                  70                  75

<210> SEQ ID NO 460
<211> LENGTH: 80
<212> TYPE: PRT
<213> ORGANISM: Artificial Sequence
<220> FEATURE:
<223> OTHER INFORMATION: Synthetic peptide

<400> SEQUENCE: 460

His Glu Lys Asp Ile Val Tyr Lys Val Glu Asp Leu Val Arg Lys Ser
1               5                   10                  15

Asp Arg Ile Ala Glu Arg Ala Arg Glu Ile Val Lys Arg Ser Arg Asp
            20                  25                  30

Ile Met Arg Glu Ile Arg Lys Asp Lys Asp Asn Lys Lys Leu Ser Asp
        35                  40                  45

Asp Leu Leu Lys Val Thr Arg Asp Leu Gln Arg Val Val Asp Glu Leu
    50                  55                  60
```

Glu Glu Leu Ser Arg Glu Leu Leu Arg Val Ala Glu Glu Ser Arg Lys
65                  70                  75                  80

<210> SEQ ID NO 461
<211> LENGTH: 13
<212> TYPE: PRT
<213> ORGANISM: Artificial Sequence
<220> FEATURE:
<223> OTHER INFORMATION: Synthetic peptide

<400> SEQUENCE: 461

Gly Ser Glu Gly Ser Gly Ser Glu Gly Ser Gly Gly Ser
1               5                   10

<210> SEQ ID NO 462
<211> LENGTH: 80
<212> TYPE: PRT
<213> ORGANISM: Artificial Sequence
<220> FEATURE:
<223> OTHER INFORMATION: Synthetic peptide

<400> SEQUENCE: 462

Asp Glu Glu Glu Ile Glu Glu Leu Leu Arg Glu Leu Glu Lys Leu Leu
1               5                   10                  15

Lys Lys Ser Glu Glu Ala Leu Glu Glu Ser Lys Lys Leu Ile Asp Glu
                20                  25                  30

Ser Glu Glu Leu Leu Arg Arg Asp Arg Leu Asp Lys Glu Lys His Val
            35                  40                  45

Arg Ala Ser Glu Glu His Val Lys Leu Ser Glu His Leu Arg Ile
        50                  55                  60

Ser Arg Glu Ile Val Lys Ile Leu Glu Lys Ala Val Tyr Ser Thr Arg
65                  70                  75                  80

<210> SEQ ID NO 463

<400> SEQUENCE: 463

000

<210> SEQ ID NO 464
<211> LENGTH: 77
<212> TYPE: PRT
<213> ORGANISM: Artificial Sequence
<220> FEATURE:
<223> OTHER INFORMATION: Synthetic peptide

<400> SEQUENCE: 464

Asp Glu Asp Asp Glu Leu Glu Arg Leu Leu Arg Glu Tyr His Arg Val
1               5                   10                  15

Leu Arg Glu Tyr Glu Lys Leu Leu Glu Glu Leu Arg Arg Leu Tyr Glu
                20                  25                  30

Glu Tyr Lys Arg Gly Glu Val Ser Glu Glu Ser Asp Arg Ile Leu
            35                  40                  45

Arg Glu Ile Lys Glu Ile Leu Asp Lys Ser Glu Arg Leu Trp Asp Leu
50                  55                  60

Ser Glu Glu Val Trp Arg Thr Leu Leu Tyr Gln Ala Glu
65                  70                  75

<210> SEQ ID NO 465

<400> SEQUENCE: 465

000

<210> SEQ ID NO 466
<211> LENGTH: 73
<212> TYPE: PRT
<213> ORGANISM: Artificial Sequence
<220> FEATURE:
<223> OTHER INFORMATION: Synthetic peptide

<400> SEQUENCE: 466

Asp Asp Glu Glu Glu Asp Lys Arg Leu Leu Glu Glu Val Lys Arg Ser
1               5                   10                  15

Leu Asp Thr Asp Glu Arg Ile Leu Glu Lys Leu Arg His Ser Leu Glu
            20                  25                  30

Arg Gln Leu Glu Asp Val Asp Lys Asp Glu Asp Ser Arg Arg Val Leu
        35                  40                  45

Arg Glu Leu Asp Glu Ile Thr Lys Arg Ser Arg Glu Val Val Lys Arg
    50                  55                  60

Leu Arg Lys Leu Ala Tyr Glu Ser Lys
65                  70

<210> SEQ ID NO 467

<400> SEQUENCE: 467

000

<210> SEQ ID NO 468
<211> LENGTH: 77
<212> TYPE: PRT
<213> ORGANISM: Artificial Sequence
<220> FEATURE:
<223> OTHER INFORMATION: Synthetic peptide

<400> SEQUENCE: 468

Pro Ser Lys Glu Tyr Gln Glu Lys Ser Ala Glu Arg Gln Lys Glu Leu
1               5                   10                  15

Leu His Glu Tyr Glu Lys Leu Val Arg His Leu Arg Glu Leu Val Glu
            20                  25                  30

Lys Leu Gln Arg Arg Glu Leu Asp Lys Glu Glu Val Leu Arg Arg Leu
        35                  40                  45

Val Glu Ile Leu Glu Arg Leu Lys Asp Leu His Lys Lys Ile Glu Asp
    50                  55                  60

Ala His Arg Lys Asn Glu Glu Ala His Lys Glu Asn Lys
65                  70                  75

<210> SEQ ID NO 469

<400> SEQUENCE: 469

000

<210> SEQ ID NO 470
<211> LENGTH: 75
<212> TYPE: PRT
<213> ORGANISM: Artificial Sequence
<220> FEATURE:
<223> OTHER INFORMATION: Synthetic peptide

<400> SEQUENCE: 470

Pro Lys Glu Glu Ser Val Glu Glu Leu Lys Arg Val Ile Asp Lys His
1               5                   10                  15

Glu Glu Ile Leu Arg Glu Leu Lys Arg Val Leu Glu Glu His Glu Arg

```
                    20                  25                  30
Val Ser His Asp Glu Asp Glu Asn Glu Leu Arg Arg Ser Leu Glu Arg
            35                  40                  45
Leu Lys His Ile Leu Asp Arg Leu His Glu Ser Leu Lys Glu Leu His
        50                  55                  60
Glu Leu Leu Lys Lys Asn Glu Tyr Thr Glu Arg
65                  70                  75
```

<210> SEQ ID NO 471

<400> SEQUENCE: 471

000

<210> SEQ ID NO 472
<211> LENGTH: 70
<212> TYPE: PRT
<213> ORGANISM: Artificial Sequence
<220> FEATURE:
<223> OTHER INFORMATION: Synthetic peptide

<400> SEQUENCE: 472

```
Asp Glu Glu Tyr Val Thr Arg Ser Gln Arg Arg Leu Lys Arg Leu Leu
1               5                   10                  15
Glu Glu Tyr Ile Lys Val Val Glu Glu His Ala Arg Leu Val Glu Arg
            20                  25                  30
Asn Glu Arg Asp Asp Lys Glu Leu Lys Arg Ser Ile Asp Glu Leu Asp
        35                  40                  45
Lys Leu Thr Lys Glu Leu Glu Leu Val Lys Arg Tyr Lys Glu Leu
    50                  55                  60
Val Asp Lys Thr Glu Thr
65                  70
```

<210> SEQ ID NO 473

<400> SEQUENCE: 473

000

<210> SEQ ID NO 474
<211> LENGTH: 73
<212> TYPE: PRT
<213> ORGANISM: Artificial Sequence
<220> FEATURE:
<223> OTHER INFORMATION: Synthetic peptide

<400> SEQUENCE: 474

```
Arg Glu Glu Glu Leu Lys Glu Ser Ala Glu Glu Leu Glu Arg Ser Val
1               5                   10                  15
Arg Glu Leu Lys Lys Glu Ala Asp Lys Tyr Lys Glu Val Asp Arg
            20                  25                  30
Leu His Tyr Arg Gly Lys Val Asp Lys Asp Trp Val Arg Val Val Glu
        35                  40                  45
Lys Leu Ile Lys Leu Val Glu Glu His Leu Glu Leu Ile Arg Glu His
    50                  55                  60
Leu Glu Leu Leu Lys Glu Glu Arg Arg
65                  70
```

<210> SEQ ID NO 475

<400> SEQUENCE: 475

-continued

000

<210> SEQ ID NO 476
<211> LENGTH: 76
<212> TYPE: PRT
<213> ORGANISM: Artificial Sequence
<220> FEATURE:
<223> OTHER INFORMATION: Synthetic peptide

<400> SEQUENCE: 476

Asp Lys Asp Glu Arg Gln Glu Arg Leu Asn Glu Ser Asp Lys Ser
1               5                   10                  15

Asn Glu Glu Ser Glu Arg Ser Asn Arg Glu Ser Glu Glu Leu Asn Arg
            20                  25                  30

Arg Ala Arg Gly Pro Asn Asp Glu Lys Glu Leu Gln Glu Ile Leu Asp
        35                  40                  45

Arg His Leu Glu Leu Leu Glu Arg Asn Gln Arg Leu Leu Asp Glu Asn
    50                  55                  60

Lys Glu Ile Leu Arg Glu Ser Gln Tyr Leu Asn Asp
65                  70                  75

<210> SEQ ID NO 477

<400> SEQUENCE: 477

000

<210> SEQ ID NO 478
<211> LENGTH: 73
<212> TYPE: PRT
<213> ORGANISM: Artificial Sequence
<220> FEATURE:
<223> OTHER INFORMATION: Synthetic peptide

<400> SEQUENCE: 478

Glu Ser Glu Tyr Thr Gln Glu Glu Ile Leu Glu Leu Leu Lys Glu Ser
1               5                   10                  15

Ile Lys Leu Leu Arg Glu Ile Leu Arg Leu Leu Glu Glu Ser Glu Glu
            20                  25                  30

Leu Trp Arg Arg Glu Asn Thr Lys Ser Glu Arg Ser Glu Glu Ile Lys
        35                  40                  45

Glu Arg Ala Lys Glu Ala Ile Lys Arg Ser Glu Glu Ile Leu Glu Arg
    50                  55                  60

Val Lys Arg Leu Ser Asp His Ser Arg
65                  70

<210> SEQ ID NO 479

<400> SEQUENCE: 479

000

<210> SEQ ID NO 480
<211> LENGTH: 78
<212> TYPE: PRT
<213> ORGANISM: Artificial Sequence
<220> FEATURE:
<223> OTHER INFORMATION: Synthetic peptide

<400> SEQUENCE: 480

Pro Glu Lys Tyr Leu Ile Lys Thr Gln Glu Glu Leu Leu Arg Arg His
1               5                   10                  15

```
Ala Glu Ile Leu Glu Asp Leu Ile Arg Lys Val Arg Gln Val Asp
            20                  25                  30

Leu Arg Arg Lys Val Asp Glu Arg Asp Glu Asp Leu Lys Arg Glu Leu
        35                  40                  45

Glu Arg Ser Leu Arg Glu Leu Glu Arg Leu Val Arg Glu Ser Ser Arg
    50                  55                  60

Leu Val Glu Glu Ile Arg Glu Leu Ser Lys Glu Ile Lys Arg
65                  70                  75
```

<210> SEQ ID NO 481

<400> SEQUENCE: 481

000

<210> SEQ ID NO 482
<211> LENGTH: 77
<212> TYPE: PRT
<213> ORGANISM: Artificial Sequence
<220> FEATURE:
<223> OTHER INFORMATION: Synthetic peptide

<400> SEQUENCE: 482

```
Glu Lys Glu Tyr Ile Glu Lys Leu Ser Arg Lys Ile Glu Glu Asp Ile
1               5                   10                  15

Arg Arg Ser Glu Glu Arg Ala Lys Asp Ser Glu Arg Leu Val Arg Arg
            20                  25                  30

Leu Glu Glu Leu Ala Lys Arg Lys Arg Leu Asp Leu Asp Asp Val Leu
        35                  40                  45

Arg Val Ala Glu Glu Asn Leu Glu Ile Leu Glu Asp Asn Leu Arg Ile
    50                  55                  60

Leu Glu Glu Ile Leu Lys Glu Gln Asp Lys Ser Asn Arg
65                  70                  75
```

<210> SEQ ID NO 483

<400> SEQUENCE: 483

000

<210> SEQ ID NO 484
<211> LENGTH: 80
<212> TYPE: PRT
<213> ORGANISM: Artificial Sequence
<220> FEATURE:
<223> OTHER INFORMATION: Synthetic peptide

<400> SEQUENCE: 484

```
Asp His Glu Asp Val Val Arg Leu His Glu Asp Leu Val Arg Lys Gln
1               5                   10                  15

Glu Asp Ala Arg Arg Val Leu Glu Glu Ile Val Arg Leu Ala Glu Glu
            20                  25                  30

Ile Val Glu Val Ile Lys Lys Asp Glu Lys Asp Lys Asp Arg Val Thr
        35                  40                  45

Arg Leu Val Glu Glu Ile Glu Lys Leu Val Glu Glu Tyr Lys Lys Lys
    50                  55                  60

Val Asp Glu Met Arg Lys Ile Ser Asp Glu Ile Lys Tyr Arg Ser Arg
65                  70                  75                  80
```

<210> SEQ ID NO 485

<400> SEQUENCE: 485

000

<210> SEQ ID NO 486
<211> LENGTH: 77
<212> TYPE: PRT
<213> ORGANISM: Artificial Sequence
<220> FEATURE:
<223> OTHER INFORMATION: Synthetic peptide

<400> SEQUENCE: 486

Arg Glu Asp Glu Glu Leu Glu Glu Ile Asp Arg Ile Arg Gln Met
1               5                   10                  15

Val Glu Tyr Glu Glu Leu Val Lys Glu Tyr Glu Glu Leu Thr Glu
            20                  25                  30

Lys Tyr Lys Gln Gly Lys Val Asp Lys Glu Glu Ser Lys Lys Ile Ile
        35                  40                  45

Glu Lys Ser Glu Arg Leu Leu Asp Leu Ser Gln Asp Ala Val Arg Lys
    50                  55                  60

Val Lys Glu Ile Ile Arg Arg Ile Leu Tyr Thr Asn Arg
65                  70                  75

<210> SEQ ID NO 487

<400> SEQUENCE: 487

000

<210> SEQ ID NO 488
<211> LENGTH: 75
<212> TYPE: PRT
<213> ORGANISM: Artificial Sequence
<220> FEATURE:
<223> OTHER INFORMATION: Synthetic peptide

<400> SEQUENCE: 488

Pro Leu Glu Glu Ile Leu Lys Ile Gln Arg Arg Ile Asn Lys Ile Gln
1               5                   10                  15

Asp Asp Ile Asn Lys Ile Leu His Glu Ile Leu Arg Met Gln Glu Lys
            20                  25                  30

Leu Asn Arg Ser Ser Asp Lys Asp Glu Val Glu Ser Leu Arg Arg
        35                  40                  45

Ile Arg Glu Leu Ile Lys Arg Ile Lys Asp Leu Ser Lys Glu Ile Glu
    50                  55                  60

Asp Leu Ser Arg Glu Val Lys Tyr Arg Thr Thr
65                  70                  75

<210> SEQ ID NO 489

<400> SEQUENCE: 489

000

<210> SEQ ID NO 490
<211> LENGTH: 77
<212> TYPE: PRT
<213> ORGANISM: Artificial Sequence
<220> FEATURE:
<223> OTHER INFORMATION: Synthetic peptide

<400> SEQUENCE: 490

```
Asp Glu Asp Glu Thr Ser Tyr Arg Ile Leu Glu Leu Leu Arg Glu Ile
1               5                   10                  15

Val Arg Ala Ser Arg Glu Leu Ile Arg Leu Ser Glu Glu Leu Leu Glu
            20                  25                  30

Val Ala Arg Arg Asp Asp Lys Asp Glu Thr Val Leu Glu Thr Leu Ile
            35                  40                  45

Arg Glu Tyr Lys Glu Leu Leu Asp Arg Tyr Arg Arg Leu Ile Glu Glu
        50                  55                  60

Leu Thr Arg Leu Val Glu Tyr Glu Glu Arg Ser Arg
65                  70                  75

<210> SEQ ID NO 491

<400> SEQUENCE: 491

000

<210> SEQ ID NO 492
<211> LENGTH: 80
<212> TYPE: PRT
<213> ORGANISM: Artificial Sequence
<220> FEATURE:
<223> OTHER INFORMATION: Synthetic peptide

<400> SEQUENCE: 492

Asp Glu Glu Leu Asn Arg Glu Leu Leu Lys Ser Lys Arg Leu
1               5                   10                  15

Val Asp Ile Asn Arg Asp Ile Ile Arg Thr Ala Gln Glu Leu Ile Glu
            20                  25                  30

Met Leu Lys Asp Ser Lys Asp Gly Arg Val Asp Glu Asp Thr Lys Arg
            35                  40                  45

Glu Leu Arg Asp Lys Leu Arg Lys Leu Glu Glu Lys Leu Glu Arg Val
        50                  55                  60

Arg Glu Glu Leu Arg Lys Tyr Glu Glu Leu Leu Arg Tyr Val Gln Arg
65                  70                  75                  80

<210> SEQ ID NO 493

<400> SEQUENCE: 493

000

<210> SEQ ID NO 494
<211> LENGTH: 77
<212> TYPE: PRT
<213> ORGANISM: Artificial Sequence
<220> FEATURE:
<223> OTHER INFORMATION: Synthetic peptide

<400> SEQUENCE: 494

Asp Glu Glu Asp Val Leu Tyr His Leu Arg Glu Leu Leu Glu Glu Leu
1               5                   10                  15

Lys Arg Val Ser Asp Asp Tyr Glu Arg Leu Val Arg Glu Ile Lys Glu
            20                  25                  30

Thr Ser Glu Arg Lys Asp Arg Asp Thr Lys Glu Asn Lys Asp Met Leu
            35                  40                  45

Asp Glu Leu Val Lys Ala His Arg Glu Gln Glu Lys Leu Leu Glu Arg
        50                  55                  60

Leu Val Arg Leu Leu Glu Glu Leu Phe Glu Arg Lys Arg
65                  70                  75
```

UNITED STATES PATENT AND TRADEMARK OFFICE
CERTIFICATE OF CORRECTION

| | | |
|---|---|---|
| PATENT NO. | : 11,820,800 B2 | Page 1 of 1 |
| APPLICATION NO. | : 17/285033 | |
| DATED | : November 21, 2023 | |
| INVENTOR(S) | : Chen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 136 days.

Signed and Sealed this
Eighth Day of July, 2025

Coke Morgan Stewart
*Acting Director of the United States Patent and Trademark Office*